(12) United States Patent
Tsukamoto et al.

(10) Patent No.: US 7,608,563 B2
(45) Date of Patent: Oct. 27, 2009

(54) 3-PHENOXY-4-PYRIDAZINOL DERIVATIVES AND HERBICIDE COMPOSITION CONTAINING THE SAME

(75) Inventors: Yoshihisa Tsukamoto, Shiga (JP); Hiroyuki Komai, Shiga (JP); Junji Kadotani, Shiga (JP); Kiyoshi Koi, Shiga (JP); Shigeru Mio, Shiga (JP); Hideo Takeshiba, Tokyo (JP)

(73) Assignee: Mitsui Agro Chemicals, Inc., Tokyo (JP)

( * ) Notice: Subject to any disclaimer, the term of this patent is extended or adjusted under 35 U.S.C. 154(b) by 601 days.

(21) Appl. No.: 10/487,013

(22) PCT Filed: Aug. 14, 2002

(86) PCT No.: PCT/JP02/08278

§ 371 (c)(1),
(2), (4) Date: Feb. 27, 2004

(87) PCT Pub. No.: WO03/016286

PCT Pub. Date: Feb. 27, 2003

(65) Prior Publication Data

US 2005/0037925 A1    Feb. 17, 2005

(30) Foreign Application Priority Data

Aug. 17, 2001  (JP)  ............................. 2001-248014
Mar. 25, 2002  (JP)  ............................. 2002-082219

(51) Int. Cl.
*A01N 43/84* (2006.01)
*A01N 43/58* (2006.01)
*C07D 413/02* (2006.01)
*C07D 403/02* (2006.01)
*C07D 237/16* (2006.01)

(52) U.S. Cl. ..................... 504/225; 504/238; 544/114; 544/238; 544/240

(58) Field of Classification Search ................. 504/116, 504/225, 238; 514/252; 544/239, 240, 114, 544/238
See application file for complete search history.

(56) References Cited

U.S. PATENT DOCUMENTS 4,661,486 A *  4/1987  Takeshiba et al. ........... 514/247
5,559,080 A    9/1996  South et al.

FOREIGN PATENT DOCUMENTS

EP    0 470 856 A1   2/1992
JP    63-264575 A    11/1988

OTHER PUBLICATIONS

Teruomi Jojima et al., "Pyridazines I. Novel Intramolecular Cycloaddition of 3-Chloro-6- (2-allylphenoxy)pyridazines", *Chem. Pharm. Bull.*, 1972, vol. 20, No. 10, pp. 2191-2203.
Donald E. Ames et al., "[1,4]Benzodioxinopyridazines", *Journal of the Chemical Society*: Perkin Transaction I, 1975, No. 6, pp. 534-538.
*The Pesticide Manual*, 11th Edition, C.D.S. Tomlin, editor, pp. 111 to 112, pp. 1049 to 1050, and pp. 1054 to 1055 (1997).
*The Pesticide Manual*, 12th Edition, C.D.S. Tomln, editor, pp. 563-564, pp. 642-644 and pp. 848-849 (2000).
P.M. Harrington et al, "Synthesis and Herbicidal Activity of Cyperin", *Journal of Agricultural and Food Chemistry*, vol. 43, No. 3, pp. 804-808 (1995).

* cited by examiner

*Primary Examiner*—Kamal A Saeed
*Assistant Examiner*—Kristin Bianchi
(74) *Attorney, Agent, or Firm*—Frishauf, Holtz, Goodman & Chick, P.C.

(57) ABSTRACT

A compound represented by the formula:

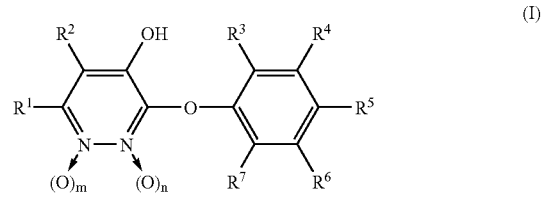

[wherein $R^1$ represents a hydrogen atom, a halogen, atom, alkyl group, etc., $R^2$ represents a hydrogen atom, a halogen atom, alkyl group, etc., $R^3$, $R^4$, $R^5$, $R^6$ and $R^7$ each independently represent a hydrogen atom, a halogen atom, a substitutable alkyl group, a substitutable alkenyl group, alkynyl group, a substituteable cycloalkyl group, etc., or $R^3$, $R^4$, $R^5$, $R^6$ and $R^7$ may form a ring which may be substituted, which is formed by the adjacent two of them with carbon atoms to which the respective substituents are bonded, m and n each independently represent 0 or 1.] a salt thereof, an ester derivative thereof and an agricultural chemical containing the same as an effective ingredient, and a herbicidal composition containing the compound and a second herbicidally active compound as effective ingredients.

18 Claims, No Drawings

3-PHENOXY-4-PYRIDAZINOL DERIVATIVES AND HERBICIDE COMPOSITION CONTAINING THE SAME

This application is the United States national phase application of International Application PCT/JP02/08278 filed Aug. 14, 2002.

TECHNICAL FIELD

The present invention relates to a 3-phenoxy-4-pyridazinol compound, its salt, its ester derivative and agricultural chemical containing the same as an effective ingredient, and a herbicidal composition containing 3-phenoxy-4-pyridazinol compound and a second herbicidally active compound as effective ingredients.

BACKGROUND ART

In Chemical Pharmaceutical Bulletin, 1972, vol. 20, No. 10, pp. 2191-2203, 3-(2-allylphenoxy)-6-chloro-4-methoxypyridazine has been disclosed but a 3-phenoxy-4-pyridazinol compound having a hydroxyl group at the 4-position of the pyridazine has not been disclosed, and there is no description about a herbicide.

In Journal of the Chemical Society: Perkin Transaction I, 1975, No. 6, pp. 534-538, 3-(2-hydroxyphenoxy)-4-methoxypyridazine and 6-chloro-3-(2-hydroxyphenoxy)-4-methoxypyridazine has been disclosed but a 3-phenoxy-4-pyridazinol compound having a hydroxyl group at the 4-position of the pyridazine has not been disclosed, and there is no description about a herbicide.

In U.S. Pat. No. 5,559,080, a 3-(phenoxy which may be substituted)pyridazine compound having a haloalkylphenoxy group at the 4-position of the pyridazine has been disclosed but a 3-phenoxy-4-pyridazinol compound having a hydroxyl group at the 4-position of the pyridazine has not been disclosed. Also, in the 3-(phenoxy which may be substituted) pyridazine compound having a haloalkylphenoxy group at the 4-position of the pyridazine, an oxygen atom bonded to the 4-position of the pyridazine is bonded by a benzene ring, and its herbicidal activity was insufficient.

Also, at present, a number of herbicides have been practically used as a herbicide for a paddy field, and widely been used for general purpose as a single agent and a mixed agent. However, there are many kinds of paddy field weeds, and germination and growth period of the respective weeds are not uniform, in particular, occurrence of perennial weeds ranges for a long period of time. Thus, it is extremely difficult to prevent from and kill all weeds with one time spread of a herbicide. Accordingly, as a herbicide, an appearance of a chemical which can kill many kinds of weeds including annual weeds and perennial weeds, that is, which has a wide weed-killing spectrum, is effective for already grown weeds, preventing and killing effects of weeds of which can be maintained for a certain period of time, and has high safety to paddy rice has earnestly been desired.

Also, as upland herbicides, a number of herbicides have now been commercially available and practically used, but there are many kinds of weeds to be prevented, and occurrence thereof ranges for a long period of time, so that a herbicide which has higher herbicidal effects, has broad weed-killing spectrum, and causes no chemical damage to crops has been desired.

One of the effective ingredient of the herbicidal composition of the present invention (hereinafter referred to as a second herbicidally active compound), 4-(2,4-dichlorobenzoyl)-1,3-dimethyl-5-pyrazolyl-p-toluenesulfonate [hereinafter referred to as Compound A. General name: Pyrazolate], 2-[4-(2,4-dichlorobenzoyl)-1,3-dimethylpyrazol-5-yloxy] acetophenone [hereinafter referred to as Compound B. General name: Pyrazoxyfen], 2-[4-(2,4-dichloro-m-toluoyl)-1,3-dimethylpyrazol-5-yloxy]-4'-methylacetophenone [hereinafter referred to as Compound C. General name: Benzofenap], 5-cyclopropyl-1,2-oxazol-4-yl α,α,α-trifluoro-2-mesyl-p-tolyl ketone [hereinafter referred to as Compound D. General name: Isoxaflutole], 2-(2-chloro-4-mesylbenzoyl) cyclohexan-1,3-dione [hereinafter referred to as Compound E. General name: sulcotrione], 2-(4-mesyl-2-nitrobenzoyl) cyclohexan-1,3-dione [hereinafter referred to as Compound F. General name: mesotrion] and 4-chloro-2-(methylsulfonyl)phenyl 5-cyclopropyl-4-isoxazolyl ketone [hereinafter referred to as Compound G. General name: Isoxachlortole] are each conventionally known herbicidal compound and each described in The Pesticide Manual 11th Edition, pp. 1049 to 1050, Ibid. pp. 1054 to 1055, Ibid. pp. 111 to 112, The Pesticide Manual, 12th Edition p. 563, Ibid. p. 848, Ibid. p. 602 and EP 470 856(1990). These compounds have high effects against annual broad-leaved weeds and a part of perennial weeds, but their effects against rice plant weeds or a part of perennial weeds are not necessarily sufficient.

DISCLOSURE OF THE INVENTION

The present inventors have earnestly studied about pyridazine derivatives having a phenoxy group at the 3-position thereof, and as a result, they have found that a compound having a hydroxyl group at the 4-position of the pyridazine ring shows substantially no chemical damage against paddy rice, and shows excellent herbicidal activity against a wide range of weeds in a paddy field with a low dosage to accomplish the present invention. Moreover, they have found that similar herbicidal activities are possessed by an ester derivative thereof in which a bonding between an oxygen atom at the 4-position of the pyridazine ring and an acyl group is cleaved in a soil or in a plant body to be converted into a compound in which a hydrogen atom binds to the oxygen atom, whereby accomplished the present invention.

Also, the present inventors have continued to search on a herbicide which can completely prevent and remove various kinds of weeds with one time spread, has extremely high safety to paddy rice or upland crops, and has extremely low toxicity against humans and animals for the purpose of overcoming the above-mentioned problems involved in the conventional herbicides such as second herbicidally active compounds A, B, C, D, E, F and G, and as a result, they have found that by formulating the above-mentioned 3-phenoxy-4-pyridazinol derivatives and the second herbicidally active compound as effective ingredients, a weed-killing spectrum can be enlarged, and serious weeds can be prevented and killed with a smaller amount of effective ingredients by their synergistic action, whereby accomplished the present invention.

The present invention relates to a compound represented by the formula:

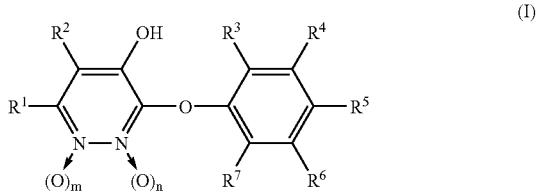

[wherein $R^1$ represents a hydrogen atom, a halogen atom, a $C_1$ to $C_6$ alkyl group, a $C_1$ to $C_6$ haloalkyl group, a $C_3$ to $C_6$ cycloalkyl group, a $C_2$ to $C_6$ alkenyl group, a cyano group, a $C_2$ to $C_7$ alkylcarbonyl group, a di($C_1$ to $C_6$ alkyl)carbamoyl group, a phenyl group which may be substituted (The substituent is a substituent selected from the following substituent Group A.), a 5 or 6-membered heterocyclic group (the heterocycle contains one nitrogen atom, oxygen atom or sulfur atom in the ring, and may contain further 1 or 2 nitrogen atom(s).), a $C_1$ to $C_6$ alkoxy group, a phenoxy group which may be substituted (The substituent is a substituent selected from the following substituent Group A.) or a 5- or 6-membered heterocycloxy group which may be substituted {the heterocycle contains one nitrogen atom, oxygen atom or sulfur atom in the ring, and may contain further 1 or 2 nitrogen atom(s). The substituent is a substituent(s) selected from the group consisting of a benzoyl group which may be substituted (The substituent is a substituent selected from the following substituent Group A.) and a $C_1$ to $C_6$ alkyl group.}, $R^2$ represents a hydrogen atom, a halogen atom, a $C_1$ to $C_6$ alkyl group, a ($C_1$ to $C_6$ alkoxy)$C_1$ to $C_6$ alkyl group, a benzoyl group which may be substituted (The substituent is a substituent selected from the following substituent Group A.), a $C_2$ to $C_7$ alkoxycarbonyl group, a phenoxy group which may be substituted (The substituent is a substituent selected from the following substituent Group A.), a phenylthio group which may be substituted (The substituent is a substituent selected from the following substituent Group A.) or a tri($C_1$ to $C_6$ alkyl)silyl group, $R^3$, $R^4$, $R^5$, $R^6$ and $R^7$ each independently represent a hydrogen atom, a halogen atom, a $C_1$ to $C_6$ alkyl group which may be substituted (The substituent is a substituent selected from the following substituent Group B.), a $C_2$ to $C_6$ alkenyl group which may be substituted (The substituent is a cyano group or a nitro group.), a $C_2$ to $C_6$ alkynyl group, a $C_3$ to $C_6$ cycloalkyl group which may be substituted (The substituent is a substituent selected from the following substituent Group C.), a $C_4$ to $C_{10}$ bicycloalkyl group, a cyano group, a formyl group, a $C_2$ to $C_7$ alkylcarbonyl group, a benzoyl group which may be substituted (The substituent is a substituent selected from the following substituent Group A.), a carboxyl group, a $C_2$ to $C_7$ alkoxycarbonyl group, a carbamoyl group, a di($C_1$ to $C_6$ alkyl)-carbamoyl group, a phenyl group which may be substituted (The substituent is a substituent selected from the following substituent Group A.), a 3- to 6-membered heterocyclic group which may be substituted (the heterocycle contains one nitrogen atom, oxygen atom or sulfur atom in the ring, and may contain further 1 or 2 nitrogen atom(s), or may be fused with a benzene ring. The substituent is a substituent selected from the following substituent Group E.), an amino group which may be substituted (The substituent is a substituent selected from the following substituent Group D.), a nitro group, a hydroxyl group, a $C_1$ to $C_6$ alkoxy group, a $C_1$ to $C_6$ haloalkoxy group, a ($C_1$ to $C_6$ alkoxy)$C_1$ to $C_6$ alkoxy group, a phenoxy group which may be substituted (The substituent is a hydroxyl group or a pyridazinyloxy group substituted by a substituent(s) selected from the group consisting of a halogen atom and a $C_1$ to $C_6$ alkoxy group.), a 5- to 6-membered heterocycloxy group which may be substituted (the heterocycle contains one nitrogen atom, oxygen atom or sulfur atom in the ring, and may contain further 1 or 2 nitrogen atom(s). The substituent is a substituent selected from the following substituent Group E.), a phenylsulfonyloxy group which may be substituted (The substituent is a substituent selected from the following substituent Group A.), a $C_1$ to $C_6$ alkylthio group, a $C_1$ to $C_6$ alkylsulfinyl group, a $C_1$ to $C_6$ alkylsulfonyl group or a tri($C_1$ to $C_6$ alkyl)silyl group, or $R^3$, $R^4$, $R^5$, $R^6$ and $R^7$ may form a 3- to 6-membered cyclic hydrocarbon group which may be substituted, which is formed by the adjacent two of them with carbon atoms to which the respective substituents are bonded (the cyclic hydrocarbon may be interrupted by the same or different 1 to 2 hetero atom(s) selected from the group consisting of a nitrogen atom, an oxygen atom and a sulfur atom. The substituent is a halogen atom, a $C_1$ to $C_6$ alkyl group, a hydroxy-$C_1$ to $C_6$ alkyl group, a $C_1$ to $C_6$ alkoxy group, an oxo group, a hydroxyimino group or a $C_1$ to $C_6$ alkoxyimino group, and when the $C_1$ to $C_6$ alkyl group is substituted, it may form another 3-membered ring by combining, with the other $C_1$ to $C_6$ alkyl group or a carbon atom(s) in the cyclic hydrocarbon.), m and n each independently represent 0 or 1, the substituent Group A is a group selected from the group consisting of a halogen atom, a $C_1$ to $C_6$ alkyl group, a $C_1$ to $C_6$ haloalkyl group, a $C_3$ to $C_6$ cycloalkyl group, a cyano group and a tri($C_1$ to $C_6$ alkyl)silyl group, the substituent Group B is a group selected from the group consisting of a halogen atom, a $C_3$ to $C_6$ cycloalkyl group, a cyano group, a $C_2$ to $C_7$ alkylcarbonyl group, a $C_2$ to $C_7$ alkoxycarbonyl group, a phenyl group, a $C_1$ to $C_6$ alkoxy group, a $C_1$ to $C_6$ alkylthio group, a $C_1$ to $C_6$ alkylsulfinyl group, a $C_1$ to $C_6$ alkylsulfonyl group, a $C_1$ to $C_4$ alkylenedioxy group, a hydroxyimino group and a $C_1$ to $C_6$ alkoxyimino group, the substituent Group C is a group selected from the group consisting of a halogen atom, a $C_1$ to $C_6$ alkyl group which may be substituted (The substituent is a substituent selected from the above-mentioned substituent Group B.), a $C_3$ to $C_6$ cycloalkyl group, a $C_2$ to $C_6$ alkenyl group, a cyano group, a $C_2$ to $C_7$ alkylcarbonyl group, a benzoyl group, a carboxyl group, a $C_2$ to $C_7$ alkoxycarbonyl group, a carbamoyl group, a di($C_1$ to $C_6$ alkyl)carbamoyl group, a phenyl group which may be substituted (The substituent is a substituent selected from the above-mentioned substituent Group A.), a 5 or 6-membered heterocyclic group (the heterocycle contains one nitrogen atom, oxygen atom or sulfur atom in the ring, and may contain further 1 or 2 nitrogen atom(s).), an amino group which may be substituted (The substituent is a substituent selected from the following substituent Group D.), a nitro group, a hydroxyl group, a $C_1$ to $C_6$ alkoxy group, a $C_1$ to $C_6$ haloalkoxy group, a phenoxy group, a $C_1$ to $C_6$ alkylthio group, a phenylthio group, a $C_1$ to $C_6$ alkylsulfinyl group and a $C_1$ to $C_6$ alkylsulfonyl group, the substituent Group D is a group selected from the group consisting of a $C_1$ to $C_6$ alkyl group, a $C_2$ to $C_7$ alkylcarbonyl group, a $C_2$ to $C_7$ alkoxycarbonyl group, a di($C_1$ to $C_6$ alkyl) carbamoyl group and a $C_1$ to $C_6$ alkylsulfonyl group, the substituent Group E is a group selected from the group consisting of a halogen atom, a $C_1$ to $C_6$ alkyl group, a $C_1$ to $C_6$ haloalkyl group, a hydroxyl group, a phenylsulfonyl group which may be substituted (The substituent is a substituent selected from the above-mentioned substituent Group A.) and a di($C_1$ to $C_6$ alkyl)sulfamoyl group.], its salt or its ester derivative, an agricultural chemical containing the same as an effective ingredient, and, a herbicidal composition containing one or more 3-phenoxy-4-pyridazinol derivatives selected from the group consisting of the above-mentioned compounds, their salt and their ester derivatives, and one or more second herbicidally active compound selected from the group consisting of 4-(2,4-dichlorobenzoyl)-1,3-dimethyl-5-pyrazolyl-p-toluenesulfonate, 2-[4-(2,4-dichlorobenzoyl)-1,3-dimethylpyrazol-5-yloxy]acetophenone, 2-[4-(2,4-dichloro-m-toluoyl)-1,3-dimethylpyrazol-5-yloxy]-4'-methylacetophenone, 5-cyclopropyl-1,2-oxazol-4-yl α,α,α-trifluoro-2-mesyl-p-tolyl ketone, 2-(2-chloro-4-mesylbenzoyl)cyclohexan-1,3-dione, 2-(4-mesyl-2-nitrobenzoyl)cyclohexan-1,3-dione and 4-chloro-2-(methylsulfonyl)phenyl 5-cyclopropyl-4-isoxazolyl ketone as effective ingredients.

In the present invention, "a halogen atom" is a fluorine atom, a chlorine atom, a bromine atom or an iodine atom, preferably a fluorine atom, a chlorine atom or a bromine atom, more preferably a chlorine atom or a bromine atom, still further preferably a chlorine atom.

In the present invention, the "$C_1$ to $C_6$ alkyl group" is a straight or branched alkyl group having 1 to 6 carbon atoms, for example, it may be methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a straight or branched alkyl group having 1 to 4 carbon atoms (a $C_1$ to $C_4$ alkyl group), more preferably a straight or branched alkyl group having 1 to 3 carbon atoms (a $C_1$ to $C_3$ alkyl group), still further preferably an alkyl group having 1 to 2 carbon atoms (a $C_1$ to $C_2$ alkyl group), particularly preferably a methyl group.

In the present invention, the "$C_1$ to $C_6$ haloalkyl group" is the "$C_1$ to $C_6$ alkyl group" to which the same or different above-mentioned 1 to 5 "a halogen atom(s)" is/are substituted, and for example, it may be chloromethyl, dichloromethyl, trichloromethyl, 1-chloroethyl, 2-chloroethyl, 2,2,2-trichloroethyl, 1-chloropropyl, 3-chloropropyl, 1-chlorobutyl, 4-chlorobutyl, fluoromethyl, difluoromethyl, trifluoromethyl, 1-fluoroethyl, 2-fluoroethyl, 2,2,2-trifluoroethyl, pentafluoroethyl, fluorochloromethyl, bromomethyl, 1-bromoethyl, 2-bromoethyl or iodomethyl group, preferably a $C_1$ to $C_3$ alkyl group substituted by the same or different 1 to 3 substituent(s) selected from the group consisting of a fluorine atom, a chlorine atom and a bromine atom, more preferably a $C_1$ to $C_2$ alkyl group substituted by the same 1 to 3 fluorine atom(s) or chlorine atom(s), still further preferably a fluoromethyl, difluoromethyl, trifluoromethyl or 2,2,2-trichloroethyl group, particularly preferably a trifluoromethyl group.

In the present invention, the "$C_3$ to $C_6$ cycloalkyl group" is a cyclopropyl, cyclobutyl, cyclopentyl or cyclohexyl group, preferably cyclopropyl or cyclobutyl group, more preferably cyclopropyl group.

In the present invention, the "$C_2$ to $C_6$ alkenyl group" is a straight or branched alkenyl group having 2 to 6 carbon atoms, for example, it may be vinyl, 1-methylvinyl, 1-propenyl, 1-methyl-1-propenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl or 5-hexenyl group, preferably a straight or branched alkenyl group having 2 to 4 carbon atoms (a $C_2$ to $C_4$ alkenyl group), more preferably a vinyl, 1-methylvinyl, 2-propenyl or 1-methyl-2-propenyl group.

In the present invention, the "$C_2$ to $C_7$ alkylcarbonyl group" is a carbonyl group to which the above-mentioned "$C_1$ to $C_6$ alkyl group" is bonded, and for example, it may be an acetyl, propionyl, butyryl, isobutyryl, valeryl, isovaleryl, pivaloyl, hexanoyl or heptanoyl group, preferably a carbonyl group to which a straight or branched alkyl group having 1 to 4 carbon atoms is bonded (a $C_2$ to $C_5$ alkylcarbonyl group), still further preferably a carbonyl group to which a straight or branched alkyl group having 1 to 3 carbon atoms is bonded (a $C_2$ to $C_4$ alkylcarbonyl group), particularly preferably an acetyl, propionyl, valeryl or pivaloyl group, most preferably an acetyl group.

In the present invention, the "di($C_1$ to $C_6$ alkyl)-carbamoyl group" is a carbamoyl group in which the same or different two above-mentioned "$C_1$ to $C_6$ alkyl groups" are bonded to a nitrogen atom, and for example, it may be a dimethylcarbamoyl, methylethylcarbamoyl, diethylcarbamoyl, dipropylcarbamoyl, dibutylcarbamoyl or dihexylcarbamoyl group, preferably a carbamoyl group in which the same two straight or branched alkyl groups having 1 to 3 carbon atoms are bonded {a di($C_1$ to $C_3$ alkyl)carbamoyl group}, more preferably a dimethylcarbamoyl group or a diethylcarbamoyl group, still further preferably a dimethylcarbamoyl group.

In the present invention, the "tri($C_1$ to $C_6$ alkyl)-silyl group" is a silicon atom to which the same or different three above-mentioned "$C_1$ to $C_6$ alkyl groups" are bonded, and for example, it may be a trimethylsilyl, triethylsilyl, triisopropylsilyl, dimethylisopropylsilyl, t-butyldimethylsilyl or trihexylsilyl group, preferably a silicon atom to which the same or different three straight or branched alkyl groups having 1 to 3 carbon atoms are bonded {a tri($C_1$ to $C_3$ alkyl)silyl group}, more preferably a trimethylsilyl or dimethylisopropylsilyl group, still further preferably a trimethylsilyl group.

In the present invention, "a phenyl group which may be substituted (The substituent is a substituent selected from the substituent Group A.)" is a phenyl group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl)-silyl group", and for example, it may be a phenyl, fluorophenyl, difluorophenyl, trifluorophenyl, chlorophenyl, dichlorophenyl, trichlorophenyl, fluorochlorophenyl, methylphenyl, dimethylphenyl, trimethylphenyl, tetramethylphenyl, pentamethylphenyl, ethylphenyl, fluoro(methyl)phenyl, chloro(methyl)phenyl, bromo(methyl)phenyl, cyclopropylphenyl, cyclopropyl(fluoro)phenyl, chloro(cyclopropyl)phenyl, cyclopropyl(methyl)phenyl, (trifluoromethyl)phenyl or fluoro(trifluoromethyl)phenyl group, preferably a phenyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a phenyl, chlorophenyl, methylphenyl, trifluorophenyl or cyanophenyl group.

In the present invention, the "5 or 6-membered heterocyclic group (the heterocycle contains one nitrogen atom, oxygen atom or sulfur atom in the ring, and may contain further 1 or 2 nitrogen atom(s).)" is a 5- to 6-membered heterocyclic group which contains one nitrogen atom, oxygen atom or sulfur atom as a hetero atom and may further contain 1 to 2 nitrogen atom(s), and for example, it may be a furyl, thienyl, pyrrolyl, pyrazolyl, imidazolyl, isoxazolyl, oxazolyl, isothiazolyl, thiazolyl, triazolyl, pyranyl, pyridyl, pyrazinyl, pyrimidinyl, pyridazinyl or triazinyl group, preferably a 5-membered heterocyclic group (the heterocycle contains one nitrogen atom, oxygen atom or sulfur atom in the ring.), more preferably a furyl or thienyl group.

In the present invention, the "$C_1$ to $C_6$ alkoxy group" is a straight or branched alkoxy group having 1 to 6 carbon atoms, and for example, it may be a methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group, preferably a straight or branched alkoxy group having 1 to 3 carbon atoms (a $C_1$ to $C_3$ alkoxy group), more preferably a methoxy or ethoxy group, still further preferably a methoxy group.

In the present invention, the "phenoxy group which may be substituted (The substituent is a substituent selected from the substituent Group A.)" is a phenoxy group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl)-silyl group", and for example, it may be a phenoxy, fluorophenoxy, difluorophenoxy, trifluorophenoxy, chlorophenoxy, dichlorophenoxy, trichlorophenoxy, fluorochlorophenoxy, methylphenoxy, dimethylphenoxy, trimethylphenoxy, tetramethylphenoxy, pentamethylphenoxy, ethylphenoxy, fluoro(methyl)phenoxy, chloro(methyl)phenoxy, bromo(methyl)phenoxy, cyclopropylphenoxy, cyclopropyl(fluoro)phenoxy, chloro(cyclopropyl)phenoxy, cyclopropyl(methyl)phenoxy, (trifluoromethyl)phenoxy or fluoro(trifluoromethyl)phenoxy group, preferably a phenoxy group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a phenoxy, chlorophenoxy, methylphenoxy, trifluorophenoxy or cyanophenoxy group.

In the present invention, "a benzoyl group which may be substituted (The substituent is a substituent selected from the substituent Group A.)" is a benzoyl group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl)silyl group", and for example, it may be a benzoyl, fluorobenzoyl, difluorobenzoyl, trifluorobenzoyl, chlorobenzoyl, dichlorobenzoyl, trichlorobenzoyl, fluorochlorobenzoyl, methylbenzoyl, dimethylbenzoyl, trimethylbenzoyl, tetramethylbenzoyl, pentamethylbenzoyl, ethylbenzoyl, fluoro(methyl)benzoyl, chloro(methyl)benzoyl, bromo(methyl)benzoyl, cyclopropylbenzoyl, cyclopropyl(fluoro)benzoyl, chloro(cyclopropyl)benzoyl, cyclopropyl(methyl)benzoyl, (trifluoromethyl)benzoyl or fluoro(trifluoromethyl)benzoyl group, preferably a benzoyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group which may be substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a benzoyl, chlorobenzoyl, dichlorobenzoyl, methylbenzoyl, trifluorobenzoyl or cyanobenzoyl group.

In the present invention, "the 5- or 6-membered heterocycloxy group which may be substituted {the heterocycle contains one nitrogen atom, oxygen atom or sulfur atom in the ring, and may contain further 1 or 2 nitrogen atom(s). The substituent may be substituted by a substituent(s) selected from the group consisting of a benzoyl group which may be substituted (The substituent is a substituent selected from the substituent Group A.) and a $C_1$ to $C_6$ alkyl group.}" is "a 5- to 6-membered heterocycloxy group which contains one nitrogen atom, oxygen atom or sulfur atom as a hetero atom, and may contain further 1 or 2 nitrogen atom(s)" which may be substituted by the same or different 1 to 3 substituent(s) selected from the group consisting of the above-mentioned "a benzoyl group which may be substituted (The substituent is a substituent selected from the substituent Group A.)" and the above-mentioned "$C_1$ to $C_6$ alkyl group", preferably a benzoyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, and "a 5-membered heterocycloxy group which contains one nitrogen atom, oxygen atom or sulfur atom as a hetero atom, and which may contain further one nitrogen atom" substituted by the same two $C_1$ to $C_3$ alkyl groups, more preferably a benzoyl group substituted by two chlorine atoms and a pyrazolyloxy group substituted by two $C_1$ to $C_2$ alkyl groups.

In the present invention, "the ($C_1$ to $C_6$ alkoxy)-$C_1$ to $C_6$ alkyl group" is the above-mentioned "$C_1$ to $C_6$ alkyl group" substituted by one of the above-mentioned "$C_1$ to $C_6$ alkoxy groups", and for example, it may be a methoxymethyl, ethoxymethyl, propoxymethyl, butoxymethyl, s-butoxymethyl, t-butoxymethyl, pentyloxymethyl, hexyloxymethyl, methoxyethyl, ethoxyethyl, propoxyethyl, butoxyethyl, methoxypropyl, methoxybutyl, methoxypentyl or methoxyhexyl group, preferably a $C_1$ to $C_6$ alkyl group substituted by one $C_1$ to $C_3$ alkoxy group, more preferably a methoxyethyl, ethoxyethyl or ethoxymethyl group.

In the present invention, "$C_2$ to $C_7$ alkoxycarbonyl group" is a carbonyl group to which the above-mentioned "$C_1$ to $C_6$ alkoxy group" is bonded, and for example, it may be a methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentoxycarbonyl, isopentoxycarbonyl, 2-methylbutoxycarbonyl, neopentoxycarbonyl, 1-ethylpropoxycarbonyl, hexyloxycarbonyl, 4-methylpentoxycarbonyl, 3-methylpentoxycarbonyl, 2-methylpentoxycarbonyl, 1-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl or 2-ethylbutoxycarbonyl group, preferably a carbonyl group to which a $C_1$ to $C_3$ alkoxy group is bonded (a $C_2$ to $C_4$ alkoxycarbonyl group), more preferably a methoxycarbonyl or ethoxycarbonyl group, still further preferably a methoxycarbonyl group.

In the present invention, "the phenylthio group which may be substituted (The substituent is a substituent selected from the substituent Group A.)" is a phenylthio group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl)silyl group", and for example, it may beta phenylthio, fluorophenylthio, difluorophenylthio, trifluorophenylthio, chlorophenylthio, dichlorophenylthio, trichlorophenylthio, fluorochlorophenylthio, methylphenylthio, dimethylphenylthio, trimethylphenylthio, tetramethylphenylthio, pentamethylphenylthio, ethylphenylthio, fluoro(methyl)phenylthio, chloro(methyl)phenylthio, bromo(methyl)phenylthio, cyclopropylphenylthio, cyclopropyl(fluoro)phenylthio, chloro(cyclopropyl)phenylthio, cyclopropyl(methyl)phenylthio, (trifluoromethyl)phenylthio or fluoro(trifluoromethyl)phenylthio group, preferably a phenylthio group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group which is substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a phenylthio, chlorophenylthio, methylphenylthio, trifluorophenylthio or cyanophenylthio group.

In the present invention, "the $C_1$ to $C_6$ alkylthio group" is a straight or branched alkylthio group having 1 to 6 carbon atoms, and for example, it may be a methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio or 2-ethylbutylthio group, preferably a straight or branched alkylthio group having 1 to 3 carbon atoms (a $C_1$ to $C_3$ alkylthio group), more preferably a methylthio or ethylthio group, still further preferably a methylthio group.

In the present invention, "the $C_1$ to $C_6$ alkylsulfinyl group" is a straight or branched alkylsulfinyl group having 1 to 6 carbon atoms, and for example, it may be a methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, isopentylsulfinyl, 2-methylbutylsulfinyl, neopentylsulfinyl, 1-ethylpropylsulfinyl, hexylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl or 2-ethylbutylsulfinyl group, preferably a straight or branched alkylsulfinyl group having 1 to 3 carbon atoms (a $C_1$ to $C_3$ alkylsulfinyl group), more preferably a methylsulfinyl or ethylsulfinyl group, still further preferably a methylsulfinyl group.

In the present invention, "the $C_1$ to $C_6$ alkylsulfonyl group" is a straight or branched alkylsulfonyl group having 1 to 6 carbon atoms, and for example, it may be a methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, isopentylsulfonyl, 2-methylbutylsulfonyl, neopentylsulfonyl, 1-ethylpropylsulfonyl, hexylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl or 2-ethylbutylsulfonyl group, preferably a straight or branched alkylsulfonyl group having 1 to 3 carbon atoms (a $C_1$ to $C_3$ alkylsulfonyl group), more preferably a methylsulfonyl or ethylsulfonyl group, still further preferably a methylsulfonyl group.

In the present invention, "the $C_1$ to $C_4$ alkylenedioxy group" is a straight or branched alkylenedioxy group having 1 to 4 carbon atoms, and for example, it may be a methylenedioxy, ethylenedioxy, propylenedioxy, trimethylenedioxy or tetramethylenedioxy group, preferably an alkylenedioxy group having 1 to 2 carbon atoms, more preferably a 1,2-ethylenedioxy group.

In the present invention, "the $C_1$ to $C_6$ alkoxyimino group" is a straight or branched alkoxyimino group having 1 to 6 carbon atoms, and for example, it may be a methoxyimino, ethoxyimino, propoxyimino, isopropoxyimino, butoxyimino, isobutoxyimino, s-butoxyimino, t-butoxyimino, pentoxyimino, isopentoxyimino, 2-methylbutoxyimino, neopentoxyimino, 1-ethylpropoxyimino, hexyloxyimino, 4-methylpentoxyimino, 3-methylpentoxyimino, 2-methylpentoxyimino, 1-methylpentoxyimino, 3,3-dimethylbutoxyimino, 2,2-dimethylbutoxyimino, 1,1-dimethylbutoxyimino, 1,2-dimethylbutoxyimino, 1,3-dimethylbutoxyimino, 2,3-dimethylbutoxyimino or 2-ethylbutoxyimino group, preferably a straight or branched alkoxyimino group having 1 to 3 carbon atoms (a $C_1$ to $C_3$ alkoxyimino group), more preferably a methoxyimino or ethoxyimino group, still further preferably a methoxyimino group.

In the present invention, "the $C_1$ to $C_6$ alkyl group which may be substituted (The substituent is a substituent selected from the substituent Group B.)" is the above-mentioned "$C_1$ to $C_6$ alkyl group" which may be substituted by the above-mentioned "a halogen atom", or by the above-mentioned "$C_3$ to $C_6$ cycloalkyl group", a cyano group, the above-mentioned "$C_2$ to $C_7$ alkylcarbonyl group", the above-mentioned "$C_2$ to $C_7$ alkoxycarbonyl group", a phenyl group, the above-mentioned "$C_1$ to $C_6$ alkoxy group", the above-mentioned "$C_1$ to $C_6$ alkylthio group", the above-mentioned "$C_1$ to $C_6$ alkylsulfinyl group", the above-mentioned "$C_1$ to $C_6$ alkylsulfonyl group", the above-mentioned "$C_1$ to $C_4$ alkylenedioxy group", a hydroxyimino group or the above-mentioned "$C_1$ to $C_6$ alkoxyimino group", and for example, it may be a fluoromethyl, difluoromethyl, trifluoromethyl, 2,2,2-trichloroethyl, cyclopropylmethyl, cyanomethyl, acetylmethyl, acetylethyl, methoxycarbonylmethyl, methoxycarbonylethyl, ethoxycarbonylmethyl, ethoxycarbonylethyl, benzyl, methoxmethyl, methoxyethyl, ethoxymethyl, ethoxyethyl, methylthiomethyl, methylthioethyl, ethylthiomethyl, ethylthioethyl, methylsulfinylmethyl, methylsulfonylmethyl, 2-(1,3-dioxolanyl), hydroxyiminomethyl or methoxyiminomethyl group, preferably a $C_1$ to $C_3$ alkyl group substituted by the same or different 1 to 3 substituent(s) selected from the group consisting of a fluorine atom, a chlorine atom and a bromine atom, or a $C_1$ to $C_3$ alkyl group which may be substituted by a $C_3$ to $C_4$ cycloalkyl group, a cyano group, a $C_2$ to $C_4$ alkylcarbonyl group, a $C_2$ to $C_4$ alkoxycarbonyl group, a phenyl group, a $C_1$ to $C_3$ alkoxy group, a $C_1$ to $C_3$ alkylthio group, a $C_1$ to $C_3$ alkylsulfinyl group, a $C_1$ to $C_3$ alkylsulfonyl group, a $C_1$ to $C_2$ alkylenedioxy group, a hydroxyimino group or a $C_1$ to $C_3$ alkoxyimino group, more preferably a $C_1$ to $C_2$ alkyl group substituted by the same 1 to 3 fluorine atom(s) or chlorine atom(s), or a $C_1$ to $C_2$ alkyl group which may be substituted by a cyclopropyl group, a cyano group, a $C_2$ to $C_3$ alkylcarbonyl group, a $C_2$ to $C_3$ alkoxycarbonyl group, a phenyl group, a $C_1$ to $C_2$ alkoxy group, a $C_1$ to $C_2$ alkylthio group, a $C_1$ to $C_2$ alkylsulfinyl group, a $C_1$ to $C_2$ alkylsulfonyl group, an ethylenedioxy group, a hydroxyimino group or a $C_1$ to $C_2$ alkoxyimino group.

In the present invention, "the substituted $C_2$ to $C_6$ alkenyl group (The substituent is a cyano group or a nitro group.)" is the above-mentioned "$C_2$ to $C_6$ alkenyl group" substituted by a cyano group or a nitro group, preferably a $C_2$ to $C_3$ alkenyl group substituted by a cyano group or a nitro group, more preferably a cyanovinyl or nitrovinyl group.

In the present invention, "the $C_2$ to $C_6$ alkynyl group" is a straight or branched alkynyl group having 2 to 6 carbon atoms, and for example, it may be ethynyl, 2-propynyl, 1-methyl-2-propynyl, 1-ethyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 1-ethyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl, preferably a straight or branched alkynyl group having 3 to 4 carbon atoms (a $C_3$ to $C_4$ alkynyl group), more preferably an ethynyl, 1-propynyl or 2-propynyl group.

In the present invention, "the amino group which may be substituted (The substituent is a substituent selected from the substituent Group D.)" is an amino group which may be substituted by the same or different 1 to 2 substituent(s) selected from the group consisting of the above-mentioned "$C_1$ to $C_6$ alkyl group", the above-mentioned "$C_2$ to $C_7$ alkylcarbonyl group", the above-mentioned "$C_2$ to $C_7$ alkoxycarbonyl group", the above-mentioned "di($C_1$ to $C_6$ alkyl)carbamoyl group" and the above-mentioned "$C_1$ to $C_6$ alkylsulfonyl group", and for example, it may be an amino, methylamino, ethylamino, propylamino, isopropylamino, butylamino, isobutylamino, s-butylamino, t-butylamino, pentylamino, isopentylamino, (2-methylbutyl)amino, neopentylamino, (1-ethylpropyl)amino, hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl)amino, (2,3-dimethylbutyl)amino, (2-ethylbutyl)amino, dimethylamino, (methyl)(ethyl)amino, diethylamino, dipropylamino, (methyl)(isopropyl)amino, di(isopropyl)amino, dibutylamino, di(isobutyl)amino, di(s-butyl)amino, di(t-butyl)amino, dipentylamino, diisopentylamino, di(2-methylbutyl)amino, dineopentylamino, di(1-ethylpropyl)amino, dihexylamino, di(4-methylpentyl)amino, di(3-methylpentyl)amino, di(2-methylpentyl)amino, di(1-methylpentyl)amino, di(3,3-dimethylbutyl)amino, di(2,2-dimethylbutyl)amino, di(1,1-dimethylbutyl)amino, di(1,2-dimethylbutyl)amino, di(1,3-dimethylbutyl)amino, di(2,3-dimethylbutyl)amino, di(2-ethylbutyl)amino, acetylamino, propionylamino, butanoylamino, (2-methylpropanoyl)amino, pentanoylamino, (2,2-dimethylpropanoyl)amino, (2,2-dimethylpentanoyl)amino, (2-methylbutanoyl)amino, (3-methylbutanoyl)amino, hexanoylamino, heptanoyl amino, (3,3-dimethylbutanoyl)amino, methoxycarbonylamino, ethoxycarbonylamino, propoxycarbonylamino, isopoxycarbonylamino, butoxycarbonylamino, isobutoxycarbonylamino, s-butoxycarbonylamino, t-butoxycarbonylamino, pentoxycarbonylamino, isopentoxycarbonylamino, (2-methylbutoxycarbonyl)amino, neopentoxycarbonylamino, (1-ethylpropoxycarbonyl)amino, hexyloxycarbonylamino, (4-methylpentoxycarbonyl)amino, (3-methylpentoxycarbonyl)amino, (2-methylpentoxycarbonyl)amino, (1-methylpentoxycarbonyl)amino, (3,3-dimethylbutoxycarbonyl)amino, (2,2-dimethylbutoxycarbonyl)amino, (1,1-dimethylbutoxycarbonyl)amino, (1,2-dimethylbutoxycarbonyl)amino, (1,3-dimethylbutoxycarbonyl)amino, (2,3-dimethylbutoxycarbonyl)amino, (2-ethylbutoxycarbonyl)amino, dimethylcarbamoylamino, (methylethylcarbamoyl)amino, diethylcarbamoylamino, dipropylcarbamoylamino, dibutylcarbamoylamino, dihexylcarbamoylamino, methylsulfonylamino, ethylsulfonylamino, propylsulfonylamino, isopropylsulfonylamino, butylsulfonylamino, t-butylsulfonylamino or hexylsulfonylamino, preferably an amino group which may be substituted by the same or different 1 to 2 $C_1$ to $C_3$ alkyl groups, or a $C_2$ to $C_4$ alkylcarbonyl group, a $C_2$ to $C_4$ alkoxycarbonyl group, a di($C_1$ to $C_3$ alkyl)carbamoyl group or a $C_1$ to $C_3$ alkylsulfonyl group, more preferably an methylamino, ethylamino, dimethylamino, diethylamino, acetylamino, propionylamino, (2-methylpropanoyl)amino, (2,2-dimethylpropanoyl)amino, methoxycarbonylamino, ethoxycarbonylamino, dimethylcarbamoylamino, diethylcarbamoylamino, methylsulfonylamino or ethylsulfonylamino group.

In the present invention, "the $C_1$ to $C_6$ haloalkoxy group" is the above-mentioned "$C_1$ to $C_6$ alkoxy group" substituted by the same or different 1 to 5 above-mentioned "halogen atoms", and for example, it may be a chloromethoxy, dichloromethoxy, trichloromethoxy, 1-chloroethoxy, 2-chloroethoxy, 2,2,2-trichloroethoxy, 1-chloropropoxy, 3-chloropropoxy, 1-chlorobutoxy, 4-chlorobutoxy, fluoromethoxy, difluoromethoxy, trifluoromethoxy, 1-fluoroethoxy, 2-fluoroethoxy, 2,2,2-trifluoroethoxy, pentafluoroethoxy, fluorochloromethoxy, bromomethoxy, 1-bromoethoxy, 2-bromoethoxy or iodomethoxy group, preferably a $C_1$ to $C_3$ alkoxy group substituted by the same or different 1 to 3 substituent(s) selected from the group consisting of a fluorine atom, a chlorine atom and a bromine atom, more preferably a $C_1$ to $C_2$ alkoxy group substituted by the same 1 to 3 fluorine atom(s) or chlorine atom(s), still further preferably a fluoromethoxy, difluoromethoxy, trifluoromethoxy or 2,2,2-trichloroethoxy group, particularly preferably a trifluoromethoxy group.

In the present invention, "the substituted $C_3$ to $C_6$ cycloalkyl group (The substituent is a substituent selected from the substituent Group C.)" is the above-mentioned "$C_3$ to $C_6$ cycloalkyl group" substituted by the same or different 1 to 5 substituent(s) selected from the group consisting of the above-mentioned "halogen atom", the above-mentioned "$C_1$ to $C_6$ alkyl group which may be substituted (The substituent is a substituent selected from the substituent Group B.)", the above-mentioned "$C_3$ to $C_6$ cycloalkyl group", the above-mentioned "$C_2$ to $C_6$ alkenyl group", a cyano group, the above-mentioned "$C_2$ to $C_7$ alkylcarbonyl group", a benzoyl group, a carboxyl group, the above-mentioned "$C_2$ to $C_7$ alkoxycarbonyl group", a carbamoyl group, the above-mentioned "di($C_1$ to $C_6$ alkyl)carbamoyl group", the above-mentioned "phenyl group which may be substituted (The substituent is a substituent selected from the substituent Group A.)", the above-mentioned "5 or 6-membered heterocyclic group (the heterocycle contains one nitrogen atom, oxygen atom or sulfur atom in the ring, and may contain further 1 or 2 nitrogen atom(s).)", the above-mentioned "amino group which may be substituted (The substituent is a substituent selected from the substituent Group D.)", a nitro group, a hydroxyl group, the above-mentioned "$C_1$ to $C_6$ alkoxy group", the above-mentioned "$C_1$ to $C_6$ haloalkoxy group", a phenoxy group, the above-mentioned "$C_1$ to $C_6$ alkylthio group", a phenylthio group, the above-mentioned "$C_1$ to $C_6$ alkylsulfinyl group" and the above-mentioned "$C_1$ to $C_6$ alkylsulfonyl group", and for example, it may be a fluorocyclopropyl, difluorocyclopropyl, chlorocyclopropyl, dichlorocyclopropyl, bromocyclopropyl, dibromocyclopropyl, iodocyclopropyl, methylcyclopropyl, ethylcyclopropyl, propylcyclopropyl, isopropylcyclopropyl, butylcyclopropyl, t-butylcyclopropyl, hexylcyclopropyl, cyclopropylcyclopropyl, cyclobutylcyclopropyl, cyclopentylcyclopropyl, (fluoromethyl)cyclopropyl, (chloromethyl)cyclopropyl, (bromomethyl)cyclopropyl, (difluoromethyl)cyclopropyl, (trifluoromethyl)cyclopropyl, (trichloromethyl)cyclopropyl, (2,2,2-trifluoroethyl)cyclopropyl, (2,2,2-trichloroethyl)cyclopropyl, vinylcyclopropyl, (methoxymethyl)cyclopropyl, (ethoxymethyl)cyclopropyl, (isopropoxymethyl)cyclopropyl, (methylthiomethyl)cyclopropyl, (ethylthiomethyl)cyclopropyl, (isopropylthiomethyl)

cyclopropyl, (methylsulfinylmethyl)cyclopropyl, (ethylsulfinylmethyl)cyclopropyl, (methylsulfonylmethyl)cyclopropyl, (ethylsulfonylmethyl)cyclopropyl, cyanocyclopropyl, (1-methoxyiminoethyl)cyclopropyl, acetylcyclopropyl, propionylcyclopropyl, benzoylcyclopropyl, carboxylcyclopropyl, methoxycarbonylcyclopropyl, ethoxycarbonylcyclopropyl, carbamoylcyclopropyl, (dimethylcarbamoyl) cyclopropyl, (diethylcarbamoyl)cyclopropyl, phenylcyclopropyl, (fluorophenyl)cyclopropyl, (chlorophenyl)cyclopropyl, tolylcyclopropyl, furylcyclo-7 propyl, thienylcyclopropyl, pyridylcyclopropyl, aminocyclopropyl, (methylamino)cyclopropyl, (dimethylamino)cyclopropyl, (acetylamino)cyclopropyl, (methoxycarbonylamino)cyclopropyl, (3,3-dimethylureido)cyclopropyl, (methylsulfonylamino)cyclopropyl, nitrocyclopropyl, hydroxycyclopropyl, methoxycyclopropyl, ethoxycyclopropyl, (trifluoromethoxy)cyclopropyl, phenoxycyclopropyl, methylthiocyclopropyl, ethylthiocyclopropyl, phenylthiocyclopropyl, methylsulfinylcyclopropyl, ethylsulfinylcyclopropyl, methylsulfonylcyclopropyl, ethylsulfonylcyclopropyl, dimethylcyclopropyl, methyl(ethyl)cyclopropyl, diethylcyclopropyl, biscyanocyclopropyl, trimethylcyclopropyl, tetramethylcyclopropyl, pentamethylcyclopropyl, methylcyclobutyl, vinylcyclobutyl, cyanocyclobutyl, carboxylcyclobutyl, acetylcyclobutyl, methoxycarbonylcyclobutyl or aminocyclobutyl group, preferably a $C_3$ to $C_4$ cycloalkyl group substituted by the same or different 1 to 5 substituent(s) selected from the group consisting of a fluorine atom, a chlorine atom, a bromine atom, a $C_1$ to $C_3$ alkyl group, a $C_3$ to $C_4$ cycloalkyl group and a cyano group, or substituted by "a $C_1$ to $C_3$ alkyl group substituted by the same or different 1 to 3 substituent(s) selected from the group consisting of a fluorine atom, a chlorine atom and a bromine atom, or a $C_1$ to $C_3$ alkyl group substituted by a $C_3$ to $C_4$ cycloalkyl group, a cyano group, a $C_2$ to $C_4$ alkylcarbonyl group, a $C_2$ to $C_4$ alkoxycarbonyl group, a phenyl group, a $C_1$ to $C_3$ alkoxy group, a $C_1$ to $C_3$ alkylthio group, a $C_1$ to $C_3$ alkylsulfinyl group, a $C_1$ to $C_3$ alkylsulfonyl group, a $C_1$ to $C_2$ alkylenedioxy group, an imino group or a $C_1$ to $C_3$ alkoxyimino group", a $C_2$ to $C_4$ alkenyl group, a $C_2$ to $C_4$ alkylcarbonyl group, a benzoyl group, a carboxyl group, a $C_2$ to $C_4$ alkoxycarbonyl group, a carbamoyl group, a di($C_1$ to $C_3$ alkyl)carbamoyl group, "a phenyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group", a 5-membered heterocyclic group (the heterocycle contains one nitrogen atom, oxygen atom or sulfur atom in the ring.), "an amino group which may be substituted by the same or different 1 to 2 $C_1$ to $C_3$ alkyl group, or by a $C_2$ to $C_4$ alkylcarbonyl group, a $C_2$ to $C_4$ alkoxycarbonyl group, a di($C_1$ to $C_3$ alkyl)carbamoyl group or a $C_1$ to $C_3$ alkylsulfonyl group", a nitro group, a hydroxyl group, a $C_1$ to $C_3$ alkoxy group, a $C_1$ to $C_3$ haloalkoxy group, a phenoxy group, a $C_1$ to $C_3$ alkylthio group, a phenylthio group, a $C_1$ to $C_3$ alkylsulfinyl group or a $C_1$ to $C_3$ alkylsulfonyl group, more preferably a cyclopropyl group substituted by the same or different 1 to 3 substituent(s) selected from the group consisting of a chlorine atom, a bromine atom, a $C_1$ to $C_2$ alkyl group, cyclopropyl group and a cyano group, or by "a $C_1$ to $C_2$ alkyl group substituted by a $C_1$ to $C_2$ alkyl group which is substituted by the same 1 to 3 substituent(s) selected from the group consisting of a chlorine atom and a bromine atom, or substituted by a cyclopropyl group, a cyano group, a $C_2$ to $C_3$ alkylcarbonyl group, a $C_2$ to $C_3$ alkoxycarbonyl group, a phenyl group, a $C_1$ to $C_2$ alkoxy group, a $C_1$ to $C_2$ alkylthio group, a $C_1$ to $C_2$ alkylsulfinyl group, a $C_1$ to $C_2$ alkylsulfonyl group, a 1,2-ethylenedioxy group, an imino group or a $C_1$ to $C_2$ alkoxyimino group", a $C_2$ to $C_3$ alkenyl group, a $C_2$ to $C_3$ alkylcarbonyl group, a benzoyl group, a carboxyl group, a $C_2$ to $C_3$ alkoxycarbonyl group, a carbamoyl group, a di($C_1$ to $C_2$ alkyl)carbamoyl group, "a phenyl group which may be substituted by the same or different 1 to 2 substituent(s) selected from the group consisting of a chlorine atom, a bromine atom, a $C_1$ to $C_2$ alkyl group, "a $C_1$ to $C_2$ alkyl group substituted by the same 1 to 3 fluorine atom(s) or chlorine atom(s)", a cyclopropyl group, a cyano group and a tri($C_1$ to $C_2$ alkyl)silyl group", a furyl group, a thienyl group, "an amino group which may be substituted by the same 1 to 2 $C_1$ to $C_2$ alkyl group(s), or by a $C_2$ to $C_3$ alkylcarbonyl group, a $C_2$ to $C_3$ alkoxycarbonyl group, a di($C_1$ to $C_2$ alkyl)carbamoyl group or a $C_1$ to $C_2$ alkylsulfonyl group", a nitro group, a hydroxyl group, a $C_1$ to $C_2$ alkoxy group, a $C_1$ to $C_2$ haloalkoxy group, a phenoxy group, a $C_1$ to $C_2$ alkylthio group, a phenylthio group, a $C_1$ to $C_2$ alkylsulfinyl group or a $C_1$ to $C_2$ alkylsulfonyl group.

In the present invention, "the $C_4$ to $C_{10}$ bicycloalkyl group" is a bicyclic hydrocarbon having 4 to 10 carbon atoms, and for example, it may be a bicyclobutyl, bicyclepentyl, bicyclohexyl, bicycloheptyl, bicyclooctyl, bicyclononyl or bicyclodecyl group, preferably a bicyclehexyl or bicycleheptyl group, more preferably a bicycle[3.1.0]hexyl or bicyclo[4.1.0]heptyl group, still further preferably a bicyclo[3.1.0] hexan-6-yl group.

In the present invention, "the phenylsulfonyl group which may be substituted (The substituent is a substituent selected from the substituent Group A.)" is a phenylsulfonyl group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl) silyl group", and for example, it may be a phenylsulfonyl, fluorophenylsulfonyl, difluorophenylsulfonyl, trifluorophenylsulfonyl, chlorophenylsulfonyl, dichlorophenylsulfonyl, trichlorophenylsulfonyl, fluorochlorophenylsulfonyl, methylphenylsulfonyl, dimethylphenylsulfonyl, trimethylphenylsulfonyl, tetramethylphenylsulfonyl, pentamethylphenylsulfonyl, ethylphenylsulfonyl, fluoro(methyl)phenylsulfonyl, chloro(methyl)phenylsulfonyl, bromo(methyl)phenylsulfonyl, cyclopropylphenylsulfonyl, cyclopropyl(fluoro)phenylsulfonyl, chloro(cyclopropyl)phenylsulfonyl, cyclopropyl (methyl)phenylsulfonyl, (trifluoromethyl)phenylsulfonyl or fluoro(trifluoromethyl)phenylsulfonyl group, preferably a phenylsulfonyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a phenylsulfonyl, chlorophenylsulfonyl, methylphenylsulfonyl, trifluorophenylsulfonyl or cyanophenylsulfonyl group.

In the present invention, "the di($C_1$ to $C_6$ alkyl)sulfamoyl group" is a sulfamoyl group in which the same or different 2 above-mentioned "$C_1$ to $C_6$ alkyl groups" are bonded to the nitrogen atom, and for example, it may be a dimethylsulfamoyl, methylethylsulfamoyl, diethylsulfamoyl, dipropylsulfamoyl, dibutylsulfamoyl or dihexylsulfamoyl, preferably a sulfamoyl group to which the same or different 2 $C_1$ to $C_3$ alkyl groups are bonded, more preferably a dimethylsulfamoyl or diethylsulfamoyl group, still further preferably a dimethylsulfamoyl group.

In the present invention, "the 3- to 6-membered heterocyclic group which may be substituted (the heterocycle contains one nitrogen atom, oxygen atom or sulfur atom in the ring, and may contain further 1 or 2 nitrogen atom(s), or may be fused with a benzene ring. The substituent is a substituent selected from the substituent Group E.)" is "a 3- to 6-membered heterocyclic group which contains one nitrogen atom, oxygen atom or sulfur atom as a hetero atom, and may contain further 1 to 2 nitrogen atom(s)" which may be substituted by the same or different 1 to 3 substituent(s) selected from the group consisting of the above-mentioned "halogen atom", the above-mentioned "$C_1$ to $C_6$ alkyl group" and the above-mentioned "$C_1$ to $C_6$ haloalkyl group", or by a hydroxyl group, the above-mentioned "phenylsulfonyl group which may be substituted (The substituent is a substituent selected from the substituent Group A.)" or the above-mentioned "di($C_1$ to $C_6$ alkyl)sulfamoyl group", or may be fused with a benzene ring, preferably "a 3- to 6-membered heterocyclic group which contains one nitrogen atom, oxygen atom or sulfur atom as a hetero atom, and may contain further one nitrogen atom" which may be substituted by the same or different 1 to 2 substituent(s) selected from the group consisting of a fluorine atom, a chlorine atom, a bromine atom, a $C_1$ to $C_3$ alkyl group and "a $C_1$ to $C_3$ alkyl group substituted by the same or different 1 to 3 substituent(s) selected from the group consisting of a fluorine atom, a chlorine atom and a bromine atom", or may be substituted by a hydroxyl group, "a phenylsulfonyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl) silyl group" or "a sulfamoyl group to which the same or different 2 $C_1$ to $C_3$ alkyl groups are bonded", or may be fused with a benzene ring, more preferably an aziridine, oxiranyl, oxetanyl, pyrrolyl, furyl, thienyl, pyrazolyl, thiazolyl, pyridyl, benzimidazolyl or benzothiazolyl, each of which may be substituted by the same 1 to 2 substituent(s) selected from the group consisting of a chlorine atom, a bromine atom, methyl group, ethyl group and trifluoromethyl group, or may be substituted by a hydroxyl group, phenylsulfonyl group, tolylsulfonyl group or dimethylsulfamoyl group, still further preferably a thienyl, pyrazolyl, thiazolyl group which may be substituted by the same or different 1 to 2 substituent(s) selected from the group consisting of a chlorine atom, methyl group and trifluoromethyl group.

In the present invention, "the ($C_1$ to $C_6$ alkoxy)$C_1$ to $C_6$ alkoxy group" is an alkoxy group having 1 to 6 carbon atoms to which an alkoxy group having 1 to 6 carbon atoms is bonded, and for example, it may be a methoxymethoxy, ethoxymethoxy, propoxymethoxy, butoxymethoxy, s-butoxymethoxy, t-butoxymethoxy, pentyloxymethoxy, hexyloxymethoxy, methoxyethoxy, ethoxyethoxy, propoxyethoxy, butoxyethoxy, methoxypropoxy, methoxybutoxy, methoxypentyloxy or methoxyhexyloxy group, preferably an alkoxy group having 1 to 3 carbon atoms to which an alkoxy group having 1 to 3 carbon atoms is substituted, more preferably a methoxyethoxy, ethoxyethoxy or ethoxymethoxy group.

In the present invention, "a phenoxy group which may be substituted (The substituent is a hydroxyl group or a pyridazinyloxy group substituted by a substituent(s) selected from the group consisting of a halogen atom and a $C_1$ to $C_6$ alkoxy group.)" is a phenoxy group which may be substituted by one hydroxyl group, or a phenoxy group substituted by a pyridazinyloxy group which is substituted by the same or different 1 to 3 substituent(s) selected from the group consisting of the above-mentioned "halogen atom" and the above-mentioned "$C_1$ to $C_6$ alkoxy group", preferably a hydroxyphenoxy group, or a phenoxy group substituted by a pyridazinyloxy group which is substituted by the same or different 1 to 2 substituent(s) selected from the group consisting of a fluorine atom, a chlorine atom, a bromine atom and $C_1$ to $C_3$ alkoxy group, more preferably a phenoxy group substituted by a pyridazinyloxy group which is substituted by each one of a chlorine atom, and a methoxy or ethoxy group.

In the present invention, "the 5- to 6-membered heterocycloxy group which may be substituted (the heterocycle contains one nitrogen atom, oxygen atom or sulfur atom in the ring, and may contain further 1 or 2 nitrogen atom(s). The substituent is a substituent selected from the substituent Group E.)" is "a 5- to 6-membered heterocycloxy group which contains one nitrogen atom, oxygen atom or sulfur atom as a heteroatom, and may contain further 1 to 2 nitrogen atom(s)" which may be substituted by the same or different 1 to 2 substituent(s) selected from the group consisting of the above-mentioned "halogen atom", the above-mentioned "$C_1$ to $C_6$ alkyl group", the above-mentioned "$C_1$ to $C_6$ haloalkyl group", a hydroxyl group, the above-mentioned "phenylsulfonyl group which may be substituted (The substituent is a substituent selected from the substituent Group A.)" and the above-mentioned "di($C_1$ to $C_6$ alkyl)sulfamoyl group", preferably "a 5- to 6-membered heterocycloxy group which contains one nitrogen atom, oxygen atom or sulfur atom as a heteroatom, and may contain further one nitrogen atom" which may be substituted by the same or different 1 to 2 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a hydroxyl group, "a phenylsulfonyl group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group" and "a sulfamoyl group to which the same or different two $C_1$ to $C_3$ alkyl groups are bonded", more preferably a pyridyloxy, pyrrolyloxy, furyloxy, thienyloxy, pyrazolyloxy, thiazolyloxy, pyrimidyloxy, pyrazinyloxy or a pyridazinyloxy group, each of which may be substituted by 1 to 2 different substituents selected from the group consisting of a chlorine atom, a bromine atom, a methyl group, an ethyl group, a trifluoromethyl group, a hydroxyl group, a phenylsulfonyl group, a tolylsulfonyl group and a dimethylsulfamoyl group, still further preferably a pyridazinyloxy group which may be substituted by a chlorine atom and a hydroxyl group.

In the present invention, "the phenylsulfonyloxy group which may be substituted (The substituent is a substituent selected from the substituent Group A.)" is a phenylsulfonyloxy group which may be substituted by the same or different 1 to 5 substituent(s) selected from the group consisting of the above-mentioned "halogen atom", the above-mentioned "$C_1$ to $C_6$ alkyl group", the above-mentioned "$C_1$ to $C_6$ haloalkyl group", the above-mentioned "$C_3$ to $C_6$ cycloalkyl group", a cyano group and the above-mentioned "tri($C_1$ to $C_6$ alkyl) silyl group", and for example, it may be a phenylsulfonyloxy, fluorophenylsulfonyloxy, difluorophenylsulfonyloxy, trifluorophenylsulfonyloxy, chlorophenylsulfonyloxy, dichlorophenylsulfonyloxy, trichlorophenylsulfonyloxy, fluorochlorophenylsulfonyloxy, methylphenylsulfonyloxy, dimethylphenylsulfonyloxy, trimethylphenylsulfonyloxy, tetramethylphenylsulfonyloxy, pentamethylphenylsulfonyloxy, ethylphenylsulfonyloxy, fluoro(methyl)phenylsulfonyloxy, chloro(methyl)phenylsulfonyloxy, bromo(methyl)phenylsulfonyloxy, cyclopropylphenylsulfonyloxy, cyclopropyl(fluoro)phenylsulfonyloxy, chloro(cyclopropyl)phenylsulfonyloxy, cyclopropyl(methyl)phenylsulfonyloxy, (trifluoromethyl)phenylsulfonyloxy or fluoro(trifluoromethyl)phenylsulfonyloxy group, preferably a phenylsulfonyloxy group which may be substituted by the same or different 1 to 3 substituent(s) selected from the group consisting of a fluorine atom, a chlorine atom, a bromine atom, a $C_1$ to $C_3$ alkyl group, "a $C_1$ to $C_3$ alkyl group substituted by the same or different 1 to 3 substituent(s) selected from the group consisting of a fluorine atom, a chlorine atom and a bromine atom", a $C_3$ to $C_4$ cycloalkyl group, a cyano group and a tri($C_1$ to $C_3$ alkyl)silyl group, more preferably a phenylsulfonyloxy, chlorophenylsulfonyloxy, methylphenylsulfonyloxy, trifluorophenylsulfonyloxy or cyanophenylsulfonyloxy group.

In $R^3$, $R^4$, $R^5$, $R^6$ and $R^7$ according to the present invention, "the 3- to 6-membered cyclic hydrocarbon group which may be substituted, which is formed by the adjacent two of them with carbon atoms to which the respective substituents are bonded (the cyclic hydrocarbon may be interrupted by 1 to 2 hetero atom(s) selected from the group consisting of a nitrogen atom, an oxygen atom and a sulfur atom. The substituent is a halogen atom, a $C_1$ to $C_6$ alkyl group, a hydroxy-$C_1$ to $C_6$ alkyl group, a $C_1$ to $C_6$ alkoxy group, an oxo group, a hydroxyimino group or a $C_1$ to $C_6$ alkoxyimino group, and when the $C_1$ to $C_6$ alkyl group is substituted, it may form another 3-membered ring by binding with the other $C_1$ to $C_6$ alkyl group or a carbon atom(s) in the cyclic hydrocarbon.)" is a saturated or unsaturated 3- to 6-membered cyclic hydrocarbon group which may be substituted by the same or different 1 to 4 substituent(s) selected from the group consisting of the above-mentioned "halogen atom", the above-mentioned "$C_1$ to $C_6$ alkyl group", the above-mentioned "$C_1$ to $C_6$ alkyl group" substituted by 1 to 2 hydroxyl group(s), the above-mentioned "$C_1$ to $C_6$ alkoxy group", an oxo group, a hydroxyimino group and the above-mentioned "$C_1$ to $C_6$ alkoxyimino group", and may be interrupted by the same or different 1 to 2 hetero atom(s) selected from the group consisting of a nitrogen atom, an oxygen atom and a sulfur atom, and further may form a cyclopropane ring on the cyclic hydrocarbon group, preferably a group represented by —$CH_2$—, —$CH_2CH_2$—, —$CH_2CH_2CH_2$—, —CH ($CH_3$) $CH_2CH_2$—, —$CH_2CH$ ($CH_3$) $CH_2$—, —C($CH_3$)$_2CH_2CH_2$—, —$CH_2C$ ($CH_3$)$_2CH_2$—, —CH (O$CH_3$) $CH_2CH_2$—, —C(O$CH_3$)$_2$ $CH_2CH_2$—, —$CH_2C$ (O$CH_3$)$_2CH_2$—, —C(=O) $CH_2CH_2$—, —$CH_2C$(=O) $CH_2$—, —C(=NO$CH_3$) $CH_2CH_2$—, —$CH_2CH_2CH_2CH_2$—, —CH ($CH_3$) $CH_2CH_2CH_2$—, —C($CH_3$)$_2CH_2CH_2CH_2$—, —CH (O$CH_3$) $CH_2CH_2CH_2$—, —CH=CH—CH=CH—, —O$CH_2CH_2$—, —OCH ($CH_3$) $CH_2$—, —O$CH_2CH$ ($CH_3$)—, —OC($CH_3$)$_2CH_2$—, —OCH=CH—, —OC($CH_3$)=CH—, —OCH=C($CH_3$)—, —SCH=CH—, —N=CH—CH=CH—, —O$CH_2O$—, —OCH ($CH_3$)O—, —OC($CH_3$)$_2$O—, —OC$F_2$O—, —O$CH_2CH_2O$—, —OCH=N—, —OC($CH_3$)=N—,

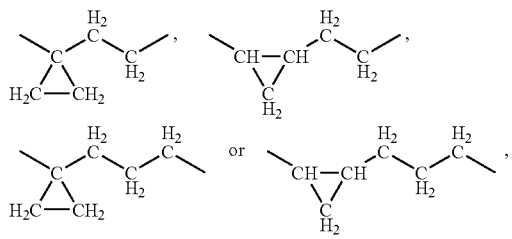

more preferably a group represented by —$CH_2CH_2$—, —$CH_2CH_2CH_2$—CH ($CH_3$) $CH_2CH_2$—, —$CH_2CH_2CH_2CH_2$—, —CH=CH—CH=CH—, —O$CH_2CH_2$—, —OCH=CH—, —OCH=C($CH_3$)—, —SCH=CH—, —N=CH—CH=CH—, —O$CH_2O$—, —O$CH_2CH_2$O—,

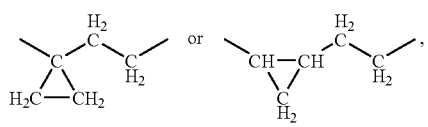

still further preferably a group represented by —$CR_2CR_2CR_2$—, —CH ($CH_3$) $CH_2CH_2$—, —O$CH_2CH_2$—, —OCH=CH— or

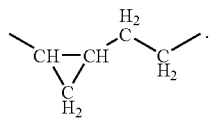

The compound (I) of the present invention can be made a salt to be generally used in agricultural chemicals, and for example, it can be made an alkali metal salt, an alkaline earth metal salt or an ammonium salt, and when a basic portion exists in the molecule, it can be made a salt, for example, a sulfate, hydrochloride, nitrate, phosphate, or the like. These salts are included in the present invention so long as they can be used as a herbicide for agricultural and horticultural chemicals.

In the present invention, "the alkali metal salt" may be, for example, a sodium salt, potassium salt or lithium salt, preferably a sodium salt or potassium salt.

In the present invention, "the alkaline earth metal salt" may be, for example, a calcium salt or magnesium salt, preferably a calcium salt.

A solvate of the compounds of the present invention is also included in the present invention.

In the compounds of the present invention, there are compounds having an asymmetric carbon(s), and in that case, the present invention also includes a kind of optical isomers and a mixture of several kinds of optical isomers with an optional ratio.

In the present invention, "ester derivative" is a compound in which an acyl group bonds to an oxygen atom of a hydroxyl group bonded at the 4-position of the pyridazine ring, and for example, a compound to which is/are bonded a $C_2$ to. $C_{15}$ alkylcarbonyl group which may be substituted [The substituent is the same or different 1 to 3 substituent(s) selected from the group consisting of a halogen atom, a $C_1$ to $C_6$ alkoxy group, a $C_2$ to $C_7$ alkoxycarbonyl group, a $C_2$ to $C_6$ alkenyloxycarbonyl group which may be substituted {The substituent is the same or different 1 to 3 substituent(s) selected from the group consisting of a $C_3$ to $C_6$ cycloalkyl group, a cyano group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a $C_3$ to $C_6$ cycloalkenyloxycarbonyl group which may be substituted {The substituent is the same or different 1 to 2 substituent(s) selected from the group consisting of an oxo group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a 5 or 6-membered heterocycloxycarbonyl group which may be substituted {the heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or deferent 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a phenyl group which may be substituted (The substituent is the same or different 1 to 3 substituent(s) selected from the group consisting of a halogen atom, a $C_1$ to $C_6$ alkyl group, a $C_1$ to $C_3$ haloalkyl group and a $C_2$ to $C_7$ alkoxycarbonyl group.), a phenoxy group and a $C_1$ to $C_6$ alkylthio group.], a $C_4$ to $C_7$ cycloalkylcarbonyl group, an adamantylcarbonyl group, a $C_3$ to $C_7$ alkenylcarbonyl group which may be substituted (The substituent is the same or different 1 to 2 substituent(s) selected from the group consisting of a halogen atom and a phenyl group.), a $C_3$ to $C_7$ alkynylcarbonyl group, a benzoyl group which may be substituted (The substituent is the same or different 1 to 3 substituent(s) selected from the group consisting of a halogen atom, a $C_1$ to $C_6$ alkyl group which may be substituted (The substituent is the same or different 1 to 3 substituent(s) selected from the group consisting of a halogen atom and a phenyl group.), a cyano group, a $C_2$ to $C_7$ alkylcarbonyl group, a $C_2$ to $C_7$ alkoxycarbonyl group, a $C_3$ to $C_7$ alkenyloxycarbonyl group which may be substituted {The substituent is the same or different 1 to 3 substituent(s) selected from the group consisting of a $C_3$ to $C_6$ cycloalkyl group, a cyano group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a $C_4$ to $C_7$ cycloalkenyloxycarbonyl group which may be substituted {The substituent is the same or different 1 to 2 substituent(s) selected from the group consisting of an oxo group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a phenyl group, a nitro group, a $C_1$ to $C_6$ alkoxy group which may be substituted (The substituent is the same or different 1 to 3 substituent(s) selected from the group consisting of a halogen atom and a phenyl group.), a phenoxy group, a 5 or 6-membered heterocyclic oxycarbonyl group which may be substituted {the heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).} and a 5 or 6-membered heterocycloxysulfonyl group which may be substituted {the heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}.], a naphthoyl group, a 3- to 6-membered heterocyclic carbonyl group which may be substituted {the heterocycle contains one nitrogen atom, oxygen atom or sulfur atom in the ring, and may contain further 1 or 2 nitrogen atom(s), or may form a 5- to 6-membered spiro ring containing 1 to 2 oxygen atom(s) on an optional carbon atom in the heterocycle. The substituent is the same or different 1 to 3 substituent(s) selected from the group consisting of a halogen atom, a $C_1$ to $C_6$ alkyl group which may be substituted (The substituent is the same or different 1 to 3 substituent(s) selected from the group consisting of a halogen atom and a phenyl group.), a $C_2$ to $C_7$ alkylcarbonyl group, a $C_2$ to $C_7$ alkoxycarbonyl group, a phenyl group which may be substituted (The substituent is the same or different 1 to 3 halogen atom(s).), a nitro group, a hydroxyl group, a $C_1$ to $C_6$ alkoxy group, a phenoxy group, a $C_1$ to $C_6$ alkylthio group, a $C_2$ to $C_6$ alkenylthio group and a phenylthio group.}, a 7 to 14-membered fused bi- or tri-cyclic heterocyclic carbonyl group which may be substituted (The heterocycle contains one nitrogen atom, oxygen atom or sulfur atom in the ring, and may contain further 1 to 2 nitrogen atom(s) or oxygen atom(s). The substituent is the same or different 1 to 3 substituent(s) selected from the group consisting of a halogen atom and a $C_1$ to $C_6$ alkyl group.), a 5 or 6-membered heterocycle carbonylcarbonyl group (The heterocycle contains one nitrogen atom, oxygen atom or sulfur atom in the ring, and may contain further 1 or 2 nitrogen atom(s).), a $C_2$ to $C_7$ alkoxycarbonyl group which may be substituted (The substituent is the same or different 1 to 3 substituent(s) selected from the group consisting of a halogen atom, a $C_1$ to $C_6$ alkoxy group and a phenyl group.), a $C_3$ to $C_7$ alkenyloxycarbonyl group, a phenoxycarbonyl group which may be substituted (The substituent is the same or different 1 to 3 substituent(s) selected from the group consisting of a halogen atom, a $C_1$ to $C_6$ alkyl group, a cyano group, a $C_2$ to $C_7$ alkylcarbonyl group, a $C_2$ to $C_7$ alkoxycarbonyl group, a nitro group and a $C_1$ to $C_6$ alkoxy group.), a fused polycyclic hydrocarbyloxycarbonyl group, a 5 or 6-membered heterocycloxycarbonyl group which may be substituted {The heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a carbamoyl group which may be substituted {The substituent is the same or different 1 to 3 substituent(s) selected from the group consisting of a $C_1$ to $C_6$ alkyl group which may be substituted (The substituent is the same or different 1 to 3 substituent(s) selected from the group consisting of a halogen atom, a $C_2$ to $C_7$ alkoxycarbonyl group, a cyano group, a phenyl group and a $C_1$ to $C_6$ alkoxy group.), a $C_3$ to $C_6$ alkenyl group, a phenyl group, a $C_2$ to $C_7$ alkylcarbonyl group, a $C_2$ to $C_7$ alkoxycarbonyl group and a $C_1$ to $C_6$ alkoxy group.}, a ($C_1$ to $C_6$ alkylthio)carbonyl group, a (phenylthio)carbonyl group, a $C_1$ to $C_8$ alkylsulfonyl group which may be substituted (The substituent is the same or different 1 to 3 halogen atom(s).), a phenylsulfonyl group which may be substituted [The substituent is the same or different 1 to 3 substituent(s) selected from the group consisting of a halogen atom, a $C_1$ to $C_6$ alkyl group, a cyano group, a $C_2$ to $C_7$ alkylcarbonyl group, a $C_2$ to $C_7$ alkoxycarbonyl group, a nitro group, a $C_1$ to $C_6$ alkoxy group, a $C_2$ to $C_6$ alkenyloxysulfonyl group which may be substituted {The substituent is the same or different 1 to 3 substituent(s) selected from the group consisting of a $C_3$ to $C_6$ cycloalkyl group, a cyano group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a $C_3$ to $C_6$ cycloalkenyloxysulfonyl group which may be substituted {The substituent is the same or different 1 to 2 substituent(s) selected from the group consisting of an oxo group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).} and a 5 or 6-membered heterocycloxysulfonyl group which may be substituted {The heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}.], a 5 or 6-membered heterocyclosulfonyl group which may be substituted {The heterocycle contains one nitrogen atom, oxygen atom or sulfur atom in the ring, and may contain further 1 or 2 nitrogen atom(s). The substituent is the same or different 1 to 3 substituent(s) selected from the group consisting of a halogen atom, a $C_1$ to $C_6$ alkyl group, a phenoxy group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_3$ to $C_6$ cycloalkyl group and a $C_2$ to $C_7$ alkoxycarbonyl group.), a 2,3-dihydro-1H-indenyloxy group and a benzoyl group which may be substituted (The substituent is the same or different 1 to 3 substituent(s) selected from the group consisting of a halogen atom, a $C_1$ to $C_6$ alkyl group, a $C_1$ to $C_3$ haloalkyl group, a $C_2$ to $C_7$ alkoxycarbonyl group, a nitro group and a $C_1$ to $C_3$ alkylsulfonyl group.).}, a di($C_1$ to $C_6$ alkyl)sulfamoyl group, a $C_1$ to $C_6$ alkoxysulfonyl group, a di($C_1$ to $C_6$ alkyl)phosphoryl group, a tri($C_1$ to $C_6$ alkyl)silyl group or a triphenylsilyl group, preferably a compound to which bonded is/arena $C_2$ to $C_{10}$ alkylcarbonyl group, a benzoyl group which may be substituted (The substituent is the same or different 1 to 2 substituent(s) selected from the group consisting of a fluorine atom, a chlorine atom, a bromine atom, a $C_1$ to $C_3$ alkyl group, a $C_1$ to $C_3$ alkoxy group or a 4-(2,4-dichlorobenzoyl)-1,3-dimethyl-1H-pyrazol-5-yloxycarbonyl group.), a pyrrolidinylcarbonyl group, azetidinylcarbonyl group, morpholinyl carbonyl group, a $C_2$ to $C_5$ alkoxycarbonyl group which may be substituted (The substituent is the same or different 1 to 3 substituent(s) selected from the group consisting of a fluorine atom, a chlorine atom and a bromine atom.), a di($C_1$ to $C_3$ alkyl)carbamoyl group, a ($C_1$ to $C_3$ alkyl) ($C_1$ to $C_3$ alkoxy)carbamoyl group, a $C_1$ to $C_3$ alkylsulfonyl group which may be substituted (The substituent is the same or different 1 to 3 substituent(s) selected from the group consisting of a fluorine atom, a chlorine atom and a bromine atom.) or a phenylsulfonyl group which may be substituted (The substituent is the same or different 1 to 2 substituent(s) selected from the group consisting of a fluorine atom, a chlorine atom, a bromine atom, a $C_1$ to $C_3$ alkyl group, a 4-(2,4-dichlorobenzoyl)-1,3-dimethyl-1H-pyrazol-5-yloxysulfonyl group and a nitro group.), more preferably a compound to which bonded is/are a $C_2$ to $C_4$ alkylcarbonyl group, a benzoyl group which may be substituted (The substituent is a methyl group or a 4-(2,4-dichlorobenzoyl)-1,3-dimethyl-1H-pyrazol-5-yloxycarbonyl group.), a 1-acetidinylcarbonyl group, a 4-morpholinylcarbonyl group, a $C_2$ to $C_3$ alkoxycarbonyl group which may be substituted (The substituent is 1 to 3 chlorine atom(s).), a dimethylcarbamoyl group, a methoxy (methyl)carbamoyl group, a $C_1$ to $C_3$ alkylsulfonyl group which may be substituted (The substituent is 1 to 3 fluorine atom(s).) or a phenylsulfonyl group which may be substituted (The substituent is a chlorine atom, a methyl group, a 4-(2,4-dichlorobenzoyl)-1,3-dimethyl-1H-pyrazol-5-yloxysulfonyl group or a nitro group.).

(a) In the present invention, $R^1$ is preferably a hydrogen atom, a fluorine atom, a chlorine atom, a bromine atom, $C_1$ to $C_3$ alkyl group, $C_1$ to $C_3$ haloalkyl group (The halogen atom is 1 to 3 fluorine atom(s).), cyclopropyl group, $C_2$ to $C_3$ alkenyl group, a cyano group, $C_2$ to $C_4$ alkylcarbonyl group, di($C_1$ to $C_3$ alkyl)carbamoyl group, a phenyl group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a furyl group, a thienyl group, a $C_1$ to $C_3$ alkoxy group, a phenoxy group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is 1 to 3 fluorine atom(s).), a cyclopropyl group, a cyano group and a tri($C_1$ to $C_3$ alkyl)silyl group.} or the substituted pyrazolyloxy group (The substituent is a benzoyl group substituted by two chlorine atoms, and two $C_1$ to $C_3$ alkyl groups.), more preferably a chlorine atom, a bromine atom, trifluoromethyl group or a cyano group, still further preferably a chlorine atom or a bromine atom, particularly preferably a chlorine atom.

(b) In the present invention, $R^2$ is preferably a hydrogen atom, a fluorine atom, a chlorine atom, a bromine atom, an iodine atom, a $C_1$ to $C_3$ alkyl group, a ($C_1$ to $C_3$ alkoxy)$C_1$ to $C_3$ alkyl group, a benzoyl group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a $C_2$ to $C_4$ alkoxycarbonyl group, a phenoxy group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a phenylthio group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.} or a tri($C_1$ to $C_3$ alkyl)silyl group, more preferably a hydrogen atom, a fluorine atom, a chlorine atom, a bromine atom, an iodine atom, a methyl group, an ethoxycarbonyl group or a trimethylsilyl group, still further preferably a hydrogen atom.

(c) In the present invention, $R^3$, $R^4$, $R^5$, $R^6$ and $R^7$ each independently represent preferably a hydrogen atom, a fluorine atom, a chlorine atom, a bromine atom, an iodine atom, a $C_1$ to $C_4$ alkyl group which may be substituted (The substituent is the same or different 1 to 3 substituent(s) selected from the group consisting of a fluorine atom, a chlorine atom and a bromine atom, or a $C_3$ to $C_4$ cycloalkyl group, a $C_1$ to $C_3$ alkylthio group or a $C_1$ to $C_3$ alkoxyimino group.), a $C_2$ to $C_3$ alkenyl group, a $C_2$ to $C_3$ alkynyl group, a $C_3$ to $C_5$ cycloalkyl group which may be substituted (The substituent is the same or different 1 to 3 substituent(s) selected from the group consisting of a fluorine atom, a chlorine atom, a bromine atom, a $C_1$ to $C_3$ alkyl group, a $C_3$ to $C_4$ cycloalkyl group, a cyano group, a $C_1$ to $C_3$ alkoxy group and a $C_1$ to $C_3$ alkylthio group.), a $C_6$ to $C_7$ bicycloalkyl group, a cyano group, a $C_2$ to $C_4$ alkylcarbonyl group, a $C_2$ to $C_4$ alkoxycarbonyl group, a phenyl group which may be substituted {The substituent is a fluorine atom, a chlorine atom, a bromine atom, a $C_1$ to $C_3$ alkyl group or a $C_1$ to $C_3$ haloalkyl group (The halogen atom is the same or different 1 to 3 halogen atom(s) selected from the group consisting of a fluorine atom, a chlorine atom and a bromine atom.).}, a 5- to 6-membered heterocyclic group which may be substituted {the heterocycle contains one nitrogen atom, oxygen atom or sulfur atom in the ring, and may contain further 1 or 2 nitrogen atom(s). The substituent is the same or different 1 to 2 substituent(s) selected from the group consisting of a fluorine atom, a chlorine atom, a bromine atom, a $C_1$ to $C_3$ alkyl group and a $C_1$ to $C_3$ haloalkyl group (The halogen atom is the same or different 1 to 3 halogen atom(s) selected from the group consisting of a fluorine atom, a chlorine atom and a bromine atom.).}, a nitro group, a $C_1$ to $C_3$ alkoxy group, a $C_1$ to $C_3$ haloalkoxy group (The halogen atom is the same or different 1 to 3 halogen atom(s) selected from the group consisting of a fluorine atom, a chlorine atom and a bromine atom.), a phenoxy group which may be substituted (The substituent is a pyridazinyloxy group substituted by a substituent(s) selected frome the group consisting of a fluorine atom, a chlorine atom, a bromine atom a $C_1$ to $C_3$ alkoxy group.) or a $C_1$ to $C_3$ alkylthio group, or $R^3$, $R^4$, $R^5$, $R^6$ and $R^7$ are a group(s) which is/are formed by the adjacent two of them with carbon atoms to which the respective substituents are bonded, and include a group represented by $CH_2CH_2$—, —$CH_2CH_2CH_2$—, —$CH(CH_3)CH_2CH_2$—, —$CH_2CH_2CH_2CH_2$—, —CH=CH—CH=CH—, —$OCH_2CH_2$—, —OCH=CH—, —OCH=C($CH_3$)—, —SCH=CH—, —N=CH—CH=CH—, —$OCH_2O$—, —$OCH_2CH_2O$—,

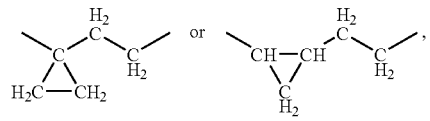

more preferably each independently represent a hydrogen atom, a fluorine atom, a chlorine atom, a bromine atom, an iodine atom, a $C_1$ to $C_4$ alkyl group which may be substituted (The substituent is 1 to 3 fluorine atom(s), or a cyclopropyl group.), a $C_3$ to $C_4$ cycloalkyl group which may be substituted (The substituent is the same 1 to 2 substituent selected from the group consisting of a fluorine atom, a chlorine atom, a bromine atom, a $C_1$ to $C_2$ alkyl group, a cyclopropyl group and a $C_1$ to $C_2$ alkoxy group.), a cyano group, $C_2$ to $C_3$ alkoxycarbonyl group, a nitro group, $C_1$ to $C_3$ alkoxy group or trifluoromethoxy group, or, $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$—, —$CH(CH_3)CH_2CH_2$—, —$OCH_2CH_2$—, —OCH=CH— or

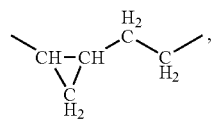

provided that $R^3$ is not a hydrogen atom, still further preferably each independently represent a hydrogen atom, a fluorine atom, a chlorine atom, a bromine atom, an iodine atom, $C_1$ to $C_3$ alkyl group, a $C_3$ to $C_4$ cycloalkyl group which may be substituted (The substituent is the same 1 to 2 substituent(s) selected from the group consisting of a chlorine atom and a $C_1$ to $C_2$ alkyl group.), a cyano group or a $C_1$ to $C_2$ alkoxy group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$— or —OCH=CH—, provided that $R^3$ is not a hydrogen atom, particularly preferably each independently represent a hydrogen atom, a fluorine atom, a chlorine atom, a bromine atom, an iodine atom, a methyl group, an ethyl group, an isopropyl group, a cyclopropyl group which may be substituted (The substituents are two chlorine atoms.) or a methoxy group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$—, provided that $R^3$ is not a hydrogen atom, most preferably $R^3$ is a fluorine atom, a chlorine atom, a bromine atom, an iodine atom, a methyl group, an ethyl group, an isopropyl group, a cyclopropyl group or a methoxy group であり, and $R^7$ is a hydrogen atom, a fluorine atom, a chlorine atom, a bromine atom, an iodine atom, a methyl group, an ethyl group, an isopropyl group, a cyclopropyl group or methoxy group, and $R^4$, $R^5$ and $R^6$ each independently represent a hydrogen atom or a methyl group.

(d) In the present invention, m and n are preferably both 0.

The compound (I) of the present invention is preferably a compound wherein (1a) $R^1$ is a hydrogen atom, a fluorine atom, a chlorine atom, a bromine atom, a $C_1$ to $C_3$ alkyl group, a $C_1$ to $C_3$ haloalkyl group (The halogen atom is 1 to 3 fluorine atom(s).), a cyclopropyl group, a $C_2$ to $C_3$ alkenyl group, a cyano group, a $C_2$ to $C_4$ alkylcarbonyl group, a di($C_1$ to $C_3$ alkyl)carbamoyl group, a phenyl group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a furyl group, a thienyl group, a $C_1$ to $C_3$ alkoxy group, a phenoxy group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is 1 to 3 fluorine atom(s).), a cyclopropyl group, a cyano group and a tri($C_1$ to $C_3$ alkyl)silyl group.} or the substituted pyrazolyloxy group (The substituent is a benzoyl group substituted by two chlorine atoms and two $C_1$ to $C_3$ alkyl groups.), (1b) $R^2$ is a hydrogen atom, a fluorine atom, a chlorine atom, a bromine atom, an iodine atom, a $C_1$ to $C_3$ alkyl group, a ($C_1$ to $C_3$ alkoxy)$C_1$ to $C_3$ alkyl group, a benzoyl group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a $C_2$ to $C_4$ alkoxycarbonyl group, a phenoxy group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl)silyl group.}, a phenylthio group which may be substituted {The substituent is the same or different 1 to 2 substituent(s) selected from the group consisting of a fluorine atom, a chlorine atom, a bromine atom, a $C_1$ to $C_3$ alkyl group, a $C_1$ to $C_3$ haloalkyl group (The halogen atom is the same or different 1 to 3 halogen atom(s) selected from the group consisting of a fluorine atom, a chlorine atom and a bromine atom.), a cyclopropyl group, a cyano group and a tri($C_1$ to $C_3$ alkyl) silyl group.} or a tri($C_1$ to $C_3$ alkyl)silyl group, (1c) $R^3$, $R^4$, $R^5$, $R^6$ and $R^7$ each independently represent a hydrogen atom, a fluorine atom, a chlorine atom, a bromine atom, an iodine atom, a $C_1$ to $C_4$ alkyl group which may be substituted (The substituent is the same or different 1 to 3 substituent(s) selected from the group consisting of a fluorine atom, a chlorine atom and a bromine atom, or a $C_3$ to $C_4$ cycloalkyl group, a $C_1$ to $C_3$ alkylthio group or a $C_1$ to $C_3$ alkoxyimino group.), a $C_2$ to $C_3$ alkenyl group, a $C_2$ to $C_3$ alkynyl group, a $C_3$ to $C_5$ cycloalkyl group which may be substituted (The substituent is the same or different 1 to 3 substituent(s) selected from the group consisting of a fluorine atom, a chlorine atom, a bromine atom, a $C_1$ to $C_3$ alkyl group, a $C_3$ to $C_4$ cycloalkyl group, a cyano group, a $C_1$ to $C_3$ alkoxy group and a $C_1$ to $C_3$ alkylthio group.), a $C_6$ to $C_7$ bicycloalkyl group, a cyano group, a $C_2$ to $C_4$ alkylcarbonyl group, a $C_2$ to $C_4$ alkoxycarbonyl group, a phenyl group which may be substituted {The substituent is a fluorine atom, a chlorine atom, a bromine atom, a $C_1$ to $C_3$ alkyl group or a $C_1$ to $C_3$ haloalkyl group (The halogen atom is the same or different 1 to 3 halogen atom(s) selected from the group consisting of a fluorine atom, a chlorine atom and a bromine atom.).}, a 5- to 6-membered heterocyclic group which may be substituted {the heterocycle contains one nitrogen atom, oxygen atom or sulfur atom in the ring, and may contain further 1 or 2 nitrogen atom(s). The substituent is the same or different 1 to 2 substituent(s) selected from the group consisting of a fluorine atom, a chlorine atom, a bromine atom, a $C_1$ to $C_3$ alkyl group and a $C_1$ to $C_3$ haloalkyl group (The halogen atom is the same or different 1 to 3 halogen atom(s) selected from the group consisting of a fluorine atom, a chlorine atom and a bromine atom.).}, a nitro group, a $C_1$ to $C_3$ alkoxy group, a $C_1$ to $C_3$ haloalkoxy group (The halogen atom is the same or different 1 to 3 halogen atom(s) selected from the group consisting of a fluorine atom, a chlorine atom and a bromine atom.), a phenoxy group which may be substituted (The substituent is a pyridazinyloxy group substituted by a substituent(s) selected from the group consisting of a fluorine atom, a chlorine atom, a bromine atom or a $C_1$ to $C_3$ alkoxy group.) or $C_1$ to $C_3$ alkylthio group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2$—, —$CH_2CH_2CH_2$—, —$CH(CH_3)CH_2CH_2$—, —$CH_2CH_2CH_2CH_2$—, —CH=CH—CH=CH—, —$OCH_2CH_2$—, —OCH=CH—, —OCH=C($CH_3$)—, —SCH=CH—, —N=CH—CH=CH—, —$OCH_2O$—, —$OCH_2CH_2O$—,

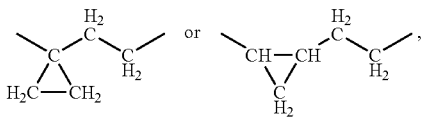

(1d) m and n are both 0,
more preferably a compound wherein
(2a) $R^1$ is a chlorine atom, a bromine atom, a trifluoromethyl group or a cyano group,
(2b) $R^2$ is a hydrogen atom, a fluorine atom, a chlorine atom, a bromine atom, an iodine atom, a methyl group, an ethoxycarbonyl group or a trimethylsilyl group,
(2c) $R^3$, $R^4$, $R^5$, $R^6$ and $R^7$ each independently represent a hydrogen atom, a fluorine atom, a chlorine atom, a bromine atom, an iodine atom, a $C_1$ to $C_4$ alkyl group which may be substituted (The substituent is 1 to 3 fluorine atom(s), or a cyclopropyl group.), a $C_3$ to $C_4$ cycloalkyl group which may be substituted (The substituent is the same 1 to 2 substituent selected from the group consisting of a fluorine atom, a chlorine atom, a bromine atom, a $C_1$ to $C_2$ alkyl group, a cyclopropyl group and a $C_1$ to $C_2$ alkoxy group.), a cyano group, a $C_2$ to $C_3$ alkoxycarbonyl group, a nitro group, a $C_1$ to $C_3$ alkoxy group or a trifluoromethoxy group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$—, —$CH(CH_3)CH_2CR_2$—, —$OCH_2CH_2$—, —$OCH=CH$— or

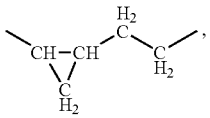

provided that $R^3$ is not a hydrogen atom,
(2d) m and n are both 0,
still further preferably a compound wherein
(3a) $R^1$ is a chlorine atom or a bromine atom,
(3b) $R^2$ is a hydrogen atom,
(3c) $R^3$, $R^4$, $R^5$, $R^6$ and $R^7$ each independently represent a hydrogen atom, a fluorine atom, a chlorine atom, a bromine atom, an iodine atom, $C_1$ to $C_3$ alkyl group, a $C_3$ to $C_4$ cycloalkyl group which may be substituted (The substituent is the same 1 to 2 substituent(s) selected from the group consisting of a chlorine atom and a $C_1$ to $C_2$ alkyl group.), a cyano group or a $C_1$ to $C_2$ alkoxy group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$— or —$OCH=CH$—, provided that $R^3$ is not a hydrogen atom,
(3d) m and n are both 0,
particularly preferably a compound wherein
(4a) $R^1$ is a chlorine atom,
(4b) $R^2$ is a hydrogen atom,
(4c) $R^3$, $R^4$, $R^5$, $R^6$ and $R^7$ each independently represent a hydrogen atom, a fluorine atom, a chlorine atom, a bromine atom, an iodine atom, a methyl group, an ethyl group, an isopropyl group, a cyclopropyl group which may be substituted (The substituents are two chlorine atoms.) or a methoxy group, or $R^3$, $R^4$, $R^5$, $R^6$ and $R^7$ are a group(s) which is/are formed by the adjacent two of them with carbon atoms to which the respective substituents are bonded, and include a group represented by —$CH_2CH_2CH_2$—, provided that $R^3$ is not a hydrogen atom,
(4d) m and n are both 0.

Representative compounds of the present invention are exemplified in the following Table 1, but the present invention is not limited by these compounds.

In the following, in $R^3$ to $R^7$, "H" means that all the $R^3$, $R^4$, $R^5$, $R^6$ and $R^7$ are hydrogen atoms, in $R^3$ to $R^7$, "2-Cl" means that $R^3$ is a chlorine atom, "Me" represents a methyl group, "Et" represents an ethyl group, "Pr" represents a propyl group, "iPr" represents an isopropyl group, "cPr" represents a cyclopropyl group, "Bu" represents a butyl group, "iBu" represents an isobutyl group, "nsBu" represents a s-butyl group, "tBu" represents a tert-butyl group, "cBu" represents a cyclobutyl group, "Pen" represents a pentyl group, "cPen" represents a cyclopentyl group, "neoPen" represents a neopentyl group, "Hx" represents a hexyl group, "cHx" represents a cyclohexyl group, in $R^3$ to $R^7$, "2-$CH_2CH_2CH_2$-3" means that $R^3$ and $R^4$ are a trimethylene group and form a 5-membered ring together with carbon atoms to which they are bonded, "=N—OMe" represents a methoxyimino group, "=O" represents a carbonyl group together with carbon atom(s) to which they are bonded, "$SO_2$ (Ph-4-Me)" represents a p-tolylsulfonyl group, "cPr-1-F" represents a 1-fluorocyclopropyl group, "cPr-cis-2-$(CH_2)_3$-cis-3" represents a group represented by

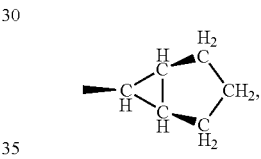

"C(—$CH_2CH_2$—)—$CH_2CH_2$" represents a group represented by

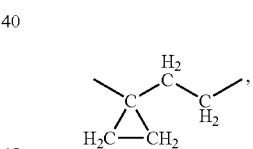

"CH($CH_2$)CH—$CH_2$" represents a group represented by

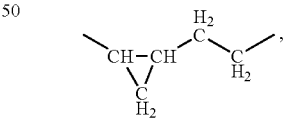

"CH($OCH_2$)$_2$" represents a group represented by

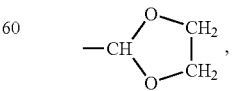

"Fur" represents a furyl group, "Thi" represents a thienyl group, "Pyr" represents a pyridyl group, "Azr" represents a aziridinyl group, "Pyrd" represents a pyrrolidinyl group, "Pyrr" represents a pyrrolyl group, "Pyza" represents a pyrazolyl group, "Thiz" represents a thiazolyl group, "Pyzn" represents a pyridazinyl group, "Np" represents a naphthyl group, "1-Ad" represents a 1-adamantyl group, "Ioxa" represents an isoxazolyl group, "Tdia" represents a 1,2,3-thiadiazolyl group, "Bfur" represents a 1-benzofuranyl group, "Bthi" represents a 1-benzothienyl group, "Bthia" represents a 1,3-benzothiazolyl group, "Boxaz" represents a 1,3-benzodioxolyl group, "Iqu" represents an isquinolyl group, "Azet" represents an azetidinyl group, "Ppri" represents a piperidyl group, "1-Ppri-4-OCH$_2$CH$_2$O-4" represents a group represented by the formula:

"Ppra" represents a piperadinyl group, "Morp" represents a morpholinyl group, "Tmor" represents a thiomorpholinyl group, "Carb" represents a carbazolyl group, "Pthia" represents a phenothiazinyl group, "Thpy" represents a tetrahydro-2H-pyranyl group, "Q$^1$" represents an oxiranyl group, "Q$^2$" represents a benzoxazolyl group, "Q$^3$" represents a benzothiazolyl group, "Q$^4$" represents a fluorenyl group, "Q$^5$" represents a 4-(2,4-dichlorobenzoyl)-1,3-dimethyl-1H-pyrazol-5-yl group, "Q$^6$" represents a 6-chloro-3-(2-methylphenoxy)-4-pyridazinyl group, "Q$^7$" represents a 6-chloro-3-(2-isopropylphenoxy)-4-pyridazinyl group, "Q$^8$" represents a 6-chloro-3-(2-cyclopropylphenoxy)-4-pyridazinyl group, "Q$^9$" represents a 6-chloro-3-(2,3-dihydro-1H-inden-4-yloxy)-4-pyridazinyl group, "Q$^{10}$" represents a 6-chloro-3-(2,6-dimethylphenoxy)-4-pyridazinyl group, "Q$^{11}$" represents a 6-chloro-3-(2-cyclopropyl-6-methylphenoxy)-4-pyridazinyl group, "Q$^{12}$" represents a 4-[2-chloro-3-(methoxycarbonyl)-4-(methylsulfonyl)benzoyl]-1-ethyl-1H-pyrazol-5-yl group, "Q$^{13}$" represents a 4-(2,4-dichloro-3-methylbenzoyl)-1,3-dimethyl-1H-pyrazol-5-yl group, "Q$^{14}$" represents a 2-[2-chloro-4-(methylsulfonyl)benzoyl]-3-oxo-1-cyclohexen-1-yl group, "Q$^{15}$" represents a 2-[4-(methylsulfonyl)-2-nitrobenzoyl]-3-oxo-1-cyclohexen-1-yl group, "Q$^{16}$" represents a 2-cyano-1-cyclopropyl-3-[2-(methylsulfonyl)-4-(trifluoromethyl)phenyl]-3-oxo-1-propenyl group, "Q$^{17}$" represents a 3-[4-chloro-2-(methylsulfonyl)phenyl]-2-cyano-1-cyclopropyl-3-oxo-1-propenyl group, and "Q$^{18}$" represents a 3,4-dihydro-2(1H)-isoquinolinyl group, respectively.

TABLE 1

| Compound No. | R$^1$ | R$^2$ | X | R$^3$ to R$^7$ | m | n |
|---|---|---|---|---|---|---|
| 1 | H | H | H | H | 0 | 0 |
| 2 | H | H | H | 2-Cl | 0 | 0 |
| 3 | H | H | H | 2-Br | 0 | 0 |
| 4 | H | H | H | 2-I | 0 | 0 |
| 5 | H | H | H | 2-Me | 0 | 0 |
| 6 | H | H | H | 2-iPr | 0 | 0 |
| 7 | H | H | H | 2-cPr | 0 | 0 |
| 8 | H | H | H | 2-cBu | 0 | 0 |
| 9 | H | H | H | 2-CH$_2$CH$_2$CH$_2$-3 | 0 | 0 |
| 10 | H | H | H | 2-cPr,5-Me | 0 | 0 |
| 11 | H | H | H | 2-OMe,5-Me | 0 | 0 |
| 12 | H | H | H | 2-F, 6-iPr | 0 | 0 |
| 13 | H | H | H | 2-Cl, 6-cPr | 0 | 0 |
| 14 | H | H | H | 2-Br, 6-Me | 0 | 0 |
| 15 | H | H | H | 2-I, 6-Me | 0 | 0 |
| 16 | H | H | H | 2, 6-Me$_2$ | 0 | 0 |
| 17 | H | H | H | 2-Me, 6-Et | 0 | 0 |
| 18 | H | H | H | 2-Me, 6-cPr | 0 | 0 |
| 19 | H | H | H | 2, 6-cPr$_2$ | 0 | 0 |
| 20 | H | H | H | 2-cPr, 3,5-Me$_2$ | 0 | 0 |
| 21 | H | H | H | 2-cPr, 5,6-Me$_2$ | 0 | 0 |
| 22 | H | H | SO$_2$ (Ph-4-Me) | 2-Cl | 0 | 0 |
| 23 | H | H | SO$_2$ (Ph-4-Me) | 2-Br | 0 | 0 |
| 24 | H | H | SO$_2$ (Ph-4-Me) | 2-I | 0 | 0 |
| 25 | H | H | SO$_2$ (Ph-4-Me) | 2-Me | 0 | 0 |
| 26 | H | H | SO$_2$ (Ph-4-Me) | 2-iPr | 0 | 0 |
| 27 | H | H | SO$_2$ (Ph-4-Me) | 2-cPr | 0 | 0 |
| 28 | H | H | SO$_2$ (Ph-4-Me) | 2-cBu | 0 | 0 |
| 29 | H | H | SO$_2$ (Ph-4-Me) | 2-CH$_2$CH$_2$CH$_2$-3 | 0 | 0 |
| 30 | H | H | SO$_2$ (Ph-4-Me) | 2-cPr, 5-Me | 0 | 0 |
| 31 | H | H | SO$_2$ (Ph-4-Me) | 2-OMe, 5-Me | 0 | 0 |
| 32 | H | H | SO$_2$ (Ph-4-Me) | 2-F, 6-iPr | 0 | 0 |
| 33 | H | H | SO$_2$ (Ph-4-Me) | 2-Cl, 6-cPr | 0 | 0 |
| 34 | H | H | SO$_2$ (Ph-4-Me) | 2-Br, 6-Me | 0 | 0 |
| 35 | H | H | SO$_2$ (Ph-4-Me) | 2-I, 6-Me | 0 | 0 |

TABLE 1-continued

| Compound No. | R¹ | R² | X | R³ to R⁷ | m | n |
|---|---|---|---|---|---|---|
| 36 | H | H | SO₂(Ph-4-Me) | 2, 6-Me₂ | 0 | 0 |
| 37 | H | H | SO₂(Ph-4-Me) | 2-Me, 6-Et | 0 | 0 |
| 38 | H | H | SO₂(Ph-4-Me) | 2-Me, 6-cPr | 0 | 0 |
| 39 | H | H | SO₂(Ph-4-Me) | 2, 6-cPr₂ | 0 | 0 |
| 40 | H | H | SO₂(Ph-4-Me) | 2-cPr, 3,5-Me₂ | 0 | 0 |
| 41 | H | H | SO₂(Ph-4-Me) | 2-cPr, 5, 6-Me₂ | 0 | 0 |
| 42 | H | Cl | H | 2-Cl | 0 | 0 |
| 43 | H | Cl | H | 2-Br | 0 | 0 |
| 44 | H | Cl | H | 2-I | 0 | 0 |
| 45 | H | Cl | H | 2-Me | 0 | 0 |
| 46 | H | Cl | H | 2-Et | 0 | 0 |
| 47 | H | Cl | H | 2-iPr | 0 | 0 |
| 48 | H | Cl | H | 2-cPr | 0 | 0 |
| 49 | H | Cl | H | 2-cBu | 0 | 0 |
| 50 | H | Cl | H | 2-CH₂CH₂CH₂-3 | 0 | 0 |
| 51 | H | Cl | H | 2-cPr, 5-Me | 0 | 0 |
| 52 | H | Cl | H | 2-OMe, 5-Me | 0 | 0 |
| 53 | H | Cl | H | 2-F, 6-iPr | 0 | 0 |
| 54 | H | Cl | H | 2-Cl, 6-cPr | 0 | 0 |
| 55 | H | Cl | H | 2-Br, 6-Me | 0 | 0 |
| 56 | H | Cl | H | 2-I, 6-Me | 0 | 0 |
| 57 | H | Cl | H | 2, 6-Me₂ | 0 | 0 |
| 58 | H | Cl | H | 2-Me, 6-Et | 0 | 0 |
| 59 | H | Cl | H | 2-Me, 6-cPr | 0 | 0 |
| 60 | H | Cl | H | 2,6-cPr₂ | 0 | 0 |
| 61 | H | Cl | H | 2-cPr, 3,5-Me₂ | 0 | 0 |
| 62 | H | Cl | H | 2-cPr, 5, 6-Me₂ | 0 | 0 |
| 63 | H | Cl | SO₂(Ph-4-Me) | 2-Cl | 0 | 0 |
| 64 | H | Cl | SO₂(Ph-4-Me) | 2-Br | 0 | 0 |
| 65 | H | Cl | SO₂(Ph-4-Me) | 2-I | 0 | 0 |
| 66 | H | Cl | SO₂(Ph-4-Me) | 2-Me | 0 | 0 |
| 67 | H | Cl | SO₂(Ph-4-Me) | 2-iPr | 0 | 0 |
| 68 | H | Cl | SO₂(Ph-4-Me) | 2-cPr | 0 | 0 |
| 69 | H | Cl | SO₂(Ph-4-Me) | 2-cBu | 0 | 0 |
| 70 | H | Cl | SO₂(Ph-4-Me) | 2-CH₂CH₂CH₂-3 | 0 | 0 |
| 71 | H | Cl | SO₂(Ph-4-Me) | 2-cPr, 5-Me | 0 | 0 |
| 72 | H | Cl | SO₂(Ph-4-Me) | 2-OMe, 5-Me | 0 | 0 |
| 73 | H | Cl | SO₂(Ph-4-Me) | 2-F, 6-iPr | 0 | 0 |
| 74 | H | Cl | SO₂(Ph-4-Me) | 2-Cl, 6-cPr | 0 | 0 |
| 75 | H | Cl | SO₂(Ph-4-Me) | 2-Br, 6-Me | 0 | 0 |
| 76 | H | Cl | SO₂(Ph-4-Me) | 2-I, 6-Me | 0 | 0 |
| 77 | H | Cl | SO₂(Ph-4-Me) | 2,6-Me₂ | 0 | 0 |
| 78 | H | Cl | SO₂(Ph-4-Me) | 2-Me, 6-Et | 0 | 0 |
| 79 | H | Cl | SO₂(Ph-4-Me) | 2-Me, 6-cPr | 0 | 0 |
| 80 | H | Cl | SO₂(Ph-4-Me) | 2,6-cPr₂ | 0 | 0 |
| 81 | H | Cl | SO₂(Ph-4-Me) | 2-cPr, 3,5-Me₂ | 0 | 0 |
| 82 | H | Cl | SO₂(Ph-4-Me) | 2-cPr, 5, 6-Me₂ | 0 | 0 |
| 83 | H | SiMe₃ | H | 2-Cl | 0 | 0 |
| 84 | H | SiMe₃ | H | 2-Br | 0 | 0 |
| 85 | H | SiMe₃ | H | 2-I | 0 | 0 |
| 86 | H | SiMe₃ | H | 2-Me | 0 | 0 |
| 87 | H | SiMe₃ | H | 2-iPr | 0 | 0 |
| 88 | H | SiMe₃ | H | 2-cPr | 0 | 0 |
| 89 | H | SiMe₃ | H | 2-cBu | 0 | 0 |
| 90 | H | SiMe₃ | H | 2-CH₂CH₂CH₂-3 | 0 | 0 |
| 91 | H | SiMe₃ | H | 2-cPr, 5-Me | 0 | 0 |
| 92 | H | SiMe₃ | H | 2-OMe, 5-Me | 0 | 0 |
| 93 | H | SiMe₃ | H | 2-F, 6-iPr | 0 | 0 |
| 94 | H | SiMe₃ | H | 2-Cl, 6-cPr | 0 | 0 |
| 95 | H | SiMe₃ | H | 2-Br, 6-Me | 0 | 0 |
| 96 | H | SiMe₃ | H | 2-I, 6-Me | 0 | 0 |
| 97 | H | SiMe₃ | H | 2,6-Me₂ | 0 | 0 |
| 98 | H | SiMe₃ | H | 2-Me, 6-Et | 0 | 0 |
| 99 | H | SiMe₃ | H | 2-Me, 6-cPr | 0 | 0 |
| 100 | H | SiMe₃ | H | 2,6-cPr₂ | 0 | 0 |
| 101 | H | SiMe₃ | H | 2-cPr, 3,5-Me₂ | 0 | 0 |

TABLE 1-continued

| Compound No. | R¹ | R² | X | R³ to R⁷ | m | n |
|---|---|---|---|---|---|---|
| 102 | H | SiMe₃ | H | 2-cPr, 5,6-Me₂ | 0 | 0 |
| 103 | H | SiMe₃ | SO₂ (Ph-4-Me) | 2-Cl | 0 | 0 |
| 104 | H | SiMe₃ | SO₂ (Ph-4-Me) | 2-Br | 0 | 0 |
| 105 | H | SiMe₃ | SO₂ (Ph-4-Me) | 2-I | 0 | 0 |
| 106 | H | SiMe₃ | SO₂ (Ph-4-Me) | 2-Me | 0 | 0 |
| 107 | H | SiMe₃ | SO₂ (Ph-4-Me) | 2-iPr | 0 | 0 |
| 108 | H | SiMe₃ | SO₂ (Ph-4-Me) | 2-cPr | 0 | 0 |
| 109 | H | SiMe₃ | SO₂ (Ph-4-Me) | 2-cBu | 0 | 0 |
| 110 | H | SiMe₃ | SO₂ (Ph-4-Me) | 2-CH₂CH₂CH₂-3 | 0 | 0 |
| 111 | H | SiMe₃ | SO₂ (Ph-4-Me) | 2-cPr, 5-Me | 0 | 0 |
| 112 | H | SiMe₃ | SO₂ (Ph-4-Me) | 2-OMe, 5-Me | 0 | 0 |
| 113 | H | SiMe₃ | SO₂ (Ph-4-Me) | 2-F, 6-iPr | 0 | 0 |
| 114 | H | SiMe₃ | SO₂ (Ph-4-Me) | 2-Cl, 6-cPr | 0 | 0 |
| 115 | H | SiMe₃ | SO₂ (Ph-4-Me) | 2-Br, 6-Me | 0 | 0 |
| 116 | H | SiMe₃ | SO₂ (Ph-4-Me) | 2-I, 6-Me | 0 | 0 |
| 117 | H | SiMe₃ | SO₂ (Ph-4-Me) | 2,6-Me₂ | 0 | 0 |
| 118 | H | SiMe₃ | SO₂ (Ph-4-Me) | 2-Me, 6-Et | 0 | 0 |
| 119 | H | SiMe₃ | SO₂ (Ph-4-Me) | 2-Me, 6-cPr | 0 | 0 |
| 120 | H | SiMe₃ | SO₂ (Ph-4-Me) | 2,6-cPr₂ | 0 | 0 |
| 121 | H | SiMe₃ | SO₂ (Ph-4-Me) | 2-cPr, 3,5-Me₂ | 0 | 0 |
| 122 | H | SiMe₃ | SO₂ (Ph-4-Me) | 2-cPr, 5,6-Me₂ | 0 | 0 |
| 123 | Cl | H | H | H | 0 | 0 |
| 124 | Cl | H | H | 2-F | 0 | 0 |
| 125 | Cl | H | H | 2-Cl | 0 | 0 |
| 126 | Cl | H | H | 2-Br | 0 | 0 |
| 127 | Cl | H | H | 2-I | 0 | 0 |
| 128 | Cl | H | H | 2-Me | 0 | 0 |
| 129 | Cl | H | H | 2-Me | 1 | 0 |
| 130 | Cl | H | H | 2-Et | 0 | 0 |
| 131 | Cl | H | H | 2-Pr | 0 | 0 |
| 132 | Cl | H | H | 2-iPr | 0 | 0 |
| 133 | Cl | H | H | 2-Bu | 0 | 0 |
| 134 | Cl | H | H | 2-iBu | 0 | 0 |
| 135 | Cl | H | H | 2-sBu | 0 | 0 |
| 136 | Cl | H | H | 2-tBu | 0 | 0 |
| 137 | Cl | H | H | 2-Pen | 0 | 0 |
| 138 | Cl | H | H | 2-Hx | 0 | 0 |
| 139 | Cl | H | H | 2-cPr | 0 | 0 |
| 140 | Cl | H | H | 2-(cPr-1-F) | 0 | 0 |
| 141 | Cl | H | H | 2-(cPr-1-Cl) | 0 | 0 |
| 142 | Cl | H | H | 2-(cPr-1-Br) | 0 | 0 |
| 143 | Cl | H | H | 2-(cPr-1-I) | 0 | 0 |
| 144 | Cl | H | H | 2-(cPr-1-Me) | 0 | 0 |
| 145 | Cl | H | H | 2-(cPr-1-Et) | 0 | 0 |
| 146 | Cl | H | H | 2-(cPr-1-Pr) | 0 | 0 |
| 147 | Cl | H | H | 2-(cPr-1-iPr) | 0 | 0 |
| 148 | Cl | H | H | 2-(cPr-1-Bu) | 0 | 0 |
| 149 | Cl | H | H | 2-(cPr-1-tBu) | 0 | 0 |
| 150 | Cl | H | H | 2-(cPr-1-Hx) | 0 | 0 |
| 151 | Cl | H | H | 2-(cPr-1-cPr) | 0 | 0 |
| 152 | Cl | H | H | 2-(cPr-1-cBu) | 0 | 0 |
| 153 | Cl | H | H | 2-(cPr-1-cPen) | 0 | 0 |
| 154 | Cl | H | H | 2-(cPr-1-CH₂F) | 0 | 0 |
| 155 | Cl | H | H | 2-(cPr-1-CH₂Cl) | 0 | 0 |
| 156 | Cl | H | H | 2-(cPr-1-CH₂Br) | 0 | 0 |
| 157 | Cl | H | H | 2-(cPr-1-CHF₂) | 0 | 0 |
| 158 | Cl | H | H | 2-(cPr-1-CF₃) | 0 | 0 |
| 159 | Cl | H | H | 2-(cPr-1-CCl₃) | 0 | 0 |
| 160 | Cl | H | H | 2-(cPr-1-CH₂CF₃) | 0 | 0 |
| 161 | Cl | H | H | 2-(cPr-1-CH₂CCl₃) | 0 | 0 |
| 162 | Cl | H | H | 2-(cPr-1-CH=CH₂) | 0 | 0 |
| 163 | Cl | H | H | 2-(cPr-1-CH₂OMe) | 0 | 0 |
| 164 | Cl | H | H | 2-(cPr-1-CH₂OEt) | 0 | 0 |
| 165 | Cl | H | H | 2-(cPr-1-CH₂OiPr) | 0 | 0 |
| 166 | Cl | H | H | 2-(cPr-1-CH₂SMe) | 0 | 0 |
| 167 | Cl | H | H | 2-(cPr-1-CH₂SEt) | 0 | 0 |

TABLE 1-continued

| Compound No. | R¹ | R² | X | R³ to R⁷ | m | n |
|---|---|---|---|---|---|---|
| 168 | Cl | H | H | 2-(cPr-1-CH₂S-iPr) | 0 | 0 |
| 169 | Cl | H | H | 2-(cPr-1-CH₂SOMe) | 0 | 0 |
| 170 | Cl | H | H | 2-(cPr-1-CH₂SOEt) | 0 | 0 |
| 171 | Cl | H | H | 2-(cPr-1-CH₂SO₂Me) | 0 | 0 |
| 172 | Cl | H | H | 2-(cPr-1-CH₂SO₂Et) | 0 | 0 |
| 173 | Cl | H | H | 2-(cPr-1-CN) | 0 | 0 |
| 174 | Cl | H | H | 2-{cPr-1-C(=NOMe)Me} | 0 | 0 |
| 175 | Cl | H | H | 2-(cPr-1-COMe) | 0 | 0 |
| 176 | Cl | H | H | 2-(cPr-1-COEt) | 0 | 0 |
| 177 | Cl | H | H | 2-(cPr-1-COPh) | 0 | 0 |
| 178 | Cl | H | H | 2-(cPr-1-CO₂H) | 0 | 0 |
| 179 | Cl | H | H | 2-(cPr-1-CO₂Me) | 0 | 0 |
| 180 | Cl | H | H | 2-(cPr-1-CO₂Et) | 0 | 0 |
| 181 | Cl | H | H | 2-(cPr-1-CONH₂) | 0 | 0 |
| 182 | Cl | H | H | 2-(cPr-1-CONMe₂) | 0 | 0 |
| 183 | Cl | H | H | 2-(cPr-1-CONEt₂) | 0 | 0 |
| 184 | Cl | H | H | 2-(cPr-1-Ph) | 0 | 0 |
| 185 | Cl | H | H | 2-{cPr-1-(Ph-2-F)} | 0 | 0 |
| 186 | Cl | H | H | 2-{cPr-1-(Ph-2-Cl)} | 0 | 0 |
| 187 | Cl | H | H | 2-{cPr-1-(Ph-2-Me)} | 0 | 0 |
| 188 | Cl | H | H | 2-{cPr-1-(Ph-4-Cl)} | 0 | 0 |
| 189 | Cl | H | H | 2-{cPr-1-(Ph-4-Me)} | 0 | 0 |
| 190 | Cl | H | H | 2-{cPr-1-(2-Fur)} | 0 | 0 |
| 191 | Cl | H | H | 2-{cPr-1-(2-Thi)} | 0 | 0 |
| 192 | Cl | H | H | 2-{cPr-1-(2-Pyr)} | 0 | 0 |
| 193 | Cl | H | H | 2-(cPr-1-NH₂) | 0 | 0 |
| 194 | Cl | H | H | 2-(cPr-1-NHMe) | 0 | 0 |
| 195 | Cl | H | H | 2-(cPr-1-NMe₂) | 0 | 0 |
| 196 | Cl | H | H | 2-(cPr-1-NHCOMe) | 0 | 0 |
| 197 | Cl | H | H | 2-(cPr-1-NHCO₂Me) | 0 | 0 |
| 198 | Cl | H | H | 2-(cPr-1-NHCONMe₂) | 0 | 0 |
| 199 | Cl | H | H | 2-(cPr-1-NHSO₂Me) | 0 | 0 |
| 200 | Cl | H | H | 2-(cPr-1-NO₂) | 0 | 0 |
| 201 | Cl | H | H | 2-(cPr-1-OH) | 0 | 0 |
| 202 | Cl | H | H | 2-(cPr-1-OMe) | 0 | 0 |
| 203 | Cl | H | H | 2-(cPr-1-OEt) | 0 | 0 |
| 204 | Cl | H | H | 2-(cPr-1-OCF₃) | 0 | 0 |
| 205 | Cl | H | H | 2-(cPr-1-OPh) | 0 | 0 |
| 206 | Cl | H | H | 2-(cPr-1-SMe) | 0 | 0 |
| 207 | Cl | H | H | 2-(cPr-1-SEt) | 0 | 0 |
| 208 | Cl | H | H | 2-(cPr-1-SPh) | 0 | 0 |
| 209 | Cl | H | H | 2-(cPr-1-SOMe) | 0 | 0 |
| 210 | Cl | H | H | 2-(cPr-1-SOEt) | 0 | 0 |
| 211 | Cl | H | H | 2-(cPr-1-SO₂Me) | 0 | 0 |
| 212 | Cl | H | H | 2-(cPr-1-SO₂Et) | 0 | 0 |
| 213 | Cl | H | H | 2-(cPr-2-F) | 0 | 0 |
| 214 | Cl | H | H | 2-(cPr-2-Cl) | 0 | 0 |
| 215 | Cl | H | H | 2-(cPr-2-Br) | 0 | 0 |
| 216 | Cl | H | H | 2-(cPr-2-I) | 0 | 0 |
| 217 | Cl | H | H | 2-(cPr-2-Me) | 0 | 0 |
| 218 | Cl | H | H | 2-(cPr-2-Et) | 0 | 0 |
| 219 | Cl | H | H | 2-(cPr-2-Pr) | 0 | 0 |
| 220 | Cl | H | H | 2-(cPr-2-iPr) | 0 | 0 |
| 221 | Cl | H | H | 2-(cPr-2-Bu) | 0 | 0 |
| 222 | Cl | H | H | 2-(cPr-2-tBu) | 0 | 0 |
| 223 | Cl | H | H | 2-(cPr-2-Hx) | 0 | 0 |
| 224 | Cl | H | H | 2-(cPr-2-cPr) | 0 | 0 |
| 225 | Cl | H | H | 2-(cPr-2-CF₃) | 0 | 0 |
| 226 | Cl | H | H | 2-(cPr-2-CN) | 0 | 0 |
| 227 | Cl | H | H | 2-(cPr-2-CH₂OMe) | 0 | 0 |
| 228 | Cl | H | H | 2-(cPr-2-CH₂OEt) | 0 | 0 |
| 229 | Cl | H | H | 2-{cPr-2-C(=NOMe)Me} | 0 | 0 |
| 230 | Cl | H | H | 2-(cPr-2-COMe) | 0 | 0 |
| 231 | Cl | H | H | 2-(cPr-2-COEt) | 0 | 0 |
| 232 | Cl | H | H | 2-(cPr-2-COPh) | 0 | 0 |
| 233 | Cl | H | H | 2-(cPr-2-CO₂H) | 0 | 0 |

TABLE 1-continued

| Compound No. | R¹ | R² | X | R³ to R⁷ | m | n |
|---|---|---|---|---|---|---|
| 234 | Cl | H | H | 2-(cPr-2-CO$_2$Me) | 0 | 0 |
| 235 | Cl | H | H | 2-(cPr-2-CO$_2$Et) | 0 | 0 |
| 236 | Cl | H | H | 2-(cPr-2-CONH$_2$) | 0 | 0 |
| 237 | Cl | H | H | 2-(cPr-2-CONMe$_2$) | 0 | 0 |
| 238 | Cl | H | H | 2-(cPr-2-CONEt$_2$) | 0 | 0 |
| 239 | Cl | H | H | 2-(cPr-2-NH$_2$) | 0 | 0 |
| 240 | Cl | H | H | 2-(cPr-2-NHMe) | 0 | 0 |
| 241 | Cl | H | H | 2-(cPr-2-NMe$_2$) | 0 | 0 |
| 242 | Cl | H | H | 2-(cPr-2-NHCOMe) | 0 | 0 |
| 243 | Cl | H | H | 2-(cPr-2-NHCO$_2$Me) | 0 | 0 |
| 244 | Cl | H | H | 2-(cPr-2-NHCONMe$_2$) | 0 | 0 |
| 245 | Cl | H | H | 2-(cPr-2-NHSO$_2$Me) | 0 | 0 |
| 246 | Cl | H | H | 2-(cPr-2-NO$_2$) | 0 | 0 |
| 247 | Cl | H | H | 2-(cPr-2-OH) | 0 | 0 |
| 248 | Cl | H | H | 2-(cPr-2-OMe) | 0 | 0 |
| 249 | Cl | H | H | 2-(cPr-2-OEt) | 0 | 0 |
| 250 | Cl | H | H | 2-(cPr-2-OCF$_3$) | 0 | 0 |
| 251 | Cl | H | H | 2-(cPr-2-OPh) | 0 | 0 |
| 252 | Cl | H | H | 2-(cPr-2-SMe) | 0 | 0 |
| 253 | Cl | H | H | 2-(cPr-2-SEt) | 0 | 0 |
| 254 | Cl | H | H | 2-(cPr-2-SPh) | 0 | 0 |
| 255 | Cl | H | H | 2-(cPr-2-SOMe) | 0 | 0 |
| 256 | Cl | H | H | 2-(cPr-2-SOEt) | 0 | 0 |
| 257 | Cl | H | H | 2-(cPr-2-SO$_2$Me) | 0 | 0 |
| 258 | Cl | H | H | 2-(cPr-2-SO$_2$Et) | 0 | 0 |
| 259 | Cl | H | H | 2-(cPr-1,2-Me$_2$) | 0 | 0 |
| 260 | Cl | H | H | 2-(cPr-1-Me-2-Et) | 0 | 0 |
| 261 | Cl | H | H | 2-(cPr-1-Et-2-Me) | 0 | 0 |
| 262 | Cl | H | H | 2-(cPr-1,2-Et$_2$) | 0 | 0 |
| 263 | Cl | H | H | 2-{cPr-1,2-(CN)$_2$} | 0 | 0 |
| 264 | Cl | H | H | 2-(cPr-2,2-F$_2$) | 0 | 0 |
| 265 | Cl | H | H | 2-(cPr-2,2-Cl$_2$) | 0 | 0 |
| 266 | Cl | H | H | 2-(cPr-2,2-Br$_2$) | 0 | 0 |
| 267 | Cl | H | H | 2-(cPr-2,2-Me$_2$) | 0 | 0 |
| 268 | Cl | H | H | 2-{cPr-2,2-(CN)$_2$} | 0 | 0 |
| 269 | Cl | H | H | 2-(cPr-2-cis-3-cis-Me$_2$) | 0 | 0 |
| 270 | Cl | H | H | 2-(cPr-2-cis-3-trans-Me$_2$) | 0 | 0 |
| 271 | Cl | H | H | 2-(cPr-2-trans-3-trans-Me$_2$) | 0 | 0 |
| 272 | Cl | H | H | 2-{cPr-cis-2-(CH$_2$)$_3$-cis-3} | 0 | 0 |
| 273 | Cl | H | H | 2-{cPr-trans-2-(CH$_2$)$_3$-trans-3} | 0 | 0 |
| 274 | Cl | H | H | 2-{cPr-cis-2-(CH$_2$)$_4$-cis-3} | 0 | 0 |
| 275 | Cl | H | H | 2-(cPr-trans-2-(CH$_2$)$_4$-trans-3) | 0 | 0 |
| 276 | Cl | H | H | 2-{cPr-2,3-(CN)$_2$} | 0 | 0 |
| 277 | Cl | H | H | 2-(cPr-1,2,2-Me$_3$) | 0 | 0 |
| 278 | Cl | H | H | 2-(cPr-1,2,3-Me$_3$) | 0 | 0 |
| 279 | Cl | H | H | 2-(cPr-2,2,3-cis-Me$_3$) | 0 | 0 |
| 280 | Cl | H | H | 2-(cPr-2,2,3-trans-Me$_3$) | 0 | 0 |
| 281 | Cl | H | H | 2-(cPr-1,2,2,3-Me$_4$) | 0 | 0 |
| 282 | Cl | H | H | 2-(cPr-2,2,3,3-Me$_4$) | 0 | 0 |
| 283 | Cl | H | H | 2-(cPr-1,2,2,3,3-Me5) | 0 | 0 |
| 284 | Cl | H | H | 2-cBu | 0 | 0 |
| 285 | Cl | H | H | 2-(cBu-1-Me) | 0 | 0 |
| 286 | Cl | H | H | 2-(cBu-1-CH=CH$_2$) | 0 | 0 |
| 287 | Cl | H | H | 2-(cBu-1-CN) | 0 | 0 |
| 288 | Cl | H | H | 2-(cBu-1-CO$_2$H) | 0 | 0 |
| 289 | Cl | H | H | 2-(cBu-1-COMe) | 0 | 0 |
| 290 | Cl | H | H | 2-(cBu-1-CO$_2$Me) | 0 | 0 |
| 291 | Cl | H | H | 2-(cBu-1-NH$_2$) | 0 | 0 |
| 292 | Cl | H | H | 2-cPen | 0 | 0 |
| 293 | Cl | H | H | 2-cHx | 0 | 0 |
| 294 | Cl | H | H | 2-CH$_2$F | 0 | 0 |
| 295 | Cl | H | H | 2-CH$_2$Cl | 0 | 0 |
| 296 | Cl | H | H | 2-CH$_2$Br | 0 | 0 |
| 297 | Cl | H | H | 2-CHF$_2$ | 0 | 0 |
| 298 | Cl | H | H | 2-CHCl$_2$ | 0 | 0 |
| 299 | Cl | H | H | 2-CHBr$_2$ | 0 | 0 |

TABLE 1-continued

| Compound No. | R¹ | R² | X | R³ to R⁷ | m | n |
|---|---|---|---|---|---|---|
| 300 | Cl | H | H | 2-CF₃ | 0 | 0 |
| 301 | Cl | H | H | 2-CCl₃ | 0 | 0 |
| 302 | Cl | H | H | 2-CBr₃ | 0 | 0 |
| 303 | Cl | H | H | 2-CH=CH₂ | 0 | 0 |
| 304 | Cl | H | H | 2-CMe=CH₂ | 0 | 0 |
| 305 | Cl | H | H | 2-CH=CHMe | 0 | 0 |
| 306 | Cl | H | H | 2-CH=CHCN | 0 | 0 |
| 307 | Cl | H | H | 2-CH₂CH=CH₂ | 0 | 0 |
| 308 | Cl | H | H | 2-C CH | 0 | 0 |
| 309 | Cl | H | H | 2-C CMe | 0 | 0 |
| 310 | Cl | H | H | 2-C CSiMe₃ | 0 | 0 |
| 311 | Cl | H | H | 2-CH₂cPr | 0 | 0 |
| 312 | Cl | H | H | 2-CH₂cBu | 0 | 0 |
| 313 | Cl | H | H | 2-CH₂cPen | 0 | 0 |
| 314 | Cl | H | H | 2-CH₂cHx | 0 | 0 |
| 315 | Cl | H | H | 2-CH₂Ph | 0 | 0 |
| 316 | Cl | H | H | 2-CH₂CN | 0 | 0 |
| 317 | Cl | H | H | 2-CHMeCN | 0 | 0 |
| 318 | Cl | H | H | 2-CMe₂CN | 0 | 0 |
| 319 | Cl | H | H | 2-CH₂COMe | 0 | 0 |
| 320 | Cl | H | H | 2-CH₂CO₂Me | 0 | 0 |
| 321 | Cl | H | H | 2-CHMeCO₂Me | 0 | 0 |
| 322 | Cl | H | H | 2-CH₂CO₂Et | 0 | 0 |
| 323 | Cl | H | H | 2-CHMeCO₂Et | 0 | 0 |
| 324 | Cl | H | H | 2-CH₂OMe | 0 | 0 |
| 325 | Cl | H | H | 2-CH₂OEt | 0 | 0 |
| 326 | Cl | H | H | 2-CH₂SMe | 0 | 0 |
| 327 | Cl | H | H | 2-CH₂SO₂Et | 0 | 0 |
| 328 | Cl | H | H | 2-CH(OMe)₂ | 0 | 0 |
| 329 | Cl | H | H | 2-CH(OCH₂)₂ | 0 | 0 |
| 330 | Cl | H | H | 2-CN | 0 | 0 |
| 331 | Cl | H | H | 2-CH=NOH | 0 | 0 |
| 332 | Cl | H | H | 2-CH=NOMe | 0 | 0 |
| 333 | Cl | H | H | 2-CMe=NOH | 0 | 0 |
| 334 | Cl | H | H | 2-CMe=NOMe | 0 | 0 |
| 335 | Cl | H | H | 2-CHO | 0 | 0 |
| 336 | Cl | H | H | 2-COMe | 0 | 0 |
| 337 | Cl | H | H | 2-COtBu | 0 | 0 |
| 338 | Cl | H | H | 2-COPh | 0 | 0 |
| 339 | Cl | H | H | 2-CO₂Me | 0 | 0 |
| 340 | Cl | H | H | 2-CO₂tBu | 0 | 0 |
| 341 | Cl | H | H | 2-CO₂H | 0 | 0 |
| 342 | Cl | H | H | 2-CONH₂ | 0 | 0 |
| 343 | Cl | H | H | 2-CONMe₂ | 0 | 0 |
| 344 | Cl | H | H | 2-Ph | 0 | 0 |
| 345 | Cl | H | H | 2-(Ph-2-Cl) | 0 | 0 |
| 346 | Cl | H | H | 2-(Ph-2-Me) | 0 | 0 |
| 347 | Cl | H | H | 2-(Ph-2-CF₃) | 0 | 0 |
| 348 (Isomer A) | Cl | H | H | 2-(Ph-3-CF₃) | 0 | 0 |
| 349 (Isomer B) | Cl | H | H | 2-(Ph-3-CF₃) | 0 | 0 |
| 350 | Cl | H | H | 2-(1-Azr) | 0 | 0 |
| 351 | Cl | H | H | 2-(2-Azr) | 0 | 0 |
| 352 | Cl | H | H | 2-{2-Azr-1-SO₂—(Ph-4-Me)} | 0 | 0 |
| 353 | Cl | H | H | 2-(2-Q¹-2-Me) | 0 | 0 |
| 354 | Cl | H | H | 2-(2-Q¹-3-Me) | 0 | 0 |
| 355 | Cl | H | H | 2-(1-Pyrd) | 0 | 0 |
| 356 | Cl | H | H | 2-(1-Pyrr) | 0 | 0 |
| 357 | Cl | H | H | 2-(2-Fur) | 0 | 0 |
| 358 | Cl | H | H | 2-(3-Fur) | 0 | 0 |
| 359 | Cl | H | H | 2-(2-Thi) | 0 | 0 |
| 360 | Cl | H | H | 2-(2-Thi-3-Cl) | 0 | 0 |
| 361 | Cl | H | H | 2-(3-Thi) | 0 | 0 |
| 362 | Cl | H | H | 2-(1-Pyza) | 0 | 0 |
| 363 | Cl | H | H | 2-(1-Pyza-3-Me) | 0 | 0 |

TABLE 1-continued

| Compound No. | R¹ | R² | X | R³ to R⁷ | m | n |
|---|---|---|---|---|---|---|
| 364 | Cl | H | H | 2-(1-Pyza-3,5-Me₂) | 0 | 0 |
| 365 | Cl | H | H | 2-(1-Pyza-3-CF₃) | 0 | 0 |
| 366 | Cl | H | H | 2-(1-Pyza-4-CF₃) | 0 | 0 |
| 367 | Cl | H | H | 2-(1-Pyza-5-CF₃) | 0 | 0 |
| 368 | Cl | H | H | 2-(3-Pyza-1-SO₂NMe₂) | 0 | 0 |
| 369 | Cl | H | H | 2-(5-Pyza-1-SO₂NMe₂) | 0 | 0 |
| 370 | Cl | H | H | 2-(2-Thiz-4-Me) | 0 | 0 |
| 371 | Cl | H | H | 2-(2-Pyr) | 0 | 0 |
| 372 | Cl | H | H | 2-(3-Pyr) | 0 | 0 |
| 373 | Cl | H | H | 2-(4-Pyr) | 0 | 0 |
| 374 | Cl | H | H | 2-(1-Pyr-2-OH) | 0 | 0 |
| 375 | Cl | H | H | 2-(2-Q²) | 0 | 0 |
| 376 | Cl | H | H | 2-(2-Q³) | 0 | 0 |
| 377 | Cl | H | H | 2-NH₂ | 0 | 0 |
| 378 | Cl | H | H | 2-NHMe | 0 | 0 |
| 379 | Cl | H | H | 2-NMe₂ | 0 | 0 |
| 380 | Cl | H | H | 2-NHCOMe | 0 | 0 |
| 381 | Cl | H | H | 2-NHCO₂Me | 0 | 0 |
| 382 | Cl | H | H | 2-NHCONMe₂ | 0 | 0 |
| 383 | Cl | H | H | 2-NO₂ | 0 | 0 |
| 384 | Cl | H | H | 2-OH | 0 | 0 |
| 385 | Cl | H | H | 2-OMe | 0 | 0 |
| 386 | Cl | H | H | 2-OEt | 0 | 0 |
| 387 | Cl | H | H | 2-OiPr | 0 | 0 |
| 388 | Cl | H | H | 2-OtBu | 0 | 0 |
| 389 | Cl | H | H | 2-OCH₂F | 0 | 0 |
| 390 | Cl | H | H | 2-OCHF₂ | 0 | 0 |
| 391 | Cl | H | H | 2-OCF₃ | 0 | 0 |
| 392 | Cl | H | H | 2-OCH₂CF₃ | 0 | 0 |
| 393 | Cl | H | H | 2-OCH₂CCl₃ | 0 | 0 |
| 394 | Cl | H | H | 2-OCH₂OMe | 0 | 0 |
| 395 | Cl | H | H | 2-OCH₂OEt | 0 | 0 |
| 396 | Cl | H | H | 2-OCH₂CH₂OMe | 0 | 0 |
| 397 | Cl | H | H | 2-OCH₂CH₂OEt | 0 | 0 |
| 398 | Cl | H | H | 2-OPh | 0 | 0 |
| 399 | Cl | H | H | 2-O(Ph-2-OH) | 0 | 0 |
| 400 | Cl | H | H | 2-O{Ph-2-O(3-Pyzn-6-Cl-4-OEt)} | 0 | 0 |
| 401 | Cl | H | H | 2-SMe | 0 | 0 |
| 402 | Cl | H | H | 2-SEt | 0 | 0 |
| 403 | Cl | H | H | 2-S-iPr | 0 | 0 |
| 404 | Cl | H | H | 2-SOMe | 0 | 0 |
| 405 | Cl | H | H | 2-SOEt | 0 | 0 |
| 406 | Cl | H | H | 2-SO₂Me | 0 | 0 |
| 407 | Cl | H | H | 2-SO₂Et | 0 | 0 |
| 408 | Cl | H | H | 2-SiMe₃ | 0 | 0 |
| 409 | Cl | H | H | 3-F | 0 | 0 |
| 410 | Cl | H | H | 3-Cl | 0 | 0 |
| 411 | Cl | H | H | 3-Br | 0 | 0 |
| 412 | Cl | H | H | 3-I | 0 | 0 |
| 413 | Cl | H | H | 3-Me | 0 | 0 |
| 414 | Cl | H | H | 3-Et | 0 | 0 |
| 415 | Cl | H | H | 3-iPr | 0 | 0 |
| 416 | Cl | H | H | 3-tBu | 0 | 0 |
| 417 | Cl | H | H | 3-cPr | 0 | 0 |
| 418 | Cl | H | H | 3-CF₃ | 0 | 0 |
| 419 | Cl | H | H | 3-(2-Fur) | 0 | 0 |
| 420 | Cl | H | H | 3-CN | 0 | 0 |
| 421 | Cl | H | H | 3-CHO | 0 | 0 |
| 422 | Cl | H | H | 3-COMe | 0 | 0 |
| 423 | Cl | H | H | 3-CO₂Me | 0 | 0 |
| 424 | Cl | H | H | 3-NO₂ | 0 | 0 |
| 425 | Cl | H | H | 3-OMe | 0 | 0 |
| 426 | Cl | H | H | 4-F | 0 | 0 |
| 427 | Cl | H | H | 4-Cl | 0 | 0 |
| 428 | Cl | H | H | 4-Br | 0 | 0 |
| 429 | Cl | H | H | 4-I | 0 | 0 |

TABLE 1-continued

| Compound No. | R¹ | R² | X | R³ to R⁷ | m | n |
|---|---|---|---|---|---|---|
| 430 | Cl | H | H | 4-Me | 0 | 0 |
| 431 | Cl | H | H | 4-Et | 0 | 0 |
| 432 | Cl | H | H | 4-iPr | 0 | 0 |
| 433 | Cl | H | H | 4-tBu | 0 | 0 |
| 434 | Cl | H | H | 4-cPr | 0 | 0 |
| 435 | Cl | H | H | 4-OMe | 0 | 0 |
| 436 | Cl | H | H | 4-SiMe₃ | 0 | 0 |
| 437 | Cl | H | H | 2,3-F₂ | 0 | 0 |
| 438 | Cl | H | H | 2-F, 3-Cl | 0 | 0 |
| 439 | Cl | H | H | 2-F, 3-Br | 0 | 0 |
| 440 | Cl | H | H | 2-F, 3-Me | 0 | 0 |
| 441 | Cl | H | H | 2-F, 3-CF₃ | 0 | 0 |
| 442 | Cl | H | H | 2-Cl, 3-F | 0 | 0 |
| 443 | Cl | H | H | 2,3-Cl₂ | 0 | 0 |
| 444 | Cl | H | H | 2-Cl, 3-Br | 0 | 0 |
| 445 | Cl | H | H | 2-Cl, 3-Me | 0 | 0 |
| 446 | Cl | H | H | 2-Cl, 3-CF₃ | 0 | 0 |
| 447 | Cl | H | H | 2-Cl, 3-OMe | 0 | 0 |
| 448 | Cl | H | H | 2-Br, 3-F | 0 | 0 |
| 449 | Cl | H | H | 2-Br, 3-Cl | 0 | 0 |
| 450 | Cl | H | H | 2-Br, 3-Me | 0 | 0 |
| 451 | Cl | H | H | 2-Br, 3-CF₃ | 0 | 0 |
| 452 | Cl | H | H | 2-Br, 3-OMe | 0 | 0 |
| 453 | Cl | H | H | 2-Me, 3-F | 0 | 0 |
| 454 | Cl | H | H | 2-Me, 3-Cl | 0 | 0 |
| 455 | Cl | H | H | 2-Me, 3-Br | 0 | 0 |
| 456 | Cl | H | H | 2,3-Me₂ | 0 | 0 |
| 457 | Cl | H | H | 2-Me, 3-CF₃ | 0 | 0 |
| 458 | Cl | H | H | 2-Me, 3-NO₂ | 0 | 0 |
| 459 | Cl | H | H | 2-Me, 3-OMe | 0 | 0 |
| 460 | Cl | H | H | 2-Me, 3-O(3-Pyzn-6-Cl-4-OH) | 0 | 0 |
| 461 | Cl | H | H | 2-Et, 3-F | 0 | 0 |
| 462 | Cl | H | H | 2-Et, 3-Cl | 0 | 0 |
| 463 | Cl | H | H | 2-Et, 3-Br | 0 | 0 |
| 464 | Cl | H | H | 2-Et, 3-Me | 0 | 0 |
| 465 | Cl | H | H | 2-iPr, 3-F | 0 | 0 |
| 466 | Cl | H | H | 2-iPr, 3-Cl | 0 | 0 |
| 467 | Cl | H | H | 2-iPr, 3-Me | 0 | 0 |
| 468 | Cl | H | H | 2-iPr, 3-Et | 0 | 0 |
| 469 | Cl | H | H | 2-cPr, 3-F | 0 | 0 |
| 470 | Cl | H | H | 2-cPr, 3-Cl | 0 | 0 |
| 471 | Cl | H | H | 2-cPr, 3-Br | 0 | 0 |
| 472 | Cl | H | H | 2-cPr, 3-Me | 0 | 0 |
| 473 | Cl | H | H | 2-cPr, 3-Et | 0 | 0 |
| 474 | Cl | H | H | 2-cPr, 3-CF₃ | 0 | 0 |
| 475 | Cl | H | H | 2-cPr, 3-CN | 0 | 0 |
| 476 | Cl | H | H | 2-cPr, 3-CO₂Me | 0 | 0 |
| 477 | Cl | H | H | 2-cPr, 3-NO₂ | 0 | 0 |
| 478 | Cl | H | H | 2-cPr, 3-OMe | 0 | 0 |
| 479 | Cl | H | H | 2-cBu, 3-F | 0 | 0 |
| 480 | Cl | H | H | 2-cBu, 3-Cl | 0 | 0 |
| 481 | Cl | H | H | 2-cBu, 3-Br | 0 | 0 |
| 482 | Cl | H | H | 2-cBu, 3-Me | 0 | 0 |
| 483 | Cl | H | H | 2-CF₃, 3-F | 0 | 0 |
| 484 | Cl | H | H | 2-CF₃, 3-Cl | 0 | 0 |
| 485 | Cl | H | H | 2-CF₃, 3-Br | 0 | 0 |
| 486 | Cl | H | H | 2-CF₃, 3-Me | 0 | 0 |
| 487 | Cl | H | H | 2-CN, 3-F | 0 | 0 |
| 488 | Cl | H | H | 2-CN, 3-Cl | 0 | 0 |
| 489 | Cl | H | H | 2-CN, 3-Br | 0 | 0 |
| 490 | Cl | H | H | 2-CN, 3-Me | 0 | 0 |
| 491 | Cl | H | H | 2-CO₂Me, 3-F | 0 | 0 |
| 492 | Cl | H | H | 2-CO₂Me, 3-Cl | 0 | 0 |
| 493 | Cl | H | H | 2-CO₂Me, 3-Br | 0 | 0 |
| 494 | Cl | H | H | 2-CO₂Me, 3-Me | 0 | 0 |
| 495 | Cl | H | H | 2-NO₂, 3-F | 0 | 0 |

TABLE 1-continued

[Structure: pyridazine core with R¹, R², OX, R³–R⁷ substituents on phenoxy group, N–N with (O)ₘ and (O)ₙ]

| Compound No. | R¹ | R² | X | R³ to R⁷ | m | n |
|---|---|---|---|---|---|---|
| 496 | Cl | H | H | 2-NO₂, 3-Cl | 0 | 0 |
| 497 | Cl | H | H | 2-NO₂, 3-Br | 0 | 0 |
| 498 | Cl | H | H | 2-NO₂, 3-Me | 0 | 0 |
| 499 | Cl | H | H | 2-OMe, 3-F | 0 | 0 |
| 500 | Cl | H | H | 2-OMe, 3-Cl | 0 | 0 |
| 501 | Cl | H | H | 2-OMe, 3-Br | 0 | 0 |
| 502 | Cl | H | H | 2-OMe, 3-Me | 0 | 0 |
| 503 | Cl | H | H | 2-OMe, 3-OMe | 0 | 0 |
| 504 | Cl | H | H | 2-CH₂-3 | 0 | 0 |
| 505 | Cl | H | H | 2-CH₂CH₂-3 | 0 | 0 |
| 506 | Cl | H | H | 2-CH₂CH₂CH₂-3 | 0 | 0 |
| 507 | Cl | H | H | 2-CHMeCH₂CH₂-3 | 0 | 0 |
| 508 | Cl | H | H | 2-CH(OMe)CH₂CH₂-3 | 0 | 0 |
| 509 | Cl | H | H | 2-CH₂CHMeCH₂-3 | 0 | 0 |
| 510 | Cl | H | H | 2-CH₂CH₂CHMe-3 | 0 | 0 |
| 511 | Cl | H | H | 2-CMe₂CH₂CH₂-3 | 0 | 0 |
| 512 | Cl | H | H | 2-C(OMe)₂CH₂CH₂-3 | 0 | 0 |
| 513 | Cl | H | H | 2-CH₂CMe₂CH₂-3 | 0 | 0 |
| 514 | Cl | H | H | 2-C(—CH₂CH₂—)—CH₂CH₂-3 | 0 | 0 |
| 515 | Cl | H | H | 2-CH(CH₂)CH—CH₂-3 | 0 | 0 |
| 516 | Cl | H | H | 2-CH₂—CH(CH₂)CH-3 | 0 | 0 |
| 517 | Cl | H | H | 2-C(=O)CH₂CH₂-3 | 0 | 0 |
| 518 | Cl | H | H | 2-CH₂C(=O)CH₂-3 | 0 | 0 |
| 519 | Cl | H | H | 2-CH₂CH₂C(=O)-3 | 0 | 0 |
| 520 | Cl | H | H | 2-C(=NOMe)CH₂CH₂-3 | 0 | 0 |
| 521 | Cl | H | H | 2-CH₂CH₂CH₂CH₂-3 | 0 | 0 |
| 522 | Cl | H | H | 2-CHMeCH₂CH₂CH₂-3 | 0 | 0 |
| 523 | Cl | H | H | 2-CMe₂CH₂CH₂CH₂-3 | 0 | 0 |
| 524 | Cl | H | H | 2-C(—CH₂CH₂—)—CH₂CH₂CH₂-3 | 0 | 0 |
| 525 | Cl | H | H | 2-CH(CH₂)CH—CH₂CH₂-3 | 0 | 0 |
| 526 | Cl | H | H | 2-CH(OMe)CH₂CH₂CH₂-3 | 0 | 0 |
| 527 | Cl | H | H | 2-CH=CHCH=CH-3 | 0 | 0 |
| 528 | Cl | H | H | 2-CH₂CH₂O-3 | 0 | 0 |
| 529 | Cl | H | H | 2-CHMeCH₂O-3 | 0 | 0 |
| 530 | Cl | H | H | 2-CH₂CHMeO-3 | 0 | 0 |
| 531 | Cl | H | H | 2-CH=CH—O-3 | 0 | 0 |
| 532 | Cl | H | H | 2-CMe=CH—O-3 | 0 | 0 |
| 533 | Cl | H | H | 2-CH=CMe-O-3 | 0 | 0 |
| 534 | Cl | H | H | 2-CH=CH—S-3 | 0 | 0 |
| 535 (Isomer A) | Cl | H | H | 2-N=CHCH=CH-3 | 0 | 0 |
| 536 (Isomer B) | Cl | H | H | 2-N=CHCH=CH-3 | 0 | 0 |
| 537 | Cl | H | H | 2-N=CH—O-3 | 0 | 0 |
| 538 | Cl | H | H | 2-N=CMe—O-3 | 0 | 0 |
| 539 | Cl | H | H | 2-OCH₂CH₂-3 | 0 | 0 |
| 540 | Cl | H | H | 2-OCMe₂CH₂-3 | 0 | 0 |
| 541 | Cl | H | H | 2-OCH=CH-3 | 0 | 0 |
| 542 | Cl | H | H | 2-OCMe=CH-3 | 0 | 0 |
| 543 | Cl | H | H | 2-OCF₂O-3 | 0 | 0 |
| 544 | Cl | H | H | 2-OCH₂O-3 | 0 | 0 |
| 545 | Cl | H | H | 2-OCHMeO-3 | 0 | 0 |
| 546 | Cl | H | H | 2-OCMe₂O-3 | 0 | 0 |
| 547 | Cl | H | H | 2-OCH₂CH₂O-3 | 0 | 0 |
| 548 | Cl | H | H | 2-OCH=N-3 | 0 | 0 |
| 549 | Cl | H | H | 2-OCMe=N-3 | 0 | 0 |
| 550 | Cl | H | H | 2,4-F₂ | 0 | 0 |
| 551 | Cl | H | H | 2-Cl, 4-F | 0 | 0 |
| 552 | Cl | H | H | 2,4-Cl₂ | 0 | 0 |
| 553 | Cl | H | H | 2-Br, 4-F | 0 | 0 |
| 554 | Cl | H | H | 2,4-Br₂ | 0 | 0 |
| 555 | Cl | H | H | 2-Br, 4-Me | 0 | 0 |
| 556 | Cl | H | H | 2-Br, 4-tBu | 0 | 0 |
| 557 | Cl | H | H | 2-Me, 4-F | 0 | 0 |
| 558 | Cl | H | H | 2-Me, 4-Cl | 0 | 0 |
| 559 | Cl | H | H | 2,4-Me₂ | 0 | 0 |

TABLE 1-continued

| Compound No. | R¹ | R² | X | R³ to R⁷ | m | n |
|---|---|---|---|---|---|---|
| 560 | Cl | H | H | 2-Et, 4-F | 0 | 0 |
| 561 | Cl | H | H | 2-Et, 4-Cl | 0 | 0 |
| 562 | Cl | H | H | 2-Et, 4-I | 0 | 0 |
| 563 | Cl | H | H | 2-Et, 4-Me | 0 | 0 |
| 564 | Cl | H | H | 2-iPr, 4-F | 0 | 0 |
| 565 | Cl | H | H | 2-iPr, 4-Cl | 0 | 0 |
| 566 | Cl | H | H | 2-iPr, 4-Br | 0 | 0 |
| 567 | Cl | H | H | 2-tBu, 4-Me | 0 | 0 |
| 568 | Cl | H | H | 2-cPr, 4-F | 0 | 0 |
| 569 | Cl | H | H | 2-cPr, 4-Cl | 0 | 0 |
| 570 | Cl | H | H | 2-cPr, 4-Br | 0 | 0 |
| 571 | Cl | H | H | 2-cPr, 4-Me | 0 | 0 |
| 572 | Cl | H | H | 2-cPr, 4-Et | 0 | 0 |
| 573 | Cl | H | H | 2-cPr, 4-CF$_3$ | 0 | 0 |
| 574 | Cl | H | H | 2-cPr, 4-CN | 0 | 0 |
| 575 | Cl | H | H | 2-cPr, 4-CO$_2$Me | 0 | 0 |
| 576 | Cl | H | H | 2-cPr, 4-NO$_2$ | 0 | 0 |
| 577 | Cl | H | H | 2-cPr, 4-OMe | 0 | 0 |
| 578 | Cl | H | H | 2-cBu, 4-F | 0 | 0 |
| 579 | Cl | H | H | 2-cBu, 4-Cl | 0 | 0 |
| 580 | Cl | H | H | 2-cBu, 4-Br | 0 | 0 |
| 581 | Cl | H | H | 2-cBu, 4-Me | 0 | 0 |
| 582 | Cl | H | H | 2-CF$_3$, 4-F | 0 | 0 |
| 583 | Cl | H | H | 2-CF$_3$, 4-Cl | 0 | 0 |
| 584 | Cl | H | H | 2-CF$_3$, 4-Br | 0 | 0 |
| 585 | Cl | H | H | 2-CF$_3$, 4-Me | 0 | 0 |
| 586 | Cl | H | H | 2-CN, 4-F | 0 | 0 |
| 587 | Cl | H | H | 2-CN, 4-Cl | 0 | 0 |
| 588 | Cl | H | H | 2-CN, 4-Br | 0 | 0 |
| 589 | Cl | H | H | 2-CN, 4-Me | 0 | 0 |
| 590 | Cl | H | H | 2-CO$_2$Me, 4-F | 0 | 0 |
| 591 | Cl | H | H | 2-CO$_2$Me, 4-Cl | 0 | 0 |
| 592 | Cl | H | H | 2-CO$_2$Me, 4-Br | 0 | 0 |
| 593 | Cl | H | H | 2-CO$_2$Me, 4-Me | 0 | 0 |
| 594 | Cl | H | H | 2-NO$_2$, 4-F | 0 | 0 |
| 595 | Cl | H | H | 2-NO$_2$, 4-Cl | 0 | 0 |
| 596 | Cl | H | H | 2-NO$_2$, 4-Br | 0 | 0 |
| 597 | Cl | H | H | 2-NO$_2$, 4-Me | 0 | 0 |
| 598 | Cl | H | H | 2-OMe, 4-F | 0 | 0 |
| 599 | Cl | H | H | 2-OMe, 4-Cl | 0 | 0 |
| 600 | Cl | H | H | 2-OMe, 4-Br | 0 | 0 |
| 601 | Cl | H | H | 2-OMe, 4-Me | 0 | 0 |
| 602 | Cl | H | H | 2,4-(OMe)$_2$ | 0 | 0 |
| 603 | Cl | H | H | 2,5-F$_2$ | 0 | 0 |
| 604 | Cl | H | H | 2-F, 5-Cl | 0 | 0 |
| 605 | Cl | H | H | 2-F, 5-Br | 0 | 0 |
| 606 | Cl | H | H | 2-F, 5-I | 0 | 0 |
| 607 | Cl | H | H | 2-F, 5-Me | 0 | 0 |
| 608 | Cl | H | H | 2-F, 5-CF$_3$ | 0 | 0 |
| 609 | Cl | H | H | 2-F, 5-OMe | 0 | 0 |
| 610 | Cl | H | H | 2-Cl, 5-F | 0 | 0 |
| 611 | Cl | H | H | 2,5-Cl$_2$ | 0 | 0 |
| 612 | Cl | H | H | 2-Cl, 5-Br | 0 | 0 |
| 613 | Cl | H | H | 2-Cl, 5-I | 0 | 0 |
| 614 | Cl | H | H | 2-Cl, 5-Me | 0 | 0 |
| 615 | Cl | H | H | 2-Cl, 5-CF$_3$ | 0 | 0 |
| 616 | Cl | H | H | 2-Cl, 5-OMe | 0 | 0 |
| 617 | Cl | H | H | 2-Me, 5-F | 0 | 0 |
| 618 | Cl | H | H | 2-Me, 5-Cl | 0 | 0 |
| 619 | Cl | H | H | 2-Me, 5-Br | 0 | 0 |
| 620 | Cl | H | H | 2-Me, 5-I | 0 | 0 |
| 621 | Cl | H | H | 2,5-Me$_2$ | 0 | 0 |
| 622 | Cl | H | H | 2-Me, 5-Et | 0 | 0 |
| 623 | Cl | H | H | 2-Me, 5-iPr | 0 | 0 |
| 624 | Cl | H | H | 2-Me, 5-CF$_3$ | 0 | 0 |
| 625 | Cl | H | H | 2-Me, 5-CN | 0 | 0 |

TABLE 1-continued

| Compound No. | R¹ | R² | X | R³ to R⁷ | m | n |
|---|---|---|---|---|---|---|
| 626 | Cl | H | H | 2-Me, 5-CO₂H | 0 | 0 |
| 627 | Cl | H | H | 2-Me, 5-NH₂ | 0 | 0 |
| 628 | Cl | H | H | 2-Me, 5-NMe₂ | 0 | 0 |
| 629 | Cl | H | H | 2-Me, 5-OMe | 0 | 0 |
| 630 | Cl | H | H | 2-Et, 5-F | 0 | 0 |
| 631 | Cl | H | H | 2-Et, 5-Cl | 0 | 0 |
| 632 | Cl | H | H | 2-Et, 5-Br | 0 | 0 |
| 633 | Cl | H | H | 2-Et, 5-Me | 0 | 0 |
| 634 | Cl | H | H | 2-Et, 5-CN | 0 | 0 |
| 635 | Cl | H | H | 2-Et, 5-OMe | 0 | 0 |
| 636 | Cl | H | H | 2-iPr, 5-F | 0 | 0 |
| 637 | Cl | H | H | 2-iPr, 5-Cl | 0 | 0 |
| 638 | Cl | H | H | 2-iPr, 5-Br | 0 | 0 |
| 639 | Cl | H | H | 2-iPr, 5-I | 0 | 0 |
| 640 | Cl | H | H | 2-iPr, 5-Me | 0 | 0 |
| 641 | Cl | H | H | 2-iPr, 5-Et | 0 | 0 |
| 642 | Cl | H | H | 2-iPr, 5-iPr | 0 | 0 |
| 643 | Cl | H | H | 2-iPr, 5-CF₃ | 0 | 0 |
| 644 | Cl | H | H | 2-iPr, 5-CN | 0 | 0 |
| 645 | Cl | H | H | 2-iPr, 5-OMe | 0 | 0 |
| 646 | Cl | H | H | 2-tBu, 5-F | 0 | 0 |
| 647 | Cl | H | H | 2-tBu, 5-Cl | 0 | 0 |
| 648 | Cl | H | H | 2-tBu, 5-Br | 0 | 0 |
| 649 | Cl | H | H | 2-tBu, 5-I | 0 | 0 |
| 650 | Cl | H | H | 2-tBu, 5-Me | 0 | 0 |
| 651 | Cl | H | H | 2-tBu, 5-Et | 0 | 0 |
| 652 | Cl | H | H | 2-tBu, 5-iPr | 0 | 0 |
| 653 | Cl | H | H | 2-tBu, 5-tBu | 0 | 0 |
| 654 | Cl | H | H | 2-tBu, 5-cPr | 0 | 0 |
| 655 | Cl | H | H | 2-tBu, 5-CF₃ | 0 | 0 |
| 656 | Cl | H | H | 2-tBu, 5-CN | 0 | 0 |
| 657 | Cl | H | H | 2-tBu, 5-OMe | 0 | 0 |
| 658 | Cl | H | H | 2-cPr, 5-F | 0 | 0 |
| 659 | Cl | H | H | 2-cPr, 5-Cl | 0 | 0 |
| 660 | Cl | H | H | 2-cPr, 5-Br | 0 | 0 |
| 661 | Cl | H | H | 2-cPr, 5-I | 0 | 0 |
| 662 | Cl | H | H | 2-cPr, 5-Me | 0 | 0 |
| 663 | Cl | H | H | 2-cPr, 5-Et | 0 | 0 |
| 664 | Cl | H | H | 2-cPr, 5-iPr | 0 | 0 |
| 665 | Cl | H | H | 2-cPr, 5-tBu | 0 | 0 |
| 666 | Cl | H | H | 2-cPr, 5-CF₃ | 0 | 0 |
| 667 | Cl | H | H | 2-cPr, 5-CN | 0 | 0 |
| 668 | Cl | H | H | 2-cPr, 5-OMe | 0 | 0 |
| 669 | Cl | H | H | 2-CF₃, 5-F | 0 | 0 |
| 670 | Cl | H | H | 2-CF₃, 5-Cl | 0 | 0 |
| 671 | Cl | H | H | 2-CF₃, 5-Br | 0 | 0 |
| 672 | Cl | H | H | 2-CF₃, 5-I | 0 | 0 |
| 673 | Cl | H | H | 2-CF₃, 5-Me | 0 | 0 |
| 674 | Cl | H | H | 2-CF₃, 5-CN | 0 | 0 |
| 675 | Cl | H | H | 2-CF₃, 5-OMe | 0 | 0 |
| 676 | Cl | H | H | 2-CH=CH₂, 5-F | 0 | 0 |
| 677 | Cl | H | H | 2-CH=CH₂, 5-Cl | 0 | 0 |
| 678 | Cl | H | H | 2-CHCH₂, 5-Me | 0 | 0 |
| 679 | Cl | H | H | 2-C=CHMe, 5-F | 0 | 0 |
| 680 | Cl | H | H | 2-CH=CHMe, 5-Cl | 0 | 0 |
| 681 | Cl | H | H | 2-CH=CHMe, 5-Me | 0 | 0 |
| 682 | Cl | H | H | 2-CMe=CH₂, 5-F | 0 | 0 |
| 683 | Cl | H | H | 2-CMe=CH₂, 5-Cl | 0 | 0 |
| 684 | Cl | H | H | 2-CMe=CH₂, 5-Me | 0 | 0 |
| 685 | Cl | H | H | 2-CN, 5-F | 0 | 0 |
| 686 | Cl | H | H | 2-CN, 5-Cl | 0 | 0 |
| 687 | Cl | H | H | 2-CN, 5-Br | 0 | 0 |
| 688 | Cl | H | H | 2-CN, 5-I | 0 | 0 |
| 689 | Cl | H | H | 2-CN, 5-Me | 0 | 0 |
| 690 | Cl | H | H | 2-CN, 5-CN | 0 | 0 |
| 691 | Cl | H | H | 2-CN, 5-OMe | 0 | 0 |

TABLE 1-continued

[Structure: pyridazine with R¹, R², OX, and phenoxy group bearing R³-R⁷, with N-oxide groups (O)ₘ and (O)ₙ]

| Compound No. | R¹ | R² | X | R³ to R⁷ | m | n |
|---|---|---|---|---|---|---|
| 692 | Cl | H | H | 2-CHO, 5-NMe₂ | 0 | 0 |
| 693 | Cl | H | H | 2-CO₂Me, 5-F | 0 | 0 |
| 694 | Cl | H | H | 2-CO₂Me, 5-Cl | 0 | 0 |
| 695 | Cl | H | H | 2-CO₂Me, 5-Br | 0 | 0 |
| 696 | Cl | H | H | 2-CO₂Me, 5-I | 0 | 0 |
| 697 | Cl | H | H | 2-CO₂Me, 5-Me | 0 | 0 |
| 698 | Cl | H | H | 2-CO₂Me, 5-CN | 0 | 0 |
| 699 | Cl | H | H | 2-CO₂Me, 5-OMe | 0 | 0 |
| 700 | Cl | H | H | 2-OMe, 5-F | 0 | 0 |
| 701 | Cl | H | H | 2-OMe, 5-Cl | 0 | 0 |
| 702 | Cl | H | H | 2-OMe, 5-Br | 0 | 0 |
| 703 | Cl | H | H | 2-OMe, 5-I | 0 | 0 |
| 704 | Cl | H | H | 2-OMe, 5-Me | 0 | 0 |
| 705 | Cl | H | H | 2-OMe, 5-Et | 0 | 0 |
| 706 | Cl | H | H | 2-OMe, 5-CF₃ | 0 | 0 |
| 707 | Cl | H | H | 2-OMe, 5-CN | 0 | 0 |
| 708 | Cl | H | H | 2-OMe, 5-NO₂ | 0 | 0 |
| 709 | Cl | H | H | 2-OMe, 5-OMe | 0 | 0 |
| 710 | Cl | H | H | 2,6-F₂ | 0 | 0 |
| 711 | Cl | H | H | 2-F, 6-Cl | 0 | 0 |
| 712 | Cl | H | H | 2-F, 6-Br | 0 | 0 |
| 713 | Cl | H | H | 2-F, 6-I | 0 | 0 |
| 714 | Cl | H | H | 2-F, 6-Me | 0 | 0 |
| 715 | Cl | H | H | 2-F, 6-Et | 0 | 0 |
| 716 | Cl | H | H | 2-F, 6-Pr | 0 | 0 |
| 717 | Cl | H | H | 2-F, 6-iPr | 0 | 0 |
| 718 | Cl | H | H | 2-F, 6-tBu | 0 | 0 |
| 719 | Cl | H | H | 2-F, 6-cPr | 0 | 0 |
| 720 | Cl | H | H | 2-F, 6-cBu | 0 | 0 |
| 721 | Cl | H | H | 2-F, 6-cPen | 0 | 0 |
| 722 | Cl | H | H | 2-F, 6-CF₃ | 0 | 0 |
| 723 | Cl | H | H | 2-F, 6-CH₂OMe | 0 | 0 |
| 724 | Cl | H | H | 2-F, 6-CH₂OEt | 0 | 0 |
| 725 | Cl | H | H | 2-F, 6-CH₂CH₂OMe | 0 | 0 |
| 726 | Cl | H | H | 2-F, 6-CH₂SMe | 0 | 0 |
| 727 | Cl | H | H | 2-F, 6-CH₂SEt | 0 | 0 |
| 728 | Cl | H | H | 2-F, 6-CHMeSEt | 0 | 0 |
| 729 | Cl | H | H | 2-F, 6-CN | 0 | 0 |
| 730 | Cl | H | H | 2-F, 6-CO₂Me | 0 | 0 |
| 731 | Cl | H | H | 2-F, 6-NO₂ | 0 | 0 |
| 732 | Cl | H | H | 2-F, 6-OMe | 0 | 0 |
| 733 | Cl | H | H | 2,6-Cl₂ | 0 | 0 |
| 734 | Cl | H | H | 2-Cl, 6-Br | 0 | 0 |
| 735 | Cl | H | H | 2-Cl, 6-I | 0 | 0 |
| 736 | Cl | H | H | 2-Cl, 6-Me | 0 | 0 |
| 737 | Cl | H | H | 2-Cl, 6-Et | 0 | 0 |
| 738 | Cl | H | H | 2-Cl, 6-iPr | 0 | 0 |
| 739 | Cl | H | H | 2-Cl, 6-tBu | 0 | 0 |
| 740 | Cl | H | H | 2-Cl, 6-cPr | 0 | 0 |
| 741 | Cl | H | H | 2-Cl, 6-cBu | 0 | 0 |
| 742 | Cl | H | H | 2-Cl, 6-cPen | 0 | 0 |
| 743 | Cl | H | H | 2-Cl, 6-CF₃ | 0 | 0 |
| 744 | Cl | H | H | 2-Cl, 6-CH=CH₂ | 0 | 0 |
| 745 | Cl | H | H | 2-Cl, 6-CH₂CH=CH₂ | 0 | 0 |
| 746 | Cl | H | H | 2-Cl, 6-CH₂CMe=CH₂ | 0 | 0 |
| 747 | Cl | H | H | 2-Cl, 6-CH₂OMe | 0 | 0 |
| 748 | Cl | H | H | 2-Cl, 6-CH₂OEt | 0 | 0 |
| 749 | Cl | H | H | 2-Cl, 6-CH₂CH₂OMe | 0 | 0 |
| 750 | Cl | H | H | 2-Cl, 6-CH₂SMe | 0 | 0 |
| 751 | Cl | H | H | 2-Cl, 6-CH₂SEt | 0 | 0 |
| 752 | Cl | H | H | 2-Cl, 6-CN | 0 | 0 |
| 753 | Cl | H | H | 2-Cl, 6-CO₂Me | 0 | 0 |
| 754 | Cl | H | H | 2-Cl, 6-NO₂ | 0 | 0 |
| 755 | Cl | H | H | 2-Cl, 6-OMe | 0 | 0 |
| 756 | Cl | H | H | 2,6-Br₂ | 0 | 0 |
| 757 | Cl | H | H | 2-Br, 6-I | 0 | 0 |

TABLE 1-continued

| Compound No. | R¹ | R² | X | R³ to R⁷ | m | n |
|---|---|---|---|---|---|---|
| 758 | Cl | H | H | 2-Br, 6-Me | 0 | 0 |
| 759 | Cl | H | H | 2-Br, 6-Et | 0 | 0 |
| 760 | Cl | H | H | 2-Br, 6-iPr | 0 | 0 |
| 761 | Cl | H | H | 2-Br, 6-tBu | 0 | 0 |
| 762 | Cl | H | H | 2-Br, 6-cPr | 0 | 0 |
| 763 | Cl | H | H | 2-Br, 6-cBu | 0 | 0 |
| 764 | Cl | H | H | 2-Br, 6-cPen | 0 | 0 |
| 765 | Cl | H | H | 2-Br, 6-cHx | 0 | 0 |
| 766 | Cl | H | H | 2-Br, 6-CF$_3$ | 0 | 0 |
| 767 | Cl | H | H | 2-Br, 6-CH=CH$_2$ | 0 | 0 |
| 768 | Cl | H | H | 2-Br, 6-CH$_2$CH=CH$_2$ | 0 | 0 |
| 769 | Cl | H | H | 2-Br, 6-CH$_2$CMe=CH$_2$ | 0 | 0 |
| 770 | Cl | H | H | 2-Br, 6-CH$_2$OMe | 0 | 0 |
| 771 | Cl | H | H | 2-Br, 6-CH$_2$OEt | 0 | 0 |
| 772 | Cl | H | H | 2-Br, 6-CH$_2$CH$_2$OMe | 0 | 0 |
| 773 | Cl | H | H | 2-Br, 6-CH$_2$SMe | 0 | 0 |
| 774 | Cl | H | H | 2-Br, 6-CH$_2$SEt | 0 | 0 |
| 775 | Cl | H | H | 2-Br, 6-CN | 0 | 0 |
| 776 | Cl | H | H | 2-Br, 6-CO$_2$Me | 0 | 0 |
| 777 | Cl | H | H | 2-Br, 6-NO$_2$ | 0 | 0 |
| 778 | Cl | H | H | 2-Br, 6-OMe | 0 | 0 |
| 779 | Cl | H | H | 2,6-I$_2$ | 0 | 0 |
| 780 | Cl | H | H | 2-I, 6-Me | 0 | 0 |
| 781 | Cl | H | H | 2-I, 6-Et | 0 | 0 |
| 782 | Cl | H | H | 2-I, 6-iPr | 0 | 0 |
| 783 | Cl | H | H | 2-I, 6-tBu | 0 | 0 |
| 784 | Cl | H | H | 2-I, 6-cPr | 0 | 0 |
| 785 | Cl | H | H | 2-I, 6-cBu | 0 | 0 |
| 786 | Cl | H | H | 2-I, 6-cPen | 0 | 0 |
| 787 | Cl | H | H | 2-I, 6-cHx | 0 | 0 |
| 788 | Cl | H | H | 2-I, 6-CF$_3$ | 0 | 0 |
| 789 | Cl | H | H | 2-I, 6-CH=CH$_2$ | 0 | 0 |
| 790 | Cl | H | H | 2-I, 6-CH$_2$CH=CH$_2$ | 0 | 0 |
| 791 | Cl | H | H | 2-I, 6-CH$_2$CMe=CH$_2$ | 0 | 0 |
| 792 | Cl | H | H | 2-I, 6-CH$_2$OMe | 0 | 0 |
| 793 | Cl | H | H | 2-I, 6-CH$_2$OEt | 0 | 0 |
| 794 | Cl | H | H | 2-I, 6-CH$_2$CH$_2$OMe | 0 | 0 |
| 795 | Cl | H | H | 2-I, 6-CH$_2$SMe | 0 | 0 |
| 796 | Cl | H | H | 2-I, 6-CH$_2$SEt | 0 | 0 |
| 797 | Cl | H | H | 2-I, 6-CN | 0 | 0 |
| 798 | Cl | H | H | 2-I, 6-CO$_2$Me | 0 | 0 |
| 799 | Cl | H | H | 2-I, 6-NO$_2$ | 0 | 0 |
| 800 | Cl | H | H | 2-I, 6-OMe | 0 | 0 |
| 801 | Cl | H | H | 2,6-Me$_2$ | 0 | 0 |
| 802 | Cl | H | H | 2-Me, 6-Et | 0 | 0 |
| 803 | Cl | H | H | 2-Me, 6-iPr | 0 | 0 |
| 804 | Cl | H | H | 2-Me, 6-sBu | 0 | 0 |
| 805 | Cl | H | H | 2-Me, 6-tBu | 0 | 0 |
| 806 | Cl | H | H | 2-Me, 6-cPr | 0 | 0 |
| 807 | Cl | H | H | 2-Me, 6-(cPr-1-F) | 0 | 0 |
| 808 | Cl | H | H | 2-Me, 6-(cPr-1-Cl) | 0 | 0 |
| 809 | Cl | H | H | 2-Me, 6-(cPr-1-Br) | 0 | 0 |
| 810 | Cl | H | H | 2-Me, 6-(cPr-1-I) | 0 | 0 |
| 811 | Cl | H | H | 2-Me, 6-(cPr-1-Me) | 0 | 0 |
| 812 | Cl | H | H | 2-Me, 6-(cPr-1-Et) | 0 | 0 |
| 813 | Cl | H | H | 2-Me, 6-(cPr-1-cPr) | 0 | 0 |
| 814 | Cl | H | H | 2-Me, 6-(cPr-1-CN) | 0 | 0 |
| 815 | Cl | H | H | 2-Me, 6-(cPr-1-OMe) | 0 | 0 |
| 816 | Cl | H | H | 2-Me, 6-(cPr-1-OEt) | 0 | 0 |
| 817 | Cl | H | H | 2-Me, 6-(cPr-2-Me) | 0 | 0 |
| 818 | Cl | H | H | 2-Me, 6-(cPr-2-Et) | 0 | 0 |
| 819 | Cl | H | H | 2-Me, 6-(cPr-2-CN) | 0 | 0 |
| 820 | Cl | H | H | 2-Me, 6-(cPr-2-OMe) | 0 | 0 |
| 821 | Cl | H | H | 2-Me, 6-(cPr-2-OEt) | 0 | 0 |
| 822 | Cl | H | H | 2-Me, 6-(cPr-2-OCF$_3$) | 0 | 0 |
| 823 | Cl | H | H | 2-Me, 6-(cPr-1,2-Me$_2$) | 0 | 0 |

TABLE 1-continued

| Compound No. | R¹ | R² | X | R³ to R⁷ | m | n |
|---|---|---|---|---|---|---|
| 824 | Cl | H | H | 2-Me, 6-{cPr-1,2-(CN)$_2$} | 0 | 0 |
| 825 | Cl | H | H | -Me, 6-(cPr-2,2-Me$_2$) | 0 | 0 |
| 826 | Cl | H | H | 2-Me, 6-(cPr-2,2-F$_2$) | 0 | 0 |
| 827 | Cl | H | H | 2-Me, 6-(cPr-2,2-Cl$_2$) | 0 | 0 |
| 828 | Cl | H | H | 2-Me, 6-(cPr-2,2-Br$_2$) | 0 | 0 |
| 829 | Cl | H | H | 2-Me, 6-{cPr-2,2-(CN)$_2$} | 0 | 0 |
| 830 | Cl | H | H | 2-Me, 6-cBu | 0 | 0 |
| 831 | Cl | H | H | 2-Me, 6-cPen | 0 | 0 |
| 832 | Cl | H | H | 2-Me, 6-cHx | 0 | 0 |
| 833 | Cl | H | H | 2-Me, 6-CF$_3$ | 0 | 0 |
| 834 | Cl | H | H | 2-Me, 6-CH=CH$_2$ | 0 | 0 |
| 835 | Cl | H | H | 2-Me, 6-CH$_2$CH=CH$_2$ | 0 | 0 |
| 836 | Cl | H | H | 2-Me, 6-CH=CH—NO$_2$ | 0 | 0 |
| 837 | Cl | H | H | 2-Me, 6-CH$_2$OMe | 0 | 0 |
| 838 | Cl | H | H | 2-Me, 6-CH$_2$OEt | 0 | 0 |
| 839 | Cl | H | H | 2-Me, 6-CH$_2$CH$_2$OMe | 0 | 0 |
| 840 | Cl | H | H | 2-Me, 6-CH$_2$SMe | 0 | 0 |
| 841 | Cl | H | H | 2-Me, 6-CH$_2$SEt | 0 | 0 |
| 842 | Cl | H | H | 2-Me, 6-CN | 0 | 0 |
| 843 | Cl | H | H | 2-Me, 6-CO$_2$Me | 0 | 0 |
| 844 | Cl | H | H | 2-Me, 6-NO$_2$ | 0 | 0 |
| 845 | Cl | H | H | 2-Me, 6-OMe | 0 | 0 |
| 846 | Cl | H | H | 2,6-Et2 | 0 | 0 |
| 847 | Cl | H | H | 2-Et, 6-iPr | 0 | 0 |
| 848 | Cl | H | H | 2-Et, 6-sBu | 0 | 0 |
| 849 | Cl | H | H | 2-Et, 6-tBu | 0 | 0 |
| 850 | Cl | H | H | 2-Et, 6-cPr | 0 | 0 |
| 851 | Cl | H | H | 2-Et, 6-(cPr-1-F) | 0 | 0 |
| 852 | Cl | H | H | 2-Et, 6-(cPr-1-Cl) | 0 | 0 |
| 853 | Cl | H | H | 2-Et, 6-(cPr-1-Br) | 0 | 0 |
| 854 | Cl | H | H | 2-Et, 6-(cPr-1-I) | 0 | 0 |
| 855 | Cl | H | H | 2-Et, 6-(cPr-1-Me) | 0 | 0 |
| 856 | Cl | H | H | 2-Et, 6-(cPr-1-Et) | 0 | 0 |
| 857 | Cl | H | H | 2-Et, 6-(cPr-1-cPr) | 0 | 0 |
| 858 | Cl | H | H | 2-Et, 6-(cPr-1-CN) | 0 | 0 |
| 859 | Cl | H | H | 2-Et, 6-(cPr-1-OMe) | 0 | 0 |
| 860 | Cl | H | H | 2-Et, 6-(cPr-1-OEt) | 0 | 0 |
| 861 | Cl | H | H | 2-Et, 6-(cPr-2-Me) | 0 | 0 |
| 862 | Cl | H | H | 2-Et, 6-(cPr-2-Et) | 0 | 0 |
| 863 | Cl | H | H | 2-Et, 6-(cPr-2-CN) | 0 | 0 |
| 864 | Cl | H | H | 2-Et, 6-(cPr-2-OMe) | 0 | 0 |
| 865 | Cl | H | H | 2-Et, 6-(cPr-2-OEt) | 0 | 0 |
| 866 | Cl | H | H | 2-Et, 6-(cPr-2-OCF$_3$) | 0 | 0 |
| 867 | Cl | H | H | 2-Et, 6-(cPr-1,2-Me$_2$) | 0 | 0 |
| 868 | Cl | H | H | 2-Et, 6-{cPr-1,2-(CN)$_2$} | 0 | 0 |
| 869 | Cl | H | H | 2-Et, 6-(cPr-2,2-Me$_2$) | 0 | 0 |
| 870 | Cl | H | H | 2-Et, 6-(cPr-2,2-F$_2$) | 0 | 0 |
| 871 | Cl | H | H | 2-Et, 6-(cPr-2,2-Cl$_2$) | 0 | 0 |
| 872 | Cl | H | H | 2-Et, 6-(cPr-2,2-Br$_2$) | 0 | 0 |
| 873 | Cl | H | H | 2-Et, 6-{cPr-2,2-(CN)$_2$} | 0 | 0 |
| 874 | Cl | H | H | 2-Et, 6-cBu | 0 | 0 |
| 875 | Cl | H | H | 2-Et, 6-cPen | 0 | 0 |
| 876 | Cl | H | H | 2-Et, 6-cHx | 0 | 0 |
| 877 | Cl | H | H | 2-Et, 6-CF$_3$ | 0 | 0 |
| 878 | Cl | H | H | 2-Et, 6-CH=CH$_2$ | 0 | 0 |
| 879 | Cl | H | H | 2-Et, 6-CH$_2$CH=CH$_2$ | 0 | 0 |
| 880 | Cl | H | H | 2-Et, 6-CH$_2$CMe=CH$_2$ | 0 | 0 |
| 881 | Cl | H | H | 2-Et, 6-CH$_2$OMe | 0 | 0 |
| 882 | Cl | H | H | 2-Et, 6-CH$_2$OEt | 0 | 0 |
| 883 | Cl | H | H | 2-Et, 6-CH$_2$CH$_2$OMe | 0 | 0 |
| 884 | Cl | H | H | 2-Et, 6-CH$_2$SMe | 0 | 0 |
| 885 | Cl | H | H | 2-Et, 6-CH$_2$SEt | 0 | 0 |
| 886 | Cl | H | H | 2-Et, 6-CN | 0 | 0 |
| 887 | Cl | H | H | 2-Et, 6-CO$_2$Me | 0 | 0 |
| 888 | Cl | H | H | 2-Et, 6-NO$_2$ | 0 | 0 |
| 889 | Cl | H | H | 2-Et, 6-OMe | 0 | 0 |

TABLE 1-continued

[Structure: pyridazine with R¹, R², OX, R³, R⁴, R⁵, R⁶, R⁷ substituents, N-N with (O)ₘ and (O)ₙ, linked via O to a phenyl ring]

| Compound No. | R¹ | R² | X | R³ to R⁷ | m | n |
|---|---|---|---|---|---|---|
| 890 | Cl | H | H | 2,6-Pr₂ | 0 | 0 |
| 891 | Cl | H | H | 2-Pr, 6-iPr | 0 | 0 |
| 892 | Cl | H | H | 2-Pr, 6-tBu | 0 | 0 |
| 893 | Cl | H | H | 2-Pr, 6-cPr | 0 | 0 |
| 894 | Cl | H | H | 2,6-iPr₂ | 0 | 0 |
| 895 | Cl | H | H | 2-iPr, 6-tBu | 0 | 0 |
| 896 | Cl | H | H | 2-iPr, 6-cPr | 0 | 0 |
| 897 | Cl | H | H | 2-iPr, 6-cBu | 0 | 0 |
| 898 | Cl | H | H | 2-iPr, 6-cPen | 0 | 0 |
| 899 | Cl | H | H | 2-iPr, 6-cHx | 0 | 0 |
| 900 | Cl | H | H | 2-iPr, 6-CF₃ | 0 | 0 |
| 901 | Cl | H | H | 2-iPr, 6-CH=CH₂ | 0 | 0 |
| 902 | Cl | H | H | 2-iPr, 6-CH₂CH=CH₂ | 0 | 0 |
| 903 | Cl | H | H | 2-iPr, 6-CH₂CMe=CH₂ | 0 | 0 |
| 904 | Cl | H | H | 2-iPr, 6-CH₂OMe | 0 | 0 |
| 905 | Cl | H | H | 2-iPr, 6-CH₂OEt | 0 | 0 |
| 906 | Cl | H | H | 2-iPr, 6-CH₂CH₂OMe | 0 | 0 |
| 907 | Cl | H | H | 2-iPr, 6-CH₂SMe | 0 | 0 |
| 908 | Cl | H | H | 2-iPr, 6-CH₂SEt | 0 | 0 |
| 909 | Cl | H | H | 2-iPr, 6-CN | 0 | 0 |
| 910 | Cl | H | H | 2-iPr, 6-CO₂Me | 0 | 0 |
| 911 | Cl | H | H | 2-iPr, 6-NO₂ | 0 | 0 |
| 912 | Cl | H | H | 2-iPr, 6-OMe | 0 | 0 |
| 913 | Cl | H | H | 2,6-tBu₂ | 0 | 0 |
| 914 | Cl | H | H | 2-tBu, 6-cPr | 0 | 0 |
| 915 | Cl | H | H | 2-tBu, 6-cBu | 0 | 0 |
| 916 | Cl | H | H | 2-tBu, 6-cPen | 0 | 0 |
| 917 | Cl | H | H | 2-tBu, 6-cHx | 0 | 0 |
| 918 | Cl | H | H | 2-tBu, 6-CF₃ | 0 | 0 |
| 919 | Cl | H | H | 2-tBu, 6-CH=CH₂ | 0 | 0 |
| 920 | Cl | H | H | 2-tBu, 6-CH₂CH=CH₂ | 0 | 0 |
| 921 | Cl | H | H | 2-tBu, 6-CH₂CMe=CH₂ | 0 | 0 |
| 922 | Cl | H | H | 2-tBu, 6-CH₂OMe | 0 | 0 |
| 923 | Cl | H | H | 2-tBu, 6-CH₂OEt | 0 | 0 |
| 924 | Cl | H | H | 2-tBu, 6-CH₂CH₂OMe | 0 | 0 |
| 925 | Cl | H | H | 2-tBu, 6-CH₂SMe | 0 | 0 |
| 926 | Cl | H | H | 2-tBu, 6-CH₂SEt | 0 | 0 |
| 927 | Cl | H | H | 2-tBu, 6-CN | 0 | 0 |
| 928 | Cl | H | H | 2-tBu, 6-CO₂Me | 0 | 0 |
| 929 | Cl | H | H | 2-tBu, 6-NO₂ | 0 | 0 |
| 930 | Cl | H | H | 2-tBu, 6-OMe | 0 | 0 |
| 931 | Cl | H | H | 2,6-cPr₂ | 0 | 0 |
| 932 | Cl | H | H | 2-cPr, 6-(cPr-1-cPr) | 0 | 0 |
| 933 | Cl | H | H | 2-cPr, 6-(cPr-1-CN) | 0 | 0 |
| 934 | Cl | H | H | 2-cPr, 6-(cPr-1-OMe) | 0 | 0 |
| 935 | Cl | H | H | 2-cPr, 6-(cPr-1-OEt) | 0 | 0 |
| 936 | Cl | H | H | 2-cPr, 6-(cPr-2-Me) | 0 | 0 |
| 937 | Cl | H | H | 2-cPr, 6-(cPr-2-Et) | 0 | 0 |
| 938 | Cl | H | H | 2-cPr, 6-(cPr-2-CN) | 0 | 0 |
| 939 | Cl | H | H | 2-cPr, 6-(cPr-2-OMe) | 0 | 0 |
| 940 | Cl | H | H | 2-cPr, 6-(cPr-2-OEt) | 0 | 0 |
| 941 | Cl | H | H | 2-cPr, 6-(cPr-2-OCF₃) | 0 | 0 |
| 942 | Cl | H | H | 2-cPr, 6-(cPr-1,2-Me₂) | 0 | 0 |
| 943 | Cl | H | H | 2-cPr, 6-{cPr-1,2-(CN)₂} | 0 | 0 |
| 944 | Cl | H | H | 2-cPr, 6-(cPr-2,2-Me₂) | 0 | 0 |
| 945 | Cl | H | H | 2-cPr, 6-(cPr-2,2-F₂) | 0 | 0 |
| 946 | Cl | H | H | 2-cPr, 6-(cPr-2,2-Cl₂) | 0 | 0 |
| 947 | Cl | H | H | 2-cPr, 6-(cPr-2,2-Br₂) | 0 | 0 |
| 948 | Cl | H | H | 2-cPr, 6-{cPr-2,2-(CN)₂} | 0 | 0 |
| 949 | Cl | H | H | 2-cPr, 6-cBu | 0 | 0 |
| 950 | Cl | H | H | 2-cPr, 6-cPen | 0 | 0 |
| 951 | Cl | H | H | 2-cPr, 6-cHx | 0 | 0 |
| 952 | Cl | H | H | 2-cPr, 6-CF₃ | 0 | 0 |
| 953 | Cl | H | H | 2-cPr, 6-CH=CH₂ | 0 | 0 |
| 954 | Cl | H | H | 2-cPr, 6-CH₂CH=CH₂ | 0 | 0 |
| 955 | Cl | H | H | 2-cPr, 6-CH₂CMe=CH₂ | 0 | 0 |

TABLE 1-continued

| Compound No. | R¹ | R² | X | R³ to R⁷ | m | n |
|---|---|---|---|---|---|---|
| 956 | Cl | H | H | 2-cPr, 6-CH$_2$OMe | 0 | 0 |
| 957 | Cl | H | H | 2-cPr, 6-CH$_2$OEt | 0 | 0 |
| 958 | Cl | H | H | 2-cPr, 6-CH$_2$CH$_2$OMe | 0 | 0 |
| 959 | Cl | H | H | 2-cPr, 6-CH$_2$SMe | 0 | 0 |
| 960 | Cl | H | H | 2-cPr, 6-CH$_2$SEt | 0 | 0 |
| 961 | Cl | H | H | 2-cPr, 6-CN | 0 | 0 |
| 962 | Cl | H | H | 2-cPr, 6-CO$_2$Me | 0 | 0 |
| 963 | Cl | H | H | 2-cPr, 6-NO$_2$ | 0 | 0 |
| 964 | Cl | H | H | 2-cPr, 6-OMe | 0 | 0 |
| 965 | Cl | H | H | 2-cPr, 6-OEt | 0 | 0 |
| 966 | Cl | H | H | 2-cPr, 6-SMe | 0 | 0 |
| 967 | Cl | H | H | 2-CF$_3$, 6-CH=CH$_2$ | 0 | 0 |
| 968 | Cl | H | H | 2-CF$_3$, 6-CH$_2$CH=CH$_2$ | 0 | 0 |
| 969 | Cl | H | H | 2-CF$_3$, 6-CH$_2$CMe=CH$_2$ | 0 | 0 |
| 970 | Cl | H | H | 2-CF$_3$, 6-CH$_2$OMe | 0 | 0 |
| 971 | Cl | H | H | 2-CF$_3$, 6-CH$_2$OEt | 0 | 0 |
| 972 | Cl | H | H | 2-CF$_3$, 6-CH$_2$CH$_2$OMe | 0 | 0 |
| 973 | Cl | H | H | 2-CF$_3$, 6-CH$_2$SMe | 0 | 0 |
| 974 | Cl | H | H | 2-CF$_3$, 6-CH$_2$SEt | 0 | 0 |
| 975 | Cl | H | H | 2-CF$_3$, 6-CN | 0 | 0 |
| 976 | Cl | H | H | 2-CF$_3$, 6-CO$_2$Me | 0 | 0 |
| 977 | Cl | H | H | 2-CF$_3$, 6-NO$_2$ | 0 | 0 |
| 978 | Cl | H | H | 2-CF$_3$, 6-OMe | 0 | 0 |
| 979 | Cl | H | H | 2,6-(CH=CHMe)$_2$ | 0 | 0 |
| 980 | Cl | H | H | 2-CH=CHMe, 6-CN | 0 | 0 |
| 981 | Cl | H | H | 2-CH=CHMe, 6-OMe | 0 | 0 |
| 982 | Cl | H | H | 2,6-(CH$_2$CH=CH$_2$)$_2$ | 0 | 0 |
| 983 | Cl | H | H | 2-CH$_2$CH=CH$_2$, 6-CN | 0 | 0 |
| 984 | Cl | H | H | 2-CH$_2$CH=CH$_2$, 6-OMe | 0 | 0 |
| 985 | Cl | H | H | 2,6-(CN)$_2$ | 0 | 0 |
| 986 | Cl | H | H | 2-CN, 6-OMe | 0 | 0 |
| 987 | Cl | H | H | 2,6-(OMe)$_2$ | 0 | 0 |
| 988 | Cl | H | H | 3,5-F$_2$ | 0 | 0 |
| 989 | Cl | H | H | 3-F, 5-Cl | 0 | 0 |
| 990 | Cl | H | H | 3-F, 5-Br | 0 | 0 |
| 991 | Cl | H | H | 3-F, 5-I | 0 | 0 |
| 992 | Cl | H | H | 3,5-Cl$_2$ | 0 | 0 |
| 993 | Cl | H | H | 3-Cl, 5-Br | 0 | 0 |
| 994 | Cl | H | H | 3-Cl, 5-I | 0 | 0 |
| 995 | Cl | H | H | 3,5-Br$_2$ | 0 | 0 |
| 996 | Cl | H | H | 3-Br, 5-I | 0 | 0 |
| 997 | Cl | H | H | 3,5-I$_2$ | 0 | 0 |
| 998 | Cl | H | H | 3,5-Me$_2$ | 0 | 0 |
| 999 | Cl | H | H | 3-Me, 5-Et | 0 | 0 |
| 1000 | Cl | H | H | 3-Me, 5-iPr | 0 | 0 |
| 1001 | Cl | H | H | 3-Me, 5-cPr | 0 | 0 |
| 1002 | Cl | H | H | 3-Me, 5-cBu | 0 | 0 |
| 1003 | Cl | H | H | 3-Me, 5-CF$_3$ | 0 | 0 |
| 1004 | Cl | H | H | 3-Me, 5-CN | 0 | 0 |
| 1005 | Cl | H | H | 3-Me, 5-NO$_2$ | 0 | 0 |
| 1006 | Cl | H | H | 3-Me, 5-OMe | 0 | 0 |
| 1007 | Cl | H | H | 3,5-iPr$_2$ | 0 | 0 |
| 1008 | Cl | H | H | 3-iPr, 5-CF$_3$ | 0 | 0 |
| 1009 | Cl | H | H | 3,5-(CF$_3$)$_2$ | 0 | 0 |
| 1010 | Cl | H | H | 2-F, 3,5-Me$_2$ | 0 | 0 |
| 1011 | Cl | H | H | 2-Cl, 3,5-Me$_2$ | 0 | 0 |
| 1012 | Cl | H | H | 2,3,5-Cl$_3$ | 0 | 0 |
| 1013 | Cl | H | H | 2-Br, 3,5-Me$_2$ | 0 | 0 |
| 1014 | Cl | H | H | 2-Br, 3,5-Cl$_2$ | 0 | 0 |
| 1015 | Cl | H | H | 2-I, 3,5-Me$_2$ | 0 | 0 |
| 1016 | Cl | H | H | 2,3,5-Me$_3$ | 0 | 0 |
| 1017 | Cl | H | H | 2-Me, 3,5-Cl$_2$ | 0 | 0 |
| 1018 | Cl | H | H | 2-Et, 3,5-Me$_2$ | 0 | 0 |
| 1019 | Cl | H | H | 2-Et, 3,5-Cl$_2$ | 0 | 0 |
| 1020 | Cl | H | H | 2-Pr, 3,5-Me$_2$ | 0 | 0 |
| 1021 | Cl | H | H | 2-iPr, 3,5-Me$_2$ | 0 | 0 |

TABLE 1-continued

Structure: pyridazine with $R^1$, $R^2$, OX substituents and phenoxy group with $R^3$–$R^7$; N-oxides $(O)_m$ and $(O)_n$.

| Compound No. | $R^1$ | $R^2$ | X | $R^3$ to $R^7$ | m | n |
|---|---|---|---|---|---|---|
| 1022 | Cl | H | H | 2-iPr, 3,5-Cl$_2$ | 0 | 0 |
| 1023 | Cl | H | H | 2-cPr, 3,5-Me$_2$ | 0 | 0 |
| 1024 | Cl | H | H | 2-cBu, 3,5-Me$_2$ | 0 | 0 |
| 1025 | Cl | H | H | 2-CN, 3,5-Me$_2$ | 0 | 0 |
| 1026 | Cl | H | H | 2-OMe, 3,5-Me$_2$ | 0 | 0 |
| 1027 | Cl | H | H | 2-SMe, 3,5-Me$_2$ | 0 | 0 |
| 1028 | Cl | H | H | 2-F, 3,6-Me$_2$ | 0 | 0 |
| 1029 | Cl | H | H | 2-F, 3-Me, 6-cPr | 0 | 0 |
| 1030 | Cl | H | H | 2-F, 3-Me, 6-OMe | 0 | 0 |
| 1031 | Cl | H | H | 2-Cl, 3,6-Me$_2$ | 0 | 0 |
| 1032 | Cl | H | H | 2-Cl, 3-Me, 6-cPr | 0 | 0 |
| 1033 | Cl | H | H | 2-Cl, 3-Me, 6-OMe | 0 | 0 |
| 1034 | Cl | H | H | 2,3,6-Cl$_3$ | 0 | 0 |
| 1035 | Cl | H | H | 2,3-Cl$_2$, 6-cPr | 0 | 0 |
| 1036 | Cl | H | H | 2-Br, 3,6-Cl$_2$ | 0 | 0 |
| 1037 | Cl | H | H | 2,6-Br$_2$, 3-Cl | 0 | 0 |
| 1038 | Cl | H | H | 2-Br, 3-Cl, 6-cPr | 0 | 0 |
| 1039 | Cl | H | H | 2,6-Br$_2$, 3-Me | 0 | 0 |
| 1040 | Cl | H | H | 2-Br, 3,6-Me$_2$ | 0 | 0 |
| 1041 | Cl | H | H | 2-Br, 3-Me, 6-cPr | 0 | 0 |
| 1042 | Cl | H | H | 2-Br, 3-Me, 6-OMe | 0 | 0 |
| 1043 | Cl | H | H | 2,2,3-CN | 0 | 0 |
| 1044 | Cl | H | H | 2-Br, 3-CN, 6-cPr | 0 | 0 |
| 1045 | Cl | H | H | 2,6-Br$_2$, 3-OMe | 0 | 0 |
| 1046 | Cl | H | H | 2-Br, 3-OMe, 6-cPr | 0 | 0 |
| 1047 | Cl | H | H | 2-I, 3,6-Me$_2$ | 0 | 0 |
| 1048 | Cl | H | H | 2-Me, 3,6-F$_2$ | 0 | 0 |
| 1049 | Cl | H | H | 2-Me, 3-F, 6-Cl | 0 | 0 |
| 1050 | Cl | H | H | 2-Me, 3-F, 6-Br | 0 | 0 |
| 1051 | Cl | H | H | 2-Me, 3-F, 6-I | 0 | 0 |
| 1052 | Cl | H | H | 2-Me, 3-F, 6-cPr | 0 | 0 |
| 1053 | Cl | H | H | 2-Me, 3-Cl, 6-Br | 0 | 0 |
| 1054 | Cl | H | H | 2-Me, 3-Cl, 6-I | 0 | 0 |
| 1055 | Cl | H | H | 2-Me, 3-Cl, 6-cPr | 0 | 0 |
| 1056 | Cl | H | H | 2,3-Me$_2$, 6-F | 0 | 0 |
| 1057 | Cl | H | H | 2,3-Me$_2$, 6-Cl | 0 | 0 |
| 1058 | Cl | H | H | 2,3-Me$_2$, 6-Br | 0 | 0 |
| 1059 | Cl | H | H | 2,3-Me$_2$, 6-I | 0 | 0 |
| 1060 | Cl | H | H | 2,3,6-Me$_3$ | 0 | 0 |
| 1061 | Cl | H | H | 2,3-Me$_2$, 6-cPr | 0 | 0 |
| 1062 | Cl | H | H | 2,3-Me$_2$, 6-CN | 0 | 0 |
| 1063 | Cl | H | H | 2,3-Me$_2$, 6-CH=NOMe | 0 | 0 |
| 1064 | Cl | H | H | 2,3-Me$_2$, 6-OMe | 0 | 0 |
| 1065 | Cl | H | H | 2-Me, 3-OMe, 6-Cl | 0 | 0 |
| 1066 | Cl | H | H | 2-Me, 3-OMe, 6-Br | 0 | 0 |
| 1067 | Cl | H | H | 2-Me, 3-OMe, 6-I | 0 | 0 |
| 1068 | Cl | H | H | 2,6-Me$_2$, 3-OMe | 0 | 0 |
| 1069 | Cl | H | H | 2-Me, 3-OMe, 6-cPr | 0 | 0 |
| 1070 | Cl | H | H | 2-cPr, 3-Me, 6-F | 0 | 0 |
| 1071 | Cl | H | H | 2-cPr, 3-Me, 6-Cl | 0 | 0 |
| 1072 | Cl | H | H | 2-cPr, 3-Me, 6-Br | 0 | 0 |
| 1073 | Cl | H | H | 2-cPr, 3,6-Me$_2$ | 0 | 0 |
| 1074 | Cl | H | H | 2-cPr, 3-Me, 6-Et | 0 | 0 |
| 1075 | Cl | H | H | 2,6-cPr$_2$, 3-Me | 0 | 0 |
| 1076 | Cl | H | H | 2-cPr, 3-Me, 6-CN | 0 | 0 |
| 1077 | Cl | H | H | 2-cPr, 3-Me, 6-OMe | 0 | 0 |
| 1078 | Cl | H | H | 2-cBu, 3,6-Me$_2$ | 0 | 0 |
| 1079 | Cl | H | H | 2-CH$_2$CH=CH$_2$, 3,6-Me$_2$ | 0 | 0 |
| 1080 | Cl | H | H | 2-CH$_2$CH=CH$_2$, 3-OMe, 6-Et | 0 | 0 |
| 1081 | Cl | H | H | 2-CN, 3,6-Me$_2$ | 0 | 0 |
| 1082 | Cl | H | H | 2-OMe, 3,6-Me$_2$ | 0 | 0 |
| 1083 | Cl | H | H | 2-CH$_2$SMe, 3,6-Me$_2$ | 0 | 0 |
| 1084 | Cl | H | H | 6-F, 2-CH$_2$CH$_2$CH$_2$-3 | 0 | 0 |
| 1085 | Cl | H | H | 6-Cl, 2-CH$_2$CH$_2$CH$_2$-3 | 0 | 0 |
| 1086 | Cl | H | H | 6-Br, 2-CH$_2$CH$_2$CH$_2$-3 | 0 | 0 |
| 1087 | Cl | H | H | 6-I, 2-CH$_2$CH$_2$CH$_2$-3 | 0 | 0 |

TABLE 1-continued

| Compound No. | R$^1$ | R$^2$ | X | R$^3$ to R$^7$ | m | n |
|---|---|---|---|---|---|---|
| 1088 | Cl | H | H | 6-Me, 2-CH$_2$CH$_2$CH$_2$-3 | 0 | 0 |
| 1089 | Cl | H | H | 6-Et, 2-CH$_2$CH$_2$CH$_2$-3 | 0 | 0 |
| 1090 | Cl | H | H | 6-iPr, 2-CH$_2$CH$_2$CH$_2$-3 | 0 | 0 |
| 1091 | Cl | H | H | 6-cPr, 2-CH$_2$CH$_2$CH$_2$-3 | 0 | 0 |
| 1092 | Cl | H | H | 6-CN, 2-CH$_2$CH$_2$CH$_2$-3 | 0 | 0 |
| 1093 | Cl | H | H | 6-OMe, 2-CH$_2$CH$_2$CH$_2$-3 | 0 | 0 |
| 1094 | Cl | H | H | 6-Cl, 2-OCH$_2$CH$_2$-3 | 0 | 0 |
| 1095 | Cl | H | H | 6-Br, 2-OCH$_2$CH$_2$-3 | 0 | 0 |
| 1096 | Cl | H | H | 6-Me, 2-OCH$_2$CH$_2$-3 | 0 | 0 |
| 1097 | Cl | H | H | 6-Et, 2-OCH$_2$CH$_2$-3 | 0 | 0 |
| 1098 | Cl | H | H | 6-cPr, 2-OCH$_2$CH$_2$-3 | 0 | 0 |
| 1099 | Cl | H | H | 6-Br, 2-OCH=CH-3 | 0 | 0 |
| 1100 | Cl | H | H | 6-Me, 2-OCH=CH-3 | 0 | 0 |
| 1101 | Cl | H | H | 6-Et, 2-OCH=CH-3 | 0 | 0 |
| 1102 | Cl | H | H | 6-cPr, 2-OCH=CH-3 | 0 | 0 |
| 1103 | Cl | H | H | 6-Cl, 2-CH$_2$CH$_2$O-3 | 0 | 0 |
| 1104 | Cl | H | H | 6-Br, 2-CH$_2$CH$_2$O-3 | 0 | 0 |
| 1105 | Cl | H | H | 6-Me, 2-CH$_2$CH$_2$O-3 | 0 | 0 |
| 1106 | Cl | H | H | 6-Et, 2-CH$_2$CH$_2$O-3 | 0 | 0 |
| 1107 | Cl | H | H | 6-cPr, 2-CH$_2$CH$_2$O-3 | 0 | 0 |
| 1108 | Cl | H | H | 6-Br, 2-CH=CHO-3 | 0 | 0 |
| 1109 | Cl | H | H | 6-Me, 2-CH=CHO-3 | 0 | 0 |
| 1110 | Cl | H | H | 6-Et, 2-CH=CHO-3 | 0 | 0 |
| 1111 | Cl | H | H | 6-cPr, 2-CH=CHO-3 | 0 | 0 |
| 1112 | Cl | H | H | 2,4,6-F$_3$ | 0 | 0 |
| 1113 | Cl | H | H | 2,4-F$_2$, 6-Me | 0 | 0 |
| 1114 | Cl | H | H | 2,4-F$_2$, 6-cPr | 0 | 0 |
| 1115 | Cl | H | H | 2-F, 4,6-cPr$_2$ | 0 | 0 |
| 1116 | Cl | H | H | 2,4,6-Cl$_3$ | 0 | 0 |
| 1117 | Cl | H | H | 2,4,6-Br$_3$ | 0 | 0 |
| 1118 | Cl | H | H | 2,4-Br$_2$, 3,6-Me$_2$ | 0 | 0 |
| 1119 | Cl | H | H | 2-Br, 4,6-Me$_2$ | 0 | 0 |
| 1120 | Cl | H | H | 2,4-I$_2$, 6-Et | 0 | 0 |
| 1121 | Cl | H | H | 2-Me, 4-F, 6-cPr | 0 | 0 |
| 1122 | Cl | H | H | 2,4,6-Me$_3$ | 0 | 0 |
| 1123 | Cl | H | H | 2,2,6-cPr | 0 | 0 |
| 1124 | Cl | H | H | 2-Br, 3,5,6-Me$_3$ | 0 | 0 |
| 1125 | Cl | H | H | 2,3,5,6-Me$_4$ | 0 | 0 |
| 1126 | Cl | H | H | 2,3,3,6-cPr | 0 | 0 |
| 1127 | Cl | H | H | 2,3,5-Me$_3$, 6-CN | 0 | 0 |
| 1128 | Cl | H | H | 2,3,3,6-OMe | 0 | 0 |
| 1129 | Cl | H | H | 5,6-Me$_2$, 2-CH$_2$CH$_2$CH$_2$-3 | 0 | 0 |
| 1130 | Cl | H | H | 5-Me, 6-cPr, 2-CH$_2$CH$_2$CH$_2$-3 | 0 | 0 |
| 1131 | Cl | H | H | 5-Me, 6-CN, 2-CH$_2$CH$_2$CH$_2$-3 | 0 | 0 |
| 1132 | Cl | H | H | 5-Me, 6-OMe, 2-CH$_2$CH$_2$CH$_2$-3 | 0 | 0 |
| 1133 | Cl | H | H | 2-CH$_2$CH$_2$CH$_2$-3,5-CH$_2$CH$_2$CH$_2$-6 | 0 | 0 |
| 1134 | Cl | H | COMe | 2-F | 0 | 0 |
| 1135 | Cl | H | COMe | 2-Cl | 0 | 0 |
| 1136 | Cl | H | COMe | 2-Br | 0 | 0 |
| 1137 | Cl | H | COMe | 2-I | 0 | 0 |
| 1138 | Cl | H | COMe | 2-Me | 0 | 0 |
| 1139 | Cl | H | COMe | 2-iPr | 0 | 0 |
| 1140 | Cl | H | COMe | 2-cPr | 0 | 0 |
| 1141 | Cl | H | COMe | 2-cBu | 0 | 0 |
| 1142 | Cl | H | COMe | 2-CH$_2$CH$_2$CH$_2$-3 | 0 | 0 |
| 1143 | Cl | H | COMe | 2-cPr, 5-Me | 0 | 0 |
| 1144 | Cl | H | COMe | 2-OMe, 5-Me | 0 | 0 |
| 1145 | Cl | H | COMe | 2-F, 6-iPr | 0 | 0 |
| 1146 | Cl | H | COMe | 2-Cl, 6-cPr | 0 | 0 |
| 1147 | Cl | H | COMe | 2-Br, 6-Me | 0 | 0 |
| 1148 | Cl | H | COMe | 2-I, 6-Me | 0 | 0 |
| 1149 | Cl | H | COMe | 2,6-Me$_2$ | 0 | 0 |
| 1150 | Cl | H | COMe | 2-Me, 6-Et | 0 | 0 |
| 1151 | Cl | H | COMe | 2-Me, 6-cPr | 0 | 0 |
| 1152 | Cl | H | COMe | 2,6-cPr$_2$ | 0 | 0 |
| 1153 | Cl | H | COMe | 2-cPr, 3,5-Me$_2$ | 0 | 0 |

TABLE 1-continued

| Compound No. | R¹ | R² | X | R³ to R⁷ | m | n |
|---|---|---|---|---|---|---|
| 1154 | Cl | H | COMe | 2-cPr, 5,6-Me₂ | 0 | 0 |
| 1155 | Cl | H | COEt | 2-Me | 0 | 0 |
| 1156 | Cl | H | COEt | 2-iPr | 0 | 0 |
| 1157 | Cl | H | COEt | 2-cPr | 0 | 0 |
| 1158 | Cl | H | COEt | 2-CH₂CH₂CH₂-3 | 0 | 0 |
| 1159 | Cl | H | COEt | 2,6-Me₂ | 0 | 0 |
| 1160 | Cl | H | COEt | 2-Me, 6-cPr | 0 | 0 |
| 1161 | Cl | H | COPr | 2-Me | 0 | 0 |
| 1162 | Cl | H | COPr | 2-iPr | 0 | 0 |
| 1163 | Cl | H | COPr | 2-cPr | 0 | 0 |
| 1164 | Cl | H | COPr | 2-CH₂CH₂CH₂-3 | 0 | 0 |
| 1165 | Cl | H | COPr | 2,6-Me₂ | 0 | 0 |
| 1166 | Cl | H | COPr | 2-Me, 6-cPr | 0 | 0 |
| 1167 | Cl | H | COiPr | 2-Me | 0 | 0 |
| 1168 | Cl | H | COiPr | 2-iPr | 0 | 0 |
| 1169 | Cl | H | COiPr | 2-cPr | 0 | 0 |
| 1170 | Cl | H | COiPr | 2-CH₂CH₂CH₂-3 | 0 | 0 |
| 1171 | Cl | H | COiPr | 2,6-Me₂ | 0 | 0 |
| 1172 | Cl | H | COiPr | 2-Me, 6-cPr | 0 | 0 |
| 1173 | Cl | H | COBu | 2-Me | 0 | 0 |
| 1174 | Cl | H | COBu | 2-iPr | 0 | 0 |
| 1175 | Cl | H | COBu | 2-cPr | 0 | 0 |
| 1176 | Cl | H | COBu | 2-CH₂CH₂CH₂-3 | 0 | 0 |
| 1177 | Cl | H | COBu | 2,6-Me₂ | 0 | 0 |
| 1178 | Cl | H | COBu | 2-Me, 6-cPr | 0 | 0 |
| 1179 | Cl | H | COiBu | 2-Me | 0 | 0 |
| 1180 | Cl | H | COiBu | 2-iPr | 0 | 0 |
| 1181 | Cl | H | COiBu | 2-cPr | 0 | 0 |
| 1182 | Cl | H | COiBu | 2-CH₂CH₂CH₂-3 | 0 | 0 |
| 1183 | Cl | H | COiBu | 2,6-Me₂ | 0 | 0 |
| 1184 | Cl | H | COiBu | 2-Me, 6-cPr | 0 | 0 |
| 1185 | Cl | H | COsBu | 2-Me | 0 | 0 |
| 1186 | Cl | H | COsBu | 2-iPr | 0 | 0 |
| 1187 | Cl | H | COsBu | 2-cPr | 0 | 0 |
| 1188 | Cl | H | COsBu | 2-CH₂CH₂CH₂-3 | 0 | 0 |
| 1189 | Cl | H | COsBu | 2,6-Me₂ | 0 | 0 |
| 1190 | Cl | H | COsBu | 2-Me, 6-cPr | 0 | 0 |
| 1191 | Cl | H | COtBu | 2-Cl | 0 | 0 |
| 1192 | Cl | H | COtBu | 2-Br | 0 | 0 |
| 1193 | Cl | H | COtBu | 2-I | 0 | 0 |
| 1194 | Cl | H | COtBu | 2-Me | 0 | 0 |
| 1195 | Cl | H | COtBu | 2-iPr | 0 | 0 |
| 1196 | Cl | H | COtBu | 2-cPr | 0 | 0 |
| 1197 | Cl | H | COtBu | 2-cBu | 0 | 0 |
| 1198 | Cl | H | COtBu | 2-CH₂CH₂CH₂-3 | 0 | 0 |
| 1199 | Cl | H | COtBu | 2-cPr, 5-Me | 0 | 0 |
| 1200 | Cl | H | COtBu | 2-OMe, 5-Me | 0 | 0 |
| 1201 | Cl | H | COtBu | 2-F, 6-iPr | 0 | 0 |
| 1202 | Cl | H | COtBu | 2-Cl, 6-cPr | 0 | 0 |
| 1203 | Cl | H | COtBu | 2-Br, 6-Me | 0 | 0 |
| 1204 | Cl | H | COtBu | 2-I, 6-Me | 0 | 0 |
| 1205 | Cl | H | COtBu | 2,6-Me₂ | 0 | 0 |
| 1206 | Cl | H | COtBu | 2-Me, 6-Et | 0 | 0 |
| 1207 | Cl | H | COtBu | 2-Me, 6-cPr | 0 | 0 |
| 1208 | Cl | H | COtBu | 2,6-cPr₂ | 0 | 0 |
| 1209 | Cl | H | COtBu | 2-cPr, 3,5-Me₂ | 0 | 0 |
| 1210 | Cl | H | COtBu | 2-cPr, 5,6-Me₂ | 0 | 0 |
| 1211 | Cl | H | COtPen | 2-Me | 0 | 0 |
| 1212 | Cl | H | COtPen | 2-iPr | 0 | 0 |
| 1213 | Cl | H | COtPen | 2-cPr | 0 | 0 |
| 1214 | Cl | H | COtPen | 2-CH₂CH₂CH₂-3 | 0 | 0 |
| 1215 | Cl | H | COtPen | 2,6-Me₂ | 0 | 0 |
| 1216 | Cl | H | COtPen | 2-Me, 6-cPr | 0 | 0 |
| 1217 | Cl | H | COHx | 2-Me | 0 | 0 |
| 1218 | Cl | H | COHx | 2-iPr | 0 | 0 |
| 1219 | Cl | H | COHx | 2-cPr | 0 | 0 |

TABLE 1-continued

| Compound No. | R¹ | R² | X | R³ to R⁷ | m | n |
|---|---|---|---|---|---|---|
| 1220 | Cl | H | COHx | 2-CH₂CH₂CH₂-3 | 0 | 0 |
| 1221 | Cl | H | COHx | 2,6-Me₂ | 0 | 0 |
| 1222 | Cl | H | COHx | 2-Me, 6-cPr | 0 | 0 |
| 1223 | Cl | H | COC₇H₁₅ | 2-Me | 0 | 0 |
| 1224 | Cl | H | COC₇H₁₅ | 2-iPr | 0 | 0 |
| 1225 | Cl | H | COC₇H₁₅ | 2-cPr | 0 | 0 |
| 1226 | Cl | H | COC₇H₁₅ | 2-CH₂CH₂CH₂-3 | 0 | 0 |
| 1227 | Cl | H | COC₇H₁₅ | 2,6-Me₂ | 0 | 0 |
| 1228 | Cl | H | COC₇H₁₅ | 2-Me, 6-cPr | 0 | 0 |
| 1229 | Cl | H | COC₈H₁₇ | 2-Me | 0 | 0 |
| 1230 | Cl | H | COC₈H₁₇ | 2-iPr | 0 | 0 |
| 1231 | Cl | H | COC₈H₁₇ | 2-cPr | 0 | 0 |
| 1232 | Cl | H | COC₈H₁₇ | 2-CH₂CH₂CH₂-3 | 0 | 0 |
| 1233 | Cl | H | COC₈H₁₇ | 2,6-Me₂ | 0 | 0 |
| 1234 | Cl | H | COC₈H₁₇ | 2-Me, 6-cPr | 0 | 0 |
| 1235 | Cl | H | COC₉H₁₉ | 2-Cl | 0 | 0 |
| 1236 | Cl | H | COC₉H₁₉ | 2-Br | 0 | 0 |
| 1237 | Cl | H | COC₉H₁₉ | 2-I | 0 | 0 |
| 1238 | Cl | H | COC₉H₁₉ | 2-Me | 0 | 0 |
| 1239 | Cl | H | COC₉H₁₉ | 2-iPr | 0 | 0 |
| 1240 | Cl | H | COC₉H₁₉ | 2-cPr | 0 | 0 |
| 1241 | Cl | H | COC₉H₁₉ | 2-cBu | 0 | 0 |
| 1242 | Cl | H | COC₉H₁₉ | 2-CH₂CH₂CH₂-3 | 0 | 0 |
| 1243 | Cl | H | COC₉H₁₉ | 2-cPr, 5-Me | 0 | 0 |
| 1244 | Cl | H | COC₉H₁₉ | 2-OMe, 5-Me | 0 | 0 |
| 1245 | Cl | H | COC₉H₁₉ | 2-F, 6-iPr | 0 | 0 |
| 1246 | Cl | H | COC₉H₁₉ | 2-Cl, 6-cPr | 0 | 0 |
| 1247 | Cl | H | COC₉H₁₉ | 2-Br, 6-Me | 0 | 0 |
| 1248 | Cl | H | COC₉H₁₉ | 2-I, 6-Me | 0 | 0 |
| 1249 | Cl | H | COC₉H₁₉ | 2,6-Me₂ | 0 | 0 |
| 1250 | Cl | H | COC₉H₁₉ | 2-Me, 6-Et | 0 | 0 |
| 1251 | Cl | H | COC₉H₁₉ | 2-Me, 6-cPr | 0 | 0 |
| 1252 | Cl | H | COC₉H₁₉ | 2,6-cPr₂ | 0 | 0 |
| 1253 | Cl | H | COC₉H₁₉ | 2-cPr, 3,5-Me₂ | 0 | 0 |
| 1254 | Cl | H | COC₉H₁₉ | 2-cPr, 5,6-Me₂ | 0 | 0 |
| 1255 | Cl | H | COC₁₄H₂₉ | 2-Me | 0 | 0 |
| 1256 | Cl | H | COC₁₄H₂₉ | 2-iPr | 0 | 0 |
| 1257 | Cl | H | COC₁₄H₂₉ | 2-cPr | 0 | 0 |
| 1258 | Cl | H | COC₁₄H₂₉ | 2-CH₂CH₂CH₂-3 | 0 | 0 |
| 1259 | Cl | H | COC₁₄H₂₉ | 2,6-Me₂ | 0 | 0 |
| 1260 | Cl | H | COC₁₄H₂₉ | 2-Me, 6-cPr | 0 | 0 |
| 1261 | Cl | H | COcPr | 2-Cl | 0 | 0 |
| 1262 | Cl | H | COcPr | 2-Br | 0 | 0 |
| 1263 | Cl | H | COcPr | 2-I | 0 | 0 |
| 1264 | Cl | H | COcPr | 2-Me | 0 | 0 |
| 1265 | Cl | H | COcPr | 2-iPr | 0 | 0 |
| 1266 | Cl | H | COcPr | 2-cPr | 0 | 0 |
| 1267 | Cl | H | COcPr | 2-cBu | 0 | 0 |
| 1268 | Cl | H | COcPr | 2-CH₂CH₂CH₂-3 | 0 | 0 |
| 1269 | Cl | H | COcPr | 2-cPr, 5-Me | 0 | 0 |
| 1270 | Cl | H | COcPr | 2-OMe, 5-Me | 0 | 0 |
| 1271 | Cl | H | COcPr | 2-F, 6-iPr | 0 | 0 |
| 1272 | Cl | H | COcPr | 2-Cl, 6-cPr | 0 | 0 |
| 1273 | Cl | H | COcPr | 2-Br, 6-Me | 0 | 0 |
| 1274 | Cl | H | COcPr | 2-I, 6-Me | 0 | 0 |
| 1275 | Cl | H | COcPr | 2,6-Me₂ | 0 | 0 |
| 1276 | Cl | H | COcPr | 2-Me, 6-Et | 0 | 0 |
| 1277 | Cl | H | COcPr | 2-Me, 6-cPr | 0 | 0 |
| 1278 | Cl | H | COcPr | 2,6-cPr₂ | 0 | 0 |
| 1279 | Cl | H | COcPr | 2-cPr, 3,5-Me₂ | 0 | 0 |
| 1280 | Cl | H | COcPr | 2-cPr, 5,6-Me₂ | 0 | 0 |
| 1281 | Cl | H | COcBu | 2-Me | 0 | 0 |
| 1282 | Cl | H | COcBu | 2-iPr | 0 | 0 |
| 1283 | Cl | H | COcBu | 2-cPr | 0 | 0 |
| 1284 | Cl | H | COcBu | 2-CH₂CH₂CH₂-3 | 0 | 0 |
| 1285 | Cl | H | COcBu | 2,6-Me₂ | 0 | 0 |

TABLE 1-continued

| Compound No. | R¹ | R² | X | R³ to R⁷ | m | n |
|---|---|---|---|---|---|---|
| 1286 | Cl | H | COcBu | 2-Me, 6-cPr | 0 | 0 |
| 1287 | Cl | H | COcPen | 2-Me | 0 | 0 |
| 1288 | Cl | H | COcPen | 2-iPr | 0 | 0 |
| 1289 | Cl | H | COcPen | 2-cPr | 0 | 0 |
| 1290 | Cl | H | COcPen | 2-CH$_2$CH$_2$CH$_2$-3 | 0 | 0 |
| 1291 | Cl | H | COcPen | 2,6-Me$_2$ | 0 | 0 |
| 1292 | Cl | H | COcPen | 2-Me, 6-cPr | 0 | 0 |
| 1293 | Cl | H | COcHx | 2-Me | 0 | 0 |
| 1294 | Cl | H | COcHx | 2-iPr | 0 | 0 |
| 1295 | Cl | H | COcHx | 2-cPr | 0 | 0 |
| 1296 | Cl | H | COcHx | 2-CH$_2$CH$_2$CH$_2$-3 | 0 | 0 |
| 1297 | Cl | H | COcHx | 2,6-Me$_2$ | 0 | 0 |
| 1298 | Cl | H | COcHx | 2-Me, 6-cPr | 0 | 0 |
| 1299 | Cl | H | COCF$_3$ | 2-Me | 0 | 0 |
| 1300 | Cl | H | COCF$_3$ | 2-iPr | 0 | 0 |
| 1301 | Cl | H | COCF$_3$ | 2-cPr | 0 | 0 |
| 1302 | Cl | H | COCF$_3$ | 2-CH$_2$CH$_2$CH$_2$-3 | 0 | 0 |
| 1303 | Cl | H | COCF$_3$ | 2,6-Me$_2$ | 0 | 0 |
| 1304 | Cl | H | COCF$_3$ | 2-Me, 6-cPr | 0 | 0 |
| 1305 | Cl | H | COCH$_2$Cl | 2-Me | 0 | 0 |
| 1306 | Cl | H | COCH$_2$Cl | 2-iPr | 0 | 0 |
| 1307 | Cl | H | COCH$_2$Cl | 2-cPr | 0 | 0 |
| 1308 | Cl | H | COCH$_2$Cl | 2-CH$_2$CH$_2$CH$_2$-3 | 0 | 0 |
| 1309 | Cl | H | COCH$_2$Cl | 2,6-Me$_2$ | 0 | 0 |
| 1310 | Cl | H | COCH$_2$Cl | 2-Me, 6-cPr | 0 | 0 |
| 1311 | Cl | H | COCCl$_3$ | 2-Me | 0 | 0 |
| 1312 | Cl | H | COCCl$_3$ | 2-iPr | 0 | 0 |
| 1313 | Cl | H | COCCl$_3$ | 2-cPr | 0 | 0 |
| 1314 | Cl | H | COCCl$_3$ | 2-CH$_2$CH$_2$CH$_2$-3 | 0 | 0 |
| 1315 | Cl | H | COCCl$_3$ | 2,6-Me$_2$ | 0 | 0 |
| 1316 | Cl | H | COCCl$_3$ | 2-Me, 6-cPr | 0 | 0 |
| 1317 | Cl | H | COCH$_2$Br | 2-Me | 0 | 0 |
| 1318 | Cl | H | COCH$_2$Br | 2-iPr | 0 | 0 |
| 1319 | Cl | H | COCH$_2$Br | 2-cPr | 0 | 0 |
| 1320 | Cl | H | COCH$_2$Br | 2-CH$_2$CH$_2$CH$_2$-3 | 0 | 0 |
| 1321 | Cl | H | COCH$_2$Br | 2,6-Me$_2$ | 0 | 0 |
| 1322 | Cl | H | COCH$_2$Br | 2-Me, 6-cPr | 0 | 0 |
| 1323 | Cl | H | COCH$_2$CF$_3$ | 2-Me | 0 | 0 |
| 1324 | Cl | H | COCH$_2$CF$_3$ | 2-iPr | 0 | 0 |
| 1325 | Cl | H | COCH$_2$CF$_3$ | 2-cPr | 0 | 0 |
| 1326 | Cl | H | COCH$_2$CF$_3$ | 2-CH$_2$CH$_2$CH$_2$-3 | 0 | 0 |
| 1327 | Cl | H | COCH$_2$CF$_3$ | 2,6-Me$_2$ | 0 | 0 |
| 1328 | Cl | H | COCH$_2$CF$_3$ | 2-Me, 6-cPr | 0 | 0 |
| 1329 | Cl | H | COCHBrEt | 2-Me | 0 | 0 |
| 1330 | Cl | H | COCHBrEt | 2-iPr | 0 | 0 |
| 1331 | Cl | H | COCHBrEt | 2-cPr | 0 | 0 |
| 1332 | Cl | H | COCHBrEt | 2-CH$_2$CH$_2$CH$_2$-3 | 0 | 0 |
| 1333 | Cl | H | COCHBrEt | 2,6-Me$_2$ | 0 | 0 |
| 1334 | Cl | H | COCHBrEt | 2-Me, 6-cPr | 0 | 0 |
| 1335 | Cl | H | COCH$_2$CH$_2$CH$_2$Cl | 2-Me | 0 | 0 |
| 1336 | Cl | H | COCH$_2$CH$_2$CH$_2$Cl | 2-iPr | 0 | 0 |
| 1337 | Cl | H | COCH$_2$CH$_2$CH$_2$Cl | 2-cPr | 0 | 0 |
| 1338 | Cl | H | COCH$_2$CH$_2$CH$_2$Cl | 2-CH$_2$CH$_2$CH$_2$-3 | 0 | 0 |
| 1339 | Cl | H | COCH$_2$CH$_2$CH$_2$Cl | 2,6-Me$_2$ | 0 | 0 |
| 1340 | Cl | H | COCH$_2$CH$_2$CH$_2$Cl | 2-Me, 6-cPr | 0 | 0 |
| 1341 | Cl | H | COCH=CH$_2$ | 2-Me | 0 | 0 |
| 1342 | Cl | H | COCH=CH$_2$ | 2-iPr | 0 | 0 |
| 1343 | Cl | H | COCH=CH$_2$ | 2-cPr | 0 | 0 |
| 1344 | Cl | H | COCH=CH$_2$ | 2-CH$_2$CH$_2$CH$_2$-3 | 0 | 0 |
| 1345 | Cl | H | COCH=CH$_2$ | 2,6-Me$_2$ | 0 | 0 |
| 1346 | Cl | H | COCH=CH$_2$ | 2-Me, 6-cPr | 0 | 0 |
| 1347 | Cl | H | COCH=CHMe | 2-Me | 0 | 0 |
| 1348 | Cl | H | COCH=CHMe | 2-iPr | 0 | 0 |
| 1349 | Cl | H | COCH=CHMe | 2-cPr | 0 | 0 |
| 1350 | Cl | H | COCH=CHMe | 2-CH$_2$CH$_2$CH$_2$-3 | 0 | 0 |
| 1351 | Cl | H | COCH=CHMe | 2,6-Me$_2$ | 0 | 0 |

TABLE 1-continued

| Compound No. | R¹ | R² | X | R³ to R⁷ | m | n |
|---|---|---|---|---|---|---|
| 1352 | Cl | H | COCH=CHMe | 2-Me, 6-cPr | 0 | 0 |
| 1353 | Cl | H | COCH=CMe₂ | 2-Me | 0 | 0 |
| 1354 | Cl | H | COCH=CMe₂ | 2-iPr | 0 | 0 |
| 1355 | Cl | H | COCH=CMe₂ | 2-cPr | 0 | 0 |
| 1356 | Cl | H | COCH=CMe₂ | 2-CH₂CH₂CH₂-3 | 0 | 0 |
| 1357 | Cl | H | COCH=CMe₂ | 2,6-Me₂ | 0 | 0 |
| 1358 | Cl | H | COCH=CMe₂ | 2-Me, 6-cPr | 0 | 0 |
| 1359 | Cl | H | COCH=CHPh | 2-Me | 0 | 0 |
| 1360 | Cl | H | COCH=CHPh | 2-iPr | 0 | 0 |
| 1361 | Cl | H | COCH=CHPh | 2-cPr | 0 | 0 |
| 1362 | Cl | H | COCH=CHPh | 2-CH₂CH₂CH₂-3 | 0 | 0 |
| 1363 | Cl | H | COCH=CHPh | 2,6-Me₂ | 0 | 0 |
| 1364 | Cl | H | COCH=CHPh | 2-Me, 6-cPr | 0 | 0 |
| 1365 | Cl | H | COC CH | 2-Me | 0 | 0 |
| 1366 | Cl | H | COC CH | 2-iPr | 0 | 0 |
| 1367 | Cl | H | COC CH | 2-cPr | 0 | 0 |
| 1368 | Cl | H | COC CH | 2-CH₂CH₂CH₂-3 | 0 | 0 |
| 1369 | Cl | H | COC CH | 2,6-Me₂ | 0 | 0 |
| 1370 | Cl | H | COC CH | 2-Me, 6-cPr | 0 | 0 |
| 1371 | Cl | H | COCH₂Ph | 2-Me | 0 | 0 |
| 1372 | Cl | H | COCH₂Ph | 2-iPr | 0 | 0 |
| 1373 | Cl | H | COCH₂Ph | 2-cPr | 0 | 0 |
| 1374 | Cl | H | COCH₂Ph | 2-CH₂CH₂CH₂-3 | 0 | 0 |
| 1375 | Cl | H | COCH₂Ph | 2,6-Me₂ | 0 | 0 |
| 1376 | Cl | H | COCH₂Ph | 2-Me, 6-cPr | 0 | 0 |
| 1377 | Cl | H | COCH₂CH₂CO₂Me | 2-Me | 0 | 0 |
| 1378 | Cl | H | COCH₂CH₂CO₂Me | 2-iPr | 0 | 0 |
| 1379 | Cl | H | COCH₂CH₂CO₂Me | 2-cPr | 0 | 0 |
| 1380 | Cl | H | COCH₂CH₂CO₂Me | 2-CH₂CH₂CH₂-3 | 0 | 0 |
| 1381 | Cl | H | COCH₂CH₂CO₂Me | 2,6-Me₂ | 0 | 0 |
| 1382 | Cl | H | COCH₂CH₂CO₂Me | 2-Me, 6-cPr | 0 | 0 |
| 1383 | Cl | H | COPh | 2-F | 0 | 0 |
| 1384 | Cl | H | COPh | 2-Cl | 0 | 0 |
| 1385 | Cl | H | COPh | 2-Br | 0 | 0 |
| 1386 | Cl | H | COPh | 2-I | 0 | 0 |
| 1387 | Cl | H | COPh | 2-Me | 0 | 0 |
| 1388 | Cl | H | COPh | 2-Et | 0 | 0 |
| 1389 | Cl | H | COPh | 2-iPr | 0 | 0 |
| 1390 | Cl | H | COPh | 2-tBu | 0 | 0 |
| 1391 | Cl | H | COPh | 2-cPr | 0 | 0 |
| 1392 | Cl | H | COPh | 2-(cPr-1-Me) | 0 | 0 |
| 1393 | Cl | H | COPh | 2-(cPr-2-Me) | 0 | 0 |
| 1394 | Cl | H | COPh | 2-(cPr-2,2-Cl₂) | 0 | 0 |
| 1395 | Cl | H | COPh | 2-cBu | 0 | 0 |
| 1396 | Cl | H | COPh | 4-SiMe₃ | 0 | 0 |
| 1397 | Cl | H | COPh | 2-CH₂CH₂CH₂-3 | 0 | 0 |
| 1398 | Cl | H | COPh | 2-CH=CHO-3 | 0 | 0 |
| 1399 | Cl | H | COPh | 2-CH₂CH₂O-3 | 0 | 0 |
| 1400 | Cl | H | COPh | 2-OCH=CH-3 | 0 | 0 |
| 1401 | Cl | H | COPh | 2-OCH₂-3 | 0 | 0 |
| 1402 | Cl | H | COPh | 2-cPr, 5-F | 0 | 0 |
| 1403 | Cl | H | COPh | 2-cPr, 5-Cl | 0 | 0 |
| 1404 | Cl | H | COPh | 2-cPr, 5-Me | 0 | 0 |
| 1405 | Cl | H | COPh | 2-OMe, 5-Me | 0 | 0 |
| 1406 | Cl | H | COPh | 2-F, 6-iPr | 0 | 0 |
| 1407 | Cl | H | COPh | 2-F, 6-cPr | 0 | 0 |
| 1408 | Cl | H | COPh | 2-Cl, 6-Me | 0 | 0 |
| 1409 | Cl | H | COPh | 2-Cl, 6-cPr | 0 | 0 |
| 1410 | Cl | H | COPh | 2-Br, 6-Me | 0 | 0 |
| 1411 | Cl | H | COPh | 2-Br, 6-Et | 0 | 0 |
| 1412 | Cl | H | COPh | 2-Br, 6-cPr | 0 | 0 |
| 1413 | Cl | H | COPh | 2-I, 6-Me | 0 | 0 |
| 1414 | Cl | H | COPh | 2-I, 6-Et | 0 | 0 |
| 1415 | Cl | H | COPh | 2,6-Me₂ | 0 | 0 |
| 1416 | Cl | H | COPh | 2-Me, 6-Et | 0 | 0 |
| 1417 | Cl | H | COPh | 2-Me, 6-cPr | 0 | 0 |

TABLE 1-continued

| Compound No. | R¹ | R² | X | R³ to R⁷ | m | n |
|---|---|---|---|---|---|---|
| 1418 | Cl | H | COPh | 2-Et, 6-cPr | 0 | 0 |
| 1419 | Cl | H | COPh | 2-iPr, 6-cPr | 0 | 0 |
| 1420 | Cl | H | COPh | 2-tBu, 6-cPr | 0 | 0 |
| 1421 | Cl | H | COPh | 2,6-cPr$_2$ | 0 | 0 |
| 1422 | Cl | H | COPh | 2-cPr, 6-OMe | 0 | 0 |
| 1423 | Cl | H | COPh | 2-Br, 3,6-Me$_2$ | 0 | 0 |
| 1424 | Cl | H | COPh | 2-cPr, 3,5-Me$_2$ | 0 | 0 |
| 1425 | Cl | H | COPh | 2-cPr,4, 6-Me$_2$ | 0 | 0 |
| 1426 | Cl | H | COPh | 2-Br, 5,6-Me$_2$ | 0 | 0 |
| 1427 | Cl | H | COPh | 2-cPr, 5,6-Me$_2$ | 0 | 0 |
| 1428 | Cl | H | COPh | 2-Br, 5-CH=CH—O-6 | 0 | 0 |
| 1429 | Cl | H | COPh | 2-Me, 5-CH$_2$CH$_2$CH$_2$-6 | 0 | 0 |
| 1430 | Cl | H | COPh | 2-Me, 5-CH$_2$CH$_2$O-6 | 0 | 0 |
| 1431 | Cl | H | COPh | 2-Me, 5-CH=CH—O-6 | 0 | 0 |
| 1432 | Cl | H | COPh | 2-Et, 5-CH$_2$CH$_2$CH$_2$-6 | 0 | 0 |
| 1433 | Cl | H | COPh | 2-cPr, 5-CH$_2$CH$_2$CH$_2$-6 | 0 | 0 |
| 1434 | Cl | H | COPh | 2-cPr, 5-CH=CH—O-6 | 0 | 0 |
| 1435 | Cl | H | COPh | 2-Br, 3,5,6-Me$_3$ | 0 | 0 |
| 1436 | Cl | H | CO(Ph-2-Cl) | 2-Me | 0 | 0 |
| 1437 | Cl | H | CO(Ph-2-Cl) | 2-iPr | 0 | 0 |
| 1438 | Cl | H | CO(Ph-2-Cl) | 2-cPr | 0 | 0 |
| 1439 | Cl | H | CO(Ph-2-Cl) | 2-CH$_2$CH$_2$CH$_2$-3 | 0 | 0 |
| 1440 | Cl | H | CO(Ph-2-Cl) | 2,6-Me$_2$ | 0 | 0 |
| 1441 | Cl | H | CO(Ph-2-Cl) | 2-Me, 6-cPr | 0 | 0 |
| 1442 | Cl | H | CO(Ph-2-Me) | 2-F | 0 | 0 |
| 1443 | Cl | H | CO(Ph-2-Me) | 2-Cl | 0 | 0 |
| 1444 | Cl | H | CO(Ph-2-Me) | 2-Br | 0 | 0 |
| 1445 | Cl | H | CO(Ph-2-Me) | 2-I | 0 | 0 |
| 1446 | Cl | H | CO(Ph-2-Me) | 2-Me | 0 | 0 |
| 1447 | Cl | H | CO(Ph-2-Me) | 2-Et | 0 | 0 |
| 1448 | Cl | H | CO(Ph-2-Me) | 2-iPr | 0 | 0 |
| 1449 | Cl | H | CO(Ph-2-Me) | 2-tBu | 0 | 0 |
| 1450 | Cl | H | CO(Ph-2-Me) | 2-sBu | 0 | 0 |
| 1451 | Cl | H | CO(Ph-2-Me) | 2-(cPr-1-Me) | 0 | 0 |
| 1452 | Cl | H | CO(Ph-2-Me) | 2-cPr | 0 | 0 |
| 1453 | Cl | H | CO(Ph-2-Me) | 2-(cPr-2,2-Cl$_2$) | 0 | 0 |
| 1454 | Cl | H | CO(Ph-2-Me) | 2-cBu | 0 | 0 |
| 1455 | Cl | H | CO(Ph-2-Me) | 2-cHx | 0 | 0 |
| 1456 | Cl | H | CO(Ph-2-Me) | 2-Ph | 0 | 0 |
| 1457 | Cl | H | CO(Ph-2-Me) | 3-tBu | 0 | 0 |
| 1458 | Cl | H | CO(Ph-2-Me) | 3-OMe | 0 | 0 |
| 1459 | Cl | H | CO(Ph-2-Me) | 2-iPr, 5-Me | 0 | 0 |
| 1460 | Cl | H | CO(Ph-2-Me) | 2-CH$_2$CH$_2$CH$_2$-3 | 0 | 0 |
| 1461 | Cl | H | CO(Ph-2-Me) | 2-CH=CH—CH=CH-3 | 0 | 0 |
| 1462 | Cl | H | CO(Ph-2-Me) | 2-CH=CHO-3 | 0 | 0 |
| 1463 | Cl | H | CO(Ph-2-Me) | 2-CH$_2$CH$_2$O-3 | 0 | 0 |
| 1464 | Cl | H | CO(Ph-2-Me) | 2-OCH=CH-3 | 0 | 0 |
| 1465 | Cl | H | CO(Ph-2-Me) | 2-OCH$_2$CH$_2$-3 | 0 | 0 |
| 1466 | Cl | H | CO(Ph-2-Me) | 2-cPr, 5-F | 0 | 0 |
| 1467 | Cl | H | CO(Ph-2-Me) | 2-cPr, 5-Cl | 0 | 0 |
| 1468 | Cl | H | CO(Ph-2-Me) | 2-cPr, 5-Me | 0 | 0 |
| 1469 | Cl | H | CO(Ph-2-Me) | 2-OMe, 5-Me | 0 | 0 |
| 1470 | Cl | H | CO(Ph-2-Me) | 2-F, 6-iPr | 0 | 0 |
| 1471 | Cl | H | CO(Ph-2-Me) | 2-F, 6-cPr | 0 | 0 |
| 1472 | Cl | H | CO(Ph-2-Me) | 2-Cl, 6-Me | 0 | 0 |
| 1473 | Cl | H | CO(Ph-2-Me) | 2-Cl, 6-cPr | 0 | 0 |
| 1474 | Cl | H | CO(Ph-2-Me) | 2-Br, 6-Me | 0 | 0 |
| 1475 | Cl | H | CO(Ph-2-Me) | 2-Br, 6-Et | 0 | 0 |
| 1476 | Cl | H | CO(Ph-2-Me) | 2-Br, 6-cPr | 0 | 0 |
| 1477 | Cl | H | CO(Ph-2-Me) | 2-I, 6-Me | 0 | 0 |
| 1478 | Cl | H | CO(Ph-2-Me) | 2-I, 6-Et | 0 | 0 |
| 1479 | Cl | H | CO(Ph-2-Me) | 2,6-Me$_2$ | 0 | 0 |
| 1480 | Cl | H | CO(Ph-2-Me) | 2-Me, 6-Et | 0 | 0 |
| 1481 | Cl | H | CO(Ph-2-Me) | 2-Me, 6-cPr | 0 | 0 |
| 1482 | Cl | H | CO(Ph-2-Me) | 2-Et, 6-cPr | 0 | 0 |
| 1483 | Cl | H | CO(Ph-2-Me) | 2-iPr, 6-cPr | 0 | 0 |

TABLE 1-continued

| Compound No. | R¹ | R² | X | R³ to R⁷ | m | n |
|---|---|---|---|---|---|---|
| 1484 | Cl | H | CO(Ph-2-Me) | 2-tBu, 6-cPr | 0 | 0 |
| 1485 | Cl | H | CO(Ph-2-Me) | 2,6-cPr$_2$ | 0 | 0 |
| 1486 | Cl | H | CO(Ph-2-Me) | 2-cPr, 6-OMe | 0 | 0 |
| 1487 | Cl | H | CO(Ph-2-Me) | 2-Br, 3,6-Me$_2$ | 0 | 0 |
| 1488 | Cl | H | CO(Ph-2-Me) | 2-cPr, 3,5-Me$_2$ | 0 | 0 |
| 1489 | Cl | H | CO(Ph-2-Me) | 2-cPr, 4, 6-Me$_2$ | 0 | 0 |
| 1490 | Cl | H | CO(Ph-2-Me) | 2-Br, 5,6-Me$_2$ | 0 | 0 |
| 1491 | Cl | H | CO(Ph-2-Me) | 2-cPr, 5,6-Me$_2$ | 0 | 0 |
| 1492 | Cl | H | CO(Ph-2-Me) | 2-Br, 5-CH=CH-O-6 | 0 | 0 |
| 1493 | Cl | H | CO(Ph-2-Me) | 2-Me, 5-CH$_2$CH$_2$CH$_2$-6 | 0 | 0 |
| 1494 | Cl | H | CO(Ph-2-Me) | 2-Me, 5-CH$_2$CH$_2$O-6 | 0 | 0 |
| 1495 | Cl | H | CO(Ph-2-Me) | 2-Me, 5-CH=CH—O-6 | 0 | 0 |
| 1496 | Cl | H | CO(Ph-2-Me) | 2-Et, 5-CH$_2$CH$_2$CH$_2$-6 | 0 | 0 |
| 1497 | Cl | H | CO(Ph-2-Me) | 2-cPr, 5-CH$_2$CH$_2$CH$_2$-6 | 0 | 0 |
| 1498 | Cl | H | CO(Ph-2-Me) | 2-cPr, 5-CH=CH—O-6 | 0 | 0 |
| 1499 | Cl | H | CO(Ph-2-Me) | 2-Br, 3,5,6-Me$_3$ | 0 | 0 |
| 1500 | Cl | H | CO(Ph-2-CN) | 2-Me | 0 | 0 |
| 1501 | Cl | H | CO(Ph-2-CN) | 2-iPr | 0 | 0 |
| 1502 | Cl | H | CO(Ph-2-CN) | 2-cPr | 0 | 0 |
| 1503 | Cl | H | CO(Ph-2-CN) | 2-CH$_2$CH$_2$CH$_2$-3 | 0 | 0 |
| 1504 | Cl | H | CO(Ph-2-CN) | 2,6-Me$_2$ | 0 | 0 |
| 1505 | Cl | H | CO(Ph-2-CN) | 2-Me, 6-cPr | 0 | 0 |
| 1506 | Cl | H | CO(Ph-2-OMe) | 2-Cl | 0 | 0 |
| 1507 | Cl | H | CO(Ph-2-OMe) | 2-Br | 0 | 0 |
| 1508 | Cl | H | CO(Ph-2-OMe) | 2-I | 0 | 0 |
| 1509 | Cl | H | CO(Ph-2-OMe) | 2-Me | 0 | 0 |
| 1510 | Cl | H | CO(Ph-2-OMe) | 2-iPr | 0 | 0 |
| 1511 | Cl | H | CO(Ph-2-OMe) | 2-cPr | 0 | 0 |
| 1512 | Cl | H | CO(Ph-2-OMe) | 2-cBu | 0 | 0 |
| 1513 | Cl | H | CO(Ph-2-OMe) | 2-CH$_2$CH$_2$CH$_2$-3 | 0 | 0 |
| 1514 | Cl | H | CO(Ph-2-OMe) | 2-cPr, 5-Me | 0 | 0 |
| 1515 | Cl | H | CO(Ph-2-OMe) | 2-OMe, 5-Me | 0 | 0 |
| 1516 | Cl | H | CO(Ph-2-OMe) | 2-F, 6-iPr | 0 | 0 |
| 1517 | Cl | H | CO(Ph-2-OMe) | 2-Cl, 6-cPr | 0 | 0 |
| 1518 | Cl | H | CO(Ph-2-OMe) | 2-Br, 6-Me | 0 | 0 |
| 1519 | Cl | H | CO(Ph-2-OMe) | 2-I, 6-Me | 0 | 0 |
| 1520 | Cl | H | CO(Ph-2-OMe) | 2,6-Me$_2$ | 0 | 0 |
| 1521 | Cl | H | CO(Ph-2-OMe) | 2-Me, 6-Et | 0 | 0 |
| 1522 | Cl | H | CO(Ph-2-OMe) | 2-Me, 6-cPr | 0 | 0 |
| 1523 | Cl | H | CO(Ph-2-OMe) | 2,6-cPr$_2$ | 0 | 0 |
| 1524 | Cl | H | CO(Ph-2-OMe) | 2-cPr, 3,5-Me$_2$ | 0 | 0 |
| 1525 | Cl | H | CO(Ph-2-OMe) | 2-cPr, 5,6-Me$_2$ | 0 | 0 |
| 1526 | Cl | H | CO(Ph-3-Me) | 2-Me | 0 | 0 |
| 1527 | Cl | H | CO(Ph-3-Me) | 2-iPr | 0 | 0 |
| 1528 | Cl | H | CO(Ph-3-Me) | 2-cPr | 0 | 0 |
| 1529 | Cl | H | CO(Ph-3-Me) | 2-CH$_2$CH$_2$CH$_2$-3 | 0 | 0 |
| 1530 | Cl | H | CO(Ph-3-Me) | 2,6-Me$_2$ | 0 | 0 |
| 1531 | Cl | H | CO(Ph-3-Me) | 2-Me, 6-cPr | 0 | 0 |
| 1532 | Cl | H | CO(Ph-4-Cl) | 2-Me | 0 | 0 |
| 1533 | Cl | H | CO(Ph-4-Cl) | 2-iPr | 0 | 0 |
| 1534 | Cl | H | CO(Ph-4-Cl) | 2-cPr | 0 | 0 |
| 1535 | Cl | H | CO(Ph-4-Cl) | 2-CH$_2$CH$_2$CH$_2$-3 | 0 | 0 |
| 1536 | Cl | H | CO(Ph-4-Cl) | 2,6-Me$_2$ | 0 | 0 |
| 1537 | Cl | H | CO(Ph-4-Cl) | 2-Me, 6-cPr | 0 | 0 |
| 1538 | Cl | H | CO(Ph-4-Br) | 2-Me | 0 | 0 |
| 1539 | Cl | H | CO(Ph-4-Br) | 2-iPr | 0 | 0 |
| 1540 | Cl | H | CO(Ph-4-Br) | 2-cPr | 0 | 0 |
| 1541 | Cl | H | CO(Ph-4-Br) | 2-CH$_2$CH$_2$CH$_2$-3 | 0 | 0 |
| 1542 | Cl | H | CO(Ph-4-Br) | 2,6-Me$_2$ | 0 | 0 |
| 1543 | Cl | H | CO(Ph-4-Br) | 2-Me, 6-cPr | 0 | 0 |
| 1544 | Cl | H | CO(Ph-4-I) | 2-Me | 0 | 0 |
| 1545 | Cl | H | CO(Ph-4-I) | 2-iPr | 0 | 0 |
| 1546 | Cl | H | CO(Ph-4-I) | 2-cPr | 0 | 0 |
| 1547 | Cl | H | CO(Ph-4-I) | 2-CH$_2$CH$_2$CH$_2$-3 | 0 | 0 |
| 1548 | Cl | H | CO(Ph-4-I) | 2,6-Me$_2$ | 0 | 0 |
| 1549 | Cl | H | CO(Ph-4-I) | 2-Me, 6-cPr | 0 | 0 |

TABLE 1-continued

[Structure: pyridazine with R¹, R², OX, R³-R⁷ substituents as shown]

| Compound No. | R¹ | R² | X | R³ to R⁷ | m | n |
|---|---|---|---|---|---|---|
| 1550 | Cl | H | CO(Ph-4-Me) | 2-Cl | 0 | 0 |
| 1551 | Cl | H | CO(Ph-4-Me) | 2-Br | 0 | 0 |
| 1552 | Cl | H | CO(Ph-4-Me) | 2-I | 0 | 0 |
| 1553 | Cl | H | CO(Ph-4-Me) | 2-Me | 0 | 0 |
| 1554 | Cl | H | CO(Ph-4-Me) | 2-iPr | 0 | 0 |
| 1555 | Cl | H | CO(Ph-4-Me) | 2-cPr | 0 | 0 |
| 1556 | Cl | H | CO(Ph-4-Me) | 2-cBu | 0 | 0 |
| 1557 | Cl | H | CO(Ph-4-Me) | 2-CH$_2$CH$_2$CH$_2$-3 | 0 | 0 |
| 1558 | Cl | H | CO(Ph-4-Me) | 2-cPr, 5-Me | 0 | 0 |
| 1559 | Cl | H | CO(Ph-4-Me) | 2-OMe, 5-Me | 0 | 0 |
| 1560 | Cl | H | CO(Ph-4-Me) | 2-F, 6-iPr | 0 | 0 |
| 1561 | Cl | H | CO(Ph-4-Me) | 2-Cl, 6-cPr | 0 | 0 |
| 1562 | Cl | H | CO(Ph-4-Me) | 2-Br, 6-Me | 0 | 0 |
| 1563 | Cl | H | CO(Ph-4-Me) | 2-I, 6-Me | 0 | 0 |
| 1564 | Cl | H | CO(Ph-4-Me) | 2,6-Me$_2$ | 0 | 0 |
| 1565 | Cl | H | CO(Ph-4-Me) | 2-Me, 6-Et | 0 | 0 |
| 1566 | Cl | H | CO(Ph-4-Me) | 2-Me, 6-cPr | 0 | 0 |
| 1567 | Cl | H | CO(Ph-4-Me) | 2-cPr$_2$ | 0 | 0 |
| 1568 | Cl | H | CO(Ph-4-Me) | 2-cPr, 3,5-Me$_2$ | 0 | 0 |
| 1569 | Cl | H | CO(Ph-4-Me) | 2-cPr, 5,6-Me$_2$ | 0 | 0 |
| 1570 | Cl | H | CO(Ph-4-tBu) | 2-Me | 0 | 0 |
| 1571 | Cl | H | CO(Ph-4-tBu) | 2-iPr | 0 | 0 |
| 1572 | Cl | H | CO(Ph-4-tBu) | 2-cPr | 0 | 0 |
| 1573 | Cl | H | CO(Ph-4-tBu) | 2-CH$_2$CH$_2$CH$_2$-3 | 0 | 0 |
| 1574 | Cl | H | CO(Ph-4-tBu) | 2,6-Me$_2$ | 0 | 0 |
| 1575 | Cl | H | CO(Ph-4-tBu) | 2-Me, 6-cPr | 0 | 0 |
| 1576 | Cl | H | CO(Ph-4-CO$_2$Me) | 2-Me | 0 | 0 |
| 1577 | Cl | H | CO(Ph-4-CO$_2$Me) | 2-iPr | 0 | 0 |
| 1578 | Cl | H | CO(Ph-4-CO$_2$Me) | 2-cPr | 0 | 0 |
| 1579 | Cl | H | CO(Ph-4-CO$_2$Me) | 2-CH$_2$CH$_2$CH$_2$-3 | 0 | 0 |
| 1580 | Cl | H | CO(Ph-4-CO$_2$Me) | 2,6-Me$_2$ | 0 | 0 |
| 1581 | Cl | H | CO(Ph-4-CO$_2$Me) | 2-Me, 6-cPr | 0 | 0 |
| 1582 | Cl | H | CO(Ph-4-COtBu) | 2-Me | 0 | 0 |
| 1583 | Cl | H | CO(Ph-4-COtBu) | 2-iPr | 0 | 0 |
| 1584 | Cl | H | CO(Ph-4-COtBu) | 2-cPr | 0 | 0 |
| 1585 | Cl | H | CO(Ph-4-COtBu) | 2-CH$_2$CH$_2$CH$_2$-3 | 0 | 0 |
| 1586 | Cl | H | CO(Ph-4-COtBu) | 2,6-Me$_2$ | 0 | 0 |
| 1587 | Cl | H | CO(Ph-4-COtBu) | 2-Me, 6-cPr | 0 | 0 |
| 1588 | Cl | H | CO(Ph-4-NO$_2$) | 2-Me | 0 | 0 |
| 1589 | Cl | H | CO(Ph-4-NO$_2$) | 2-iPr | 0 | 0 |
| 1590 | Cl | H | CO(Ph-4-NO$_2$) | 2-cPr | 0 | 0 |
| 1591 | Cl | H | CO(Ph-4-NO$_2$) | 2-CH$_2$CH$_2$CH$_2$-3 | 0 | 0 |
| 1592 | Cl | H | CO(Ph-4-NO$_2$) | 2,6-Me$_2$ | 0 | 0 |
| 1593 | Cl | H | CO(Ph-4-NO$_2$) | 2-Me, 6-cPr | 0 | 0 |
| 1594 | Cl | H | CO(Ph-4-OMe) | 2-Me | 0 | 0 |
| 1595 | Cl | H | CO(Ph-4-OMe) | 2-iPr | 0 | 0 |
| 1596 | Cl | H | CO(Ph-4-OMe) | 2-cPr | 0 | 0 |
| 1597 | Cl | H | CO(Ph-4-OMe) | 2-CH$_2$CH$_2$CH$_2$-3 | 0 | 0 |
| 1598 | Cl | H | CO(Ph-4-OMe) | 2,6-Me$_2$ | 0 | 0 |
| 1599 | Cl | H | CO(Ph-4-OMe) | 2-Me, 6-cPr | 0 | 0 |
| 1600 | Cl | H | CO(Ph-2,4-Cl$_2$) | 2-Cl | 0 | 0 |
| 1601 | Cl | H | CO(Ph-2,4-Cl$_2$) | 2-Br | 0 | 0 |
| 1602 | Cl | H | CO(Ph-2,4-Cl$_2$) | 2-I | 0 | 0 |
| 1603 | Cl | H | CO(Ph-2, 4-Cl$_2$) | 2-Me | 0 | 0 |
| 1604 | Cl | H | CO(Ph-2,4-Cl$_2$) | 2-iPr | 0 | 0 |
| 1605 | Cl | H | CO(Ph-2,4-Cl$_2$) | 2-cPr | 0 | 0 |
| 1606 | Cl | H | CO(Ph-2,4-Cl$_2$) | 2-cBu | 0 | 0 |
| 1607 | Cl | H | CO(Ph-2,4-Cl$_2$) | 2-CH$_2$CH$_2$CH$_2$-3 | 0 | 0 |
| 1608 | Cl | H | CO(Ph-2,4-Cl$_2$) | 2-cPr, 5-Me | 0 | 0 |
| 1609 | Cl | H | CO(Ph-2,4-Cl$_2$) | 2-OMe, 5-Me | 0 | 0 |
| 1610 | Cl | H | CO(Ph-2,4-Cl$_2$) | 2-F, 6-iPr | 0 | 0 |
| 1611 | Cl | H | CO(Ph-2,4-Cl$_2$) | 2-Cl, 6-cPr | 0 | 0 |
| 1612 | Cl | H | CO(Ph-2,4-Cl$_2$) | 2-Br, 6-Me | 0 | 0 |
| 1613 | Cl | H | CO(Ph-2,4-Cl$_2$) | 2-I, 6-Me | 0 | 0 |
| 1614 | Cl | H | CO(Ph-2,4-Cl$_2$) | 2,6-Me$_2$ | 0 | 0 |
| 1615 | Cl | H | CO(Ph-2,4-Cl$_2$) | 2-Me, 6-Et | 0 | 0 |

TABLE 1-continued

| Compound No. | R¹ | R² | X | R³ to R⁷ | m | n |
|---|---|---|---|---|---|---|
| 1616 | Cl | H | CO(Ph-2,4-Cl$_2$) | 2-Me, 6-cPr | 0 | 0 |
| 1617 | Cl | H | CO(Ph-2,4-Cl$_2$) | 2,6-cPr$_2$ | 0 | 0 |
| 1618 | Cl | H | CO(Ph-2,4-Cl$_2$) | 2-cPr, 3,5-Me$_2$ | 0 | 0 |
| 1619 | Cl | H | CO(Ph-2,4-Cl$_2$) | 2-cPr, 5,6-Me$_2$ | 0 | 0 |
| 1620 | Cl | H | CO(Ph-2-CO$_2$Q$^5$) | 2-Me | 0 | 0 |
| 1621 | Cl | H | CO(Ph-2-CO$_2$Q$^5$) | 2-iPr | 0 | 0 |
| 1622 | Cl | H | CO(Ph-2-CO$_2$Q$^5$) | 2-cPr | 0 | 0 |
| 1623 | Cl | H | CO(Ph-2-CO$_2$Q$^5$) | 2-CH$_2$CH$_2$CH$_2$-3 | 0 | 0 |
| 1624 | Cl | H | CO(Ph-2-CO$_2$Q$^5$) | 2,6-Me$_2$ | 0 | 0 |
| 1625 | Cl | H | CO(Ph-2-CO$_2$Q$^5$) | 2-Me, 6-cPr | 0 | 0 |
| 1626 | Cl | H | CO(Ph-3-CO$_2$Q$^5$) | 2-Me | 0 | 0 |
| 1627 | Cl | H | CO(Ph-3-CO$_2$Q$^5$) | 2-iPr | 0 | 0 |
| 1628 | Cl | H | CO(Ph-3-CO$_2$Q$^5$) | 2-cPr | 0 | 0 |
| 1629 | Cl | H | CO(Ph-3-CO$_2$Q$^5$) | 2-CH$_2$CH$_2$CH$_2$-3 | 0 | 0 |
| 1630 | Cl | H | CO(Ph-3-CO$_2$Q$^5$) | 2,6-Me$_2$ | 0 | 0 |
| 1631 | Cl | H | CO(Ph-3-CO$_2$Q$^5$) | 2-Me, 6-cPr | 0 | 0 |
| 1632 | Cl | H | CO(Ph-4-CO$_2$Q$^5$) | 2-Me | 0 | 0 |
| 1633 | Cl | H | CO(Ph-4-CO$_2$Q$^5$) | 2-iPr | 0 | 0 |
| 1634 | Cl | H | CO(Ph-4-CO$_2$Q$^5$) | 2-cPr | 0 | 0 |
| 1635 | Cl | H | CO(Ph-4-CO$_2$Q$^5$) | 2-CH$_2$CH$_2$CH$_2$-3 | 0 | 0 |
| 1636 | Cl | H | CO(Ph-4-CO$_2$Q$^5$) | 2,6-Me$_2$ | 0 | 0 |
| 1637 | Cl | H | CO(Ph-4-CO$_2$Q$^5$) | 2-Me, 6-cPr | 0 | 0 |
| 1638 | Cl | H | CO(2-Fur) | 2-Me | 0 | 0 |
| 1639 | Cl | H | CO(2-Fur) | 2-iPr | 0 | 0 |
| 1640 | Cl | H | CO(2-Fur) | 2-cPr | 0 | 0 |
| 1641 | Cl | H | CO(2-Fur) | 2-CH$_2$CH$_2$CH$_2$-3 | 0 | 0 |
| 1642 | Cl | H | CO(2-Fur) | 2,6-Me$_2$ | 0 | 0 |
| 1643 | Cl | H | CO(2-Fur) | 2-Me, 6-cPr | 0 | 0 |
| 1644 | Cl | H | CO(2-Thi) | 2-Me | 0 | 0 |
| 1645 | Cl | H | CO(2-Thi) | 2-iPr | 0 | 0 |
| 1646 | Cl | H | CO(2-Thi) | 2-cPr | 0 | 0 |
| 1647 | Cl | H | CO(2-Thi) | 2-CH$_2$CH$_2$CH$_2$-3 | 0 | 0 |
| 1648 | Cl | H | CO(2-Thi) | 2,6-Me$_2$ | 0 | 0 |
| 1649 | Cl | H | CO(2-Thi) | 2-Me, 6-cPr | 0 | 0 |
| 1650 | Cl | H | CO$_2$Me | 2-F | 0 | 0 |
| 1651 | Cl | H | CO$_2$Me | 2-Cl | 0 | 0 |
| 1652 | Cl | H | CO$_2$Me | 2-Br | 0 | 0 |
| 1653 | Cl | H | CO$_2$Me | 2-I | 0 | 0 |
| 1654 | Cl | H | CO$_2$Me | 2-Me | 0 | 0 |
| 1655 | Cl | H | CO$_2$Me | 2-Et | 0 | 0 |
| 1656 | Cl | H | CO$_2$Me | 2-iPr | 0 | 0 |
| 1657 | Cl | H | CO$_2$Me | 2-tBu | 0 | 0 |
| 1658 | Cl | H | CO$_2$Me | 2-cPr | 0 | 0 |
| 1659 | Cl | H | CO$_2$Me | 2-(cPr-1-Me) | 0 | 0 |
| 1660 | Cl | H | CO$_2$Me | 2-(cPr-2-Me) | 0 | 0 |
| 1661 | Cl | H | CO$_2$Me | 2-(cPr-2,2-Cl$_2$) | 0 | 0 |
| 1662 | Cl | H | CO$_2$Me | 2-cBu | 0 | 0 |
| 1663 | Cl | H | CO$_2$Me | 2-CH$_2$CH$_2$CH$_2$-3 | 0 | 0 |
| 1664 | Cl | H | CO$_2$Me | 2-CH=CH—O-3 | 0 | 0 |
| 1665 | Cl | H | CO$_2$Me | 2-CH$_2$CH$_2$O-3 | 0 | 0 |
| 1666 | Cl | H | CO$_2$Me | 2-OCH=CH-3 | 0 | 0 |
| 1667 | Cl | H | CO$_2$Me | 2-OCH$_2$CH$_2$3 | 0 | 0 |
| 1668 | Cl | H | CO$_2$Me | 2-cPr, 5-F | 0 | 0 |
| 1669 | Cl | H | CO$_2$Me | 2-cPr, 5-Cl | 0 | 0 |
| 1670 | Cl | H | CO$_2$Me | 2-cPr, 5-Me | 0 | 0 |
| 1671 | Cl | H | CO$_2$Me | 2-OMe, 5-Me | 0 | 0 |
| 1672 | Cl | H | CO$_2$Me | 2-F, 6-iPr | 0 | 0 |
| 1673 | Cl | H | CO$_2$Me | 2-F, 6-cPr | 0 | 0 |
| 1674 | Cl | H | CO$_2$Me | 2-Cl, 6-Me | 0 | 0 |
| 1675 | Cl | H | CO$_2$Me | 2-Cl, 6-cPr | 0 | 0 |
| 1676 | Cl | H | CO$_2$Me | 2-Br, 6-Me | 0 | 0 |
| 1677 | Cl | H | CO$_2$Me | 2-Br, 6-Et | 0 | 0 |
| 1678 | Cl | H | CO$_2$Me | 2-Br, 6-cPr | 0 | 0 |
| 1679 | Cl | H | CO$_2$Me | 2-I, 6-Me | 0 | 0 |
| 1680 | Cl | H | CO$_2$Me | 2-I, 6-Et | 0 | 0 |
| 1681 | Cl | H | CO$_2$Me | 2,6-Me$_2$ | 0 | 0 |

TABLE 1-continued

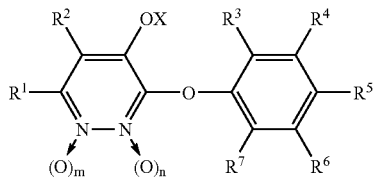

| Compound No. | $R^1$ | $R^2$ | X | $R^3$ to $R^7$ | m | n |
|---|---|---|---|---|---|---|
| 1682 | Cl | H | $CO_2Me$ | 2-Me, 6-Et | 0 | 0 |
| 1683 | Cl | H | $CO_2Me$ | 2-Me, 6-cPr | 0 | 0 |
| 1684 | Cl | H | $CO_2Me$ | 2-Et, 6-cPr | 0 | 0 |
| 1685 | Cl | H | $CO_2Me$ | 2-iPr, 6-cPr | 0 | 0 |
| 1686 | Cl | H | $CO_2Me$ | 2-tBu, 6-cPr | 0 | 0 |
| 1687 | Cl | H | $CO_2Me$ | 2,6-$cPr_2$ | 0 | 0 |
| 1688 | Cl | H | $CO_2Me$ | 2-cPr, 6-OMe | 0 | 0 |
| 1689 | Cl | H | $CO_2Me$ | 2-Br, 3,6-$Me_2$ | 0 | 0 |
| 1690 | Cl | H | $CO_2Me$ | 2-cPr, 3,2 | 0 | 0 |
| 1691 | Cl | H | $CO_2Me$ | 2-cPr, 4,6-$Me_2$ | 0 | 0 |
| 1692 | Cl | H | $CO_2Me$ | 2-Br, 5,6-$Me_2$ | 0 | 0 |
| 1693 | Cl | H | $CO_2Me$ | 2-cPr, 5,6-$Me_2$ | 0 | 0 |
| 1694 | Cl | H | $CO_2Me$ | 2-Br, 5-CH=CH—O-6 | 0 | 0 |
| 1695 | Cl | H | $CO_2Me$ | 2-Me, 5-$CH_2CH_2CH_2$-6 | 0 | 0 |
| 1696 | Cl | H | $CO_2Me$ | 2-Me, 5-$CH_2CH_2O$-6 | 0 | 0 |
| 1697 | Cl | H | $CO_2Me$ | 2-Me, 5-CH=CH—O-6 | 0 | 0 |
| 1698 | Cl | H | $CO_2Me$ | 2-Et, 5-$CH_2CH_2CH_2$-6 | 0 | 0 |
| 1699 | Cl | H | $CO_2Me$ | 2-cPr, 5-$CH_2CH_2CH_2$-6 | 0 | 0 |
| 1700 | Cl | H | $CO_2Me$ | 2-cPr, 5-CH=CH—O-6 | 0 | 0 |
| 1701 | Cl | H | $CO_2Me$ | 2-Br, 3,5,6-$Me_3$ | 0 | 0 |
| 1702 | Cl | H | $CO_2Et$ | 2-F | 0 | 0 |
| 1703 | Cl | H | $CO_2Et$ | 2-Cl | 0 | 0 |
| 1704 | Cl | H | $CO_2Et$ | 2-Br | 0 | 0 |
| 1705 | Cl | H | $CO_2Et$ | 2-I | 0 | 0 |
| 1706 | Cl | H | $CO_2Et$ | 2-Me | 0 | 0 |
| 1707 | Cl | H | $CO_2Et$ | 2-Et | 0 | 0 |
| 1708 | Cl | H | $CO_2Et$ | 2-iPr | 0 | 0 |
| 1709 | Cl | H | $CO_2Et$ | 2-tBu | 0 | 0 |
| 1710 | Cl | H | $CO_2Et$ | 2-cPr | 0 | 0 |
| 1711 | Cl | H | $CO_2Et$ | 2-(cPr-1-Me) | 0 | 0 |
| 1712 | Cl | H | $CO_2Et$ | 2-(cPr-2-Me) | 0 | 0 |
| 1713 | Cl | H | $CO_2Et$ | 2-(cPr-2,2-$Cl_2$) | 0 | 0 |
| 1714 | Cl | H | $CO_2Et$ | 2-cBu | 0 | 0 |
| 1715 | Cl | H | $CO_2Et$ | 2-$CH_2CH_2CH_2$-3 | 0 | 0 |
| 1716 | Cl | H | $CO_2Et$ | 2-CH=CH—O-3 | 0 | 0 |
| 1717 | Cl | H | $CO_2Et$ | 2-$CH_2CH_2O$-3 | 0 | 0 |
| 1718 | Cl | H | $CO_2Et$ | 2-OCH=CH-3 | 0 | 0 |
| 1719 | Cl | H | $CO_2Et$ | 2-$OCH_2CH_2$-3 | 0 | 0 |
| 1720 | Cl | H | $CO_2Et$ | 2-cPr, 5-F | 0 | 0 |
| 1721 | Cl | H | $CO_2Et$ | 2-cPr, 5-Cl | 0 | 0 |
| 1722 | Cl | H | $CO_2Et$ | 2-cPr, 5-Me | 0 | 0 |
| 1723 | Cl | H | $CO_2Et$ | 2-OMe, 5-Me | 0 | 0 |
| 1724 | Cl | H | $CO_2Et$ | 2-F, 6-iPr | 0 | 0 |
| 1725 | Cl | H | $CO_2Et$ | 2-F, 6-cPr | 0 | 0 |
| 1726 | Cl | H | $CO_2Et$ | 2-Cl, 6-Me | 0 | 0 |
| 1727 | Cl | H | $CO_2Et$ | 2-Cl, 6-cPr | 0 | 0 |
| 1728 | Cl | H | $CO_2Et$ | 2-Br, 6-Me | 0 | 0 |
| 1729 | Cl | H | $CO_2Et$ | 2-Br, 6-Et | 0 | 0 |
| 1730 | Cl | H | $CO_2Et$ | 2-Br, 6-cPr | 0 | 0 |
| 1731 | Cl | H | $CO_2Et$ | 2-I, 6-Me | 0 | 0 |
| 1732 | Cl | H | $CO_2Et$ | 2-I, 6-Et | 0 | 0 |
| 1733 | Cl | H | $CO_2Et$ | 2,6-$Me_2$ | 0 | 0 |
| 1734 | Cl | H | $CO_2Et$ | 2-Me, 6-Et | 0 | 0 |
| 1735 | Cl | H | $CO_2Et$ | 2-Me, 6-cPr | 0 | 0 |
| 1736 | Cl | H | $CO_2Et$ | 2-Et, 6-cPr | 0 | 0 |
| 1737 | Cl | H | $CO_2Et$ | 2-iPr, 6-cPr | 0 | 0 |
| 1738 | Cl | H | $CO_2Et$ | 2-tBu, 6-cPr | 0 | 0 |
| 1739 | Cl | H | $CO_2Et$ | 2,6-$cPr_2$ | 0 | 0 |
| 1740 | Cl | H | $CO_2Et$ | 2-cPr, 6-OMe | 0 | 0 |
| 1741 | Cl | H | $CO_2Et$ | 2-Br, 3,6-$Me_2$ | 0 | 0 |
| 1742 | Cl | H | $CO_2Et$ | 2-cPr, 3,5-$Me_2$ | 0 | 0 |
| 1743 | Cl | H | $CO_2Et$ | 2-cPr, 4,6-$Me_2$ | 0 | 0 |
| 1744 | Cl | H | $CO_2Et$ | 2-Br, 5,6-$Me_2$ | 0 | 0 |
| 1745 | Cl | H | $CO_2Et$ | 2-cPr, 5,6-$Me_2$ | 0 | 0 |
| 1746 | Cl | H | $CO_2Et$ | 2-Br, 5-CH=CH—O-6 | 0 | 0 |
| 1747 | Cl | H | $CO_2Et$ | 2-Me, 5-$CH_2CH_2CH_2$-6 | 0 | 0 |

TABLE 1-continued

| Compound No. | R¹ | R² | X | R³ to R⁷ | m | n |
|---|---|---|---|---|---|---|
| 1748 | Cl | H | CO$_2$Et | 2-Me, 5-CH$_2$CH$_2$O-6 | 0 | 0 |
| 1749 | Cl | H | CO$_2$Et | 2-Me, 5-CH=CH—O-6 | 0 | 0 |
| 1750 | Cl | H | CO$_2$Et | 2-Et, 5-CH$_2$CH$_2$CH$_2$-6 | 0 | 0 |
| 1751 | Cl | H | CO$_2$Et | 2-cPr, 5-CH$_2$CH$_2$CH$_2$-6 | 0 | 0 |
| 1752 | Cl | H | CO$_2$Et | 2-cPr, 5-CH=CH—O-6 | 0 | 0 |
| 1753 | Cl | H | CO$_2$Et | 2-Br, 3,5,6-Me$_3$ | 0 | 0 |
| 1754 | Cl | H | CO$_2$iBu | 2-Cl | 0 | 0 |
| 1755 | Cl | H | CO$_2$iBu | 2-Br | 0 | 0 |
| 1756 | Cl | H | CO$_2$iBu | 2-I | 0 | 0 |
| 1757 | Cl | H | CO$_2$iBu | 2-Me | 0 | 0 |
| 1758 | Cl | H | CO$_2$iBu | 2-iPr | 0 | 0 |
| 1759 | Cl | H | CO$_2$iBu | 2-cPr | 0 | 0 |
| 1760 | Cl | H | CO$_2$iBu | 2-cBu | 0 | 0 |
| 1761 | Cl | H | CO$_2$iBu | 2-CH$_2$CH$_2$CH$_2$-3 | 0 | 0 |
| 1762 | Cl | H | CO$_2$iBu | 2-cPr, 5-Me | 0 | 0 |
| 1763 | Cl | H | CO$_2$iBu | 2-OMe, 5-Me | 0 | 0 |
| 1764 | Cl | H | CO$_2$iBu | 2-F, 6-iPr | 0 | 0 |
| 1765 | Cl | H | CO$_2$iBu | 2-Cl, 6-cPr | 0 | 0 |
| 1766 | Cl | H | CO$_2$iBu | 2-Br, 6-Me | 0 | 0 |
| 1767 | Cl | H | CO$_2$iBu | 2-I, 6-Me | 0 | 0 |
| 1768 | Cl | H | CO$_2$iBu | 2,6-Me$_2$ | 0 | 0 |
| 1769 | Cl | H | CO$_2$iBu | 2-Me, 6-Et | 0 | 0 |
| 1770 | Cl | H | CO$_2$iBu | 2-Me, 6-cPr | 0 | 0 |
| 1771 | Cl | H | CO$_2$iBu | 2,6-cPr$_2$ | 0 | 0 |
| 1772 | Cl | H | CO$_2$iBu | 2-cPr, 3,5-Me$_2$ | 0 | 0 |
| 1773 | Cl | H | CO$_2$iBu | 2-cPr, 5,6-Me$_2$ | 0 | 0 |
| 1774 | Cl | H | CO$_2$Bu | 2-Me | 0 | 0 |
| 1775 | Cl | H | CO$_2$Bu | 2-iPr | 0 | 0 |
| 1776 | Cl | H | CO$_2$Bu | 2-cPr | 0 | 0 |
| 1777 | Cl | H | CO$_2$Bu | 2-CH$_2$CH$_2$CH$_2$-3 | 0 | 0 |
| 1778 | Cl | H | CO$_2$Bu | 2,6-Me$_2$ | 0 | 0 |
| 1779 | Cl | H | CO$_2$Bu | 2-Me, 6-cPr | 0 | 0 |
| 1780 | Cl | H | CO$_2$CH$_2$Cl | 2-Me | 0 | 0 |
| 1781 | Cl | H | CO$_2$CH$_2$Cl | 2-iPr | 0 | 0 |
| 1782 | Cl | H | CO$_2$CH$_2$Cl | 2-cPr | 0 | 0 |
| 1783 | Cl | H | CO$_2$CH$_2$Cl | 2-CH$_2$CH$_2$CH$_2$-3 | 0 | 0 |
| 1784 | Cl | H | CO$_2$CH$_2$Cl | 2,6-Me$_2$ | 0 | 0 |
| 1785 | Cl | H | CO$_2$CH$_2$Cl | 2-Me, 6-cPr | 0 | 0 |
| 1786 | Cl | H | CO$_2$CH$_2$CCl$_3$ | 2-Cl | 0 | 0 |
| 1787 | Cl | H | CO$_2$CH$_2$CCl$_3$ | 2-Br | 0 | 0 |
| 1788 | Cl | H | CO$_2$CH$_2$CCl$_3$ | 2-I | 0 | 0 |
| 1789 | Cl | H | CO$_2$CH$_2$CCl$_3$ | 2-Me | 0 | 0 |
| 1790 | Cl | H | CO$_2$CH$_2$CCl$_3$ | 2-iPr | 0 | 0 |
| 1791 | Cl | H | CO$_2$CH$_2$CCl$_3$ | 2-cPr | 0 | 0 |
| 1792 | Cl | H | CO$_2$CH$_2$CCl$_3$ | 2-cBu | 0 | 0 |
| 1793 | Cl | H | CO$_2$CH$_2$CCl$_3$ | 2-CH$_2$CH$_2$CH$_2$-3 | 0 | 0 |
| 1794 | Cl | H | CO$_2$CH$_2$CCl$_3$ | 2-cPr, 5-Me | 0 | 0 |
| 1795 | Cl | H | CO$_2$CH$_2$CCl$_3$ | 2-OMe, 5-Me | 0 | 0 |
| 1796 | Cl | H | CO$_2$CH$_2$CCl$_3$ | 2-F, 6-iPr | 0 | 0 |
| 1797 | Cl | H | CO$_2$CH$_2$CCl$_3$ | 2-Cl, 6-cPr | 0 | 0 |
| 1798 | Cl | H | CO$_2$CH$_2$CCl$_3$ | 2-Br, 6-Me | 0 | 0 |
| 1799 | Cl | H | CO$_2$CH$_2$CCl$_3$ | 2-I, 6-Me | 0 | 0 |
| 1800 | Cl | H | CO$_2$CH$_2$CCl$_3$ | 2,6-Me$_2$ | 0 | 0 |
| 1801 | Cl | H | CO$_2$CH$_2$CCl$_3$ | 2-Me, 6-Et | 0 | 0 |
| 1802 | Cl | H | CO$_2$CH$_2$CCl$_3$ | 2-Me, 6-cPr | 0 | 0 |
| 1803 | Cl | H | CO$_2$CH$_2$CCl$_3$ | 2,6-cPr$_2$ | 0 | 0 |
| 1804 | Cl | H | CO$_2$CH$_2$CCl$_3$ | 2-cPr, 3,5-Me$_2$ | 0 | 0 |
| 1805 | Cl | H | CO$_2$CH$_2$CCl$_3$ | 2-cPr, 5,6-Me$_2$ | 0 | 0 |
| 1806 | Cl | H | CO$_2$CH$_2$CH=CH$_2$ | 2-Me | 0 | 0 |
| 1807 | Cl | H | CO$_2$CH$_2$CH=CH$_2$ | 2-iPr | 0 | 0 |
| 1808 | Cl | H | CO$_2$CH$_2$CH=CH$_2$ | 2-cPr | 0 | 0 |
| 1809 | Cl | H | CO$_2$CH$_2$CH=CH$_2$ | 2-CH$_2$CH$_2$CH$_2$-3 | 0 | 0 |
| 1810 | Cl | H | CO$_2$CH$_2$CH=CH$_2$ | 2,6-Me$_2$ | 0 | 0 |
| 1811 | Cl | H | CO$_2$CH$_2$CH=CH$_2$ | 2-Me, 6-cPr | 0 | 0 |
| 1812 | Cl | H | CO$_2$CH$_2$Ph | 2-Me | 0 | 0 |
| 1813 | Cl | H | CO$_2$CH$_2$Ph | 2-iPr | 0 | 0 |

TABLE 1-continued

| Compound No. | R¹ | R² | X | R³ to R⁷ | m | n |
|---|---|---|---|---|---|---|
| 1814 | Cl | H | $CO_2CH_2Ph$ | 2-cPr | 0 | 0 |
| 1815 | Cl | H | $CO_2CH_2Ph$ | 2-$CH_2CH_2CH_2$-3 | 0 | 0 |
| 1816 | Cl | H | $CO_2CH_2Ph$ | 2,6-$Me_2$ | 0 | 0 |
| 1817 | Cl | H | $CO_2CH_2Ph$ | 2-Me, 6-cPr | 0 | 0 |
| 1818 | Cl | H | $CO_2CH_2CH_2OMe$ | 2-Me | 0 | 0 |
| 1819 | Cl | H | $CO_2CH_2CH_2OMe$ | 2-iPr | 0 | 0 |
| 1820 | Cl | H | $CO_2CH_2CH_2OMe$ | 2-cPr | 0 | 0 |
| 1821 | Cl | H | $CO_2CH_2CH_2OMe$ | 2-$CH_2CH_2CH_2$-3 | 0 | 0 |
| 1822 | Cl | H | $CO_2CH_2CH_2OMe$ | 2,6-$Me_2$ | 0 | 0 |
| 1823 | Cl | H | $CO_2CH_2CH_2OMe$ | 2-Me, 6-cPr | 0 | 0 |
| 1824 | Cl | H | $CO_2Ph$ | 2-Cl | 0 | 0 |
| 1825 | Cl | H | $CO_2Ph$ | 2-Br | 0 | 0 |
| 1826 | Cl | H | $CO_2Ph$ | 2-I | 0 | 0 |
| 1827 | Cl | H | $CO_2Ph$ | 2-Me | 0 | 0 |
| 1828 | Cl | H | $CO_2Ph$ | 2-iPr | 0 | 0 |
| 1829 | Cl | H | $CO_2Ph$ | 2-cPr | 0 | 0 |
| 1830 | Cl | H | $CO_2Ph$ | 2-cBu | 0 | 0 |
| 1831 | Cl | H | $CO_2Ph$ | 2-$CH_2CH_2CH_2$-3 | 0 | 0 |
| 1832 | Cl | H | $CO_2Ph$ | 2-cPr, 5-Me | 0 | 0 |
| 1833 | Cl | H | $CO_2Ph$ | 2-OMe, 5-Me | 0 | 0 |
| 1834 | Cl | H | $CO_2Ph$ | 2-F, 6-iPr | 0 | 0 |
| 1835 | Cl | H | $CO_2Ph$ | 2-Cl, 6-cPr | 0 | 0 |
| 1836 | Cl | H | $CO_2Ph$ | 2-Br, 6-Me | 0 | 0 |
| 1837 | Cl | H | $CO_2Ph$ | 2-I, 6-Me | 0 | 0 |
| 1838 | Cl | H | $CO_2Ph$ | 2,6-$Me_2$ | 0 | 0 |
| 1839 | Cl | H | $CO_2Ph$ | 2-Me, 6-Et | 0 | 0 |
| 1840 | Cl | H | $CO_2Ph$ | 2-Me, 6-cPr | 0 | 0 |
| 1841 | Cl | H | $CO_2Ph$ | 2,6-$cPr_2$ | 0 | 0 |
| 1842 | Cl | H | $CO_2Ph$ | 2-cPr, 3,5-$Me_2$ | 0 | 0 |
| 1843 | Cl | H | $CO_2Ph$ | 2-cPr, 5,6-$Me_2$ | 0 | 0 |
| 1844 | Cl | H | $CO_2$(Ph-4-Cl) | 2-Me | 0 | 0 |
| 1845 | Cl | H | $CO_2$(Ph-4-Cl) | 2-iPr | 0 | 0 |
| 1846 | Cl | H | $CO_2$(Ph-4-Cl) | 2-cPr | 0 | 0 |
| 1847 | Cl | H | $CO_2$(Ph-4-Cl) | 2-$CH_2CH_2CH_2$-3 | 0 | 0 |
| 1848 | Cl | H | $CO_2$(Ph-4-Cl) | 2,6-$Me_2$ | 0 | 0 |
| 1849 | Cl | H | $CO_2$(Ph-4-Cl) | 2-Me, 6-cPr | 0 | 0 |
| 1850 | Cl | H | $CO_2$(Ph-4-$NO_2$) | 2-Me | 0 | 0 |
| 1851 | Cl | H | $CO_2$(Ph-4-$NO_2$) | 2-iPr | 0 | 0 |
| 1852 | Cl | H | $CO_2$(Ph-4-$NO_2$) | 2-cPr | 0 | 0 |
| 1853 | Cl | H | $CO_2$(Ph-4-$NO_2$) | 2-$CH_2CH_2CH_2$-3 | 0 | 0 |
| 1854 | Cl | H | $CO_2$(Ph-4-$NO_2$) | 2,6-$Me_2$ | 0 | 0 |
| 1855 | Cl | H | $CO_2$(Ph-4-$NO_2$) | 2-Me, 6-cPr | 0 | 0 |
| 1856 | Cl | H | $CO_2$(1-Np) | 2-Me | 0 | 0 |
| 1857 | Cl | H | $CO_2$(1-Np) | 2-iPr | 0 | 0 |
| 1858 | Cl | H | $CO_2$(1-Np) | 2-cPr | 0 | 0 |
| 1859 | Cl | H | $CO_2$(1-Np) | 2-$CH_2CH_2CH_2$-3 | 0 | 0 |
| 1860 | Cl | H | $CO_2$(1-Np) | 2,6-$Me_2$ | 0 | 0 |
| 1861 | Cl | H | $CO_2$(1-Np) | 2-Me, 6-cPr | 0 | 0 |
| 1862 | Cl | H | $CO_2$(9-$Q^4$) | 2-Me | 0 | 0 |
| 1863 | Cl | H | $CO_2$(9-$Q^4$) | 2-iPr | 0 | 0 |
| 1864 | Cl | H | $CO_2$(9-$Q^4$) | 2-cPr | 0 | 0 |
| 1865 | Cl | H | $CO_2$(9-$Q^4$) | 2-$CH_2CH_2CH_2$-3 | 0 | 0 |
| 1866 | Cl | H | $CO_2$(9-$Q^4$) | 2,6-$Me_2$ | 0 | 0 |
| 1867 | Cl | H | $CO_2$(9-$Q^4$) | 2-Me, 6-cPr | 0 | 0 |
| 1868 | Cl | H | $CO_2Q^5$ | 2-Me | 0 | 0 |
| 1869 | Cl | H | $CO_2Q^5$ | 2-iPr | 0 | 0 |
| 1870 | Cl | H | $CO_2Q^5$ | 2-cPr | 0 | 0 |
| 1871 | Cl | H | $CO_2Q^5$ | 2-$CH_2CH_2CH_2$-3 | 0 | 0 |
| 1872 | Cl | H | $CO_2Q^5$ | 2,6-$Me_2$ | 0 | 0 |
| 1873 | Cl | H | $CO_2Q^5$ | 2-Me, 6-cPr | 0 | 0 |
| 1874 | Cl | H | $CONMe_2$ | 2-Cl | 0 | 0 |
| 1875 | Cl | H | $CONMe_2$ | 2-Br | 0 | 0 |
| 1876 | Cl | H | $CONMe_2$ | 2-I | 0 | 0 |
| 1877 | Cl | H | $CONMe_2$ | 2-Me | 0 | 0 |
| 1878 | Cl | H | $CONMe_2$ | 2-iPr | 0 | 0 |
| 1879 | Cl | H | $CONMe_2$ | 2-cPr | 0 | 0 |

TABLE 1-continued

| Compound No. | R¹ | R² | X | R³ to R⁷ | m | n |
|---|---|---|---|---|---|---|
| 1880 | Cl | H | CONMe$_2$ | 2-cBu | 0 | 0 |
| 1881 | Cl | H | CONMe$_2$ | 3-CF$_3$ | 0 | 0 |
| 1882 | Cl | H | CONMe$_2$ | 2-CH$_2$CH$_2$CH$_2$-3 | 0 | 0 |
| 1883 | Cl | H | CONMe$_2$ | 2-cPr, 5-Me | 0 | 0 |
| 1884 | Cl | H | CONMe$_2$ | 2-OMe, 5-Me | 0 | 0 |
| 1885 | Cl | H | CONMe$_2$ | 2-F, 6-iPr | 0 | 0 |
| 1886 | Cl | H | CONMe$_2$ | 2-Cl, 6-cPr | 0 | 0 |
| 1887 | Cl | H | CONMe$_2$ | 2-Br, 6-Me | 0 | 0 |
| 1888 | Cl | H | CONMe$_2$ | 2-I, 6-Me | 0 | 0 |
| 1889 | Cl | H | CONMe$_2$ | 2,6-Me$_2$ | 0 | 0 |
| 1890 | Cl | H | CONMe$_2$ | 2-Me, 6-Et | 0 | 0 |
| 1891 | Cl | H | CONMe$_2$ | 2-Me, 6-cPr | 0 | 0 |
| 1892 | Cl | H | CONMe$_2$ | 2,6-cPr$_2$ | 0 | 0 |
| 1893 | Cl | H | CONMe$_2$ | 2-cPr, 3,5-Me$_2$ | 0 | 0 |
| 1894 | Cl | H | CONMe$_2$ | 2-cPr, 5,6-Me$_2$ | 0 | 0 |
| 1895 | Cl | H | CONEt$_2$ | 2-Cl | 0 | 0 |
| 1896 | Cl | H | CONEt$_2$ | 2-Br | 0 | 0 |
| 1897 | Cl | H | CONEt$_2$ | 2-I | 0 | 0 |
| 1898 | Cl | H | CONEt$_2$ | 2-Me | 0 | 0 |
| 1899 | Cl | H | CONEt$_2$ | 2-iPr | 0 | 0 |
| 1900 | Cl | H | CONEt$_2$ | 2-cPr | 0 | 0 |
| 1901 | Cl | H | CONEt$_2$ | 2-cBu | 0 | 0 |
| 1902 | Cl | H | CONEt$_2$ | 2-CH$_2$CH$_2$CH$_2$-3 | 0 | 0 |
| 1903 | Cl | H | CONEt$_2$ | 2-cPr, 5-Me | 0 | 0 |
| 1904 | Cl | H | CONEt$_2$ | 2-OMe, 5-Me | 0 | 0 |
| 1905 | Cl | H | CONEt$_2$ | 2-F, 6-iPr | 0 | 0 |
| 1906 | Cl | H | CONEt$_2$ | 2-Cl, 6-cPr | 0 | 0 |
| 1907 | Cl | H | CONEt$_2$ | 2-Br, 6-Me | 0 | 0 |
| 1908 | Cl | H | CONEt$_2$ | 2-I, 6-Me | 0 | 0 |
| 1909 | Cl | H | CONEt$_2$ | 2,6-Me$_2$ | 0 | 0 |
| 1910 | Cl | H | CONEt$_2$ | 2-Me, 6-Et | 0 | 0 |
| 1911 | Cl | H | CONEt$_2$ | 2-Me, 6-cPr | 0 | 0 |
| 1912 | Cl | H | CONEt$_2$ | 2,6-cPr$_2$ | 0 | 0 |
| 1913 | Cl | H | CONEt$_2$ | 2-cPr, 3,5-Me$_2$ | 0 | 0 |
| 1914 | Cl | H | CONEt$_2$ | 2-cPr, 5,6-Me$_2$ | 0 | 0 |
| 1915 | Cl | H | CON(iPr)$_2$ | 2-Me | 0 | 0 |
| 1916 | Cl | H | CON(iPr)$_2$ | 2-iPr | 0 | 0 |
| 1917 | Cl | H | CON(iPr)$_2$ | 2-cPr | 0 | 0 |
| 1918 | Cl | H | CON(iPr)$_2$ | 2-CH$_2$CH$_2$CH$_2$-3 | 0 | 0 |
| 1919 | Cl | H | CON(iPr)$_2$ | 2,6-Me$_2$ | 0 | 0 |
| 1920 | Cl | H | CON(iPr)$_2$ | 2-Me, 6-cPr | 0 | 0 |
| 1921 | Cl | H | CO-1-Pyrd | 2-Cl | 0 | 0 |
| 1922 | Cl | H | CO-1-Pyrd | 2-Br | 0 | 0 |
| 1923 | Cl | H | CO-1-Pyrd | 2-I | 0 | 0 |
| 1924 | Cl | H | CO-1-Pyrd | 2-Me | 0 | 0 |
| 1925 | Cl | H | CO-1-Pyrd | 2-iPr | 0 | 0 |
| 1926 | Cl | H | CO-1-Pyrd | 2-cPr | 0 | 0 |
| 1927 | Cl | H | CO-1-Pyrd | 2-cBu | 0 | 0 |
| 1928 | Cl | H | CO-1-Pyrd | 2-CH$_2$CH$_2$CH$_2$-3 | 0 | 0 |
| 1929 | Cl | H | CO-1-Pyrd | 2-cPr, 5-Me | 0 | 0 |
| 1930 | Cl | H | CO-1-Pyrd | 2-OMe, 5-Me | 0 | 0 |
| 1931 | Cl | H | CO-1-Pyrd | 2-F, 6-iPr | 0 | 0 |
| 1932 | Cl | H | CO-1-Pyrd | 2-Cl, 6-cPr | 0 | 0 |
| 1933 | Cl | H | CO-1-Pyrd | 2-Br, 6-Me | 0 | 0 |
| 1934 | Cl | H | CO-1-Pyrd | 2-I, 6-Me | 0 | 0 |
| 1935 | Cl | H | CO-1-Pyrd | 2,6-Me$_2$ | 0 | 0 |
| 1936 | Cl | H | CO-1-Pyrd | 2-Me, 6-Et | 0 | 0 |
| 1937 | Cl | H | CO-1-Pyrd | 2-Me, 6-cPr | 0 | 0 |
| 1938 | Cl | H | CO-1-Pyrd | 2,6-cPr$_2$ | 0 | 0 |
| 1939 | Cl | H | CO-1-Pyrd | 2-cPr, 3,5-Me$_2$ | 0 | 0 |
| 1940 | Cl | H | CO-1-Pyrd | 2-cPr, 5,6-Me$_2$ | 0 | 0 |
| 1941 | Cl | H | CONMePh | 2-Me | 0 | 0 |
| 1942 | Cl | H | CONMePh | 2-iPr | 0 | 0 |
| 1943 | Cl | H | CONMePh | 2-cPr | 0 | 0 |
| 1944 | Cl | H | CONMePh | 2-CH$_2$CH$_2$CH$_2$-3 | 0 | 0 |
| 1945 | Cl | H | CONMePh | 2,6-Me$_2$ | 0 | 0 |

TABLE 1-continued

[Structure: pyridazine with R¹, R², OX, R³-R⁷ substituents, (O)m and (O)n on nitrogens]

| Compound No. | R¹ | R² | X | R³ to R⁷ | m | n |
|---|---|---|---|---|---|---|
| 1946 | Cl | H | CONMePh | 2-Me, 6-cPr | 0 | 0 |
| 1947 | Cl | H | CONPh$_2$ | 2-Me | 0 | 0 |
| 1948 | Cl | H | CONPh$_2$ | 2-iPr | 0 | 0 |
| 1949 | Cl | H | CONPh$_2$ | 2-cPr | 0 | 0 |
| 1950 | Cl | H | CONPh$_2$ | 2-CH$_2$CH$_2$CH$_2$-3 | 0 | 0 |
| 1951 | Cl | H | CONPh$_2$ | 2,6-Me$_2$ | 0 | 0 |
| 1952 | Cl | H | CONPh$_2$ | 2-Me, 6-cPr | 0 | 0 |
| 1953 | Cl | H | COSMe | 2-Me | 0 | 0 |
| 1954 | Cl | H | COSMe | 2-iPr | 0 | 0 |
| 1955 | Cl | H | COSMe | 2-cPr | 0 | 0 |
| 1956 | Cl | H | COSMe | 2-CH$_2$CH$_2$CH$_2$-3 | 0 | 0 |
| 1957 | Cl | H | COSMe | 2,6-Me$_2$ | 0 | 0 |
| 1958 | Cl | H | COSMe | 2-Me, 6-cPr | 0 | 0 |
| 1959 | Cl | H | COSC$_7$H$_{15}$ | 2-Me | 0 | 0 |
| 1960 | Cl | H | COSC$_7$H$_{15}$ | 2-iPr | 0 | 0 |
| 1961 | Cl | H | COSC$_7$H$_{15}$ | 2-cPr | 0 | 0 |
| 1962 | Cl | H | COSC$_7$H$_{15}$ | 2-CH$_2$CH$_2$CH$_2$-3 | 0 | 0 |
| 1963 | Cl | H | COSC$_7$H$_{15}$ | 2,6-Me$_2$ | 0 | 0 |
| 1964 | Cl | H | COSC$_7$H$_{15}$ | 2-Me, 6-cPr | 0 | 0 |
| 1965 | Cl | H | COScHx | 2-Me | 0 | 0 |
| 1966 | Cl | H | COScHx | 2-iPr | 0 | 0 |
| 1967 | Cl | H | COScHx | 2-cPr | 0 | 0 |
| 1968 | Cl | H | COScHx | 2-CH$_2$CH$_2$CH$_2$-3 | 0 | 0 |
| 1969 | Cl | H | COScHx | 2,6-Me$_2$ | 0 | 0 |
| 1970 | Cl | H | COScHx | 2-Me, 6-cPr | 0 | 0 |
| 1971 | Cl | H | COSPh | 2-Me | 0 | 0 |
| 1972 | Cl | H | COSPh | 2-iPr | 0 | 0 |
| 1973 | Cl | H | COSPh | 2-cPr | 0 | 0 |
| 1974 | Cl | H | COSPh | 2-CH$_2$CH$_2$CH$_2$-3 | 0 | 0 |
| 1975 | Cl | H | COSPh | 2,6-Me$_2$ | 0 | 0 |
| 1976 | Cl | H | COSPh | 2-Me, 6-cPr | 0 | 0 |
| 1977 | Cl | H | SO$_2$Me | 2-F | 0 | 0 |
| 1978 | Cl | H | SO$_2$Me | 2-Cl | 0 | 0 |
| 1979 | Cl | H | SO$_2$Me | 2-Br | 0 | 0 |
| 1980 | Cl | H | SO$_2$Me | 2-I | 0 | 0 |
| 1981 | Cl | H | SO$_2$Me | 2-Me | 0 | 0 |
| 1982 | Cl | H | SO$_2$Me | 2-Et | 0 | 0 |
| 1983 | Cl | H | SO$_2$Me | 2-iPr | 0 | 0 |
| 1984 | Cl | H | SO$_2$Me | 2-tBu | 0 | 0 |
| 1985 | Cl | H | SO$_2$Me | 2-cPr | 0 | 0 |
| 1986 | Cl | H | SO$_2$Me | 2-(cPr-1-Me) | 0 | 0 |
| 1987 | Cl | H | SO$_2$Me | 2-(cPr-2-Me) | 0 | 0 |
| 1988 | Cl | H | SO$_2$Me | 2-(cPr-2,2-Cl$_2$) | 0 | 0 |
| 1989 | Cl | H | SO$_2$Me | 2-cBu | 0 | 0 |
| 1990 | Cl | H | SO$_2$Me | 2-CH$_2$CH$_2$CH$_2$-3 | 0 | 0 |
| 1991 | Cl | H | SO$_2$Me | 2-CH=CH—O-3 | 0 | 0 |
| 1992 | Cl | H | SO$_2$Me | 2-CH$_2$CH$_2$O-3 | 0 | 0 |
| 1993 | Cl | H | SO$_2$Me | 2-OCH=CH-3 | 0 | 0 |
| 1994 | Cl | H | SO$_2$Me | 2OCH$_2$CH$_2$-3 | 0 | 0 |
| 1995 | Cl | H | SO$_2$Me | 2-cPr, 5-F | 0 | 0 |
| 1996 | Cl | H | SO$_2$Me | 2-cPr, 5-Cl | 0 | 0 |
| 1997 | Cl | H | SO$_2$Me | 2-cPr, 5-Me | 0 | 0 |
| 1998 | Cl | H | SO$_2$Me | 2-OMe, 5-Me | 0 | 0 |
| 1999 | Cl | H | SO$_2$Me | 2-F, 6-iPr | 0 | 0 |
| 2000 | Cl | H | SO$_2$Me | 2-F, 6-cPr | 0 | 0 |
| 2001 | Cl | H | SO$_2$Me | 2-Cl, 6-Me | 0 | 0 |
| 2002 | Cl | H | SO$_2$Me | 2-Cl, 6-cPr | 0 | 0 |
| 2003 | Cl | H | SO$_2$Me | 2-Br, 6-Me | 0 | 0 |
| 2004 | Cl | H | SO$_2$Me | 2-Br, 6-Et | 0 | 0 |
| 2005 | Cl | H | SO$_2$Me | 2-Br, 6-cPr | 0 | 0 |
| 2006 | Cl | H | SO$_2$Me | 2-I, 6-Me | 0 | 0 |
| 2007 | Cl | H | SO$_2$Me | 2-I, 6-Et | 0 | 0 |
| 2008 | Cl | H | SO$_2$Me | 2,6-Me$_2$ | 0 | 0 |
| 2009 | Cl | H | SO$_2$Me | 2-Me, 6-Et | 0 | 0 |
| 2010 | Cl | H | SO$_2$Me | 2-Me, 6-cPr | 0 | 0 |
| 2011 | Cl | H | SO$_2$Me | 2-Et, 6-cPr | 0 | 0 |

TABLE 1-continued

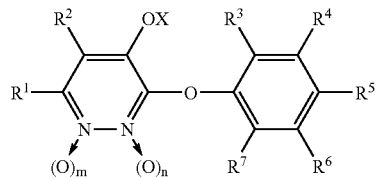

| Compound No. | R¹ | R² | X | R³ to R⁷ | m | n |
|---|---|---|---|---|---|---|
| 2012 | Cl | H | SO$_2$Me | 2-iPr, 6-cPr | 0 | 0 |
| 2013 | Cl | H | SO$_2$Me | 2-tBu, 6-cPr | 0 | 0 |
| 2014 | Cl | H | SO$_2$Me | 2,6-cPr$_2$ | 0 | 0 |
| 2015 | Cl | H | SO$_2$Me | 2-cPr, 6-OMe | 0 | 0 |
| 2016 | Cl | H | SO$_2$Me | 2-Br, 3,6-Me$_2$ | 0 | 0 |
| 2017 | Cl | H | SO$_2$Me | 2-cPr, 3,5-Me$_2$ | 0 | 0 |
| 2018 | Cl | H | SO$_2$Me | 2-cPr, 4, 6-Me$_2$ | 0 | 0 |
| 2019 | Cl | H | SO$_2$Me | 2-Br, 5,6-Me$_2$ | 0 | 0 |
| 2020 | Cl | H | SO$_2$Me | 2-cPr, 5,6-Me$_2$ | 0 | 0 |
| 2021 | Cl | H | SO$_2$Me | 2-Br, 5-CH=CH—O-6 | 0 | 0 |
| 2022 | Cl | H | SO$_2$Me | 2-Me, 5-CH$_2$CH$_2$CH$_2$-6 | 0 | 0 |
| 2023 | Cl | H | SO$_2$Me | 2-Me, 5-CH$_2$CH$_2$O-6 | 0 | 0 |
| 2024 | Cl | H | SO$_2$Me | 2-Me, 5-CH=CH—O-6 | 0 | 0 |
| 2025 | Cl | H | SO$_2$Me | 2-Et, 5-CH$_2$CH$_2$CH$_2$-6 | 0 | 0 |
| 2026 | Cl | H | SO$_2$Me | 2-cPr, 5-CH$_2$CH$_2$CH$_2$-6 | 0 | 0 |
| 2027 | Cl | H | SO$_2$Me | 2-cPr, 5-CH=CH—O-6 | 0 | 0 |
| 2028 | Cl | H | SO$_2$Me | 2-Br, 3,5,6-Me$_3$ | 0 | 0 |
| 2029 | Cl | H | SO$_2$Et | 2-Me | 0 | 0 |
| 2030 | Cl | H | SO$_2$Et | 2-iPr | 0 | 0 |
| 2031 | Cl | H | SO$_2$Et | 2-cPr | 0 | 0 |
| 2032 | Cl | H | SO$_2$Et | 2-CH$_2$CH$_2$CH$_2$-3 | 0 | 0 |
| 2033 | Cl | H | SO$_2$Et | 2,6-Me$_2$ | 0 | 0 |
| 2034 | Cl | H | SO$_2$Et | 2-Me, 6-cPr | 0 | 0 |
| 2035 | Cl | H | SO$_2$Pr | 2-Cl | 0 | 0 |
| 2036 | Cl | H | SO$_2$Pr | 2-Br | 0 | 0 |
| 2037 | Cl | H | SO$_2$Pr | 2-I | 0 | 0 |
| 2038 | Cl | H | SO$_2$Pr | 2-Me | 0 | 0 |
| 2039 | Cl | H | SO$_2$Pr | 2-iPr | 0 | 0 |
| 2040 | Cl | H | SO$_2$Pr | 2-cPr | 0 | 0 |
| 2041 | Cl | H | SO$_2$Pr | 2-cBu | 0 | 0 |
| 2042 | Cl | H | SO$_2$Pr | 2-CH$_2$CH$_2$CH$_2$-3 | 0 | 0 |
| 2043 | Cl | H | SO$_2$Pr | 2-cPr, 5-Me | 0 | 0 |
| 2044 | Cl | H | SO$_2$Pr | 2-OMe, 5-Me | 0 | 0 |
| 2045 | Cl | H | SO$_2$Pr | 2-F, 6-iPr | 0 | 0 |
| 2046 | Cl | H | SO$_2$Pr | 2-Cl, 6-cPr | 0 | 0 |
| 2047 | Cl | H | SO$_2$Pr | 2-Br, 6-Me | 0 | 0 |
| 2048 | Cl | H | SO$_2$Pr | 2-I, 6-Me | 0 | 0 |
| 2049 | Cl | H | SO$_2$Pr | 2,6-Me$_2$ | 0 | 0 |
| 2050 | Cl | H | SO$_2$Pr | 2-Me, 6-Et | 0 | 0 |
| 2051 | Cl | H | SO$_2$Pr | 2-Me, 6-cPr | 0 | 0 |
| 2052 | Cl | H | SO$_2$Pr | 2,6-cPr$_2$ | 0 | 0 |
| 2053 | Cl | H | SO$_2$Pr | 2-cPr, 3,5-Me$_2$ | 0 | 0 |
| 2054 | Cl | H | SO$_2$Pr | 2-cPr, 5,6-Me$_2$ | 0 | 0 |
| 2055 | Cl | H | SO$_2$iPr | 2-Me | 0 | 0 |
| 2056 | Cl | H | SO$_2$iPr | 2-iPr | 0 | 0 |
| 2057 | Cl | H | SO$_2$iPr | 2-cPr | 0 | 0 |
| 2058 | Cl | H | SO$_2$iPr | 2-CH$_2$CH$_2$CH$_2$-3 | 0 | 0 |
| 2059 | Cl | H | SO$_2$iPr | 2,6-Me$_2$ | 0 | 0 |
| 2060 | Cl | H | SO$_2$iPr | 2-Me, 6-cPr | 0 | 0 |
| 2061 | Cl | H | SO$_2$C$_8$H$_{17}$ | 2-Me | 0 | 0 |
| 2062 | Cl | H | SO$_2$C$_8$H$_{17}$ | 2-iPr | 0 | 0 |
| 2063 | Cl | H | SO$_2$C$_8$H$_{17}$ | 2-cPr | 0 | 0 |
| 2064 | Cl | H | SO$_2$C$_8$H$_{17}$ | 2-CH$_2$CH$_2$CH$_2$-3 | 0 | 0 |
| 2065 | Cl | H | SO$_2$C$_8$H$_{17}$ | 2,6-Me$_2$ | 0 | 0 |
| 2066 | Cl | H | SO$_2$C$_8$H$_{17}$ | 2Me, 6-cPr | 0 | 0 |
| 2067 | Cl | H | SO$_2$CH$_2$Cl | 2-Me | 0 | 0 |
| 2068 | Cl | H | SO$_2$CH$_2$Cl | 2-iPr | 0 | 0 |
| 2069 | Cl | H | SO$_2$CH$_2$Cl | 2-cPr | 0 | 0 |
| 2070 | Cl | H | SO$_2$CH$_2$Cl | 2-CH$_2$CH$_2$CH$_2$-3 | 0 | 0 |
| 2071 | Cl | H | SO$_2$CH$_2$Cl | 2,6-Me$_2$ | 0 | 0 |
| 2072 | Cl | H | SO$_2$CH$_2$Cl | 2-Me, 6-cPr | 0 | 0 |
| 2073 | Cl | H | SO$_2$CF$_3$ | 2-F | 0 | 0 |
| 2074 | Cl | H | SO$_2$CF$_3$ | 2-Cl | 0 | 0 |
| 2075 | Cl | H | SO$_2$CF$_3$ | 2-Br | 0 | 0 |
| 2076 | Cl | H | SO$_2$CF$_3$ | 2-I | 0 | 0 |
| 2077 | Cl | H | SO$_2$CF$_3$ | 2-Me | 0 | 0 |

TABLE 1-continued

| Compound No. | R¹ | R² | X | R³ to R⁷ | m | n |
|---|---|---|---|---|---|---|
| 2078 | Cl | H | $SO_2CF_3$ | 2-Et | 0 | 0 |
| 2079 | Cl | H | $SO_2CF_3$ | 2-iPr | 0 | 0 |
| 2080 | Cl | H | $SO_2CF_3$ | 2-tBu | 0 | 0 |
| 2081 | Cl | H | $SO_2CF_3$ | 2-cPr | 0 | 0 |
| 2082 | Cl | H | $SO_2CF_3$ | 2-(cPr-1-Me) | 0 | 0 |
| 2083 | Cl | H | $SO_2CF_3$ | 2-(cPr-2-Me) | 0 | 0 |
| 2084 | Cl | H | $SO_2CF_3$ | 2-(cPr-2,2-Cl₂) | 0 | 0 |
| 2085 | Cl | H | $SO_2CF_3$ | 2-cBu | 0 | 0 |
| 2086 | Cl | H | $SO_2CF_3$ | 2-CH₂CH₂CH₂-3 | 0 | 0 |
| 2087 | Cl | H | $SO_2CF_3$ | 2-CH=CH—O-3 | 0 | 0 |
| 2088 | Cl | H | $SO_2CF_3$ | 2-CH₂CH₂O-3 | 0 | 0 |
| 2089 | Cl | H | $SO_2CF_3$ | 2-OCH=CH-3 | 0 | 0 |
| 2090 | Cl | H | $SO_2CF_3$ | 2-OCH₂CH₂-3 | 0 | 0 |
| 2091 | Cl | H | $SO_2CF_3$ | 2-cPr, 5-F | 0 | 0 |
| 2092 | Cl | H | $SO_2CF_3$ | 2-cPr, 5-Cl | 0 | 0 |
| 2093 | Cl | H | $SO_2CF_3$ | 2-cPr, 5-Me | 0 | 0 |
| 2094 | Cl | H | $SO_2CF_3$ | 2-OMe, 5-Me | 0 | 0 |
| 2095 | Cl | H | $SO_2CF_3$ | 2-F, 6-iPr | 0 | 0 |
| 2096 | Cl | H | $SO_2CF_3$ | 2-F, 6-cPr | 0 | 0 |
| 2097 | Cl | H | $SO_2CF_3$ | 2-Cl, 6-Me | 0 | 0 |
| 2098 | Cl | H | $SO_2CF_3$ | 2-Cl, 6-cPr | 0 | 0 |
| 2099 | Cl | H | $SO_2CF_3$ | 2-Br, 6-Me | 0 | 0 |
| 2100 | Cl | H | $SO_2CF_3$ | 2-Br, 6-Et | 0 | 0 |
| 2101 | Cl | H | $SO_2CF_3$ | 2-Br, 6-cPr | 0 | 0 |
| 2102 | Cl | H | $SO_2CF_3$ | 2-I, 6-Me | 0 | 0 |
| 2103 | Cl | H | $SO_2CF_3$ | 2-I, 6-Et | 0 | 0 |
| 2104 | Cl | H | $SO_2CF_3$ | 2,6-Me₂ | 0 | 0 |
| 2105 | Cl | H | $SO_2CF_3$ | 2-Me, 6-Et | 0 | 0 |
| 2106 | Cl | H | $SO_2CF_3$ | 2-Me, 6-cPr | 0 | 0 |
| 2107 | Cl | H | $SO_2CF_3$ | 2-Et, 6-cPr | 0 | 0 |
| 2108 | Cl | H | $SO_2CF_3$ | 2-iPr, 6-cPr | 0 | 0 |
| 2109 | Cl | H | $SO_2CF_3$ | 2-tBu, 6-cPr | 0 | 0 |
| 2110 | Cl | H | $SO_2CF_3$ | 2,6-cPr₂ | 0 | 0 |
| 2111 | Cl | H | $SO_2CF_3$ | 2-cPr, 6-OMe | 0 | 0 |
| 2112 | Cl | H | $SO_2CF_3$ | 2-Br, 3,6-Me₂ | 0 | 0 |
| 2113 | Cl | H | $SO_2CF_3$ | 2-cPr, 3,5-Me₂ | 0 | 0 |
| 2114 | Cl | H | $SO_2CF_3$ | 2-cPr, 4, 6-Me₂ | 0 | 0 |
| 2115 | Cl | H | $SO_2CF_3$ | 2-Br, 5,6-Me₂ | 0 | 0 |
| 2116 | Cl | H | $SO_2CF_3$ | 2-cPr, 5,6-Me₂ | 0 | 0 |
| 2117 | Cl | H | $SO_2CF_3$ | 2-Br, 5-CH=CH—O—6 | 0 | 0 |
| 2118 | Cl | H | $SO_2CF_3$ | 2-Me, 5-CH₂CH₂CH₂-6 | 0 | 0 |
| 2119 | Cl | H | $SO_2CF_3$ | 2-Me, 5-CH₂CH₂O-6 | 0 | 0 |
| 2120 | Cl | H | $SO_2CF_3$ | 2-Me, 5-CH=CH—O—6 | 0 | 0 |
| 2121 | Cl | H | $SO_2CF_3$ | 2-Et, 5-CH₂CH₂CH₂-6 | 0 | 0 |
| 2122 | Cl | H | $SO_2CF_3$ | 2-cPr, 5-CH₂CH₂CH₂-6 | 0 | 0 |
| 2123 | Cl | H | $SO_2CF_3$ | 2-cPr, 5-CH=CH—O—6 | 0 | 0 |
| 2124 | Cl | H | $SO_2CF_3$ | 2-Br, 3,5,6-Me₃ | 0 | 0 |
| 2125 | Cl | H | $SO_2CCl_3$ | 2-Me | 0 | 0 |
| 2126 | Cl | H | $SO_2CCl_3$ | 2-iPr | 0 | 0 |
| 2127 | Cl | H | $SO_2CCl_3$ | 2-cPr | 0 | 0 |
| 2128 | Cl | H | $SO_2CCl_3$ | 2-CH₂CH₂CH₂-3 | 0 | 0 |
| 2129 | Cl | H | $SO_2CCl_3$ | 2,6-Me₂ | 0 | 0 |
| 2130 | Cl | H | $SO_2CCl_3$ | 2-Me, 6-cPr | 0 | 0 |
| 2131 | Cl | H | $SO_2CH_2CF_3$ | 2-Me | 0 | 0 |
| 2132 | Cl | H | $SO_2CH_2CF_3$ | 2-iPr | 0 | 0 |
| 2133 | Cl | H | $SO_2CH_2CF_3$ | 2-cPr | 0 | 0 |
| 2134 | Cl | H | $SO_2CH_2CF_3$ | 2-CH₂CH₂CH₂-3 | 0 | 0 |
| 2135 | Cl | H | $SO_2CH_2CF_3$ | 2,6-Me₂ | 0 | 0 |
| 2136 | Cl | H | $SO_2CH_2CF_3$ | 2-Me, 6-cPr | 0 | 0 |
| 2137 | Cl | H | $SO_2CH_2CH_2CH_2Cl$ | 2-Me | 0 | 0 |
| 2138 | Cl | H | $SO_2CH_2CH_2CH_2Cl$ | 2-iPr | 0 | 0 |
| 2139 | Cl | H | $SO_2CH_2CH_2CH_2Cl$ | 2-cPr | 0 | 0 |
| 2140 | Cl | H | $SO_2CH_2CH_2CH_2Cl$ | 2-CH₂CH₂-3 | 0 | 0 |
| 2141 | Cl | H | $SO_2CH_2CH_2CH_2Cl$ | 2,6-Me₂ | 0 | 0 |
| 2142 | Cl | H | $SO_2CH_2CH_2CH_2Cl$ | 2-Me, 6-cPr | 0 | 0 |
| 2143 | Cl | H | $SO_2Ph$ | 2-F | 0 | 0 |

TABLE 1-continued

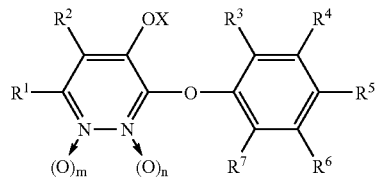

| Compound No. | $R^1$ | $R^2$ | X | $R^3$ to $R^7$ | m | n |
|---|---|---|---|---|---|---|
| 2144 | Cl | H | $SO_2Ph$ | 2-Cl | 0 | 0 |
| 2145 | Cl | H | $SO_2Ph$ | 2-Br | 0 | 0 |
| 2146 | Cl | H | $SO_2Ph$ | 2-I | 0 | 0 |
| 2147 | Cl | H | $SO_2Ph$ | 2-Me | 0 | 0 |
| 2148 | Cl | H | $SO_2Ph$ | 2-Et | 0 | 0 |
| 2149 | Cl | H | $SO_2Ph$ | 2-iPr | 0 | 0 |
| 2150 | Cl | H | $SO_2Ph$ | 2-tBu | 0 | 0 |
| 2151 | Cl | H | $SO_2Ph$ | 2-cPr | 0 | 0 |
| 2152 | Cl | H | $SO_2Ph$ | 2-(cPr-1-Me) | 0 | 0 |
| 2153 | Cl | H | $SO_2Ph$ | 2-(cPr-2-Me) | 0 | 0 |
| 2154 | Cl | H | $SO_2Ph$ | 2-(cPr-2,2-$Cl_2$) | 0 | 0 |
| 2155 | Cl | H | $SO_2Ph$ | 2-cBu | 0 | 0 |
| 2156 | Cl | H | $SO_2Ph$ | 2-$CH_2CH_2CH_2$-3 | 0 | 0 |
| 2157 | Cl | H | $SO_2Ph$ | 2-CH=CHO-3 | 0 | 0 |
| 2158 | Cl | H | $SO_2Ph$ | 2-$CH_2CH_2$O-3 | 0 | 0 |
| 2159 | Cl | H | $SO_2Ph$ | 2-OCH=CH-3 | 0 | 0 |
| 2160 | Cl | H | $SO_2Ph$ | 2-OCH$_2$CH$_2$-3 | 0 | 0 |
| 2161 | Cl | H | $SO_2Ph$ | 2-cPr, 5-F | 0 | 0 |
| 2162 | Cl | H | $SO_2Ph$ | 2-cPr, 5-Cl | 0 | 0 |
| 2163 | Cl | H | $SO_2Ph$ | 2-cPr, 5-Me | 0 | 0 |
| 2164 | Cl | H | $SO_2Ph$ | 2-OMe, 5-Me | 0 | 0 |
| 2165 | Cl | H | $SO_2Ph$ | 2-F, 6-iPr | 0 | 0 |
| 2166 | Cl | H | $SO_2Ph$ | 2-F, 6-cPr | 0 | 0 |
| 2167 | Cl | H | $SO_2Ph$ | 2-Cl, 6-Me | 0 | 0 |
| 2168 | Cl | H | $SO_2Ph$ | 2-Cl, 6-cPr | 0 | 0 |
| 2169 | Cl | H | $SO_2Ph$ | 2-Br, 6-Me | 0 | 0 |
| 2170 | Cl | H | $SO_2Ph$ | 2-Br, 6-Et | 0 | 0 |
| 2171 | Cl | H | $SO_2Ph$ | 2-Br, 6-cPr | 0 | 0 |
| 2172 | Cl | H | $SO_2Ph$ | 2-I, 6-Me | 0 | 0 |
| 2173 | Cl | H | $SO_2Ph$ | 2-I, 6-Et | 0 | 0 |
| 2174 | Cl | H | $SO_2Ph$ | 2,6-$Me_2$ | 0 | 0 |
| 2175 | Cl | H | $SO_2Ph$ | 2-Me, 6-Et | 0 | 0 |
| 2176 | Cl | H | $SO_2Ph$ | 2-Me, 6-cPr | 0 | 0 |
| 2177 | Cl | H | $SO_2Ph$ | 2-Et, 6-cPr | 0 | 0 |
| 2178 | Cl | H | $SO_2Ph$ | 2-iPr, 6-cPr | 0 | 0 |
| 2179 | Cl | H | $SO_2Ph$ | 2-tBu, 6-cPr | 0 | 0 |
| 2180 | Cl | H | $SO_2Ph$ | 2,6-$cPr_2$ | 0 | 0 |
| 2181 | Cl | H | $SO_2Ph$ | 2-cPr, 6-OMe | 0 | 0 |
| 2182 | Cl | H | $SO_2Ph$ | 2-Br, 3,6-$Me_2$ | 0 | 0 |
| 2183 | Cl | H | $SO_2Ph$ | 2-cPr, 3,5-$Me_2$ | 0 | 0 |
| 2184 | Cl | H | $SO_2Ph$ | 2-cPr, 4, 6-$Me_2$ | 0 | 0 |
| 2185 | Cl | H | $SO_2Ph$ | 2-Br, 5,6-$Me_2$ | 0 | 0 |
| 2186 | Cl | H | $SO_2Ph$ | 2-cPr, 5,6-$Me_2$ | 0 | 0 |
| 2187 | Cl | H | $SO_2Ph$ | 2-Br, 5-CH=CH—O-6 | 0 | 0 |
| 2188 | Cl | H | $SO_2Ph$ | 2-Me, 5-$CH_2CH_2CH_2$-6 | 0 | 0 |
| 2189 | Cl | H | $SO_2Ph$ | 2-Me, 5-$CH_2CH_2$O-6 | 0 | 0 |
| 2190 | Cl | H | $SO_2Ph$ | 2-Me, 5-CH=CH—O-6 | 0 | 0 |
| 2191 | Cl | H | $SO_2Ph$ | 2-Et, 5-$CH_2CH_2CH_2$-6 | 0 | 0 |
| 2192 | Cl | H | $SO_2Ph$ | 2-cPr, 5-$CH_2CH_2CH_2$-6 | 0 | 0 |
| 2193 | Cl | H | $SO_2Ph$ | 2-cPr, 5-CH=CH—O-6 | 0 | 0 |
| 2194 | Cl | H | $SO_2Ph$ | 2-Br, 3,5,6-$Me_3$ | 0 | 0 |
| 2195 | Cl | H | $SO_2$ (Ph-4-Cl) | 2-Cl | 0 | 0 |
| 2196 | Cl | H | $SO_2$ (Ph-4-Cl) | 2-Br | 0 | 0 |
| 2197 | Cl | H | $SO_2$ (Ph-4-cl) | 2-I | 0 | 0 |
| 2198 | Cl | H | $SO_2$ (Ph-4-Cl) | 2-Me | 0 | 0 |
| 2199 | Cl | H | $SO_2$ (Ph-4-Cl) | 2-iPr | 0 | 0 |
| 2200 | Cl | H | $SO_2$ (Ph-4-Cl) | 2-tBu | 0 | 0 |
| 2201 | Cl | H | $SO_2$ (Ph-4-Cl) | 2-cPr | 0 | 0 |
| 2202 | Cl | H | $SO_2$ (Ph-4-Cl) | 2-cBu | 0 | 0 |
| 2203 | Cl | H | $SO_2$ (Ph-4-Cl) | 2-$CH_2CH_2CH_2$-3 | 0 | 0 |
| 2204 | Cl | H | $SO_2$ (Ph-4-Cl) | 2-cPr, 5-Me | 0 | 0 |
| 2205 | Cl | H | $SO_2$ (Ph-4-Cl) | 2-OMe, 5-Me | 0 | 0 |
| 2206 | Cl | H | $SO_2$ (Ph-4-Cl) | 2-F, 6-iPr | 0 | 0 |
| 2207 | Cl | H | $SO_2$ (Ph-4-Cl) | 2-Cl, 6-cPr | 0 | 0 |
| 2208 | Cl | H | $SO_2$ (Ph-4-Cl) | 2-Br, 6-Me | 0 | 0 |
| 2209 | Cl | H | $SO_2$ (Ph-4-Cl) | 2-I, 6-Me | 0 | 0 |

TABLE 1-continued

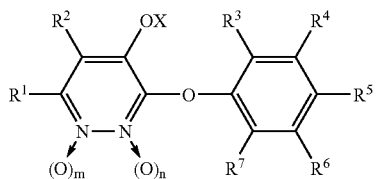

| Compound No. | $R^1$ | $R^2$ | X | $R^3$ to $R^7$ | m | n |
|---|---|---|---|---|---|---|
| 2210 | Cl | H | $SO_2$ (Ph-4-Cl) | 2,6-$Me_2$ | 0 | 0 |
| 2211 | Cl | H | $SO_2$ (Ph-4-Cl) | 2-Me, 6-Et | 0 | 0 |
| 2212 | Cl | H | $SO_2$ (Ph-4-Cl) | 2-Me, 6-cPr | 0 | 0 |
| 2213 | Cl | H | $SO_2$ (Ph-4-Cl) | 2,6-$cPr_2$ | 0 | 0 |
| 2214 | Cl | H | $SO_2$ (Ph-4-Cl) | 2-cPr, 3,5-$Me_2$ | 0 | 0 |
| 2215 | Cl | H | $SO_2$ (Ph-4-Cl) | 2-cPr, 5,6-$Me_2$ | 0 | 0 |
| 2216 | Cl | H | $SO_2$ (Ph-4-Me) | 2-F | 0 | 0 |
| 2217 | Cl | H | $SO_2$ (Ph-4-Me) | 2-Cl | 0 | 0 |
| 2218 | Cl | H | $SO_2$ (Ph-4-Me) | 2-Br | 0 | 0 |
| 2219 | Cl | H | $SO_2$ (Ph-4-Me) | 2-I | 0 | 0 |
| 2220 | Cl | H | $SO_2$ (Ph-4-Me) | 2-Me | 0 | 0 |
| 2221 | Cl | H | $SO_2$ (Ph-4-Me) | 2-Et | 0 | 0 |
| 2222 | Cl | H | $SO_2$ (Ph-4-Me) | 2-iPr | 0 | 0 |
| 2223 | Cl | H | $SO_2$ (Ph-4-Me) | 2-sBu | 0 | 0 |
| 2224 | Cl | H | $SO_2$ (Ph-4-Me) | 2-tBu | 0 | 0 |
| 2225 | Cl | H | $SO_2$ (Ph-4-Me) | 2-cPr | 0 | 0 |
| 2226 | Cl | H | $SO_2$ (Ph-4-Me) | 2-(cPr-1-Me) | 0 | 0 |
| 2227 | Cl | H | $SO_2$ (Ph-4-Me) | 2-(cPr-2-Me) | 0 | 0 |
| 2228 | Cl | H | $SO_2$ (Ph-4-Me) | 2-(cPr-2,2-$Cl_2$) | 0 | 0 |
| 2229 | Cl | H | $SO_2$ (Ph-4-Me) | 2-cBu | 0 | 0 |
| 2230 | Cl | H | $SO_2$ (Ph-4-Me) | 2-cHx | 0 | 0 |
| 2231 | Cl | H | $SO_2$ (Ph-4-Me) | 2-Ph | 0 | 0 |
| 2232 | Cl | H | $SO_2$ (Ph-4-Me) | 2-OMe | 0 | 0 |
| 2233 | Cl | H | $SO_2$ (Ph-4-Me) | 2-$OSO_2$ (Ph-4-Me) | 0 | 0 |
| 2234 | Cl | H | $SO_2$ (Ph-4-Me) | 3-Cl | 0 | 0 |
| 2235 | Cl | H | $SO_2$ (Ph-4-Me) | 3-tBu | 0 | 0 |
| 2236 | Cl | H | $SO_2$ (Ph-4-Me) | 3-$CF_3$ | 0 | 0 |
| 2237 | Cl | H | $SO_2$ (Ph-4-Me) | 3-CN | 0 | 0 |
| 2238 | Cl | H | $SO_2$ (Ph-4-Me) | 3-OMe | 0 | 0 |
| 2239 | Cl | H | $SO_2$ (Ph-4-Me) | 2-$CH_2CH_2CH_2$-3 | 0 | 0 |
| 2240 | Cl | H | $SO_2$ (Ph-4-Me) | 2-CH=CH=CH=CH-3 | 0 | 0 |
| 2241 | Cl | H | $SO_2$ (Ph-4-Me) | 2-CH=CH—O-3 | 0 | 0 |
| 2242 | Cl | H | $SO_2$ (Ph-4-Me) | 2-$CH_2CH_2$O-3 | 0 | 0 |
| 2243 | Cl | H | $SO_2$ (Ph-4-Me) | 2-OCH=CH-3 | 0 | 0 |
| 2244 | Cl | H | $SO_2$ (Ph-4-Me) | 2-O$CH_2CH_2$-3 | 0 | 0 |
| 2245 | Cl | H | $SO_2$ (Ph-4-Me) | 2-Br, 4-tBu | 0 | 0 |
| 2246 | Cl | H | $SO_2$ (Ph-4-Me) | 2-Me, 4-Cl | 0 | 0 |
| 2247 | Cl | H | $SO_2$ (Ph-4-Me) | 2, 4-$Me_2$ | 0 | 0 |
| 2248 | Cl | H | $SO_2$ (Ph-4-Me) | 2-iPr, 4-Br | 0 | 0 |
| 2249 | Cl | H | $SO_2$ (Ph-4-Me) | 2-iPr, 5-Me | 0 | 0 |
| 2250 | Cl | H | $SO_2$ (Ph-4-Me) | 2-cPr, 5-F | 0 | 0 |
| 2251 | Cl | H | $SO_2$ (Ph-4-Me) | 2-cPr, 5-Cl | 0 | 0 |
| 2252 | Cl | H | $SO_2$ (Ph-4-Me) | 2-cPr, 5-Me | 0 | 0 |
| 2253 | Cl | H | $SO_2$ (Ph-4-Me) | 2-OMe, 5-Me | 0 | 0 |
| 2254 | Cl | H | $SO_2$ (Ph-4-Me) | 2-F, 6-iPr | 0 | 0 |
| 2255 | Cl | H | $SO_2$ (Ph-4-Me) | 2-F, 6-cPr | 0 | 0 |
| 2256 | Cl | H | $SO_2$ (Ph-4-Me) | 2-Cl, 6-Me | 0 | 0 |
| 2257 | Cl | H | $SO_2$ (Ph-4-Me) | 2-Cl, 6-cPr | 0 | 0 |
| 2258 | Cl | H | $SO_2$ (Ph-4-Me) | 2-Br, 6-Me | 0 | 0 |
| 2259 | Cl | H | $SO_2$ (Ph-4-Me) | 2-Br, 6-Et | 0 | 0 |
| 2260 | Cl | H | $SO_2$ (Ph-4-Me) | 2-Br, 6-cPr | 0 | 0 |
| 2261 | Cl | H | $SO_2$ (Ph-4-Me) | 2-I, 6-Me | 0 | 0 |
| 2262 | Cl | H | $SO_2$ (Ph-4-Me) | 2-I, 6-Et | 0 | 0 |
| 2263 | Cl | H | $SO_2$ (Ph-4-Me) | 2,6-$Me_2$ | 0 | 0 |
| 2264 | Cl | H | $SO_2$ (Ph-4-Me) | 2-Me, 6-Et | 0 | 0 |
| 2265 | Cl | H | $SO_2$ (Ph-4-Me) | 2-Me, 6-cPr | 0 | 0 |
| 2266 | Cl | H | $SO_2$ (Ph-4-Me) | 2-Et, 6-cPr | 0 | 0 |
| 2267 | Cl | H | $SO_2$ (Ph-4-Me) | 2-iPr, 6-cPr | 0 | 0 |
| 2268 | Cl | H | $SO_2$ (Ph-4-Me) | 2-tBu, 6-cPr | 0 | 0 |
| 2269 | Cl | H | $SO_2$ (Ph-4-Me) | 2,6-$cPr_2$ | 0 | 0 |
| 2270 | Cl | H | $SO_2$ (Ph-4-Me) | 2-cPr, 6-OMe | 0 | 0 |
| 2271 | Cl | H | $SO_2$ (Ph-4-Me) | 2-Br, 3,6-$Me_2$ | 0 | 0 |
| 2272 | Cl | H | $SO_2$ (Ph-4-Me) | 2-cPr, 3,5-$Me_2$ | 0 | 0 |
| 2273 | Cl | H | $SO_2$ (Ph-4-Me) | 2-cPr, 4, 6-$Me_2$ | 0 | 0 |
| 2274 | Cl | H | $SO_2$ (Ph-4-Me) | 2-Br, 5,6-$Me_2$ | 0 | 0 |
| 2275 | Cl | H | $SO_2$ (Ph-4-Me) | 2-cPr, 5,6-$Me_2$ | 0 | 0 |

TABLE 1-continued

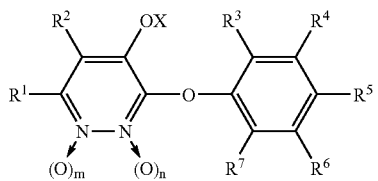

| Compound No. | $R^1$ | $R^2$ | X | $R^3$ to $R^7$ | m | n |
|---|---|---|---|---|---|---|
| 2276 | Cl | H | $SO_2$ (Ph-4-Me) | 2-Br, 5-CH=CH—O-6 | 0 | 0 |
| 2277 | Cl | H | $SO_2$ (Ph-4-Me) | 2-Me, 5-$CH_2CH_2CH_2$-6 | 0 | 0 |
| 2278 | Cl | H | $SO_2$ (Ph-4-Me) | 2-Me, 5-$CH_2CH_2O$-6 | 0 | 0 |
| 2279 | Cl | H | $SO_2$ (Ph-4-Me) | 2-Me, 5-CH=CH—O-6 | 0 | 0 |
| 2280 | Cl | H | $SO_2$ (Ph-4-Me) | 2-Et, 5-$CH_2CH_2CH_2$-6 | 0 | 0 |
| 2281 | Cl | H | $SO_2$ (Ph-4-Me) | 2-cPr, 5-$CH_2CH_2CH_2$-6 | 0 | 0 |
| 2282 | Cl | H | $SO_2$ (Ph-4-Me) | 2-cPr, 5-CH=CH—O-6 | 0 | 0 |
| 2283 | Cl | H | $SO_2$ (Ph-4-Me) | 2-Br, 3,5,6-$Me_3$ | 0 | 0 |
| 2284 | Cl | H | $SO_2$ (Ph-4-No2) | 2-Cl | 0 | 0 |
| 2285 | Cl | H | $SO_2$ (Ph-4-NO_2) | 2-Br | 0 | 0 |
| 2286 | Cl | H | $SO_2$ (Ph-4-NO_2) | 2-I | 0 | 0 |
| 2287 | Cl | H | $SO_2$ (Ph-4-NO_2) | 2-Me | 0 | 0 |
| 2288 | Cl | H | $SO_2$ (Ph-4-NO_2) | 2-iPr | 0 | 0 |
| 2289 | Cl | H | $SO_2$ (Ph-4-NO_2) | 2-cPr | 0 | 0 |
| 2290 | Cl | H | $SO_2$ (Ph-4-NO_2) | 2-cBu | 0 | 0 |
| 2291 | Cl | H | $SO_2$ (Ph-4-NO_2) | 2-$CH_2CH_2CH_2$-3 | 0 | 0 |
| 2292 | Cl | H | $SO_2$ (Ph-4-NO_2) | 2-cPr, 5-Me | 0 | 0 |
| 2293 | Cl | H | $SO_2$ (Ph-4-NO_2) | 2-OMe, 5-Me | 0 | 0 |
| 2294 | Cl | H | $SO_2$ (Ph-4-NO_2) | 2-F, 6-iPr | 0 | 0 |
| 2295 | Cl | H | $SO_2$ (Ph-4-NO_2) | 2-Cl, 6-cPr | 0 | 0 |
| 2296 | Cl | H | $SO_2$ (Ph-4-NO2) | 2-Br, 6-Me | 0 | 0 |
| 2297 | Cl | H | $SO_2$ (Ph-4-NO_2) | 2-I, 6-Me | 0 | 0 |
| 2298 | Cl | H | $SO_2$ (Ph-4-NO_2) | 2,6-$Me_2$ | 0 | 0 |
| 2299 | Cl | H | $SO_2$ (Ph-4-NO_2) | 2-Me, 6-Et | 0 | 0 |
| 2300 | Cl | H | $SO_2$ (Ph-4-NO_2) | 2-Me, 6-cPr | 0 | 0 |
| 2301 | Cl | H | $SO_2$ (Ph-4-NO_2) | 2,6-$cPr_2$ | 0 | 0 |
| 2302 | Cl | H | $SO_2$ (Ph-4-NO_2) | 2-cPr, 3,5-$Me_2$ | 0 | 0 |
| 2303 | Cl | H | $SO_2$ (Ph-4-NO_2) | 2-cPr, 5,6-$Me_2$ | 0 | 0 |
| 2304 | Cl | H | $SO_2$ (Ph-4-OMe) | 2-Me | 0 | 0 |
| 2305 | Cl | H | $SO_2$ (Ph-4-OMe) | 2-iPr | 0 | 0 |
| 2306 | Cl | H | $SO_2$ (Ph-4-OMe) | 2-cPr | 0 | 0 |
| 2307 | Cl | H | $SO_2$ (Ph-4-OMe) | 2-$CH_2CH_2CH_2$-3 | 0 | 0 |
| 2308 | Cl | H | $SO_2$ (Ph-4-OMe) | 2,6-$Me_2$ | 0 | 0 |
| 2309 | Cl | H | $SO_2$ (Ph-4-OMe) | 2-Me, 6-cPr | 0 | 0 |
| 2310 | Cl | H | $SO_2$ (Ph-2,4,6-$Me_3$) | 2-Me | 0 | 0 |
| 2311 | Cl | H | $SO_2$ (Ph-2,4,6-$Me_3$) | 2-iPr | 0 | 0 |
| 2312 | Cl | H | $SO_2$ (Ph-2,4,6-$Me_3$) | 2-cPr | 0 | 0 |
| 2313 | Cl | H | $SO_2$ (Ph-2,4,6-$Me_3$) | 2-$CH_2CH_2CH_2$-3 | 0 | 0 |
| 2314 | Cl | H | $SO_2$ (Ph-2,4,6-$Me_3$) | 2,6-$Me_2$ | 0 | 0 |
| 2315 | Cl | H | $SO_2$ (Ph-2,4,6-$Me_3$) | 2-Me, 6-cPr | 0 | 0 |
| 2316 | Cl | H | $SO_2$ (Ph-2,4,6-$iPr_3$) | 2-Me | 0 | 0 |
| 2317 | Cl | H | $SO_2$ (Ph-2,4,6-$iPr_3$) | 2-iPr | 0 | 0 |
| 2318 | Cl | H | $SO_2$ (Ph-2,4,6-$iPr_3$) | 2-cPr | 0 | 0 |
| 2319 | Cl | H | $SO_2$ (Ph-2,4,6-$iPr_3$) | 2-$CH_2CH_2CH_2$-3 | 0 | 0 |
| 2320 | Cl | H | $SO_2$ (Ph-2,4,6-$iPr_3$) | 2,6-$Me_2$ | 0 | 0 |
| 2321 | Cl | H | $SO_2$ (Ph-2,4,6-$iPr_3$) | 2-Me, 6-cPr | 0 | 0 |
| 2322 | Cl | H | $SO_2$ (Ph-2-$SO_2OQ^5$) | 2-Me | 0 | 0 |
| 2323 | Cl | H | $SO_2$ (Ph-2-$SO_2OQ^5$) | 2-iPr | 0 | 0 |
| 2324 | Cl | H | $SO_2$ (Ph-2-$SO_2OQ^5$) | 2-cPr | 0 | 0 |
| 2325 | Cl | H | $SO_2$ (Ph-2-$SO_2OQ^5$) | 2-$CH_2CH_2CH_2$-3 | 0 | 0 |
| 2326 | Cl | H | $SO_2$ (Ph-2-$SO_2OQ^5$) | 2,6-$Me_2$ | 0 | 0 |
| 2327 | Cl | H | $SO_2$ (Ph-2-$SO_2OQ^5$) | 2-Me, 6-cPr | 0 | 0 |
| 2328 | Cl | H | $SO_2$ (Ph-3-$SO_2OQ^5$) | 2-Me | 0 | 0 |
| 2329 | Cl | H | $SO_2$ (Ph-3-$SO_2OQ^5$) | 2-iPr | 0 | 0 |
| 2330 | Cl | H | $SO_2$ (Ph-3-$SO_2OQ^5$) | 2-cPr | 0 | 0 |
| 2331 | Cl | H | $SO_2$ (Ph-3-$SO_2OQ^5$) | 2-$CH_2CH_2CH_2$-3 | 0 | 0 |
| 2332 | Cl | H | $SO_2$ (Ph-3-$SO_2OQ^5$) | 2,6-$Me_2$ | 0 | 0 |
| 2333 | Cl | H | $SO_2$ (Ph-3-$SO_2OQ^5$) | 2-Me, 6-cPr | 0 | 0 |
| 2334 | Cl | H | $SO_2$ (Ph-4-$SO_2OQ^5$) | 2-Me | 0 | 0 |
| 2335 | Cl | H | $SO_2$ (Ph-4-$SO_2OQ^5$) | 2-iPr | 0 | 0 |
| 2336 | Cl | H | $SO_2$ (Ph-4-$SO_2OQ^5$) | 2-cPr | 0 | 0 |
| 2337 | Cl | H | $SO_2$ (Ph-4-$SO_2OQ^5$) | 2-$CH_2CH_2CH_2$-3 | 0 | 0 |
| 2338 | Cl | H | $SO_2$ (Ph-4-$SO_2OQ^5$) | 2,6-$Me_2$ | 0 | 0 |
| 2339 | Cl | H | $SO_2$ (Ph-4-$SO_2OQ^5$) | 2-Me, 6-cPr | 0 | 0 |
| 2340 | Cl | H | $SO_2OQ^5$ | 2-Me | 0 | 0 |
| 2341 | Cl | H | $SO_2OQ^5$ | 2-iPr | 0 | 0 |

TABLE 1-continued

| Compound No. | R¹ | R² | X | R³ to R⁷ | m | n |
|---|---|---|---|---|---|---|
| 2342 | Cl | H | SO$_2$OQ$^5$ | 2-cPr | 0 | 0 |
| 2343 | Cl | H | SO$_2$OQ$^5$ | 2-CH$_2$CH$_2$CH$_2$-3 | 0 | 0 |
| 2344 | Cl | H | SO$_2$OQ$^5$ | 2,6-Me$_2$ | 0 | 0 |
| 2345 | Cl | H | SO$_2$OQ$^5$ | 2-Me, 6-cPr | 0 | 0 |
| 2346 | Cl | H | SO$_2$NMe$_2$ | 2-Cl | 0 | 0 |
| 2347 | Cl | H | SO$_2$NMe$_2$ | 2-Br | 0 | 0 |
| 2348 | Cl | H | SO$_2$NMe$_2$ | 2-I | 0 | 0 |
| 2349 | Cl | H | SO$_2$NMe$_2$ | 2-Me | 0 | 0 |
| 2350 | Cl | H | SO$_2$NMe$_2$ | 2-iPr | 0 | 0 |
| 2351 | Cl | H | SO$_2$NMe$_2$ | 2-cPr | 0 | 0 |
| 2352 | Cl | H | SO$_2$NMe$_2$ | 2-cBu | 0 | 0 |
| 2353 | Cl | H | SO$_2$NMe$_2$ | 2-CH$_2$CH$_2$CH$_2$-3 | 0 | 0 |
| 2354 | Cl | H | SO$_2$NMe$_2$ | 2-cPr, 5-Me | 0 | 0 |
| 2355 | Cl | H | SO$_2$NMe$_2$ | 2-OMe, 5-Me | 0 | 0 |
| 2356 | Cl | H | SO$_2$NMe$_2$ | 2-F, 6-iPr | 0 | 0 |
| 2357 | Cl | H | SO$_2$NMe$_2$ | 2-Cl, 6-cPr | 0 | 0 |
| 2358 | Cl | H | SO$_2$NMe$_2$ | 2-Br, 6-Me | 0 | 0 |
| 2359 | Cl | H | SO$_2$NMe$_2$ | 2-I, 6-Me | 0 | 0 |
| 2360 | Cl | H | SO$_2$NMe$_2$ | 2,6-Me$_2$ | 0 | 0 |
| 2361 | Cl | H | SO$_2$NMe$_2$ | 2-Me, 6-Et | 0 | 0 |
| 2362 | Cl | H | SO$_2$NMe$_2$ | 2-Me, 6-cPr | 0 | 0 |
| 2363 | Cl | H | SO$_2$NMe$_2$ | 2,6-cPr$_2$ | 0 | 0 |
| 2364 | Cl | H | SO$_2$NMe$_2$ | 2-cPr, 3,5-Me$_2$ | 0 | 0 |
| 2365 | Cl | H | SO$_2$NMe | 2-cPr, 5,6-Me$_2$ | 0 | 0 |
| 2366 | Cl | H | SO$_2$OEt | 2-Me | 0 | 0 |
| 2367 | Cl | H | SO$_2$OEt | 2-iPr | 0 | 0 |
| 2368 | Cl | H | SO$_2$OEt | 2-cPr | 0 | 0 |
| 2369 | Cl | H | SO$_2$OEt | 2-CH$_2$CH$_2$CH$_2$-3 | 0 | 0 |
| 2370 | Cl | H | SO$_2$OEt | 2,6-Me$_2$ | 0 | 0 |
| 2371 | Cl | H | SO$_2$OEt | 2-Me, 6-cPr | 0 | 0 |
| 2372 | Cl | Me | H | 2-Me | 0 | 0 |
| 2373 | Cl | Me | H | 2-iPr | 0 | 0 |
| 2374 | Cl | Me | H | 2-cPr | 0 | 0 |
| 2375 | Cl | Me | H | 2-CH$_2$CH$_2$CH$_2$-3 | 0 | 0 |
| 2376 | Cl | Me | H | 2,6-Me$_2$ | 0 | 0 |
| 2377 | Cl | Me | H | 2-Me, 6-cPr | 0 | 0 |
| 2378 | Cl | CH$_2$OMe | H | 2-Me | 0 | 0 |
| 2379 | Cl | CH$_2$OMe | H | 2-iPr | 0 | 0 |
| 2380 | Cl | CH$_2$OMe | H | 2-cPr | 0 | 0 |
| 2381 | Cl | CH$_2$OMe | H | 2-CH$_2$CH$_2$CH$_2$-3 | 0 | 0 |
| 2382 | Cl | CH$_2$OMe | H | 2,6-Me$_2$ | 0 | 0 |
| 2383 | Cl | CH$_2$OMe | H | 2-Me, 6-cPr | 0 | 0 |
| 2384 | Cl | CO$_2$Et | H | 2-Me | 0 | 0 |
| 2385 | Cl | CO$_2$Et | H | 2-iPr | 0 | 0 |
| 2386 | Cl | CO$_2$Et | H | 2-tBu | 0 | 0 |
| 2387 | Cl | CO$_2$Et | H | 2-cPr | 0 | 0 |
| 2388 | Cl | CO$_2$Et | H | 2-CH$_2$CH$_2$CH$_2$-3 | 0 | 0 |
| 2389 | Cl | CO$_2$Et | H | 2,6-Me$_2$ | 0 | 0 |
| 2390 | Cl | CO$_2$Et | H | 2-Me, 6-cPr | 0 | 0 |
| 2391 | Cl | CO(Ph-2-F) | H | 2-tBu | 0 | 0 |
| 2392 | Cl | OMe | H | 2-Me | 0 | 0 |
| 2393 | Cl | O(Ph-2,4-F$_2$) | H | 2,4-F$_2$ | 0 | 0 |
| 2394 | Cl | O(Ph-2,6-F$_2$) | H | 2,6-F$_2$ | 0 | 0 |
| 2395 | Cl | O(Ph-2-Me) | H | 2-Me | 0 | 0 |
| 2396 | Cl | O(Ph-2-Me) | H | 2-iPr | 0 | 0 |
| 2397 | Cl | O(Ph-2-Me) | H | 2-cPr | 0 | 0 |
| 2398 | Cl | O(Ph-2-Me) | H | 2-CH$_2$CH$_2$CH$_2$-3 | 0 | 0 |
| 2399 | Cl | O(Ph-2-Me) | H | 2,6-Me$_2$ | 0 | 0 |
| 2400 | Cl | O(Ph-2-Me) | H | 2-Me, 6-cPr | 0 | 0 |
| 2401 | Cl | SPh | H | 2-Me | 0 | 0 |
| 2402 | Cl | SiMe$_3$ | H | H | 0 | 0 |
| 2403 | Cl | SiMe$_3$ | H | 2-Me | 0 | 0 |
| 2404 | Cl | SiMe$_3$ | H | 2-iPr | 0 | 0 |
| 2405 | Cl | SiMe$_3$ | H | 2-tBu | 0 | 0 |
| 2406 | Cl | SiMe$_3$ | H | 2-cPr | 0 | 0 |
| 2407 | Cl | SiMe$_3$ | H | 2-CH$_2$CH$_2$CH$_2$-3 | 0 | 0 |

TABLE 1-continued

| Compound No. | R¹ | R² | X | R³ to R⁷ | m | n |
|---|---|---|---|---|---|---|
| 2408 | Cl | SiMe₃ | H | 2,6-Me₂ | 0 | 0 |
| 2409 | Cl | SiMe₃ | H | 2-Me, 6-cPr | 0 | 0 |
| 2410 | Br | H | H | 2-Cl | 0 | 0 |
| 2411 | Br | H | H | 2-Me | 0 | 0 |
| 2412 | Br | H | H | 2-iPr | 0 | 0 |
| 2413 | Br | H | H | 2-cPr | 0 | 0 |
| 2414 | Br | H | H | 2-CH₂CH₂CH₂-3 | 0 | 0 |
| 2415 | Br | H | H | 2,6-Me₂ | 0 | 0 |
| 2416 | Br | H | H | 2-Me, 6-cPr | 0 | 0 |
| 2417 | Me | H | H | 2-Me | 0 | 0 |
| 2418 | Me | H | H | 2-iPr | 0 | 0 |
| 2419 | Me | H | H | 2-cPr | 0 | 0 |
| 2420 | Me | H | H | 2-CH₂CH₂CH₂-3 | 0 | 0 |
| 2421 | Me | H | H | 2,6-Me₂ | 0 | 0 |
| 2422 | Me | H | H | 2-Me, 6-cPr | 0 | 0 |
| 2423 | cPr | H | H | 2-Me | 0 | 0 |
| 2424 | cPr | H | H | 2-iPr | 0 | 0 |
| 2425 | cPr | H | H | 2-cPr | 0 | 0 |
| 2426 | cPr | H | H | 2-CH₂CH₂CH₂-3 | 0 | 0 |
| 2427 | cPr | H | H | 2,6-Me₂ | 0 | 0 |
| 2428 | cPr | H | H | 2-Me, 6-cPr | 0 | 0 |
| 2429 | CF₃ | H | H | 2-Cl | 0 | 0 |
| 2430 | CF₃ | H | H | 2-Me | 0 | 0 |
| 2431 | CF₃ | H | H | 2-iPr | 0 | 0 |
| 2432 | CF₃ | H | H | 2-cPr | 0 | 0 |
| 2433 | CF₃ | H | H | 2-CH₂CH₂CH₂-3 | 0 | 0 |
| 2434 | CF₃ | H | H | 2,6-Me₂ | 0 | 0 |
| 2435 | CF₃ | H | H | 2-Me, 6-cPr | 0 | 0 |
| 2436 | CH=CH₂ | H | H | 2-Me | 0 | 0 |
| 2437 | CH=CH₂ | H | H | 2-iPr | 0 | 0 |
| 2438 | CH=CH₂ | H | H | 2-cPr | 0 | 0 |
| 2439 | CH=CH₂ | H | H | 2-CH₂CH₂CH₂-3 | 0 | 0 |
| 2440 | CH=CH₂ | H | H | 2,6-Me₂ | 0 | 0 |
| 2441 | CH=CH₂ | H | H | 2-Me, 6-cPr | 0 | 0 |
| 2442 | CH=CHMe | H | H | 2-Me | 0 | 0 |
| 2443 | CH=CHMe | H | H | 2-iPr | 0 | 0 |
| 2444 | CH=CHMe | H | H | 2-cPr | 0 | 0 |
| 2445 | CH=CHMe | H | H | 2-CH₂CH₂CH₂-3 | 0 | 0 |
| 2446 | CH=CHMe | H | H | 2,6-Me₂ | 0 | 0 |
| 2447 | CH=CHMe | H | H | 2-Me, 6-cPr | 0 | 0 |
| 2448 | CH₂CH=CH₂ | H | H | 2-Me | 0 | 0 |
| 2449 | CN | H | H | 2-Me | 0 | 0 |
| 2450 | CN | H | H | 2-iPr | 0 | 0 |
| 2451 | CN | H | H | 2-cPr | 0 | 0 |
| 2452 | CN | H | H | 2-CH₂CH₂CH₂-3 | 0 | 0 |
| 2453 | CN | H | H | 2,6-Me₂ | 0 | 0 |
| 2454 | CN | H | H | 2-Me, 6-cPr | 0 | 0 |
| 2455 | COMe | H | H | 2-Me | 0 | 0 |
| 2456 | COMe | H | H | 2-iPr | 0 | 0 |
| 2457 | COMe | H | H | 2-cPr | 0 | 0 |
| 2458 | COMe | H | H | 2-CH₂CH₂CH₂-3 | 0 | 0 |
| 2459 | COMe | H | H | 2,6-Me₂ | 0 | 0 |
| 2460 | COMe | H | H | 2-Me, 6-cPr | 0 | 0 |
| 2461 | COBu | H | H | 2,6-Me₂ | 0 | 0 |
| 2462 | CONMe₂ | H | H | 2,6-Me₂ | 0 | 0 |
| 2463 | CONMe₂ | SiMe₃ | H | 2,6-Me₂ | 0 | 0 |
| 2464 | Ph | H | H | 2-Me | 0 | 0 |
| 2465 | Ph | H | H | 2-iPr | 0 | 0 |
| 2466 | Ph | H | H | 2-cPr | 0 | 0 |
| 2467 | Ph | H | H | 2-CH₂CH₂CH₂-3 | 0 | 0 |
| 2468 | Ph | H | H | 2,6-Me₂ | 0 | 0 |
| 2469 | Ph | H | H | 2-Me, 6-cPr | 0 | 0 |
| 2470 | Ph | H | H | 3-CN | 0 | 0 |
| 2471 | Ph-3-CF₃ | H | H | 2-Me | 0 | 0 |
| 2472 | Ph-3-CN | H | H | 2-iPr | 0 | 0 |
| 2473 | Ph-3-CN | H | H | 2-cPr | 0 | 0 |

TABLE 1-continued

Structure: R² and OX on adjacent positions, R¹ on pyridazine ring with N–N (with (O)ₘ and (O)ₙ), linked via O to a phenyl ring with R³, R⁴, R⁵, R⁶, R⁷.

| Compound No. | R¹ | R² | X | R³ to R⁷ | m | n |
|---|---|---|---|---|---|---|
| 2474 | Ph-3-CN | H | H | 2-CH₂CH₂CH₂-3 | 0 | 0 |
| 2475 | Ph-3-CN | H | H | 2,6-Me₂ | 0 | 0 |
| 2476 | Ph-3-CN | H | H | 2-Me, 6-cPr | 0 | 0 |
| 2477 | 2-Fur | H | H | 2-Me | 0 | 0 |
| 2478 | 2-Thi | H | H | 2-Me | 0 | 0 |
| 2479 | 2-Thi | H | H | 2-iPr | 0 | 0 |
| 2480 | 2-Thi | H | H | 2-cPr | 0 | 0 |
| 2481 | 2-Thi | H | H | 2-CH₂CH₂CH₂-3 | 0 | 0 |
| 2482 | 2-Thi | H | H | 2,6-Me₂ | 0 | 0 |
| 2483 | 2-Thi | H | H | 2-Me, 6-cPr | 0 | 0 |
| 2484 | OMe | H | H | 2-Me | 0 | 0 |
| 2485 | O(Ph-2-F) | H | H | 2-F | 0 | 0 |
| 2486 | O(Ph-2-F) | H | H | 2-Me | 0 | 0 |
| 2487 | O(Ph-2-F) | H | H | 2-iPr | 0 | 0 |
| 2488 | O(Ph-2-F) | H | H | 2-cPr | 0 | 0 |
| 2489 | O(Ph-2-F) | H | H | 2-CH₂CH₂CH₂-3 | 0 | 0 |
| 2490 | O(Ph-2-F) | H | H | 2,6-Me₂ | 0 | 0 |
| 2491 | O(Ph-2-F) | H | H | 2-Me, 6-cPr | 0 | 0 |
| 2492 | O(Ph-2-Me) | H | H | 2-Me | 0 | 0 |
| 2493 | O(Ph-2-Me) | H | H | 2-iPr | 0 | 0 |
| 2494 | O(Ph-2-Me) | H | H | 2-cPr | 0 | 0 |
| 2495 | O(Ph-2-Me) | H | H | 2-CH₂CH₂CH₂-3 | 0 | 0 |
| 2496 | O(Ph-2-Me) | H | H | 2,6-Me₂ | 0 | 0 |
| 2497 | O(Ph-2-Me) | H | H | 2-Me, 6-cPr | 0 | 0 |
| 2498 | O(Ph-2-Me) | CO₂Et | H | 2-Me | 0 | 0 |
| 2499 | O(Ph-4-tBu) | H | H | 4-tBu | 0 | 0 |
| 2500 | O(Ph-2-iPr-5-Me) | H | H | 2-iPr, 5-Me | 0 | 0 |
| 2501 | O(Ph-2,3,5-Me₃) | H | H | 2,3,5-Me₃ | 0 | 0 |
| 2502 | O(Ph-2,4,6-Me₃) | H | H | 2,4,6-Me₃ | 0 | 0 |
| 2503 | O(Ph-2-cHx) | H | H | 2-cHx | 0 | 0 |
| 2504 | O(Ph-3-cN) | H | H | 3-CN | 0 | 0 |
| 2505 | O(Ph-4-SiMe₃) | H | H | 4-SiMe₃ | 0 | 0 |
| 2506 | OQ⁵ | H | H | 2-Me | 0 | 0 |
| 2507 | OQ⁵ | H | H | 2-iPr | 0 | 0 |
| 2508 | OQ⁵ | H | H | 2-cPr | 0 | 0 |
| 2509 | OQ⁵ | H | H | 2-CH₂CH₂CH₂-3 | 0 | 0 |
| 2510 | OQ⁵ | H | H | 2,6-Me₂ | 0 | 0 |
| 2511 | OQ⁵ | H | H | 2-Me, 6-cPr | 0 | 0 |
| 2512 | Cl | H | H | 2-(cPr-1-F-2-F) | 0 | 0 |
| 2513 | Cl | H | H | 2-(cPr-1-F-2-Cl) | 0 | 0 |
| 2514 | Cl | H | H | 2-(cPr-1,2-Cl₂) | 0 | 0 |
| 2515 | Cl | H | H | 2-(cPr-1-Cl-2-Br) | 0 | 0 |
| 2516 | Cl | H | H | 2-(cPr-1,2-Br₂) | 0 | 0 |
| 2517 | Cl | H | H | 2-(cPr-1-Me-2-Cl) | 0 | 0 |
| 2518 | Cl | H | H | 2-(cPr-1-Me-2-Br) | 0 | 0 |
| 2519 | Cl | H | H | 2-(cPr-2-F-2-Cl) | 0 | 0 |
| 2520 | Cl | H | H | 2-(cPr-2-F-2-Br) | 0 | 0 |
| 2521 | Cl | H | H | 2-(cPr-2-Cl-2-Br) | 0 | 0 |
| 2522 | Cl | H | H | 2-(cPr-1-Me-2,2-Cl₂) | 0 | 0 |
| 2523 | Cl | H | H | 2-(cPr-1-Me-2,2-Br₂) | 0 | 0 |
| 2524 | Cl | H | H | 2-(cPr-1-Me-2-F-2-Cl) | 0 | 0 |
| 2525 | Cl | H | H | 2-C(F)=CH₂ | 0 | 0 |
| 2526 | Cl | H | H | 2-C(Cl)=CH₂ | 0 | 0 |
| 2527 | Cl | H | H | 2-C(Br)=CH₂ | 0 | 0 |
| 2528 | Cl | H | H | 2-C(Et)=CH₂ | 0 | 0 |
| 2529 | Cl | H | H | 2-C(iPr)=CH₂ | 0 | 0 |
| 2530 | Cl | H | H | 2-C(tBu)=CH₂ | 0 | 0 |
| 2531 | Cl | H | H | 2-C(CN)=CH₂ | 0 | 0 |
| 2532 | Cl | H | H | 2-CH=CHF | 0 | 0 |
| 2533 | Cl | H | H | 2-CH=CHCl | 0 | 0 |
| 2534 | Cl | H | H | 2-CH=CHBr | 0 | 0 |
| 2535 | Cl | H | H | 2-CCl=CHC | 0 | 0 |
| 2536 | Cl | H | H | 2-CMe=CHCl | 0 | 0 |
| 2537 | Cl | H | H | 2-CH=CF₂ | 0 | 0 |
| 2538 | Cl | H | H | 2-CH=CCl₂ | 0 | 0 |
| 2539 | Cl | H | H | 2-CH=CBr₂ | 0 | 0 |

TABLE 1-continued

| Compound No. | R¹ | R² | X | R³ to R⁷ | m | n |
|---|---|---|---|---|---|---|
| 2540 | Cl | H | H | 2-CH=CMe₂ | 0 | 0 |
| 2541 | Cl | H | H | 2-CCl=CCl₂ | 0 | 0 |
| 2542 | Cl | H | H | 2-CMe=CMe₂ | 0 | 0 |
| 2543 | Cl | H | H | 2-CH=C(CN)₂ | 0 | 0 |
| 2544 | Cl | H | H | 3-OH | 0 | 0 |
| 2545 | Cl | H | H | 4-OH | 0 | 0 |
| 2546 | Cl | H | H | 2-OCH₂Ph | 0 | 0 |
| 2547 | Cl | H | H | 3-OCH₂Ph | 0 | 0 |
| 2548 | Cl | H | H | 4-OCH₂Ph | 0 | 0 |
| 2549 | Cl | H | H | 2-I, 3-F | 0 | 0 |
| 2550 | Cl | H | H | 2-I, 3-Me | 0 | 0 |
| 2551 | Cl | H | H | 2-I, 3-OMe | 0 | 0 |
| 2552 | Cl | H | H | 2-CHMeCH₂-3 | 0 | 0 |
| 2553 | Cl | H | H | 2-CMe₂CH₂-3 | 0 | 0 |
| 2554 | Cl | H | H | 2-CH₂CHMe-3 | 0 | 0 |
| 2555 | Cl | H | H | 2-CH₂CH{(CH₂)₃OH}-3 | 0 | 0 |
| 2556 | Cl | H | H | 2-CH₂CMe₂-3 | 0 | 0 |
| 2557 | Cl | H | H | 2-CH(CH₂)CH-3 | 0 | 0 |
| 2558 | Cl | H | H | 2-CH(—CH₂CH₂—)CH₂-3 | 0 | 0 |
| 2559 | Cl | H | H | 2-CHOMeCH₂-3 | 0 | 0 |
| 2560 | Cl | H | H | 2-C(=O)CH₂-3 | 0 | 0 |
| 2561 | Cl | H | H | 2-CH₂C(=O)-3 | 0 | 0 |
| 2562 | Cl | H | H | 2-C(=O)C(=O)-3 | 0 | 0 |
| 2563 | Cl | H | H | 2-CH₂CH₂NMe-3 | 0 | 0 |
| 2564 | Cl | H | H | 2-CH=CHNH-3 | 0 | 0 |
| 2565 | Cl | H | H | 2-CH=CHNMe-3 | 0 | 0 |
| 2566 | Cl | H | H | 2-NMeCH₂CH₂-3 | 0 | 0 |
| 2567 | Cl | H | H | 2-NHCH=CH-3 | 0 | 0 |
| 2568 | Cl | H | H | 2-NMeCH=CH-3 | 0 | 0 |
| 2569 | Cl | H | H | 2-N(COMe)CH=CH-3 | 0 | 0 |
| 2570 | Cl | H | H | 2-Me, 4-COMe | 0 | 0 |
| 2571 | Cl | H | H | 2-Me, 4-C(=NOMe)Me | 0 | 0 |
| 2572 | Cl | H | H | 2-Me, 4-OCOMe | 0 | 0 |
| 2573 | Cl | H | H | 2-Me, 4-OCOPh | 0 | 0 |
| 2574 | Cl | H | H | 2-OMe, 5-CO₂Me | 0 | 0 |
| 2575 | Cl | H | H | 2-Me, 6-CH₂F | 0 | 0 |
| 2576 | Cl | H | H | 2-Me, 6-CHF₂ | 0 | 0 |
| 2577 | Cl | H | H | 2-Me, 6-CMe=CH₂ | 0 | 0 |
| 2578 | Cl | H | H | 2-Me, 6-COMe | 0 | 0 |
| 2579 | Cl | H | H | 2-Me, 6-C(=NOMe)Me | 0 | 0 |
| 2580 | Cl | H | H | 2-OMe, 6-CO₂Me | 0 | 0 |
| 2581 | Cl | H | H | 2-Me, 6-OCOMe | 0 | 0 |
| 2582 | Cl | H | H | 2-Me, 6-OCOPh | 0 | 0 |
| 2583 | Cl | H | H | 3-Me, 4-F | 0 | 0 |
| 2584 | Cl | H | H | 3-CH₂CH₂CH₂-4 | 0 | 0 |
| 2585 | Cl | H | H | 3-CH₂CH₂CMe₂-4 | 0 | 0 |
| 2586 | Cl | H | H | 2,6-Me₂, 3-Br | 0 | 0 |
| 2587 | Cl | H | H | 2-Me, 3-Br, 6-cPr | 0 | 0 |
| 2588 | Cl | H | H | 2,6-Me₂, 3-NO₂ | 0 | 0 |
| 2589 | Cl | H | H | 2-Me, 3-NO₂,6-cPr | 0 | 0 |
| 2590 | Cl | H | H | 6-Cl, 2-CH₂OCH₂-3 | 0 | 0 |
| 2591 | Cl | H | H | 6-Br, 2-CH₂OCH₂-3 | 0 | 0 |
| 2592 | Cl | H | H | 6-Me, 2-CH₂OCH₂-3 | 0 | 0 |
| 2593 | Cl | H | H | 6-Et, 2-CH₂OCH₂-3 | 0 | 0 |
| 2594 | Cl | H | H | 6-iPr, 2-CH₂OCH₂-3 | 0 | 0 |
| 2595 | Cl | H | H | 6-cPr, 2-CH₂OCH₂-3 | 0 | 0 |
| 2596 | Cl | H | H | 2,4-Br₂, 5-SEt | 0 | 0 |
| 2597 | Cl | H | H | 2-F, 3,5,6-Me₃ | 0 | 0 |
| 2598 | Cl | H | H | 2,3,5,6-Cl₄ | 0 | 0 |
| 2599 | Cl | H | H | 2-Cl, 3,5,6-Me₃ | 0 | 0 |
| 2600 | Cl | H | H | 2-I, 3,5,6-Me₃ | 0 | 0 |
| 2601 | Cl | H | H | 2,3,3,6-Et | 0 | 0 |
| 2602 | Cl | H | H | 2,3,5-Me₃, 6-iPr | 0 | 0 |
| 2603 | Cl | H | H | 2,3,5-Me₃, 6-CH=CH₂ | 0 | 0 |
| 2604 | Cl | H | H | 2,3,5-Me₃, 6-CCl=CH₂ | 0 | 0 |
| 2605 | Cl | H | H | 2,3,5-Me₃, 6-CMe=CH₂ | 0 | 0 |

TABLE 1-continued

| Compound No. | R¹ | R² | X | R³ to R⁷ | m | n |
|---|---|---|---|---|---|---|
| 2606 | Cl | H | H | 2,3,5-Me$_3$, 6-CH(SEt)Me | 0 | 0 |
| 2607 | Cl | H | H | 2,3,5-Me$_3$, 6-COMe | 0 | 0 |
| 2608 | Cl | H | H | 2,3,5-Me$_3$, 6-NO$_2$ | 0 | 0 |
| 2609 | Cl | H | H | 2,4-Cl$_2$, 3,5,6-Me$_3$ | 0 | 0 |
| 2610 | Cl | H | H | 2,3,4,5,6-F$_5$ | 0 | 0 |
| 2611 | Cl | H | H | 2,3,4,5,6-Cl$_5$ | 0 | 0 |
| 2612 | Cl | H | H | 2-Cl, 3,4,5,6-Me$_4$ | 0 | 0 |
| 2613 | Cl | H | H | 2-Br, 3,4,5,6-Me$_4$ | 0 | 0 |
| 2614 | Cl | H | H | 2,3,4,5,6-Me$_5$ | 0 | 0 |
| 2615 | Cl | H | H | 2,3,4,4,6-Et | 0 | 0 |
| 2616 | Cl | H | H | 2,3,4,5-Me$_4$, 6-iPr | 0 | 0 |
| 2617 | Cl | H | H | 2,3,4,5-Me$_4$, 6-cPr | 0 | 0 |
| 2618 | Cl | H | COEt | 2-Cl | 0 | 0 |
| 2619 | Cl | H | COEt | 2-Br | 0 | 0 |
| 2620 | Cl | H | COEt | 2-I | 0 | 0 |
| 2621 | Cl | H | COEt | 2-cBu | 0 | 0 |
| 2622 | Cl | H | COEt | 2-cPr, 5-Me | 0 | 0 |
| 2623 | Cl | H | COEt | 2-OMe, 5-Me | 0 | 0 |
| 2624 | Cl | H | COEt | 2-F, 6-iPr | 0 | 0 |
| 2625 | Cl | H | COEt | 2-Cl, 6-cPr | 0 | 0 |
| 2626 | Cl | H | COEt | 2-Br, 6-Me | 0 | 0 |
| 2627 | Cl | H | COEt | 2-I, 6-Me | 0 | 0 |
| 2628 | Cl | H | COEt | 2-Me, 6-Et | 0 | 0 |
| 2629 | Cl | H | COEt | 2,6-cPr$_2$ | 0 | 0 |
| 2630 | Cl | H | COEt | 2-cPr, 3,5-Me$_2$ | 0 | 0 |
| 2631 | Cl | H | COEt | 2-cPr, 3,6-Me$_2$ | 0 | 0 |
| 2632 | Cl | H | COiPr | 2-Cl | 0 | 0 |
| 2633 | Cl | H | COiPr | 2-Br | 0 | 0 |
| 2634 | Cl | H | COiPr | 2-I | 0 | 0 |
| 2635 | Cl | H | COiPr | 2-cBu | 0 | 0 |
| 2636 | Cl | H | COiPr | 2-cPr, 5-Me | 0 | 0 |
| 2637 | Cl | H | COiPr | 2-OMe, 5-Me | 0 | 0 |
| 2638 | Cl | H | COiPr | 2-F, 6-iPr | 0 | 0 |
| 2639 | Cl | H | COiPr | 2-Cl, 6-cPr | 0 | 0 |
| 2640 | Cl | H | COiPr | 2-Br, 6-Me | 0 | 0 |
| 2641 | Cl | H | COiPr | 2-I, 6-Me | 0 | 0 |
| 2642 | Cl | H | COiPr | 2-Me, 6-Et | 0 | 0 |
| 2643 | Cl | H | COiPr | 2,6-cPr$_2$ | 0 | 0 |
| 2644 | Cl | H | COiPr | 2-cPr, 3,5-Me$_2$ | 0 | 0 |
| 2645 | Cl | H | COiPr | 2-cPr, 3,6-Me$_2$ | 0 | 0 |
| 2646 | Cl | H | COneoPen | 2-Cl | 0 | 0 |
| 2647 | Cl | H | COneoPen | 2-Br | 0 | 0 |
| 2648 | Cl | H | COneoPen | 2-I | 0 | 0 |
| 2649 | Cl | H | COneoPen | 2-Me | 0 | 0 |
| 2650 | Cl | H | COneoPen | 2-iPr | 0 | 0 |
| 2651 | Cl | H | COneoPen | 2-cPr | 0 | 0 |
| 2652 | Cl | H | COneoPen | 2-cBu | 0 | 0 |
| 2653 | Cl | H | COneoPen | 2-CH$_2$CH$_2$CH$_2$-3 | 0 | 0 |
| 2654 | Cl | H | COneoPen | 2-cPr, 5-Me | 0 | 0 |
| 2655 | Cl | H | COneoPen | 2-OMe, 5-Me | 0 | 0 |
| 2656 | Cl | H | COneoPen | 2-F, 6-iPr | 0 | 0 |
| 2657 | Cl | H | COneoPen | 2-Cl, 6-cPr | 0 | 0 |
| 2658 | Cl | H | COneoPen | 2-Br, 6-Me | 0 | 0 |
| 2659 | Cl | H | COneoPen | 2-I, 6-Me | 0 | 0 |
| 2660 | Cl | H | COneoPen | 2,6-Me$_2$ | 0 | 0 |
| 2661 | Cl | H | COneoPen | 2-Me, 6-Et | 0 | 0 |
| 2662 | Cl | H | COneoPen | 2-Me, 6-cPr | 0 | 0 |
| 2663 | Cl | H | COneoPen | 2,6-cPr$_2$ | 0 | 0 |
| 2664 | Cl | H | COneoPen | 2-cPr, 3,5-Me$_2$ | 0 | 0 |
| 2665 | Cl | H | COneoPen | 2-cPr, 3,6-Me$_2$ | 0 | 0 |
| 2666 | Cl | H | CO(1-Ad) | 2-Me | 0 | 0 |
| 2667 | Cl | H | CO(1-Ad) | 2-iPr | 0 | 0 |
| 2668 | Cl | H | CO(1-Ad) | 2-cPr | 0 | 0 |
| 2669 | Cl | H | CO(1-Ad) | 2-CH$_2$CH$_2$CH$_2$-3 | 0 | 0 |
| 2670 | Cl | H | CO(1-Ad) | 2,6-Me$_2$ | 0 | 0 |
| 2671 | Cl | H | CO(1-Ad) | 2-Me, 6-cPr | 0 | 0 |

TABLE 1-continued

| Compound No. | R¹ | R² | X | R³ to R⁷ | m | n |
|---|---|---|---|---|---|---|
| 2672 | Cl | H | COCMe=CH₂ | 2-Me | 0 | 0 |
| 2673 | Cl | H | COCMe=CH₂ | 2-iPr | 0 | 0 |
| 2674 | Cl | H | COCMe=CH₂ | 2-cPr | 0 | 0 |
| 2675 | Cl | H | COCMe=CH₂ | 2-CH₂CH₂CH₂-3 | 0 | 0 |
| 2676 | Cl | H | COCMe=CH₂ | 2,6-Me₂ | 0 | 0 |
| 2677 | Cl | H | COCMe=CH₂ | 2-Me, 6-cPr | 0 | 0 |
| 2678 | Cl | H | COCH=CMe₂ | 2-Cl | 0 | 0 |
| 2679 | Cl | H | COCH=CMe₂ | 2-Br | 0 | 0 |
| 2680 | Cl | H | COCH=CMe₂ | 2-I | 0 | 0 |
| 2681 | Cl | H | COCH=CMe₂ | 2-cBu | 0 | 0 |
| 2682 | Cl | H | COCH=CMe₂ | 2-cPr, 5-Me | 0 | 0 |
| 2683 | Cl | H | COCH=CMe₂ | 2-OMe, 5-Me | 0 | 0 |
| 2684 | Cl | H | COCH=CMe₂ | 2-F, 6-iPr | 0 | 0 |
| 2685 | Cl | H | COCH=CMe₂ | 2-Cl, 6-cPr | 0 | 0 |
| 2686 | Cl | H | COCH=CMe₂ | 2-Br, 6-Me | 0 | 0 |
| 2687 | Cl | H | COCH=CMe₂ | 2-I, 6-Me | 0 | 0 |
| 2688 | Cl | H | COCH=CMe₂ | 2-Me, 6-Et | 0 | 0 |
| 2689 | Cl | H | COCH=CMe₂ | 2,6-cPr₂ | 0 | 0 |
| 2690 | Cl | H | COCH=CMe₂ | 2-cPr, 3,5-Me₂ | 0 | 0 |
| 2691 | Cl | H | COCH=CMe₂ | 2-cPr, 3,6-Me₂ | 0 | 0 |
| 2692 | Cl | H | COCMe₂Br | 2-Me | 0 | 0 |
| 2693 | Cl | H | COCMe₂Br | 2-iPr | 0 | 0 |
| 2694 | Cl | H | COCMe₂Br | 2-cPr | 0 | 0 |
| 2695 | Cl | H | COCMe₂Br | 2-CH₂CH₂CH₂-3 | 0 | 0 |
| 2696 | Cl | H | COCMe₂Br | 2,6-Me₂ | 0 | 0 |
| 2697 | Cl | H | COCMe₂Br | 2-Me, 6-cPr | 0 | 0 |
| 2698 | Cl | H | COCMe₂CH₂Cl | 2-Me | 0 | 0 |
| 2699 | Cl | H | COCMe₂CH₂Cl | 2-iPr | 0 | 0 |
| 2700 | Cl | H | COCMe₂CH₂Cl | 2-cPr | 0 | 0 |
| 2701 | Cl | H | COCMe₂CH₂Cl | 2-CH₂CH₂CH₂-3 | 0 | 0 |
| 2702 | Cl | H | COCMe₂CH₂Cl | 2,6-Me₂ | 0 | 0 |
| 2703 | Cl | H | COCMe₂CH₂Cl | 2-Me, 6-cPr | 0 | 0 |
| 2704 | Cl | H | COCH₂CH₂CH₂CH₂Br | 2-Me | 0 | 0 |
| 2705 | Cl | H | COCH₂CH₂CH₂CH₂Br | 2-iPr | 0 | 0 |
| 2706 | Cl | H | COCH₂CH₂CH₂CH₂Br | 2-cPr | 0 | 0 |
| 2707 | Cl | H | COCH₂CH₂CH₂CH₂Br | 2-CH₂CH₂CH₂-3 | 0 | 0 |
| 2708 | Cl | H | COCH₂CH₂CH₂CH₂Br | 2,6-Me₂ | 0 | 0 |
| 2709 | Cl | H | COCH₂CH₂CH₂CH₂Br | 2-Me, 6-cPr | 0 | 0 |
| 2710 | Cl | H | COCHMePh | 2-Me | 0 | 0 |
| 2711 | Cl | H | COCHMePh | 2-iPr | 0 | 0 |
| 2712 | Cl | H | COCHMePh | 2-cPr | 0 | 0 |
| 2713 | Cl | H | COCHMePh | 2-CH₂CH₂CH₂-3 | 0 | 0 |
| 2714 | Cl | H | COCHMePh | 2,6-Me₂ | 0 | 0 |
| 2715 | Cl | H | COCHMePh | 2-Me, 6-cPr | 0 | 0 |
| 2716 | Cl | H | COCH₂(Ph-4-OMe) | 2-Me | 0 | 0 |
| 2717 | Cl | H | COCH₂(Ph-4-OMe) | 2-iPr | 0 | 0 |
| 2718 | Cl | H | COCH₂(Ph-4-OMe) | 2-cPr | 0 | 0 |
| 2719 | Cl | H | COCH₂(Ph-4-OMe) | 2-CH₂CH₂CH₂-3 | 0 | 0 |
| 2720 | Cl | H | COCH₂(Ph-4-OMe) | 2,6-Me₂ | 0 | 0 |
| 2721 | Cl | H | COCH₂(Ph-4-OMe) | 2-Me, 6-cPr | 0 | 0 |
| 2722 | Cl | H | COCH₂CH₂CO₂Et | 2-Me | 0 | 0 |
| 2723 | Cl | H | COCH₂CH₂CO₂Et | 2-iPr | 0 | 0 |
| 2724 | Cl | H | COCH₂CH₂CO₂Et | 2-cPr | 0 | 0 |
| 2725 | Cl | H | COCH₂CH₂CO₂Et | 2-CH₂CH₂CH₂-3 | 0 | 0 |
| 2726 | Cl | H | COCH₂CH₂CO₂Et | 2,6-Me₂ | 0 | 0 |
| 2727 | Cl | H | COCH₂CH₂CO₂Et | 2-Me, 6-cPr | 0 | 0 |
| 2728 | Cl | H | CO(CH₂)₂CO₂Q⁶ | 2-Me | 0 | 0 |
| 2729 | Cl | H | CO(CH₂)₂CO₂Q⁷ | 2-iPr | 0 | 0 |
| 2730 | Cl | H | CO(CH₂)₂CO₂Q⁸ | 2-cPr | 0 | 0 |
| 2731 | Cl | H | CO(CH₂)₂CO₂Q⁹ | 2-CH₂CH₂CH₂-3 | 0 | 0 |
| 2732 | Cl | H | CO(CH₂)₂CO₂Q¹⁰ | 2,6-Me₂ | 0 | 0 |
| 2733 | Cl | H | CO(CH₂)₂CO₂Q¹¹ | 2-Me, 6-cPr | 0 | 0 |
| 2734 | Cl | H | CO(CH₂)₃CO₂Q⁵ | 2-Me | 0 | 0 |
| 2735 | Cl | H | CO(CH₂)₃CO₂Q⁵ | 2-iPr | 0 | 0 |
| 2736 | Cl | H | CO(CH₂)₃CO₂Q⁵ | 2-cPr | 0 | 0 |
| 2737 | Cl | H | CO(CH₂)₃CO₂Q⁵ | 2-CH₂CH₂CH₂-3 | 0 | 0 |

TABLE 1-continued

| Compound No. | R¹ | R² | X | R³ to R⁷ | m | n |
|---|---|---|---|---|---|---|
| 2738 | Cl | H | CO(CH$_2$)$_3$CO$_2$Q$^5$ | 2,6-Me$_2$ | 0 | 0 |
| 2739 | Cl | H | CO(CH$_2$)$_3$CO$_2$Q$^5$ | 2-Me, 6-cPr | 0 | 0 |
| 2740 | Cl | H | CO(CH$_2$)$_3$CO$_2$Q$^{12}$ | 2-Me, 6-cPr | 0 | 0 |
| 2741 | Cl | H | CO(CH$_2$)$_3$CO$_2$Q$^{13}$ | 2-Me, 6-cPr | 0 | 0 |
| 2742 | Cl | H | CO(CH$_2$)$_3$CO$_2$Q$^{14}$ | 2-Me, 6-cPr | 0 | 0 |
| 2743 | Cl | H | CO(CH$_2$)$_3$CO$_2$Q$^{15}$ | 2-Me, 6-cPr | 0 | 0 |
| 2744 | Cl | H | CO(CH$_2$)$_3$CO$_2$Q$^{16}$ | 2-Me, 6-cPr | 0 | 0 |
| 2745 | Cl | H | CO(CH$_2$)$_3$CO$_2$Q$^{17}$ | 2-Me, 6-cPr | 0 | 0 |
| 2746 | Cl | H | CO(CH$_2$)$_3$CO$_2$Q$^{11}$ | 2-Me, 6-cPr | 0 | 0 |
| 2747 | Cl | H | COCH$_2$OMe | 2-Me | 0 | 0 |
| 2748 | Cl | H | COCH$_2$OMe | 2-iPr | 0 | 0 |
| 2749 | Cl | H | COCH$_2$OMe | 2-cPr | 0 | 0 |
| 2750 | Cl | H | COCH$_2$OMe | 2-CH$_2$CH$_2$CH$_2$-3 | 0 | 0 |
| 2751 | Cl | H | COCH$_2$OMe | 2,6-Me$_2$ | 0 | 0 |
| 2752 | Cl | H | COCH$_2$OMe | 2-Me, 6-cPr | 0 | 0 |
| 2753 | Cl | H | COCH$_2$OPh | 2-Me | 0 | 0 |
| 2754 | Cl | H | COCH$_2$OPh | 2-iPr | 0 | 0 |
| 2755 | Cl | H | COCH$_2$OPh | 2-cPr | 0 | 0 |
| 2756 | Cl | H | COCH$_2$OPh | 2-CH$_2$CH$_2$CH$_2$-3 | 0 | 0 |
| 2757 | Cl | H | COCH$_2$OPh | 2,6-Me$_2$ | 0 | 0 |
| 2758 | Cl | H | COCH$_2$OPh | 2-Me, 6-cPr | 0 | 0 |
| 2759 | Cl | H | COCH(Me)OPh | 2-Me | 0 | 0 |
| 2760 | Cl | H | COCH(Me)OPh | 2-iPr | 0 | 0 |
| 2761 | Cl | H | COCH(Me)OPh | 2-cPr | 0 | 0 |
| 2762 | Cl | H | COCH(Me)OPh | 2-CH$_2$CH$_2$CH$_2$-3 | 0 | 0 |
| 2763 | Cl | H | COCH(Me)OPh | 2,6-Me$_2$ | 0 | 0 |
| 2764 | Cl | H | COCH(Me)OPh | 2-Me, 6-cPr | 0 | 0 |
| 2765 | Cl | H | COCH(OMe)Ph | 2-Me | 0 | 0 |
| 2766 | Cl | H | COCH(OMe)Ph | 2-iPr | 0 | 0 |
| 2767 | Cl | H | COCH(OMe)Ph | 2-cPr | 0 | 0 |
| 2768 | Cl | H | COCH(OMe)Ph | 2-CH$_2$CH$_2$CH$_2$-3 | 0 | 0 |
| 2769 | Cl | H | COCH(OMe)Ph | 2,6-Me$_2$ | 0 | 0 |
| 2770 | Cl | H | COCH(OMe)Ph | 2-Me, 6-cPr | 0 | 0 |
| 2771 | Cl | H | COCH$_2$CH$_2$SMe | 2-Me | 0 | 0 |
| 2772 | Cl | H | COCH$_2$CH$_2$SMe | 2-iPr | 0 | 0 |
| 2773 | Cl | H | COCH$_2$CH$_2$SMe | 2-cPr | 0 | 0 |
| 2774 | Cl | H | COCH$_2$CH$_2$SMe | 2-CH$_2$CH$_2$CH$_2$-3 | 0 | 0 |
| 2775 | Cl | H | COCH$_2$CH$_2$SMe | 2,6-Me$_2$ | 0 | 0 |
| 2776 | Cl | H | COCH$_2$CH$_2$SMe | 2-Me, 6-cPr | 0 | 0 |
| 2777 | Cl | H | COCO(2-Thi) | 2-Me | 0 | 0 |
| 2778 | Cl | H | COCO(2-Thi) | 2-iPr | 0 | 0 |
| 2779 | Cl | H | COCO(2-Thi) | 2-cPr | 0 | 0 |
| 2780 | Cl | H | COCO(2-Thi) | 2-CH$_2$CH$_2$CH$_2$-3 | 0 | 0 |
| 2781 | Cl | H | COCO(2-Thi) | 2,6-Me$_2$ | 0 | 0 |
| 2782 | Cl | H | COCO(2-Thi) | 2-Me, 6-cPr | 0 | 0 |
| 2783 | Cl | H | CO(Ph-2-F) | 2-Me | 0 | 0 |
| 2784 | Cl | H | CO(Ph-2-F) | 2-iPr | 0 | 0 |
| 2785 | Cl | H | CO(Ph-2-F) | 2-cPr | 0 | 0 |
| 2786 | Cl | H | CO(Ph-2-F) | 2-CH$_2$CH$_2$CH$_2$-3 | 0 | 0 |
| 2787 | Cl | H | CO(Ph-2-F) | 2,6-Me$_2$ | 0 | 0 |
| 2788 | Cl | H | CO(Ph-2-F) | 2-Me, 6-cPr | 0 | 0 |
| 2789 | Cl | H | CO(Ph-2-Br) | 2-Cl | 0 | 0 |
| 2790 | Cl | H | CO(Ph-2-Br) | 2-Br | 0 | 0 |
| 2791 | Cl | H | CO(Ph-2-Br) | 2-I | 0 | 0 |
| 2792 | Cl | H | CO(Ph-2-Br) | 2-Me | 0 | 0 |
| 2793 | Cl | H | CO(Ph-2-Br) | 2-iPr | 0 | 0 |
| 2794 | Cl | H | CO(Ph-2-Br) | 2-cPr | 0 | 0 |
| 2795 | Cl | H | CO(Ph-2-Br) | 2-cBu | 0 | 0 |
| 2796 | Cl | H | CO(Ph-2-Br) | 2-CH$_2$CH$_2$CH$_2$-3 | 0 | 0 |
| 2797 | Cl | H | CO(Ph-2-Br) | 2-cPr, 5-Me | 0 | 0 |
| 2798 | Cl | H | CO(Ph-2-Br) | 2-OMe, 5-Me | 0 | 0 |
| 2799 | Cl | H | CO(Ph-2-Br) | 2-F, 6-iPr | 0 | 0 |
| 2800 | Cl | H | CO(Ph-2-Br) | 2-Cl, 6-cPr | 0 | 0 |
| 2801 | Cl | H | CO(Ph-2-Br) | 2-Br, 6-Me | 0 | 0 |
| 2802 | Cl | H | CO(Ph-2-Br) | 2-I, 6-Me | 0 | 0 |
| 2803 | Cl | H | CO(Ph-2-Br) | 2,6-Me$_2$ | 0 | 0 |

TABLE 1-continued

| Compound No. | R¹ | R² | X | R³ to R⁷ | m | n |
|---|---|---|---|---|---|---|
| 2804 | Cl | H | CO(Ph-2-Br) | 2-Me, 6-Et | 0 | 0 |
| 2805 | Cl | H | CO(Ph-2-Br) | 2-Me, 6-cPr | 0 | 0 |
| 2806 | Cl | H | CO(Ph-2-Br) | 2,6-cPr$_2$ | 0 | 0 |
| 2807 | Cl | H | CO(Ph-2-Br) | 2-cPr, 3,5-Me$_2$ | 0 | 0 |
| 2808 | Cl | H | CO(Ph-2-Br) | 2-cPr, 3,6-Me$_2$ | 0 | 0 |
| 2809 | Cl | H | CO(Ph-2-I) | 2-Me | 0 | 0 |
| 2810 | Cl | H | CO(Ph-2-I) | 2-iPr | 0 | 0 |
| 2811 | Cl | H | CO(Ph-2-I) | 2-cPr | 0 | 0 |
| 2812 | Cl | H | CO(Ph-2-I) | 2-CH$_2$CH$_2$CH$_2$-3 | 0 | 0 |
| 2813 | Cl | H | CO(Ph-2-I) | 2,6-Me$_2$ | 0 | 0 |
| 2814 | Cl | H | CO(Ph-2-I) | 2-Me, 6-cPr | 0 | 0 |
| 2815 | Cl | H | CO(Ph-2-CF$_3$) | 2-Me | 0 | 0 |
| 2816 | Cl | H | CO(Ph-2-CF$_3$) | 2-iPr | 0 | 0 |
| 2817 | Cl | H | CO(Ph-2-CF$_3$) | 2-cPr | 0 | 0 |
| 2818 | Cl | H | CO(Ph-2-CF$_3$) | 2-CH$_2$CH$_2$CH$_2$-3 | 0 | 0 |
| 2819 | Cl | H | CO(Ph-2-CF$_3$) | 2,6-Me$_2$ | 0 | 0 |
| 2820 | Cl | H | CO(Ph-2-CF$_3$) | 2-Me, 6-cPr | 0 | 0 |
| 2821 | Cl | H | CO(Ph-2-CH$_2$Ph) | 2-Me | 0 | 0 |
| 2822 | Cl | H | CO(Ph-2-CH$_2$Ph) | 2-iPr | 0 | 0 |
| 2823 | Cl | H | CO(Ph-2-CH$_2$Ph) | 2-cPr | 0 | 0 |
| 2824 | Cl | H | CO(Ph-2-CH$_2$Ph) | 2-CH$_2$CH$_2$CH$_2$-3 | 0 | 0 |
| 2825 | Cl | H | CO(Ph-2-CH$_2$Ph) | 2,6-Me$_2$ | 0 | 0 |
| 2826 | Cl | H | CO(Ph-2-CH$_2$Ph) | 2-Me, 6-cPr | 0 | 0 |
| 2827 | Cl | H | CO(Ph-2-CO$_2$Q$^6$) | 2-Me | 0 | 0 |
| 2828 | Cl | H | CO(Ph-2-CO$_2$Q$^{12}$) | 2-Me | 0 | 0 |
| 2829 | Cl | H | CO(Ph-2-CO$_2$Q$^{13}$) | 2-Me | 0 | 0 |
| 2830 | Cl | H | CO(Ph-2-CO$_2$Q$^{14}$) | 2-Me | 0 | 0 |
| 2831 | Cl | H | CO(Ph-2-CO$_2$Q$^{15}$) | 2-Me | 0 | 0 |
| 2832 | Cl | H | CO(Ph-2-CO$_2$Q$^{16}$) | 2-Me | 0 | 0 |
| 2833 | Cl | H | CO(Ph-2-CO$_2$Q$^{17}$) | 2-Me | 0 | 0 |
| 2834 | Cl | H | CO(Ph-2-CO$_2$Q$^7$) | 2-iPr | 0 | 0 |
| 2835 | Cl | H | CO(Ph-2-CO$_2$Q$^8$) | 2-cPr | 0 | 0 |
| 2836 | Cl | H | CO(Ph-2-CO$_2$Q$^9$) | 2-CH$_2$CH$_2$CH$_2$-3 | 0 | 0 |
| 2837 | Cl | H | CO(Ph-2-CO$_2$Q$^{10}$) | 2,6-Me$_2$ | 0 | 0 |
| 2838 | Cl | H | CO(Ph-2-CO$_2$Q$^{11}$) | 2-Me, 6-cPr | 0 | 0 |
| 2839 | Cl | H | CO(Ph-2-CO$_2$Q$^{12}$) | 2-Me, 6-cPr | 0 | 0 |
| 2840 | Cl | H | CO(Ph-2-CO$_2$Q$^{13}$) | 2-Me, 6-cPr | 0 | 0 |
| 2841 | Cl | H | CO(Ph-2-CO$_2$Q$^{14}$) | 2-Me, 6-cPr | 0 | 0 |
| 2842 | Cl | H | CO(Ph-2-CO$_2$Q$^{15}$) | 2-Me, 6-cPr | 0 | 0 |
| 2843 | Cl | H | CO(Ph-2-CO$_2$Q$^{16}$) | 2-Me, 6-cPr | 0 | 0 |
| 2844 | Cl | H | CO(Ph-2-CO$_2$Q$^{17}$) | 2-Me, 6-cPr | 0 | 0 |
| 2845 | Cl | H | CO(Ph-2-NO$_2$) | 2-Me | 0 | 0 |
| 2846 | Cl | H | CO(Ph-2-NO$_2$) | 2-iPr | 0 | 0 |
| 2847 | Cl | H | CO(Ph-2-NO$_2$) | 2-cPr | 0 | 0 |
| 2848 | Cl | H | CO(Ph-2-NO$_2$) | 2-CH$_2$CH$_2$CH$_2$-3 | 0 | 0 |
| 2849 | Cl | H | CO(Ph-2-NO$_2$) | 2,6-Me$_2$ | 0 | 0 |
| 2850 | Cl | H | CO(Ph-2-NO$_2$) | 2-Me, 6-cPr | 0 | 0 |
| 2851 | Cl | H | CO(Ph-2-OPh) | 2-Me | 0 | 0 |
| 2852 | Cl | H | CO(Ph-2-OPh) | 2-iPr | 0 | 0 |
| 2853 | Cl | H | CO(Ph-2-OPh) | 2-cPr | 0 | 0 |
| 2854 | Cl | H | CO(Ph-2-OPh) | 2-CH$_2$CH$_2$CH$_2$-3 | 0 | 0 |
| 2855 | Cl | H | CO(Ph-2-OPh) | 2,6-Me$_2$ | 0 | 0 |
| 2856 | Cl | H | CO(Ph-2-OPh) | 2-Me, 6-cPr | 0 | 0 |
| 2857 | Cl | H | CO(Ph-3-F) | 2-Me | 0 | 0 |
| 2858 | Cl | H | CO(Ph-3-F) | 2-iPr | 0 | 0 |
| 2859 | Cl | H | CO(Ph-3-F) | 2-cPr | 0 | 0 |
| 2860 | Cl | H | CO(Ph-3-F) | 2-CH$_2$CH$_2$CH$_2$-3 | 0 | 0 |
| 2861 | Cl | H | CO(Ph-3-F) | 2,6-Me$_2$ | 0 | 0 |
| 2862 | Cl | H | CO(Ph-3-F) | 2-Me, 6-cPr | 0 | 0 |
| 2863 | Cl | H | CO(Ph-3-Cl) | 2-Me | 0 | 0 |
| 2864 | Cl | H | CO(Ph-3-Cl) | 2-iPr | 0 | 0 |
| 2865 | Cl | H | CO(Ph-3-Cl) | 2-cPr | 0 | 0 |
| 2866 | Cl | H | CO(Ph-3-Cl) | 2-CH$_2$CH$_2$CH$_2$-3 | 0 | 0 |
| 2867 | Cl | H | CO(Ph-3-Cl) | 2,6-Me$_2$ | 0 | 0 |
| 2868 | Cl | H | CO(Ph-3-Cl) | 2-Me, 6-cPr | 0 | 0 |
| 2869 | Cl | H | CO(Ph-3-Br) | 2-Me | 0 | 0 |

TABLE 1-continued

| Compound No. | R¹ | R² | X | R³ to R⁷ | m | n |
|---|---|---|---|---|---|---|
| 2870 | Cl | H | CO(Ph-3-Br) | 2-iPr | 0 | 0 |
| 2871 | Cl | H | CO(Ph-3-Br) | 2-cPr | 0 | 0 |
| 2872 | Cl | H | CO(Ph-3-Br) | 2-$CH_2CH_2CH_2$-3 | 0 | 0 |
| 2873 | Cl | H | CO(Ph-3-Br) | 2,6-$Me_2$ | 0 | 0 |
| 2874 | Cl | H | CO(Ph-3-Br) | 2-Me, 6-cPr | 0 | 0 |
| 2875 | Cl | H | CO(Ph-3-I) | 2-Me | 0 | 0 |
| 2876 | Cl | H | CO(Ph-3-I) | 2-iPr | 0 | 0 |
| 2877 | Cl | H | CO(Ph-3-I) | 2-cPr | 0 | 0 |
| 2878 | Cl | H | CO(Ph-3-I) | 2-$CH_2CH_2CH_2$-3 | 0 | 0 |
| 2879 | Cl | H | CO(Ph-3-I) | 2,6-$Me_2$ | 0 | 0 |
| 2880 | Cl | H | CO(Ph-3-I) | 2-Me, 6-cPr | 0 | 0 |
| 2881 | Cl | H | CO(Ph-3-Me) | 2-Cl | 0 | 0 |
| 2882 | Cl | H | CO(Ph-3-Me) | 2-Br | 0 | 0 |
| 2883 | Cl | H | CO(Ph-3-Me) | 2-I | 0 | 0 |
| 2884 | Cl | H | CO(Ph-3-Me) | 2-cBu | 0 | 0 |
| 2885 | Cl | H | CO(Ph-3--Me) | 2-cPr, 5-Me | 0 | 0 |
| 2886 | Cl | H | CO(Ph-3-Me) | 2-OMe, 5-Me | 0 | 0 |
| 2887 | Cl | H | CO(Ph-3-Me) | 2-F, 6-iPr | 0 | 0 |
| 2888 | Cl | H | CO(Ph-3-Me) | 2-Cl, 6-cPr | 0 | 0 |
| 2889 | Cl | H | CO(Ph-3-Me) | 2-Br, 6-Me | 0 | 0 |
| 2890 | Cl | H | CO(Ph-3-Me) | 2-I, 6-Me | 0 | 0 |
| 2891 | Cl | H | CO(Ph-3-Me) | 2-Me, 6-Et | 0 | 0 |
| 2892 | Cl | H | CO(Ph-3-Me) | 2,6-$cPr_2$ | 0 | 0 |
| 2893 | Cl | H | CO(Ph-3-Me) | 2-cPr, 3,5-$Me_2$ | 0 | 0 |
| 2894 | Cl | H | CO(Ph-3-Me) | 2-cPr, 3,6-$Me_2$ | 0 | 0 |
| 2895 | Cl | H | CO(Ph-3-$CF_3$) | 2-Me | 0 | 0 |
| 2896 | Cl | H | CO(Ph-3-$CF_3$) | 2-iPr | 0 | 0 |
| 2897 | Cl | H | CO(Ph-3-$CF_3$) | 2-cPr | 0 | 0 |
| 2898 | Cl | H | CO(Ph-3-$CF_3$) | 2-$CH_2CH_2CH_2$-3 | 0 | 0 |
| 2899 | Cl | H | CO(Ph-3-$CF_3$) | 2,6-$Me_2$ | 0 | 0 |
| 2900 | Cl | H | CO(Ph-3-$CF_3$) | 2-Me, 6-cPr | 0 | 0 |
| 2901 | Cl | H | CO(Ph-3-$CO_2Q^6$) | 2-Me | 0 | 0 |
| 2902 | Cl | H | CO(Ph-3-$CO_2Q^7$) | 2-iPr | 0 | 0 |
| 2903 | Cl | H | CO(Ph-3-$CO_2Q^8$) | 2-cPr | 0 | 0 |
| 2904 | Cl | H | CO(Ph-3-$CO_2Q^9$) | 2-$CH_2CH_2CH_2$-3 | 0 | 0 |
| 2905 | Cl | H | CO(Ph-3-$CO_2Q^{10}$) | 2,6-$Me_2$ | 0 | 0 |
| 2906 | Cl | H | CO(Ph-3-$CO_2Q^{11}$) | 2-Me, 6-cPr | 0 | 0 |
| 2907 | Cl | H | CO(Ph-3-$CO_2Q^{12}$) | 2-Me, 6-cPr | 0 | 0 |
| 2908 | Cl | H | CO(Ph-3-$CO_2Q^{13}$) | 2-Me, 6-cPr | 0 | 0 |
| 2909 | Cl | H | CO(Ph-3-$CO_2Q^{14}$) | 2-Me, 6-cPr | 0 | 0 |
| 2910 | Cl | H | CO(Ph-3-$CO_2Q^{15}$) | 2-Me, 6-cPr | 0 | 0 |
| 2911 | Cl | H | CO(Ph-3-$CO_2Q^{16}$) | 2-Me, 6-cPr | 0 | 0 |
| 2912 | Cl | H | CO(Ph-3-$CO_2Q^{17}$) | 2-Me., 6-cPr | 0 | 0 |
| 2913 | Cl | H | CO(Ph-3-$NO_2$) | 2-Me | 0 | 0 |
| 2914 | Cl | H | CO(Ph-3-$NO_2$) | 2-iPr | 0 | 0 |
| 2915 | Cl | H | CO(Ph-3-$NO_2$) | 2-cPr | 0 | 0 |
| 2916 | Cl | H | CO(Ph-3-$NO_2$) | 2-$CH_2CH_2CH_2$-3 | 0 | 0 |
| 2917 | Cl | H | CO(Ph-3-$NO_2$) | 2,6-$Me_2$ | 0 | 0 |
| 2918 | Cl | H | CO(Ph-3-$NO_2$) | 2-Me, 6-cPr | 0 | 0 |
| 2919 | Cl | H | CO(Ph-3-OPh) | 2-Me | 0 | 0 |
| 2920 | Cl | H | CO(Ph-3-OPh) | 2-iPr | 0 | 0 |
| 2921 | Cl | H | CO(Ph-3-OPh) | 2-cPr | 0 | 0 |
| 2922 | Cl | H | CO(Ph-3-OPh) | 2-$CH_2CH_2CH_2$-3 | 0 | 0 |
| 2923 | Cl | H | CO(Ph-3-OPh) | 2,6-$Me_2$ | 0 | 0 |
| 2924 | Cl | H | CO(Ph-3-OPh) | 2-Me, 6-cPr | 0 | 0 |
| 2925 | Cl | H | CO(Ph-4-F) | 2-Me | 0 | 0 |
| 2926 | Cl | H | CO(Ph-4-F) | 2-iPr | 0 | 0 |
| 2927 | Cl | H | CO(Ph-4-F) | 2-cPr | 0 | 0 |
| 2928 | Cl | H | CO(Ph-4-F) | 2-$CH_2CH_2CH_2$-3 | 0 | 0 |
| 2929 | Cl | H | CO(Ph-4-F) | 2,6-$Me_2$ | 0 | 0 |
| 2930 | Cl | H | CO(Ph-4-F) | 2-Me, 6-cPr | 0 | 0 |
| 2931 | Cl | H | CO(Ph-4-Br) | 2-Cl | 0 | 0 |
| 2932 | Cl | H | CO(Ph-4-Br) | 2-Br | 0 | 0 |
| 2933 | Cl | H | CO(Ph-4-Br) | 2-I | 0 | 0 |
| 2934 | Cl | H | CO(Ph-4-Br) | 2-cBu | 0 | 0 |
| 2935 | Cl | H | CO(Ph-4-Br) | 2-cPr, 5-Me | 0 | 0 |

TABLE 1-continued

Structure: pyridazine core with R¹, R², OX, R³-R⁷ substituents on phenoxy, N-oxides (O)m and (O)n.

| Compound No. | R¹ | R² | X | R³ to R⁷ | m | n |
|---|---|---|---|---|---|---|
| 2936 | Cl | H | CO(Ph-4-Br) | 2-OMe, 5-Me | 0 | 0 |
| 2937 | Cl | H | CO(Ph-4-Br) | 2-F, 6-iPr | 0 | 0 |
| 2938 | Cl | H | CO(Ph-4-Br) | 2-Cl, 6-cPr | 0 | 0 |
| 2939 | Cl | H | CO(Ph-4-Br) | 2-Br, 6-Me | 0 | 0 |
| 2940 | Cl | H | CO(Ph-4-Br) | 2-I, 6-Me | 0 | 0 |
| 2941 | Cl | H | CO(Ph-4-Br) | 2-Me, 6-Et | 0 | 0 |
| 2942 | Cl | H | CO(Ph-4-Br) | 2,6-cPr$_2$ | 0 | 0 |
| 2943 | Cl | H | CO(Ph-4-Br) | 2-cPr, 3,5-Me$_2$ | 0 | 0 |
| 2944 | Cl | H | CO(Ph-4-Br) | 2-cPr, 3,6-Me$_2$ | 0 | 0 |
| 2945 | Cl | H | CO(Ph-4-Et) | 2-Cl | 0 | 0 |
| 2946 | Cl | H | CO(Ph-4-Et) | 2-Br | 0 | 0 |
| 2947 | Cl | H | CO(Ph-4-Et) | 2-I | 0 | 0 |
| 2948 | Cl | H | CO(Ph-4-Et) | 2-Me | 0 | 0 |
| 2949 | Cl | H | CO(Ph-4-Et) | 2-iPr | 0 | 0 |
| 2950 | Cl | H | CO(Ph-4-Et) | 2-cPr | 0 | 0 |
| 2951 | Cl | H | CO(Ph-4-Et) | 2-cBu | 0 | 0 |
| 2952 | Cl | H | CO(Ph-4-Et) | 2-CH$_2$CH$_2$CH$_2$-3 | 0 | 0 |
| 2953 | Cl | H | CO(Ph-4-Et) | 2-cPr, 5-Me | 0 | 0 |
| 2954 | Cl | H | CO(Ph-4-Et) | 2-OMe, 5-Me | 0 | 0 |
| 2955 | Cl | H | CO(Ph-4-Et) | 2-F, 6-iPr | 0 | 0 |
| 2956 | Cl | H | CO(Ph-4-Et) | 2-Cl, 6-cPr | 0 | 0 |
| 2957 | Cl | H | CO(Ph-4-Et) | 2-Br, 6-Me | 0 | 0 |
| 2958 | Cl | H | CO(Ph-4-Et) | 2-I, 6-Me | 0 | 0 |
| 2959 | Cl | H | CO(Ph-4-Et) | 2,6-Me$_2$ | 0 | 0 |
| 2960 | Cl | H | CO(Ph-4-Et) | 2-Me, 6-Et | 0 | 0 |
| 2961 | Cl | H | CO(Ph-4-Et) | 2-Me, 6-cPr | 0 | 0 |
| 2962 | Cl | H | CO(Ph-4-Et) | 2,6-cPr$_2$ | 0 | 0 |
| 2963 | Cl | H | CO(Ph-4-Et) | 2-cPr, 3,5-Me$_2$ | 0 | 0 |
| 2964 | Cl | H | CO(Ph-4-Et) | 2-cPr, 3,6-Me$_2$ | 0 | 0 |
| 2965 | Cl | H | CO(Ph-4-Pr) | 2-Me | 0 | 0 |
| 2966 | Cl | H | CO(Ph-4-Pr) | 2-iPr | 0 | 0 |
| 2967 | Cl | H | CO(Ph-4-Pr) | 2-cPr | 0 | 0 |
| 2968 | Cl | H | CO(Ph-4-Pr) | 2-CH$_2$CH$_2$CH$_2$-3 | 0 | 0 |
| 2969 | Cl | H | CO(Ph-4-Pr) | 2,6-Me$_2$ | 0 | 0 |
| 2970 | Cl | H | CO(Ph-4-Pr) | 2-Me, 6-cPr | 0 | 0 |
| 2971 | Cl | H | CO(Ph-4-iPr) | 2-Me | 0 | 0 |
| 2972 | Cl | H | CO(Ph-4-iPr) | 2-iPr | 0 | 0 |
| 2973 | Cl | H | CO(Ph-4-iPr) | 2-cPr | 0 | 0 |
| 2974 | Cl | H | CO(Ph-4-iPr) | 2-CH$_2$CH$_2$CH$_2$-3 | 0 | 0 |
| 2975 | Cl | H | CO(Ph-4-iPr) | 2,6-Me$_2$ | 0 | 0 |
| 2976 | Cl | H | CO(Ph-4-iPr) | 2-Me, 6-cPr | 0 | 0 |
| 2977 | Cl | H | CO(Ph-4-Bu) | 2-Me | 0 | 0 |
| 2978 | Cl | H | CO(Ph-4-Bu) | 2-iPr | 0 | 0 |
| 2979 | Cl | H | CO(Ph-4-Bu) | 2-cPr | 0 | 0 |
| 2980 | Cl | H | CO(Ph-4-Bu) | 2-CH$_2$CH$_2$CH$_2$-3 | 0 | 0 |
| 2981 | Cl | H | CO(Ph-4-Bu) | 2,6-Me$_2$ | 0 | 0 |
| 2982 | Cl | H | CO(Ph-4-Bu) | 2-Me, 6-cPr | 0 | 0 |
| 2983 | Cl | H | CO(Ph-4-CF$_3$) | 2-Me | 0 | 0 |
| 2984 | Cl | H | CO(Ph-4-CF$_3$) | 2-iPr | 0 | 0 |
| 2985 | Cl | H | CO(Ph-4-CF$_3$) | 2-cPr | 0 | 0 |
| 2986 | Cl | H | CO(Ph-4-CF$_3$) | 2-CH$_2$CH$_2$CH$_2$-3 | 0 | 0 |
| 2987 | Cl | H | CO(Ph-4-CF$_3$) | 2,6-Me$_2$ | 0 | 0 |
| 2988 | Cl | H | CO(Ph-4-CF$_3$) | 2-Me, 6-cPr | 0 | 0 |
| 2989 | Cl | H | CO(Ph-4-CN) | 2-Me | 0 | 0 |
| 2990 | Cl | H | CO(Ph-4-CN) | 2-iPr | 0 | 0 |
| 2991 | Cl | H | CO(Ph-4-CN) | 2-cPr | 0 | 0 |
| 2992 | Cl | H | CO(Ph-4-CN) | 2-CH$_2$CH$_2$CH$_2$-3 | 0 | 0 |
| 2993 | Cl | H | CO(Ph-4-CN) | 2,6-Me$_2$ | 0 | 0 |
| 2994 | Cl | H | CO(Ph-4-CN) | 2-Me, 6-cPr | 0 | 0 |
| 2995 | Cl | H | CO(Ph-4-CO$_2$Q$^5$) | 2-Cl, 6-cPr | 0 | 0 |
| 2996 | Cl | H | CO(Ph-4-CO$_2$Q$^6$) | 2-Me | 0 | 0 |
| 2997 | Cl | H | CO(Ph-4-CO$_2$Q$^7$) | 2-iPr | 0 | 0 |
| 2998 | Cl | H | CO(Ph-4-CO$_2$Q$^8$) | 2-cPr | 0 | 0 |
| 2999 | Cl | H | CO(Ph-4-CO$_2$Q$^9$) | 2-CH$_2$CH$_2$CH$_2$-3 | 0 | 0 |
| 3000 | Cl | H | CO(Ph-4-CO$_2$Q$^{10}$) | 2,6-Me$_2$ | 0 | 0 |
| 3001 | Cl | H | CO(Ph-4-CO$_2$Q$^{11}$) | 2-Me, 6-cPr | 0 | 0 |

TABLE 1-continued

[Structure: pyridazine ring with R¹, R², OX, R³-R⁷ substituents on phenoxy group, with (O)ₘ and (O)ₙ on the nitrogens]

| Compound No. | R¹ | R² | X | R³ to R⁷ | m | n |
|---|---|---|---|---|---|---|
| 3002 | Cl | H | CO(Ph-4-CO$_2$Q$^{12}$) | 2-Me, 6-cPr | 0 | 0 |
| 3003 | Cl | H | CO(Ph-4-CO$_2$Q$^{13}$) | 2-Me, 6-cPr | 0 | 0 |
| 3004 | Cl | H | CO(Ph-4-CO$_2$Q$^{14}$) | 2-Me, 6-cPr | 0 | 0 |
| 3005 | Cl | H | CO(Ph-4-CO$_2$Q$^{15}$) | 2-Me, 6-cPr | 0 | 0 |
| 3006 | Cl | H | CO(Ph-4-CO$_2$Q$^{16}$) | 2-Me, 6-cPr | 0 | 0 |
| 3007 | Cl | H | CO(Ph-4-CO$_2$Q$^{17}$) | 2-Me, 6-cPr | 0 | 0 |
| 3008 | Cl | H | CO(Ph-2-SO$_2$OQ$^5$) | 2-Me, 6-cPr | 0 | 0 |
| 3009 | Cl | H | CO(Ph-3-SO$_2$OQ$^5$) | 2-Me, 6-cPr | 0 | 0 |
| 3010 | Cl | H | CO(Ph-4-SO$_2$OQ$^5$) | 2-Me, 6-cPr | 0 | 0 |
| 3011 | Cl | H | CO(Ph-4-Ph) | 2-Me | 0 | 0 |
| 3012 | Cl | H | CO(Ph-4-Ph) | 2-iPr | 0 | 0 |
| 3013 | Cl | H | CO(Ph-4-Ph) | 2-cPr | 0 | 0 |
| 3014 | Cl | H | CO(Ph-4-Ph) | 2-CH$_2$CH$_2$CH$_2$-3 | 0 | 0 |
| 3015 | Cl | H | CO(Ph-4-Ph) | 2,6-Me$_2$ | 0 | 0 |
| 3016 | Cl | H | CO(Ph-4-Ph) | 2-Me, 6-cPr | 0 | 0 |
| 3017 | Cl | H | CO(Ph-4-OCF$_3$) | 2-Me | 0 | 0 |
| 3018 | Cl | H | CO(Ph-4-OCF$_3$) | 2-iPr | 0 | 0 |
| 3019 | Cl | H | CO(Ph-4-OCF$_3$) | 2-cPr | 0 | 0 |
| 3020 | Cl | H | CO(Ph-4-OCF$_3$) | 2-CH$_2$CH$_2$CH$_2$-3 | 0 | 0 |
| 3021 | Cl | H | CO(Ph-4-OCF$_3$) | 2,6-Me$_2$ | 0 | 0 |
| 3022 | Cl | H | CO(Ph-4-OCF$_3$) | 2-Me, 6-cPr | 0 | 0 |
| 3023 | Cl | H | CO(Ph-4-OCH$_2$Ph) | 2-Me | 0 | 0 |
| 3024 | Cl | H | CO(Ph-4-OCH$_2$Ph) | 2-iPr | 0 | 0 |
| 3025 | Cl | H | CO(Ph-4-OCH$_2$Ph) | 2-cPr | 0 | 0 |
| 3026 | Cl | H | CO(Ph-4-OCH$_2$Ph) | 2-CH$_2$CH$_2$CH$_2$-3 | 0 | 0 |
| 3027 | Cl | H | CO(Ph-4-OCH$_2$Ph) | 2,6-Me$_2$ | 0 | 0 |
| 3028 | Cl | H | CO(Ph-4-OCH$_2$Ph) | 2-Me, 6-cPr | 0 | 0 |
| 3029 | Cl | H | CO(Ph-2,3-F$_2$) | 2-Me | 0 | 0 |
| 3030 | Cl | H | CO(Ph-2,3-F$_2$) | 2-iPr | 0 | 0 |
| 3031 | Cl | H | CO(Ph-2,3-F$_2$) | 2-cPr | 0 | 0 |
| 3032 | Cl | H | CO(Ph-2,3-F$_2$) | 2-CH$_2$CH$_2$CH$_2$-3 | 0 | 0 |
| 3033 | Cl | H | CO(Ph-2,3-F$_2$) | 2,6-Me$_2$ | 0 | 0 |
| 3034 | Cl | H | CO(Ph-2,3-F$_2$) | 2-Me, 6-cPr | 0 | 0 |
| 3035 | Cl | H | CO(Ph-2-F-3-CF$_3$) | 2-Me | 0 | 0 |
| 3036 | Cl | H | CO(Ph-2-F-3-CF$_3$) | 2-iPr | 0 | 0 |
| 3037 | Cl | H | CO(Ph-2-F-3-CF$_3$) | 2-cPr | 0 | 0 |
| 3038 | Cl | H | CO(Ph-2-F-3-CF$_3$) | 2-CH$_2$CH$_2$CH$_2$-3 | 0 | 0 |
| 3039 | Cl | H | CO(Ph-2-F-3-CF$_3$) | 2,6-Me$_2$ | 0 | 0 |
| 3040 | Cl | H | CO(Ph-2-F-3-CF$_3$) | 2-Me, 6-cPr | 0 | 0 |
| 3041 | Cl | H | CO(Ph-2,3-Me$_2$) | 2-Me | 0 | 0 |
| 3042 | Cl | H | CO(Ph-2,3-Me$_2$) | 2-iPr | 0 | 0 |
| 3043 | Cl | H | CO(Ph-2,3-Me$_2$) | 2-cPr | 0 | 0 |
| 3044 | Cl | H | CO(Ph-2,3-Me$_2$) | 2-CH$_2$CH$_2$CH$_2$-3 | 0 | 0 |
| 3045 | Cl | H | CO(Ph-2,3-Me$_2$) | 2,6-Me$_2$ | 0 | 0 |
| 3046 | Cl | H | CO(Ph-2,3-Me$_2$) | 2-Me, 6-cPr | 0 | 0 |
| 3047 | Cl | H | CO(Ph-2-Me-3-Cl) | 2-Me | 0 | 0 |
| 3048 | Cl | H | CO(Ph-2-Me-3-Cl) | 2-iPr | 0 | 0 |
| 3049 | Cl | H | CO(Ph-2-Me-3-Cl) | 2-cPr | 0 | 0 |
| 3050 | Cl | H | CO(Ph-2-Me-3-Cl) | 2-CH$_2$CH$_2$CH$_2$-3 | 0 | 0 |
| 3051 | Cl | H | CO(Ph-2-Me-3-Cl) | 2,6-Me$_2$ | 0 | 0 |
| 3052 | Cl | H | CO(Ph-2-Me-3-Cl) | 2-Me, 6-cPr | 0 | 0 |
| 3053 | Cl | H | CO(Ph-2,4-F$_2$) | 2-Me | 0 | 0 |
| 3054 | Cl | H | CO(Ph-2,4-F$_2$) | 2-iPr | 0 | 0 |
| 3055 | Cl | H | CO(Ph-2,4-F$_2$) | 2-cPr | 0 | 0 |
| 3056 | Cl | H | CO(Ph-2,4-F$_2$) | 2-CH$_2$CH$_2$CH$_2$-3 | 0 | 0 |
| 3057 | Cl | H | CO(Ph-2,4-F$_2$) | 2,6-Me$_2$ | 0 | 0 |
| 3058 | Cl | H | CO(Ph-2,4-F$_2$) | 2-Me, 6-cPr | 0 | 0 |
| 3059 | Cl | H | CO(Ph-2-F-4-Cl) | 2-Me | 0 | 0 |
| 3060 | Cl | H | CO(Ph-2-F-4-Cl) | 2-iPr | 0 | 0 |
| 3061 | Cl | H | CO(Ph-2-F-4-Cl) | 2-cPr | 0 | 0 |
| 3062 | Cl | H | CO(Ph-2-F-4-Cl) | 2-CH$_2$CH$_2$CH$_2$-3 | 0 | 0 |
| 3063 | Cl | H | CO(Ph-2-F-4-Cl) | 2,6-Me$_2$ | 0 | 0 |
| 3064 | Cl | H | CO(Ph-2-F-4-Cl) | 2-Me, 6-cPr | 0 | 0 |
| 3065 | Cl | H | CO(Ph-2-F-4-CF$_3$) | 2-Me | 0 | 0 |
| 3066 | Cl | H | CO(Ph-2-F-4-CF$_3$) | 2-iPr | 0 | 0 |
| 3067 | Cl | H | CO(Ph-2-F-4-CF$_3$) | 2-cPr | 0 | 0 |

TABLE 1-continued

| Compound No. | R¹ | R² | X | R³ to R⁷ | m | n |
|---|---|---|---|---|---|---|
| 3068 | Cl | H | CO(Ph-2-F-4-CF$_3$) | 2-CH$_2$CH$_2$CH$_2$-3 | 0 | 0 |
| 3069 | Cl | H | CO(Ph-2-F-4-CF$_3$) | 2,6-Me$_2$ | 0 | 0 |
| 3070 | Cl | H | CO(Ph-2-F-4-CF$_3$) | 2-Me, 6-cPr | 0 | 0 |
| 3071 | Cl | H | CO(Ph-2-Cl-4-F) | 2-Me | 0 | 0 |
| 3072 | Cl | H | CO(Ph-2-Cl-4-F) | 2-iPr | 0 | 0 |
| 3073 | Cl | H | CO(Ph-2-Cl-4-F) | 2-cPr | 0 | 0 |
| 3074 | Cl | H | CO(Ph-2-Cl-4-F) | 2-CH$_2$CH$_2$CH$_2$-3 | 0 | 0 |
| 3075 | Cl | H | CO(Ph-2-Cl-4-F) | 2,6-Me$_2$ | 0 | 0 |
| 3076 | Cl | H | CO(Ph-2-Cl-4-F) | 2-Me, 6-cPr | 0 | 0 |
| 3077 | Cl | H | CO(Ph-2-Cl-4-Br) | 2-Me | 0 | 0 |
| 3078 | Cl | H | CO(Ph-2-Cl-4-Br) | 2-iPr | 0 | 0 |
| 3079 | Cl | H | CO(Ph-2-Cl-4-Br) | 2-cPr | 0 | 0 |
| 3080 | Cl | H | CO(Ph-2-Cl-4-Br) | 2-CH$_2$CH$_2$CH$_2$-3 | 0 | 0 |
| 3081 | Cl | H | CO(Ph-2-Cl-4-Br) | 2,6-Me$_2$ | 0 | 0 |
| 3082 | Cl | H | CO(Ph-2-Cl-4-Br) | 2-Me, 6-cPr | 0 | 0 |
| 3083 | Cl | H | CO(Ph-2-Me-4-Br) | 2-Me | 0 | 0 |
| 3084 | Cl | H | CO(Ph-2-Me-4-Br) | 2-iPr | 0 | 0 |
| 3085 | Cl | H | CO(Ph-2-Me-4-Br) | 2-cPr | 0 | 0 |
| 3086 | Cl | H | CO(Ph-2-Me-4-Br) | 2-CH$_2$CH$_2$CH$_2$-3 | 0 | 0 |
| 3087 | Cl | H | CO(Ph-2-Me-4-Br) | 2,6-Me$_2$ | 0 | 0 |
| 3088 | Cl | H | CO(Ph-2-Me-4-Br) | 2-Me, 6-cPr | 0 | 0 |
| 3089 | Cl | H | CO(Ph-2,4-Me$_2$) | 2-Me | 0 | 0 |
| 3090 | Cl | H | CO(Ph-2,4-Me$_2$) | 2-iPr | 0 | 0 |
| 3091 | Cl | H | CO(Ph-2,4-Me$_2$) | 2-cPr | 0 | 0 |
| 3092 | Cl | H | CO(Ph-2,4-Me$_2$) | 2-CH$_2$CH$_2$CH$_2$-3 | 0 | 0 |
| 3093 | Cl | H | CO(Ph-2,4-Me$_2$) | 2,6-Me$_2$ | 0 | 0 |
| 3094 | Cl | H | CO(Ph-2,4-Me$_2$) | 2-Me, 6-cPr | 0 | 0 |
| 3095 | Cl | H | CO(Ph-2,5-Cl$_2$) | 2-Me | 0 | 0 |
| 3096 | Cl | H | CO(Ph-2,5-Cl$_2$) | 2-iPr | 0 | 0 |
| 3097 | Cl | H | CO(Ph-2,5-Cl$_2$) | 2-cPr | 0 | 0 |
| 3098 | Cl | H | CO(Ph-2,5-Cl$_2$) | 2-CH$_2$CH$_2$CH$_2$-3 | 0 | 0 |
| 3099 | Cl | H | CO(Ph-2,5-Cl$_2$) | 2,6-Me$_2$ | 0 | 0 |
| 3100 | Cl | H | CO(Ph-2,5-Cl$_2$) | 2-Me, 6-cPr | 0 | 0 |
| 3101 | Cl | H | CO(Ph-2-Cl-5-Br) | 2-Me | 0 | 0 |
| 3102 | Cl | H | CO(Ph-2-Cl-5-Br) | 2-iPr | 0 | 0 |
| 3103 | Cl | H | CO(Ph-2-Cl-5-Br) | 2-cPr | 0 | 0 |
| 3104 | Cl | H | CO(Ph-2-Cl-5-Br) | 2-CH$_2$CH$_2$CH$_2$-3 | 0 | 0 |
| 3105 | Cl | H | CO(Ph-2-Cl-5-Br) | 2,6-Me$_2$ | 0 | 0 |
| 3106 | Cl | H | CO(Ph-2-Cl-5-Br) | 2-Me, 6-cPr | 0 | 0 |
| 3107 | Cl | H | CO(Ph-2-Br-5-OMe) | 2-Me | 0 | 0 |
| 3108 | Cl | H | CO(Ph-2-Br-5-OMe) | 2-iPr | 0 | 0 |
| 3109 | Cl | H | CO(Ph-2-Br-5-OMe) | 2-cPr | 0 | 0 |
| 3110 | Cl | H | CO(Ph-2-Br-5-OMe) | 2-CH$_2$CH$_2$CH$_2$-3 | 0 | 0 |
| 3111 | Cl | H | CO(Ph-2-Br-5-OMe) | 2,6-Me$_2$ | 0 | 0 |
| 3112 | Cl | H | CO(Ph-2-Br-5-OMe) | 2-Me, 6-cPr | 0 | 0 |
| 3113 | Cl | H | CO(Ph-2,5-Me$_2$) | 2-Cl | 0 | 0 |
| 3114 | Cl | H | CO(Ph-2,5-Me$_2$) | 2-Br | 0 | 0 |
| 3115 | Cl | H | CO(Ph-2,5-Me$_2$) | 2-I | 0 | 0 |
| 3116 | Cl | H | CO(Ph-2,5-Me$_2$) | 2-Me | 0 | 0 |
| 3117 | Cl | H | CO(Ph-2,5-Me$_2$) | 2-iPr | 0 | 0 |
| 3118 | Cl | H | CO(Ph-2,5-Me$_2$) | 2-cPr | 0 | 0 |
| 3119 | Cl | H | CO(Ph-2,5-Me$_2$) | 2-cBu | 0 | 0 |
| 3120 | Cl | H | CO(Ph-2,5-Me$_2$) | 2-CH$_2$CH$_2$CH$_2$-3 | 0 | 0 |
| 3121 | Cl | H | CO(Ph-2,5-Me$_2$) | 2-cPr, 5-Me | 0 | 0 |
| 3122 | Cl | H | CO(Ph-2,5-Me$_2$) | 2-OMe, 5-Me | 0 | 0 |
| 3123 | Cl | H | CO(Ph-2,5-Me$_2$) | 2-F, 6-iPr | 0 | 0 |
| 3124 | Cl | H | CO(Ph-2,5-Me$_2$) | 2-Cl, 6-cPr | 0 | 0 |
| 3125 | Cl | H | CO(Ph-2,5-Me$_2$) | 2-Br, 6-Me | 0 | 0 |
| 3126 | Cl | H | CO(Ph-2,5-Me$_2$) | 2-I, 6-Me | 0 | 0 |
| 3127 | Cl | H | CO(Ph-2,5-Me$_2$) | 2,6-Me$_2$ | 0 | 0 |
| 3128 | Cl | H | CO(Ph-2,5-Me$_2$) | 2-Me, 6-Et | 0 | 0 |
| 3129 | Cl | H | CO(Ph-2,5-Me$_2$) | 2-Me, 6-cPr | 0 | 0 |
| 3130 | Cl | H | CO(Ph-2,5-Me$_2$) | 2,6-cPr$_2$ | 0 | 0 |
| 3131 | Cl | H | CO(Ph-2,5-Me$_2$) | 2-cPr, 3,5-Me$_2$ | 0 | 0 |
| 3132 | Cl | H | CO(Ph-2,5-Me$_2$) | 2-cPr, 3,6-Me$_2$ | 0 | 0 |
| 3133 | Cl | H | CO(Ph-2,6-F$_2$) | 2-Me | 0 | 0 |

TABLE 1-continued

| Compound No. | R¹ | R² | X | R³ to R⁷ | m | n |
|---|---|---|---|---|---|---|
| 3134 | Cl | H | CO(Ph-2,6-F$_2$) | 2-iPr | 0 | 0 |
| 3135 | Cl | H | CO(Ph-2,6-F$_2$) | 2-cPr | 0 | 0 |
| 3136 | Cl | H | CO(Ph-2,6-F$_2$) | 2-CH$_2$CH$_2$CH$_2$-3 | 0 | 0 |
| 3137 | Cl | H | CO(Ph-2,6-F$_2$) | 2,6-Me$_2$ | 0 | 0 |
| 3138 | Cl | H | CO(Ph-2,6-F$_2$) | 2-Me, 6-cPr | 0 | 0 |
| 3139 | Cl | H | CO(Ph-2-F-6-Cl) | 2-Me | 0 | 0 |
| 3140 | Cl | H | CO(Ph-2-F-6-Cl) | 2-iPr | 0 | 0 |
| 3141 | Cl | H | CO(Ph-2-F-6-Cl) | 2-cPr | 0 | 0 |
| 3142 | Cl | H | CO(Ph-2-F-6-Cl) | 2-CH$_2$CH$_2$CH$_2$-3 | 0 | 0 |
| 3143 | Cl | H | CO(Ph-2-F-6-Cl) | 2,6-Me$_2$ | 0 | 0 |
| 3144 | Cl | H | CO(Ph-2-F-6-Cl) | 2-Me, 6-cPr | 0 | 0 |
| 3145 | Cl | H | CO(Ph-2,6-Cl$_2$) | 2-Me | 0 | 0 |
| 3146 | Cl | H | CO(Ph-2,6-Cl$_2$) | 2-iPr | 0 | 0 |
| 3147 | Cl | H | CO(Ph-2,6-Cl$_2$) | 2-cPr | 0 | 0 |
| 3148 | Cl | H | CO(Ph-2,6-Cl$_2$) | 2-CH$_2$CH$_2$CH$_2$-3 | 0 | 0 |
| 3149 | Cl | H | CO(Ph-2,6-Cl$_2$) | 2,6-Me$_2$ | 0 | 0 |
| 3150 | Cl | H | CO(Ph-2,6-Cl$_2$) | 2-Me, 6-cPr | 0 | 0 |
| 3151 | Cl | H | CO(Ph-2,6-Me$_2$) | 2-Me | 0 | 0 |
| 3152 | Cl | H | CO(Ph-2,6-Me$_2$) | 2-iPr | 0 | 0 |
| 3153 | Cl | H | CO(Ph-2,6-Me$_2$) | 2-cPr | 0 | 0 |
| 3154 | Cl | H | CO(Ph-2,6-Me$_2$) | 2-CH$_2$CH$_2$CH$_2$-3 | 0 | 0 |
| 3155 | Cl | H | CO(Ph-2,6-Me$_2$) | 2,6-Me$_2$ | 0 | 0 |
| 3156 | Cl | H | CO(Ph-2,6-Me$_2$) | 2-Me, 6-cPr | 0 | 0 |
| 3157 | Cl | H | CO{Ph-2,6-(OMe)$_2$} | 2-Me | 0 | 0 |
| 3158 | Cl | H | CO{Ph-2,6-(OMe)$_2$} | 2-iPr | 0 | 0 |
| 3159 | Cl | H | CO{Ph-2,6-(OMe)$_2$} | 2-cPr | 0 | 0 |
| 3160 | Cl | H | CO{Ph-2,6-(OMe)$_2$} | 2-CH$_2$CH$_2$CH$_2$-3 | 0 | 0 |
| 3161 | Cl | H | CO{Ph-2,6-(OMe)$_2$} | 2,6-Me$_2$ | 0 | 0 |
| 3162 | Cl | H | CO{Ph-2,6-(OMe)$_2$} | 2-Me, 6-cPr | 0 | 0 |
| 3163 | Cl | H | CO(Ph-3,4-F$_2$) | 2-Me | 0 | 0 |
| 3164 | Cl | H | CO(Ph-3,4-F$_2$) | 2-iPr | 0 | 0 |
| 3165 | Cl | H | CO(Ph-3,4-F$_2$) | 2-cPr | 0 | 0 |
| 3166 | Cl | H | CO(Ph-3,4-F$_2$) | 2-CH$_2$CH$_2$CH$_2$-3 | 0 | 0 |
| 3167 | Cl | H | CO(Ph-3,4-F$_2$) | 2,6-Me$_2$ | 0 | 0 |
| 3168 | Cl | H | CO(Ph-3,4-F$_2$) | 2-Me, 6-cPr | 0 | 0 |
| 3169 | Cl | H | CO(Ph-3-F-4-Me) | 2-Cl | 0 | 0 |
| 3170 | Cl | H | CO(Ph-3-F-4-Me) | 2-Br | 0 | 0 |
| 3171 | Cl | H | CO(Ph-3-F-4-Me) | 2-I | 0 | 0 |
| 3172 | Cl | H | CO(Ph-3-F-4-Me) | 2-Me | 0 | 0 |
| 3173 | Cl | H | CO(Ph-3-F-4-Me) | 2-iPr | 0 | 0 |
| 3174 | Cl | H | CO(Ph-3-F-4-Me) | 2-cPr | 0 | 0 |
| 3175 | Cl | H | CO(Ph-3-F-4-Me) | 2-cBu | 0 | 0 |
| 3176 | Cl | H | CO(Ph-3-F-4-Me) | 2-CH$_2$CH$_2$CH$_2$-3 | 0 | 0 |
| 3177 | Cl | H | CO(Ph-3-F-4-Me) | 2-cPr, 5-Me | 0 | 0 |
| 3178 | Cl | H | CO(Ph-3-F-4-Me) | 2-OMe, 5-Me | 0 | 0 |
| 3179 | Cl | H | CO(Ph-3-F-4-Me) | 2-F, 6-iPr | 0 | 0 |
| 3180 | Cl | H | CO(Ph-3-F-4-Me) | 2-Cl, 6-cPr | 0 | 0 |
| 3181 | Cl | H | CO(Ph-3-F-4-Me) | 2-Br, 6-Me | 0 | 0 |
| 3182 | Cl | H | CO(Ph-3-F-4-Me) | 2-I, 6-Me | 0 | 0 |
| 3183 | Cl | H | CO(Ph-3-F-4-Me) | 2,6-Me$_2$ | 0 | 0 |
| 3184 | Cl | H | CO(Ph-3-F-4-Me) | 2-Me, 6-Et | 0 | 0 |
| 3185 | Cl | H | CO(Ph-3-F-4-Me) | 2-Me, 6-cPr | 0 | 0 |
| 3186 | Cl | H | CO(Ph-3-F-4-Me) | 2,6-cPr$_2$ | 0 | 0 |
| 3187 | Cl | H | CO(Ph-3-F-4-Me) | 2-cPr, 3,5-Me$_2$ | 0 | 0 |
| 3188 | Cl | H | CO(Ph-3-F-4-Me) | 2-cPr, 3,6-Me$_2$ | 0 | 0 |
| 3189 | Cl | H | CO(Ph-3,4-Cl$_2$) | 2-Me | 0 | 0 |
| 3190 | Cl | H | CO(Ph-3,4-Cl$_2$) | 2-iPr | 0 | 0 |
| 3191 | Cl | H | CO(Ph-3,4-Cl$_2$) | 2-cPr | 0 | 0 |
| 3192 | Cl | H | CO(Ph-3,4-Cl$_2$) | 2-CH$_2$CH$_2$CH$_2$-3 | 0 | 0 |
| 3193 | Cl | H | CO(Ph-3,4-Cl$_2$) | 2,6-Me$_2$ | 0 | 0 |
| 3194 | Cl | H | CO(Ph-3,4-Cl$_2$) | 2-Me, 6-cPr | 0 | 0 |
| 3195 | Cl | H | CO(Ph-3-NO$_2$-4-Cl) | 2-Me | 0 | 0 |
| 3196 | Cl | H | CO(Ph-3-NO$_2$-4-Cl) | 2-iPr | 0 | 0 |
| 3197 | Cl | H | CO(Ph-3-NO$_2$-4-Cl) | 2-cPr | 0 | 0 |
| 3198 | Cl | H | CO(Ph-3-NO$_2$-4-Cl) | 2-CH$_2$CH$_2$CH$_2$-3 | 0 | 0 |
| 3199 | Cl | H | CO(Ph-3-NO$_2$-4-Cl) | 2,6-Me$_2$ | 0 | 0 |

TABLE 1-continued

[Structure: pyridazine with $R^1$, $R^2$, OX substituents, N-N with $(O)_m$ and $(O)_n$, linked via O to phenyl ring with $R^3$, $R^4$, $R^5$, $R^6$, $R^7$]

| Compound No. | $R^1$ | $R^2$ | X | $R^3$ to $R^7$ | m | n |
|---|---|---|---|---|---|---|
| 3200 | Cl | H | CO(Ph-3-NO$_2$-4-Cl) | 2-Me, 6-cPr | 0 | 0 |
| 3201 | Cl | H | CO(Ph-3,5-F$_2$) | 2-Cl | 0 | 0 |
| 3202 | Cl | H | CO(Ph-3,5-F$_2$) | 2-Br | 0 | 0 |
| 3203 | Cl | H | CO(Ph-3,5-F$_2$) | 2-I | 0 | 0 |
| 3204 | Cl | H | CO(Ph-3,5-F$_2$) | 2-Me | 0 | 0 |
| 3205 | Cl | H | CO(Ph-3,5-F$_2$) | 2-iPr | 0 | 0 |
| 3206 | Cl | H | CO(Ph-3,5-F$_2$) | 2-cPr | 0 | 0 |
| 3207 | Cl | H | CO(Ph-3,5-F$_2$) | 2-cBu | 0 | 0 |
| 3208 | Cl | H | CO(Ph-3,5-F$_2$) | 2-CH$_2$CH$_2$CH$_2$-3 | 0 | 0 |
| 3209 | Cl | H | CO(Ph-3,5-F$_2$) | 2-cPr, 5-Me | 0 | 0 |
| 3210 | Cl | H | CO(Ph-3,5-F$_2$) | 2-OMe, 5-Me | 0 | 0 |
| 3211 | Cl | H | CO(Ph-3,5-F$_2$) | 2-F, 6-iPr | 0 | 0 |
| 3212 | Cl | H | CO(Ph-3,5-F$_2$) | 2-Cl, 6-cPr | 0 | 0 |
| 3213 | Cl | H | CO(Ph-3,5-F$_2$) | 2-Br, 6-Me | 0 | 0 |
| 3214 | Cl | H | CO(Ph-3,5-F$_2$) | 2-I, 6-Me | 0 | 0 |
| 3215 | Cl | H | CO(Ph-3,5-F$_2$) | 2,6-Me$_2$ | 0 | 0 |
| 3216 | Cl | H | CO(Ph-3,5-F$_2$) | 2-Me, 6-Et | 0 | 0 |
| 3217 | Cl | H | CO(Ph-3,5-F$_2$) | 2-Me, 6-cPr | 0 | 0 |
| 3218 | Cl | H | CO(Ph-3,5-F$_2$) | 2,6-cPr$_2$ | 0 | 0 |
| 3219 | Cl | H | CO(Ph-3,5-F$_2$) | 2-cPr, 3,5-Me$_2$ | 0 | 0 |
| 3220 | Cl | H | CO(Ph-3,5-F$_2$) | 2-cPr, 3,6-Me$_2$ | 0 | 0 |
| 3221 | Cl | H | CO(Ph-3,5-Cl$_2$) | 2-Me | 0 | 0 |
| 3222 | Cl | H | CO(Ph-3,5-Cl$_2$) | 2-iPr | 0 | 0 |
| 3223 | Cl | H | CO(Ph-3,5-Cl$_2$) | 2-cPr | 0 | 0 |
| 3224 | Cl | H | CO(Ph-3,5-Cl$_2$) | 2-CH$_2$CH$_2$CH$_2$-3 | 0 | 0 |
| 3225 | Cl | H | CO(Ph-3,5-Cl$_2$) | 2,6-Me$_2$ | 0 | 0 |
| 3226 | Cl | H | CO(Ph-3,5-Cl$_2$) | 2-Me, 6-cPr | 0 | 0 |
| 3227 | Cl | H | CO(Ph-3,5-Me$_2$) | 2-Cl | 0 | 0 |
| 3228 | Cl | H | CO(Ph-3,5-Me$_2$) | 2-Br | 0 | 0 |
| 3229 | Cl | H | CO(Ph-3,5-Me$_2$) | 2-I | 0 | 0 |
| 3230 | Cl | H | CO(Ph-3,5-Me$_2$) | 2-Me | 0 | 0 |
| 3231 | Cl | H | CO(Ph-3,5-Me$_2$) | 2-iPr | 0 | 0 |
| 3232 | Cl | H | CO(Ph-3,5-Me$_2$) | 2-cPr | 0 | 0 |
| 3233 | Cl | H | CO(Ph-3,5-Me$_2$) | 2-cBu | 0 | 0 |
| 3234 | Cl | H | CO(Ph-3,5-Me$_2$) | 2-CH$_2$CH$_2$CH$_2$-3 | 0 | 0 |
| 3235 | Cl | H | CO(Ph-3,5-Me$_2$) | 2-cPr, 5-Me | 0 | 0 |
| 3236 | Cl | H | CO(Ph-3,5-Me$_2$) | 2-OMe, 5-Me | 0 | 0 |
| 3237 | Cl | H | CO(Ph-3,5-Me$_2$) | 2-F, 6-iPr | 0 | 0 |
| 3238 | Cl | H | CO(Ph-3,5-Me$_2$) | 2-Cl, 6-cPr | 0 | 0 |
| 3239 | Cl | H | CO(Ph-3,5-Me$_2$) | 2-Br, 6-Me | 0 | 0 |
| 3240 | Cl | H | CO(Ph-3,5-Me$_2$) | 2-I, 6-Me | 0 | 0 |
| 3241 | Cl | H | CO(Ph-3,5-Me$_2$) | 2,6-Me$_2$ | 0 | 0 |
| 3242 | Cl | H | CO(Ph-3,5-Me$_2$) | 2-Me, 6-Et | 0 | 0 |
| 3243 | Cl | H | CO(Ph-3,5-Me$_2$) | 2-Me, 6-cPr | 0 | 0 |
| 3244 | Cl | H | CO(Ph-3,5-Me$_2$) | 2,6-cPr$_2$ | 0 | 0 |
| 3245 | Cl | H | CO(Ph-3,5-Me$_2$) | 2-cPr, 3,5-Me$_2$ | 0 | 0 |
| 3246 | Cl | H | CO(Ph-3,5-Me$_2$) | 2-cPr, 3,6-Me$_2$ | 0 | 0 |
| 3247 | Cl | H | CO{Ph-3,5-(OMe)$_2$} | 2-Me | 0 | 0 |
| 3248 | Cl | H | CO{Ph-3,5-(OMe)$_2$} | 2-iPr | 0 | 0 |
| 3249 | Cl | H | CO{Ph-3,5-(OMe)$_2$} | 2-cPr | 0 | 0 |
| 3250 | Cl | H | CO{Ph-3,5-(OMe)$_2$} | 2-CH$_2$CH$_2$CH$_2$-3 | 0 | 0 |
| 3251 | Cl | H | CO{Ph-3,5-(OMe)$_2$} | 2,6-Me$_2$ | 0 | 0 |
| 3252 | Cl | H | CO{Ph-3,5-(OMe)$_2$} | 2-Me, 6-cPr | 0 | 0 |
| 3253 | Cl | H | CO(Ph-2,4,6-Cl$_3$) | 2-Me | 0 | 0 |
| 3254 | Cl | H | CO(Ph-2,4,6-Cl$_3$) | 2-iPr | 0 | 0 |
| 3255 | Cl | H | CO(Ph-2,4,6-Cl$_3$) | 2-cPr | 0 | 0 |
| 3256 | Cl | H | CO(Ph-2,4,6-Cl$_3$) | 2-CH$_2$CH$_2$CH$_2$-3 | 0 | 0 |
| 3257 | Cl | H | CO(Ph-2,4,6-Cl$_3$) | 2,6-Me$_2$ | 0 | 0 |
| 3258 | Cl | H | CO(Ph-2,4,6-Cl$_3$) | 2-Me, 6-cPr | 0 | 0 |
| 3259 | Cl | H | CO{Ph-3,4,5-(OMe)$_3$} | 2-Me | 0 | 0 |
| 3260 | Cl | H | CO{Ph-3,4,5-(OMe)$_3$} | 2-iPr | 0 | 0 |
| 3261 | Cl | H | CO{Ph-3,4,5-(OMe)$_3$} | 2-cPr | 0 | 0 |
| 3262 | Cl | H | CO{Ph-3,4,5-(OMe)$_3$} | 2-CH$_2$CH$_2$CH$_2$-3 | 0 | 0 |
| 3263 | Cl | H | CO{Ph-3,4,5-(OMe)$_3$} | 2,6-Me$_2$ | 0 | 0 |
| 3264 | Cl | H | CO{Ph-3,4,5-(OMe)$_3$} | 2-Me, 6-cPr | 0 | 0 |
| 3265 | Cl | H | CO(1-Np) | 2-Me | 0 | 0 |

TABLE 1-continued

[Structure: pyridazine with R¹, R², OX substituents and phenoxy group with R³-R⁷ substituents, N-oxides (O)ₘ and (O)ₙ]

| Compound No. | R¹ | R² | X | R³ to R⁷ | m | n |
|---|---|---|---|---|---|---|
| 3266 | Cl | H | CO(1-Np) | 2-iPr | 0 | 0 |
| 3267 | Cl | H | CO(1-Np) | 2-cPr | 0 | 0 |
| 3268 | Cl | H | CO(1-Np) | 2-CH₂CH₂CH₂-3 | 0 | 0 |
| 3269 | Cl | H | CO(1-Np) | 2,6-Me₂ | 0 | 0 |
| 3270 | Cl | H | CO(1-Np) | 2-Me, 6-cPr | 0 | 0 |
| 3271 | Cl | H | CO(2-Np) | 2-Me | 0 | 0 |
| 3272 | Cl | H | CO(2-Np) | 2-iPr | 0 | 0 |
| 3273 | Cl | H | CO(2-Np) | 2-cPr | 0 | 0 |
| 3274 | Cl | H | CO(2-Np) | 2-CH₂CH₂CH₂-3 | 0 | 0 |
| 3275 | Cl | H | CO(2-Np) | 2,6-Me₂ | 0 | 0 |
| 3276 | Cl | H | CO(2-Np) | 2-Me, 6-cPr | 0 | 0 |
| 3277 | Cl | H | CO(2-Pyrr-1-Me) | 2-Me | 0 | 0 |
| 3278 | Cl | H | CO(2-Pyrr-1-Me) | 2-iPr | 0 | 0 |
| 3279 | Cl | H | CO(2-Pyrr-1-Me) | 2-cPr | 0 | 0 |
| 3280 | Cl | H | CO(2-Pyrr-1-Me) | 2-CH₂CH₂CH₂-3 | 0 | 0 |
| 3281 | Cl | H | CO(2-Pyrr-1-Me) | 2,6-Me₂ | 0 | 0 |
| 3282 | Cl | H | CO(2-Pyrr-1-Me) | 2-Me, 6-cPr | 0 | 0 |
| 3283 | Cl | H | CO(2-Fur-5-Br) | 2-Me | 0 | 0 |
| 3284 | Cl | H | CO(2-Fur-5-Br) | 2-iPr | 0 | 0 |
| 3285 | Cl | H | CO(2-Fur-5-Br) | 2-cPr | 0 | 0 |
| 3286 | Cl | H | CO(2-Fur-5-Br) | 2-CH₂CH₂CH₂-3 | 0 | 0 |
| 3287 | Cl | H | CO(2-Fur-5-Br) | 2,6-Me₂ | 0 | 0 |
| 3288 | Cl | H | CO(2-Fur-5-Br) | 2-Me, 6-cPr | 0 | 0 |
| 3289 | Cl | H | CO(3-Fur) | 2-Me | 0 | 0 |
| 3290 | Cl | H | CO(3-Fur) | 2-iPr | 0 | 0 |
| 3291 | Cl | H | CO(3-Fur) | 2-cPr | 0 | 0 |
| 3292 | Cl | H | CO(3-Fur) | 2-CH₂CH₂CH₂-3 | 0 | 0 |
| 3293 | Cl | H | CO(3-Fur) | 2,6-Me₂ | 0 | 0 |
| 3294 | Cl | H | CO(3-Fur) | 2-Me, 6-cPr | 0 | 0 |
| 3295 | Cl | H | CO(3-Fur-2-Me-5-tBu) | 2-Me | 0 | 0 |
| 3296 | Cl | H | CO(3-Fur-2-Me-5-tBu) | 2-iPr | 0 | 0 |
| 3297 | Cl | H | CO(3-Fur-2-Me-5-tBu) | 2-cPr | 0 | 0 |
| 3298 | Cl | H | CO(3-Fur-2-Me-5-tBu) | 2-CH₂CH₂CH₂-3 | 0 | 0 |
| 3299 | Cl | H | CO(3-Fur-2-Me-5-tBu) | 2,6-Me₂ | 0 | 0 |
| 3300 | Cl | H | CO(3-Fur-2-Me-5-tBu) | 2-Me, 6-cPr | 0 | 0 |
| 3301 | Cl | H | CO(3-Fur-2-CF₃-5-Me) | 2-Me | 0 | 0 |
| 3302 | Cl | H | CO(3-Fur-2-CF₃-5-Me) | 2-iPr | 0 | 0 |
| 3303 | Cl | H | CO(3-Fur-2-CF₃-5-Me) | 2-cPr | 0 | 0 |
| 3304 | Cl | H | CO(3-Fur-2-CF₃-5-Me) | 2-CH₂CH₂CH₂-3 | 0 | 0 |
| 3305 | Cl | H | CO(3-Fur-2-CF₃-5-Me) | 2,6-Me₂ | 0 | 0 |
| 3306 | Cl | H | CO(3-Fur-2-CF₃-5-Me) | 2-Me, 6-cPr | 0 | 0 |
| 3307 | Cl | H | CO{3-Fur-2-CF₃-5-(Ph-4-Cl)} | 2-Me | 0 | 0 |
| 3308 | Cl | H | CO{3-Fur-2-CF₃-5-(Ph-4-Cl)} | 2-iPr | 0 | 0 |
| 3309 | Cl | H | CO{3-Fur-2-CF₃-5-(Ph-4-Cl)} | 2-cPr | 0 | 0 |
| 3310 | Cl | H | CO{3-Fur-2-CF₃-5-(Ph-4-Cl)} | 2-CH₂CH₂CH₂-3 | 0 | 0 |
| 3311 | Cl | H | CO{3-Fur-2-CF₃-5-(Ph-4-Cl)} | 2,6-Me₂ | 0 | 0 |
| 3312 | Cl | H | CO{3-Fur-2-CF₃-5-(Ph-4-Cl)} | 2-Me, 6-cPr | 0 | 0 |
| 3313 | Cl | H | CO(2-Thi-3-Cl) | 2-Me | 0 | 0 |
| 3314 | Cl | H | CO(2-Thi-3-Cl) | 2-iPr | 0 | 0 |
| 3315 | Cl | H | CO(2-Thi-3-Cl) | 2-cPr | 0 | 0 |
| 3316 | Cl | H | CO(2-Thi-3-Cl) | 2-CH₂CH₂CH₂-3 | 0 | 0 |
| 3317 | Cl | H | CO(2-Thi-3-Cl) | 2,6-Me₂ | 0 | 0 |
| 3318 | Cl | H | CO(2-Thi-3-Cl) | 2-Me, 6-cPr | 0 | 0 |
| 3319 | Cl | H | CO(2-Thi-3-Me) | 2-Me | 0 | 0 |
| 3320 | Cl | H | CO(2-Thi-3-Me) | 2-iPr | 0 | 0 |
| 3321 | Cl | H | CO(2-Thi-3-Me) | 2-cPr | 0 | 0 |
| 3322 | Cl | H | CO(2-Thi-3-Me) | 2-CH₂CH₂CH₂-3 | 0 | 0 |
| 3323 | Cl | H | CO(2-Thi-3-Me) | 2,6-Me₂ | 0 | 0 |
| 3324 | Cl | H | CO(2-Thi-3-Me) | 2-Me, 6-cPr | 0 | 0 |
| 3325 | Cl | H | CO(2-Thi-3-OEt) | 2-Me | 0 | 0 |
| 3326 | Cl | H | CO(2-Thi-3-OEt) | 2-iPr | 0 | 0 |
| 3327 | Cl | H | CO(2-Thi-3-OEt) | 2-cPr | 0 | 0 |
| 3328 | Cl | H | CO(2-Thi-3-OEt) | 2-CH₂CH₂CH₂-3 | 0 | 0 |
| 3329 | Cl | H | CO(2-Thi-3-OEt) | 2,6-Me₂ | 0 | 0 |
| 3330 | Cl | H | CO(2-Thi-3-OEt) | 2-Me, 6-cPr | 0 | 0 |
| 3331 | Cl | H | CO(2-Thi-5-Cl) | 2-Me | 0 | 0 |

TABLE 1-continued

| Compound No. | R¹ | R² | X | R³ to R⁷ | m | n |
|---|---|---|---|---|---|---|
| 3332 | Cl | H | CO(2-Thi-5-Cl) | 2-iPr | 0 | 0 |
| 3333 | Cl | H | CO(2-Thi-5-Cl) | 2-cPr | 0 | 0 |
| 3334 | Cl | H | CO(2-Thi-5-Cl) | 2-CH$_2$CH$_2$CH$_2$-3 | 0 | 0 |
| 3335 | Cl | H | CO(2-Thi-5-Cl) | 2,6-Me$_2$ | 0 | 0 |
| 3336 | Cl | H | CO(2-Thi-5-Cl) | 2-Me, 6-cPr | 0 | 0 |
| 3337 | Cl | H | CO(2-Thi-5-Br) | 2-Me | 0 | 0 |
| 3338 | Cl | H | CO(2-Thi-5-Br) | 2-iPr | 0 | 0 |
| 3339 | Cl | H | CO(2-Thi-5-Br) | 2-cPr | 0 | 0 |
| 3340 | Cl | H | CO(2-Thi-5-Br) | 2-CH$_2$CH$_2$CH$_2$-3 | 0 | 0 |
| 3341 | Cl | H | CO(2-Thi-5-Br) | 2,6-Me$_2$ | 0 | 0 |
| 3342 | Cl | H | CO(2-Thi-5-Br) | 2-Me, 6-cPr | 0 | 0 |
| 3343 | Cl | H | CO(2-Thi-5-Me) | 2-Me | 0 | 0 |
| 3344 | Cl | H | CO(2-Thi-5-Me) | 2-iPr | 0 | 0 |
| 3345 | Cl | H | CO(2-Thi-5-Me) | 2-cPr | 0 | 0 |
| 3346 | Cl | H | CO(2-Thi-5-Me) | 2-CH$_2$CH$_2$CH$_2$-3 | 0 | 0 |
| 3347 | Cl | H | CO(2-Thi-5-Me) | 2,6-Me$_2$ | 0 | 0 |
| 3348 | Cl | H | CO(2-Thi-5-Me) | 2-Me, 6-cPr | 0 | 0 |
| 3349 | Cl | H | CO(2-Thi-5-COMe) | 2-Me | 0 | 0 |
| 3350 | Cl | H | CO(2-Thi-5-COMe) | 2-iPr | 0 | 0 |
| 3351 | Cl | H | CO(2-Thi-5-COMe) | 2-cPr | 0 | 0 |
| 3352 | Cl | H | CO(2-Thi-5-COMe) | 2-CH$_2$CH$_2$CH$_2$-3 | 0 | 0 |
| 3353 | Cl | H | CO(2-Thi-5-COMe) | 2,6-Me$_2$ | 0 | 0 |
| 3354 | Cl | H | CO(2-Thi-5-COMe) | 2-Me, 6-cPr | 0 | 0 |
| 3355 | Cl | H | CO(3-Thi-5-NO$_2$) | 2-Me | 0 | 0 |
| 3356 | Cl | H | CO(3-Thi-5-NO$_2$) | 2-iPr | 0 | 0 |
| 3357 | Cl | H | CO(3-Thi-5-NO$_2$) | 2-cPr | 0 | 0 |
| 3358 | Cl | H | CO(3-Thi-5-NO$_2$) | 2-CH$_2$CH$_2$CH$_2$-3 | 0 | 0 |
| 3359 | Cl | H | CO(3-Thi-5-NO$_2$) | 2,6-Me$_2$ | 0 | 0 |
| 3360 | Cl | H | CO(3-Thj-5-NO$_2$) | 2-Me, 6-cPr | 0 | 0 |
| 3361 | Cl | H | CO(2-Thi-4,5-Br$_2$) | 2-Me | 0 | 0 |
| 3362 | Cl | H | CO(2-Thi-4,5-Br$_2$) | 2-iPr | 0 | 0 |
| 3363 | Cl | H | CO(2-Thi-4,5-Br$_2$) | 2-cPr | 0 | 0 |
| 3364 | Cl | H | CO(2-Thi-4,5-Br$_2$) | 2-CH$_2$CH$_2$CH$_2$-3 | 0 | 0 |
| 3365 | Cl | H | CO(2-Thi-4,5-Br$_2$) | 2,6-Me$_2$ | 0 | 0 |
| 3366 | Cl | H | CO(2-Thi-4,5-Br$_2$) | 2-Me, 6-cPr | 0 | 0 |
| 3367 | Cl | H | CO(3-Thi) | 2-Me | 0 | 0 |
| 3368 | Cl | H | CO(3-Thi) | 2-iPr | 0 | 0 |
| 3369 | Cl | H | CO(3-Thi) | 2-cPr | 0 | 0 |
| 3370 | Cl | H | CO(3-Thi) | 2-CH$_2$CH$_2$CH$_2$-3 | 0 | 0 |
| 3371 | Cl | H | CO(3-Thi) | 2,6-Me$_2$ | 0 | 0 |
| 3372 | Cl | H | CO(3-Thi) | 2-Me, 6-cPr | 0 | 0 |
| 3373 | Cl | H | CO(3-Thi-4-OMe) | 2-Me | 0 | 0 |
| 3374 | Cl | H | CO(3-Thi-4-OMe) | 2-iPr | 0 | 0 |
| 3375 | Cl | H | CO(3-Thi-4-OMe) | 2-cPr | 0 | 0 |
| 3376 | Cl | H | CO(3-Thi-4-OMe) | 2-CH$_2$CH$_2$CH$_2$-3 | 0 | 0 |
| 3377 | Cl | H | CO(3-Thi-4-OMe) | 2,6-Me$_2$ | 0 | 0 |
| 3378 | Cl | H | CO(3-Thi-4-OMe) | 2-Me, 6-cPr | 0 | 0 |
| 3379 | Cl | H | CO(5-Pyza-1-CH$_2$Ph-3-tBu) | 2-Me | 0 | 0 |
| 3380 | Cl | H | CO(5-Pyza-1-CH$_2$Ph-3-tBu) | 2-iPr | 0 | 0 |
| 3381 | Cl | H | CO(5-Pyza-1-CH$_2$Ph-3-tBu) | 2-cPr | 0 | 0 |
| 3382 | Cl | H | CO(5-Pyza-1-CH$_2$Ph-3-tBu) | 2-CH$_2$CH$_2$CH$_2$-3 | 0 | 0 |
| 3383 | Cl | H | CO(5-Pyza-1-CH$_2$Ph-3-tBu) | 2,6-Me$_2$ | 0 | 0 |
| 3384 | Cl | H | CO(5-Pyza-1-CH$_2$Ph-3-tBu) | 2-Me, 6-cPr | 0 | 0 |
| 3385 | Cl | H | CO(4-Pyza-1,3-Me$_2$-5-Cl) | 2-Me | 0 | 0 |
| 3386 | Cl | H | CO(4-Pyza-1,3-Me$_2$-5-Cl) | 2-iPr | 0 | 0 |
| 3387 | Cl | H | CO(4-Pyza-1,3-Me$_2$-5-Cl) | 2-cPr | 0 | 0 |
| 3388 | Cl | H | CO(4-Pyza-1,3-Me$_2$-5-Cl) | 2-CH$_2$CH$_2$CH$_2$-3 | 0 | 0 |
| 3389 | Cl | H | CO(4-Pyza-1,3-Me$_2$-5-Cl) | 2,6-Me$_2$ | 0 | 0 |
| 3390 | Cl | H | CO(4-Pyza-1,3-Me$_2$-5-Cl) | 2-Me, 6-cPr | 0 | 0 |
| 3391 | Cl | H | CO{4-Ioxa-5-Me-3-(Ph-2-Cl)} | 2-Me | 0 | 0 |
| 3392 | Cl | H | CO{4-Ioxa-5-Me-3-(Ph-2-Cl)} | 2-iPr | 0 | 0 |
| 3393 | Cl | H | CO{4-Ioxa-5-Me-3-(Ph-2-Cl)} | 2-cPr | 0 | 0 |
| 3394 | Cl | H | CO{4-Ioxa-5-Me-3-(Ph-2-Cl)} | 2-CH$_2$CH$_2$CH$_2$-3 | 0 | 0 |
| 3395 | Cl | H | CO{4-Ioxa-5-Me-3-(Ph-2-Cl)} | 2,6-Me$_2$ | 0 | 0 |
| 3396 | Cl | H | CO{4-Ioxa-5-Me-3-(Ph-2-Cl)} | 2-Me, 6-cPr | 0 | 0 |
| 3397 | Cl | H | CO(5-Tdia-4-Me) | 2-Me | 0 | 0 |

TABLE 1-continued

| Compound No. | R¹ | R² | X | R³ to R⁷ | m | n |
|---|---|---|---|---|---|---|
| 3398 | Cl | H | CO(5-Tdia-4-Me) | 2-iPr | 0 | 0 |
| 3399 | Cl | H | CO(5-Tdia-4-Me) | 2-cPr | 0 | 0 |
| 3400 | Cl | H | CO(5-Tdia-4-Me) | 2-$CH_2CH_2CH_2$-3 | 0 | 0 |
| 3401 | Cl | H | CO(5-Tdia-4-Me) | 2,6-$Me_2$ | 0 | 0 |
| 3402 | Cl | H | CO(5-Tdia-4-Me) | 2-Me, 6-cPr | 0 | 0 |
| 3403 | Cl | H | CO(2-Pyr-6-Me) | 2-Me | 0 | 0 |
| 3404 | Cl | H | CO(2-Pyr-6-Me) | 2-iPr | 0 | 0 |
| 3405 | Cl | H | CO(2-Pyr-6-Me) | 2-cPr | 0 | 0 |
| 3406 | Cl | H | CO(2-Pyr-6-Me) | 2-$CH_2CH_2CH_2$-3 | 0 | 0 |
| 3407 | Cl | H | CO(2-Pyr-6-Me) | 2,6-$Me_2$ | 0 | 0 |
| 3408 | Cl | H | CO(2-Pyr-6-Me) | 2-Me, 6-cPr | 0 | 0 |
| 3409 | Cl | H | CO(2-Pyr-5-Bu) | 2-Me | 0 | 0 |
| 3410 | Cl | H | CO(2-Pyr-5-Bu) | 2-iPr | 0 | 0 |
| 3411 | Cl | H | CO(2-Pyr-5-Bu) | 2-cPr | 0 | 0 |
| 3412 | Cl | H | CO(2-Pyr-5-Bu) | 2-$CH_2CH_2CH_2$-3 | 0 | 0 |
| 3413 | Cl | H | CO(2-Pyr-5-Bu) | 2,6-$Me_2$ | 0 | 0 |
| 3414 | Cl | H | CO(2-Pyr-5-Bu) | 2-Me, 6-cPr | 0 | 0 |
| 3415 | Cl | H | CO(3-Pyr) | 2-Me | 0 | 0 |
| 3416 | Cl | H | CO(3-Pyr) | 2-iPr | 0 | 0 |
| 3417 | Cl | H | CO(3-Pyr) | 2-cPr | 0 | 0 |
| 3418 | Cl | H | CO(3-Pyr) | 2-$CH_2CH_2CH_2$-3 | 0 | 0 |
| 3419 | Cl | H | CO(3-Pyr) | 2,6-$Me_2$ | 0 | 0 |
| 3420 | Cl | H | CO(3-Pyr) | 2-Me, 6-cPr | 0 | 0 |
| 3421 | Cl | H | CO(3-Pyr-2-Cl) | 2-Me | 0 | 0 |
| 3422 | Cl | H | CO(3-Pyr-2-Cl) | 2-iPr | 0 | 0 |
| 3423 | Cl | H | CO(3-Pyr-2-Cl) | 2-cPr | 0 | 0 |
| 3424 | Cl | H | CO(3-Pyr-2-Cl) | 2-$CH_2CH_2CH_2$-3 | 0 | 0 |
| 3425 | Cl | H | CO(3-Pyr-2-Cl) | 2,6-$Me_2$ | 0 | 0 |
| 3426 | Cl | H | CO(3-Pyr-2-Cl) | 2-Me, 6-cPr | 0 | 0 |
| 3427 | Cl | H | CO(3-Pyr-2-Me) | 2-Me | 0 | 0 |
| 3428 | Cl | H | CO(3-Pyr-2-Me) | 2-iPr | 0 | 0 |
| 3429 | Cl | H | CO(3-Pyr-2-Me) | 2-cPr | 0 | 0 |
| 3430 | Cl | H | CO(3-Pyr-2-Me) | 2-$CH_2CH_2CH_2$-3 | 0 | 0 |
| 3431 | Cl | H | CO(3-Pyr-2-Me) | 2,6-$Me_2$ | 0 | 0 |
| 3432 | Cl | H | CO(3-Pyr-2-Me) | 2-Me, 6-cPr | 0 | 0 |
| 3433 | Cl | H | CO(3-Pyr-2-OPh) | 2-Me | 0 | 0 |
| 3434 | Cl | H | CO(3-Pyr-2-OPh) | 2-iPr | 0 | 0 |
| 3435 | Cl | H | CO(3-Pyr-2-OPh) | 2-cPr | 0 | 0 |
| 3436 | Cl | H | CO(3-Pyr-2-OPh) | 2-$CH_2CH_2CH_2$-3 | 0 | 0 |
| 3437 | Cl | H | CO(3-Pyr-2-OPh) | 2,6-$Me_2$ | 0 | 0 |
| 3438 | Cl | H | CO(3-Pyr-2-OPh) | 2-Me, 6-cPr | 0 | 0 |
| 3439 | Cl | H | CO(3-Pyr-2-SMe) | 2-Me | 0 | 0 |
| 3440 | Cl | H | CO(3-Pyr-2-SMe) | 2-iPr | 0 | 0 |
| 3441 | Cl | H | CO(3-Pyr-2-SMe) | 2-cPr | 0 | 0 |
| 3442 | Cl | H | CO(3-Pyr-2-SMe) | 2-$CH_2CH_2CH_2$-3 | 0 | 0 |
| 3443 | Cl | H | CO(3-Pyr-2-SMe) | 2,6-$Me_2$ | 0 | 0 |
| 3444 | Cl | H | CO(3-Pyr-2-SMe) | 2-Me, 6-cPr | 0 | 0 |
| 3445 | Cl | H | CO(3-Pyr-2-$SCH_2CH=CH_2$) | 2-Me | 0 | 0 |
| 3446 | Cl | H | CO(3-Pyr-2-$SCH_2CH=CH_2$) | 2-iPr | 0 | 0 |
| 3447 | Cl | H | CO(3-Pyr-2-$SCH_2CH=CH_2$) | 2-cPr | 0 | 0 |
| 3448 | Cl | H | CO(3-Pyr-2-$SCH_2CH=CH_2$) | 2-$CH_2CH_2CH_2$-3 | 0 | 0 |
| 3449 | Cl | H | CO(3-Pyr-2-$SCH_2CH=CH_2$) | 2,6-$Me_2$ | 0 | 0 |
| 3450 | Cl | H | CO(3-Pyr-2-$SCH_2CH=CH_2$) | 2-Me, 6-cPr | 0 | 0 |
| 3451 | Cl | H | CO(3-Pyr-2-SPh) | 2-Me | 0 | 0 |
| 3452 | Cl | H | CO(3-Pyr-2-SPh) | 2-iPr | 0 | 0 |
| 3453 | Cl | H | CO(3-Pyr-2-SPh) | 2-cPr | 0 | 0 |
| 3454 | Cl | H | CO(3-Pyr-2-SPh) | 2-$CH_2CH_2CH_2$-3 | 0 | 0 |
| 3455 | Cl | H | CO(3-Pyr-2-SPh) | 2,6-$Me_2$ | 0 | 0 |
| 3456 | Cl | H | CO(3-Pyr-2-SPh) | 2-Me, 6-cPr | 0 | 0 |
| 3457 | Cl | H | CO(3-Pyr-4-$CF_3$) | 2-Me | 0 | 0 |
| 3458 | Cl | H | CO(3-Pyr-4-$CF_3$) | 2-iPr | 0 | 0 |
| 3459 | Cl | H | CO(3-Pyr-4-$CF_3$) | 2-cPr | 0 | 0 |
| 3460 | Cl | H | CO(3-Pyr-4-$CF_3$) | 2-$CH_2CH_2CH_2$-3 | 0 | 0 |
| 3461 | Cl | H | CO(3-Pyr-4-$CF_3$) | 2,6-$Me_2$ | 0 | 0 |
| 3462 | Cl | H | CO(3-Pyr-4-$CF_3$) | 2-Me, 6-cPr | 0 | 0 |
| 3463 | Cl | H | CO(3-Pyr-6-Cl) | 2-Me | 0 | 0 |

TABLE 1-continued

[Structure: pyridazine with R², OX, R¹ substituents, N-N with (O)ₘ and (O)ₙ, linked via O to phenyl ring with R³, R⁴, R⁵, R⁶, R⁷]

| Compound No. | R¹ | R² | X | R³ to R⁷ | m | n |
|---|---|---|---|---|---|---|
| 3464 | Cl | H | CO(3-Pyr-6-Cl) | 2-iPr | 0 | 0 |
| 3465 | Cl | H | CO(3-Pyr-6-Cl) | 2-cPr | 0 | 0 |
| 3466 | Cl | H | CO(3-Pyr-6-Cl) | 2-CH₂CH₂CH₂-3 | 0 | 0 |
| 3467 | Cl | H | CO(3-Pyr-6-Cl) | 2,6-Me₂ | 0 | 0 |
| 3468 | Cl | H | CO(3-Pyr-6-Cl) | 2-Me, 6-cPr | 0 | 0 |
| 3469 | Cl | H | CO(3-Pyr-2,6-Cl₂) | 2-Me | 0 | 0 |
| 3470 | Cl | H | CO(3-Pyr-2,6-Cl₂) | 2-iPr | 0 | 0 |
| 3471 | Cl | H | CO(3-Pyr-2,6-Cl₂) | 2-cPr | 0 | 0 |
| 3472 | Cl | H | CO(3-Pyr-2,6-Cl₂) | 2-CH₂CH₂CH₂-3 | 0 | 0 |
| 3473 | Cl | H | CO(3-Pyr-2,6-Cl₂) | 2,6-Me₂ | 0 | 0 |
| 3474 | Cl | H | CO(3-Pyr-2,6-Cl₂) | 2-Me, 6-cPr | 0 | 0 |
| 3475 | Cl | H | CO(3-Pyr-2-Cl-6-Me) | 2-Me | 0 | 0 |
| 3476 | Cl | H | CO(3-Pyr-2-Cl-6-Me) | 2-iPr | 0 | 0 |
| 3477 | Cl | H | CO(3-Pyr-2-Cl-6-Me) | 2-cPr | 0 | 0 |
| 3478 | Cl | H | CO(3-Pyr-2-Cl-6-Me) | 2-CH₂CH₂CH₂-3 | 0 | 0 |
| 3479 | Cl | H | CO(3-Pyr-2-Cl-6-Me) | 2,6-Me₂ | 0 | 0 |
| 3480 | Cl | H | CO(3-Pyr-2-Cl-6-Me) | 2-Me, 6-cPr | 0 | 0 |
| 3481 | Cl | H | CO(3-Pyr-5,6-Cl₂) | 2-Me | 0 | 0 |
| 3482 | Cl | H | CO(3-Pyr-5,6-Cl₂) | 2-iPr | 0 | 0 |
| 3483 | Cl | H | CO(3-Pyr-5,6-Cl₂) | 2-cPr | 0 | 0 |
| 3484 | Cl | H | CO(3-Pyr-5,6-Cl₂) | 2-CH₂CH₂CH₂-3 | 0 | 0 |
| 3485 | Cl | H | CO(3-Pyr-5,6-Cl₂) | 2,6-Me₂ | 0 | 0 |
| 3486 | Cl | H | CO(3-Pyr-5,6-Cl₂) | 2-Me, 6-cPr | 0 | 0 |
| 3487 | Cl | H | CO(4-Pyr-2-Cl) | 2-Me | 0 | 0 |
| 3488 | Cl | H | CO(4-Pyr-2-Cl) | 2-iPr | 0 | 0 |
| 3489 | Cl | H | CO(4-Pyr-2-Cl) | 2-cPr | 0 | 0 |
| 3490 | Cl | H | CO(4-Pyr-2-Cl) | 2-CH₂CH₂CH₂-3 | 0 | 0 |
| 3491 | Cl | H | CO(4-Pyr-2-Cl) | 2,6-Me₂ | 0 | 0 |
| 3492 | Cl | H | CO(4-Pyr-2-Cl) | 2-Me, 6-cPr | 0 | 0 |
| 3493 | Cl | H | CO(2-Bfur) | 2-Me | 0 | 0 |
| 3494 | Cl | H | CO(2-Bfur) | 2-iPr | 0 | 0 |
| 3495 | Cl | H | CO(2-Bfur) | 2-cPr | 0 | 0 |
| 3496 | Cl | H | CO(2-Bfur) | 2-CH₂CH₂CH₂-3 | 0 | 0 |
| 3497 | Cl | H | CO(2-Bfur) | 2,6-Me₂ | 0 | 0 |
| 3498 | Cl | H | CO(2-Bfur) | 2-Me, 6-cPr | 0 | 0 |
| 3499 | Cl | H | CO(2-Bthi) | 2-Me | 0 | 0 |
| 3500 | Cl | H | CO(2-Bthi) | 2-iPr | 0 | 0 |
| 3501 | Cl | H | CO(2-Bthi) | 2-cPr | 0 | 0 |
| 3502 | Cl | H | CO(2-Bthi) | 2-CH₂CH₂CH₂-3 | 0 | 0 |
| 3503 | Cl | H | CO(2-Bthi) | 2,6-Me₂ | 0 | 0 |
| 3504 | Cl | H | CO(2-Bthi) | 2-Me, 6-cPr | 0 | 0 |
| 3505 | Cl | H | CO(6-Bthia) | 2-Me | 0 | 0 |
| 3506 | Cl | H | CO(6-Bthia) | 2-iPr | 0 | 0 |
| 3507 | Cl | H | CO(6-Bthia) | 2-cPr | 0 | 0 |
| 3508 | Cl | H | CO(6-Bthia) | 2-CH₂CH₂CH₂-3 | 0 | 0 |
| 3509 | Cl | H | CO(6-Bthia) | 2,6-Me₂ | 0 | 0 |
| 3510 | Cl | H | CO(6-Bthia) | 2-Me, 6-cPr | 0 | 0 |
| 3511 | Cl | H | CO(5-Boxaz) | 2-Me | 0 | 0 |
| 3512 | Cl | H | CO(5-Boxaz) | 2-iPr | 0 | 0 |
| 3513 | Cl | H | CO(5-Boxaz) | 2-cPr | 0 | 0 |
| 3514 | Cl | H | CO(5-Boxaz) | 2-CH₂CH₂CH₂-3 | 0 | 0 |
| 3515 | Cl | H | CO(5-Boxaz) | 2,6-Me₂ | 0 | 0 |
| 3516 | Cl | H | CO(5-Boxaz) | 2-Me, 6-cPr | 0 | 0 |
| 3517 | Cl | H | CO(1-Iqu) | 2-Me | 0 | 0 |
| 3518 | Cl | H | CO(1-Iqu) | 2-iPr | 0 | 0 |
| 3519 | Cl | H | CO(1-Iqu) | 2-cPr | 0 | 0 |
| 3520 | Cl | H | CO(1-Iqu) | 2-CH₂CH₂CH₂-3 | 0 | 0 |
| 3521 | Cl | H | CO(1-Iqu) | 2,6-Me₂ | 0 | 0 |
| 3522 | Cl | H | CO(1-Iqu) | 2-Me, 6-cPr | 0 | 0 |
| 3523 | Cl | H | CONMe(tBu) | 2-Me | 0 | 0 |
| 3524 | Cl | H | CONMe(tBu) | 2-iPr | 0 | 0 |
| 3525 | Cl | H | CONMe(tBu) | 2-cPr | 0 | 0 |
| 3526 | Cl | H | CONMe(tBu) | 2-CH₂CH₂CH₂-3 | 0 | 0 |
| 3527 | Cl | H | CONMe(tBu) | 2,6-Me₂ | 0 | 0 |
| 3528 | Cl | H | CONMe(tBu) | 2-Me, 6-cPr | 0 | 0 |
| 3529 | Cl | H | CONBu₂ | 2-Me | 0 | 0 |

TABLE 1-continued

Structure: pyridazine with R¹, R², OX, R³-R⁷ substituents on phenoxy group, with (O)ₘ and (O)ₙ on the ring nitrogens.

| Compound No. | R¹ | R² | X | R³ to R⁷ | m | n |
|---|---|---|---|---|---|---|
| 3530 | Cl | H | CONBu$_2$ | 2-iPr | 0 | 0 |
| 3531 | Cl | H | CONBu$_2$ | 2-cPr | 0 | 0 |
| 3532 | Cl | H | CONBu$_2$ | 2-CH$_2$CH$_2$CH$_2$-3 | 0 | 0 |
| 3533 | Cl | H | CONBu$_2$ | 2,6-Me$_2$ | 0 | 0 |
| 3534 | Cl | H | CONBu$_2$ | 2-Me, 6-cPr | 0 | 0 |
| 3535 | Cl | H | CONMe(CH$_2$Ph) | 2-Me | 0 | 0 |
| 3536 | Cl | H | CONMe(CH$_2$Ph) | 2-iPr | 0 | 0 |
| 3537 | Cl | H | CONMe(CH$_2$Ph) | 2-cPr | 0 | 0 |
| 3538 | Cl | H | CONMe(CH$_2$Ph) | 2-CH$_2$CH$_2$CH$_2$-3 | 0 | 0 |
| 3539 | Cl | H | CONMe(CH$_2$Ph) | 2,6-Me$_2$ | 0 | 0 |
| 3540 | Cl | H | CONMe(CH$_2$Ph) | 2-Me, 6-cPr | 0 | 0 |
| 3541 | Cl | H | CONMe(CH$_2$CN) | 2-Me | 0 | 0 |
| 3542 | Cl | H | CONMe(CH$_2$CN) | 2-iPr | 0 | 0 |
| 3543 | Cl | H | CONMe(CH$_2$CN) | 2-cPr | 0 | 0 |
| 3544 | Cl | H | CONMe(CH$_2$CN) | 2CH$_2$CH$_2$CH$_2$-3 | 0 | 0 |
| 3545 | Cl | H | CONMe(CH$_2$CN) | 2,6-Me$_2$ | 0 | 0 |
| 3546 | Cl | H | CONMe(CH$_2$CN) | 2-Me, 6-cPr | 0 | 0 |
| 3547 | Cl | H | CONMe(CH$_2$CO$_2$Et) | 2-Me | 0 | 0 |
| 3548 | Cl | H | CONMe(CH$_2$CO$_2$Et) | 2-iPr | 0 | 0 |
| 3549 | Cl | H | CONMe(CH$_2$CO$_2$Et) | 2-cPr | 0 | 0 |
| 3550 | Cl | H | CONMe(CH$_2$CO$_2$Et) | 2-CH$_2$CH$_2$CH$_2$-3 | 0 | 0 |
| 3551 | Cl | H | CONMe(CH$_2$CO$_2$Et) | 2,6-Me$_2$ | 0 | 0 |
| 3552 | Cl | H | CONMe(CH$_2$CO$_2$Et) | 2-Me, 6-cPr | 0 | 0 |
| 3553 | Cl | H | CONMe(2-Pyr) | 2-Me | 0 | 0 |
| 3554 | Cl | H | CONMe(2-Pyr) | 2-iPr | 0 | 0 |
| 3555 | Cl | H | CONMe(2-Pyr) | 2-cPr | 0 | 0 |
| 3556 | Cl | H | CONMe(2-Pyr) | 2-CH$_2$CH$_2$CH$_2$-3 | 0 | 0 |
| 3557 | Cl | H | CONMe(2-Pyr) | 2,6-Me$_2$ | 0 | 0 |
| 3558 | Cl | H | CONMe(2-Pyr) | 2-Me, 6-cPr | 0 | 0 |
| 3559 | Cl | H | CONMe(OMe) | 2-Me | 0 | 0 |
| 3560 | Cl | H | CONMe(OMe) | 2-iPr | 0 | 0 |
| 3561 | Cl | H | CONMe(OMe) | 2-cPr | 0 | 0 |
| 3562 | Cl | H | CONMe(OMe) | 2-CH$_2$CH$_2$CH$_2$-3 | 0 | 0 |
| 3563 | Cl | H | CONMe(OMe) | 2,6-Me$_2$ | 0 | 0 |
| 3564 | Cl | H | CONMe(OMe) | 2-Me, 6-cPr | 0 | 0 |
| 3565 | Cl | H | CON(CH$_2$CH$_2$Cl)$_2$ | 2-Me | 0 | 0 |
| 3566 | Cl | H | CON(CH$_2$CH$_2$Cl)$_2$ | 2-iPr | 0 | 0 |
| 3567 | Cl | H | CON(CH$_2$CH$_2$Cl)$_2$ | 2-cPr | 0 | 0 |
| 3568 | Cl | H | CON(CH$_2$CH$_2$Cl)$_2$ | 2-CH$_2$CH$_2$CH$_2$-3 | 0 | 0 |
| 3569 | Cl | H | CON(CH$_2$CH$_2$Cl)$_2$ | 2,6-Me$_2$ | 0 | 0 |
| 3570 | Cl | H | CON(CH$_2$CH$_2$Cl)$_2$ | 2-Me, 6-cPr | 0 | 0 |
| 3571 | Cl | H | CON(CH$_2$CH=CH$_2$)$_2$ | 2-Me | 0 | 0 |
| 3572 | Cl | H | CON(CH$_2$CH=CH$_2$)$_2$ | 2-iPr | 0 | 0 |
| 3573 | Cl | H | CON(CH$_2$CH=CH$_2$)$_2$ | 2-cPr | 0 | 0 |
| 3574 | Cl | H | CON(CH$_2$CH=CH$_2$)$_2$ | 2-CH$_2$CH$_2$CH$_2$-3 | 0 | 0 |
| 3575 | Cl | H | CON(CH$_2$CH=CH$_2$)$_2$ | 2,6-Me$_2$ | 0 | 0 |
| 3576 | Cl | H | CON(CH$_2$CH=CH$_2$)$_2$ | 2-Me, 6-cPr | 0 | 0 |
| 3577 | Cl | H | CON(CH$_2$CN)$_2$ | 2-Me | 0 | 0 |
| 3578 | Cl | H | CON(CH$_2$CN)$_2$ | 2-iPr | 0 | 0 |
| 3579 | Cl | H | CON(CH$_2$CN)$_2$ | 2-cPr | 0 | 0 |
| 3580 | Cl | H | CON(CH$_2$CN)$_2$ | 2-CH$_2$CH$_2$CH$_2$-3 | 0 | 0 |
| 3581 | Cl | H | CON(CH$_2$CN)$_2$ | 2,6-Me$_2$ | 0 | 0 |
| 3582 | Cl | H | CON(CH$_2$CN)$_2$ | 2-Me, 6-cPr | 0 | 0 |
| 3583 | Cl | H | CON(CH$_2$CH$_2$CN)$_2$ | 2-Me | 0 | 0 |
| 3584 | Cl | H | CON(CH$_2$CH$_2$CN)$_2$ | 2-iPr | 0 | 0 |
| 3585 | Cl | H | CON(CH$_2$CH$_2$CN)$_2$ | 2-cPr | 0 | 0 |
| 3586 | Cl | H | CON(CH$_2$CH$_2$CN)$_2$ | 2-CH$_2$CH$_2$CH$_2$-3 | 0 | 0 |
| 3587 | Cl | H | CON(CH$_2$CH$_2$CN)$_2$ | 2,6-Me$_2$ | 0 | 0 |
| 3588 | Cl | H | CON(CH$_2$CH$_2$CN)$_2$ | 2-Me, 6-cPr | 0 | 0 |
| 3589 | Cl | H | CON(CH$_2$CO$_2$Et)$_2$ | 2-Me | 0 | 0 |
| 3590 | Cl | H | CON(CH$_2$CO$_2$Et)$_2$ | 2-iPr | 0 | 0 |
| 3591 | Cl | H | CON(CH$_2$CO$_2$Et)$_2$ | 2-cPr | 0 | 0 |
| 3592 | Cl | H | CON(CH$_2$cO$_2$Et)$_2$ | 2-CH$_2$CH$_2$CH$_2$-3 | 0 | 0 |
| 3593 | Cl | H | CON(CH$_2$CO$_2$Et)$_2$ | 2,6-Me$_2$ | 0 | 0 |
| 3594 | Cl | H | CON(CH$_2$CO$_2$Et)$_2$ | 2-Me, 6-cPr | 0 | 0 |
| 3595 | Cl | H | CON(CH$_2$CH$_2$OMe)$_2$ | 2-Me | 0 | 0 |

TABLE 1-continued

[Structure: pyridazine with R¹, R², OX, R³–R⁷ substituents on phenoxy group, N-oxides (O)ₘ and (O)ₙ]

| Compound No. | R¹ | R² | X | R³ to R⁷ | m | n |
|---|---|---|---|---|---|---|
| 3596 | Cl | H | CON(CH₂CH₂OMe)₂ | 2-iPr | 0 | 0 |
| 3597 | Cl | H | CON(CH₂CH₂OMe)₂ | 2-cPr | 0 | 0 |
| 3598 | Cl | H | CON(CH₂CH₂OMe)₂ | 2-CH₂CH₂CH₂-3 | 0 | 0 |
| 3599 | Cl | H | CON(CH₂CH₂OMe)₂ | 2,6-Me₂ | 0 | 0 |
| 3600 | Cl | H | CON(CH₂CH₂OMe)₂ | 2-Me, 6-cPr | 0 | 0 |
| 3601 | Cl | H | CON(CH₂CH₂OEt)₂ | 2-Me | 0 | 0 |
| 3602 | Cl | H | CON(CH₂CH₂OEt)₂ | 2-iPr | 0 | 0 |
| 3603 | Cl | H | CON(CH₂CH₂OEt)₂ | 2-cPr | 0 | 0 |
| 3604 | Cl | H | CON(CH₂CH₂OEt)₂ | 2-CH₂CH₂CH₂-3 | 0 | 0 |
| 3605 | Cl | H | CON(CH₂CH₂OEt)₂ | 2,6-Me₂ | 0 | 0 |
| 3606 | Cl | H | CON(CH₂CH₂OEt)₂ | 2-Me, 6-cPr | 0 | 0 |
| 3607 | Cl | H | CO(1-Azet) | 2-Me | 0 | 0 |
| 3608 | Cl | H | CO(1-Azet) | 2-iPr | 0 | 0 |
| 3609 | Cl | H | CO(1-Azet) | 2-cPr | 0 | 0 |
| 3610 | Cl | H | CO(1-Azet) | 2-CH₂CH₂CH₂-3 | 0 | 0 |
| 3611 | Cl | H | CO(1-Azet) | 2,6-Me₂ | 0 | 0 |
| 3612 | Cl | H | CO(1-Azet) | 2-Me, 6-cPr | 0 | 0 |
| 3613 | Cl | H | CO(1-Pyrd-2-CO₂Me) | 2-Me | 0 | 0 |
| 3614 | Cl | H | CO(1-Pyrd-2-CO₂Me) | 2-iPr | 0 | 0 |
| 3615 | Cl | H | CO(1-Pyrd-2-CO₂Me) | 2-cPr | 0 | 0 |
| 3616 | Cl | H | CO(1-Pyrd-2-CO₂Me) | 2-CH₂CH₂CH₂-3 | 0 | 0 |
| 3617 | Cl | H | CO(1-Pyrd-2-CO₂Me) | 2,6-Me₂ | 0 | 0 |
| 3618 | Cl | H | CO(1-Pyrd-2-CO₂Me) | 2-Me, 6-cPr | 0 | 0 |
| 3619 | Cl | H | CO(1-Pyrd-3-OH) | 2-Me | 0 | 0 |
| 3620 | Cl | H | CO(1-Pyrd-3-OH) | 2-iPr | 0 | 0 |
| 3621 | Cl | H | CO(1-Pyrd-3-OH) | 2-cPr | 0 | 0 |
| 3622 | Cl | H | CO(1-Pyrd-3-OH) | 2-CH₂CH₂CH₂-3 | 0 | 0 |
| 3623 | Cl | H | CO(1-Pyrd-3-OH) | 2,6-Me₂ | 0 | 0 |
| 3624 | Cl | H | CO(1-Pyrd-3-OH) | 2-Me, 6-cPr | 0 | 0 |
| 3625 | Cl | H | CO(1-Pyrr-2,5-Me₂) | 2-Me | 0 | 0 |
| 3626 | Cl | H | CO(1-Pyrr-2,5-Me₂) | 2-iPr | 0 | 0 |
| 3627 | Cl | H | CO(1-Pyrr-2,5-Me₂) | 2-cPr | 0 | 0 |
| 3628 | Cl | H | CO(1-Pyrr-2,5-Me₂) | 2-CH₂CH₂CH₂-3 | 0 | 0 |
| 3629 | Cl | H | CO(1-Pyrr-2,5-Me₂) | 2,6-Me₂ | 0 | 0 |
| 3630 | Cl | H | CO(1-Pyrr-2,5-Me₂) | 2-Me, 6-cPr | 0 | 0 |
| 3631 | Cl | H | CO(1-Ppri) | 2-Me | 0 | 0 |
| 3632 | Cl | H | CO(1-Ppri) | 2-iPr | 0 | 0 |
| 3633 | Cl | H | CO(1-Ppri) | 2-cPr | 0 | 0 |
| 3634 | Cl | H | CO(1-Ppri) | 2-CH₂CH₂CH₂-3 | 0 | 0 |
| 3635 | Cl | H | CO(1-Ppri) | 2,6-Me₂ | 0 | 0 |
| 3636 | Cl | H | CO(1-Ppri) | 2-Me, 6-cPr | 0 | 0 |
| 3637 | Cl | H | CO(1-Ppri-2-CO₂Me) | 2-Me | 0 | 0 |
| 3638 | Cl | H | CO(1-Ppri-2-CO₂Me) | 2-iPr | 0 | 0 |
| 3639 | Cl | H | CO(1-Ppri-2-CO₂Me) | 2-cPr | 0 | 0 |
| 3640 | Cl | H | CO(1-Ppri-2-CO₂Me) | 2-CH₂CH₂CH₂-3 | 0 | 0 |
| 3641 | Cl | H | CO(1-Ppri-2-CO₂Me) | 2,6-Me₂ | 0 | 0 |
| 3642 | Cl | H | CO(1-Ppri-2-CO₂Me) | 2-Me, 6-cPr | 0 | 0 |
| 3643 | Cl | H | CO(1-Ppri-4-Br) | 2-Me | 0 | 0 |
| 3644 | Cl | H | CO(1-Ppri-4-Br) | 2-iPr | 0 | 0 |
| 3645 | Cl | H | CO(1-Ppri-4-Br) | 2-cPr | 0 | 0 |
| 3646 | Cl | H | CO(1-Ppri-4-Br) | 2-CH₂CH₂CH₂-3 | 0 | 0 |
| 3647 | Cl | H | CO(1-Ppri-4-Br) | 2,6-Me₂ | 0 | 0 |
| 3648 | Cl | H | CO(1-Ppri-4-Br) | 2-Me, 6-cPr | 0 | 0 |
| 3649 | Cl | H | CO(1-Ppri-4-Me) | 2-Me | 0 | 0 |
| 3650 | Cl | H | CO(1-Ppri-4-Me) | 2-iPr | 0 | 0 |
| 3651 | Cl | H | CO(1-Ppri-4-Me) | 2-cPr | 0 | 0 |
| 3652 | Cl | H | CO(1-Ppri-4-Me) | 2-CH₂CH₂CH₂-3 | 0 | 0 |
| 3653 | Cl | H | CO(1-Ppri-4-Me) | 2,6-Me₂ | 0 | 0 |
| 3654 | Cl | H | CO(1-Ppri-4-Me) | 2-Me, 6-cPr | 0 | 0 |
| 3655 | Cl | H | CO(1-Ppri-4-CO₂Me) | 2-Me | 0 | 0 |
| 3656 | Cl | H | CO(1-Ppri-4-CO₂Me) | 2-iPr | 0 | 0 |
| 3657 | Cl | H | CO(1-Ppri-4-CO₂Me) | 2-cPr | 0 | 0 |
| 3658 | Cl | H | CO(1-Ppri-4-CO₂Me) | 2-CH₂CH₂CH₂-3 | 0 | 0 |
| 3659 | Cl | H | CO(1-Ppri-4-CO₂Me) | 2,6-Me₂ | 0 | 0 |
| 3660 | Cl | H | CO(1-Ppri-4-CO₂Et) | 2-Me, 6-cPr | 0 | 0 |
| 3661 | Cl | H | CO(1-Ppri-4-OCH₂CH₂O-4) | 2-Me | 0 | 0 |

TABLE 1-continued

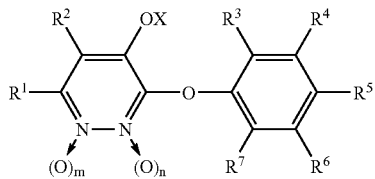

| Compound No. | R¹ | R² | X | R³ to R⁷ | m | n |
|---|---|---|---|---|---|---|
| 3662 | Cl | H | CO(1-Ppri-4-OCH$_2$CH$_2$O-4) | 2-iPr | 0 | 0 |
| 3663 | Cl | H | CO(1-Ppri-4-OCH$_2$CH$_2$O-4) | 2-cPr | 0 | 0 |
| 3664 | Cl | H | CO(1-Ppri-4-OCH$_2$CH$_2$O-4) | 2-CH$_2$CH$_2$CH$_2$-3 | 0 | 0 |
| 3665 | Cl | H | CO(1-Ppri-4-OCH$_2$CH$_2$O-4) | 2,6-Me$_2$ | 0 | 0 |
| 3666 | Cl | H | CO(1-Ppri-4-OCH$_2$CH$_2$O-4) | 2-Me, 6-cPr | 0 | 0 |
| 3667 | Cl | H | CO(1-Ppri-2,2,6,6-Me$_4$) | 2-Me | 0 | 0 |
| 3668 | Cl | H | CO(1-Ppri-2,2,6,6-Me$_4$) | 2-iPr | 0 | 0 |
| 3669 | Cl | H | CO(1-Ppri-2,2,6,6-Me$_4$) | 2-cPr | 0 | 0 |
| 3670 | Cl | H | CO(1-Ppri-2,2,6,6-Me$_4$) | 2-CH$_2$CH$_2$CH$_2$-3 | 0 | 0 |
| 3671 | Cl | H | CO(1-Ppri-2,2,6,6-Me$_4$) | 2,6-Me$_2$ | 0 | 0 |
| 3672 | Cl | H | CO(1-Ppri-2,2,6,6-Me$_4$) | 2-Me, 6-cPr | 0 | 0 |
| 3673 | Cl | H | CO(1-Ppra-4-Me) | 2-Me | 0 | 0 |
| 3674 | Cl | H | CO(1-Ppra-4-Me) | 2-iPr | 0 | 0 |
| 3675 | Cl | H | CO(1-Ppra-4-Me) | 2-cPr | 0 | 0 |
| 3676 | Cl | H | CO(1-Ppra-4-Me) | 2-CH$_2$CH$_2$CH$_2$-3 | 0 | 0 |
| 3677 | Cl | H | CO(1-Ppra-4-Me) | 2,6-Me$_2$ | 0 | 0 |
| 3678 | Cl | H | CO(1-Ppra-4-Me) | 2-Me, 6-cPr | 0 | 0 |
| 3679 | Cl | H | CO(1-Ppra-4-Ph) | 2-Me | 0 | 0 |
| 3680 | Cl | H | CO(1-Ppra-4-Ph) | 2-iPr | 0 | 0 |
| 3681 | Cl | H | CO(1-Ppra-4-Ph) | 2-cPr | 0 | 0 |
| 3682 | Cl | H | CO(1-Ppra-4-Ph) | 2-CH$_2$CH$_2$CH$_2$-3 | 0 | 0 |
| 3683 | Cl | H | CO(1-Ppra-4-Ph) | 2,6-Me$_2$ | 0 | 0 |
| 3684 | Cl | H | CO(1-Ppra-4-Ph) | 2-Me, 6-cPr | 0 | 0 |
| 3685 | Cl | H | CO-4-Morp | 2-Me | 0 | 0 |
| 3686 | Cl | H | CO-4-Morp | 2-iPr | 0 | 0 |
| 3687 | Cl | H | CO-4-Morp | 2-cPr | 0 | 0 |
| 3688 | Cl | H | CO-4-Morp | 2-CH$_2$CH$_2$CH$_2$-3 | 0 | 0 |
| 3689 | Cl | H | CO-4-Morp | 2,6-Me$_2$ | 0 | 0 |
| 3690 | Cl | H | CO-4-Morp | 2-Me, 6-cPr | 0 | 0 |
| 3691 | Cl | H | CO(4-Morp-2,6-Me$_2$) | 2-Me | 0 | 0 |
| 3692 | Cl | H | CO(4-Morp-2,6-Me$_2$) | 2-iPr | 0 | 0 |
| 3693 | Cl | H | CO(4-Morp-2,6-Me$_2$) | 2-cPr | 0 | 0 |
| 3694 | Cl | H | CO(4-Morp-2,6-Me$_2$) | 2-CH$_2$CH$_2$CH$_2$-3 | 0 | 0 |
| 3695 | Cl | H | CO(4-Morp-2,6-Me$_2$) | 2,6-Me$_2$ | 0 | 0 |
| 3696 | Cl | H | CO(4-Morp-2,6-Me$_2$) | 2-Me, 6-cPr | 0 | 0 |
| 3697 | Cl | H | CO-4-Tmor | 2-Me | 0 | 0 |
| 3698 | Cl | H | CO-4-Tmor | 2-iPr | 0 | 0 |
| 3699 | Cl | H | CO-4-Tmor | 2-cPr | 0 | 0 |
| 3700 | Cl | H | CO-4-Tmor | 2-CH$_2$CH$_2$CH$_2$-3 | 0 | 0 |
| 3701 | Cl | H | CO-4-Tmor | 2,6-Me$_2$ | 0 | 0 |
| 3702 | Cl | H | CO-4-Tmor | 2-Me, 6-cPr | 0 | 0 |
| 3703 | Cl | H | COQ$^{18}$ | 2-Me | 0 | 0 |
| 3704 | Cl | H | COQ$^{18}$ | 2-iPr | 0 | 0 |
| 3705 | Cl | H | COQ$^{18}$ | 2-cPr | 0 | 0 |
| 3706 | Cl | H | COQ$^{18}$ | 2-CH$_2$CH$_2$CH$_2$-3 | 0 | 0 |
| 3707 | Cl | H | COQ$^{18}$ | 2,6-Me$_2$ | 0 | 0 |
| 3708 | Cl | H | COQ$^{18}$ | 2-Me, 6-cPr | 0 | 0 |
| 3709 | Cl | H | CO(9-Carb) | 2-Me | 0 | 0 |
| 3710 | Cl | H | CO(9-Carb) | 2-iPr | 0 | 0 |
| 3711 | Cl | H | CO(9-Carb) | 2-cPr | 0 | 0 |
| 3712 | Cl | H | CO(9-Carb) | 2-CH$_2$CH$_2$CH$_2$-3 | 0 | 0 |
| 3713 | Cl | H | CO(9-Carb) | 2,6-Me$_2$ | 0 | 0 |
| 3714 | Cl | H | CO(9-Carb) | 2-Me, 6-cPr | 0 | 0 |
| 3715 | Cl | H | CO(10-Pthia) | 2-Me | 0 | 0 |
| 3716 | Cl | H | CO(10-Pthia) | 2-iPr | 0 | 0 |
| 3717 | Cl | H | CO(10-Pthia) | 2-cPr | 0 | 0 |
| 3718 | Cl | H | CO(10-Pthia) | 2-CH$_2$CH$_2$CH$_2$-3 | 0 | 0 |
| 3719 | Cl | H | CO(10-Pthia) | 2,6-Me$_2$ | 0 | 0 |
| 3720 | Cl | H | CO(10-Pthia) | 2-Me, 6-cPr | 0 | 0 |
| 3721 | Cl | H | SO$_2$(Ph-2-CO$_2$Q$^5$) | 2-Me, 6-cPr | 0 | 0 |
| 3722 | Cl | H | SO$_2$(Ph-3-CO$_2$Q$^5$) | 2-Me, 6-cPr | 0 | 0 |
| 3723 | Cl | H | SO$_2$(Ph-4-CO$_2$Q$^5$) | 2-Me, 6-cPr | 0 | 0 |
| 3724 | Cl | H | SO$_2$(Ph-4-OMe) | 2-Cl | 0 | 0 |
| 3725 | Cl | H | SO$_2$(Ph-4-OMe) | 2-Br | 0 | 0 |
| 3726 | Cl | H | SO$_2$(Ph-4-OMe) | 2-I | 0 | 0 |
| 3727 | Cl | H | SO$_2$(Ph-4-OMe) | 2-cBu | 0 | 0 |

TABLE 1-continued

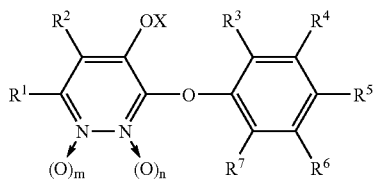

| Compound No. | R¹ | R² | X | R³ to R⁷ | m | n |
|---|---|---|---|---|---|---|
| 3728 | Cl | H | $SO_2$ (Ph-4-OMe) | 2-cPr, 5-Me | 0 | 0 |
| 3729 | Cl | H | $SO_2$ (Ph-4-OMe) | 2-OMe, 5-Me | 0 | 0 |
| 3730 | Cl | H | $SO_2$ (Ph-4-OMe) | 2-F, 6-iPr | 0 | 0 |
| 3731 | Cl | H | $SO_2$ (Ph-4-OMe) | 2-Cl, 6-cPr | 0 | 0 |
| 3732 | Cl | H | $SO_2$ (Ph-4-OMe) | 2-Br, 6-Me | 0 | 0 |
| 3733 | Cl | H | $SO_2$ (Ph-4-OMe) | 2-I, 6-Me | 0 | 0 |
| 3734 | Cl | H | $SO_2$ (Ph-4-OMe) | 2-Me, 6-Et | 0 | 0 |
| 3735 | Cl | H | $SO_2$ (Ph-4-OMe) | 2,6-cPr₂ | 0 | 0 |
| 3736 | Cl | H | $SO_2$ (Ph-4-OMe) | 2-cPr, 3,5-Me₂ | 0 | 0 |
| 3737 | Cl | H | $SO_2$ (Ph-4-OMe) | 2-cPr, 3,6-Me₂ | 0 | 0 |
| 3738 | Cl | H | $SO_2$ (Ph-2-$SO_2OQ^6$) | 2-Me | 0 | 0 |
| 3739 | Cl | H | $SO_2$ (Ph-2-$SO_2OQ^7$) | 2-iPr | 0 | 0 |
| 3740 | Cl | H | $SO_2$ (Ph-2-$SO_2OQ^8$) | 2-cPr | 0 | 0 |
| 3741 | Cl | H | $SO_2$ (Ph-2-$SO_2OQ^9$) | 2-$CH_2CH_2CH_2$-3 | 0 | 0 |
| 3742 | Cl | H | $SO_2$ (Ph-2-$SO_2OQ^{10}$) | 2,6-Me₂ | 0 | 0 |
| 3743 | Cl | H | $SO_2$ (Ph-2-$SO_2OQ^{11}$) | 2-Me, 6-cPr | 0 | 0 |
| 3744 | Cl | H | $SO_2$ (Ph-2-$SO_2OQ^{12}$) | 2-Me, 6-cPr | 0 | 0 |
| 3745 | Cl | H | $SO_2$ (Ph-2-$SO_2OQ^{13}$) | 2-Me, 6-cPr | 0 | 0 |
| 3746 | Cl | H | $SO_2$ (Ph-2-$SO_2OQ^{14}$) | 2-Me, 6-cPr | 0 | 0 |
| 3747 | Cl | H | $SO_2$ (Ph-2-$SO_2OQ^{15}$) | 2-Me, 6-cPr | 0 | 0 |
| 3748 | Cl | H | $SO_2$ (Ph-2-$SO_2OQ^{16}$) | 2-Me, 6-cPr | 0 | 0 |
| 3749 | Cl | H | $SO_2$ (Ph-2-$SO_2OQ^{17}$) | 2-Me, 6-cPr | 0 | 0 |
| 3750 | Cl | H | $SO_2$ (Ph-3-$SO_2OQ^6$) | 2-Me | 0 | 0 |
| 3751 | Cl | H | $SO_2$ (Ph-3-$SO_2OQ^7$) | 2-iPr | 0 | 0 |
| 3752 | Cl | H | $SO_2$ (Ph-3-$SO_2OQ^8$) | 2-cPr | 0 | 0 |
| 3753 | Cl | H | $SO_2$ (Ph-3-$SO_2OQ^9$) | 2-$CH_2CH_2CH_2$-3 | 0 | 0 |
| 3754 | Cl | H | $SO_2$ (Ph-3-$SO_2OQ^{10}$) | 2,6-Me₂ | 0 | 0 |
| 3755 | Cl | H | $SO_2$ (Ph-3-$SO_2OQ^{11}$) | 2-Me, 6-cPr | 0 | 0 |
| 3756 | Cl | H | $SO_2$ (Ph-3-$SO_2OQ^{12}$) | 2-Me, 6-cPr | 0 | 0 |
| 3757 | Cl | H | $SO_2$ (Ph-3-$SO_2OQ^{13}$) | 2-Me, 6-cPr | 0 | 0 |
| 3758 | Cl | H | $SO_2$ (Ph-3-$SO_2OQ^{14}$) | 2-Me, 6-cPr | 0 | 0 |
| 3759 | Cl | H | $SO_2$ (Ph-3-$SO_2OQ^{15}$) | 2-Me, 6-cPr | 0 | 0 |
| 3760 | Cl | H | $SO_2$ (Ph-3-$SO_2OQ^{16}$) | 2-Me, 6-cPr | 0 | 0 |
| 3761 | Cl | H | $SO_2$ (Ph-3-$SO_2OQ^{17}$) | 2-Me, 6-cPr | 0 | 0 |
| 3762 | Cl | H | $SO_2$ (Ph-4-$SO_2OQ^5$) | 2-Cl, 6-cPr | 0 | 0 |
| 3763 | Cl | H | $SO_2$ (Ph-4-$SO_2OQ^6$) | 2-Me | 0 | 0 |
| 3764 | Cl | H | $SO_2$ (Ph-4-$SO_2OQ^7$) | 2-iPr | 0 | 0 |
| 3765 | Cl | H | $SO_2$ (Ph-4-$SO_2OQ^8$) | 2-cPr | 0 | 0 |
| 3766 | Cl | H | $SO_2$ (Ph-4-$SO_2OQ^9$) | 2-$CH_2CH_2CH_2$-3 | 0 | 0 |
| 3767 | Cl | H | $SO_2$ (Ph-4-$SO_2OQ^{10}$) | 2,6-Me₂ | 0 | 0 |
| 3768 | Cl | H | $SO_2$ (Ph-4-$SO_2OQ^{11}$) | 2-Me, 6-cPr | 0 | 0 |
| 3769 | Cl | H | $SO_2$ (Ph-4-$SO_2OQ^{12}$) | 2-Me, 6-cPr | 0 | 0 |
| 3770 | Cl | H | $SO_2$ (Ph-4-$SO_2OQ^{13}$) | 2-Me, 6-cPr | 0 | 0 |
| 3771 | Cl | H | $SO_2$ (Ph-4-$SO_2OQ^{14}$) | 2-Me, 6-cPr | 0 | 0 |
| 3772 | Cl | H | $SO_2$ (Ph-4-$SO_2OQ^{15}$) | 2-Me, 6-cPr | 0 | 0 |
| 3773 | Cl | H | $SO_2$ (Ph-4-$SO_2OQ^{16}$) | 2-Me, 6-cPr | 0 | 0 |
| 3774 | Cl | H | $SO_2$ (Ph-4-$SO_2OQ^{17}$) | 2-Me, 6-cPr | 0 | 0 |
| 3775 | Cl | H | $SO_2$ (Ph-2,5-Cl₂) | 2-Me | 0 | 0 |
| 3776 | Cl | H | $SO_2$ (Ph-2,5-Cl₂) | 2-iPr | 0 | 0 |
| 3777 | Cl | H | $SO_2$ (Ph-2,5-Cl₂) | 2-cPr | 0 | 0 |
| 3778 | Cl | H | $SO_2$ (Ph-2,5-Cl₂) | 2-$CH_2CH_2CH_2$-3 | 0 | 0 |
| 3779 | Cl | H | $SO_2$ (Ph-2,5-Cl₂) | 2,6-Me₂ | 0 | 0 |
| 3780 | Cl | H | $SO_2$ (Ph-2,5-Cl₂) | 2-Me, 6-cPr | 0 | 0 |
| 3781 | Cl | H | $SO_2$ (Ph-3-$NO_2$-4-Cl) | 2-Me | 0 | 0 |
| 3782 | Cl | H | $SO_2$ (Ph-3-$NO_2$-4-Cl) | 2-iPr | 0 | 0 |
| 3783 | Cl | H | $SO_2$ (Ph-3-$NO_2$-4-Cl) | 2-cPr | 0 | 0 |
| 3784 | Cl | H | $SO_2$ (Ph-3-$NO_2$-4-Cl) | 2-$CH_2CH_2CH_2$-3 | 0 | 0 |
| 3785 | Cl | H | $SO_2$ (Ph-3-$NO_2$-4-Cl) | 2,6-Me₂ | 0 | 0 |
| 3786 | Cl | H | $SO_2$ (Ph-3-$NO_2$-4-Cl) | 2-Me, 6-cPr | 0 | 0 |
| 3787 | Cl | H | $SO_2$ (2-Thi) | 2-Me | 0 | 0 |
| 3788 | Cl | H | $SO_2$ (2-Thi) | 2-iPr | 0 | 0 |
| 3789 | Cl | H | $SO_2$ (2-Thi) | 2-cPr | 0 | 0 |
| 3790 | Cl | H | $SO_2$ (2-Thi) | 2-$CH_2CH_2CH_2$-3 | 0 | 0 |
| 3791 | Cl | H | $SO_2$ (2-Thi) | 2,6-Me₂ | 0 | 0 |
| 3792 | Cl | H | $SO_2$ (2-Thi) | 2-Me, 6-cPr | 0 | 0 |
| 3793 | Cl | H | N(Bu)₄ | 2-Me | 0 | 0 |

TABLE 1-continued

| Compound No. | R¹ | R² | X | R³ to R⁷ | m | n |
|---|---|---|---|---|---|---|
| 3794 | Cl | H | N(Bu)$_4$ | 2-iPr | 0 | 0 |
| 3795 | Cl | H | N(Bu)$_4$ | 2-cPr | 0 | 0 |
| 3796 | Cl | H | N(Bu)$_4$ | 2-CH$_2$CH$_2$CH$_2$-3 | 0 | 0 |
| 3797 | Cl | H | N(Bu)$_4$ | 2,6-Me$_2$ | 0 | 0 |
| 3798 | Cl | H | N(Bu)$_4$ | 2-Me, 6-cPr | 0 | 0 |
| 3799 | Cl | H | Li | 2-Me, 6-cPr | 0 | 0 |
| 3800 | Cl | H | Na | 2-Me | 0 | 0 |
| 3801 | Cl | H | Na | 2-iPr | 0 | 0 |
| 3802 | Cl | H | Na | 2-cPr | 0 | 0 |
| 3803 | Cl | H | Na | 2CH$_2$CH$_2$CH$_2$-3 | 0 | 0 |
| 3804 | Cl | H | Na | 2,6-Me$_2$ | 0 | 0 |
| 3805 | Cl | H | Na | 2-Me, 6-cPr | 0 | 0 |
| 3806 | Cl | H | K | 2-Me | 0 | 0 |
| 3807 | Cl | H | K | 2-iPr | 0 | 0 |
| 3808 | Cl | H | K | 2-cPr | 0 | 0 |
| 3809 | Cl | H | K | 2-CH$_2$CH$_2$CH$_2$-3 | 0 | 0 |
| 3810 | Cl | H | K | 2,6-Me$_2$ | 0 | 0 |
| 3811 | Cl | H | K | 2-Me, 6-cPr | 0 | 0 |
| 3812 | Cl | H | Rb | 2-Me, 6-cPr | 0 | 0 |
| 3813 | Cl | H | Cs | 2-Me, 6-cPr | 0 | 0 |
| 3814 | Cl | H | Mg | 2-Me, 6-cPr | 0 | 0 |
| 3815 | Cl | H | Ca | 2-Me, 6-cPr | 0 | 0 |
| 3816 | Cl | H | Ba | 2-Me, 6-cPr | 0 | 0 |
| 3817 | Cl | H | Sc | 2-Me, 6-cPr | 0 | 0 |
| 3818 | Cl | H | Ti | 2-Me, 6-cPr | 0 | 0 |
| 3819 | Cl | H | Mn | 2-Me, 6-cPr | 0 | 0 |
| 3820 | Cl | H | Fe | 2-Me, 6-cPr | 0 | 0 |
| 3821 | Cl | H | Cu | 2-Me, 6-cPr | 0 | 0 |
| 3822 | Cl | H | Ag | 2-Me, 6-cPr | 0 | 0 |
| 3823 | Cl | H | Au | 2-Me, 6-cPr | 0 | 0 |
| 3824 | Cl | H | Zn | 2-Me, 6-cPr | 0 | 0 |
| 3825 | Cl | H | Al | 2-Me, 6-cPr | 0 | 0 |
| 3826 | Cl | F | H | 2-Me | 0 | 0 |
| 3827 | Cl | F | H | 2-iPr | 0 | 0 |
| 3828 | Cl | F | H | 2-cPr | 0 | 0 |
| 3829 | Cl | F | H | 2-CH$_2$CH$_2$CH$_2$-3 | 0 | 0 |
| 3830 | Cl | F | H | 2,6-Me$_2$ | 0 | 0 |
| 3831 | Cl | F | H | 2-Me, 6-cPr | 0 | 0 |
| 3832 | Cl | Cl | H | 2-Me | 0 | 0 |
| 3833 | Cl | Cl | H | 2-iPr | 0 | 0 |
| 3834 | Cl | Cl | H | 2-cPr | 0 | 0 |
| 3835 | Cl | Cl | H | 2-CH$_2$CH$_2$CH$_2$-3 | 0 | 0 |
| 3836 | Cl | Cl | H | 2,6-Me$_2$ | 0 | 0 |
| 3837 | Cl | Cl | H | 2-Me, 6-cPr | 0 | 0 |
| 3838 | Cl | Br | H | 2-Me | 0 | 0 |
| 3839 | Cl | Br | H | 2-iPr | 0 | 0 |
| 3840 | Cl | Br | H | 2-cPr | 0 | 0 |
| 3841 | Cl | Br | H | 2-CH$_2$CH$_2$CH$_2$-3 | 0 | 0 |
| 3842 | Cl | Br | H | 2,6-Me$_2$ | 0 | 0 |
| 3843 | Cl | Br | H | 2-Me, 6-cPr | 0 | 0 |
| 3844 | Cl | I | H | 2-Me | 0 | 0 |
| 3845 | Cl | I | H | 2-iPr | 0 | 0 |
| 3846 | Cl | I | H | 2-cPr | 0 | 0 |
| 3847 | Cl | I | H | 2-CH$_2$CH$_2$CH$_2$-3 | 0 | 0 |
| 3848 | Cl | I | H | 2,6-Me$_2$ | 0 | 0 |
| 3849 | Cl | I | H | 2-Me, 6-cPr | 0 | 0 |
| 3850 | Cl | H | OCOPh | 2-Me, 4-OCOPh | 0 | 0 |
| 3851 | Cl | H | CO-4-Thpy | 2-Me | 0 | 0 |
| 3852 | Cl | H | CO-4-Thpy | 2-iPr | 0 | 0 |
| 3853 | Cl | H | CO-4-Thpy | 2-cPr | 0 | 0 |
| 3854 | Cl | H | CO-4-Thpy | 2-CH$_2$CH$_2$CH$_2$-3 | 0 | 0 |
| 3855 | Cl | H | CO-4-Thpy | 2,6-Me$_2$ | 0 | 0 |
| 3856 | Cl | H | CO-4-Thpy | 2-Me, 6-cPr | 0 | 0 |

Among the above-mentioned exemplary compounds, preferred compounds are Compounds Nos. 124, 125, 126, 127, 128, 130, 131, 132, 134, 136, 139, 140, 144, 145, 151, 163, 173, 202, 207, 217, 226, 249, 264, 265, 266, 267, 269, 270, 271, 272, 273, 279, 280, 284, 287, 292, 300, 304, 305, 306, 307, 308, 309, 311, 330, 334, 336, 339, 344, 359, 361, 362, 364, 365, 370, 377, 385, 386, 387, 390, 391, 400, 401, 403, 410, 412, 413, 417, 422, 426, 437, 438, 441, 443, 446, 450, 456, 459, 472, 478, 498, 505, 506, 507, 514, 515, 516, 521, 527, 528, 529, 531, 532, 534, 535, 539, 541, 544, 547, 557, 562, 566, 571, 614, 618, 621, 623, 629, 640, 642, 658, 659, 662, 663, 664, 667, 700, 701, 702, 704, 707, 708, 710, 711, 712, 716, 717, 719, 728, 732, 733, 734, 735, 736, 737, 738, 740, 756, 758, 759, 760, 761, 762, 775, 778, 780, 781, 782, 801, 802, 803, 804, 805, 806, 827, 834, 844, 845, 846, 850, 890, 894, 896, 911, 914, 931, 964, 965, 979, 982, 987, 998, 1000, 1007, 1009, 1013, 1016, 1020, 1023, 1027, 1040, 1050, 1052, 1053, 1055, 1058, 1060, 1061, 1063, 1064, 1066, 1069, 1073, 1083, 1086, 1088, 1089, 1091, 1096, 1099, 1100, 1102, 1109, 1115, 1118, 1119, 1120, 1122, 1123, 1124, 1125, 1126, 1128, 1129, 1133, 1140, 1151, 1160, 1172, 1178, 1184, 1207, 1251, 1260, 1266, 1286, 1298, 1334, 1340, 1358, 1364, 1382, 1387, 1391, 1417, 1441, 1446, 1448, 1456, 1459, 1461, 1481, 1509, 1522, 1531, 1537, 1543, 1549, 1553, 1554, 1566, 1575, 1593, 1599, 1603, 1616, 1620, 1625, 1631, 1643, 1649, 1658, 1706, 1710, 1757, 1770, 1789, 1811, 1840, 1877, 1879, 1891, 1898, 1911, 1920, 1924, 1937, 1946, 1952, 1958, 1981, 1985, 2010, 2034, 2038, 2040, 2042, 2051, 2060, 2066, 2072, 2081, 2106, 2136, 2147, 2151, 2176, 2198, 2199, 2200, 2212, 2220, 2221, 2222, 2224, 2225, 2263, 2265, 2287, 2289, 2300, 2309, 2315, 2321, 2327, 2333, 2411, 2431, 2453, 2519, 2529, 2540, 2542, 2547, 2548, 2551, 2555, 2556, 2565, 2568, 2570, 2571, 2572, 2574, 2576, 2577, 2585, 2587, 2589, 2592, 2596, 2597, 2599, 2600, 2601, 2603, 2605, 2606, 2607, 2608, 2609, 2614, 2662, 2671, 2677, 2697, 2703, 2709, 2715, 2721, 2727, 2733, 2739, 2746, 2752, 2758, 2764, 2770, 2776, 2782, 2788, 2805, 2814, 2820, 2826, 2827, 2838, 2850, 2856, 2862, 2868, 2874, 2880, 2900, 2906, 2918, 2924, 2930, 2961, 2970, 2976, 2982, 2988, 2994, 3001, 3016, 3022, 3028, 3034, 3040, 3046, 3052, 3058, 3064, 3070, 3076, 3082, 3088, 3094, 3100, 3106, 3112, 3129, 3138, 3144, 3150, 3156, 3162, 3168, 3185, 3194, 3200, 3217, 3226, 3243, 3252, 3258, 3264, 3270, 3276, 3282, 3288, 3294, 3300, 3306, 3312, 3318, 3324, 3330, 3336, 3342, 3348, 3354, 3360, 3366, 3372, 3378, 3384, 3390, 3396, 3402, 3408, 3414, 3420, 3426, 3432, 3438, 3444, 3450, 3456, 3462, 3468, 3474, 3480, 3486, 3492, 3498, 3504, 3510, 3516, 3522, 3528, 3534, 3540, 3546, 3552, 3558, 3564, 3570, 3576, 3582, 3588, 3594, 3600, 3606, 3612, 3618, 3624, 3630, 3636, 3642, 3648, 3654, 3660, 3666, 3672, 3678, 3684, 3690, 3696, 3702, 3708, 3714, 3720, 3755, 3780, 3786, 3792, 3798, 3805, 3811, 3837, 3843 or 3849, more preferably compounds of Compounds Nos. 124, 125, 126, 127, 128, 130, 132, 136, 139, 140, 144, 145, 151, 163, 173, 202, 217, 249, 264, 265, 266, 267, 269, 270, 271, 284, 287, 300, 304, 308, 309, 311, 334, 336, 339, 361, 362, 377, 385, 386, 387, 390, 391, 401, 437, 438, 459, 472, 505, 506, 507, 515, 516, 521, 528, 529, 531, 532, 534, 539, 541, 544, 547, 571, 621, 658, 659, 662, 663, 664, 667, 700, 701, 702, 704, 707, 708, 711, 712, 717, 719, 732, 733, 734, 735, 736, 737, 738, 740, 756, 758, 759, 760, 762, 775, 778, 780, 781, 782, 801, 802, 803, 806, 827, 834, 845, 846, 850, 896, 914, 931, 964, 965, 998, 1013, 1016, 1023, 1040, 1050, 1052, 1053, 1055, 1058, 1060, 1061, 1063, 1064, 1066, 1069, 1073, 1086, 1088, 1089, 1091, 1096, 1099, 1100, 1102, 1109, 1115, 1118, 1119, 1120, 1123, 1124, 1125, 1126, 1129, 1133, 1140, 1151, 1160, 1172, 1178, 1184, 1207, 1260, 1266, 1286, 1298, 1334, 1340, 1358, 1364, 1382, 1387, 1391, 1417, 1441, 1446, 1448, 1481, 1522, 1531, 1537, 1543, 1549, 1566, 1575, 1593, 1599, 1616, 1620, 1625, 1631, 1643, 1649, 1658, 1710, 1770, 1789, 1811, 1840, 1879, 1891, 1911, 1937, 1946, 1958, 1981, 1985, 2010, 2034, 2038, 2040, 2042, 2051, 2060, 2066, 2072, 2081, 2106, 2136, 2151, 2176, 2200, 2212, 2220, 2225, 2265, 2289, 2300, 2309, 2327, 2333, 2411, 2519, 2529, 2540, 2542, 2556, 2565, 2568, 2576, 2577, 2587, 2597, 2599, 2600, 2601, 2605, 2609, 2614, 2662, 2671, 2677, 2697, 2703, 2709, 2715, 2721, 2727, 2733, 2739, 2746, 2752, 2758, 2764, 2770, 2776, 2782, 2788, 2805, 2814, 2820, 2826, 2850, 2856, 2862, 2868, 2874, 2880, 2900, 2906, 2918, 2924, 2930, 2961, 2970, 2976, 2982, 2988, 2994, 3022, 3028, 3034, 3040, 3046, 3052, 3058, 3064, 3070, 3076, 3082, 3088, 3094, 3100, 3106, 3112, 3129, 3138, 3144, 3162, 3168, 3185, 3194, 3200, 3217, 3226, 3243, 3252, 3258, 3264, 3270, 3276, 3282, 3288, 3294, 3300, 3306, 3312, 3318, 3324, 3330, 3336, 3342, 3348, 3354, 3360, 3366, 3372, 3378, 3384, 3390, 3396, 3402, 3408, 3414, 3420, 3426, 3432, 3438, 3444, 3450, 3456, 3462, 3468, 3474, 3480, 3486, 3492, 3498, 3504, 3510, 3516, 3528, 3534, 3540, 3546, 3552, 3558, 3564, 3570, 3576, 3582, 3588, 3594, 3600, 3606, 3612, 3618, 3624, 3630, 3636, 3642, 3648, 3654, 3660, 3666, 3672, 3678, 3684, 3690, 3696, 3702, 3708, 3714, 3720, 3755, 3780, 3786, 3792, 3798, 3805, 3811, 3837, 3843 or 3849, still further preferably compounds of Compounds Nos. 125, 126, 127, 128, 130, 132, 139, 140, 144, 145, 151, 163, 217, 249, 264, 265, 266, 284, 304, 308, 387, 390, 391, 459, 472, 506, 507, 515, 516, 531, 539, 541, 621, 658, 659, 662, 700, 701, 702, 704, 711, 717, 719, 733, 734, 735, 740, 758, 759, 762, 775, 780, 781, 801, 802, 803, 806, 827, 834, 846, 850, 931, 964, 965, 1023, 1040, 1050, 1052, 1053, 1055, 1058, 1061, 1064, 1066, 1069, 1073, 1088, 1089, 1091, 1096, 1099, 1100, 1102, 1109, 1119, 1124, 1125, 1126, 1129, 1133, 1151, 1160, 1172, 1178, 1184, 1207, 1260, 1286, 1298, 1334, 1340, 1358, 1382, 1417, 1441, 1481, 1522, 1531, 1537, 1543, 1549, 1566, 1593, 1599, 1616, 1625, 1631, 1643, 1649, 1770, 1811, 1891, 1958, 2034, 2051, 2060, 2072, 2136, 2176, 2212, 2265, 2309, 2327, 2333, 2519, 2556, 2577, 2587, 2597, 2599, 2600, 2601, 2609, 2614, 2662, 2677, 2697, 2709, 2715, 2721, 2727, 2733, 2739, 2746, 2752, 2758, 2764, 2770, 2776, 2782, 2788, 2805, 2814, 2820, 2826, 2850, 2862, 2868, 2874, 2900, 2918, 2924, 2930, 2961, 2970, 2988, 2994, 3022, 3034, 3046, 3058, 3064, 3076, 3082, 3094, 3106, 3112, 3129, 3144, 3162, 3168, 3185, 3217, 3243, 3252, 3264, 3282, 3288, 3294, 3306, 3324, 3330, 3336, 3354, 3378, 3390, 3396, 3402, 3408, 3414, 3420, 3426, 3432, 3438, 3450, 3462, 3468, 3474, 3486, 3492, 3510, 3516, 3546, 3552, 3564, 3582, 3588, 3594, 3600, 3606, 3612, 3618, 3624, 3642, 3654, 3660, 3678, 3690, 3696, 3702, 3780, 3786, 3798, 3805, 3811, 3837, 3843 or 3849, particularly preferably compounds of Compounds Nos. 127, 128, 132, 139, 144, 217, 265, 284, 304, 391, 472, 506, 507, 515, 516, 539, 541, 621, 658, 659, 662, 704, 711, 717, 719, 733, 735, 740, 758, 759, 762, 780, 781, 801, 802, 803, 806, 827, 846, 850, 931, 964, 965, 1023, 1040, 1052, 1058, 1061, 1088, 1089, 1091, 1096, 1099, 1100, 1102, 1109, 1124, 1125, 1151, 1160, 1172, 1184, 1207, 1286, 1298, 1334, 1358, 1417, 1441, 1481, 1522, 1531, 1537, 1543, 1566, 1593, 1599, 1616, 1625, 1631, 1643, 1770, 1811, 1891, 1958, 2034, 2051, 2176, 2212, 2265, 2309, 2327, 2333, 2597, 2599, 2614, 2662, 2677, 2727, 2733, 2739, 2746, 2752, 2805, 2814, 2850, 2900, 2918, 2961, 2994, 3022, 3046, 3064, 3094, 3129, 3144, 3168, 3185, 3217, 3243, 3264, 3288, 3402, 3408, 3426, 3432, 3450, 3462, 3546, 3552, 3564, 3582, 3588, 3594, 3600, 3606, 3612, 3618, 3624, 3642, 3654, 3660, 3678, 3690, 3696, 3702, 3805 or 3811, most preferably compounds of 6-chloro-3-(2-methylphenoxy)-4-pyridazinol (Compound No. 128), 6-chloro-3-(2-isopropylphenoxy)-4-pyridazinol (Compound No. 132), 6-chloro-3-(2-cyclopropylphenoxy)-4-pyridazinol (Compound No. 139), 6-chloro-3-[2-(2,2-dichlorocyclopropyl)phenoxy]-4-pyridazinol (Compound No. 265), 6-chloro-3-(2,3-dihydro-1H-inden-4-yloxy)-4-pyridazinol (Compound No. 506), 6-chloro-3-(2-cyclopropyl-5-methylphenoxy)-4-pyridazinol (Compound No. 662), 6-chloro-3-(2-fluoro-6-isopropylphenoxy)-4-pyridazinol (Compound No. 717), 6-chloro-3-(2-chloro-6-cyclopropylphenoxy)-4-pyridazinol (Compound No. 740), 6-chloro-3-(2,6-dimethylphenoxy)-4-pyridazinol (Compound No. 801), 6-chloro-3-(2-cyclopropyl-6-methylphenoxy)-4-pyridazinol (Compound No. 806), 6-chloro-3-[2-(2,2-dichlorocyclopropyl)-6-methylphenoxy]-4-pyridazinol (Compound No. 827), 6-chloro-3-(2-cyclopropyl-3,5-dimethylphenoxy)-4-pyridazinol (Compound No. 1023), 6-chloro-3-(6-cyclopropyl-3-fluoro-2-methylphenoxy)-4-pyridazinol (Compound No. 1052), 6-chloro-3-(6-cyclopropyl-2,3-dimethylphenoxy)-4-pyridazinol (Compound No. 1061), 6-chloro-3-(2,3,5,6-tetramethylphenoxy)-4-pyridazinol (Compound No. 1125), 6-chloro-3-(2-cyclopropyl-6-methylphenoxy)-4-pyridazinyl acetate (Compound No. 1151), 6-chloro-3-(2-cyclopropyl-6-methylphenoxy)-4-pyridazinyl propionate (Compound No. 1160), 6-chloro-3-(2-cyclopropyl-6-methylphenoxy)-4-pyridazinyl 2-methylpropanoate (Compound No. 1172), 6-chloro-3-(2-cyclopropyl-6-methylphenoxy)-4-pyridazinyl pivalate (Compound No. 1207), 6-chloro-3-(2-cyclopropyl-6-methylphenoxy)-4-pyridazinyl 3-methyl-2-butenoate (Compound No. 1358), 6-chloro-3-(2-cyclopropyl-6-methylphenoxy)-4-pyridazinyl benzoate (Compound No. 1417), 6-chloro-3-(2-cyclopropyl-6-methylphenoxy)-4-pyridazinyl 2-methylbenzoate (Compound No. 1481), 6-chloro-3-(2-cyclopropyl-6-methylphenoxy)-4-pyridazinyl 2-methoxybenzoate (Compound No. 1522), 6-chloro-3-(2-cyclopropyl-6-methylphenoxy)-4-pyridazinyl 3-methylbenzoate (Compound No. 1531), 6-chloro-3-(2-cyclopropyl-6-methylphenoxy)-4-pyridazinyl 4-bromobenzoate (Compound No. 1543), 6-chloro-3-(2-cyclopropyl-6-methylphenoxy)-4-pyridazinyl 4-methylbenzoate (Compound No. 1566), 6-chloro-3-(2-cyclopropyl-6-methylphenoxy)-4-pyridazinyl 4-(2,4-dichlorobenzoyl)-1,3-dimethyl-1H-pyrazol-5-yl phthalate (Compound No. 1625), 6-chloro-3-(2-cyclopropyl-6-methylphenoxy)-4-pyridazinyl 4-(2,4-dichlorobenzoyl)-1,3-dimethyl-1H-pyrazol-5-yl isophthalate (Compound No. 1631), 6-chloro-3-(2-cyclopropyl-6-methylphenoxy)-4-pyridazinyl isobutylcarbonate (Compound No. 1770), 6-chloro-3-(2-cyclopropyl-6-methylphenoxy)-4-pyridazinyl dimethylcarbamate (Compound No. 1891), 6-chloro-3-(2-cyclopropyl-6-methylphenoxy)-4-pyridazinyl 1-propanesulfonate (Compound No. 2051), 6-chloro-3-(2-cyclopropyl-6-methylphenoxy)-4-pyridazinyl benzene sulfonate (Compound No. 2176), 6-chloro-3-(2-cyclopropyl-6-methylphenoxy)-4-pyridazinyl 4-chlorobenzene sulfonate (Compound No. 2212), 6-chloro-3-(2-cyclopropyl-6-methylphenoxy)-4-pyridazinyl 4-methylbenzene sulfonate (Compound No. 2265), 6-chloro-3-(2-cyclopropyl-6-methylphenoxy)-4-pyridazinyl 4-methoxybenzene sulfonate (Compound No. 2309), 6-chloro-3-(2-cyclopropyl-6-methylphenoxy)-4-pyridazinyl 4-(2,4-dichlorobenzoyl)-1,3-dimethyl-1H-pyrazoyl-5-yl 1,2-benzene disulfonate (Compound No. 2327), 6-chloro-3-(2-cyclopropyl-6-methylphenoxy)-4-pyridazinyl 4-(2,4-dichlorobenzoyl)-1,3-dimethyl-1H-pyrazol-5-yl 1,3-benzene disulfonate (Compound No. 2333), 6-chloro-3-(2-cyclopropyl-6-methylphenoxy)-4-pyridazinyl 3,3-dimethylbutanoate (Compound No. 2662), 6-chloro-3-(2-cyclopropyl-6-methylphenoxy)-4-pyridazinyl ethyl succinate (Compound No. 2727), bis[6-chloro-3-(2-cyclopropyl-6-methylphenoxy)-4-pyridazinyl] succinate (Compound No. 2733), 6-chloro-3-(2-cyclopropyl-6-methylphenoxy)-4-pyridazinyl 4-(2,4-dichlorobenzoyl)-1,3-dimethyl-1H-pyrazol-5-yl pentanedioate (Compound No. 2739), bis[6-chloro-3-(2-cyclopropyl-6-methylphenoxy)-4-pyridazinyl] pentanedioate (Compound No. 2746), 6-chloro-3-(2-cyclopropyl-6-methylphenoxy)-4-pyridazinyl 2-bromobenzoate (Compound No. 2805), 6-chloro-3-(2-cyclopropyl-6-methylphenoxy)-4-pyridazinyl 4-ethylbenzoate (Compound No. 2961), 6-chloro-3-(2-cyclopropyl-6-methylphenoxy)-4-pyridazinyl 2,5-dimethylbenzoate (Compound No. 3129), 6-chloro-3-(2-cyclopropyl-6-methylphenoxy)-4-pyridazinyl 3-fluoro-4-methylbenzoate (Compound No. 3185), 6-chloro-3-(2-cyclopropyl-6-methylphenoxy)-4-pyridazinyl 3,5-difluorobenzoate (Compound No. 3217), 6-chloro-3-(2-cyclopropyl-6-methylphenoxy)-4-pyridazinyl 3,5-dimethylbenzoate (Compound No. 3243), 6-chloro-3-(2-cyclopropyl-6-methylphenoxy)-4-pyridazinyl methoxy(methyl)carbamate (Compound No. 3564), 6-chloro-3-(2-cyclopropyl-6-methylphenoxy)-4-pyridazinyl bis(2-methoxyethyl)carbamate (Compound No. 3600), 6-chloro-3-(2-cyclopropyl-6-methylphenoxy)-4-pyridazinyl 1-azetizincarboxylate (Compound No. 3612) or 6-chloro-3-(2-cyclopropyl-6-methylphenoxy)-4-pyridazinyl 4-morpholinecarboxylate (Compound No. 3690).

The 3-phenoxy-4-pyridazinol compound and its ester derivative of the present invention can be produced by the methods described in the following Steps A to N.

(Step A)

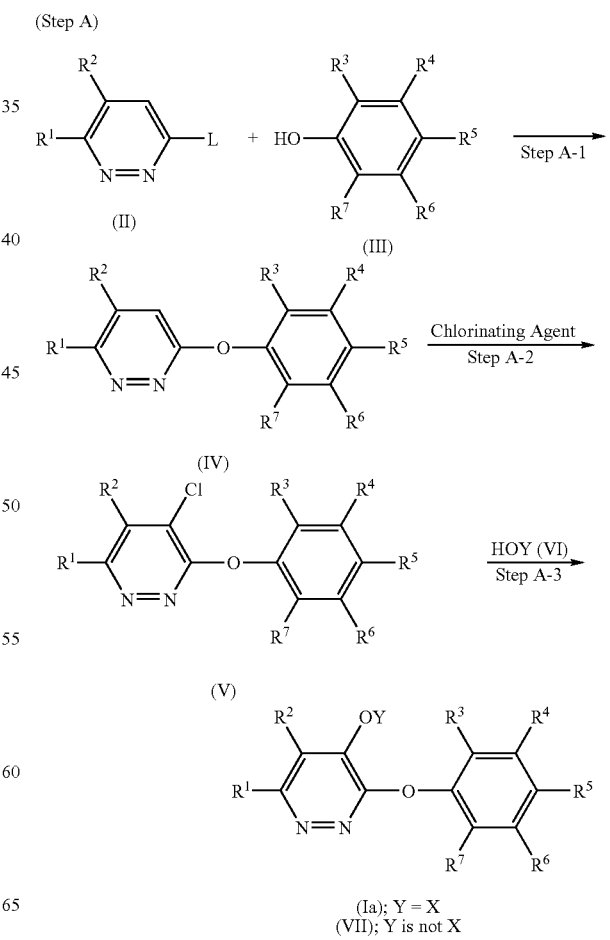

(VII) $\xrightarrow[\text{Step A-4}]{\text{Deprotection}}$

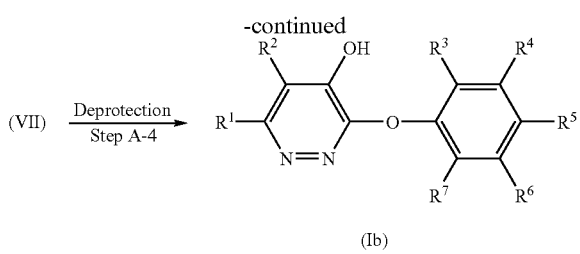

(Ib)

In the above formula, $R^1$, $R^2$, $R^3$, $R^4$, $R^5$, $R^6$ and $R^7$ have the same meanings as defined in the above, L represents a leaving group, and for example, it may be a halogen atom, a $C_1$ to $C_6$ alkylsulfonyloxy group or a phenylsulfonyloxy group (the phenylsulfonyloxy group may be substituted by the same or different 1 to 5 halogen atom(s) or $C_1$ to $C_6$ alkyl group(s).),
X repersents a hydrogen atom or an acyl group,
Y represents, in addition to X, other protective groups for the hydroxyl group, and for example, it may be a methyl group, a methoxymethyl group, a methoxyethoxymethyl group or a benzyl group.

Step A is a step to produce Compound (Ia) of the present invention or a compound represented by the formula (VII), in which a hydroxyl group is protected, by reacting a phenol compound represented by the formula (III) with a pyridazine compound represented by the formula (II), then, chlorinating the resulting compound, and futher reacting an oxygen nucleophilic agent, and further a step to produce Compound (Ib) of the present invention by removing the protective group of Compound (VII).

(Step A-1)

Step A-1 is a step to produce a phenoxypyridazine compound represented by the formula (IV) by reacting Compound (II) with Compound (III) in the presence or absence of a solvent, and if necessary, in the presence of a base.

The base to be used is not specifically limited so long as it is a base showing generally a pH of 8 or more, and for example, it may be alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal hydrides such as sodium hydride, potassium hydride, etc.; alkali metals such as sodium, potassium, etc.; aliphatic tertiary amines such as triethylamine, tributylamine, diisopropylethylamine, etc.; aliphatic cyclic tertiary amines such as 1,4-diazabicyclo[2.2.2]-octane (DABCO), 1,8-diazabicyclo[5.4.0]undec-7-ene (DBU), etc.; pyridines such as pyridine, collidine, 4-(N,N-dimethylamino)pyridine, etc.; organic metal bases such as n-butyl lithiums, s-butyl lithium, lithium diisopropylamide, sodium bis(trimehylsilyl)amide, lithium bis(trimethylsilyl)amide, etc., preferably alkali metal hydroxides, alkali metal carbonates, metal alkoxides, alkali metal hydrides or alkali metals, more preferably potassium carbonate, potassium t-butoxide, sodium hydride or sodium.

An amount of the base to be used is generally 0.5 to 5 mol, preferably 1 to 3 mol based on 1 mol of the compound (II).

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above, preferably nitriles, halogenated hdyrocarbons, ethers, aromatic hydrocarbons, amides or sulfoxides, more preferably dioxane, toluene, dimethylformamide or dimethylsulfoxide.

The reaction temperature may vary depending on the starting compounds, reaction reagents and solvent, etc., and is generally −90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

(Step A-2)

Step A-2 is a step to producing a compound represented by the formula (V) in which a chlorine atom is introduced into the 4-position of a pyridazine ring by chlorinating Compound (IV) with a chlorinating agent in the presence or absence of a solvent.

As the chlorinating agent to be used, it is not specifically limited so long as it can chlorinate an aromatic ring, and for example, it may be chlorine, chlorine-iron chloride, sulfuryl chloride, copper chloride, N-chlorosuccinimide or phosphorus pentachloride, preferably chlorine.

An amount of the chlorinating agent to be used is generally 0.5 to 10 mol, preferably 1 to 2 mol based on 1 mol of the compound (IV).

The solvent to be used is not specifically limited so long as it does not inhibit the reaction, and dissolves starting material(s) with a certain extent, and for example, it may be phosphorus oxychloride; water; alcohols such as methanol, ethanol, t-butanol, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, heptane, etc.; or a mixed solvent of the above, preferably phosphorus oxychloride, water, halogenated hdyrocarbons or ethers, more preferably phosphorus oxychloride.

The reaction temperature may vary depending on the starting compounds, reaction reagents and a kind of the solvent to be used, etc., and is generally −90° C. to 200° C., preferably 0° C. to 50° C.

The reaction time may vary mainly depending on a reaction temperature, starting materials, reaction reagents and a kind of the solvent to be used, and usually 5 minutes to 24 hours, preferably 15 minutes to 6 hours.

(Step A-3)

Step A-3 is a step to produce Compound (Ia) of the present invention or a compound represented by the formula (VII), in which a hydroxyl group is protected, by reacting Compound (V) with an oxygen nucleophilic agent represented by the formula (VI) in the presence or absence of a solvent, and if necessary, in the presence of a base.

The base to be used is not specifically limited so long as it is a base showing generally a pH of 8 or more, and for example, it may be alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal salts of an organic acid such as sodium acetate, potassium acetate, sodium formate, potassium formate, etc.; alkali metal hydrides such as sodium hydride, potassium hydride, etc.;

alkali metals such as sodium, potassium, etc.; aliphatic tertiary amines such as triethylamine, tributylamine, diisopropylethylamine, etc.; aliphatic cyclic tertiary amines such as 1,4-diazabicyclo-[2.2.2]octane (DABCO), 1,8-diazabicyclo[5.4.0]undec-7-ene (DBU), etc.; pyridines such as pyridine, collidine, 4-(N,N-dimethylamino)pyridine, etc.; organic metal bases such as n-butyl lithiums, s-butyl lithium, lithium diisopropylamide, sodium bis(trimehylsilyl)amide, lithium bis(trimethylsilyl)amide, etc., preferably alkali metal hydroxides, alkali metal carbonates, metal alkoxide, alkali metal salts of an organic acid, alkali metal hydrides or alkali metals, more preferably sodium hydroxide, potassium hydroxide, potassium carbonate, potassium t-butoxide, sodium acetate, sodium formate, sodium hydride or sodium.

The solvent to be used is not specifically limited so long as it does not inhibit the reaction, and dissolves starting material(s) with a certain extent, for example, water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above, preferably water, alcohols, nitriles, ethers, amides or sulfoxides, more preferably water, methanol, acetonitrile, tetrahydrofuran, dioxane, dimethylformamide or dimethylsulfoxide.

The reaction temperature may vary depending on the starting compounds, reaction reagents and a kind of the solvent to be used, etc., and is generally −90° C. to 200° C., preferably 0° C. to 100° C.

The reaction time may vary mainly depending on a reaction temperature, starting materials, reaction reagents and a kind of the solvent to be used, and is usually 5 minutes to 24 hours, preferably 15 minutes to 6 hours.

Incidentally, in the present step, the compound (VI) may be used in the present step after making a salt by previously reacting with a base.

(Step A-4)

Step A-4 is a step to produce Compound (Ib) of the present invention by removing the protective group for a hydroxyl group of Compound (VII).

The protective group to be used in the present step is not specifically limited so long as it can selectively removed from Compound (VII) to provide Compound (Ib), and for example, it may be a methyl group, methoxymethyl group, benzyloxymethyl group, methoxyethoxymethyl group, 2-(trimethylsilyl)ethoxymethyl group, methylthiomethyl group, phenylthiomethyl group, 2,2-dichloro-1,1-difluoroethyl group, tetrahydropyranyl group, phenacyl group, p-bromophenacyl group, cyclopropylmethyl group, allyl group, isopropyl group, cyclohexyl group, t-butyl group, benzyl group, 2,6-dimethylbenzyl group, 4-methoxybenzyl group, 2-nitrobenzyl group, 2,6-dichlorobenzyl group, 4-(dimethylaminocarbonyl)benzyl group, 9-anthrylmethyl group, 4-picolyl group, heptafluoro-p-tolyl group or tetrafluoro-4-pyridyl group, preferably a methyl group, methoxymethyl group, methoxyethoxymethyl group, methylthiomethyl group, tetrahydropyranyl group, phenacyl group, allyl group or benzyl group, more preferably a methyl group.

A method for removing the protective group to be used in the present step is not specifically limited so long as it can selectively remove the protective group for a hydroxyl group, and it can be carried out by the conventionally known method (for example, a method described in Protective Groups in Organic Synthesis, 13$^{th}$ Edition, written by Theodora W. Greene and Peter G. M. Wuts, JOHN WILEY & SONS, INC.) with regard to the respective protecttive groups or in accordance with these methods. For example, when the protective group is a methyl group, removal of the methyl group can be carried out, for example, by reacting with a potassium salt or sodium salt of 2-hydroxypyridine in dimethylsulfoxide, a sodium salt of ethanethiol in dimethylformamide, or boron tribromide in methylene chloride. For example, when the protective group is a methoxymethyl group, removal of the methoxymethyl group can be carried out, for example, by reacting with trifluoroacetic acid. For example, when the protective group is a methoxyethoxymethyl group, removal of the methoxyethoxymethyl group can be carried out, for example, by reacting with trifluoroacetic acid. Also, for example, when the protective group is a benzyl group, removal of the benzyl group can be carried out by catalytic hydrogenation.

(Step B)

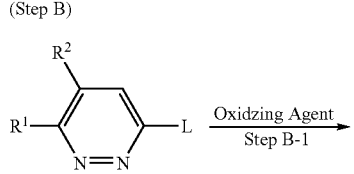

(II)

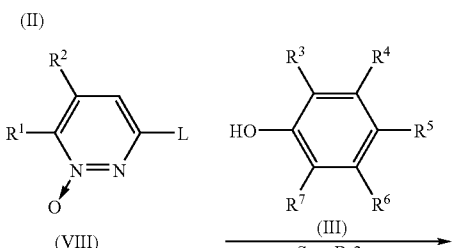

(VIII)     (III)

Step B-2

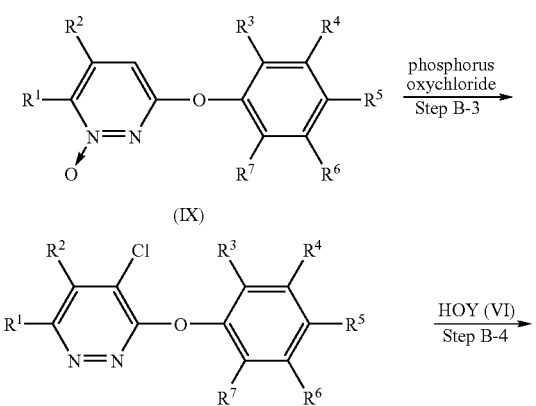

(IX)

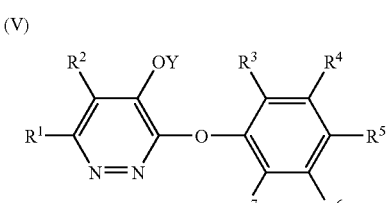

(V)

(Ia); Y = X
(VII); Y is not X

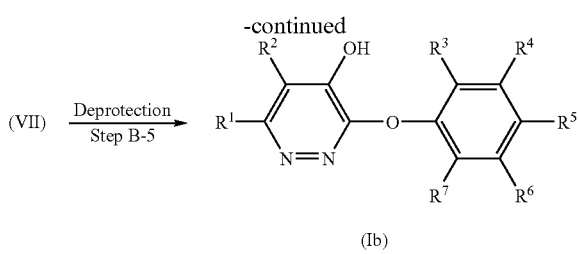

In the above formula, $R^1$, $R^2$, $R^3$, $R^4$, $R^5$, $R^6$, $R^7$, L, X and Y have the same meanings as defined in the above.

Step B is a step to produce Compound (Ia) of the present invention or a compound represented by the formula (VII), in which a hydroxyl group is protected, by oxidizing a pyridazine compound represented by the formula (II), reacting a phenol compound represented by the formula (III) to the resulting compound, then chlorinating the resulting compound, and further reacting an oxygen nucleophilic agent, or a step to produce Compound (Ib) of the present invention by removing the protective group of Compound (VII).

(Step B-1)

Step B-1 is a step to produce Pyridazine N-oxide represented by the formula (VIII) by oxidizing Compound (II) with an oxidizing agent in the presence or absence of a solvent.

The oxidizing agent to be used is not specifically limited so long as it can convert an amine into an N-oxide, and for example, it may be peroxides such as m-chloroperbenzoic acid (mcpba), peracetic acid, pertrifluoroacetic acid, trifluoroacetic anhydride-hydrogen peroxide, peroxydichloromaleic acid, dichloromaleic acid-hydrogen peroxide, peroxymaleic acid, maleic acid-hydrogen peroxide, t-butylhydroperoxide, t-butylhydroperoxide-vanadium oxyacetylacetonate, t-butylhydroperoxide-molybdenum chloride, hydrogen peroxide, etc.; ozone; or oxygen, preferably m-chloroperbenzoic acid (mcpba), trifluoroacetic anhydride-hydrogen peroxide or dichloromaleic acid-hydrogen peroxide.

An amount of the oxidizing agent to be used in the reaction is usually 0.5 to 100 mol, preferably 1 to 2 mol based on 1 mol of Compound (II).

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above, preferably halogenated hdyrocarbons, more preferably methylene chloride.

The reaction temperature may vary depending on the starting compounds, reaction reagents and solvents, etc., and is generally −90° C. to 200° C., preferably 0° C. to 100° C.

The reaction time may vary mainly depending on a reaction temperature, starting materials, reaction reagents and a kind of the solvent to be used, and usually 5 minutes to 24 hours, preferably 15 minutes to 6 hours.

According to the present step, an isomer in which other nitrogen atom is oxidized may be by-produced in some cases, and an objective Pyridazine N-oxide can be obtained by purifying the resulting materials after completion of the present step, or carrying out the subsequent steps in a state of admixture and by purifying the resulting materials after completion of the step.

(Step B-2)

Step B-2 is a step to produce a phenoxypyridazine compound represented by the formula (IX) by reacting Compound (VIII) with Compound (III) in the presence or absence of a solvent, and if necessary, in the presence of a base.

The present step can be carried out in accordance with Step A-1.

(Step B-3)

Step B-3 is a step to produce Compound (V) by reacting Compound (IX) with phosphorus oxychloride in the presence or absence of a solvent.

An amount of the phosphorus oxychloride to be used in the present step is generally 0.5 to 100 mol, preferably 1 to 5 mol based on 1 mol of Compound (IX).

The solvent to be used is not specifically limited so long as it does not inhibit the reaction, and dissolves starting material(s) with a certain extent, and for example, it may be ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, etc.; or a mixed solvent of the above, preferably halogenated hdyrocarbons, more preferably methylene chloride or chloroform.

The reaction temperature may vary depending on the starting compounds, reaction reagents and solvents, etc., and is generally −90° C. to 200° C., preferably 0° C. to 100° C.

The reaction time may vary mainly depending on a reaction temperature, starting materials, reaction reagents and a kind of the solvent to be used, and usually 5 minutes to 72 hours, preferably 30 minutes to 24 hours.

(Step B-4)

Step B-4 is a step to produce Compound (Ia) of the present invention or a compound represented by the formula (VII), in which a hydroxyl group is protected, by reacting Compound (V) with an oxygen nucleophilic agent represented by the formula (VI) in the presence or absence of a solvent, and if necessary, in the presence of a base.

The present step is similar to Step A-3.

(Step B-5)

Step B-5 is a step to produce Compound (Ib) of the present invention by removing the protective group for a hydroxyl group of Compound (VII).

The present step is similar to Step A-4.

(Step C)

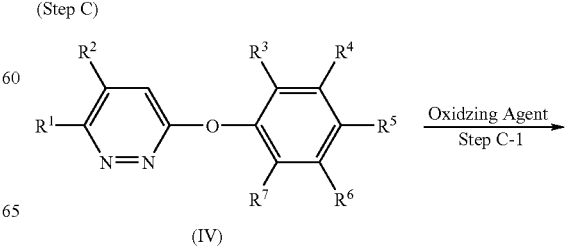

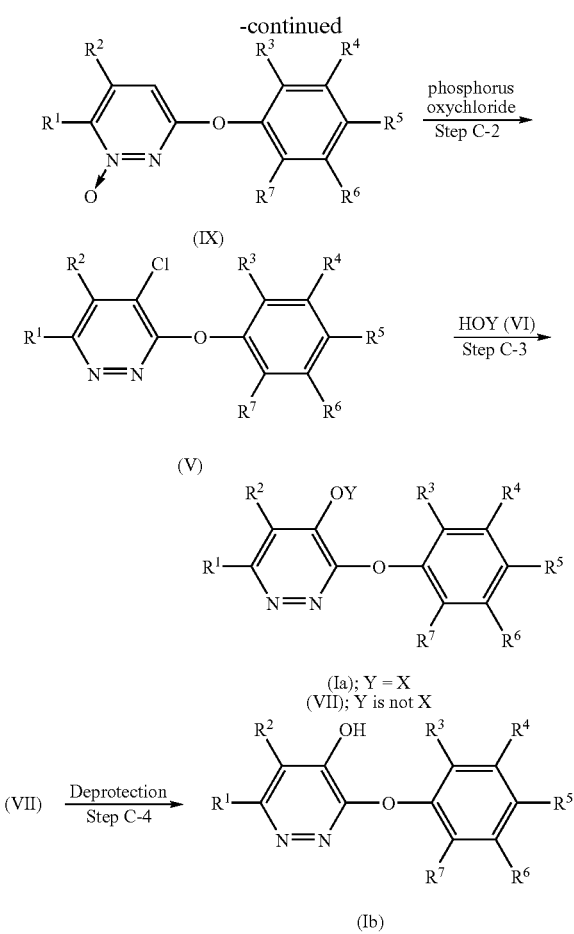

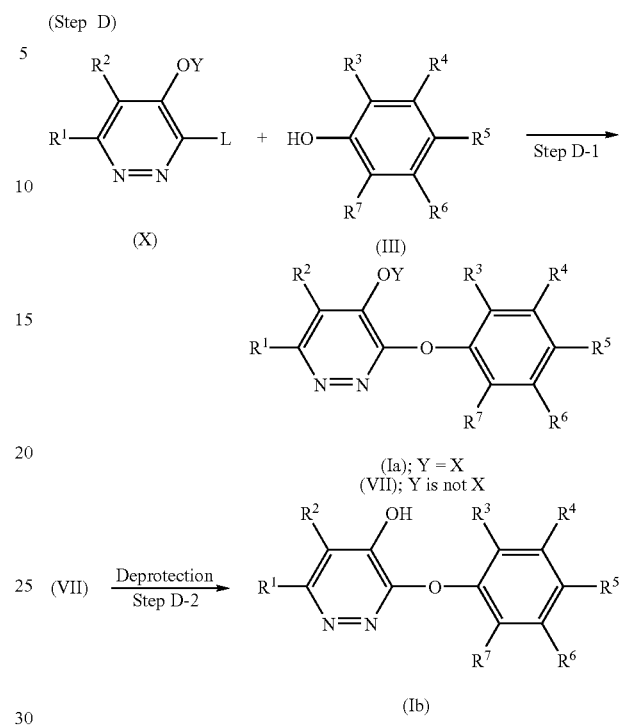

In the above formula, $R^1$, $R^2$, $R^3$, $R^4$, $R^5$, $R^6$, $R^7$, X and Y have the same meanings as defined in the above.

Step C is a step to produce Compound (Ia) of the present invention or a compound represented by the formula (VII), in which a hydroxyl group is protected, by oxidizing Compound (IV), then chlorinating the resulting material, and then reacting the same with an oxygen nucleophilic agent, and further a step to produce Compound (Ib) of the present invention by removing the protective group of Compound (VII).

(Step C-1)

Step C-1 is a step to produce Pyridazine N-oxide represented by the formula (IX) by oxidizing Compound (IV) with an oxidizing agent in the presence or absence of a solvent.

The present step can be carried out in accordance with Step B-1.

(Step C-2)

Step C-2 is a step to produce Compound (V) by reacting Compound (IX) with phosphorus oxychloride in the presence or absence of a solvent.

The present step is similar to Step B-3.

(Step C-3)

Step C-3 is a step to produce Compound (Ia) of the present invention or a compound represented by the formula (VII), in which a hydroxyl group is protected, by reacting Compound (V) with an oxygen nucleophilic agent represented by the formula (VI) in the presence or absence of a solvent, and if necessary, in the presence of a base.

The present step is similar to Step A-3 or B-4.

(Step C-4)

Step C-4 is a step to produce Compound (Ib) of the present invention by removing the protective group for a hydroxyl group of Compound (VII).

The present step is similar to Step A-4 or B-5.

In the above formula, $R^1$, $R^2$, $R^3$, $R^4$, $R^5$, $R^{6,}$ $R^7$, L, X and Y have the same meanings as defined above.

Step D is a step to produce Compound (Ia) of the present invention or a compound represented by the formula (VII), in which a hydroxyl group is protected, by reacting a pyridazine compound represented by the formula (X), into which an oxygen functional group has previously been substituted, with a phenol represented by the formula (III), and further a step to produce Compound (Ib) of the present invention by removing the protective group of Compound (VII).

(Step D-1)

Step D-1 is a step to produce Compound (Ia) of the present invention or a compound represented by the formula (VII), in which a hydroxyl group is protected, by reacting Compound (X) with Compound (III) in the presence or absence of a solvent, and if necessary, in the presence of a base.

The present step can be carried out in accordance with Step A-1 or B-2.

(Step D-2)

Step D-2 is a step to produce Compound (Ib) of the present invention by removing the protective group for a hydroxyl group for Compound (VII).

The present step is similar to Step A-4, B-5 or C-4.

(Step E)

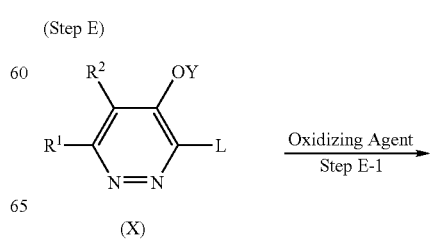

-continued

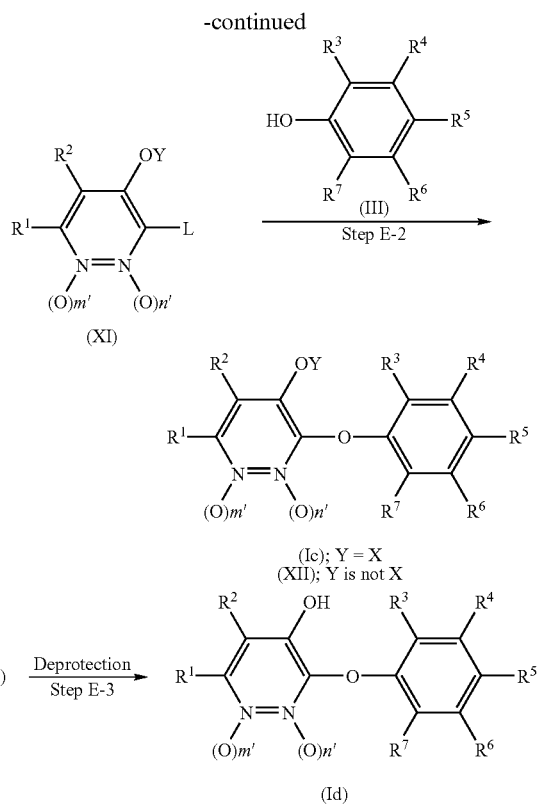

(XI)

(Ic); Y = X
(XII); Y is not X (XII) —Deprotection→ (Id)
Step E-3

In the above formula, $R^1$, $R^2$, $R^3$, $R^4$, $R^5$, $R^6$, $R^7$, L, X and Y have the same meanings as defined above, m' and n' each represent 0 or 1, provided that m' and n' are not simultaneously 0.

Step E is a step to produce Compound (Ic) of the present invention or a compound represented by the formula (XII), in which a hydroxyl group is protected, by oxidizing a pyridazine compound to which an oxygen functional group has previously been substituted represented by the formula (X), and then reacting a phenol represented by the formula (III), and further a step to produce Compound (Id) of the present invention by removing the protective group of Compound (XII).

(Step E-1)

Step E-1 is a step to produce Pyridazine N-oxide represented by the formula (XI) by oxidizing Compound (X) with an oxidizing agent in the presence or absence of a solvent.

The present step can be carried out in accordance with Step B-1 or C-1 in the case where m'=0 or n'=0, and when m'=n'=1, it can be carried out under severer conditions by making an amount of the oxidizing agent in excessive, by using an oxidizing agent having higher reactivity to carry out the oxidation, and the like.

(Step E-2)

Step E-2 is a step to produce Compound (Ic) of the present invention or a compound represented by the formula (XII), in which a hydroxyl group is protected, by reacting Compound (XI) with Compound (III) in the presence or absence of a solvent, and if necessary, in the presence of a base.

The present step can be carried out in accordance with Step A-1, B-2 or D-1.

(Step E-3)

Step E-3 is a step to produce Compound (Id) of the present invention by removing the protective group for a hydroxyl group of Compound (XII).

The present step is similar to Step A-4, B-5, C-4 or D-2.

(Step F)

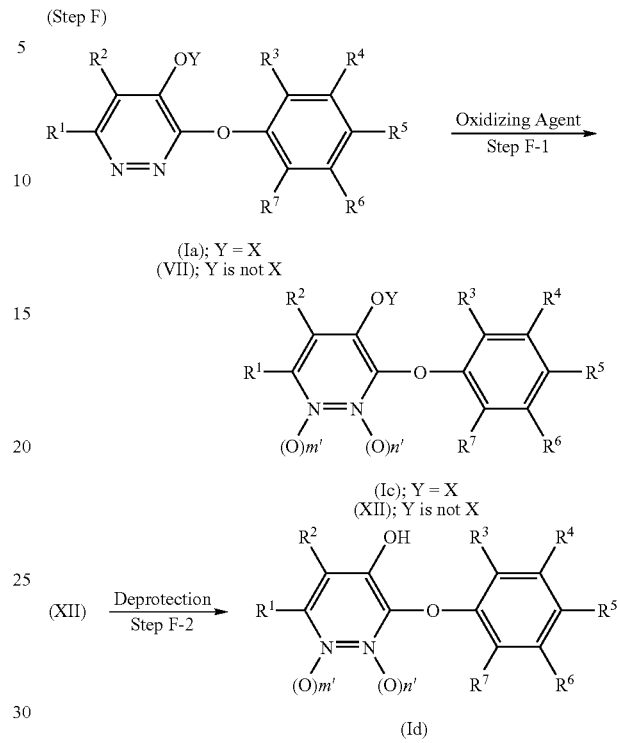

(Ia); Y = X
(VII); Y is not X (Ic); Y = X
(XII); Y is not X (XII) —Deprotection→ (Id)
Step F-2

In the above formula, $R^1$, $R^2$, $R^3$, $R^4$, $R^5$, $R^6$, $R^7$, X, Y, m' and n' have the same meanings as defined above.

Step F is a step to produce Compound (Ic) of the present invention or a compound represented by the formula (XII), in which a hydroxyl group is protected, by oxidizing Compound (Ia) of the present invention or a compound represented by the formula (VII) in which a hydroxyl group is protected, and further is a step to produce Compound (Id) of the present invention by removing the protective group of Compound (XII).

(Step F-1)

Step F-1 is a step to produce Compound (Ic) of the present invention or a compound represented by the formula (XII), in which a hydroxyl group is protected, by oxidizing Compound (Ia) of the present invention or Compound (VII) with an oxidizing agent in the presence or absence of a solvent.

The present step can be carried out in accordance with Step E-1.

(Step F-2)

Step F-2 is a step to produce Compound (Id) of the present invention by removing the protective group for a hydroxyl group of Compound (XII).

The present step is similar to Step A-4, B-5, C-4, D-2 or E-3.

(Step G)

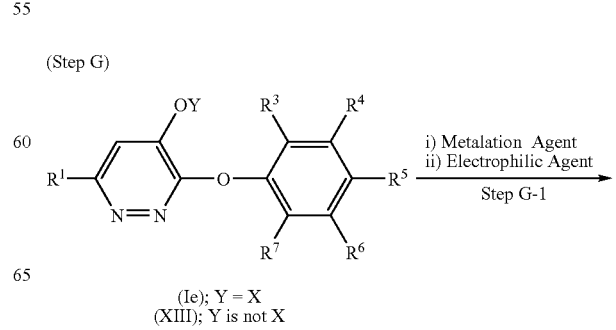

(Ie); Y = X
(XIII); Y is not X

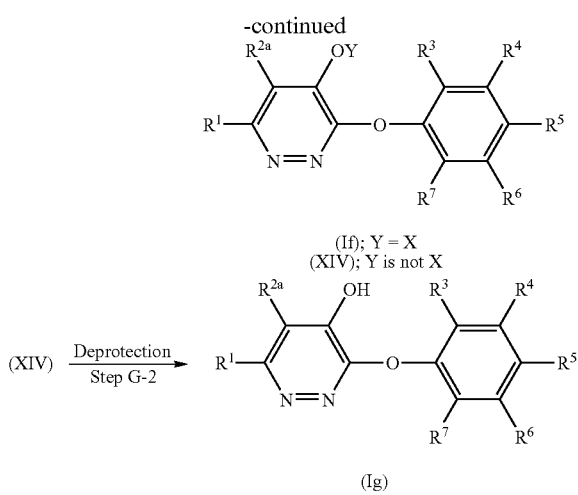

(If); Y = X
(XIV); Y is not X

In the above formula, $R^1$, $R^3$, $R^4$, $R^5$, $R^6$, $R^7$, X and Y have the same meanings as defined above, $R^{2a}$ has the same meaning as $R^2$ except for removing a hydrogen atom.

Step G is a step to produce Compound (If) of the present invention or a compound represented by the formula (XIV), in which a hydroxyl group is protected, by subjecting the 5-position of the pyridazine ring of Compound (Ie) of the present invention or a compound represented by the formula (XIII), in which a hydroxyl group is protected, to metalation, and then reacting an electrophilic agent to the resulting material, and further is a step to produce Compound (Ig) of the present invention by removing the protective group of Compound (XIV).

(Step G-1)

Step G-1 is a step to produce Compound (If) of the present invention or a compound represented by the formula (XIV), in which a hydroxyl group is protected, by reacting Compound (Ie) of the present invention or a compound represented by the formula (XIII), in which a hydroxyl group is protected, with a metalating agent in the presence or absence of a solvent, and then, reacting with an electrophilic agent.

The metalating agent to be used is not specifically limited so long as it can metalate an aromatic ring, and for example, it may be organic lithium compounds such as methyl lithium, butyl lithium, s-butyl lithium, t-butyl lithium, phenyl lithium, etc.; organic magnesium compounds such as methylmagnesium chloride, methyl magnesium bromide, ethyl magnesium bromide, phenylmagnesium bromide, etc.; organometal amides such as lithium diisopropylamide, sodium bis(trimethylsilyl)amide, lithium bis(trimethylsilyl)amide, etc.; metal alkoxides such as sodium methoxide, sodium ethoxide, potassium t-butoxide, etc.; alkali metal hydrides such as sodium hydride, potassium hydride, etc.; alkali metals such as lithium, sodium, potassium, etc.; alkaline earth metals such as magnesium, etc., preferably organic lithium compounds, more preferably butyl lithium.

An amount of the metalating agent to be used in the reaction is generally 0.5 to 10 mol, preferably 1 to 2 mol based on 1 mol of Compound (Ie) or Compound (XIII).

The electrophilic agent to be used in the reaction is not specifically limited so long as it can be a nucleophilic agent capable of reacting with an organometallic compound, and for example, it may be silylating agents such as trimethylsilyl chloride, triethylsilyl chloride, t-butyldimethylsilyl chloride, trimethylsilyl trifluoromethane sulfonate, etc.; acylating agents such as acetyl chloride, benzoyl chloride, ethyl chlorocarbonate, methyl chlorocarbonate, N,N-dimethylformamide, methyl formate, etc.; carbonyl compounds such as acetaldehyde, benzaldehyde, acetone, cyclohexanone, etc.; alkylating agents such as methyl iodide, methyl bromide, benzyl bromide, etc.; halogenating agents such as fluorine, chlorine, bromine, iodine, N-fluorobenzene sulfonamide, 1-fluoro-2,6-dichloropyridinium triflate, N-chlorosuccinimide (NCS), N-bromosuccinimide (NBS), etc.; or carbon dioxide, preferably a silylating agent, acylating agent, alkylating agent or halogenating agent, more preferably trimethylsilyl chloride, benzoyl chloride, ethyl chlorocarbonate or methyl iodide.

An amount of the electrophilic agent to be used in the reaction is generally 0.5 to 10 mol, preferably 1 to 3 mol based on 1 mol of Compound (Ie) or Compound (XIII).

The solvent to be used is not specifically limited so long as it does not inhibit the reaction, and dissolves starting material(s) with a certain extent, and for example, it may be halogenated hydrocarbons such as methylene chloride, chloroform, dichloroethane, etc.; ethers such as diethyl ether, tetrahydrofuran, dioxane, etc.; aromatic hydrocarbons such as toluene, etc.; aliphatic hydrocarbons such as hexane, cyclohexane, etc.; or a mixed solvent of the above, preferably ethers, more preferably tetrahydrofuran.

The reaction temperature may vary depending on starting materials, reaction reagents and a kind of the solvent to be used, etc., and usually −90° C. to 100° C., preferably −70° C. to 30° C.

The reaction time may vary mainly depending on a reaction temperature, starting materials, reaction reagents and a kind of the solvent to be used, and usually 5 minutes to 24 hours, preferably 30 minutes to 12 hours.

(Step G-2)

Step G-2 is a step to produce Compound (Ig) of the present invention by removing the protective group for a hydroxyl group of Compound (XIV).

The present step is similar to Step A-4, B-5, C-4, D-2, E-3 or F-2.

(Step H)

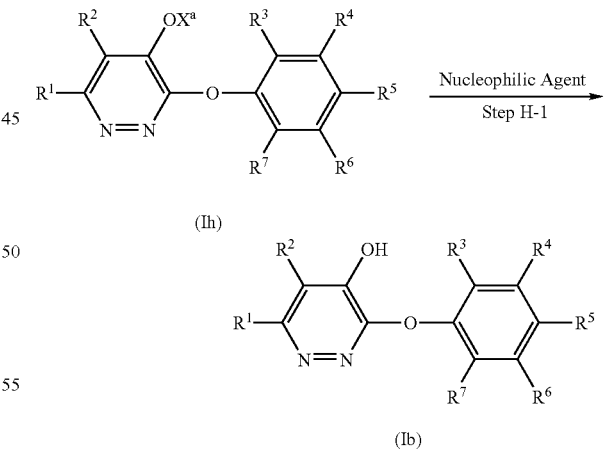

In the above formula, $R^1$, $R^2$, $R^3$, $R^4$, $R^5$, $R^6$ and $R^7$ have the same meanings as defined above, $X^a$ represents the same meanings as X except for removing a hydrogen atom.

Step H is a step to convert an ester derivative represented by the formula (Ih) of the present invention into a hydroxy compound represented by the formula (Ib) of the present invention.

(Step H-1)

Step H-1 is a step to produce Compound (Ib) of the present invention by reacting Compound (Ih) of the present invention with a nucleophilic agent in the presence or absence of a solvent.

The nucleophilic agent to be used is not specifically limited so long as it can nucleophilically attack an ester derivative, and cleave the ester bonding to an acid portion and an alcohol portion, and for example, it may be water; hydroxides of an alkali metal such as lithium hydroxide, sodium hydroxide, potassium hydroxide, etc.; hydroxides of an alkaline earth metal such as magnesium hydroxide, calcium hydroxide, etc.; metal alkoxides such as sodium methoxide, sodium ethoxide, 2-hydroxypyridine potassium salt, 2-hydroxypyridine sodium salt, etc.; alkali metal salts of an organic acid such as sodium acetate, potassium acetate, sodium formate, potassium formate, etc.; fluorides such as tetrabutylammonium fluoride, potassium fluoride, etc.; chlorides such as lithium chloride, sodium chloride, etc.; bromides such as lithium bromide, sodium bromide, etc.; iodides such as sodium iodide, potassium iodide, etc.; or metal salts of a sulfur compound such as methanethiol sodium salt, ethanethiol sodium salt, etc., preferably water, hydroxides of an alkali metal, metal alkoxides or alkali metal salts of an organic acid, more preferably water, sodium hydroxide, potassium hydroxide or sodium acetate.

An amount of the nucleophilic agent to be used is generally 1 to 10 mol, preferably 1 to 5 mol based on 1 mol of Compound (Ih).

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitrites such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above, preferably water, alcohols, nitrites, ethers, amides or sulfoxides, more preferably water, methanol, ethanol, tetrahydrofuran, dioxane, dimethylformamide or dimethylsulfoxide.

The reaction temperature may vary depending on starting materials, reaction reagents and a kind of the solvent to be used, etc., and usually −90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

Incidentally, in the present step, a conventionally known method can be employed as usual deprotection of a hydroxyl group.

(Step I)

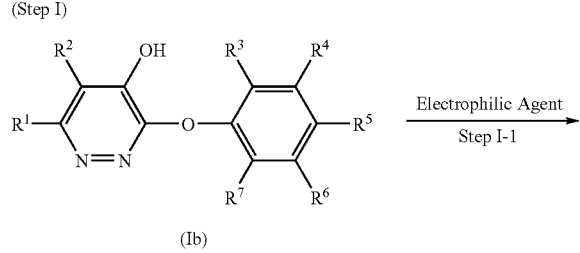

(Ib)

-continued

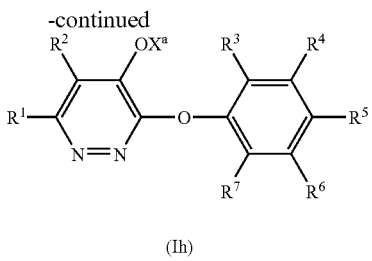

(Ih)

In the above formula, $R^1$, $R^2$, $R^3$, $R^4$, $R^5$, $R^6$, $R^7$ and $X^a$ have the same meanings as defined above.

Step I is a step to convert the hydroxy compound represented by the formula (Ib) of the present invention tinot an ester derivative represented by the formula (Ih) of the present invention.

(Step I-1)

Step I-1 is a step to produce Compound (Ih) of the present invention by reacting Compound (Ib) of the present invention with an esterifyng agent in the presence or absence of a solvent.

The esterifying agent to be used is not specifically limited so long as it can esterify a hydroxyl group, and for example, it may be acylating agents such as acetyl chloride, acetyl bromide, acetic anhydride, trifluoroacetic anhydride, benzoyl chloride, methyl chlorocarbonate, ethyl chlorocarbonate, N,N-dimethylcarbamoyl chloride, methyl chlorothioformate, etc.; or sulfonylating agents such as methanesulfonyl chloride, propanesulfonyl chloride, p-toluenesulfonyl chloride, trifluoromethanesulfonic acid anhydride, N,N-dimethylsulfamoyl chloride, etc., preferably acetyl chloride, acetic anhydride, trifluoroacetic anhydride, benzoyl chloride, methyl chlorocarbonate, ethyl chlorocarbonate, methanesulfonyl chloride, propanesulfonyl chloride, p-toluenesulfonyl chloride or trifluoromethanesulfonic acid anhydride, more preferably benzoyl chloride, p-toluenesulfonyl chloride or trifluoromethanesulfonic acid anhydride.

An amount of the esterifying agent to be used in the reaction is generally 0.5 to 10 mols, preferably 1 to 3 mols based on 1 mol of Compound (Ib).

The reaction is preferably carried out in the presence of a base.

The base to be used is not specifically limited so long as it is a base showing a pH of 8 or more, and for example, it may be alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal hydrides such as sodium hydride, potassium hydride, etc.; aliphatic tertiary amines such as triethylamine, tributylamine, diisopropylethylamine, etc.; aliphatic cyclic tertiary amines such as 1,4-diazabicyclo-[2.2.2]octane (DABCO), 1,8-diazabicyclo[5.4.0]undec-7-ene (DBU), etc.; pyridines such as pyridine, collidine, 4-(N,N-dimethylamino)pyridine, etc.; or organic metal bases such as n-butyl lithiums, s-butyl lithium, lithium diisopropylamide, sodium bis(trimehylsilyl)amide, lithium bis(trimethylsilyl)amide, etc., preferably aliphatic tertiary amines, aliphatic cyclic tertiary amines or pyridines, more preferably triethylamine, 1,4-diazabicyclo[2.2.2]octane (DABCO), pyridine or 4-(N,N-dimethylamino)pyridine.

An amount of the base to be used in the reaction is generally 0.5 to 20 mols, preferably 1 to 5 mols based on 1 mol of Compound (Ib).

The solvent to be used is not specifically limited so long as it does not inhibit the reaction, and dissolves starting material(s) with a certain extent, and for example, it may be ketones such as acetone, methyl isobutyl ketone, etc.; nitrites such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; aliphatic hydrocarbons such as hexane, cyclohexane, etc.; amides such as dimethylformamide, dimethylacetamide, etc.; sulfoxides such as dimethylsulfoxide, etc.; or a mixed solvent of the above, preferably nitriles, halogenated hdyrocarbons or ethers, more preferably acetonitrile or methylene chloride.

The reaction temperature may vary mainly depending on starting materials, reaction reagents and a kind of the solvent to be used, and usually −90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

Incidentally, in the present step, a conventionally known method can be employed as usual protection of a hydroxyl group.

(Step J)

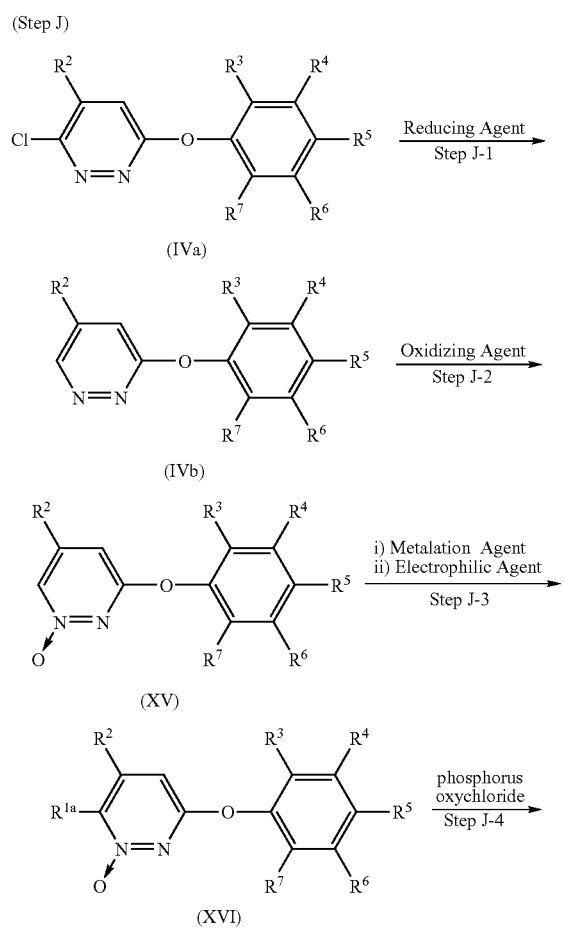

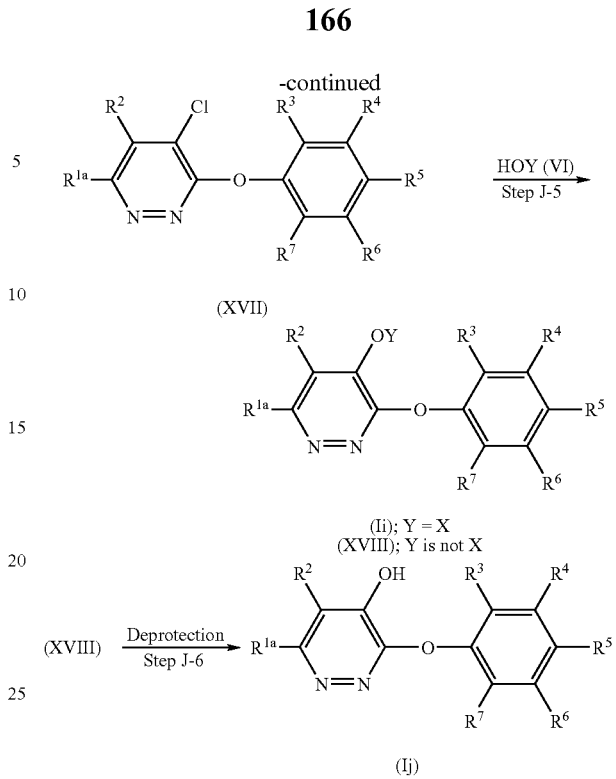

In the above formula, $R^2$, $R^3$, $R^4$, $R^5$, $R^6$, $R^7$, X and Y have the same meanings as defined above, $R^{1a}$ represents the same meaning as $R^1$ except for removing a hydrogen atom.

Step J is a step to produce Compound (Ii) of the present invention or a compound represented by the formula (XVIII), in which a hydroxyl group is protected, by reducing, oxidizing and then metalating a 6-chloropyridazine derivative represented by the formula (IVa), and reacting the resulting material with an electrophilic agent to introduce a substituent on the 6-position of a pyridazine ring, and further subjecting to chlorination, and substitution reaction with an oxygen nucleophilic agent, and further, a step to produce Compound (Ij) of the present invention by removing the protective group of Compound (XVIII).

(Step J-1)

Step J-1 is a step to produce Compound (IVb) in which $R^1$ in Compound (IV) is a hydrogen atom by reacting Compound (IVa) in which $R^1$ in Compound (IV) is a chlorine atom with a reducing agent in the presence or absence of a solvent.

The reducing agent to be used in the reaction is not specifically limited so long as it can reduce a chlorine atom on an aromatic ring, and for example, it may be a reducing agent to be used in a usual hydrogenation reaction, preferably hydrogen-palladium catalyst.

When the hydrogenation reaction is carried out in the present step, a hydrogen pressure is generally 1 atm to 100 atms, preferably 1 to 3 atms.

An amount of the palladium to be used in the hydrogenation reaction is generally 0.001 to 10 mols, preferably 0.01 to 1 mol based on 1 mol of Compound (IVa).

The hydrogenation reaction is preferably carried out in the presence of a base.

The base to be used is not specifically limited so long as it is a base showing a pH of generally 8 or more, and for example, alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal hydrides such as sodium hydride, potassium hydride, etc.; aqueous ammonia; aliphatic tertiary amines such as triethylamine, tri-n-butylamine, diisopropylethylamine, etc.; aliphatic cyclic tertiary amines such as 1,4-diazabicyclo[2.2.2]octane (DABCO), 1,8-diazabicyclo-[5.4.0]undec-7-ene (DBU), etc.; pyridines such as pyridine, collidine, 4-(N,N-dimethylamino)pyridine, etc.; or organometallic bases such as butyl lithium, s-butyl lithium, lithium diisopropylamide, sodium bis(trimethylsilyl)amide, lithium bis(trimethylsilyl)amide, etc., preferably aqueous ammonia or aliphatic tertiary amines, more preferably aqueous ammonia or triethylamine.

An amount of the base to be used in the reaction is generally 0.1 to 100 mols, preferably 1 to 3 mols based on 1 mol of Compound (IVa).

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, etc.; or a mixed solvent of the above, preferably alcohols, more preferably methanol or ethanol.

The reaction temperature may vary mainly depending on starting materials, reaction reagents and a kind of the solvent to be used, and usually −90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

(Step J-2)

Step J-2 is a step to produce Pyridazine N-oxide represented by the formula (XV) by oxidizing Compound (IVb) with an oxidizing agent in the presence or absence of a solvent.

The present step can be carried out in accordance with Step B-1 or C-1.

(Step J-3)

Step J-3 is a step to produce Compound (XVI) of the present invention by reacting Compound (XV) with a metalating agent in the presence or absence of a solvent, and then, reacting with an electrophilic agent.

The present step can be carried out in accordance with Step G-1.

(Step J-4)

Step J-4 is a step to produce Compound (XVII) by reacting Compound (XVI) with phosphorus oxychloride in the presence or absence of a solvent.

The present step is similar to Step B-3 or C-2.

(Step J-5)

Step J-5 is a step to produce Compound (Ii) of the present invention or a compound represented by the formula (XVIII), in which a hydroxyl group is protected, by reacting Compound (XVII) with an oxygen nucleophilic agent represented by the formula (VI) in the presence or absence of a solvent, and if necessary, in the presence of a base.

The present step is similar to Step A-3, B-4 or C-3.

(Step J-6)

Step J-6 is a step to produce Compound (Ij) of the present invention by removing the protective group for a hydroxyl group of Compound (XVIII).

The present step is similar to Step A-4, B-5, C-4, D-2, E-3, F-2 or G-2.

(Step K)

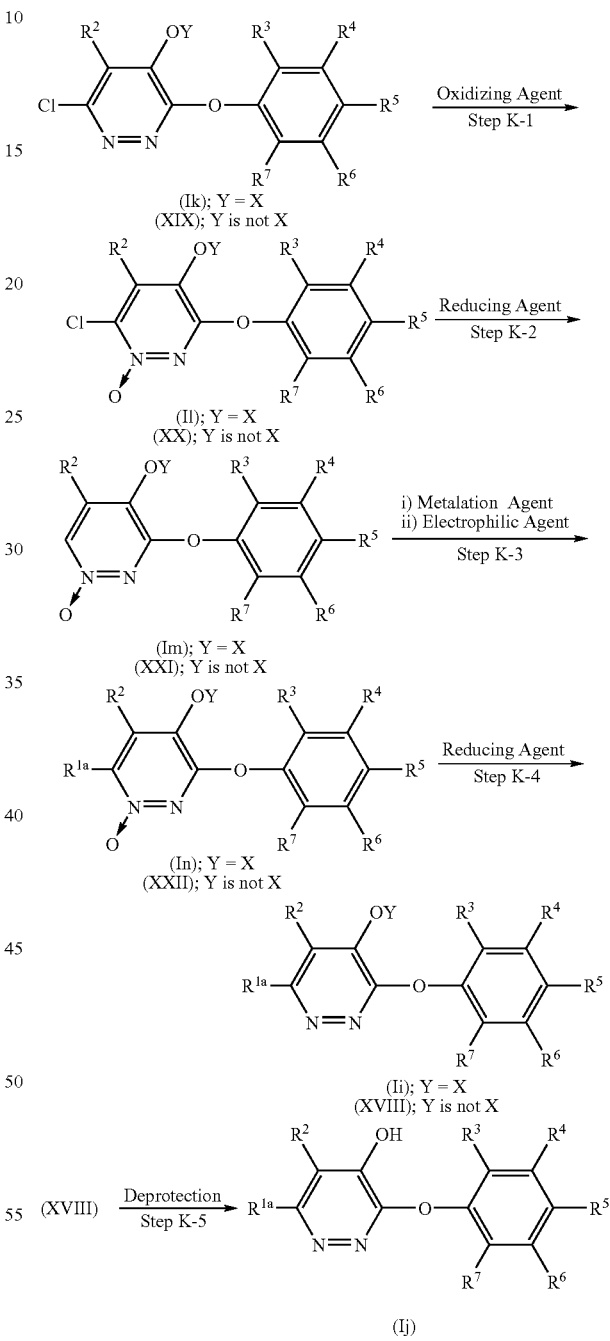

In the above formula, $R^{1a}$, $R^2$, $R^3$, $R^4$, $R^5$, $R^6$, $R^7$, X and Y have the same meanings as defined above.

Step K is a step to produce Compound (Ii) of the present invention or a compound represented by the formula (XVIII), in which a hydroxyl group is protected, by oxidizing, dechlorinating and then metalating 6-chloropyridazine derivative represented by the formula (Ik) of the present invention or a 6-chloropyridazine derivative represented by the formula (XIX) in which a hydroxyl group is protected, then introducing an electrophilic agent and finally reducing the resulting material, and further a step to produce Compound (Ij) of the present invention by removing the protective group of Compound (XVIII).

(Step K-1)

Step K-1 is a step to produce a N-oxypyridazine compound represented by the formula (Il) or (XX) by oxidizing Compound (Ik) or Compound (XIX) with an oxidizing agent in the presence or absence of a solvent.

The present step can be carried out in accordance with Step B-1, C-1 or J-2.

(Step K-2)

Step K-2 is a step to produce a N-oxide compound (Im) or (XXI), in which the 6-position of the pyridazine ring is a hydrogen atom, by reacting a N-oxide compound (Il) or (XX), in which the 6-position of the pyridazine ring is a chlorine atom, with a reducing agent in the presence or absence of a solvent.

The present step can be carried out in accordance with Step J-1.

(Step K-3)

Step K-3 is a step to produce Compound (In) of the present invention or a compound represented by the formula (XXII), in which a hydroxyl group is protected, by reacting Compound (Im) or (XXI) with a metalating agent in the presence or absence of a solvent, and then, reacting with an electrophilic agent.

The present step can be carried out in accordance with Step G-1 or J-3.

(Step K-4)

Step K-4 is a step to produce Compound (Ii) of the present invention or a compound represented by the formula (XVIII), in which a hydroxyl group is protected, by reacting a N-oxide derivative represented by the formula (In) or (XXII) with phosphorus trichloride or phosphorus tribromide in the presence or absence of a solvent.

An amount of the phosphorus trichloride or phosphorus tribromide to be used is generally 0.5 to 100 mols, preferably 1 to 20 mols based on 1 mol of Compound (In) or (XXII).

The solvent to be used is not specifically limited so long as it does not inhibit the reaction, and dissolves starting material(s) with a certain extent, and for example, it may be halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, heptane, etc.; or a mixed solvent of the above, preferably halogenated hydrocarbons, more preferably chloroform.

The reaction temperature may vary mainly depending on starting materials, reaction reagents and a kind of the solvent to be used, and usually –90° C. to 200° C., preferably 0° C. to 100° C.

The reaction time may vary mainly depending on a reaction temperature, starting materials, reaction reagents and a kind of the solvent to be used, and usually 5 minutes to 24 hours, preferably 15 minutes to 6 hours.

(Step K-5)

Step K-5 is a step to produce Compound (Ij) of the present invention by removing the protective group for a hydroxyl group of Compound (XVIII).

The present step is similar to Step A-4, B-5, C-4, D-2, E-3, F-2, G-2 or J-6.

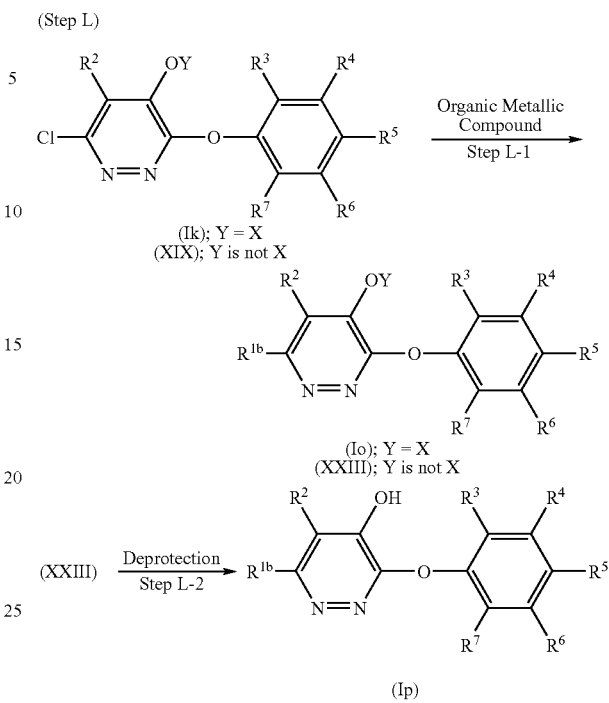

In the above formula, $R^2$, $R^3$, $R^4$, $R^5$, $R^6$, $R^7$, X and Y have the same meanings as defined above, $R^{1b}$ represents the same meaning as $R^1$ except for removing a hydrogen atom and a halogen atom.

Step L is a step to produce Compound (Io) or a compound represented by the formula (XXIII), in which a hydroxyl group is protected, by reacting a 6-chloropyridazine derivative represented by the formula (Ik) or (XIX) with an organometallic compound, and further a step to produce Compound (Ip) of the present invention by removing the protective group of Compound (XXIII).

(Step L-1)

Step L-1 is a step to produce Compound (Io) of the present invention or a compound represented by the formula (XXIII), in which a hydroxyl group is protected, by reacting Compound (Ik) or (XIX) with an organometallic compound in the presence or absence of a solvent and in the presence of a metal catalyst.

The organometallic compound to be used is not specifically limited so long as it is used for a cross-coupling reaction in which a $R^{1b}$ group is substituted by a chlorine atom, and for example, it may be organic magnesium compounds such as methyl magnesium chloride, ethyl magnesium bromide, phenylmagnesium chloride, etc.; organic zinc compounds such as phenyl zinc chloride, etc.; organic aluminum compounds such as (diisobutyl)(1-hexenyl)aluminum, etc.; organic tin compounds such as (vinyl)trimethyl tin, (1-ethoxyvinyl)tributyltin, (2-furyl)tributyltin, (2-thienyl)tributyltin, etc.; organic boron compounds such as phenylboronic acid, etc.; organic silicate compounds such as trimethylvinylsilicon-tris(dimethylamino)sulfonium difluorotrimethyl silicate, etc.; potassium cyanide, and acetylene compounds such as trimethylsilyl acetylene, phenyl acetylene, etc. may be used similarly in the presence of amines such as triethylamine, etc., as in the above-mentioned organometallic compounds, preferably organic tin compounds or organic boron compounds.

An amount of the organometallic compound to be used in the reaction is generally 0.5 to 10 mols, preferably 1 to 2 mols based on 1 mol of Compound (Ik) or (XIX).

The metal catalyst to be used in the present step is not specifically limited so long as it can be used in a cross-coupling reaction, and for example, it may be a nickel catalyst or a palladium catalyst.

An amount of the metal catalyst to be used in the reaction is generally 0.0001 to 10 mols, preferably 0.01 to 0.5 mol based on 1 mol of Compound (Ik) or (XIX).

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitrites such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, etc.; organic amines such as triethylamine, pyridine, etc.; or a mixed solvent of the above, preferably ethers, aromatic hydrocarbons or amides, more preferably ether, tetrahydrofuran, toluene or dimethylformamide.

The reaction temperature may vary mainly depending on starting materials, reaction reagents and a kind of the solvent to be used, and usually −90° C. to 200° C., preferably 0° C. to 130° C.

The reaction time may vary mainly depending on a reaction temperature, starting materials, reaction reagents and a kind of the solvent to be used, and usually 5 minutes to 48 hours, preferably 15 minutes to 24 hours.

(Step L-2)

Step L-2 is a step to produce Compound (Ip) of the present invention by removing the protective group for a hydroxyl group of Compound (XXIII).

The present step is similar to Step A-4, B-5, C-4, D-2, E-3, F-2, G-2, J-6 or K-5.

(Step M)

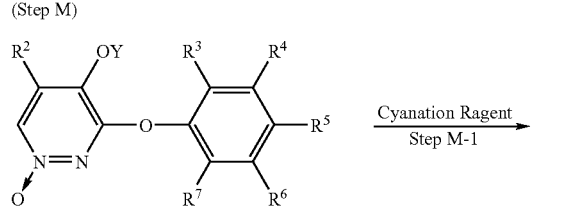

(Im); Y = X
(XXI); Y is not X

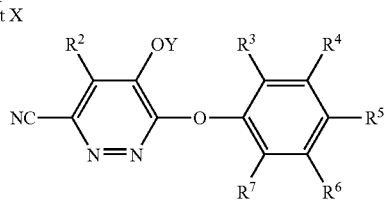

(Iq); Y = X
(XXIV); Y is not X

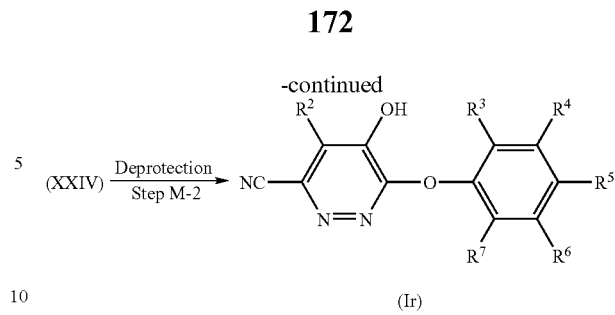

(Ir)

In the above formula, $R^2$, $R^3$, $R^4$, $R^5$, $R^6$, $R^7$, X and Y have the same meanings as defined above.

Step M is a step to produce Compound (Iq) of the present invention or a compound represented by the formula (XXIV), in which a hydroxyl group is protected, by cyanation of 6-position unsubstituted Pyridazine N-oxide derivative represented by the formula (Im) or (XXI), and also a step to produce Compound (Ir) of the present invention by removing the protective group of Compound (XXIV).

(Step M-1)

Step M-1 is a step to produce Compound (Iq) of the present invention or a compound represented by the formula (XXIV), in which a hydroxyl group is protected, by reacting Compound (Im) or (XXI) with a cyanation reagent in the presence or absence of a solvent.

The present step can be carried out in accordance with the conventionally known Reissert-Henze reaction (JOC, 48, 1983, 1375 to 1377; Heterocycles, 15, 1981, 981 to 984; Synthesis, 1983, 316 to 319, etc.).

(Step M-2)

Step M-2 is a step to produce Compound (Ir) of the present invention by removing the protective group for a hydroxyl group of Compound (XXIV).

The present step is similar to Step A-4, B-5, C-4, D-2, E-3, F-2, G-2, J-6, K-5 or L-2.

(Step N)

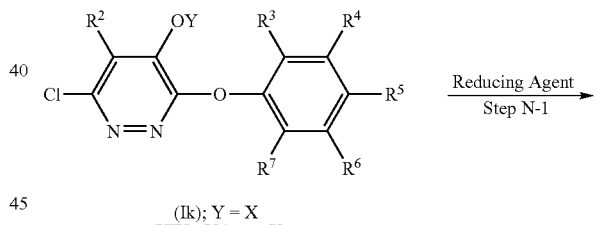

(Ik); Y = X
(XIX); Y is not X

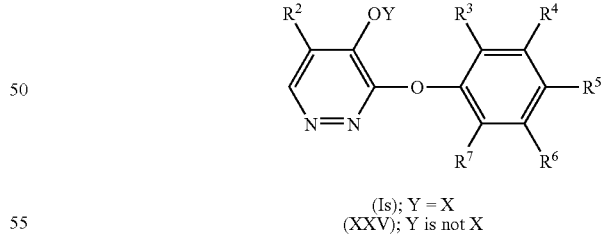

(Is); Y = X
(XXV); Y is not X

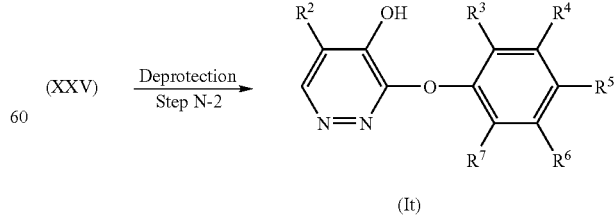

(It)

In the above formula, $R^2$, $R^3$, $R^4$, $R^5$, $R^6$, $R^7$, X and Y have the same meanings as defined above.

Step N is a step to produce Compound (Is) of the present invention or a compound represented by the formula (XXV), in which a hydroxyl group is protected, by dechlorinating a 6-chloropyridazine derivative represented by the formula (Ik) or (XIX), and further a step to produce Compound (It) of the present invention by removing the protective group of Compound (XXV).

(Step N-1)

Step N-1 is a step to produce Compound (Is) of the present invention or a compound represented by the formula (XXV), in which a hydroxyl group is protected, by reacting Compound (Ik) or (XIX) with a reducing agent in the presence or absence of a solvent.

The present step can be carried out in accordance with Step J-1 or K-2.

(Step N-2)

Step N-2 is a step to produce Compound (It) of the present invention by removing the protective group for a hydroxyl group of Compound (XXV).

The present step is similar to Step A-4, B-5, C-4, D-2, E-3, F-2, G-2, J-6, K-5, L-2 or M-2.

(Step O)

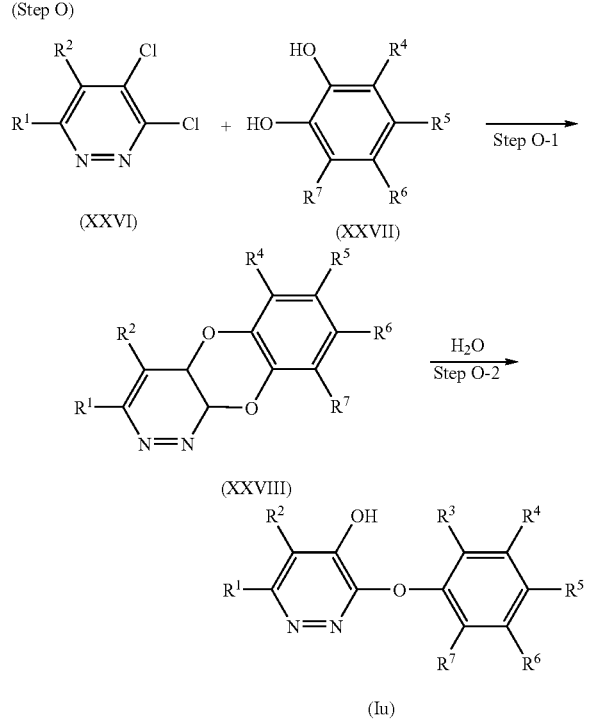

In the above formula, $R^1$, $R^2$, $R^4$, $R^5$, $R^6$ and $R^7$ have the same meanings as defined above.

Step O is a step to produce Compound (Iu) of the present invention by reacting a 3,4-dichloropyridazine derivative represented by the formula (XXVI) with a catechol derivative represented by the formula (XXVII) and then subjecting the resulting material to hydrolysis.

(Step O-1)

Step O-1 is a step to produce a condensed compound represented by the formula (XXVIII) by reacting Compound (XXVI) with Compound (XXVII) in the presence or absence of a solvent, and if necessary, in the presence of a base.

The present step can be carried out in accordance with Step A-1, B-2, D-1 or E-2, and an amount of the base to be used is generally 1 to 10 mols, preferably 2 to 6 mols based on 1 mol of Compound (XXVI).

(Step O-2)

Step O-2 is a step to produce Compound (Iu) of the present invention by subjecting Compound (XXVIII) to hydrolysis.

The present step can be carried out in accordance with the case where Y is a hydrogen atom in Step A-3, B-4 or C-3, and a reaction temperature is preferably 80° C. to 100° C.

(Step P)

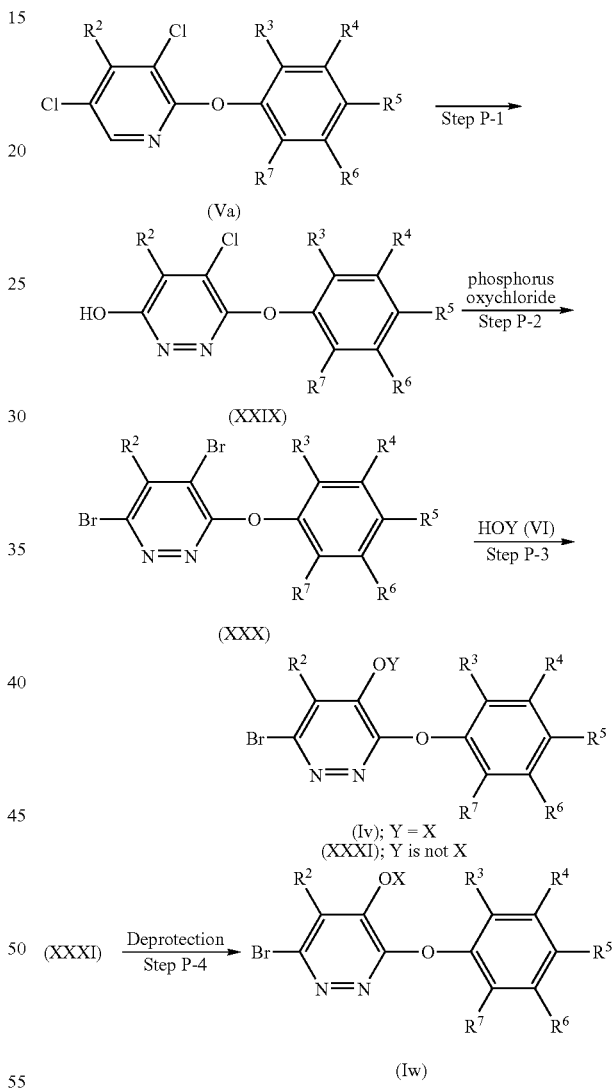

In the above formula, $R^2$, $R^3$, $R^4$, $R^5$, $R^6$ and $R^7$ have the same meanings as defined above.

Step P is a step to produce Compound (Iv) of the present invention or a compound represented by the formula (XXXI), in which a hydroxyl group is protected, by selectively subjecting 6-position of a 4,6-dichloropyridazine derivative represented by the formula (Va) to hydrolysis to prepare Compound (XXIX), then, brominating 4,6-positions thereof with phosphorus oxybromide, and then selectively reacting an oxygen nucleophilic agent at 4-position thereof, and a step to produce Compound (Iw) of the present invention by removing the protective group of Compound (XXXI).

(Step P-1)

Step P-1 is a step to produce a compound represented by the formula (XXIX) by subjecting Compound (Va) to hydrolysis in the presence or absence of a solvent and in the presence of an acid to selectively convert a chlorine atom at the 6-position into a hydroxyl group.

An acid to be used is not specifically limited so long as it is an acid showing a pH of 6 or less, and for example, it may be organic acids such as formic acid, acetic acid, oxalic acid, propionic acid, succinic acid, maleic acid, fumalic acid, benzoic acid, etc.; mineral acids such as hydrofluoric acid, hydrochloric acid, hydrobromic acid, hydroiodic acid, sulfuric acid, nitric acid, phosphoric acid, etc.; or Lewis acids such as aluminum chloride, iron chloride, titanium chloride, boron trifluoride, etc., preferably organic acids, more preferably formic acid or acetic acid.

The present step is carried out preferably in the presence of a metal salt of an acid.

The metal salt of an acid to be used may inclide, for example, alkali metal salts of an organic acid such as sodium formate, potassium formate, lithium acetate, sodium acetate, potassium acetate, cesium acetate, sodium benzoate, etc.; alkaline earth metal salts of an organic acid such as magnesium formate, calcium formate, magnesium acetate, calcium acetate, magnesium benzoate, etc.; alkali metal salts or alkaline earth metal salts of carbonic acid such as sodium carbonate, potassium carbonate, calcium carbonate, sodium hydrogen carbonate, potassium hydrogen carbonate, etc.; or alkali metal salts or alkaline earth metal salts of a mineral acid such as sodium fluoride, potassium fluoride, sodium chloride, potassium chloride, sodium bromide, potassium bromide, sodium iodide, potassium iodide, sodium sulfate, sodium hydrogen sulfate, potassium sulfate, potassium hydrogen sulfate, magnesium sulfate, sodium phosphate, disodium hydrogen phosphate, sodium dihydrogen phosphate, potassium phosphate, dipotassium hydrogen phosphate, potassium dihydrogen phosphate, etc., preferably alkali metal salts of an organic acid, more preferably sodium formate, potassium formate, sodium acetate or potassium acetate.

The solvent to be used is not specifically limited so long as it does not inhibit the reaction, and dissolves starting material(s) with a certain extent, and for example, it may be water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; organic acids such as formic acid, acetic acid, propionic acid, etc.; or a mixed solvent of the above, preferably water, nitriles, ethers, amides, sulfoxides or organic acids, more preferably water, acetonitrile, tetrahydrofuran, dioxane, dimethylformamide, dimethylsulfoxide, formic acid or acetic acid.

The reaction temperature may vary depending on the starting compounds, reaction reagents and a kind of the solvent to be used, etc., and is generally –90° C. to 200° C., preferably 0° C. to 150° C.

The reaction time may vary mainly depending on a reaction temperature, starting materials, reaction reagents and a kind of the solvent to be used, and usually, 5 minutes to 24 hours, preferably 15 minutes to 12 hours.

(Step P-2)

Step P-2 is a step to produce Compound (XXX) by reacting Compound (XXIX) with phosphorus oxybromide in the presence or absence of a solvent.

An amount of the phosphorus oxybromide to be used in the present step is generally 0.5 to 100 mols, preferably 1 to 10 mols based on 1 mol of Compound (XXIX).

The solvent to be used is not specifically limited so long as it does not inhibit the reaction, and dissolves starting material(s) with a certain extent, and for example, it may be ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; aliphatic hydrocarbons such as hexane, cyclohexane, etc.; or a mixed solvent of the above, preferably halogenated hydrocarbons, more preferably methylene chloride, chloroform.

The reaction temperature may vary depending on starting materials, reaction reagents and a kind of the solvent to be used, and usually –90° C. to 200° C., preferably 0° C. to 100° C.

The reaction time may vary mainly depending on a reaction temperature, starting materials, reaction reagents and a kind of the solvent to be used, and usually 5 minutes to 72 hours, preferably 30 minutes to 24 hours.

(Step P-3)

Step P-3 is a step to produce Compound (Iv) of the present invention or a compound represented by the formula (XXXI), in which a hydroxyl group is protected, by reacting Compound (XXX) with an oxygen nucleophilic agent represented by the formula (VI) in the presence or absence of a solvent, and if necessary, in the presence of a base.

The present step is similar to Step A-3, B-4, C-3 or J-5.

(Step P-4)

Step P-4 is a step to produce Compound (Iw) of the present invention by removing the protective group for a hydroxyl group of Compound (XXXI).

The present step is similar to Step A-4, B-5, C-4, D-2, E-3, F-2, G-2, J-6, K-5, L-2, M-2 or N-2.

(Step Q)

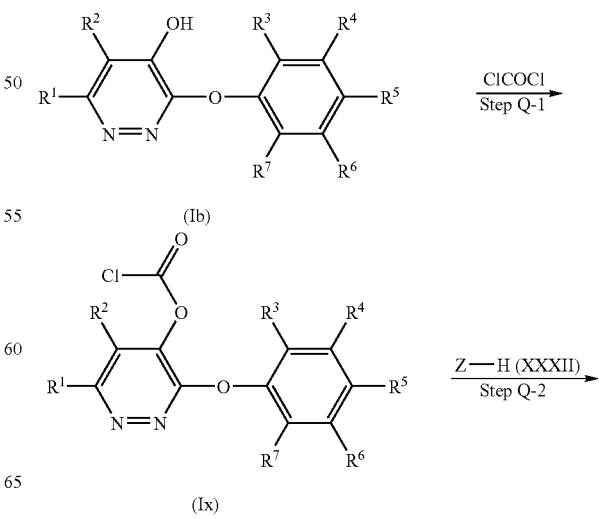

-continued

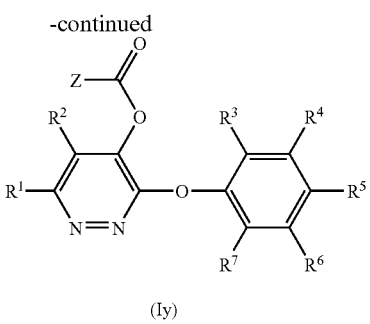

(Iy)

In the above formula, $R^1$, $R^2$, $R^3$, $R^4$, $R^5$, $R^6$ and $R^7$ have the same meanings as defined above, a compound represented by the formula (XXXII) represents an oxygen nucleophilic agent, a sulfur nucleophilic agent or a nitrogen nucleophilic agent, Z represents a substituent in which a proton is removed from the oxygen nucleophilic agent, the sulfur nucleophilic agent or the nitrogen nucleophilic agent, and for example, it may be an alkoxy group, a thioalkoxy group, a dialkylamino group, etc.

Step Q is a step to convert a hydroxy isomer represented by the formula (Ib) of the present invention into an ester derivative represented by the formula (Iy) of the present invention.

(Step Q-1)

Step Q-1 is a step to produce Compound (Ix) of the present invention by reacting Compound (Ib) of the present invention with phosgene in the presence or absence of a solvent.

An amount of the phosgene to be used in the reaction is generally 0.5 to 10 mols, preferably 1 to 3 mols based on 1 mol of Compound (Ib).

The reaction is preferably carried out in the presence of a base.

The base to be used is not specifically limited so long as it is a base generally showing a pH of 8 or more, and for example, alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal hydrides such as sodium hydride, potassium hydride, etc.; aliphatic tertiary amines such as triethylamine, tributylamine, diisopropylethylamine, etc.; aliphatic cyclic tertiary amines such as 1,4-diazabicyclo-[2.2.2]octane (DABCO), 1,8-diazabicyclo[5.4.0]undec-7-ene (DBU), etc.; pyridines such as pyridine, collidine, 4-(N,N-dimethylamino)pyridine, etc.; or, organic metal bases such as n-butyl lithiums, s-butyl lithium, lithium diisopropylamide, sodium bis(trimehylsilyl)amide, lithium bis(trimethylsilyl)amide, etc., preferably aliphatic tertiary amines, aliphatic cyclic tertiary amines or pyridines, more preferably triethylamine, 1,4-diazabicyclo[2.2.2]octane (DABCO), pyridine or 4-(N,N-dimethylamino)pyridine.

An amount of the base to be used in the reaction is generally 0.5 to 20 mols, preferably 1 to 5 mols based on 1 mol of Compound (Ib).

The solvent to be used is not specifically limited so long as it does not inhibit the reaction, and dissolves starting material(s) with a certain extent, and for example, it may be ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; aliphatic hydrocarbons such as hexane, cyclohexane, etc.; amides such as dimethylformamide, dimethylacetamide, etc.; sulfoxides such as dimethylsulfoxide, etc.; or a mixed solvent of the above, preferably nitriles, halogenated hydrocarbons or ethers, more preferably acetonitrile or methylene chloride.

The reaction temperature may vary mainly depending on starting materials, reaction reagents and a kind of the solvent to be used, and usually −90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

(Step Q-2)

Step Q-2 is a step to produce Compound (Iy) of the present invention by reacting Compound (Ix) of the present invention with a nucleophilic agent represented by the formula (XXXII) in the presence or absence of a solvent, and if necessary, in the presence of a base.

The solvent to be used is not specifically limited so long as it does not inhibit the reaction, and dissolves starting material(s) with a certain extent, and for example, it may be ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; aliphatic hydrocarbons such as hexane, cyclohexane, etc.; amides such as dimethylformamide, dimethylacetamide, etc.; sulfoxides such as dimethylsulfoxide, etc.; or a mixed solvent of the above, preferably nitriles, halogenated hydrocarbons or ethers, more preferably acetonitrile or methylene chloride.

The base to be used is not specifically limited so long as it is a base generally showing a pH of 8 or more, and for example, alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal hydrides such as sodium hydride, potassium hydride, etc.; aliphatic tertiary amines such as triethylamine, tributylamine, diisopropylethylamine, etc.; aliphatic cyclic tertiary amines such as 1,4-diazabicyclo-[2.2.2]octane (DABCO), 1,8-diazabicyclo[5.4.0]undec-7-ene (DBU), etc.; pyridines such as pyridine, collidine, 4-(N,N-dimethylamino)pyridine, etc.; or organic metal bases such as n-butyl lithiums, s-butyl lithium, lithium diisopropylamide, sodium bis(trimehylsilyl)amide, lithium bis(trimethylsilyl)amide, etc., preferably aliphatic tertiary amines, aliphatic cyclic tertiary amines or pyridines, more preferably triethylamine, 1,4-diazabicyclo[2.2.2]octane (DABCO), pyridine or 4-(N,N-dimethylamino)pyridine.

An amount of the base to be used in the reaction is generally 0.5 to 20 mols, preferably 1 to 5 mols based on 1 mol of Compound (Ix).

The nucleophilic agent (XXXII) to be used in the reaction is not specifically limited so long as it can substitute a chlorine atom of chlorocarbonic acid ester (Ix), and the oxygen nucleophilic agent may include, for example, alcohols such as methanol, ethanol, propanol, etc.; or phenols such as phenol, 4-chlorophenol, etc., also, the sulfur nucleophilic agent may include, for example, thiols such as methanethiol, ethanethiol, propanethiol, etc.; or thiophenols such as thiophenol, etc., and, the nitrogen nucleophilic agent may include, for example, aliphatic linear amines such as methylamine, dimethylamine, diethylamine, methyl(t-butyl)amine, methyl(cyanomethyl)amine, methyl(ethoxycarbonylmethyl)

amine, bis(cyanomethyl)amine, bis(2-cyanoethyl)amine, bis (ethoxycarbonylmethyl)amine, bis(2-methoxyethyl)amine, bis(2-ethoxyethyl)amine, bis(2-chloroethyl)amine, N,O-dimethylhydroxylamine, etc.; aromatic amines such as methyl(phenyl)amine, methyl(pyridyl)amine, etc.; aliphatic cyclic amines such as aziridine, azetidine, pyrrolidine, piperidine, morpholine, thiomorpholine, N-methylpiperazine, N-phenylpiperazine, 2-methoxycarbonylpyrrolidine, 3-hydroxypyrrolidine, 4-bromopiperidine, 4-methylpiperidine, 2,2,6,6-tetramethylpiperidine, 2-ethoxycarbonylpiperidine, 4-ethoxycarbonylpiperidine, 2,6-dimethyl morpholine, 1,2,3,4-tetrahydroisoquinoline, etc.; aromatic cyclic amines such as carbazole, 2,5-dimethylpyrrole, etc., preferably methanol, ethanol, methanethiol, ethanethiol, methylamine, dimethylamine, methyl(cyanomethyl)amine, methyl(ethoxycarbonylmethyl)amine, bis(cyanomethyl)amine, bis(2-cyanoethyl)amine, bis(ethoxycarbonylmethyl)amine, bis(2-methoxyethyl)amine, bis(2-ethoxyethyl)amine, bis(2-chloroethyl)amine, N,O-dimethylhydroxylamine, methyl (pyridyl)amine, azetidine, pyrrolidine, piperidine, morpholine, thio morpholine, N-methylpiperazine, 2-methoxycarbonylpyrrolidine, 3-hydroxypyrrolidine, 2-ethoxycarbonylpiperidine, 4-ethoxycarbonylpiperidine, 2,6-dimethyl morpholine, 2,5-dimethylpyrrole, more preferably dimethylamine, methyl(cyanomethyl)amine, methyl(ethoxycarbonylmethyl)amine, bis(cyanomethyl)amine, bis(ethoxycarbonylmethyl)amine, bis(2-methoxyethyl)amine, bis(2-ethoxyethyl)amine, N,O-dimethylhydroxylamine, azetidine, morpholine, thiomorpholine, N-methylpiperazine, 2-methoxycarbonylpyrrolidine, 3-hydroxypyrrolidine, 2-ethoxycarbonylpiperidine, 4-ethoxycarbonylpiperidine, 2,6-dimethyl morpholine.

An amount of the nucleophilic agent to be used in the reaction is generally 0.5 to 20 mols, preferably 1 to 5 mols based on 1 mol of Compound (Ix).

The reaction temperature may vary mainly depending on starting materials, reaction reagents and a kind of the solvent to be used, and usually –90° C. to 200° C., preferably 0° C. to 100° C.

The reaction time may vary mainly depending on a reaction temperature, starting materials, reaction reagents and a kind of the solvent to be used, and usually 5 minutes to 48 hours, preferably 15 minutes to 12 hours.

Incidentally, after completion of the above-mentioned respective steps, and before the steps subsequent thereto, the functional group(s) in $R^1$ to $R^7$ of the desired compound of the respective steps can be converted to the other functional group so long as it is within the definitions for $R^1$ to $R^7$.

Also, in Steps A-1, B-2, D-1 and E-2, when at least one of $R^1$ and $R^2$ is a chlorine atom, depending on the reaction conditions, in the Step, a chlorine atom of $R^1$ or $R^2$ is substituted by the group

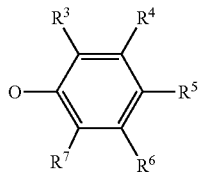

in some cases, and further, in Steps A-3, B-4, C-3 and J-5, when at least either one of $R^1$ and $R^2$ is a chlorine atom, depending on the reaction conditions, in the Step, a chlorine atom of $R^1$ or $R^2$ is substituted by the group OY in some cases, and further, in Step P-3, a bromine atom at the 6-position of the pyridazine ring or a chlorine atom of $R^2$ when $R^2$ is a chlorine atom is substituted by the group OY in some cases.

Starting Compound (II) in Step A and B may be used those commercially available, or may be produced by the method disclosed in, for example, Kogyo Kagaku Zasshi (Journal of Industrial Chemistry), 1971, vol. 74, No. 7, pp. 1490-1491; Tetrahedron, 1999, vol. 55, No. 52, pp. 15067 to 15070; The Journal of Organic Chemistry, 1963, vol. 28, pp. 218 to 221 or in accordance with these methods.

The starting Compound (X) of Steps D and E can be produced by the method disclosed in, for example, Helvetica Chimica Acta, 1956, vol. 39, pp. 1755 to 1764; Monatshefte fur Chemie, 1968, vol. 99, pp. 15-81 (in the present specification, the letter u in Monatshefte fur Chemie represents u-umlaut.); German Patent 1,912,472, Nov. 12, 1970 (filed on Apr. 12, 1969) (Ger. Offen. 1,912,472, 12 Nov. 1970, Appl. 12 Mar. 1969), or in accordance with these methods.

The phenol Compound (III) to be used in Steps A, B, D and E may be used those commercially available, or may be produced by using the conventionally known method or in accordance with these methods.

2-Isobutylphenol can be produced by the method disclosed in, for example, Canadian Journal of Chemistry, 1956, vol. 34, pp. 851-854.

2-Pentylphenol can be produced by the method disclosed in, for example, Tetrahedron Letters, 1989, vol. 30, No. 35, pp. 4741-4744.

2-Hexylphenol can be produced by the method disclosed in, for example, Journal of the Chemical Society: Parkin transaction I, 2000, vol. 7, pp. 1109-1116 (coversion of vinyl group into hexyl group), and Journal of Medicinal Chemistry, 1977, vol. 20, No. 10, pp. 1317-1323 (conversion of phenylmethyl ether into phenol, demethylation reaction) from commercially available 1-methoxy-2-vinylbenzene.

2-Cyclopropylphenol can be produced by the method disclosed in, for example, Bioorganic & Medicinal Chemistry, 1997, vol. 5, No. 10, pp. 1959-1968.

2-(1-Methylcyclopropyl)phenol can be produced in accordance with the method disclosed in, for example, from commercially available 1-(2-methoxyphenyl)ethanone, The Journal of Organic Chemistry, 1963, vol. 28, p. 1128 or Synthetic Communications, 1985, vol. 15, No. 10, pp. 855-864 (conversion of carbonyl group into olefin, Wittg reaction), and by the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(1-Ethylcyclopropyl)phenol can be produced in accordance with the method disclosed in, for example, from commercially available 1-(2-methoxyphenyl)-1-propanone, The Journal of Organic Chemistry, 1963, vol. 28, p. 1128 or Synthetic Communications, 1985, vol. 15, No. 10, pp. 855-864 (conversion of carbonyl group into olefin, Wittg reaction), and by the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and by the method disclosed in Bioscience, Biotechnology, and Biochemistry, 1993, vol. 57, No.

9, pp. 1572-1574 or Japanese Provisional Patent Publication No. 11-322755 (conversion of phenylmethyl ether into phenol, demethylation reaction).

2-(1-Cyclopropylcyclopropyl)phenol can be produced in accordance with the method disclosed in, for example, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction) from cyclopropyl(2-hydroxyphenyl) methanone produced by the method disclosed in Journal of the Chemical Society: Parkin transaction I, 1990, pp. 689-693 from commercially available 2,3-dihydro-4H-chromen-4-one.

1-(2-Hydroxyphenyl)cyclopropanecarbonitrile can be produced by producing 1-(2-methoxyphenyl)cyclopropanecarbonitrile in accordance with the method disclosed in, for example, Journal of the American Chemical Society, 2000, vol. 122, No. 4, pp. 712-713, and by the method disclosed in Organic Synthesis, Collective Volume, vol. 5, pp. 412-414 (conversion of phenylmethyl ether into phenol, demethylation reaction).

2-(1-Phenylcyclopropyl)phenol can be produced in accordance with the method disclosed in, for example, from commercially available 1-(2-methoxyphenyl)(phenyl)methanone, The Journal of Organic Chemistry, 1963, vol. 28, p. 1128 or Synthetic Communications, 1985, vol. 15, No. 10, pp. 855-864 (conversion of carbonyl group into olefin, Wittg reaction), and by the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(2-Methylcyclopropyl)phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(2,2-Dimethylcyclopropyl)phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Cis-2,cis-3-dimethyl)-ref-1-cyclopropyl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Cis-2,trans-3-dimethyl)-ref-1-cyclopropyl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Trans-2,trans-3-dimethyl)-ref-1-cyclopropyl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Ref-1,cis-5,cis-6)-bicyclo[3.1.0]hexa-6-yl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Ref-1,cis-5,trans-6)-bicyclo[3.1.0]hexa-6-yl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Ref-1,cis-6,cis-7)-bicyclo[4.1.0]hept-7-yl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(Ref-1,cis-6,trans-7)-bicyclo[4.1.0]hept-7-yl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp.

1572-1574 or Japanese Provisional Patent Publication No. 11-322755 (conversion of phenylmethyl ether into phenol, demethylation reaction).

2-[(2,2,Cis-3-trimethyl)-ref-1-cyclopropyl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-[(2,2,trans-3-trimethyl)-ref-1-cyclopropyl]phenol can be produced in accordance with the method disclosed in, for example, from commercially available 1-(chloromethyl)-2-methoxybenzene, Journal of the American Chemical Society, 1973, vol. 95, No. 2, pp. 581-582 (construction of cyclopropyl group), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclobutylphenol can be produced by the method disclosed in, for example, German Patent DE-2825388.

1-(2-Hydroxyphenyl)cyclobutancarbonitrile can be produced by the method disclosed in, for example, Pharmaceutical Chemistry Journal (English Translation), 1980, vol. 14, No. 2, pp. 114-118.

1-(2-Hydroxyphenyl)cyclobutanecarboxylic acid can be produced by the method disclosed in, for example, Pharmaceutical Chemistry Journal (English Translation), 1980, vol. 14, No. 2, pp. 114-118.

2-(1-Propynyl)phenol can be produced by the method disclosed in, for example, Journal of the Chemical Society: Parkin transaction I, 1998, pp. 477-484.

2-(Cyclopropylmethyl)phenol can be produced in accordance with the method disclosed in, for example, Organic Reactions, 1941, vol, 1, p. 155 (Clemmensen reduction) from cyclopropyl(2-hydroxyphenyl)methanone which can be produced by the method disclosed in Journal of the Chemical Society: Parkin transaction I, 1990, pp. 689-693 from commercially available 2,3-dihydro-4H-chromen-4-one.

2-(Methoxymethyl)phenol can be produced by the method disclosed in, for example, Tetrahedron Letters, 1999, vol. 40, p. 6049.

2-(Ethoxymethyl)phenol can be produced by the method disclosed in, for example, Tetrahedron Letters, 1999, vol. 40, p. 6049.

2-(1,3-Dioxolan-2-yl)phenol can be produced by the method disclosed in, for example, Tetrahedron Letters, 1989, vol. 30, No. 13, pp. 1609-1612.

1-(2-Hydroxyphenyl)ethanone O-methyloxime can be produced in accordance with the method disclosed in, for example, commercially available 1-(2-hydroxyphenyl)ethanone, Journal of the American Chemical Society, 1986, vol. 108, pp. 6016-6023.

3'-(Trifluoromethyl)[1,1'-biphenyl]-2-ol can be produced in accordance with the method disclosed in, for example, from commercially available 2-iodophenol and 3-(trifluoromethyl)phenylboronic acid, Chemical Reviews, 1995, vol. 95, pp. 2457-2483 (phenylation reaction, Suzuki-Miyaura coupling reaction).

2-(1H-pyrrole-1-yl)phenol can be produced by the method disclosed in, for example, The Journal of Antibiotics, 1994, vol. 47, No. 5, pp. 602-605.

2-(2-Thienyl)phenol can be produced by the method disclosed in, for example, Journal of Heterocyclic Chemistry, 1985, vol. 22, pp. 1667-1669.

2-(3-Thienyl)phenol can be produced by the method disclosed in, for example, Journal of Heterocyclic Chemistry, 1985, vol. 22, pp. 1667-1669.

2-(1H-pyrazol-1-yl)phenol can be produced by the method disclosed in, for example, Canadian Journal of Chemistry, 1963, vol. 41, pp. 2086-2092.

2-(3,5-Dimethyl-1H-pyrazol-1-yl)phenol can be produced by the method disclosed in, for example, Heterocycles, 1982, vol. 19, No. 8, pp. 1487-1495.

2-[3-(Trifluoromethyl)-1H-pyrazol-1-yl]phenol can be produced, for example, by preparing 1-(2-methoxyphenyl)-3-(trifluoromethyl)-1H-pyrazol from commercially available 1-(2-methoxyphenyl)hydrazine hydrochloride by the method disclosed in Journal of Fluorine Chemistry 1998, vol. 92, p. 23, and in accordance with the method disclosed in Organic Synthesis, Collective Volume, vol. 5, pp. 412-414 (conversion of phenylmethyl ether into phenol, demethylation reaction).

2-[4-(Trifluoromethyl)-1H-pyrazol-1-yl]phenol can be produced, for example, by preparing 1-(2-methoxyphenyl)-4-(trifluoromethyl)-1H-pyrazole from commercially available 1-(2-methoxyphenyl)hydrazine hydrochloride by the method disclosed in Tetrahedron Letters, 1996, vol. 37, No. 11, p. 1829, and in accordance with the method disclosed in Organic Synthesis, Collective Volume, vol. 5, pp. 412-414 (conversion of phenylmethyl ether into phenol, demethylation reaction).

2-[5-(Trifluoromethyl)-1H-pyrazol-1-yl]phenol can be produced, for example, by preparing 1-(2-methoxyphenyl)-5-(trifluoromethyl)-1H-pyrazole from commercially available 1-(2-methoxyphenyl)hydrazine hydrochloride by the method disclosed in Journal of Fluorine Chemistry, 1998, vol. 92, p. 23, and in accordance with the method disclosed in Organic Synthesis, Collective Volume, vol. 5, pp. 412-414 (conversion of phenylmethyl ether into phenol, demethylation reaction).

5-(2-Hydroxyphenyl)-N,N-dimethyl-1H-pyrazol-1-sulfonamide can be produced, for example, from 5-(5-chloro-2-hydroxyphenyl)-N,N-dimethyl-1H-pyrazol-1-sulfonamide, which can be produced from commercially available 4-chloro-2-(1H-pyrazol-5-yl)phenol in accordance with the method disclosed in Journal of Medicinal Chemistry, 1998, vol. 41, No. 12, pp. 2019-2028, in accordance with the method disclosed in, Jikken Kagaku Koza (Experimental Chemistry Lecture), 4th Edition, vol. 26, pp. 251-266 (catalytic hydrogenation reaction).

3-(2-Hydroxyphenyl)-N,N-dimethyl-1H-pyrazol-1-sulfonamide can be produced, for example, from 3-(5-chloro-2-hydroxyphenyl)-N,N-dimethyl-1H-pyrazol-1-sulfonamide, which can be produced from commercially available 4-chloro-2-(1H-pyrazol-5-yl)phenol in accordance with the method disclosed in Journal of Medicinal Chemistry, 1998, vol. 41, No. 12, pp. 2019-2028, in accordance with the method disclosed in, Jikken Kagaku Koza (Experimental Chemistry Lecture), 4th Edition, vol. 26, pp. 251-266 (catalytic hydrogenation reaction).

2-(4-Methyl-1,3-thiazol-2-yl)phenol can be produced by the method disclosed in, for example, from commercially available 2-hydroxybenzonitrile, Japanese Provisional Patent Publication No. 11-60552 (thioamidation reaction of a cyano group), and the method disclosed in Liebigs Annalen der Chemie, 1890, vol. 259, p. 236.

2-(1,3-Benzothiazol-2-yl)phenol can be produced by the method disclosed in, for example, The Journal of Organic Chemistry, 1970, vol. 35, pp. 3147-3149.

2-(Dimethylamino)phenol can be produced by the method disclosed in, for example, Journal of Medicinal Chemistry, 1998, vol. 41, pp. 4800-4818.

2-(2-Methoxyethoxy)phenol can be produced in accordance with the method disclosed in, for example, Journal of the Chemical Society: Parkin transaction I, 1980, pp. 756-758 from commercially available pyrocatechol.

2-(Isopropylsulfanyl)phenol can be produced by the method disclosed in, for example, Tetrahedron, 1970, vol. 26, pp. 4449-4471.

3-Cyclopropylphenol can be produced by the method disclosed in, for example, from commercially available 1-bromo-3-methoxybenzene, Tetrahedron Letters, 2000, vol. 41, pp. 4251-4255 (construction of cyclopropyl group, Suzuki-Miyaura coupling reaction), and in accordance with the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3-(2-Furyl)phenol can be produced, for example, by producing 2-(3-methoxyphenyl)furan by the method disclosed in The Journal of Organic Chemistry, 1993, vol. 58, No. 17, pp. 4722-4726, and in accordance with the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

4-Cyclopropylphenol can be produced in accordance with the method disclosed in, for example, from commercially available 1-bromo-4-methoxybenzene, Tetrahedron Letters, 2000, vol. 41, pp. 4251-4255 (construction of cyclopropyl group, Suzuki-Miyaura coupling reaction), and by the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Bromo-3-methylphenol can be produced in accordance with the method disclosed in, for example, from commercially available 2-methoxy-6-methylaniline, Organic Synthesis, Collective Volume, vol. 3, pp. 185-187 or the method disclosed in The Journal of Organic Chemistry, 1977, vol. 42, pp. 2426-2430 (conversion of anilines into bromobenzene, Sandmeyer reaction, etc.) and, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3-Fluoro-2-methylphenol can be produced in accordance with the method disclosed in Journal of the Chemical Society: Parkin transaction I, 1974, p. 1353 from commercially available 3-fluoro-2-methylbenzaldehyde.

3-Chloro-2-methylphenol can be produced in accordance with the method disclosed in Organic Synthesis, Collective Volume, vol. 5, pp. 412-414 (conversion of phenylmethyl ether into phenol, demethylation reaction) from commercially available 1-chloro-3-methoxy-2-methylbenzene.

3-Methoxy-2-methylphenol can be produced in accordance with the method disclosed in, Organic Synthesis, Collective Volume, vol. 4, pp. 836-838 (conversion of phenol into phenyl methyl ether, methylation reaction) from commercially available 2-methyl-1,3-benzene diol.

2-Cyclopropyl-3-methylphenol can be produced in accordance with the method disclosed in, for example, from commercially available 2-methoxy-6-methylaniline, Organic Synthesis, Collective Volume, vol. 3, pp. 185-187 or the method disclosed in The Journal of Organic Chemistry, 1977, vol. 42, pp. 2426-2430 (conversion of anilines into bromobenzene, Sandmeyer reaction, etc.), and the method disclosed in Tetrahedron Letters, 1979, vol. 20, pp. 4159-4162 or the method disclosed in Tetrahedron, 1997, vol. 53, No. 43, pp. 14599-14614 or the method disclosed in Bulletin of the Chemical Society of Japan, 1971, vol. 44, pp. 2237-2248 (conversion reaction of aromatic bromide into aromatic aldehyde), and the method disclosed in The Journal of Organic Chemistry, 1963, vol. 2.8, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, 3428 or the method disclosed in Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclopropyl-3-methoxyphenol can be produced in accordance with the method disclosed in, for example, from commercially available 2,6-dimethoxybenzaldehyde, The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

4-indanol can be produced in accordance with the method disclosed in, for example, Organic Reactions, 1941, vol. 1, p. 155 (Clemmensen reduction) from commercially available 4-hydroxy-1-indanone.

3-methyl-4-indanol can be produced by the method disclosed in, for example, Journal of Applied Chemistry, 1959, vol. 9, pp. 629 and 637.

1-Methyl-4-indanol can be produced by the method disclosed in, for example, Journal of the Chemical Society, 1961, pp. 2773-2777.

2,2-Dimethyl-4-indanol can be produced by the method disclosed in, for example, Journal of Chemical Research Miniprint, 1985, vol. 8, pp. 2724-2747.

Spiro[cyclopropane-1,3'-(2',3'-dihydro-1'H-inden-4'-ol)] can be produced in accordance with the method disclosed in, for example, from commercially available 2,3-dihydro-4H-chromen-4-ol, Bioorganic and Medicinal Chemistry, 1999, vol. 7, No. 12, pp. 2801-2810 (synthesis of 7-hydroxy-1-indanone), and the method disclosed in Organic Synthesis, Collective Volume vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

7-hydroxy-2,3-dihydro-1H-inden-1-one O-methyloxime can be produced in accordance with the method disclosed in, for example, from commercially available 2,3-dihydro-4H-chromen-4-ol, Bioorganic and Medicinal Chemistry, 1999, vol. 7, No. 12, pp. 2801-2810 (synthesis of 7-hydroxy-1-indanone), and the method disclosed in Organic Synthesis, Collective Volume vol. 4, pp. 836-838 (conversion of phenol into phenyl methyl ether, methylation reaction), and the method disclosed in Chemical Pharmaceutical Bulletin, 1988, vol. 36, No. 8, pp. 3134-3137 (conversion of carbonyl group into oxime), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2,3-Dihydro-1-benzofuran-4-ol can be produced by the method disclosed in, for example, Journal of the Chemical Society, 1948, p. 894 (reduction of olefin) from 1-benzofuran-4-ol which is obtained by the method disclosed in Helvetica Chimica Acta, 1933, vol. 16, pp. 121-129.

3-Methyl-2,3-dihydro-1-benzofuran-4-ol can be produced in accordance with the method disclosed in, for example, Journal of the Chemical Society, 1948, p. 894 (reduction of olefin) from 3-methyl-1-benzofuran-4-ol which is obtained by the method disclosed in Journal of the Chemical Society, 1951, pp. 3229-3234.

1-Benzofuran-4-ol can be produced by the method disclosed in, for example, Helvetica Chimica Acta, 1933, vol. 16, pp. 121-129.

3-Methyl-1-benzofuran-4-ol can be produced by the method disclosed in, for example, Journal of the Chemical Society, 1951, pp. 3229-3234.

1-Benzothiophen-4-ol can be produced by the method disclosed in, for example, Journal of the American Chemical Society, 1935, vol. 57, pp. 1611-1615.

2-Methyl-1,3-benzoxazol-4-ol can be produced in accordance with the method disclosed in, for example, Journal of Medicinal Chemistry, 1987, vol. 30, No. 1, pp. 62-67.

2,3-Dihydro-1-benzofuran-7-ol can be produced in accordance with the method disclosed in, for example, from commercially available 7-methoxy-1-benzofuran, Journal of the Chemical Society, 1948, p. 894 (hydrogenation reaction of benzofuran), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

1-Benzofuran-7-ol can be produced in accordance with the method disclosed in, for example, from commercially available 7-methoxy-1-benzofuran, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

1,3-Benzodioxol-4-ol can be produced by the method disclosed in, for example, Chemical Pharmaceutical Bulletin, 1981, vol. 29, No. 10, pp. 2893-2898 from commercially available 1,2,3-benzene triol.

2,3-Dihydro-1,4-benzodioxyn-5-ol can be produced by the method disclosed in, for example, Journal of the Chemical Society: Parkin transaction I, 1988, pp. 511 to 520 from commercially available 1,2,3-benzene triol.

2-Methyl-1,3-benzoxazol-7-ol can be produced in accordance with the method disclosed in, for example, Liebigs Annalen der Chemie, 1957, vol. 608, p. 128 (reduction of a nitro group into an amino group), and the method disclosed in Journal of Medicinal Chemistry, 1987, vol. 30, No. 1, pp. 62-67 from commercially available 3-nitro-1,2-benzene diol.

2-Bromo-4-tert-butylphenol can be produced by the method disclosed in, for example, Tetrahedron, 1999, vol. 55, No. 28, pp. 8377-8384.

2-Ethyl-4-iodophenol can be produced by the method disclosed in, The Journal of Organic Chemistry, 1951, vol. 16, pp. 1117-1120 from commercially available 2-ethylphenol.

4-Bromo-2-isopropylphenol can be produced by the method disclosed in, for example, Journal of Medicinal Chemistry, 1971, vol. 14, No. 9, pp. 789-792.

3-Cyclopropyl-4-methylphenol can be produced in accordance with the method disclosed in, for example, from commercially available 2-bromo-1-methoxy-4-methylbenzene, Tetrahedron Letters, 2000, vol. 41, pp. 4251-4255 (construction of cyclopropyl group, Suzuki-Miyaura coupling reaction) and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

5-(Dimethylamino)-2-methylphenol can be produced by the method disclosed in, for example, Journal of the Chemical Society, 1947, pp. 182-191.

5-Methoxy-2-methylphenol can be produced by the method disclosed in, for example, Chemical Abstracts, 1938, p. 2519.

2-Ethyl-5-methoxyphenol can be produced by the method disclosed in, for example, Chemical and Pharmaceutical Bulletin, 1979, vol. 27, No. 6, pp. 1490-1494.

2,5-Diisopropylphenol can be produced by the method disclosed in, for example, The Journal of Organic Chemistry, 1980, vol. 45, No. 22, pp. 4326-4329.

2-Cyclopropyl-5-fluorophenol can be produced in accordance with the method disclosed in, for example, from commercially available 2-bromo-5-fluorophenol, Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

5-Chloro-2-cyclopropylphenol can be produced in accordance with the method disclosed in, for example, from commercially available 4-chloro-2-methoxyphenol, The Journal of Organic Chemistry, 1997, vol. 62, No. 2, pp. 261-274 (trifluoromethanesulfonylation of phenol), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclopropyl-5-methylphenol can be produced in accordance with the method disclosed in, for example, from commercially available 2-methoxy-4-methylphenol, The Journal of Organic Chemistry, 1997, vol. 62, No. 2, pp. 261-274 (trifluoromethanesulfonylation of phenol), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp.

1572-1574 or Japanese Provisional Patent Publication No. 11-322755 (conversion of phenylmethyl ether into phenol, demethylation reaction).

2-Cyclopropyl-5-ethylphenol can be produced in accordance with the method disclosed in, for example, from commercially available 4-ethyl-2-methoxyphenol, The Journal of Organic Chemistry, 1997, vol. 62, No. 2, pp. 261-274 (trifluoromethanesulfonylation of phenol), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclopropyl-5-isopropylphenol can be produced in accordance with the method disclosed in, for example, from commercially available 3-isopropylphenol, Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

4-Cyclopropyl-3-hydroxybenzonitrile can be produced in accordance with the method disclosed in, for example, from commercially available 4-hydroxy-3-methoxybenzonitrile, The Journal of Organic Chemistry, 1997, vol. 62, No. 2, pp. 261-274 (trifluoromethanesulfonylation of phenol), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

5-Fluoro-2-[(1E)-1-propenyl]phenol can be produced in accordance with the method disclosed in, for example, Journal of the Chemical Society: Parkin transaction I, 1994, pp. 1823-1831 (synthesis of 4-fluoro-2-hydroxybenzaldehyde), and the method disclosed in Organic Synthesis, Collective Volume, vol. 4, pp. 836-838 (conversion of phenol into phenyl methyl ether, methylation reaction), and the method disclosed in Synthetic Communications, 1985, vol. 15, No. 10, pp. 855-864 (conversion of carbonyl group into olefin, Wittg reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

5-Chloro-2-[(1E)-1-propenyl]phenol can be produced in accordance with the method disclosed in, for example, The Journal of Organic Chemistry, 1964, vol. 29, pp. 2693-2698 (synthesis of 4-chloro-2-hydroxybenzaldehyde), and the method disclosed in Organic Synthesis, Collective Volume, vol. 4, pp. 836-838 (conversion of phenol into phenyl methyl ether, methylation reaction), the method disclosed in Synthetic Communications, 1985, vol. 15, No. 10, pp. 855-864 (conversion of carbonyl group into olefin, Wittg reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

4-(Dimethylamino)-2-hydroxybenzaldehyde can be produced by the method disclosed in, for example, German Patent (DE 105103).

5-Chloro-2-methoxyphenol can be produced in accordance with the method disclosed in, for example, Organic Synthesis, Collective Volume, vol. 2, pp. 130-133 (conversion of anilines into chlorobenzene, Sandmeyer reaction, etc.) from commercially available 5-amino-2-methoxyphenol.

5-Bromo-2-methoxyphenol can be produced in accordance with the method disclosed in, for example, Organic Synthesis, Collective Volume, vol. 3, pp. 185-187 or the method disclosed in The Journal of Organic Chemistry, 1977, vol. 42, pp. 2426-2430 (conversion of anilines into bromobenzene, Sandmeyer reaction, etc.) from commercially available 5-amino-2-methoxyphenol.

3-Hydroxy-4-methoxybenzonitrile can be produced by the method disclosed in, for example, Synthesis, 1998, pp. 329-332 from commercially available methyl 3,4-dimethoxybenzoate.

2,5-Dimethoxyphenol can be produced by the method disclosed in, for example, The Journal of Organic Chemistry, 1987, vol. 57, p. 4485.

2-Bromo-6-fluorophenol can be produced in accordance with the method disclosed in, for example, Tetrahedron Letters, 1998, vol. 39, p. 2947 (bromination reaction of phenol) from commercially available 2-fluorophenol.

2-Fluoro-6-propylphenol can be produced in accordance with the method disclosed in, for example, from commercially available 2-fluorophenol, Organic Reactions, 1949, vol. 2, pp. 1-48 (allyllation of phenol, Claisen transition reaction), and the method disclosed in Journal of the American Chemical Society, 1951, vol. 73, pp. 4152-4156 (conversion of an allyl group into a propyl group, hydrogenation reaction).

2-Fluoro-6-isopropylphenol can be produced in accordance with the method disclosed in, for example, from commercially available 2-isopropyl-6-nitrophenol, Organic Synthesis, Collective Volume vol. 4, pp. 836-838 (conversion of phenol into phenyl methyl ether, methylation reaction), the method disclosed in Liebigs Annalen der Chemie, 1975, vol. 608, p. 128 (Reduction of a nitro group into an amino group), the method disclosed in Synthesis, 1989, p. 905 (conversion reaction of an amino group into a fluorine atom), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclopropyl-6-fluorophenol can be produced in accordance with the method disclosed in, for example, from commercially available 2-fluorophenol, Tetrahedron Letters, 1998, vol. 39, p. 2947 (bromination reaction of phenol), and the method disclosed in Helvetica Chemica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2-Chloro-6-iodophenol can be produced by the method disclosed in, for example, The Journal of Organic Chemistry, 1988, vol. 53, No. 22, pp. 5281-5287.

2-Chloro-6-ethylphenol can be produced by the method disclosed in, for example, Journal of Chemical and Engineering Data, 1969, vol. 14, p. 392.

2-Chloro-6-cyclopropylphenol can be produced in accordance with the method disclosed in, for example, from commercially available 2-chlorophenol, Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2-Chloro-6-(2-methyl-2-propenyl)phenol can be produced in accordance with the method disclosed in, for example, Organic Reactions, 1949, vol. 2, pp. 1-48 (allylation of phenol, Claisen transition reaction) from commercially available 2-chlorophenol.

2-Bromo-6-methylphenol can be produced by the method disclosed in, for example, Tetrahedron Letters, 1998, vol. 39, p. 2947.

2-Bromo-6-ethylphenol can be produced in accordance with the method disclosed in, for example, Tetrahedron Letters, 1998, vol. 39, p. 2947 (bromination reaction of phenol) from commercially available 2-ethylphenol.

2-Bromo-6-cyclopropylphenol can be produced in accordance with the method disclosed in, for example, from commercially available 2,6-dibromophenol, Organic Synthesis, Collective Volume vol. 4, pp. 836-838 (conversion of phenol into phenyl methyl ether, methylation reaction), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3-Bromo-2-hydroxybenzonitrile can be produced in accordance with the method disclosed in, for example, Tetrahedron Letters, 1998, vol. 39, p. 2947 (bromination reaction of phenol) from commercially available 2-hydroxybenzonitrile.

2-Bromo-6-methoxyphenol can be produced by the method disclosed in, for example, Synthesis, 1999, vol. 7, pp. 1127-1134.

2-Iodo-6-methylphenol can be produced by the method disclosed in, for example, Australian Journal of Chemistry, 1997, vol. 50, No. 7, pp. 767-770.

2-Ethyl-6-iodophenol can be produced in accordance with the method disclosed in, Australian Journal of Chemistry, 1997, vol. 50, No. 7, pp. 767-770 (iodation reaction of phenol) from commercially available 2-ethylphenol.

2-Iodo-6-isopropylphenol can be produced in accordance with the method disclosed in, Australian Journal of Chemistry, 1997, vol. 50, No. 7, pp. 767-770 (iodation reaction of phenol) from commercially available 2-isopropylphenol.

2-Isopropyl-6-methylphenol can be produced by the method disclosed in, for example, Bulletin de la Societe Chemique de France, 1962, pp. 1700-1705.

2-s-Butyl-6-methylphenol can be produced by the method disclosed in, for example, Angewandte Chemie, 1957, vol. 69, p. 699, p. 703. Also, for example, it can be produced in accordance with the method disclosed in Organic Reactions, 1949, vol. 2, pp. 1-48 (allylation of phenol, Claisen transition reaction), and Journal of the American Chemical Society, 1951, vol. 73, pp. 4152-4156 (conversion of allyl group into propyl group, hydrogenation reaction) from commercially available 2-methylphenol.

2-Cyclopropyl-6-methylphenol can be produced from commercially available 2-hydroxy-3-methylbenzaldehyde in accordance with the method disclosed in, for example, Organic Synthesis, Collective Volume, vol. 4, pp. 836-838 (conversion of phenol into phenyl methyl ether, methylation reaction), and The Journal of Organic Chemistry, 1963, vol. 28, 1128 or Synthetic Communications, 1985, vol. 15, No. 10, pp. 855-864 (conversion of carbonyl group into olefin, Wittg reaction), and Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Methoxy-6-methylphenol can be produced by the method disclosed in, for example, Synthetic Communications, 1996, vol. 26, No. 1, pp. 49-62 from commercially available 1,2-dimethoxy-3-methylbenzene.

2,6-Diethylphenol can be produced by the method disclosed in, for example, Journal of Medicinal Chemistry, 1960, vol. 2, pp. 201-212.

2-Cyclopropyl-6-ethylphenol can be produced from commercially available 2-ethylphenol in accordance with the method disclosed in, for example, Tetrahedron Letters, 1998, vol. 39, p. 2947 (bromination reaction of phenol), and Helvetica Chimica Acta, 1992, vol. 75, p. 457 (conversion of phenol into phenylmethoxymethyl ether, methoxymethylation reaction), and Tetrahedron Letters, 2000, vol. 41, pp. 4251-4255 (construction of cyclopropyl group, Suzuki-Miyaura coupling reaction), and Tetrahedron, 1998, vol. 54, pp. 15861-15869 (conversion of phenylmethoxymethyl ether into phenol, demethoxymethylation reaction).

2,6-Dipropylphenol can be produced by the method disclosed in, for example, Liebigs Annalen der Chemie, 1919, vol. 418, pp. 90-91 (synthesis of 2,6-diallylphenol), and Bulletin de la Societe Chemique de France, 1937, vol. 5, No. 4, pp. 1080-1083 (conversion of allyl group into propyl group, hydrogenation reaction).

3-Cyclopropyl-6-isopropylphenol can be produced in accordance with the method disclosed in, for example, Journal of the Chemical Society: Parkin transaction I, 1980, pp. 1862-1865 (synthesis of 2-hydroxy-3-isopropylbenzaldehyde), and Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3-tert-Butyl-6-cyclopropylphenol can be produced in accordance with the method disclosed in, for example, commercially available 3-tert-butyl-2-hydroxybenzaldehyde より, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2,6-Dicyclopropylphenol can be produced in accordance with the method disclosed in, for example, Tetrahedron Letters, 1997, vol. 38, No. 17, pp. 3111-3114 (synthesis of 2-hydroxyisophthalaldehyde), and the method disclosed in Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Cyclopropyl-6-methoxyphenol can be produced from commercially available 2-hydroxy-3-methoxybenzaldehyde in accordance with the method disclosed in, for example, Helvetica Chimica Acta, 1992, vol. 75, p. 457 (conversion of phenol into phenylmethoxymethyl ether, methoxymethylation reaction), and The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Tetrahedron, 1998, vol. 54, pp. 15861-15869 (conversion of phenylmethoxymethyl ether into phenol, demethoxymethylation reaction).

2-Cyclopropyl-6-ethoxyphenol can be produced from commercially available 3-ethoxy-2-hydroxybenzaldehyde in accordance with the method disclosed in, for example, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2,6-Di[(1E)-1-propenyl]phenol can be produced by the method disclosed in, for example, Liebigs Annalen der Chemie, 1919, vol. 418, pp. 90-91 (synthesis of 2,6-diallylphenol), and the method disclosed in Journal of the American Chemical Society, 1956, vol. 78, pp. 1709-1713(isomerization reaction).

2,6-Diallylphenol can be produced by the method disclosed in, for example, Liebigs Annalen der Chemie, 1919, vol. 418, pp. 90-91.

3,5-Diisopropylphenol can be produced by the method disclosed in, for example, U.S. Patent (U.S. Pat. No. 2,790, 010).

2-Bromo-3,5-dimethylphenol can be produced in accordance with the method disclosed in, Bulletin of the Chemical Society of Japan, 1993, vol. 66, p. 1576 (brominetion reaction of phenol) from commercially available 3,5-dimethylphenol.

3,5-Dimethyl-2-propylphenol can be produced by the method disclosed in, for example, Bulletin of the Chemical Society of Japan, 1968, vol. 41, No. 3, pp. 745-746.

2-Cyclopropyl-3,5-dimethylphenol can be produced from commercially available 3,5-dimethylphenol in accordance with the method disclosed in, for example, Tetrahedron, 1998, vol. 39, p. 2947 (bromination reaction of phenol), and Organic Synthesis, Collective Volume vol. 4, pp. 836-838 (conversion of phenol into phenyl methyl ether, methylation reaction), and the method disclosed in Tetrahedron Letters, 1979, vol. 20, pp. 4159-4162 or the method disclosed in Tetrahedron, 1997, vol. 53, No. 43, pp. 14599-14614 or the method disclosed in Bulletin of the Chemical Society of Japan, 1971, vol. 44, pp. 2237-2248 (conversion reaction of aromatic bromide into aromatic aldehyde), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3,5-Dimethyl-2-(methylsulfanyl)phenol can be produced by the method disclosed in, for example, Tetrahedron Letters, 1999, vol. 40, No. 35, pp. 6357-6358.

2-Bromo-3,6-dimethylphenol can be produced in accordance with the method disclosed in, for example, Tetrahedron Letters, 1998, vol. 39, p. 2947 (bromination reaction of phenol) from commercially available 3,6-dimethylphenol.

6-Bromo-3-fluoro-2-methylphenol can be produced, from 3-fluoro-2-methylphenol which can be produced from commercially available 3-fluoro-2-methylbenzaldehyde in accordance with the method disclosed in Journal of the Chemical Society: Parkin transaction I, 1974, p. 1353, in accordance with the method disclosed in, for example, Tetrahedron Letters, 1998, vol. 39, p. 2947 (bromination reaction of phenol).

6-Bromo-3-chloro-2-methylphenol can be produced in accordance with the method disclosed in Tetrahedron Letters, 1998, vol. 39, p. 2947 (bromination reaction of phenol) from 3-chloro-2-methylphenol which can be produced from commercially available 1-chloro-3-methoxy-2-methylbenzene in accordance with the method disclosed in Organic Synthesis, Collective Volume, vol. 5, pp. 412-414 (conversion of phenylmethyl ether into phenol, demethylation reaction).

3-Chloro-6-cyclopropyl-2-methylphenol can be produced from 3-chloro-2-methylphenol which can be produced from commercially available 1-chloro-3-methoxy-2-methylbenzene in accordance with the method disclosed in Organic Synthesis, Collective Volume, vol. 5, pp. 412-414 (conversion of phenylmethyl ether into phenol, demethylation reaction), in accordance with the method disclosed in Tetrahedron Letters, 1998, vol. 39, p. 2947. (bromination reaction of phenol) and Helvetica Chimica Acta, 1992, vol. 75, p. 457 (conversion of phenol into phenylmethoxymethyl ether, methoxymethylation reaction), and Tetrahedron Letters, 2000, vol. 41, pp. 4251-4255 (construction of cyclopropyl group, Suzuki-Miyaura coupling reaction), and Tetrahedron, 1998, vol. 54, pp. 15861-15869 (conversion of phenylmethoxymethyl ether into phenol, demethoxymethylation reaction).

6-Bromo-2,3-dimethylphenol can be produced in accordance with the method disclosed in, for example, Tetrahedron Letters, 1998, vol. 39, p. 2947 (bromination reaction of phenol) from commercially available 2,3-dimethylphenol.

6-Cyclopropyl-2,3-dimethylphenol can be produced from commercially available 2,3-dimethylphenol in accordance with the method disclosed in, for example, Tetrahedron Letters, 1998, vol. 39, p. 2947 (bromination reaction of phenol), and Helvetica Chimica Acta, 1992, vol. 75, p. 457 (conversion of phenol into phenylmethoxymethyl ether, methoxymethylation reaction), and Tetrahedron Letters, 2000, vol. 41, pp. 4251-4255 (construction of cyclopropyl group, Suzuki-Miyaura coupling reaction), and Tetrahedron, 1998, vol. 54, pp. 15861-15869 (conversion of phenylmethoxymethyl ether into phenol, demethoxymethylation reaction).

2-Hydroxy-3,4-dimethylbenzaldehyde O-methyloxime can be produced from commercially available 2,3-dimethylphenol in accordance with the method disclosed in, for example, Tetrahedron Letters, 1998, vol. 39, p. 2947 (bromination reaction of phenol), and Helvetica Chimica Acta, 1992, vol. 75, p. 457 (conversion of phenol into phenylmethoxymethyl ether, methoxymethylation reaction), and the method disclosed in Tetrahedron Letters, 1979, vol. 20, pp. 4159-4162 or the method disclosed in Tetrahedron, 1997, vol. 53, No. 43, pp. 14599-14614 or the method disclosed in Bulletin of the Chemical Society of Japan, 1971, vol. 44, pp. 2237-2248 (conversion reaction of aromatic bromide into aromatic aldehyde), and the method disclosed in Journal of the Chemical Society: Perkin transactions I, 1979, pp. 643-645 (oximation reaction), and Tetrahedron, 1998, vol. 54, pp. 15861-15869 (conversion of phenylmethoxymethyl ether into phenol, demethoxymethylation reaction).

6-Methoxy-2,3-dimethylphenol can be produced from commercially available 3,4-dimethylphenol in accordance with the method disclosed in, for example, Tetrahedron Letters, 1998, vol. 39, p. 2947 (bromination reaction of phenol) and the method disclosed in Tetrahedron Letters, 1979, vol. 20, pp. 4159-4162 or the method disclosed in Tetrahedron, 1997, vol. 53, No. 43, pp. 14599-14614 or the method disclosed in Bulletin of the Chemical Society of Japan, 1971, vol. 44, pp. 2237-2248 (conversion reaction of aromatic bromide into aromatic aldehyde), and the method disclosed in Journal of the Chemical Society: Parkin transaction I, 1974, p. 1353.

6-Bromo-3-methoxy-2-methylphenol can be produced in accordance with the method disclosed in, Tetrahedron Letters, 1998, vol. 39, p. 2947 (bromination reaction of phenol) from 3-methoxy-2-methylphenol which can be produced from commercially available 2-methyl-1,3-benzene diol in accordance with the method disclosed in Organic Synthesis, Collective Volume, vol. 4, pp. 836-838 (conversion of phenol into phenyl methyl ether, methylation reaction).

6-Cyclopropyl-3-methoxy-2-methylphenol can be produced from 3-methoxy-2-methylphenol which can be produced from commercially available 2-methyl-1,3-benzene diol in accordance with the method disclosed in Organic Synthesis, Collective Volume, vol. 4, pp. 836-838 (conversion of phenol into phenyl methyl ether, methylation reaction), in accordance with the method disclosed in Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2-Cyclopropyl-3,6-dimethylphenol can be produced from commercially available 2,5-dimethylphenol in accordance with the method disclosed in, for example, Tetrahedron Letters, 1998, vol. 39, p. 2947 (bromination reaction of phenol), and the method disclosed in Organic Synthesis, Collective Volume, vol. 4, pp. 836-838 (conversion of phenol into phenyl methyl ether, methylation reaction), and the method disclosed in Tetrahedron Letters, 1979, vol. 20, pp. 4159-4162 or the method disclosed in Tetrahedron, 1997, vol. 53, No. 43, pp. 14599-14614 or the method disclosed in Bulletin of the Chemical Society of Japan, 1971, vol. 44, pp. 2237-2248 (conversion reaction of aromatic bromide into aromatic aldehyde), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittg reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-Allyl-6-ethyl-3-methoxyphenol can be produced from 2-ethyl-5-methoxyphenol which can be produced in accordance with the method disclosed in Chemical and Pharmaceutical Bulletin, 1979, vol. 27, No. 6, pp. 1490-1494, in accordance with the method disclosed in, for example, Organic Reactions, 1949, vol. 2, pp. 1-48 (allylation reaction of phenol, Claisen transition).

3,6-Dimethyl-2-[(methylsulfanyl)methyl]phenol can be produced by the method disclosed in, for example, Journal of the American Chemical Society, 1966, vol. 88, No. 24, pp. 5855-5864.

5-Bromo-4-indanol can be produced in accordance with the method disclosed in, for example, Journal of the American Chemical Society, 1946, vol. 68, p. 2487 (reduction of carbonyl group, Wolff-Kishner Reduction), and Tetrahedron Letters, 1998, vol. 39, p. 2947 (bromination reaction of phenol) from commercially available 4-hydroxy-1-indanone.

5-Methyl-4-indanol can be produced from commercially available 4-hydroxy-1-indanone in accordance with the method disclosed in, for example, Journal of the American Chemical Society, 1946, vol. 68, p. 2487 (reduction of carbonyl group, Wolff-Kishner Reduction), and the method disclosed in Tetrahedron Letters, 1998, vol. 39, p. 2947 (bromination reaction of phenol), and the method disclosed in Helvetica Chimica Acta, 1990, vol. 75, p. 457 (conversion of phenol into phenylmethoxymethyl ether, methoxymethylation reaction), and the method disclosed in Helvetica Chimica Acta, 1990, vol. 73, pp. 417-425 (conversion reaction of bromo group into methyl group), and the method disclosed in Tetrahedron, 1998, vol. 54, pp. 15861-15869 (conversion of phenylmethoxymethyl ether into phenol, demethoxymethylation reaction).

5-Ethyl-4-indanol can be produced from commercially available 4-hydroxy-1-indanone in accordance with the method disclosed in, for example, Journal of the American Chemical Society, 1946, vol. 68, p. 2487 (reduction of carbonyl group, Wolff-Kishner Reduction), and the method disclosed in Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Helvetica Chimica Acta, 1990, vol. 73, pp. 417-425 (conversion reaction of bromo group into ethyl group), and the method disclosed in Tetrahedron, 1998, vol. 54, pp. 15861-15869 (conversion of phenylmethoxymethyl ether into phenol, demethoxymethylation reaction).

5-Cyclopropyl-4-indanol can be produced from commercially available 4-hydroxy-1-indanone in accordance with the method disclosed in, for example, Journal of the American Chemical Society, 1946, vol. 68, p. 2487 (reduction of carbonyl group, Wolff-Kishner Reduction), and the method disclosed in Tetrahedron Letters, 1998, vol. 39, p. 2947 (bromination reaction of phenol) and the method disclosed in Organic Synthesis, Collective Volume, vol. 4, pp. 836-838 (conversion of phenol into phenyl methyl ether, methylation reaction), and Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

6-Methyl-2,3-dihydro-1-benzofuran-7-ol can be produced in accordance with the method disclosed in, for example, Journal of the Chemical Society, 1948, p. 894 (reduction of olefin) from 6-methyl-1-benzofuran-7-ol. 6-Methyl-1-benzofuran-7-ol can be produced, for example, from 2-methoxy-3-methylphenol which can be produced by the method disclosed in Tetrahedron Letters, 1998, vol. 39, p. 2947, in accordance with the method disclosed in Journal of the Chemical Society: Perkin transactions I, 1988, p. 3029 (construction of benzofuran ring), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

6-Bromo-1-benzofuran-7-ol can be produced from commercially available 7-methoxy-1-benzofuran in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction), and Tetrahedron Letters, 1998, vol. 39, p. 2947 (bromination reaction of phenol).

6-Methyl-1-benzofuran-7-ol can be produced from 2-methoxy-3-methylphenol which can be produced by the method disclosed in Tetrahedron Letters, 1998, vol. 39, p. 2947, in accordance with the method disclosed in, for example, Journal of the Chemical Society: Perkin transactions I, 1988, p. 3029 (construction of benzofuran ring), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

6-Cyclopropyl-1-benzofuran-7-ol can be produced from commercially available 7-methoxy-1-benzofuran in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction), and the method disclosed in Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2,4-Dicyclopropyl-6-fluorophenol can be produced from commercially available 2-fluorophenol in accordance with the method disclosed in, for example, Tetrahedron Letters, 1998, vol. 39, p. 2947 (bromination reaction of phenol), and Helvetica Chimica Acta, 1992, vol. 75, p. 457 (conversion of phenol into phenylmethoxymethyl ether, methoxymethylation reaction), and Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2,4-Dibromo-3,6-dimethylphenol can be produced in accordance with the method disclosed in, for example, Tetrahedron Letters, 1998, vol. 39, p. 2947 (bromination reaction of phenol) from commercially available 3,6-dimethylphenol.

2-Bromo-4,6-dimethylphenol can be produced in accordance with the method disclosed in, for example, Tetrahedron Letters, 1998, vol. 39, p. 2947 (bromination reaction of phenol) from commercially available 2,4-dimethylphenol.

2-Ethyl-4,6-diiodophenol can be produced in accordance with the method disclosed in, Australian Journal of Chemistry, 1997, vol. 50, No. 7, pp. 767-770 (iodation reaction of phenol) from commercially available 2-ethylphenol.

2-Cyclopropyl-4,6-dimethylphenol can be produced from commercially available 2,4-dimethylphenol in accordance with the method disclosed in, for example, Tetrahedron Letters, 1998, vol. 39, p. 2947 (bromination reaction of phenol), and the method disclosed in Helvetica Chimica Acta, 1992, vol. 75, p. 457 (conversion of phenol into phenylmethoxymethyl ether, methoxymethylation reaction), and the method disclosed in Tetrahedron Letters, 2000, vol. 41, pp. 4251-4255 (construction of cyclopropyl group, Suzuki-Miyaura coupling reaction), and the method disclosed in Tetrahedron, 1998, vol. 54, pp. 15861-15869 (conversion of phenylmethoxymethyl ether into phenol, demethoxymethylation reaction).

2-Bromo-3,5,6-trimethylphenol can be produced in accordance with the method disclosed in, for example, Tetrahedron Letters, 1998, vol. 39, p. 2947 (bromination reaction of phenol) from commercially available 2,3,5-trimethylphenol.

5,6-Dimethyl-4-indanol can be produced from commercially available 7-methyl-2H-chromen-2-one in accordance with the method disclosed in, for example, Nihon Kagakukaishi (Journal of Japan Chemical Association), 1974, pp. 136-146, and the method disclosed in Organic Reactions, 1941, vol. 1, p. 155 (Clemmensen reduction).

1,2,3,5,6,7-Hexahydro-s-indacen-4-ol can be produced from commercially available indane by the method disclosed in, for example, Journal of the American Chemical Society, 1977, vol. 99, pp. 8007-8014, and the method disclosed in Organic Reactions, 1941, vol. 1, p. 155 (Clemmensen reduction), and the method disclosed in The Journal of Organic Chemistry, 1977, vol. 42, pp. 3260-3264.

3-(1,3-Dioxolan-2-yl)phenol can be produced in accordance with the method disclosed in, for example, Tetrahedron Letters, 1989, vol. 30, No. 13, pp. 1609-1612 from 3-hydroxybenzaldehyde.

3'-(Trifluoromethyl)[1,1'-biphenyl]-3-ol can be produced in accordance with the method disclosed in, for example, Chemical Reviews, 1995, vol. 95, pp. 2457-2483 (phenylation reaction, Suzuki-Miyaura coupling reaction) from commercially available 3-iodophenol and 3-(trifluoromethyl)phenylboronic acid.

3-Hydroxy-4-methylbenzonitrile can be produced by the method disclosed in, for example, Monatshefte fur Chemie, 1957, vol. 88, pp. 228, 230.

Ethyl 3-hydroxy-4-methylbenzoate can be produced by the method disclosed in, for example, The Journal of Organic Chemistry, 1961, vol. 26, pp. 1732-1734.

3-Hydroxy-4-methylbenzamide can be produced in accordance with the method disclosed in, for example, Phosphorus and Sulfur, 1980, vol. 9, pp. 155-164 from commercially available 3-hydroxy-4-methylbenzoic acid.

3,6-Dimethyl-2-propylphenol can be produced by the method disclosed in, for example, Journal of Polymer Science, 1948, vol. 3, p. 448, p. 452.

2-Hydroxy-3,4,6-trimethylbenzaldehyde can be produced by the method disclosed in, for example, Liebigs Annalen der Chemie, 1906, vol. 347, p. 379.

2-Hydroxy-3,4,6-trimethylbenzaldehyde O-methyloxime can be produced in accordance with the method disclosed in, for example, Liebigs Annalen der Chemie, 1906, vol. 347, p. 379 (synthesis of 2-hydroxy-3,4,6-trimethylbenzaldehyde), and in accordance with the method disclosed in Chemical Pharmaceutical Bulletin, 1988, vol. 36, No. 8, pp. 3134-3137.

2-[1-(Methoxymethyl)cyclopropyl]phenol can be produced from 2-methoxy-1-(2-methoxyphenyl)ethanone which can be obtained by the method disclosed in The Journal of Organic Chemistry, 1942, vol. 7, pp. 444-456, in accordance with the method disclosed in, for example, The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(1-Methoxycyclopropyl)phenol can be produced from 1-methoxy-2-(1-methoxyvinyl)benzene which can be produced by the method disclosed in The Journal of Organic Chemistry, 1998, vol. 63, pp. 4632-4635, in accordance with the method disclosed in, for example, Organic Reactions, 1973, vol. 20, pp. 1-131 or Journal of the American Chemical Society, 1975, vol. 97, p. 3428 or Tetrahedron Letters, 1998, vol. 39, pp. 8621-8624 (construction of cyclopropyl group, Simmons-Smith reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(2-Hydroxyphenyl)cyclopropanecarbonitrile can be produced from 3-(2-methoxyphenyl)acrylonitrile which can be produced by the method disclosed in Journal of Medicinal Chemistry, 1988, vol. 31, No. 1, pp. 37-54, in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction), and the method disclosed in Helvetica Chimica Acta, 1992, vol. 75, p. 457 (conversion of phenol into phenylmethoxymethyl ether, methoxymethylation reaction), and the method disclosed in The Journal of Organic Chemistry, 1973, vol. 38, pp. 1793-1797 or The Journal of Organic Chemistry, 1970, vol. 35, pp. 374-379 (cyclopropanation reaction), and the method disclosed in Tetrahedron, 1998, vol. 54, pp. 15861-15869 (conversion of phenylmethoxymethyl ether into phenol, demethoxymethylation reaction).

2-(2-Ethoxycyclopropyl)phenol can be produced in accordance with the method disclosed in, for example, The Journal of Organic Chemistry, 1981, vol. 46, pp. 5143-5147 (conversion of benzyl alcohol into benzyl chloride), and the method disclosed in Journal of the American Chemical Society, 1973, vol. 95, No. 2, pp. 581-582 (construction of cyclopropyl group), and the method disclosed in Tetrahedron, 1998, vol. 54, pp. 15861-15869 (conversion of phenylmethoxymethyl ether into phenol, demethoxymethylation reaction) from [2-(methoxymethoxy)phenyl]methanol which can be produced by the method disclosed in Heterocycles, 1998, vol. 48, No. 7, pp. 1373-1394.

2-(2,2-Difluorocyclopropyl)phenol can be produced in accordance with the method disclosed in, for example, The Journal of Organic Chemistry, 1973, vol. 38, pp. 1793-1797 or The Journal of Organic Chemistry, 1970, vol. 35, pp. 374-379 (cyclopropanization reaction), and the method disclosed in Organic Synthesis, Collective Volume, vol. 5, pp. 412-414 (conversion of phenylmethyl ether into phenol, demethylation reaction) from 1-(2,2-difluorovinyl)-2-methoxybenzene which can be produced by the method disclosed in Bulletin de la Societe Chemique de France, 1995, pp. 850-856.

2-(2,2-Dichlorocyclopropyl)phenol can be produced in accordance with the method disclosed in, for example, The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Synthetic Communications, 1999, vol. 29, No. 23, pp. 4101-4112 (conversion of olefin into dichlorocyclopropane), and the method disclosed in Tetrahedron, 1998, vol. 54, pp. 15861-15869 (conversion of phenylmethoxymethyl ether into phenol, demethoxymethylation reaction) from 2-(methoxymethoxy)benzaldehyde which can be produced by the method disclosed in Heterocycles, 1998, vol. 48, No. 7, pp. 1373-1394.

2-(2,2-Dibromocyclopropyl)phenol can be produced in accordance with the method disclosed in, for example, from commercially available 1-methoxy-2-vinylbenzene, Synthetic Communications, 1999, vol. 29, No. 23, pp. 4101-4112 (using bromoform in place of chloroform. Conversion of olefin into dibromocyclopropane), and the method disclosed in Organic Synthesis, Collective Volume, vol. 5, pp. 412-414 (conversion of phenylmethyl ether into phenol, demethylation reaction).

2-Isopropenylphenol can be produced in accordance with the method disclosed in, for example, from commercially available 1-(2-methoxyphenyl)ethanone, The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

3-(2-Hydroxyphenyl)acrylonitrile can be produced in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction) from 3-(2-methoxyphenyl)acrylonitrile which can be produced by the method disclosed in Journal of Medicinal Chemistry, 1988, vol. 31, No. 1, pp. 37-54.

2-Ethynylphenol can be produced by the method disclosed in, for example, Canadian Journal of Chemistry, 1997, vol. 75, No. 9, pp. 1256-1263 from commercially available 1-benzofuran.

Bicyclo[4.2.0]octa-1,3,5-trien-2-ol can be produced in accordance with the method disclosed in, for example, Organic Reactions, 1941, vol. 1, p. 155 (Clemmensen reduction), and the method disclosed in Bioscience, Biotechnology, and Biochemistry, 1993, vol. 57, No. 9, pp. 1572-1574 or Japanese Provisional Patent Publication No. 11-322755 or Organic Synthesis, Collective Volume, vol. 5, pp. 412-414 (conversion of phenylmethyl ether into phenol, demethylation reaction) from 5-methoxybicyclo[4.2.0]octa-1,3,5-trien-7-one which can be produced by the method disclosed in The Journal of Organic Chemistry, 1982, vol. 47, pp. 2393-2396.

2-Bromo-6-chlorophenol can be produced in accordance with the method disclosed in, for example, Tetrahedron Letters, 1998, vol. 39, p. 2947 (bromination reaction of phenol) from commercially available 2-chlorophenol.

3-Bromo-2-hydroxybenzonitrile can be produced in accordance with the method disclosed in, for example, Tetrahedron Letters, 1998, vol. 39, p. 2947 (bromination reaction of phenol) from commercially available 2-hydroxybenzonitrile.

2-(2,2-Dichlorocyclopropyl)-6-methylphenol can be produced in accordance with the method disclosed in, for example, from commercially available 2-hydroxy-3-methylbenzaldehyde, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Synthetic Communications, 1999, vol. 29, No. 23, pp. 4101-4112 (conversion of olefin into dichlorocyclopropane), and the method disclosed in Organic Synthesis, Collective Volume, vol. 5, pp. 412-414 (conversion of phenylmethyl ether into phenol, demethylation reaction).

2-Methyl-6-vinylphenol can be produced in accordance with the method disclosed in, for example, for example, from commercially available 2-hydroxy-3-methylbenzaldehyde, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

6-Cyclopropyl-3-fluoro-2-methylphenol can be produced in accordance with the method disclosed in, for example, from commercially available 3-fluoro-2-methylbenzaldehyde, The Journal of Organic Chemistry, 1999, vol. 64, pp. 7921-7928 or Journal of the Chemical Society: Parkin transaction I) 1974, p. 1353 (Baeyer-Villiger oxidation, convertion of an aromatic aldehyde into phenol), and the method disclosed in Tetrahedron Letters, 1998, vol. 39, p. 2947 (bromination reaction of phenol), and the method disclosed in Organic Synthesis, Collective Volume, vol. 4, pp. 836-838 (conversion of phenol into phenyl methyl ether, methylation reaction) and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

5-Methyl-1-benzofuran-4-ol can be produced from methyl 4-hydroxy-1-benzofuran-5-carboxylate which can be produced by the method disclosed in Tetrahedron, 1995, vol. 51, pp. 4009-4022, in accordance with the method disclosed in, for example, Organic Synthesis, Collective Volume, vol. 4, pp. 836-838 (conversion of phenol into phenyl methyl ether, methylation reaction), and the method disclosed in The Journal of Organic Chemistry, 2001, vol. 66, pp. 4965-4972 (reduction of ester to alcohol), and the method disclosed in Journal of Medicinal Chemistry, 1999, vol. 42, No. 6, pp. 1007-1017 (conversion of benzyl alcohol into benzylmethanesulfonyl ester), and the method disclosed in The Journal of Organic Chemistry, 1969, vol. 34, p. 3923 or Synthetic Communications, 2001, vol. 31, No. 9, pp. 1373-1382 (reduction of halogen compound, tosylate, and mesylate), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

2-(2-Chloro-2-fluorocyclopropyl)phenol can be produced from 2-(methoxymethoxy)benzaldehyde which can be produced by the method disclosed in Heterocycles, 1998, vol. 48, No. 7, pp. 1373-1394, in accordance with the method disclosed in, for example, Journal of Fluorine Chemistry, 1983, vol. 23, pp. 339-357 (conversion of carbonyl group into chlorofluoroolefin), and the method disclosed in The Journal of Organic Chemistry, 1973, vol. 38, pp. 1793-1797 or The Journal of Organic Chemistry, 1970, vol. 35, pp. 374-379 (cyclopropanation reaction), and the method disclosed in Organic Synthesis, Collective Volume, vol. 5, pp. 412-414 (conversion of phenylmethyl ether into phenol, demethylation reaction).

3-(Benzyloxy)phenol can be produced by the method disclosed in, for example, The Journal of Organic Chemistry, 1997, vol. 62, No. 10, pp. 3062-3075.

1-Methyl-1H-indol-4-ol can be produced in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction) from commercially available 4-methoxy-1-methyl-1H-indole.

1-Methyl-1H-indol-7-ol can be produced in accordance with the method disclosed in, for example, Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction) from 7-methoxy-1-methyl-1H-indole which can be produced by the method disclosed in Journal of Medicinal Chemistry, 1992, vol. 35, No. 1, pp. 177-184.

1-(4-Hydroxy-3-methylphenyl)ethanone O-methyloxime can be produced in accordance with the method disclosed in, for example, Journal of the American Chemical Society, 1986, vol. 108, pp. 6016-6023 from commercially available 1-(4-hydroxy-3-methylphenyl)ethanone.

2-Isopropenyl-6-methylphenol can be produced from 1-(2-hydroxy-3-methylphenyl)ethanone which can be produced by the method disclosed in Chemische Berichte, 1925, vol. 58, p. 41, in accordance with the method disclosed in, for example, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

1,1-Dimethyl-5-indanol can be produced in accordance with the method disclosed in, for example, Organic Synthesis, Collective Volume, vol. 5, pp. 412-414 (conversion of phenylmethyl ether into phenol, demethylation reaction) from 5-methoxy-1,1-dimethylindane which can be produced by the method disclosed in Bulletin of the Chemical Society of Japan, 2000, vol. 73, No. 12, pp. 2779-2782.

3-Bromo-6-cyclopropyl-2-methylphenol can be produced from commercially available 2-methyl-3-nitrophenol, in accordance with the method disclosed in Tetrahedron Letters, 1998, vol. 39, p. 2947 (bromination reaction of phenol), and the method disclosed in Organic Synthesis, Collective Volume, vol. 4, pp. 836-838 (conversion of phenol into phenyl methyl ether, methylation reaction), and the modified method of the method disclosed in Organic Synthesis, Collective Volume, vol. 1, pp. 445-447 (reduction of nitrophenol to aniline; 8.5 equivalents of zinc powder and 25 equivalents of ammonium chloride are used based on nitrophenol, reaction is carried out at room temperature), and the method disclosed in Tetrahedron Letters, 2000, vol. 41, pp. 4251-4255 (construction of cyclopropyl group, Suzuki-Miyaura coupling reaction), and the method disclosed in Organic Synthesis, Collective Volume, vol. 3, pp. 185-187 or the method disclosed in The Journal of Organic Chemistry, 1977, vol. 42, pp. 2426-2430 (conversion of anilines into bromobenzene, Sandmeyer reaction, etc.) and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

6-Cyclopropyl-2-methyl-3-nitrophenol can be produced from commercially available 2-methyl-3-nitrophenol, in accordance with the method disclosed in Tetrahedron Letters, 1998, vol. 39, p. 2947 (bromination reaction of phenol), and the method disclosed in Organic Synthesis, Collective Volume, vol. 4, pp. 836-838 (conversion of phenol into phenyl methyl ether, methylation reaction), and the modified method of the method disclosed in Organic Synthesis, Collective Volume, vol. 1, pp. 445-447 (reduction of nitrophenol to aniline; 8.5 equivalents of zinc powder and 25 equivalents of ammonium chloride are used based on nitrophenol, reaction is carried out at room temperature), and the method disclosed in Tetrahedron Letters, 2000, vol. 41, pp. 4251-4255 (construction of cyclopropyl group, Suzuki-Miyaura coupling reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction), and the method disclosed in Tetrahedron, 1987, vol. 43, No. 8, pp. 1753-1758 (conversion of aniline derivative into nitrobenzene).

5-Methyl-1,3-dihydro-2-benzofuran-4-ol can be produced in accordance with the method disclosed in, for example, Journal of the American Chemical Society, 2000, vol. 122, pp. 11553-11554.

2-Fluoro-3,5,6-trimethylphenol can be produced from 2,3,5-trimethyl-6-nitrophenol which can be produced by the method disclosed in Chemische Berichte, 1922, vol. 55, p. 2384, in accordance with the method disclosed in, for example, Organic Synthesis, Collective Volume, vol. 4, pp. 836-838 (conversion of phenol into phenyl methyl ether, methylation reaction), and the method disclosed in Liebigs Annalen der Chemie, 1957, vol. 608, p. 128, or the method disclosed in Organic Synthesis, Collective Volume, vol. 5, 829-833 (Reduction of a nitro group into an amino group), and the method disclosed in Synthesis, 1989, pp. 905-908 (conversion of aromatic amine into aromatic fluoride), and the method disclosed in Organic Synthesis, Collective Volume, vol. 5, pp. 412-414 (conversion of phenylmethyl ether into phenol, demethylation reaction).

2-Chloro-3,5,6-trimethylphenol can be produced in accordance with the method disclosed in, for example, Tetrahedron Letters, 1998, vol. 39, p. 2947 (chlorication reaction of phenol; using N-chlorosuccinimide in place of N-bromosuccinimide) from commercially available 2,3,5-trimethylphenol.

2-Iodo-3,5,6-trimethylphenol can be produced in accordance with the method disclosed in, for example, Tetrahedron Letters, 1998, vol. 39, p. 2947 (iodation reaction of phenol; using N-iodosuccinimide in place of N-bromosuccinimide) from commercially available 2,3,5-trimethylphenol.

2-Ethyl-3,5,6-trimethylphenol can be produced in accordance with the method disclosed in, for example, Journal of the American Chemical Society, 1946, vol. 68, p. 2487 (reduction of carbonyl group, Wolff-Kishner reduction) from 1-(2-hydroxy-3,4,6-trimethylphenyl)ethanone which can be produced by the method disclosed in Chemical Research in Toxicology, 1997, vol. 10, No. 3, pp. 335-343.

2-Isopropenyl-3,5,6-trimethylphenol can be produced from 1-(2-hydroxy-3,4,6-trimethylphenyl)ethanone which can be produced by the method disclosed in Chemical Research in Toxicology, 1997, vol. 10, No. 3, pp. 335-343, in accordance with the method disclosed in, for example, Organic Synthesis, Collective Volume, vol. 4, pp. 836-838 (conversion of phenol into phenyl methyl ether, methylation reaction), and the method disclosed in The Journal of Organic Chemistry, 1963, vol. 28, p. 1128 or Synthetic Communications, 1985, vol. 15, No. 10, pp. 855-864 (conversion of carbonyl group into olefin, Wittig reaction), and the method disclosed in Bioscience, Biotechnology, and Biochemistry, 1993, vol. 57, No. 9, pp. 1572-1574 or Japanese Provisional Patent Publication No. 11-322755 (conversion of phenylmethyl ether into phenol, demethylation reaction).

1-(2-Hydroxy-3,4,6-trimethylphenyl)ethanone can be produced by the method disclosed in, for example, Chemical Research in Toxicology, 1997, vol. 10, No. 3, pp. 335-343.

2,3,5-Trimethyl-6-nitrophenol can be produced by the method disclosed in, for example, Chemische Berichte, 1922, vol. 55, p. 2384.

2,4-Dichloro-3,5,6-trimethylphenol can be produced in accordance with the method disclosed in, for example, Tetrahedron Letters, 1998, vol. 39, p. 2947 (chlorination reaction of phenol; using N-chlorosuccinimide in place of N-bromosuccinimide) from commercially available 2,3,5-trimethylphenol.

Pentamethylphenol can be produced by the method disclosed in, for example, Journal of the Chemical Society, 1949, p. 624.

After completion of the above-mentioned respective reaction steps, the objective compounds of the respective steps can be collected from the reaction mixture according to the conventional manner. For example, the reaction mixture is optionally neutralized, and also, after removing insoluble materials by filtration when insoluble materials exist, an organic solvent which is immiscible with water is added to the mixture, and after washing with water, it can be obtained by distillation of the solvent. The obtained desired compound can be further purified according to the conventional manner, if necessary, for example, recrystallization, reprecipitation or chromatography, etc.

Compound (I) of the present invention can be made a salt. These salts are included in the present invention so long as they can be used as an agricultural and horticultural herbicide.

A salt of Compound (I) of the present invention may include, for example, alkali metal salts such as lithium, sodium, potassium, etc.; alkaline earth metal salts such as magnesium, calcium, etc.; aluminum salts; transition metal salts such as iron, copper, etc.; amine salts such as ammonium, trimethyl ammonium, triethyl ammonium, tetramethyl ammonium, pyridinium, etc.; inorganic mineral acid salts such as hydrochloride, sulfate, phosphate, etc.; or organic acid salts such as formate, acetate, toluenesulfonate, oxalate, etc.

When a pyridazine derivative is an acid component of the salt, the salt can be produced by, for example, mixing the pyridazine derivative and a base in the presence or absence of a solvent, and removing the solvent.

The base to be used is not specifically limited so long as it is a base generally showing a pH 8 or more, and for example, it may be alkali metal hydroxides such as sodium hydroxide, potassium hydroxide, etc.; alkali metal carbonates such as sodium carbonate, potassium carbonate, cesium carbonate, etc.; metal alkoxides such as sodium methoxide, sodium ethoxide, potassium t-butoxide, etc.; alkali metal salts of an organic acid such as sodium acetate, potassium acetate, sodium formate, potassium formate, etc.; alkali metal hydrides such as sodium hydride, potassium hydride, etc.; alkali metals such as sodium, potassium, etc.; aliphatic tertiary amines such as triethylamine, tributylamine, diisopropylethylamine, etc.; aliphatic cyclic tertiary amines such as 1,4-diazabicyclo-[2.2.2]octane (DABCO), 1,8-diazabicyclo [5.4.0]undece-7-ene (DBU), etc.; pyridines such as pyridine, collidine, 4-(N,N-dimethylamino)pyridine, etc.; metal amides such as lithium amide, sodium amide, etc.; or organometallic bases such as butyl lithium, s-butyl lithium, lithium diisopropylamide, sodium bis(trimethylsilyl)amide, lithium bis(trimethylsilyl)amide, etc.

The solvent to be used is not specifically limited so long as it does not inhibit the reaction, and dissolves starting material(s) with a certain extent, for example, water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above.

When the pyridazine derivative is a base component of a salt, the salt can be prepared by, for example, mixing the pyridazine derivative and an acid in the presence or absence of a solvent, and removing the solvent.

The acid to be used is not specifically limited so long as it is an acid generally showing a pH of 6 or less, and for example, it may be inorganic mineral acids such as hydrochloric acid, hydrobromic acid, sulfuric acid, nitric acid, phosphoric acid, etc.; or organic acids such as formic acid, acetic acid, toluenesulfonic acid, oxalic acid, benzoic acid, etc.

The solvent to be used is not specifically limited so long as it does not inhibit the reaction, and dissolves starting material(s) with a certain extent, for example, water; alcohols such as methanol, ethanol, t-butanol, etc.; ketones such as acetone, methyl isobutyl ketone, etc.; nitriles such as acetonitrile, etc.; esters such as ethyl acetate, etc.; halogenated hydrocarbons such as methylene chloride, chloroform, dichloroethane, etc.; ethers such as diethyl ether, tetrahydrofuran, dioxane, etc.; aromatic hydrocarbons such as toluene, etc.; amides such as dimethylformamide, dimethylacetamide, etc.; sulfoxides such as dimethylsulfoxide, etc.; or a mixed solvent of the above.

The composition of the present invention shows herbicidal activity against various kinds of weeds which cause problems in a paddy field, for example, broad-leaved weeds such as *Lindernia* spp., *Vandellia angustifolia* Benth., *Rotala indica*, *Elatine triandra*, *Dopatirum junceum* (Roxb.) Hamilt, *Ammannia coccinea* (Rottb.), *Monochoria vaginaris*, etc.; *Cyperaceous* weeds such as smallflower umbrella sedge, *Scirpus juncoides*, needle spikerush, *Cyperus serotinus*, *Scirpus nipponicus* Makino etc.; and Arrowhead plant weeds such as *Sagittaria pygmaea*, arrowhead, *Alisma canaliculatum*, and shows no crop injury, which causes any problem, to rice.

The composition of the present invention shows herbicidal activities both by foliar application and soil application against various kinds of weeds, which are troublesome in upland fields, including, for example, broad-leaved weeds such as Common purslane, Common chickweed, Common lambsquarters, *Amaranthus retroflexus* L.i, *Sinapis arvensis*, shepherdspurse, velvetleaf, *Sida spinosa*, field pansy, Cleavers, *Lamium purpureum, henbit, Datura stramonium* L., *Solanum nigrum* L., Persian speedwell, *Matricaria indora*, etc.; *Commelinaceae* weeds such as asiatic dayflower; and *Cyperaceous* weeds such as *Cyperus iria, Cyperus rotundus*, etc., and shows no crop injury which causes a problem, against corn, wheat, soybean, etc.

The composition of the present invention can be used not only in an upland and a paddy field, but also in an orchard, a mulberry field and a non-crop land.

Synergistic effects of the present invention can be admitted in a wide range of a mixing ratio, and when the second herbicidally active compound is Compound A, B or C, the second herbicidally active compound is mixed with a ratio of, in general, 0.1 to 50 parts by weight based on 1 part by weight of Compound (I) to prepare a useful herbicidal composition, and the ratio is preferably 0.2 to 20 parts by weight, more preferably 0.5 to 10 parts by weight, and when the second herbicidally active compound is Compound D, E, F or G, the second herbicidally active compound is mixed with a ratio of, in general, 0.01 to 100 parts by weight based on 1 part by weight of Compound (I) to prepare a useful herbicidal composition, and the ratio is preferably 0.02 to 50 parts by weight, more preferably 0.1 to 10 parts by weight. The thus accomplished herbicidal composition of the present invention gives high herbicidal effects by applying it before germination of weeds and subjecting to a soil treatment or a foliar treatment after germination.

In the present invention, 3-phenoxy-4-pyridazinol derivatives and the second herbicidally active compound may be mixed and spread as a preparation, may be spread simultaneously without mixing both effective ingredients, or may be spread one of these effective ingredients firstly and then spread the remaining effective ingredient later. Also, an order of spreading may be optional.

The composition of the present invention may be spread a raw material itself, or may be used by mixing with a carrier and, if necessary, with the other auxiliaries, and prepared in a preparation form which is generally used as a herbicidal composition, for example, dust powder, coarse dust powder, fine dust powder, granules, wettable powder, emulsifiable concentrate, aqueous suspension, water dispersible granules, suspension concentrate in water or oil, Jumbo (Throw-in Packed) formulation, etc.

The compound of the present invention is used by mixing with a carrier and, if necessary, with the other auxiliaries (a surfactant, etc.), and prepared in a preparation form which is generally used as a herbicidal composition, for example, dust powder, coarse dust powder, granules, fine granules, wettable powder, water-soluble agent, emulsifiable concentrate, liquid agent, etc. The carrier herein mentioned means a synthetic or natural inorganic or organic substance which is mixed in the herbicidal composition to aid reachability of the effective ingredient compound to plants or to make storage, transportation or handling of the effective ingredient easy.

A suitable solid carrier may be, for example, clays represented by kaolinite group, montmorllironite group, attapulgite group, etc.; inorganic substances such as talc, mica, pyrophyllite, pumice, vermiculite, gypsum, dolomite, diatomaceous earth, magnesium lime, phosphorus lime, zeolite, silicic acid anhydride, synthetic calcium silicate, kaolin, bentonite, calcium carbonate, etc.; vegetable organic substances such as soybean powder, tobacco powder, walnut powder, wheat flour, wood powder, starch powder, crystalline cellulose, etc.; synthetic or natural polymer compounds such as coumarone resin, petroleum resin, alkyd resin, polyvinyl chloride, polyalkylene glycol, ketone resin, ester gum, copal gum, dammar gum, etc.; waxes such as carnauba wax, paraffin wax, bees wax, etc.; or urea.

Suitable liquid carriers may include, for example, paraffin series or naphthene series hydrocarbons such as kerosine, mineral oil, spindle oil, white oil, etc.; aromatic hydrocarbons such as benzene, toluene, xylene, ethylbenzene, cumene, methylnaphthalene, etc.; chlorinated hydrocarbons such as carbon tetrachloride, chloroform, trichloroethylene, monochlorobenzene, chlorotoluene, etc.; ethers such as dioxane, tetrahydrofuran, etc.; ketones such as acetone, methylethylketone, diisobutylketone, cyclohexanone, acetophenone, isophorone, etc.; esters such as ethyl acetate, amyl acetate, ethylene glycol acetate, diethylene glycol acetate, dibutyl maleate, diethyl succinate, etc.; alcohols such as methanol, hexanole, ethylene glycol, diethylene glycol, cyclohexanol, benzyl alcohol, etc.; ether alcohols such as ethylene glycol ethyl ether, ethylene glycol phenyl ether, diethylene glycol ethyl ether, diethylene glycol butyl ether, etc.; polar solvents such as dimethylformamide, dimethylsulfoxide, etc.; or water.

A surfactant which is used for the purpose of emulsification, dispersion, wetting, spreading, binding, controlling disintegration, stabilization of effective ingredient(s), improvement in fluidity, antirust, promotion of absorption into plants, etc., may be ionic or nonionic one.

Suitable nonionic surfactants may include, for example, sucrose ester of aliphatic acid, ethylene oxide polymerized adducts of higher fatty acids such as lauryl alcohol, stearyl alcohol, oleyl alcohol, etc., ethylene oxide polymerized adducts of alkylphenols such as isooctylphenol, nonylphenol, etc., ethylene oxide polymerized adducts of alkyl naphthol such as butylnaphthol, octylnaphthol, etc., ethylene oxide polymerized adducts of higher fatty acids such as palmitic acid, stearic acid, oleic acid, etc., ethylene oxide polymerized adducts of mono- or dialkylphosphates such as stearyl phosphate, dilauryl phosphate, etc., ethylene oxide polymerized adducts of higher fatty amines such as dodecylamine, stearic amide, etc., higher fatty acid esters of polyvalent alcohols such as sorbitan, etc. and their ethylene oxide polymerized adducts and copolymers of ethylene oxide and propylene oxide, and the like.

Suitable anionic surfactants may include, for example, alkylsulfuric acid ester salts such as sodium lauryl sulfate, oleyl alcohol sulfuric acid ester amine salt, etc., aliphatic acid salts such as sodium sulfosuccinate dioctyl ester, sodium oleate, sodium stearate, etc., alkylarylsulfonic acid salts such as sodium isopropylnaphthalene sulfonate, sodium methylenebisnaphthalene sulfonate, sodium lignosulfonate, sodium dodecylbenzenesulfonate, etc.

Suitable cationic surfactants may include, for example, higher aliphatic amines, quaternary ammonium salts, alkylpyridinium salts, etc.

Moreover, in the herbicide of the present invention,

A surfactant which is used for the purpose of emulsification, dispersion, wetting, spreading, binding, controlling disintegration, stabilization of effective ingredient(s), improvement in fluidity, antirust, promotion of absorption into plants, etc., may be ionic or nonionic one.

Suitable nonionic surfactants may include, for example, sucrose ester of aliphatic acid, ethylene oxide polymerized adducts of higher fatty acids such as lauryl alcohol, stearyl alcohol, oleyl alcohol, etc., ethylene oxide polymerized adducts of alkylphenols such as isooctylphenol, nonylphenol, etc., ethylene oxide polymerized adducts of alkyl naphthol such as butylnaphthol, octylnaphthol, etc., ethylene oxide polymerized adducts of higher fatty acids such as palmitic acid, stearic acid, oleic acid, etc., ethylene oxide polymerized adducts of mono- or dialkylphosphates such as stearyl phosphate, dilauryl phosphate, etc., ethylene oxide polymerized adducts of higher fatty amines such as dodecylamine, stearic amide, etc., higher fatty acid esters of polyvalent alcohols such as sorbitan, etc. and their ethylene oxide polymerized adducts and copolymers of ethylene oxide and propylene oxide, and the like.

Suitable anionic surfactants may include, for example, alkylsulfuric acid ester salts such as sodium lauryl sulfate, oleyl alcohol sulfuric acid ester amine salt, etc., aliphatic acid salts such as sodium sulfosuccinate dioctyl ester, sodium oleate, sodium stearate, etc., alkylarylsulfonic acid salts such as sodium isopropylnaphthalene sulfonate, sodium methylenebisnaphthalene sulfonate, sodium lignosulfonate, sodium dodecylbenzenesulfonate, etc.

Suitable cationic surfactants may include, for example, higher aliphatic amines, quaternary ammonium salts, alkylpyridinium salts, etc.

Moreover, in the herbicide of the present invention, for the purpose of improving characteristics of the preparation and heightening biological effects, for example, polymer compounds such as gelatin, Gum Arabic, caseine, albumin, glue, sodium arginate, polyvinyl alcohol, carboxymethyl cellulose, methyl cellulose, hydroxymethyl cellulose, etc., thixotropic agents such as sodium polyphosphate, bentonite, etc. and other auxiliaries may be contained as other components.

Dust powder or crude dust powder generally contains, for example, 0.1 to 25 parts by weight of an effective ingredient, and the reminder is a solid carrier.

Wettable powder or granular wettable powder generally contains, for example, 1 to 90 parts by weight of an effective ingredient, and the reminder is a solid carrier and a dispersing or wetting agent, and a protective colloidal agent, thixotropic agent and defoaming agent are added depending on necessity. These preparations are suspended and dispersed when they are thrown into water and stirred.

Granules or fine dust powder generally contain(s), for example, 0.1 to 35 parts by weight of an effective ingredient, and the reminder is a solid carrier in almost all the part. The effective ingredient compound is uniformly mixed with a solid carrier, or firmly fixed or adsorbed on the surface of the solid carrier, and a size of the grain is generally 0.2 to 1.5 mm.

Emulsifiable concentrate generally contains, for example, 1 to 70 parts by weight of an effective ingredient compound, and further 5 to 20 parts by weight of an emulsifying agent is contained therein, and the reminder is a liquid carrier, and other auxiliaries such as a rust proof agent, etc. may be added if necessary.

Aqueous suspension or oil suspension is one in which the effective ingredient is suspended or emulsified and dispersed in water or an organic solvent with a high boiling point by using a suitable surfactant, and stability with a lapse of time is maintained by adding a thickening agent, etc., if necessary.

The Jumbo (Throw-in Packed) formulation can be prepared by making an active ingredient suitable preparation forms, for example, dust powder, granule, tablet, emulsifiable concentrate, clumpy tablet, etc., and if necessary, they are dividedly packed in a water-soluble film or a container, and at the time of use, they are directry thrown into a paddy field with several to several hundred preparations.

The compound of the present invention thus prepared in various types of formulations may be applied, for example, at dosage of 1 g to 1000 g, preferably 10 g to 300 g of an active ingredient per 10 are when it is subjected to soil treatment in a paddy field before or after germination of weeds, whereby weeds can be effectively eliminated.

As a method for treating the compound of the present invention, it can be applied, generally by preparing a formulation, as a soil treatment, a foliar treatment or a submerged treatment at pre-emergence or post-emergence within about one month after germination of weeds. In the soil treatment, there are soil surface treatment, soil incorporation, etc., in the foliar treatment, in addition to a treatment from upward of a plant canopy, there is a directed treatment in which weeds alone are treated so that the compound is not adhered to crops, etc., and in the submerged treatment, there are spreading or injection treatment of granules or flowable agent to water surface, etc.

Into the herbicidal composition of the present invention, other herbicides may be added to broaden weeding spectrum.

The herbicidal composition of the present invention can be used by mixing with, for example, a plant growth regulator, fungicide, insecticide, acaricide, nematocide or fertilizer, etc.

BEST MODE FOR CARRYING OUT THE INVENTION

In the following, Examples, Preparation examples and Test examples of the present invention are shown to explain the invention more specifically, but the present invention is not limited by these. Incidentally, in the following Preparation examples, "%" means % by weight.

EXAMPLE 1

6-Chloro-3-(2-methylphenoxy)-4-pyridazinol (Compound No. 128)

(1) 3-Chloro-6-(2-methylphenoxy)pyridazine (Step A-1)

A mixture of 278.7 g (1.87 mol) of 3,6-dichloropyridazine, 202.3 g (1.87 mol) of 2-methylphenol and 259 g (1.87 mol) of potassium carbonate was stirred at 160° C. for 6 hours. The reaction mixture was cooled to 70° C. and 2 L of ethyl acetate was added. This mixture was washed successively with 1 mol/L sodium hydroxide aqueous solution (4×500 mL), water (4×500 mL) and brine (50 mL), and dried over anhydrous magnesium sulfate. The solvent was removed, and isopropyl ether was added to the residue to form crystal. The crystal was collected by filtration to obtain 234.2 g (1.06 mol, Yield: 56.7%) of 3-chloro-6-(2-methylphenoxy)pyridazine.

(2) 4,6-Dichloro-3-(2-methylphenoxy)pyridazine (Step A-2)

In phosphorus oxychloride (1.85 L) was dissolved 6-chloro-3-(2-methylphenoxy)pyridazine (234.2 g, 1.06 mol) obtained in (1), and 76.7 g (1.08 mol) of a chlorine gas was passed into the solution over 4 hours. A nitrogen gas was passed into the reaction mixture to remove excess chlorine gas, and then phosphorus oxychloride was removed. The residue was dissolved in ethyl acetate (1.5 L), washed successively with water (4×500 mL) and brine(200 mL), and dried over anhydrous magnesium sulfate. The solvent was removed, and the resulting residue was washed with 500 mL of hexane to obtain 193.1 g of a crude product. This crude product was recrystallized form a mixed solvent of hexane-ethyl acetate (400 mL-240 mL) to obtain 114.4 g (0.448 mol, Yield: 42.3%) of 4,6-dichloro-3-(2-methylphenoxy)pyridazine.

(3) 6-Chloro-3-(2-methylphenoxy)-4-pyridazinol (Compound No. 128, Step A-3)

In 1,4-dioxane (1 L) was dissolved 100.0 g (0.392 mol) of 4,6-dichloro-3-(2-methylphenoxy)pyridazine obtained in (2), and to the solution were added an aqueous solution (400 mL of water) containing sodium hydroxide (purity 96%, 19.6 g, 0.470 mol) and 1.09 g (4.78 mmol) of tetrabutylammonium chloride, and the resulting mixture was stirred for 4 hours under reflux. The reaction mixture was concentrated under reduced pressure, and the total amount was made about 100 mL. To the residue were added an aqueous sodium hydroxide solution (13.1 g of sodium hydroxide was dissolved in 1.4 L of water) and 500 mL of ethyl acetate. The aqueous layer was washed with ethyl acetate (3×200 mL), cooled in an ice-bath, and then conc. hydrochloric acid was added to adjust the pH thereof to 5. Precipitated solid was collected by suction filtration, washed with 1 L of water and air dried. The resulting solid was recrystallized from acetonitrile to obtain 34.4 g (0.145 mol, Yield: 37.0%) of 6-chloro-3-(2-methylphenoxy)-4-pyridazinol (Compound No. 128). Also, the organic layer was dried over magnesium sulfate, and the solvent was removed. The obtained residue was purified by silica gel column chromatography (YMC GEL, SIL60, 350/250 mesh, hexane-ethyl acetate, gradient) to obtain 13.5 g (0.0414 mol, Yield: 10.5%) of 6-chloro-3,4-bis(2-methylphenoxy)pyridazine.

$^1$H-NMR (200 MHz, DMSO-d$_6$) δ ppm: 7.35-7.08 (4H, m), 6.84 (1H, brs), 2.11 (3H, s). Melting point (° C.): 211-213.

EXAMPLE 2

3-(2-Methylphenoxy)-4-pyridazinol (Compound No. 5)

(1) 6-Chloro-4-methoxy-3-(2-methylphenoxy)pyridazine (Step A-3)

In methanol (60 mL) was dissolved 3.00 g (11.8 mmol) of 4,6-dichloro-3-(2-methylphenoxy)pyridazine obtained in Example 1 (2), 1.00 g (17.6 mmol) of 95% sodium methoxide was added to the solution at room temperature and the mixture was stirred at 60° C. for 4 hours. Moreover, 1.00 g (17.6 mmol) of 95% sodium methoxide was further added and after stirring the mixture at 60° C. for 1 hour, it was allowed to stand at room temperature overnight. The reaction mixture was concentrated, ethyl acetate was added to the residue, and the mixture was successively washed with water and brine. After drying over anhydrous sodium sulfate, the solvent was removed, and the obtained residue was purified by silica gel column chromatography (eluted with hexane:ethyl acetate=4:1) to obtain 2.75 g (11.0 mmol, Yield: 93.2%) of 6-chloro-4-methoxy-3-(2-methylphenoxy)pyridazine.

(2) 4-Methoxy-3-(2-methylphenoxy)pyridazine (Step N-1)

In methanol (40 mL) was dissolved 2.00 g (7.98 mmol) of 6-chloro-4-methoxy-3-(2-methylphenoxy)pyridazine obtained in (1), 0.20 g of 5% palladium-carbon was added to the solution and the mixture was stirred under hydrogen atmosphere (1 atm) for 4 hours. The reaction mixture was filtered through Celite, and the filtrate was concentrated. The residue was purified by silica gel column chromatography (eluted with ethyl acetate and then dichloromethane: methanol=5:1) to obtain 1.59 g (7.36 mmol, Yield: 92.2%) of 4-methoxy-3-(2-methylphenoxy)pyridazine.

(3) 3-(2-Methylphenoxy)-4-pyridazinol (Compound No. 5, Step N-2)

A mixture comprising 1.08 g (5.00 mmol) of 4-methoxy-3-(2-methylphenoxy)pyridazine obtained in (2), 0.24 g (6.0 mmol) of sodium hydroxide, water (5 mL) and 1,4-dioxane (5 mL) was stirred overnight. The reaction mixture was washed with ethyl acetate, the aqueous layer was made acidic with hydrochloric acid, and extracted with ethyl acetate. The solvent was removed to obtain 0.21 g (10 mmol, Yield: 20%) of 3-(2-methylphenoxy)-4-pyridazinol (Compound No. 5).

$^1$H-NMR (60 MHz, DMF-d$_7$) δ ppm: 8.30 (1H, d, J=7.2 Hz), 7.43-7.00 (5H, m), 6.43 (1H, d, J=7.2 Hz), 2.18 (3H, s). Melting point (° C.): 169-171.

EXAMPLE 3

5-Chloro-3-(2-methylphenoxy)-4-pyridazinol (Compound No. 45)

(1) 4,5-Dichloro-3-(2-methylphenoxy)pyridazine 16.4 g (88.2 mmol) of 3-(2-methylphenoxy)pyridazine {which can be produced by the method described in Agricultural and Biological Chemistry, 1968, vol. 32, p. 1376 and Agricultural and Biological Chemistry, 1969, vol. 33, p. 96.} and phosphorus oxychloride (200 mL) were mixed, the mixture was heated to 80° C., and 8.5 g (120 mmol) of a chlorine gas was introduced therein. Phosphorus oxychloride was removed from the reaction mixture by distillation, the residue was poured into ice-cold water, and extracted with ethyl acetate. The organic layers were combined, washed with water, and dried over anhydrous sodium sulfate. The solvent was removed, and the residue was purified by silica gel column chromatography (available from Merck Co., 9385, hexane:ethyl acetate gradient) to obtain 6.61 g (25.9 mmol, Yield: 29.4%) of 4,5-dichloro-3-(2-methylphenoxy)pyridazine, 8.14 g (36.9 mmol, Yield: 41.8%) of 5-chloro-3-(2-methylphenoxy)pyridazine and 1.20 g (5.44 mmol, Yield: 6.17%) of 4-chloro-3-(2-methylphenoxy)pyridazine.

(2) 5-Chloro-4-methoxy-3-(2-methylphenoxy)pyridazine (Step A-3)

5.10 g (20.0 mmol) of 4,5-dichloro-3-(2-methylphenoxy)pyridazine obtained in (1) and methanol (70 mL) were mixed, and 0.46 g (20 mmol) of sodium was added to the mixture at −8° C., and the resulting mixture was stirred at −8° C. for 30 minutes, and in an ice bath for 8 hours and 30 minutes. Ice-cold water was added to the reaction mixture, pH was made 3 with hydrochloric acid, and then the mixture was extracted with ethyl acetate. The organic layers were combined, washed with water, and dried over anhydrous sodium sulfate. The solvent was removed, and the residue was purified by silica gel column chromatography (available from Merck Co., 9385, hexane:ethyl acetate, gradient) to obtain 1.15 g (4.58 mmol, Yield: 22.9%) of 5-chloro-4-methoxy-3-(2-methylphenoxy)pyridazine and 3.27 g (13.0 mmol, Yield: 65%) of 4-chloro-5-methoxy-3-(2-methylphenoxy)pyridazine.

(3) 5-Chloro-3-(2-methylphenoxy)-4-pyridazinol (Compound No. 45, Step A-4, etc.)

750 mg (2.99 mmol) of 5-chloro-4-methoxy-3-(2-methylphenoxy)pyridazine obtained in (2), 156 mg (3.9 mmol) of sodium hydroxide, 1,4-dioxane (5 mL) and water (10 mL) were mixed, and the mixture was refluxed with stirring for 2 hours and 30 minutes. The reaction mixture was poured into ice-cold water, and made acidic with hydrochloric acid. The precipitated solid was collected by filtration, and washed with water and then with hexane. 525 mg (2.22 mmol, Yield: 74.2%) of 5-chloro-3-(2-methylphenoxy)-4-pyridazinol (Compound No. 45) was obtained.

$^1$H-NMR (60 MHz, DMF-d$_7$) δ ppm: 8.68 (1H, s), 7.38-6.80 (4H, m), 5.32 (1H, brs), 2.13 (3H, s). Melting point (° C.): 238-243.

EXAMPLE 4

5-Chloro-3-(2-methylphenoxy)-4-pyridazinyl 4-methylbenzene sulfonate (Compound No. 66, Step I-1)

237 mg (1.00 mmol) of 5-chloro-3-(2-methylphenoxy)-4-pyridazinol (Compound No. 45) obtained in Example 3 and acetonitrile (8 mL) were mixed, and 112 mg (1.00 mmol) of 1,4-diazabicyclo[2,2,2]octane was added to the mixture with stirring, and then, 191 mg (1.00 mmol) of 4-methylbenzene sulfonyl chloride was added thereto, and the resulting mixture was stirred at room temperature for 1 hour and 30 minutes. Water was added to the reaction mixture, the mixture was made acidic with hydrochloric acid, and extracted with ethyl acetate. The organic layers were combined, washed with water, and dried over anhydrous sodium sulfate. The solvent was removed, and the residue was purified by silica gel column chromatography (Wako gel C-100, hexane:ethyl acetate=3:1) to obtain 379 mg (0.969 mmol, Yield: 96.9%) of 5-chloro-3-(2-methylphenoxy)-4-pyridazinyl 4-methylbenzene sulfonate (Compound No. 66).

$^1$H-NMR (60 MHz, CDCl$_3$) δ ppm: 8.80 (1H, s), 7.77-6.75 (8H, m), 2.47 (3H, s), 1.98 (3H, s). Melting point (° C.): 140-143.

EXAMPLE 5

6-Chloro-3-(2-methylphenoxy)-4-pyridazinol 1-oxide (Compound No. 129, Step F-1)

135 mg (0.572 mmol) of 6-chloro-3-(2-methylphenoxy)-4-pyridazinol (Compound No. 128) obtained in Example 1 and methylene chloride (6 mL) were mixed, 247 mg (purity 80%, 1.14 mmol) of m-chloroperbenzoic acid was added to the mixture and the resulting mixture was refluxed for 16 hours with stirring. The mixture was allowed to stand at room temperature for 2 days, the reaction mixture was poured in a saturated aqueous sodium sulfite solution, and washed with methylene chloride. The aqueous layer was made acidic with hydrochloric acid, extracted with methylene chloride, then washed with brine, and dried over anhydrous sodium sulfate. The solvent was removed, and the obtained residue was purified by silica gel column chromatography (YMC GEL, SIL60, 350/250 mesh, eluted with ethyl acetate) to obtain 32.6 mg (0.129 mmol, Yield: 22.6%) of 6-chloro-3-(2-methylphenoxy)-4-pyridazinol 1-oxide (Compound No. 129).

$^1$H-NMR (200 MHz, CD$_3$OD) δ ppm: 7.34 (1H, s), 7.34-7.10 (4H, m), 2.20 (3H, s). Melting point (° C.): 194-196.

EXAMPLE 6

6-Chloro-3-(2-cyclopropylphenoxy)-4-pyridazinol (Compound No. 139)

(1) Mixture of 6-chloro-3-(2-cyclopropylphenoxy)pyridazine 1-oxide and 3-chloro-6-(2-cyclopropylphenoxy)pyridazine 1-oxide (Step B-2)

25.3 g (189 mmol) of 2-cyclopropylphenol, 1,4-dioxane (120 mL) and dimethylsulfoxide (120 mL) were mixed, 23.2 g (207 mmol) of potassium tert-butoxide was added to the mixture in an ice bath and the resulting mixture was stirred for 10 minutes. To the mixture was added 32.0 g (194 mmol) of 3,6-dichloropyridazine 1-oxide which is a known compound, and the mixture was allowed to stand at room temperature for 5 days. The reaction mixture was poured into ice-cold water, and extracted with ethyl acetate. The organic layers were combined, washed successsively with water and brine, and dried over anhydrous sodium sulfate. The solvent was removed, and the residue was purified by silica gel column chromatography (hexane:ethyl acetate, gradient) to obtain 43.3 g (165 mmol, Yield: 87.3%) of a mixture of 6-chloro-3-(2-cyclopropylphenoxy)pyridazine 1-oxide and 3-chloro-6-(2-cyclopropylphenoxy)pyridazine 1-oxide.

(2) 4,6-Dichloro-3-(2-cyclopropylphenoxy)pyridazine (Step B-3)

43.3 g (165 mmol) of a mixture of 6-chloro-3-(2-cyclopropylphenoxy)pyridazine 1-oxide and 3-chloro-6-(2-cyclopropylphenoxy)pyridazine 1-oxide obtained in (1), chloroform (30 mL) and 18.0 mL (194 mmol) of phosphorus oxychloride were mixed, and the mixture was heated to 60° C. and dissolved. The solution was stirred at room temperature overnight, and concentrated. The residue was purified by silica gel column chromatography (hexane:ethyl acetate, gradient) to obtain 32.5 g (116 mmol, Yield: 70.3%) of 4,6-dichloro-3-(2-cyclopropylphenoxy)pyridazine.

(3) 6-Chloro-3-(2-cyclopropylphenoxy)-4-pyridazinol (Compound No. 139, Step B-4)

In dimethylsulfoxide (500 mL) was dissolved 32.5 g (116 mmol) of 4,6-dichloro-3-(2-cyclopropylphenoxy)pyridazine obtained in (2), 84 mL (210 mmol) of 10% (w/v) aqueous sodium hydroxide solution was added to the solution, and the mixture was stirred at room temperature overnight. The reaction mixture was poured into ice-cold 1 mol/L aqueous sodium hydroxide solution, and washed with ether. The aqueous layer was made acidic with hydrochloric acid, the precipitated solid was collected by filtration, and washed with water. To the resulting solid was added acetonitrile and the mixture was heated. The mixture was cooled overnight by allowing to stand, and crystals (14.04 g) were collected by filtration. The filtrate was concentrated, the residue was recrystallized from ethanol to obtain 2.64 g of crystals. These crystals were combined to obtain 16.7 g (63.5 mmol, Yield: 54.7%) of 6-chloro-3-(2-cyclopropylphenoxy)-4-pyridazinol (Compound No. 139).

$^1$H-NMR (200 MHz, DMSO-d$_6$) δ ppm: 7.28-6.97 (4H, m), 6.82 (1H, s), 1.89-1.77 (1H, m), 0.87-0.73 (2H, m), 0.73-0.58 (2H, m). Melting point (° C.): 229-231.

EXAMPLE 7

6-Chloro-3-[2-(1-fluorocyclopropyl)phenoxy]-4-pyridazinol (Compound No. 140)

(1) 2-(Methoxymethoxy)benzaldehyde

In N,N-dimethylformamide (20 mL) was dissolved 5.01 g (41.1 mmol) of commercially available salicylaldehyde, 1.80 g (45.0 mmol) of 60% sodium hydride was added to the solution in an ice bath, and after stirring the mixture in an ice bath for 10 minutes, 3.43 mL (45.2 mmol) of chloro(methoxy)methane was gradually added dropwise to the mixture and the resulting mixture was stirred in an ice bath for 1 hour. The reaction mixture was poured into water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 6.54 g (39.4 mmol, Yield: 95.9%) of 2-(methoxymethoxy)benzaldehyde.

(2) 1-(Methoxymethoxy)-2-vinylbenzene

Under nitrogen atmosphere, 877 mg (21.9 mmol) of 60% sodium hydride washed with hexane was suspended in dry dimethylsulfoxide (10 mL), the suspension was heated at 85° C. for 30 minutes with stirring, cooled to room temperature, and then, in an ice bath, a dry dimethylsulfoxide (20 mL) solution containing 7.83 g (21.9 mmol) of methyl(triphenyl)phosphonium bromide was gradually added dropwise thereto. After stirring at room temperature for 15 minutes, a dry dimethylsulfoxide (9 mL) solution containing 3.02 g (18.2 mmol) of 2-(methoxymethoxy)benzaldehyde obtained in (1) was added dropwise thereto, and the mixture was stirred at room temperature for 15 minutes. The reaction mixture was poured into water, and extracted with diethyl ether. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 2.54 g (15.5 mmol, Yield: 85.2%) of 1-(methoxymethoxy)-2-vinylbenzene.

(3) 1-(2-Bromo-1-fluoroethyl)-2-(methoxymethoxy)benzene

To a methylene chloride (10 mL) solution containing 1.47 g (9.13 mmol) of N,N,N-triethylamine hydrotrifluoric acid (MEC-82) was added dropwise a methylene chloride (5 mL) solution containing 1.00 g (6.09 mmol) of 1-(methoxymethoxy)-2-vinylbenzene obtained in (2), and 1.19 g (6.70 mmol) of N-bromosuccinimide was added thereto in an ice bath. The mixture was stirred in an ice bath as such for 2 hours, it was warmed to room temperature and stirred for further 30 minutes. The reaction mixture was poured into a saturated aqueous sodium hydrogen carbonate solution and extracted with methylene chloride. The organic layer was successively washed with diluted hydrochloric acid, water and brine, and dried over anhydrous magnesium sulfate. The solvent was distilled off and the obtained residue was purified by preparative thin-layer chromatography (available from MERCK CO., 1.05717, 4 plates were used, developed by ethyl acetate:hexane=4:1), and then, purified by preparative thin-layer chromatography (available from MERCK CO., 1.05744, 4 plates were used, developed by ethyl acetate:hexane=10:1) to obtain 1.24 g of a crude product of 1-(2-bromo-1-fluoroethyl)-2-(methoxymethoxy)benzene.

(4) 1-(1-Fluorovinyl)-2-(methoxymethoxy)benzene

In dry dimethylsulfoxide (10 mL) was added 736.2 mg (11.15 mmol) of 85% potassium hydroxide, the mixture was stirred at room temperature for 1 hour and 30 minutes, a dry dimethylsulfoxide (6 mL) solution containing 978.2 mg of a crude purified product of 1-(2-bromo-1-fluoroethyl)-2-(methoxymethoxy)benzene obtained in (3) was added dropwise to the mixture, and the resulting mixture was stirred for 2 hours and then stirred at 60° C. for 2 hours. The reaction mixture was poured into water and extracted with hexane. The organic layer was successively washed with water and brine, and dried over anhydrous magnesium sulfate. The solvent was removed to obtain 632.7 mg of a crude product of 1-(1-fluorovinyl)-2-(methoxymethoxy)benzene.

(5) 1-(1-Fluorocyclopropyl)-2-(methoxymethoxy)benzene

Under nitrogen atmosphere, dry diethyl ether (5 mL) was charged in a dry flask, 1.97 mL (1.97 mmol) of diethylzinc (1M hexane solution) was added dropwise thereto, and then, a dry diethyl ether (3 mL) solution containing 143.6 mg of a crude product of 1-(1-fluorovinyl)-2-(methoxymethoxy)benzene obtained in (4) was added dropwise thereto. After stirring at room temperature for 10 minutes, 0.19 mL (2.3 mmol) of diiodomethane was added dropwise to the mixture and the resulting mixture was refluxed for 4 hours and 30 minutes. The reaction mixture was poured into a saturated aqueous ammonium chloride solution, then, a saturated aqueous sodium hydrogen carbonate solution was added and the mixture was stirred for a while, and extracted with diethyl ether. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=4:1) to obtain 80.5 mg of a crude product of 1-(1-fluorocyclopropyl)-2-(methoxymethoxy)benzene.

(6) 2-(1-Fluorocyclopropyl)phenol

Conc. hydrochloric acid (0.3 mL) was added dropwise to a methanol (6 mL) solution containing 43.8 mg of a crude product of 1-(1-fluorocyclopropyl)-2-(methoxymethoxy)benzene obtained in (5), and the mixture was stirred at 60° C. for 3 hours. The reaction mixture was poured into water, and extracted with ethyl acetate. The organic layer was successively washed with water and brine, and dried over anhydrous magnesium sulfate. The solvent was removed to obtain 42.8 mg of a crude product of 2-(1-fluorocyclopropyl)phenol.

(7) 6-Chloro-3-[2-(1-fluorocyclopropyl)phenoxy]pyridazine 1-oxide (Step B-2)

In a mixed solvent of 1,4-dioxane(3 mL) and dimethylsulfoxide (3 mL) was dissolved 42.8 mg of a crude product of 2-(1-fluorocyclopropyl)phenol obtained in (6), 34.7 mg (0.310 mmol) of potassium tert-butoxide was added to the solution, and then, 46.4 mg.(0.281 mmol) of 3,6-dichloropyridazine 1-oxide was added to the mixture and the resulting mixture was stirred at room temperature overnight. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 2 plates were used, developed by ethyl acetate:hexane=2:1) to obtain 28.0 mg (0.0996 mmol) of 6-chloro-3-[2-(1-fluorocyclopropyl)phenoxy]pyridazine 1-oxide.

(8) 4,6-Dichloro-3-[2-(1-fluorocyclopropyl)phenoxy]-pyridazine (Step B-3)

In phosphorus oxychloride (1 mL) was dissolved 28.0 mg (0.0996 mmol) of 6-chloro-3-[2-(1-fluorocyclopropyl)phenoxy]pyridazine 1-oxide obtained in (7), and the solution was stirred at room temperature overnight. To the mixture were added water and methylene chloride, and after stirring for 30 minutes, the mixture was extracted with methylene chloride. The organic layer was successively washed with water and brine, and dried over anhydrous magnesium sulfate. The solvent was distilled off and the obtained residue was purified by preparative thin-layer chromatography (available from MERCK CO., 1.05744, 2 plates were used, developed by ethyl acetate:hexane=2:1) to obtain 5.1 mg (0.017 mmol, Yield: 17%) of 4,6-dichloro-3-[2-(1-fluorocyclopropyl)phenoxy]pyridazine.

(9) 6-Chloro-3-[2-(1-fluorocyclopropyl)phenoxy]-4-pyridazinol (Compound No. 140, Step B-4)

In a mixed solvent of 1,4-dioxane (2 mL) and dimethylsulfoxide (2 mL) was dissolved 5.1 mg (0.017 mmol) of 4,6-dichloro-3-[2-(1-fluorocyclopropyl)phenoxy]pyridazine obtained in (8), and to the solution was added 0.1 mL of 2 mol/L of aqueous sodium hydroxide solution, and the resulting mixture was stirred at room temperature overnight. The reaction mixture was poured into water, diluted hydrochloric acid was added to the mixture to adjust pH 2, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 1 plate was used, developed by ethyl acetate) to obtain 4.0 mg (0.014 mmol, Yield: 82%) of 6-chloro-3-[2-(1-fluorocyclopropyl)phenoxy]-4-pyridazinol (Compound No. 140).

$^1$H-NMR (200 MHz, CD$_3$OD) δ ppm: 7.57-7.52 (1H, m), 7.39-7.31 (1H, m), 7.22-7.13 (1H, m), 7.00 (1H, d, J=8.1 Hz), 6.48 (1H, s), 1.32-1.22 (2H, m), 1.16-1.08 (2H, m). Melting point (° C.): 152-157.

EXAMPLE 8

6-Chloro-3-{2-[1-(ethylsulfanyl)cyclopropyl]phenoxy}-4-pyridazinol (Compound No. 207)

(1) 1-Methoxy-2-vinylbenzene

Under nitrogen atmosphere, in dry dimethylsulfoxide (15 mL) was suspended 1.92 g (48.0 mmol) of 60% sodium hydride washed with hexane, after stirring the suspension at 85° C. for 30 minutes, it was cooled to room temperature and then, in an ice bath, a dry dimethylsulfoxide (35 mL) solution containing 17.2 g (48.2 mmol) of methyl(triphenyl)phosphonium bromide was gradually added dropwise thereto. After stirring at room temperature for 20 minutes, 4.83 mL (40.1 mmol) of commercially available 2-methoxybenzaldehyde was added dropwise thereto, and the resulting mixture was stirred at room temperature for 1 hour and then at 65° C. for 3 hours. The reaction mixture was poured into ice water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 3.29 g (24.5 mmol, Yield: 61.1%) of 1-methoxy-2-vinylbenzene.

(2) 1-(2-Bromo-1-fluoroethyl)-2-methoxybenzene

To a methylene chloride (20 mL) solution containing 3.60 g (22.4 mmol) of N,N,N-triethylamine hydrotrifluoric acid (MEC-82) was added dropwise a methylene chloride (6 mL) solution containing 2.01 g (15.0 mmol) of 1-methoxy-2-vinylbenzene obtained in (1), and 2.92 g (16.4 mmol) of N-bromosuccinimide was added in an ice bath. Stirring was continued in an ice bath for 25 minutes, and the mixture was warmed to room temperature and further stirred for 1 hour and 30 minutes. The reaction mixture was poured into a saturated aqueous sodium hydrogen carbonate solution and extracted with methylene chloride. The organic layer was successively washed with diluted hydrochloric acid, water and brine, and dried over anhydrous magnesium sulfate. The solvent was removed, and the obtained residue was purified by silica gel column chromatography (Wako gel C-100, hexane-ethyl acetate, gradient) to obtain 1.39 g of a crude product of 1-(2-bromo-1-fluoroethyl)-2-methoxybenzene.

(3) 1-(1-Fluorovinyl)-2-methoxybenzene

To dry dimethylsulfoxide (10 mL) was added 1.28 g (19.4 mmol) of 85% potassium hydroxide, the mixture was stirred at room temperature for 30 minutes, and then, a dry dimethylsulfoxide (10 mL) solution containing 1.50 g of a crude product of 1-(2-bromo-1-fluoroethyl)-2-methoxybenzene obtained in (2) was added dropwise thereto, and the mixture was stirred overnight. The reaction mixture was poured into water and extracted with hexane. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 1.21 g of a crude product of 1-(1-fluorovinyl)-2-methoxybenzene.

(4) 1-(1-Fluorocyclopropyl)-2-methoxybenzene

Under nitrogen atmosphere, dry diethyl ether (8 mL) was charged in a dry flask, 19.88 mL (19.88 mmol) of diethylzinc (1 mol/L hexane solution) was added dropwise thereto, and a dry diethyl ether (8 mL) solution containing 1.21 g of a crude product of 1-(1-fluorovinyl)-2-methoxybenzene obtained in (3) was added dropwise thereto. After stirring at room temperature for 10 minutes, 1.92 mL (23.86 mmol) of diiodomethane was added dropwise thereto, and the mixture was refluxed for 6 hours. After allowing to stand at room temperature overnight, the reaction mixture was poured into a saturated aqueous ammonium chloride solution, and then, a saturated aqueous sodium hydrogen carbonate solution was added thereto and the mixture was stirred for a while, and extracted with diethyl ether. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 1.06 g of a crude product of 1-(1-fluorocyclopropyl)-2-methoxybenzene.

(5) 2-[1-(ethylsulfanyl)cyclopropyl]phenol

Under nitrogen atmosphere, in dry N,N-dimethylformamide (8 mL) was suspended 765.3 mg (19.1 mmol) of 60% sodium hydride, and to the suspension was gradually added dropwise 1.46 mL (19.8 mmol) of ethanethiol and after stirring for 15 minutes, a dry N,N-dimethylformamide (5 mL) solution containing 1.06 g of a crude product of 1-(1-fluorocyclopropyl)-2-methoxybenzene obtained in (4) was added dropwise thereto and the resulting mixture was stirred at 160° C. for 5 hours. After cooling by allowing to stand, 1 mol/L of aqueous potassium hydroxide solution and diethyl ether were added to the reaction mixture. The aqueous layer was separated, and washed with diethyl ether. To the mixture was added diluted hydrochloric acid to adjust pH to 2, and extracted with diethyl ether. The organic layer was successively washed with water and brine, and dried over anhydrous magnesium sulfate. The solvent was removed, and the obtained residue was purified by silica gel column chromatography (Wako gel C-100, hexaneethyl acetate, gradient) to obtain 0.26 g of a crude product of 2-[1-(ethylsulfanyl)cyclopropyl]phenol.

(6) 6-Chloro-3-{2-[1-(ethylsulfanyl)cyclopropyl]phenoxy}-pyridazine 1-oxide (Step B-2)

In a mixed solvent of 1,4-dioxane (3 mL) and dimethylsulfoxide (3 mL) was dissolved 0.26 g of a crude product of 2-[1-(ethylsulfanyl)cyclopropyl]phenol obtained in (5), 265.5 mg (2.37 mmol) of potassium tert-butoxide was added to the solution, and then, 390.3 mg (2.37 mmol) of 3,6- dichloropyridazine 1-oxide was added to the same, and the resulting mixture was stirred at room temperature overnight. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=2:1) to obtain 138.4 mg (0.428 mmol) of 6-chloro-3-{2-[1-(ethylsulfanyl)cyclopropyl]phenoxy}pyridazine 1-oxide.

(7) 4,6-Dichloro-3-{2-[1-(ethylsulfanyl)cyclopropyl]-phenoxy}pyridazine (Step B-3)

In phosphorus oxychloride (1 mL) was dissolved 138.4 mg (0.428 mmol) of 6-chloro-3-{2-[1-(ethylsulfanyl)cyclopropyl]phenoxy}pyridazine 1-oxide obtained in (6), and the solution was stirred at room temperature overnight. To the reaction mixture were added water and methylene chloride, and the mixture was stirred for 30 minutes and extracted with methylene chloride. The organic layer was successsively washed with water and brine, and dried over anhydrous magnesium sulfate. The solvent was distilled off and the obtained residue was purified by preparative thin-layer chromatography (available from MERCK CO., 1.05744, 2 plates were used, developed by ethyl acetate:hexane=4:1) to obtain 94.4 mg (0.277 mmol, Yield: 64.7%) of 4,6-dichloro-3-{2-[1-(ethylsulfanyl)cyclopropyl]phenoxy}pyridazine.

(8) 6-Chloro-3-{2-[1-(ethylsulfanyl)cyclopropyl]phenoxy}-4-pyridazinol (Compound No. 207, Step B-4)

In a mixed solvent of 1,4-dioxane (1 mL) and dimethylsulfoxide (1 mL) was dissolved 94.4 mg (0.277 mmol) of 4,6-dichloro-3-{2-[1-(ethylsulfanyl)cyclopropyl]phenoxy}pyridazine obtained in (7), 0.69 mL (1.38 mmol) of 2 mol/L aqueous sodium hydroxide solution was added to the solution, and the mixture was stirred at room temperature overnight. To the reaction mixture were added water and ethyl acetate, the aqueous layer was separated and washed with ethyl acetate. Diluted hydrochloric acid was added thereto to adjust pH to 2, and the mixture was extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 2 plates were used, developed by ethyl acetate) to obtain 47.5 mg (0.147 mmol, Yield: 53.1%) of 6-chloro-3-{2-[1-(ethylsulfanyl)cyclopropyl]phenoxy}-4-pyridazinol (Compound No. 207).

$^1$H-NMR (200 MHz, CD$_3$OD) δ ppm: 7.45-7.07 (4H, m), 6.69 (1H, s), 2.46 (2H, q, J=7.3 Hz), 1.28-1.02 (9H, m). Melting point (° C.): 88.

EXAMPLE 9

6-Chloro-3-[2-(2,2-dichlorocyclopropyl)phenoxy]-4-pyridazinol (Compound No. 265)

(1) 1-(2,2-dichlorocyclopropyl)-2-(methoxymethoxy)benzene

In chloroform (12 mL) was dissolved 305 mg (1.86 mmol) of 1-(methoxymethoxy)-2-vinylbenzene obtained in Example 7(2), 5 mL (63 mmol) of 50% aqueous sodium hydroxide solution was added dropwise to the solution, and then, 54.1 mg (0.237 mmol) of benzyl(triethyl)ammonium chloride was added to the same and the resulting mixture was stirred at room temperature overnight. The reaction mixture was poured into water, and extracted with chloroform. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=1:2) to obtain 387 mg (1.57 mmol, Yield: 84.4%) of 1-(2,2-dichlorocyclopropyl)-2-(methoxymethoxy)benzene.

(2) 2-(2,2-Dichlorocyclopropyl)phenol

In methanol (5 mL) was dissolved 203 mg (0.822 mmol) of 1-(2,2-dichlorocyclopropyl)-2-(methoxymethoxy)benzene obtained in (1), 0.1 mL of conc. hydrochloric acid was added to the solution, and the resulting mixture was stirred at 60° C. for 2 hours. After confirming disappearance of the starting materials by thin layer chromatography, the reaction mixture was poured into water, and extracted with ethyl acetate. The organic layers were combined, washed successively with water and brine, and dried over anhydrous magnesium sulfate. The solvent was removed to obtain 194 mg of a crude product of 2-(2,2-dichlorocyclopropyl)phenol.

(3) 6-Chloro-3-[2-(2,2-dichlorocyclopropyl)phenoxy]-pyridazine 1-oxide (Step B-2)

In a mixed solvent of 1,4-dioxane (3 mL) and dimethylsulfoxide (3 mL) was mixed 194 mg of a crude product of 2-(2,2-dichlorocyclopropyl)phenol obtained in (2), 118 mg (1.05 mmol) of potassium tert-butoxide was added to the mixture in an ice bath, and the resulting mixture was stirred for 10 minutes. To the mixture was added 157 mg (0.952 mmol) of 3,6-dichloropyridazine 1-oxide, and the mixture was stirred at room temperature overnight. The reaction mixture was poured into ice-cold water, and extracted with ethyl acetate. The organic layers were combined, washed successively with water and brine, and dried over anhydrous magnesium sulfate. The solvent was distilled off and the residue was purified by preparative thin-layer chromatography (available from MERCK CO., 1.05744, 3 plates were used, developed by ethyl acetate:hexane=1:2) to obtain 268 mg of a crude product of 6-chloro-3-[2-(2,2-dichlorocyclopropyl)phenoxy]pyridazine 1-oxide.

(4) 4,6-Dichloro-3-[2-(2,2-dichlorocyclopropyl)phenoxy]-pyridazine (Step B-3)

268 mg of a crude product of 6-chloro-3-[2-(2,2-dichlorocyclopropyl)phenoxy]pyridazine 1-oxide obtained in (3) and 3 mL of phosphorus oxychloride were mixed, and the mixture was stirred at room temperature overnight. To the reaction mixture were added water and dichloromethane, and the resulting mixture was stirred for 30 minutes. The mixture was separated, and the organic layer was successively washed with water and brine, and dried over anhydrous magnesium sulfate. The solvent was distilled off and the residue was purified by preparative thin-layer chromatography (available from MERCK CO., 1.05744, 3 plates were used, developed by ethyl acetate:hexane=1:2) to obtain 162 mg (0.463 mmol, Yield with 3 steps from 1-(2,2-dichlorocyclopropyl)-2-(methoxymethoxy)benzene: 56.3%) of 4,6-dichloro-3-[2-(2,2-dichlorocyclopropyl)phenoxy]pyridazine.

(5) 6-Chloro-3-[2-(2,2-dichlorocyclopropyl)phenoxy]-4-pyridazinol (Compound No. 265, Step B-4)

162 mg (0.463 mmol) of 4,6-dichloro-3-[2-(2,2-dichlorocyclopropyl)phenoxy]pyridazine obtained in (4), 1,4-dioxane (3 mL) and dimethylsulfoxide (3 mL) were mixed, to the mixture was added 1.15 mL (2.30 mmol) of 2 mol/L aqueous sodium hydroxide solution, and the mixture was stirred at room temperature overnight. The reaction mixture was poured into water, and made acidic with diluted hydrochloric acid. The mixture was extracted with dichloromethane. The organic layers were combined, washed successively with water and brine, and dried over anhydrous magnesium sulfate. The solvent was distilled off and the residue was purified by preparative thin-layer chromatography (available from MERCK CO., 1.05744, 3 plates were used, developed by ethyl acetate) to obtain 50.0 mg (0.151 mmol, Yield: 32.6%) of 6-chloro-3-[2-(2,2-dichlorocyclopropyl)phenoxy]-4-pyridazinol (Compound No. 265).
$^1$H-NMR (200 MHz, CD$_3$OD) δ ppm: 7.55-7.15 (4H, m), 6.69 (1H, s), 2.90 (1H, dd, J=10.6, 8.8 Hz), 2.07-1.89 (2H, m). Melting point (° C.): 158-163.

EXAMPLE 10

6-Chloro-3-(2-hydroxyphenoxy)-4-pyridazinol (Compound No. 384)

(1) 3-Chloro[1,4]benzodioxino[2,3-c]pyridazine(Step O-1)

In 1,4-dioxane (30 mL) was suspended 3.49 g (80.0 mmol) of 55% sodium hydride, and to the suspension were added a 1,4-dioxane (30 mL) solution containing 4.40 g (40 mmol) of pyrocatechol, then a 1,4-dioxane (30 mL) solution containing 7.30 g (39.9 mmol) of 3,4,6-trichloropyridazine {described in The Journal of Organic Chemistry, 1963, vol. 28, pp. 218 to 221}, and the mixture was refluxed for 2 hours. The reaction mixture was poured into ice-cold water, and extracted with ethyl acetate. The organic layers were combined, washed successively with 1 mol/L sodium hydroxide and water, and dried over anhydrous magnesium sulfate. The solvent was removed, and the residue was recrystallized from methyl isobutyl ketone to obtain 6.15 g (27.8 mmol, Yield: 69.7%) of 3-chloro[1,4]benzodioxino[2,3-c]pyridazine.

(2) 6-Chloro-3-(2-hydroxyphenoxy)-4-pyridazinol (Compound No. 384, Step O-2)

A mixture comprising 5.52 g (25.0 mmol) of 3-chloro[1,4]benzodioxino[2,3-c]pyridazine obtained in (1), 1.30 g (31.2 mmol) of 96% sodium hydroxide, dimethylsulfoxide (55 mL) and water (15 mL) was stirred at 90° C. for 1 hour. The reaction mixture was poured into ice-cold water, made acidic with hydrochloric acid, and extracted with ethyl acetate. The solvent was removed, and the residue was washed with isopropyl ether to obtain 4.90 g (20.5 mmol, Yield: 82.0%) of 6-chloro-3-(2-hydroxyphenoxy)-4-pyridazinol (Compound No. 384).
$^1$H-NMR (60 MHz, DMF-d$_7$) δ ppm: 7.25-6.40 (5H, m). Melting point (° C.): 216-219.

EXAMPLE 11

6-Chloro-3-[2-(methylsulfinyl)phenoxy]-4-pyridazinol (Compound No. 404)

(1) 6-Chloro-3-[2-(methylsulfanyl)phenoxy]pyridazine 1-oxide (Step B-2)

In a mixed solvent of 1,4-dioxane (5 mL) and dimethylsulfoxide (5 mL) was dissolved 454 mg (3.24 mmol) of 2-(methylsulfanyl)phenol, to the solution was added 519 mg (4.63 mmol) of potassium tert-butoxide and the mixture was stirred for 35 minutes. To the mixture was added 424 mg (2.57 mmol) of 3,6-dichloropyridazine 1-oxide and the resulting mixture was stirred for 3 hours. The reaction mixture was poured into water and extracted with ethyl acetate. The organic layers were combined, washed with brine, and dried over anhydrous magnesium sulfate. The solvent was removed, and the obtained residue was purified by silica gel chromatography (Wakogel C-100, eluted with hexane:ethyl acetate=3:1) to obtain 391 mg (1.46 mmol, Yield: 56.8%) of 6-chloro-3-[2-(methylsulfanyl)phenoxy]pyridazine 1-oxide.

(2) 4,6-Dichloro-3-[2-(methylsulfanyl)phenoxy]pyridazine (Step B-3)

288 mg (1.07 mmol) of 6-chloro-3-[2-(methylsulfanyl)phenoxy]pyridazine 1-oxide obtained in (1) and 1.00 mL (10.8 mmol) of phosphorus oxychloride were mixed, and the mixture was stirred overnight. The reaction mixture was poured into water, and extracted with ethyl acetate. The organic layer was washed successively with a saturated aqueous sodium hydrogen carbonate solution and brine, and dried over anhydrous magnesium sulfate. The solvent was distilled off and the residue was purified by preparative thin-layer chromatography (available from Merck Co., 1.05744, developed by hexane/ethyl acetate=3/1) to obtain 118 mg (0.411 mmol, Yield: 38.4%) of 4,6-dichloro-3-[2-(methylsulfanyl)phenoxy]pyridazine.

(3) 4,6-Dichloro-3-[2-(methylsulfinyl)phenoxy]pyridazine

In 1,2-dichloroethane (4 mL) was dissolved 118 mg (0.411 mmol) of 4,6-dichloro-3-[2-(methylsulfanyl)phenoxy]pyridazine obtained in (2), 96.3 mg (purity 80%, 0.446 mmol) of m-chloroperbenzoic acid was added to the solution and the resulting mixture was stirred at room temperature for 5 hours. The reaction mixture was poured into 10% aqueous sodium sulfite solution, extracted with ethyl acetate, then washed with brine, and dried over anhydrous magnesium sulfate. The solvent was distilled off and the obtained residue was purified by preparative thin-layer chromatography (available from Merck Co., 1.05744, developed by hexane:ethyl acetate=1:1, then, 3:1, and then, 1:1) to obtain 21.1 mg (0.0696 mmol, Yield: 16.9%) of 4,6-dichloro-3-[2-(methylsulfinyl)phenoxy]pyridazine.

(4) 6-Chloro-3-[2-(methylsulfinyl)phenoxy]-4-pyridazinol (Compound No. 404, Step B-4)

In 1,4-dioxane (0.5 mL) was dissolved 21.1 mg (0.0696 mmol) of 4,6-dichloro-3-[2-(methylsulfinyl)phenoxy]pyridazine obtained in (3), 0.12 mL (0.36 mmol) of 3 mol/L aqueous sodium hydroxide solution was added to the solution, and the resulting mixture was stirred for 45 minutes. To the mixture was added dimethylsulfoxide (0.5 mL), and after stirring for 3 hours, the reaction mixture was poured into 10% hydrochloric acid and extracted with ethyl acetate. The organic layer was successively washed with water and brine, and dried over anhydrous magnesium sulfate. The solvent was distilled off and the obtained residue was purified by preparative thin-layer chromatography (available from Merck Co., 1.05744, chloroform:methanol=10:1) to obtain 2.1 mg (0.0074 mmol, Yield: 11%) of 6-chloro-3-[2-(methylsulfinyl)phenoxy]-4-pyridazinol (Compound No. 404).

¹H-NMR (200 MHz, CD₃OD) δ ppm: 7.90-7.84 (1H, m), 7.60-7.42 (2H, m), 7.14 (1H, dd, J=9.2, 1.1 Hz), 6.62 (1H, s), 2.92 (3H, s). Appearance: amorphous.

EXAMPLE 12

6-Chloro-3-[2-(methylsulfonyl)phenoxy]-4-pyridazinol (Compound No. 406)

(1) 6-Chloro-3-[2-(methylsulfonyl)phenoxy]pyridazine 1-oxide

In 1,2-dichloroethane (5 mL) was dissolved 208 mg (0.774 mmol) of 6-chloro-3-[2-(methylsulfanyl)phenoxy]pyridazine 1-oxide obtained in Example 11 (1), 829 mg (3.84 mmol) of 80% m-chloroperbenzoic acid was added to the solution and the resulting mixture was stirred at room temperature for 4 hours. The reaction mixture was poured into 10% aqueous sodium sulfite solution, and extracted with ethyl acetate. The organic layers were combined, washed with brine and dried over anhydrous magnesium sulfate. The solvent was distilled off and the obtained residue was purified by preparative thin-layer chromatography (available from Merck Co., 1.05744, developed by hexane:ethyl acetate=1:1) to obtain 132 mg (0.439 mmol, Yield: 56.7%) of 6-chloro-3-[2-(methylsulfonyl)phenoxy]pyridazine 1-oxide.

(2) 4,6-Dichloro-3-[2-(methylsulfonyl)phenoxy]pyridazine (Step B-3)

111 mg (0.369 mmol) of 6-chloro-3-[2-(methylsulfonyl)phenoxy]pyridazine 1-oxide obtained in (1) and 1.00 mL (10.8 mmol) of phosphorus oxychloride were mixed, and the mixture was stirred overnight. The reaction mixture was poured into water, and extracted with ethyl acetate. The organic layer was successively washed with a saturated sodium hydrogen carbonate and brine, and dried over anhydrous magnesium sulfate. The solvent was distilled off and the residue was purified by preparative thin-layer chromatography (available from Merck Co., 1.05744, developed by hexane:ethyl acetate=1:1) to obtain 70.8 mg (0.222 mmol, Yield: 60.2%) of 4,6-dichloro-3-[2-(methylsulfonyl)phenoxy]pyridazine.

(3) 6-Chloro-3-[2-(methylsulfonyl)phenoxy]-4-pyridazinol (Compound No. 406, Step B-4)

In 1,4-dioxane (2.0 mL) was dissolved 70.8 mg (0.222 mmol) of 4,6-dichloro-3-[2-(methylsulfonyl)phenoxy]pyridazine obtained in (2), 0.45 mL (1.4 mmol) of 3 mol/L aqueous sodium hydroxide solution was added to the solution, and the resulting mixture was stirred for 30 minutes. To the mixture was added dimethylsulfoxide (2.0 mL), the mixture was stirred overnight, poured into water and washed with a mixed solvent of hexane-ethyl acetate. To the aqueous layer was added 10% hydrochloric acid to make it acidic, and the mixture was extracted with ethyl acetate. The organic layer was successively washed with water and brine, and dried over anhydrous magnesium sulfate. The solvent was distilled off and the obtained residue was purified by preparative thin-layer chromatography (available from Merck Co., 1.05744, developed by chloroform:methanol=10:1) to obtain 18.0 mg (0.0599 mmol, Yield: 27.0%) of 6-chloro-3-[2-(methylsulfonyl)phenoxy]-4-pyridazinol (Compound No. 406).

¹H-NMR (200 MHz, CD₃OD) δ ppm: 8.00 (1H, dd, J=7.7, 1.8 Hz), 7.71 (1H, ddd, J=7.7, 7.7, 1.8 Hz), 7.43 (1H, ddd, J=7.7, 7.7, 1.1 Hz), 7.32 (1H, br.d, J=7.7 Hz), 6.62 (1H, s), 3.36 (3H, s). Appearance: amorphous.

EXAMPLE 13

6-Chloro-3-(2-cyclopropyl-3-methoxyphenoxy)-4-pyridazinol (Compound No. 478)

(1) 6-Chloro-3-(2-cyclopropyl-3-methoxyphenoxy)-4-methoxy-pyridazine (Step D-1)

In a mixed solvent of 1,4-dioxane (2.5 mL) and dimethylsulfoxide (2.5 mL) was dissolved 190 mg (1.16 mmol) of 2-cyclopropyl-3-methoxyphenol, 146 mg (1.30 mmol) of potassium tert-butoxide was added to the solution and the resulting mixture was stirred for 10 minutes. To the mixture was added 170 mg (0.950 mmol) of 3,6-dichloro-4-methoxypyridazine and the resulting mixture was stirred overnight. The reaction mixture was poured into ice water and extracted with ethyl acetate. The organic layers were combined, washed successively with water and brine, and dried over anhydrous magnesium sulfate. The solvent was removed, and the obtained residue was purified by silica gel chromatography (Wakogel C-100, hexane-ethyl acetate, gradient) to obtain 90.1 mg (0.293 mmol, Yield: 30.8%) of 6-chloro-3-(2-cyclopropyl-3-methoxyphenoxy)-4-methoxypyridazine and 114 mg (0.371 mmol, Yield: 39.1%) of 3-chloro-6-(2-cyclopropyl-3-methoxyphenoxy)-4-methoxypyridazine.

(2) 6-Chloro-3-(2-cyclopropyl-3-methoxyphenoxy)-4-pyridazinol (Compound No. 478, Step D-2)

In dry N,N-dimethylformamide (DMF, 2 mL) was suspended 24 mg (0.60 mmol) of 60% sodium hydride, 0.05 mL (0.7 mmol) of ethanethiol was added dropwise to the suspension in an ice bath and the resulting mixture was stirred at room temperature for 10 minutes. To the mixture was added a dry N,N-dimethylformamide (DMF, 1.5 mL) solution containing 60.0 mg (0.195 mmol,) of 6-chloro-3-(2-cyclopropyl-3-methoxyphenoxy)-4-methoxypyridazine obtained in (1), and the resulting mixture was refluxed for 2 hours. The reaction mixture was cooled, and poured into ice-cold 1 mol/L aqueous sodium hydroxide solution, and washed with ethyl acetate. Ice-cold conc. hydrochloric acid was added to the aqueous layer to adjust pH to 4, and the mixture was extracted with ethyl acetate. The ethyl acetate extracts were combined, washed successively with water and brine, and dried over sodium sulfate. The solvent was distilled off and the obtained residue was purified by preparative thin-layer chromatography (available from Merck Co., 1.05744, 3 plates were used, developed by hexane:ethyl acetate=1:1) to obtain 15.2 mg (0.0519 mmol, Yield: 26.6%) of 6-chloro-3-(2-cyclopropyl-3-methoxyphenoxy)-4-pyridazinol (Compound No. 478).

¹H-NMR (200 MHz, CDCl₃) δ ppm: 7.19 (1H, dd, J=8.1, 8.4 Hz), 6.76 (1H, d, J=8.1 Hz), 6.69 (1H, d, J=8.4 Hz), 6.60 (1H, s), 3.85 (3H, s), 1.55-1.35 (1H, m), 0.85-0.60 (4H, m). Melting point (° C.): 184-185.

EXAMPLE 14

3-(1,1a,6,6a-Tetrahydrocyclopropa[a]inden-2-yloxy)-6-chloro-4-pyridazinol (Compound No. 515)

(1) 7-hydroxy-1-indanone 37.0 g (278 mmol) of aluminum chloride was mixed with 3.70 g (61.3 mmol) of sodium chloride, the mixture was dissolved at 150° C. under heating, 6.40 g (43.2 mmol) of commercially available 2,3-dihydro-4H-chromen-4-one dissolved by heating (50° C.) was added to the mixture and the resulting mixture was stirred at 200° C. for 20 minutes. The reaction mixture (gum state) was cooled, and added to ice-cold hydrochloric acid (100 ml of conc. hydrochloric acid and ice were combined to make them 200 ml) little by little and stirred for 30 minutes. Methylene chloride was added to the mixture and the mixture was separated. The aqueous layer was filtered, and the filtrate was extracted with methylene chloride. The organic layers were combined, washed successively with water and brine, and dried over sodium sulfate. The solvent was removed, and the obtained residue was purified by silica gel chromatography (Wakogel C-100, hexane-ethyl acetate, gradient) to obtain 4.82 g (32.6 mmol, Yield: 75.2%) of 7-hydroxy-1-indanone.

(2) 7-(Methoxymethoxy)-1-indanone

In N,N-dimethylformamide (DMF, 33 mL) was dissolved 1.00 g (6.76 mmol) of 7-hydroxy-1-indanone obtained in (1), the solution was cooled in an ice bath, and 0.330 g (8.25 mmol) of 60% sodium hydride was added by dividing into four times and the resulting mixture was stirred for 30 minutes. To the mixture was added dropwise 0.80 mL (11 mmol) of chloromethoxymethane, and the mixture was stirred at room temperature for 2 hours. The reaction mixture was poured into an ice-cold saturated aqueous ammonium chloride solution (100 mL) and extracted with ethyl acetate. The organic layer was washed successively with water and and brine, dried over sodium sulfate. The solvent was removed, and the obtained residue was purified by silica gel chromatography (Wakogel C-100, hexane-ethyl acetate, gradient) to obtain 1.04 g (5.42 mmol, Yield: 80.2%) of 7-(methoxymethoxy)-1-indanone.

(3) 7-(Methoxymethoxy)-1-indanol

In methanol(20 mL) was dissolved 1.04 g (5.42 mmol) of 7-methoxymethoxy-1-indanone obtained in (2), the solution was cooled in an ice bath, and 164 mg (4.34 mmol) of sodium borohydride was added to the solution and the resulting mixture was stirred at room temperature for 4 hours. The reaction mixture was poured into ice water, and extracted with ethyl acetate. The organic layers were combined, washed successively with water and brine, and dried over sodium sulfate. The solvent was removed, and the obtained residue was purified by silica gel chromatography (Wakogel C-100, hexane-ethyl acetate, gradient) to obtain 1.05 g (5.42 mmol, Yield: 100%) of 7-(methoxymethoxy)-1-indanol.

(4) Mixture of 4-(methoxymethoxy)-1H-indene and 7-(methoxymethoxy)-1H-indene

In methylene chloride (3 mL) was dissolved 500 mg (2.58 mmol) of 7-(methoxymethoxy)-1-indanol obtained in (3), the solution was cooled in an ice bath, and 0.50 mL (3.7 mmol) of triethylamine and 0.25 mL (3.3 mmol) of methanesulfonyl chloride were added to the solution and the resulting mixture was stirred for 2 hours. To the mixture was added 0.80 mL (5.7 mmol) of triethylamine and the mixture was stirred for 1 hour, then the mixture was poured into water and extracted with methylene chloride. The organic layer was successively washed with water and brine, and dried over anhydrous magnesium sulfate. The solvent was removed, and the resulting residue was dissolved in pyridine (3 mL), and the mixture was refluxed for 4 hours. After allowing to stand at room temperature overnight, the reaction mixture was poured into water and extracted with ethyl acetate. The organic layers were combined, washed successively with water and brine, and dried over anhydrous sodium sulfate. The solvent was removed, and the obtained residue was purified by silica gel chromatography (Wakogel C-100, hexane-ethyl acetate, gradient) to obtain 280 mg (1.59 mmol, Yield: 61.6%) of a mixture of 4-(methoxymethoxy)-1H-indene and 7-(methoxymethoxy)-1H-indene.

(5) Mixture of (2-(methoxymethoxy)-1,1a,6,6a-tetrahydrocyclopropa[a]indene and 5-(methoxymethoxy)-1,1a,6,6a-tetrahydrocyclopropa[a]indene In 30 mL of eggplant type flask was charged dry diethyl ether (5 mL) under nitrogen atmosphere, and cooled in an ice bath. To the solution were successively added dropwise 6.3 mL (6.3 mmol) of diethylzinc (1.0 mol/L hexane solution), and 0.70 mL (8.5 mmol) of diiodomethane, and the mixture was stirred for 10 minutes. To the mixture was gradually added dropwise an ether solution (9 mL) containing 250 mg (1.42 mmol) of a mixture comprising 4-(methoxymethoxy)-1H-indene and 7-(methoxymethoxy)-1H-indene obtained in (4). The resulting mixture was refluxed for 4 hours. The reaction mixture was cooled, and poured into a saturated aqueous ammonium chloride solution. To the mixture was added the same volume of a saturated aqueous sodium hydrogen carbonate solution, and then, extracted with ether. The organic layers were combined, washed successively with water and brine, and dried over anhydrous magnesium sulfate. The solvent was removed, and the obtained residue was purified by silica gel chromatography (Wakogel C-100, hexane-ethyl acetate, gradient) to obtain 150 mg (0.789 mmol, Yield: 55.6%) of a mixture of 2-(methoxymethoxy)-1,1a,6,6a-tetrahydrocyclopropa[a]indene and 5-(methoxymethoxy)-1,1a,6,6a-tetrahydrocyclopropa[a]-indene.

(6) Mixture of 1,1a,6,6a-tetrahydrocyclopropa[a]inden-2-ol and 1,1a,6,6a-tetrahydrocyclopropa[a]inden-5-ol In methanol (6 mL) was dissolved 150 mg (0.789 mmol) of a mixture of 2-(methoxymethoxy)-1,1a,6,6a-tetrahydrocyclopropa[a]indene and 5-(methoxymethoxy)-1,1a,6,6a-tetrahydrocyclopropa[a]indene obtained in (5), two drops of conc. hydrochloric acid were added to the solution and the resulting mixture was stirred at room temperature for 1 hour and then at 60° C. for 20 minutes. The reaction mixture was cooled, poured into water and extracted with ethyl acetate. The organic layers were combined, washed successively with water and brine, and dried over anhydrous sodium sulfate. The solvent was distilled off and the obtained residue was purified by preparative thin-layer chromatography (available from Merck Co., 1.05744, developed by hexane:ethyl acetate=2:1) to obtain 80.0 mg (0.548 mmol, Yield: 69.5%) of a mixture of 1,1a,6,6a-tetrahydrocyclopropa[a]inden-2-ol and 1,1a,6,6a-tetrahydrocyclopropa[a]inden-5-ol.

(7) Mixture of 3-(1,1a,6,6a-tetrahydrocyclopropa[a]inden-2-yloxy)-6-chloropyridazine 1-oxide and 3-(1,1a,6,6a-tetrahydrocyclopropa[a]inden-5-yloxy)-6-chloropyridazine 1-oxide (Step B-2)

In a mixed solvent of 1,4-dioxane (2 mL) and dimethylsulfoxide (2 mL) was dissolved 80.0 mg (0.548 mmol) of a mixture of 1,1a,6,6a-tetrahydrocyclopropa[a]inden-2-ol and 1,1a,6,6a-tetrahydrocyclopropa[a]inden-5-ol obtained in (6), and 85 mg (0.76 mmol) of potassium tert-butoxide was added to the solution and the mixture was stirred for 10 minutes. To the mixture was added 82 mg (0.50 mmol) of 3,6-dichloropyridazine 1-oxide, and the resulting mixture was stirred at room temperature overnight. The reaction mixture was poured into water and extracted with ethyl acetate. The organic layers were combined, washed successively with water and brine, and dried over anhydrous magnesium sulfate. The solvent was distilled off and the obtained residue was purified by preparative thin-layer chromatography (available from Merck Co., 1.05744, 4 plates were used, developed by hexane:ethyl acetate=2:1) to obtain 75.0 mg (0.273 mmol, Yield: 49.8%) of a mixture of 3-(1,1a,6,6a-tetrahydrocyclopropa[a]inden-2-yloxy)-6-chloropyridazine 1-oxide and 3-(1,1a,6,6a-tetrahydrocyclopropa-[a]inden-5-yloxy)-6-chloropyridazine 1-oxide.

(8) 3-(1,1a,6,6a-Tetrahydrocyclopropa[a]inden-2-yloxy)-4,6-dichloropyridazine and 3-(1,1a,6,6a-tetrahydrocyclopropa-[a]inden-5-yloxy)-4,6-dichloropyridazine (Step B-3)

75.0 mg (0.273 mmol) of a mixture of 3-(1,1a,6,6a-tetrahydrocyclopropa[a]inden-2-yloxy)-6-chloropyridazine 1-oxide and 3-(1,1a,6,6a-tetrahydrocyclopropa[a]inden-5-yloxy)-6-chloropyridazine 1-oxide obtained in (7) was mixed with 0.30 mL (3.2 mmol) of phosphorus oxychloride, and the mixture was stirred overnight. The reaction mixture was concentrated under reduced pressure to remove phosphorus oxychloride, and the residue was purified by preparative thin-layer chromatography (available from Merck Co., 1.05744, 3 plates were used, developed by hexane/ethyl acetate=9/1 four times repeatedly) to obtain 21.4 mg (0.0730 mmol, Yield: 26.7%) of 3-(1,1a,6,6a-tetrahydrocyclopropa[a]inden-2-yloxy)-4,6-dichloropyridazine and 32.6 mg (0.111 mmol, Yield: 40.7%) of 3-(1,1a,6,6a-tetrahydrocyclopropa[a]inden-5-yloxy)-4,6-dichloropyridazine.

(9) 3-(1,1a,6,6a-Tetrahydrocyclopropa[a]inden-2-yloxy)-6-chloro-4-pyridazinol (Compound No. 515, Step B-4)

To a dimethylsulfoxide (3 mL) solution containing 21.4 mg (0.0730 mmol) of 3-(1,1a,6,6a-tetrahydrocyclopropa[a]inden-2-yloxy)-4,6-dichloropyridazine obtained in (8) was added 0.1 mL (0.2 mmol) of 2 mol/L aqueous sodium hydroxide solution, and the mixture was stirred at room temperature for 3 hours. The reaction mixture was poured into ice-cold 1 mol/L aqueous sodium hydroxide solution, and extracted with ethyl acetate. The aqueous layer was separated, conc. hydrochloric acid was added thereto to adjust pH to 4 in an ice bath, and the mixture was extracted with ethyl acetate. The organic layers were combined, washed successively with water and brine, dried over sodium sulfate. The solvent was distilled off and the obtained residue was purified by preparative thin-layer chromatography (available from Merck Co., 1.05744, 1 plate was used, developed by chloroform:methanol=10:1) to obtain 10.3 mg (0.0375 mmol, Yield: 51.4%) of 3-(1,1a,6,6a-tetrahydrocyclopropa[a]inden-2-yloxy)-6-chloro-4-pyridazinol (Compound No. 515).

$^1$H-NMR (200 MHz, CD$_3$OD) δ ppm: 7.08 (1H, t, J=7.7 Hz), 6.98 (1H, d, J=7.7 Hz), 6.84 (1H, d, J=7.7 Hz), 6.59 (1H, s), 3.20 (1H, dd, J=17.2, 6.2 Hz), 2.94 (1H, d, J=17.2 Hz), 2.30-2.15 (1H, m), 1.90-1.75 (1H, m), 1.05-0.90 (1H, m). Melting point (° C.): 245-247.

EXAMPLE 15

3-(1,1a,6,6a-Tetrahydrocyclopropa[a]inden-5-yloxy)-6-chloro-4-pyridazinol (Compound No. 516, Step B-4)

In dimethylsulfoxide (3 mL) was dissolved 32.6 mg (0.111 mmol) of 3-(1,1a,6,6a-tetrahydrocyclopropa[a]inden-5-yloxy)-4,6-dichloropyridazine obtained in Example 14(8), and 0.1 mL (0.2 mmol) of 2 mol/L aqueous sodium hydroxide solution was added to the solution and the resulting mixture was stirred at room temperature for 4 hours. The reaction mixture was poured into ice-cold 1 mol/L aqueous sodium hydroxide solution, and washed with ethyl acetate. The aqueous layer was separated, conc. hydrochloric acid was added thereto to adjust pH to 4 in an ice bath, and extracted with ethyl acetate. The organic layers were combined, washed successively with water and brine, dried over sodium sulfate. The solvent was distilled off and the obtained residue was purified by preparative thin-layer chromatography (available from Merck Co., 1.05744, 1 plate was used, developed by chloroform:methanol=10:1) to obtain 13.4 mg (0.0487 mmol, Yield: 43.9%) of 3-(1,1a,6,6a-tetrahydrocyclopropa[a]inden-5-yloxy)-6-chloro-4-pyridazinol (Compound No. 516).

$^1$H-NMR (200 MHz, CD$_3$OD) δ ppm: 7.25-7.05 (2H, m), 6.83 (1H, dd, J=6.6, 2.6 Hz), 6.67 (1H, s), 3.00 (1H, dd, J=17.2, 6.6 Hz), 2.78 (1H, d, J=17.2 Hz), 2.50-2.35 (1H, m), 2.00-1.80 (1H, m), 1.15-1.00 (1H, m), 0.10-0.00 (1H, m). Melting point (° C.): 211-213.

EXAMPLE 16

6-Chloro-3-(2-methoxy-5-methylphenoxy)-4-pyridazinol (Compound No. 704)

(1) 6-Chloro-3-(2-methoxy-5-methylphenoxy)pyridazine 1-oxide (Step B-2)

In a mixed solvent of 1,4-dioxane (3 mL) and dimethylsulfoxide (3 mL) was dissolved 167.5 mg (1.21 mmol) of commercially available 2-methoxy-5-methylphenol, and 142.8 mg (1.27 mmol) of potassium tert-butoxide was added to the solution, then 202.9 mg (1.23 mmol) of 3,6-dichloropyridazine 1-oxide was added to the mixture and the resulting mixture was stirred at room temperature overnight. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=2:1) to obtain 226.5 mg (0.849 mmol, Yield: 70.2%) of 6-chloro-3-(2-methoxy-5-methylphenoxy)pyridazine 1-oxide.

(2) 4,6-Dichloro-3-(2-methoxy-5-methylphenoxy)pyridazine (Step B-3)

In phosphorus oxychloride (1 mL) was dissolved 226.5 mg (0.849 mmol) of 6-chloro-3-(2-methoxy-5-methylphenoxy)-pyridazine 1-oxide obtained in (1), and the solution was stirred at room temperature overnight. To the reaction mixture were added water and methylene chloride, and after stirring for 30 minutes, it was extracted with methylene chloride. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=2:1) to obtain 205.3 mg (0.720 mmol, Yield: 84.8%) of 4,6-dichloro-3-(2-methoxy-5-methylphenoxy)pyridazine.

(3) 6-Chloro-3-(2-methoxy-5-methylphenoxy)-4-pyridazinol (Compound No. 704, Step B-4)

In a mixed solvent of 1,4-dioxane (5 mL) and dimethylsulfoxide (5 mL) was dissolved 205.3 mg (0.720 mmol) of 4,6-dichloro-3-(2-methoxy-5-methylphenoxy)pyridazine obtained in (2), and 1.8 mL (3.6 mmol) of 2 mol/L aqueous sodium hydroxide solution was added to the solution, and the resulting mixture was stirred at room temperature overnight. Water was added to the reaction mixture, diluted hydrochloric acid was added thereto to adjust pH to 2, and the mixture was extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate) to obtain 148.1 mg (0.555 mmol, Yield: 77.1%) of 6-chloro-3-(2-methoxy-5-methylphenoxy)-4-pyridazinol (Compound No. 704).
$^1$H-NMR (200 MHz, CD$_3$OD) δ ppm: 7.04-6.91 (3H, m), 6.66 (1H, s), 3.70 (3H, s), 2.27 (3H, s). Melting point (° C.): 126-134.

EXAMPLE 17

6-Chloro-3-{2-[1-(ethylsulfanyl)ethyl]-6-fluorophenoxy}-4-pyridazinol (Compound No. 728)

(1) 3-Fluoro-2-methoxybenzaldehyde

To an acetonitrile (50 mL) solution containing 3.01 g (21.5 mmol) of commercially available 3-fluoro-2-hydroxybenzaldehyde were added 5.92 g (42.8 mmol) of potassium carbonate and 6.66 mL (107 mmol) of methyl iodide, and the mixture was stirred at 90° C. for 3 hours. After allowing to stand at room temperature overnight, the reaction mixture was poured into water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 3.22 g of a crude product of 3-fluoro-2-methoxybenzaldehyde.

(2) 1-Fluoro-2-methoxy-3-vinylbenzene

Under nitrogen atmosphere, 273.2 mg (6.83 mmol) of 60% sodium hydride washed with hexane was suspended in dry dimethylsulfoxide (3 mL), and the suspension was stirred at 85° C. for 30 minutes, cooled to room temperature and then, in an ice bath, a dry dimethylsulfoxide (8 mL) solution containing 2.44 g (6.83 mmol) of methyl(triphenyl)phosphonium bromide was gradually added dropwise. After stirring at room temperature for 30 minutes, a dry dimethylsulfoxide (5 mL) solution containing 877.4 mg of a crude product of 3-fluoro-2-methoxybenzaldehyde obtained in (1) was added dropwise, and the mixture was stirred at room temperature for 30 minutes. The reaction mixture was poured into water, and extracted with ethyl acetate. The organic layer was washed successively with water and brine, and dried over anhydrous magnesium sulfate. The solvent was removed, and the obtained residue was purified by silica gel column chromatography (Wako gel C-100, hexane-ethyl acetate, gradient) to obtain 0.38 g (2.5 mmol) of 1-fluoro-2-methoxy-3-vinylbenzene.

(3) 1-Cyclopropyl-3-fluoro-2-methoxybenzene

Under nitrogen atmosphere, dry diethyl ether (5 mL) was charged in a dry flask, 9.20 mL (9.20 mmol) of diethyl-zinc (1 mol/L hexane solution) was then added dropwise, and a dry diethyl ether (10 mL) solution containing 0.56 g (3.7 mmol) of 1-fluoro-2-methoxy-3-vinylbenzene obtained in (2) was added dropwise thereto. After stirring at room temperature for 5 minutes, 1.48 mL (18.4 mmol) of diiodomethane was added dropwise thereto, and the resulting mixture was refluxed for 5 hours. After cooling to room temperature, 9.20 mL (9.20 mmol) of diethylzinc (1 mol/L hexane solution) and 1.48 mL (18.4 mmol) of diiodomethane were additionally added, and the resulting mixture was again refluxed for 4 hours. After allowing to stand at room temperature overnight, the reaction mixture was poured into a saturated aqueous ammonium chloride solution. To the mixture was added a saturated aqueous sodium hydrogen carbonate solution and after stirring for 30 minutes, and the mixture was extracted with diethyl ether. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 0.82 g of a crude product of 1-cyclopropyl-3-fluoro-2-methoxybenzene.

(4) 6-Chloro-3-{2-[1-(ethylsulfanyl)ethyl]-6-fluorophenoxy}pyridazine 1-oxide (Step B-2)

Under nitrogen atmosphere, 288.8 mg (7.22 mmol) of 60% sodium hydride was suspended in dry N,N-dimethylformamide (3 mL), and 0.55 mL (7.5 mmol) of ethanethiol was gradually added dropwise to the suspension. After stirring for 15 minutes, a dry N,N-dimethylformamide (6 mL) solution containing 402.1 mg of a crude product of 1-cyclopropyl-3-fluoro-2-methoxybenzene obtained in (3) was added dropwise thereto, and the resulting mixture was stirred at 160° C. for 5 hours. After allowing to stand at room temperature overnight, 1 mol/L aqueous potassium hydroxide solution and diethyl ether were added to the reaction mixture. The aqueous layer was separated, washed with diethyl ether, and added thereto diluted hydrochloric acid to adjust pH to 2. The mixture was extracted with diethyl ether, ether extracts were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate: hexane=4:1) to obtain 299.9 mg of a mixture.
In a mixed solvent of 1,4-dioxane (3 mL) and dimethylsulfoxide (3 mL) was dissolved 152.7 mg of the mixture, 116.1 mg (1.03 mmol) of potassium tert-butoxide was added to the solution, then 162.6 mg (0.988 mmol) of 3,6-dichloropyridazine 1-oxide was added thereto, and the resulting mixture was stirred at room temperature over-night. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=2:1) to obtain 46.6 mg (0.144 mmol) of 6-chloro-3-{2-[1-(ethylsulfanyl)ethyl]-6-fluorophenoxy}pyridazine 1-oxide.

(5) 4,6-Dichloro-3-{2-[1-(ethylsulfanyl)ethyl]-6-fluorophenoxy}pyridazine (Step B-3)

A phosphorus oxychloride (0.5 mL) solution containing 46.6 mg (0.144 mmol) of 6-chloro-3-{2-[1-(ethylsulfanyl)-ethyl]-6-fluorophenoxy}pyridazine 1-oxide obtained in (4) was stirred at room temperature overnight. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 1 plate was used, developed by ethyl acetate:hexane=4:1) to obtain 9.8 mg (0.028 mmol, Yield: 19%) of 4,6-dichloro-3-{2-[1-(ethylsulfanyl)ethyl]-6-fluorophenoxy}pyridazine.

(6) 6-Chloro-3-{2-[1-(ethylsulfanyl)ethyl]-6-fluorophenoxy}-4-pyridazinol (Compound No. 728, Step B-4)

In a mixed solvent of 1,4-dioxane (1 mL) and dimethylsulfoxide (1 mL) was dissolved 9.8 mg (0.028 mmol) of 4,6-dichloro-3-{2-[1-(ethylsulfanyl)ethyl]-6-fluorophenoxy}pyridazine obtained in (5), 0.07 mL (0.14 mmol) of 2 mol/L aqueous sodium hydroxide solution was added to the solution, and the resulting mixture was stirred at room temperature overnight. The reaction mixture was poured into water, diluted hydrochloric acid was added thereto to adjust pH to 2, and the mixture was extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, 1 plate was used, developed by ethyl acetate) to obtain 2.2 mg (0.0067 mmol, Yield: 24%) of 6-chloro-3-{2-[1-(ethylsulfanyl)ethyl]-6-fluorophenoxy}-4-pyridazinol (Compound No. 728).

$^1$H-NMR (200 MHz, CD$_3$OD) δ ppm: 7.42 (1H, d, J=8.1 Hz), 7.26-7.15 (1H, m), 7.07-6.97 (1H, m), 6.46 (1H, s), 4.33 (1H, q, J=7.0 Hz), 2.42-2.20 (2H, m), 1.43 (3H, d, J=7.0 Hz), 1.02 (3H, t, J=7.0 Hz). Appearance: amorphous.

EXAMPLE 18

6-Chloro-3-(2-chloro-6-isopropylphenoxy)-4-pyridazinol (Compound No. 738)

(1) 1-Isopropyl-2-[(2-methoxyethoxy)methoxy]benzene

In dry tetrahydrofuran (60 mL) was suspended 4.80 g (120 mmol) of 60% sodium hydride, and a dry tetrahydrofuran (80 mL) solution containing 13.6 g (100 mmol) of 2-isopropylphenol was added dropwise to the suspension at 0° C. After stirring at 0° C. for 10 minutes, a dry tetrahydrofuran (80 mL) solution containing 14.9 g (119 mmol) of 2-methoxyethoxymethyl chloride was added dropwise thereto. The reaction mixture was stirred in an ice bath for 2 hours, poured into ice-cold water (250 mL), and extracted with ethyl acetate. The organic layers were combined, washed succeccively with 1 mol/L aqueous sodium hydroxide solution and brine, and dried over anhydrous sodium sulfate. The solvent was removed, and the residue was purified by silica gel column chromatography (eluted with hexane:ethyl acetate=50:1) to obtain 18.1 g (80.8 mmol, Yield: 80.8%) of 1-isopropyl-2-[(2-methoxyethoxy)methoxy]benzene.

(2) 1-Chloro-3-isopropyl-2-[(2-methoxyethoxy)methoxy]-benzene

In a dry ether (100 mL) was dissolved 8.00 g (35.7 mmol) of 1-isopropyl-2-[(2-methoxyethoxy)methoxy]benzene obtained in (1), and 34.4 mL (55.0 mmol) of n-butyl lithium-hexane solution (1.60M) was added to the solution in an ice bath (reaction solution temperature: 5-10° C.), and the mixture was stirred in an ice bath for 5 hours. To the mixture was passed through 2.51 g (35.4 mmol) of a chlorine gas while keeping the reaction solution temperature to 5-10° C. The reaction mixture was stirred in an ice bath for 1 hour, poured into 1 mol/L hydrochloric acid (300 mL), and extracted with ether. The organic layers were combined, dried over anhydrous sodium sulfate, and the solvent was removed. The residue was purified by silica gel column chromatography (eluted with hexane:ethyl acetate=100:1) to obtain 4.38 g (16.9 mmol, Yield: 47.3%) of 1-chloro-3-isopropyl-2-[(2-methoxyethoxy)methoxy]benzene.

(3) 2-Chloro-6-isopropylphenol

In dichloromethane (15 mL) was dissolved 4.38 g (16.9 mmol) of 1-chloro-3-isopropyl-2-[(2-methoxyethoxy)methoxy]-benzene obtained in (2), 2.70 g (23.7 mmol) of trifluoroacetic acid was added to the solution, and the resulting mixture was stirred at room temperature overnight. The reaction mixture was poured into 1 mol/L hydrochloric acid, and extracted with ethyl acetate. The organic layers were combined, and dried over anhydrous sodium sulfate. The solvent was removed, and the residue was purified by silica gel column chromatography (eluted with hexane) to obtain 2.50 g (14.7 mmol, Yield: 87.0%) of 2-chloro-6-isopropylphenol.

(4) 3-Chloro-6-(2-chloro-6-isopropylphenoxy)pyridazine (Step A-1)

1.98 g (17.7 mmol) of potassium tert-butoxide, 1,4-dioxane (100 mL) and 2.50 g (14.7 mmol) of 2-chloro-6-isopropylphenol obtained in (3) were mixed, and the mixture was stirred at room temperature for 20 minutes. To the mixture was added 2.18 g (14.6 mmol) of 3,6-dichloropyridazine and the mixture was refluxed for 4 hours. To the reaction mixture was further added 0.50 g (4.5 mmol) of potassium tert-butoxide, and the mixture was refluxed for further 3 hours. The reaction mixture was allowed to stand for cooling, poured into 1N hydrochloric acid (100 mL), and extracted with ethyl acetate. The organic layers were combined, washed successively with water and brine, and dried over anhydrous sodium sulfate. The solvent was removed, and the obtained residue was purified by silica gel column chromatography (hexane:ethyl acetate, gradient) to obtain 3.18 g (11.2 mmol, Yield: 76.2%) of 3-chloro-6-(2-chloro-6-isopropylphenoxy)pyridazine.

(5) Mixture of 6-chloro-3-(2-chloro-6-isopropylphenoxy)-pyridazine 1-oxide and 3-chloro-6-(2-chloro-6-isopropylphenoxy)pyridazine 1-oxide (Step C-1)

In dry dichloromethane (90 mL) was dissolved 3.17 g (11.2 mmol) of 3-chloro-6-(2-chloro-6-isopropylphenoxy)-pyridazine obtained in (4), 2.90 g (13.4-14.3 mmol) of 80-85% m-chloroperbenzoic acid was added to the solution, and the mixture was refluxed for 13 hours. The reaction mixture was poured into 1N aqueous sodium hydroxide solution, and extracted with ethyl acetate. The organic layers were combined, washed successively with water and brine, and dried over anhydrous sodium sulfate. The solvent was removed, and the obtained residue was purified by silica gel column chromatography (hexane:ethyl acetate, gradient) to obtain 2.82 g (9.43 mmol, Yield: 84.2%) of a mixture of 6-chloro-3-(2-chloro-6-isopropylphenoxy)pyridazine 1-oxide and 3-chloro-6-(2-chloro-6-isopropylphenoxy)pyridazine 1-oxide.

(6) Mixture of 4,6-dichloro-3-(2-chloro-6-isopropylphenoxy)pyridazine and 3,4-dichloro-6-(2-chloro-6-isopropylphenoxy)pyridazine (Step C-2)

2.80 g (9.36 mmol) of a mixture of 6-chloro-3-(2-chloro-6-isopropylphenoxy)pyridazine 1-oxide and 3-chloro-6-(2-chloro-6-isopropylphenoxy)pyridazine 1-oxide obtained in (5) was mixed with 17.5 mL (189 mmol) of phosphorus oxychloride, and the mixture was refluxed for 2 hours and 30 minutes. The reaction mixture was allowed to stand for cooling, poured into ice-cold water, and extracted with ethyl acetate. The organic layers were combined, washed successively with water and brine, and dried over anhydrous sodium sulfate. The solvent was removed, and the obtained residue was purified by silica gel column chromatography (hexane:ethyl acetate=20:1) to obtain 0.850 g (2.67 mmol, m.p. 90-91° C.) of 4,6-dichloro-3-(2-chloro-6-isopropylphenoxy)pyridazine, and 1.78 g (5.60 mmol) of a mixture of 4,6-dichloro-3-(2-chloro-6-isopropylphenoxy)pyridazine and 3,4-dichloro-6-(2-chloro-6-isopropylphenoxy)pyridazine.

(7) 6-Chloro-3-(2-chloro-6-isopropylphenoxy)-4-methoxypyridazine and 3-chloro-6-(2-chloro-6-isopropylphenoxy)-4-methoxypyridazine (Step C-3)

To methanol (10 mL) was added 0.080 g (3.5 mmol) of sodium, and the mixture was stirred at room temperature for 30 minutes. To the mixture was added 0.830 g (2.61 mmol) of 4,6-dichloro-3-(2-chloro-6-isopropylphenoxy)pyridazine obtained in (6), and the mixture was stirred at room temperature for 2 hours. The reaction mixture was poured into ice-cold water, and extracted with ethyl acetate. The organic layers were combined, dried over anhydrous sodium sulfate, and the solvent was removed. The obtained residue was purified by silica gel column chromatography (hexane: ethyl acetate=10:1), washed with hexane and crystallized to obtain 0.720 g (2.30 mmol, Yield: 88.1%) of 6-chloro-3-(2-chloro-6-isopropylphenoxy)-4-methoxypyridazine. On the other hand, 1.78 g (5.60 mmol) of the mixture of 4,6-dichloro-3-(2-chloro-6-isopropylphenoxy)pyridazine and 3,4-dichloro-6-(2-chloro-6-isopropylphenoxy)pyridazine was reacted in the same manner as mentioned above to obtain 1.25 g (3.99 mmol, Yield: 71.3%) of 6-chloro-3-(2-chloro-6-isopropylphenoxy)-4-methoxypyridazine and 0.300 g (0.958 mmol, Yield: 17.1%) of 3-chloro-6-(2-chloro-6-isopropylphenoxy)-4-methoxypyridazine.

(8) 6-Chloro-3-(2-chloro-6-isopropylphenoxy)-4-pyridazinol (Compound No. 738, Step C-4)

In dimethylsulfoxide (13 mL) was dissolved 1.46 g (4.66 mmol) of 6-chloro-3-(2-chloro-6-isopropylphenoxy)-4-methoxypyridazine obtained in (7), 3 mL (6.0 mmol) of 2 mol/L aqueous sodium hydroxide solution was added to the solution, and the resulting mixture was stirred at 80° C. for 3 hours. The reaction mixture was poured into water, and made acidic with hydrochloric acid. The precipitated solid was collected by filtration, washed with water, and air dried. 6-Chloro-3-(2-chloro-6-isopropylphenoxy)-4-pyridazinol (Compound No. 738) was obtained in an amount of 1.33 g (4.45 mmol, Yield: 95.5%).

$^1$H-NMR (60 MHz, DMSO-$d_6$) δ ppm: 7.40-7.05 (3H, m), 6.70 (1H, s), 2.98 (1H, septet, J=6.2 Hz), 1.13 (6H, d, J=6.2 Hz). Melting point (° C.): 218-233.

EXAMPLE 19

3-(2-Bromo-6-isopropylphenoxy)-6-chloro-4-pyridazinol (Compound No. 760)

(1) 1-Bromo-3-isopropyl-2-[(2-methoxyethoxy)methoxy]benzene

In dry ether (100 mL) was dissolved 5.18 g (23.1 mmol) of 1-isopropyl-2-[(2-methoxyethoxy)methoxy]benzene obtained in Example 18(1), 22.3 mL (35.7 mmol) of n-butyl lithium-hexane solution (1.60M) was added dropwise to the solution in an ice bath (reaction solution temperature: 5-10° C.), and the mixture was stirred in an ice bath for 5 hours. To the reaction mixture was added 8.20 g (69.7 mmol) of 90% cyanogen bromide while maintaining the reaction solution temperature to 5-10° C. The reaction mixture was stirred in an ice bath for 2 hours, poured into ice-cold water (300 mL), and extracted with ether. The organic layers were combined, dried over anhydrous sodium sulfate, and the solvent was removed. The residue was purified by silica gel column chromatography (eluted with hexane:ethyl acetate=100:1) to obtain 3.40 g (11.2 mmol, Yield: 48.5%) of 1-bromo-3-isopropyl-2-[(2-methoxyethoxy)-methoxy]benzene.

(2) 2-Bromo-6-isopropylphenol

In dichloromethane (10 mL) was dissolved 3.40 g (11.2 mmol) of 1-bromo-3-isopropyl-2-[(2-methoxyethoxy)methoxy]-benzene obtained in (1), 2.50 g (21.9 mmol) of trifluoroacetic acid was added to the solution, and the mixture was stirred at room temperature overnight. The reaction mixture was poured into 1 mol/L hydrochloric acid, and extracted with ethyl acetate. The organic layers were combined, and dried over anhydrous sodium sulfate. The solvent was removed, and the residue was purified by silica gel column chromatography (eluted with hexane) to obtain 2.27 g (10.6 mmol, Yield: 94.6%) of 2-bromo-6-isopropylphenol.

(3) 3-(2-Bromo-6-isopropylphenoxy)-6-chloropyridazine (Step A-1)

1.52 g (13.6 mmol) of potassium tert-butoxide, 1,4-dioxane (60 mL) and 2.27 g (10.6 mmol) of 2-bromo-6-isopropylphenol obtained in (2) were mixed, and the mixture was stirred at room temperature for 20 minutes. To the mixture was added 1.58 g (10.6 mmol) of 3,6-dichloropyridazine, and the resulting mixture was refluxed for 7 hours and 20 minutes. The reaction mixture was allowed to stand for cooling, poured into ice-cold water (110 mL), and extracted with ethyl acetate. The organic layers were combined, washed with brine, and dried over anhydrous sodium sulfate. The solvent was removed, the obtained residue was recrystallized (from isopropyl ether), then, purified by silica gel column chromatography (hexane:ethyl acetate, gradient) to obtain 2.68 g (8.17 mmol, Yield: 77.1%) of 3-(2-bromo-6-isopropylphenoxy)-6-chloropyridazine.

(4) Mixture of 3-(2-bromo-6-isopropylphenoxy)-6-chloropyridazine 1-oxide and 6-(2-bromo-6-isopropylphenoxy)-3-chloropyridazine 1-oxide (Step C-1)

In dry dichloromethane (35 mL) was dissolved 2.68 g (8.17 mmol) of 3-(2-bromo-6-isopropylphenoxy)-6-chloropyridazine obtained in (3), 2.12 g (9.80-10.4 mmol) of 80-85% m-chloroperbenzoic acid was added to the solution, and the mixture was refluxed for 12 hours and 30 minutes. The reaction mixture was poured into 1 mol/L aqueous sodium hydroxide solution, and extracted with ethyl acetate. The organic layers were combined, washed with brine, and dried over anhydrous sodium sulfate. The solvent was removed, and the obtained residue was purified by silica gel column chromatography (hexane:ethyl acetate=5:1) to obtain 2.26 g (6.57 mmol, Yield: 80.4%) of a mixture of 3-(2-bromo-6-isopropylphenoxy)-6-chloropyridazine 1-oxide and 6-(2-bromo-6-isopropylphenoxy)-3-chloropyridazine 1-oxide.

(5) Mixture of 3-(2-bromo-6-isopropylphenoxy)-4,6-dichloropyridazine and 6-(2-bromo-6-isopropylphenoxy)-3,4-dichloropyridazine (Step C-2)

A mixture of 2.14 g (6.22 mmol) of 3-(2-bromo-6-isopropylphenoxy)-6-chloropyridazine 1-oxide and 6-(2-bromo-6-isopropylphenoxy)-3-chloropyridazine 1-oxide obtained in (4) was mixed with 11.6 mL (125 mmol) of phosphorus oxychloride, and the resulting mixture was refluxed for 3 hours. The reaction mixture was cooled by allowing to stand, poured into ice-cold water, and extracted with ethyl acetate. The organic layers were combined, washed successively with 1 mol/L of an aqueous sodium hydroxide solution, water and brine, and dried over anhydrous sodium sulfate. The solvent was removed, and the obtained residue was purified by silica gel column chromatography (hexane:ethyl acetate=20:1) to obtain 2.22 g (6.13 mmol, Yield: 98.6%) of a mixture of 3-(2-bromo-6-isopropylphenoxy)-4,6-dichloropyridazine and 6-(2-bromo-6-isopropylphenoxy)-3,4-dichloropyridazine.

(6) 3-(2-Bromo-6-isopropylphenoxy)-6-chloro-4-methoxypyridazine (Step-C-3)

To methanol (20 mL) was added 0.180 g (7.8 mmol) of sodium, and the mixture was stirred at room temperature for 30 minutes. To the mixture was added 2.22 g (6.13 mmol) of a mixture of 3-(2-bromo-6-isopropylphenoxy)-4,6-dichloropyridazine and 6-(2-bromo-6-isopropylphenoxy)-3,4-dichloropyridazine obtained in (5) and the resulting mixture was stirred at room temperature for 4 hours. The reaction mixture was poured into ice-cold water, and extracted with ethyl acetate. The organic layers were combined, washed with brine, and dried over anhydrous sodium sulfate. The solvent was removed, and the obtained residue was purified by silica gel column chromatography (hexane:ethyl acetate=15:1), and washed with hexane to crystallize to obtain 1.48 g (4.13 mmol, Yield: 67.4%) of 3-(2-bromo-6-isopropylphenoxy)-6-chloro-4-methoxypyridazine. Also, 0.21 g (0.59 mmol, Yield: 9.6%) of 6-(2-bromo-6-isopropylphenoxy)-3-chloro-4-methoxypyridazine was simultaneously obtained.

(7) 3-(2-Bromo-6-isopropylphenoxy)-6-chloro-4-pyridazinol (Compound No. 760, Step C-4)

In dimethylsulfoxide (10 mL) was dissolved 0.72 g (2.0 mmol) of 3-(2-bromo-6-isopropylphenoxy)-6-chloro-4-methoxypyridazine obtained in (6), an aqueous sodium hydroxide solution (prepared by dissolving 100 mg of sodium hydroxide in 1.5 mL of water, 2.4 mmol) was added to the solution, and the resulting mixture was stirred at 80° C. for 3 hours. The reaction mixture was poured into water, and made acidic by hydrochloric acid. The precipitated solid was collected by filtration, washed with water, and air-dried. Thus, 0.56 g (1.6 mmol, Yield: 80%) of 3-(2-bromo-6-isopropylphenoxy)-6-chloro-4-pyridazinol (Compound No. 760) was obtained.

$^1$H-NMR (60 MHz, DMF-$d_7$) δ ppm: 7.70-7.00 (3H, m), 6.89 (1H, s), 2.94 (1H, septet, J=7.0 Hz), 1.16 (6H, d, J=7.0 Hz). Melting point (° C.): 232-253 (dec.).

EXAMPLE 20

3-(2-Bromo-6-tert-butylphenoxy)-6-chloro-4-pyridazinol (Compound No. 761)

(1) tert-Butyl-2-[(2-methoxyethoxy)methoxy]benzene

In dry tetrahydrofuran (25 mL) was suspended 4.80 g (120 mmol) of 60% sodium hydride, and a dry tetrahydrofuran (80 mL) solution containing 15.0 g (100 mmol) of 2-tert-butylphenol was added dropwise to this suspension at 0° C. After stirring the mixture at 0° C. for 10 minutes, a dry tetrahydrofuran (80 mL) solution containing 14.9 g (119 mmol) of 2-methoxyethoxymethyl chloride was added dropwise to the mixture. The reaction mixture was stirred in an ice bath for 4 hours and 30 minutes, and allowed to stand at room temperature overnight. To the reaction mixture were further added 1.20 g (30 mmol) of 60% sodium hydride and 3.8 g (30 mmol) of 2-methoxyethoxymethyl chloride at 0° C., and the mixture was stirred at 0° C. for 7 hours. The reaction mixture was poured into ice-cold water (250 mL), and extracted with ethyl acetate. The organic layers were combined, washed with 2N aqueous sodium hydroxide solution and brine, and dried over anhydrous sodium sulfate. The solvent was removed, and the residue was purified by silica gel column chromatography (eluted with hexane:ethyl acetate=20:1) to obtain 19.7 g (82.8 mmol, Yield: 82.8%) of tert-butyl-2-[(2-methoxyethoxy)methoxy]benzene.

(2) 1-Bromo-3-tert-butyl-2-[(2-methoxyethoxy)methoxy]-benzene

In dry ether (120 mL) was dissolved 10.0 g (42.0 mmol) of tert-butyl-2-[(2-methoxyethoxy)methoxy]benzene obtained in (1), 42.1 mL (64.4 mmol) of n-butyl lithium-hexane solution (1.53M) was added dropwise to the solution in an ice bath, and the mixture was stirred in an ice bath for 3 hours. To the mixture was added dropwise a dry ether (20 mL) solution containing 14.8 g (126 mmol) of 90% cyanogen bromide. The reaction mixture was stirred in an ice bath for 3 hours, poured into ice-cold water (300 mL), and extracted with ether. The organic layers were combined, washed with brine, and dried over anhydrous sodium sulfate. The solvent was removed, and the residue was purified by silica gel column chromatography (eluted with hexane:ethyl acetate=20:1) to obtain 8.48 g (26.8 mmol, Yield: 63.8%) of 1-bromo-3-tert-butyl-2-[(2-methoxyethoxy)methoxy]benzene.

(3) 2-Bromo-6-tert-butylphenol

In dichloromethane (30 mL) was dissolved 8.38 g (26.4 mmol) of 1-bromo-3-tert-butyl-2-[(2-methoxyethoxy)methoxy]-benzene obtained in (2), a dichloromethane (20 mL) solution containing 9.03 g (79.2 mmol) of trifluoroacetic acid was added to the solution, and the mixture was stirred at room temperature overnight. The reaction mixture was poured into ice-cold 1 mol/L of hydrochloric acid, and extracted with ethyl acetate. The organic layers were combined, washed with brine, and dried over anhydrous sodium sulfate. The solvent was removed, and the residue was purified by silica gel column chromatography (eluted with hexane) to obtain 5.68 g (24.8 mmol, Yield: 93.9%) of 2-bromo-6-tert-butylphenol.

(4) 3-(2-Bromo-6-tert-butylphenoxy)-6-fluoropyridazine (Step A-1)

In 1,4-dioxane (40 mL) was dissolved 4.84 g (21.1 mmol) of 2-bromo-6-tert-butylphenol obtained in (3), 3.55 g (31.7 mmol) of potassium tert-butoxide and 1,4-dioxane (40 mL) were added to the solution, and the mixture was stirred at room temperature for 15 minutes. To the mixture was added 2.45 g (21.1 mmol) of 3,6-difluoropyridazine and the resulting mixture was refluxed for 24 hours with stirring. The reaction mixture was allowed to stand for cooling, poured into ice-cold water, and extracted with ethyl acetate. The organic layers were combined, washed with brine, and dried over anhydrous sodium sulfate. The solvent was removed, and the obtained residue was purified by silica gel column chromatography (hexane: ethyl acetate, gradient) to obtain 1.70 g (5.23 mmol, Yield: 24.8%) of 3-(2-bromo-6-tert-butylphenoxy)-6-fluoropyridazine.

(5) 6-(2-Bromo-6-tert-butylphenoxy)-3-pyridazinol 1.04 g (10.6 mmol) of potassium acetate was added to a mixture of acetic acid (9 mL) and 1.70 g (5.23 mmol) of 3-(2-bromo-6-tert-butylphenoxy)-6-fluoropyridazine obtained in (4), and the resulting mixture was stirred at 130-140° C. for 3 hours. The reaction mixture was allowed to stand for cooling, poured into ice-cold water, and extracted with ethyl acetate. The organic layers were combined, washed with brine, and dried over anhydrous sodium sulfate. The solvent was removed, and the obtained residue was washed with benzene to obtain 1.54 g (4.77 mmol, Yield: 91.2%, m.p. 255-257° C.) of 6-(2-bromo-6-tert-butylphenoxy)-3-pyridazinol.

(6) 3-(2-Bromo-6-tert-butylphenoxy)-6-chloropyridazine 1.54 g (4.77 mmol) of 6-(2-bromo-6-tert-butylphenoxy)-3-pyridazinol obtained in (5) was mixed with 15 mL (162 mmol) of phosphorus oxychloride, and the mixture was refluxed for 70 minutes. Phosphorus oxychloride was removed from the reaction mixture by distillation, the reaction mixture was poured into ice-cold water, and extracted with ethyl acetate. The organic layers were combined, washed with brine, and dried over anhydrous sodium sulfate. The solvent was removed to obtain 1.55 g (4.53 mmol, Yield: 95.0%) of 3-(2-bromo-6-tert-butylphenoxy)-6-chloropyridazine.

(7) Mixture of 3-(2-bromo-6-tert-butylphenoxy)-6-chloropyridazine 1-oxide and 6-(2-bromo-6-tert-butylphenoxy)-3-chloropyridazine 1-oxide (Step C-1)

In dry dichloromethane (20 mL) was dissolved 1.42 g (4.15 mmol) of 3-(2-bromo-6-tert-butylphenoxy)-6-chloropyridazine obtained in (6), a dry dichloromethane (10 mL) solution containing 1.08 g (4.99 mmol) of 80% m-chloroperbenzoic acid was added to the solution, and the mixture was refluxed for 20 hours. To the reaction mixture was additionally added 0.275 g (1.27 mmol) of 80% m-chloroperbenzoic acid, and after refluxing for 3 hours and 30 minutes, the reaction mixture was poured into 1 mol/L aqueous sodium hydroxide solution, and extracted with ethyl acetate. The organic layers were combined, washed with brine, and dried over anhydrous sodium sulfate. The solvent was removed, and the obtained residue was purified by silica gel column chromatography (hexane: ethyl acetate=10:1) to obtain 0.704 g (1.97 mmol, Yield: 47.5%) of a mixture of 3-(2-bromo-6-tert-butylphenoxy)-6-chloropyridazine 1-oxide and 6-(2-bromo-6-tert-butylphenoxy)-3-chloropyridazine 1-oxide.

(8) 3-(2-Bromo-6-tert-butylphenoxy)-4,6-dichloropyridazine and 6-(2-bromo-6-tert-butylphenoxy)-3,4-dichloropyridazine (Step C-2)

0.704 g (1.97 mmol) of a mixture of 3-(2-bromo-6-tert-butylphenoxy)-6-chloropyridazine 1-oxide and 6-(2-bromo-6-tert-butylphenoxy)-3-chloropyridazine 1-oxide obtained in (7) was mixed with 5 mL (54 mmol) of phosphorus oxychloride, and the resulting mixture was refluxed for 2 hours. The reaction mixture was allowed to stand for cooling, poured into ice-cold water, and extracted with ethyl acetate. The organic layers were combined, washed with brine, and dried over anhydrous sodium sulfate. The solvent was removed, and the obtained residue was purified by silica gel column chromatography (hexane:ethyl acetate=20:1) to obtain 0.474 g (1.26 mmol, Yield: 64.0%) of 3-(2-bromo-6-tert-butylphenoxy)-4,6-dichloropyridazine and 0.119 g (0.316 mmol, Yield: 16.0%) of 6-(2-bromo-6-tert-butylphenoxy)-3,4-dichloropyridazine.

(9) 3-(2-Bromo-6-tert-butylphenoxy)-6-chloro-4-methoxypyridazine (Step C-3)

In methanol (10 mL) was dissolved 0.443 g (1.18 mmol) of 3-(2-bromo-6-tert-butylphenoxy)-4,6-dichloropyridazine obtained in (8), and 0.545 g (2.83 mmol) of 28% sodium methoxide-methanol solution and methanol (5 mL) were added to the solution, and the resulting mixture was stirred at room temperature for 80 minutes. To the reaction mixture was additionally added 0.10 g (0.52 mmol) of 28% sodium methoxide-methanol solution, after stirring at room temperature for 2 hours, 0.15 g (0.78 mmol) of 28% sodium methoxide-methanol solution was further additionally added to the mixture and the resulting mixture was stirred at room temperature overnight. The reaction mixture was poured into ice-cold water, and extracted with ethyl acetate. The organic layers were combined, washed with brine, and dried over anhydrous sodium sulfate. The solvent was removed to obtain 0.428 g (1.15 mmol, Yield: 97.5%) of 3-(2-bromo-6-tert-butylphenoxy)-6-chloro-4-methoxypyridazine:

(10) 3-(2-Bromo-6-tert-butylphenoxy)-6-chloro-4-pyridazinol (Compound No. 761, Step C-4)

In dimethylsulfoxide (5 mL) was dissolved 0.395 g (1.06 mmol) of 3-(2-bromo-6-tert-butylphenoxy)-6-chloro-4-methoxypyridazine obtained in (9), aqueous sodium hydroxide solution (prepared by dissolving 50.8 mg of sodium hydroxide in 3 mL of water, 1.27 mmol) was added to the solution, and the resulting mixture was stirred at 80° C. for 3 hours. Aqueous sodium hydroxide solution (prepared by dissolving 42 mg of sodium hydroxide in 3 mL of water, 1.1 mmol) and dimethylsulfoxide (10 mL) were additionally added thereto, and the mixture was further stirred at 80° C. for 5 hours. After cooling by allowing to stand, the reaction mixture was poured into ice-cold water, and made acidic by hydrochloric acid. The precipitated solid was collected by filtration, washed successively with water, hexane and isopropyl ether, and air-dried. 0.309 g (0.863 mmol, Yield: 81.4%) of 3-(2-bromo-6-tert-butylphenoxy)-6-chloro-4-pyridazinol (Compound No. 761) was obtained.

$^1$H-NMR (270 MHz, CDCl$_3$) δ ppm: 9.55 (1H, brs), 7.47 (1H, dd, J=8.1, 1.7 Hz), 7.41 (1H, dd, J=8.1, 1.7 Hz), 7.08 (1H, t, J=8.1 Hz), 6.58 (1H, brs), 1.34 (9H, s). Melting point (° C.): 240-247.

EXAMPLE 21

6-Chloro-3-(2,6-dimethylphenoxy)-4-pyridazinol (Compound No. 801)

(1) 6-Chloro-3-(2,6-dimethylphenoxy)pyridazine 1-oxide (Step B-2)

268 mg (2.20 mmol) of 2,6-dimethylphenol, 1,4-dioxane (3 mL) and dimethylsulfoxide (3 mL) were mixed, 270 mg (2.41 mmol) of potassium tert-butoxide was added to the mixture in an ice bath, and the resulting mixture was stirred for 10 minutes. To the mixture was added 370 mg (2.24 mmol) of 3,6-dichloropyridazine 1-oxide, and the resulting mixture was stirred at room temperature for 10 hours and allowed to stand for 2 days. The reaction mixture was poured into ice-cold water, and extracted with ethyl acetate. The organic layers were combined, washed successively with water and brine, and dried over anhydrous sodium sulfate. The solvent was removed, and the residue was purified by silica gel column chromatography (hexane: ethyl acetate, gradient) to obtain 350 mg (1.39 mmol, Yield: 63.1%) of 6-chloro-3-(2,6-dimethylphenoxy)pyridazine 1-oxide.

(2) 4,6-Dichloro-3-(2,6-dimethylphenoxy)pyridazine (Step B-3)

330 mg (1.31 mmol) of 6-chloro-3-(2,6-dimethylphenoxy)pyridazine 1-oxide obtained in (1) was mixed with dichloromethane (0.6 mL) and phosphorus oxychloride 0.60 mL (6.5 mmol), and the mixture was stirred for 1 hour and allowed to stand for further 5 days. The reaction mixture was poured into ice-cold water, and extracted with ethyl acetate. The organic layers were combined, washed successively with water and brine, and dried over anhydrous sodium sulfate. The solvent was removed, and the residue was purified by silica gel column chromatography (hexane: ethyl acetate, gradient) to obtain 322 mg (1.20 mmol, Yield: 91.6%) of 4,6-dichloro-3-(2,6-dimethylphenoxy)-pyridazine.

(3) 6-Chloro-3-(2,6-dimethylphenoxy)-4-pyridazinol (Compound No. 801, Step B-4)

In dimethylsulfoxide (8 mL) was dissolved 300 mg (1.12 mmol) of 4,6-dichloro-3-(2,6-dimethylphenoxy)-pyridazine obtained in (2), 0.80 mL (2.0 mmol) of 10% (W/V) aqueous sodium hydroxide solution was added to the solution, and the resulting mixture was stirred at room temperature overnight. To the mixture was further added. 0.80 mL (2.0 mmol) of 10% (W/V) aqueous sodium hydroxide solution, and after disappearance of the starting materials, the reaction mixture was poured into ice-cold water. The mixture was made acidic with hydrochloric acid, and then, extracted with ethyl acetate. The organic layers were combined, washed successively with water and brine, and dried over anhydrous sodium sulfate. The solvent was removed, and the residue was purified by silica gel column chromatography (hexane:ethyl acetate, gradient) and purified by preparative thin-layer chromatography (available from Merck Co., 1.05744, developed by dichloromethane: methanol=9:1) to obtain 128 mg (0.510 mmol, Yield: 45.5%) of 6-chloro-3-(2,6-dimethylphenoxy)-4-pyridazinol (Compound No. 801).

$^1$H-NMR (200 MHz, DMSO-d$_6$) δ ppm: 7.18-7.05 (3H, m), 6.83 (1H, s), 2.05 (6H, s). Melting point (° C.): 214-215.

EXAMPLE 22

3-(2-tert-Butyl-6-methylphenoxy)-6-chloro-4-pyridazinol (Compound No. 805)

(1) 3-(2-tert-Butyl-6-methylphenoxy)-6-chloropyridazine (Step A-1)

17.5 g (107 mmol) of 2-tert-butyl-6-methylphenol, 11.9 g (106 mmol) of potassium tert-butoxide and 1,4-dioxane (250 mL) were mixed, and the mixture was stirred at room temperature for 30 minutes. To the mixture was added 15.0 g (101 mmol) of 2,6-dichloropyridazine and the resulting mixture was stirred at 100° C. for 3 hours and 15 minutes. The reaction mixture was poured into ice water, and extracted with ethyl acetate. The organic layer was washed successively with water and brine, and dried over anhydrous sodium sulfate. The solvent was removed, and the residue was crystallized form isopropyl ether to obtain 15.3 g (55.2 mmol, Yield: 54.6%) of 3-(2-tert-butyl-6-methylphenoxy)-6-chloropyridazine.

(2) 3-(2-tert-Butyl-6-methylphenoxy)-6-chloropyridazine 1-oxide (Step C-1)

8.00 g (28.9 mmol) of 3-(2-tert-butyl-6-methylphenoxy)-6-chloropyridazine obtained in (1) was mixed with dry dichloromethane (200 mL) and 8.50 g (34.4 mmol) of 70% m-chloroperbenzoic acid, and the mixture was stirred at room temperature for 4 days. The reaction mixture was poured into an ice-coled saturated aqueous sodium sulfite solution, and extracted with dichloromethane. The organic layers were combined, washed successively with water and brine, and dried over anhydrous sodium sulfate. The solvent was removed, and the residue was crystallized from a mixed solvent of ether-hexane or purified by silica gel column chromatography to obtain 7.04 g (24.0 mmol, Yield: 83.0%) of 3-(2-tert-butyl-6-methylphenoxy)-6-chloropyridazine 1-oxide.

(3) 3-(2-tert-Butyl-6-methylphenoxy)-4,6-dichloropyridazine (Step C-2)

1.00 g (3.41 mmol) of 3-(2-tert-butyl-6-methylphenoxy)-6-chloropyridazine 1-oxide obtained in (2) was mixed with chloroform (10 mL) and 0.48 mL (5.2 mmol) of phosphorus oxychloride, and the mixture was stirred under reflux for 24 hours and at room temperature for 2 days. The reaction mixture was poured into ice-cold water, and extracted with dichloromethane. The organic layers were combined, washed successively with a saturated aqueous sodium hydrogen carbonate solution, water and brine, and dried over anhydrous sodium sulfate. The solvent was removed and the residue was crystallized from a mixed solvent of ether-hexane to obtain 0.767 g (2.47 mmol, Yield: 72.4%) of 3-(2-tert-butyl-6-methylphenoxy)-4,6-dichloropyridazine.

(4) 3-(2-tert-Butyl-6-methylphenoxy)-6-chloro-4-pyridazinol (Compound No. 805, Step C-3)

354 mg (1.14 mmol) of 3-(2-tert-butyl-6-methylphenoxy)-4,6-dichloropyridazine obtained in (3) was mixed with dimethylsulfoxide (10 mL) and 1.6 mL (1.6 mmol) of 1 mol/L aqueous sodium hydroxide solution, and the mixture was stirred at room temperature for 2 hours and 30 minutes. The reaction mixture was poured into ice-cold water, and washed with ether. The aqueous layer was made acidic with hydrochloric acid, and extracted with ethyl acetate. The organic layer was washed with brine, and dried over anhydrous sodium sulfate. The solvent was removed, and the residue was crystallized from a mixed solvent of ether-hexane to obtain 172 mg (0.587 mmol, Yield: 51.5%) of 3-(2-tert-butyl-6-methylphenoxy)-6-chloro-4-pyridazinol (Compound No. 805).
$^1$H-NMR (90 MHz, CDCl$_3$) δ ppm: 7.35-6.80 (3H, m), 6.50 (1H, s), 1.80 (3H, s), 1.18 (9H, s). Melting point (° C.): 135-136.

EXAMPLE 23

6-Chloro-3-(2-cyclopropyl-6-methylphenoxy)-4-pyridazinol (Compound No. 806)

(1) 6-Chloro-3-(2-cyclopropyl-6-methylphenoxy)pyridazine 1-oxide and 3-chloro-6-(2-cyclopropyl-6-methylphenoxy)pyridazine 1-oxide (Step B-2)

221 mg (1.49 mmol) of 2-cyclopropyl-6-methylphenol was mixed with 1,4-dioxane (2 mL) and dimethylsulfoxide (2 mL), 184 mg (1.64 mmol) of potassium tert-butoxide was added to the mixture in an ice bath, and the resulting mixture was stirred for 10 minutes. To the mixture was added 258 mg (1.56 mmol) of 3,6-dichloropyridazine 1-oxide, and the resulting mixture was stirred at room temperature for 10 hours, and then, allowed to stand for 3 days. The reaction mixture was poured into ice-cold water, and extracted with ethyl acetate. The organic layers were combined, washed successively with water and brine, and dried over anhydrous sodium sulfate. The solvent was removed, and the residue was purified by silica gel column chromatography (hexane:ethyl acetate, gradient) to obtain 222 mg (0.801 mmol, Yield: 53.8%) of a mixture of 6-chloro-3-(2-cyclopropyl-6-methylphenoxy)pyridazine 1-oxide and 3-chloro-6-(2-cyclopropyl-6-methylphenoxy)pyridazine 1-oxide.

(2) 4,6-Dichloro-3-(2-cyclopropyl-6-methylphenoxy)-pyridazine (Step B-3)

In chloroform (1 mL) was dissolved 210 mg (0.758 mmol) of a mixture of 6-chloro-3-(2-cyclopropyl-6-methylphenoxy)pyridazine 1-oxide and 3-chloro-6-(2-cyclopropyl-6-methylphenoxy)pyridazine 1-oxide obtained in (1), 0.106 mL (1.14 mmol) of phosphorus oxychloride was added to the mixture, and after removing almost all the chloroform with a nitrogen-stream, the mixture was stirred at room temperature for 2 days. Further, chloroform (2 mL) and 0.150 mL (1.62 mmol) of phosphorus oxychloride were added to the mixture, and after removing almost all the chloroform with a nitrogen stream, the mixture was stirred for 3 hours. The reaction mixture was poured into ice-cold water, and extracted with ethyl acetate. The organic layers were combined, washed successively with water, brine, and dried over anhydrous sodium sulfate. The solvent was removed, and the residue was purified by silica gel column chromatography (hexane:ethyl acetate, gradient) to obtain 167 mg (0.566 mmol, Yield: 74.7%) of 4,6-dichloro-3-(2-cyclopropyl-6-methylphenoxy)pyridazine.

(3) 6-Chloro-3-(2-cyclopropyl-6-methylphenoxy)-4-pyridazinol (Compound No. 806, Step B-4)

In dimethylsulfoxide (3 mL) was dissolved 150 mg (0.508 mmol) of 4,6-dichloro-3-(2-cyclopropyl-6-methylphenoxy)pyridazine obtained in (2), 0.37 mL (0.925 mmol) of 10% (W/V) aqueous sodium hydroxide solution was added to the solution, and the mixture was stirred at room temperature for 4 days. The reaction mixture was poured into an ice-coled 5% aqueous sodium hydroxide solution, and extracted with ether. The aqueous layer was made acidic with hydrochloric acid, and extracted with ether. The organic layer was dried and concentrated. The residue was purified by preparative thin-layer chromatography (available from Merck Co., 1.05744, developed by dichloromethane: methanol=20:1) to obtain 114 mg (0.412 mmol, Yield: 81.1%) of 6-chloro-3-(2-cyclopropyl-6-methylphenoxy)-4-pyridazinol (Compound No. 806).
$^1$H-NMR (200 MHz, DMSO-d$_6$) δ ppm: 7.13-7.03 (2H, m), 6.84-6.79 (2H, m), 2.06 (3H, s), 1.83-1.68 (1H, m), 0.82-0.72 (2H, m), 0.64-0.51 (2H, m). Melting point (° C.): 201-202.

EXAMPLE 24

6-Chloro-3-[2-(2,2-dichlorocyclopropyl)-6-methylphenoxy]-4-pyridazinol (Compound No. 827)

(1) 1-(2,2-Dichlorocyclopropyl)-2-methoxy-3-methylbenzene

In chloroform (12 mL) was dissolved 304 mg (2.05 mmol) of 2-methoxy-1-methyl-3-vinylbenzene, 5 mL (63 mmol) of 50% aqueous sodium hydroxide solution was added dropwise to the solution, then, 59.9 mg (0.263 mmol) of benzyl-(triethyl)ammonium chloride was added to the mixture, and the resulting mixture was stirred at room temperature overnight. The reaction mixture was poured into water, and extracted with chloroform. The organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by hexane:ethyl acetate=4:1) to obtain 390 mg (1.69 mmol, Yield: 82.4%) of 1-(2,2-dichlorocyclopropyl)-2-methoxy-3-methylbenzene.

(2) 2-(2,2-Dichlorocyclopropyl)-6-methylphenol

In dichloromethane (5 mL) was dissolved 102 mg (0.442 mmol) of 1-(2,2-dichlorocyclopropyl)-2-methoxy-3-methylbenzene obtained in (1), the solution was cooled in an ice bath, and 0.045 mL (0.47 mmol) of boron tribromide was added dropwise to the solution with stirring. The reaction mixture was stirred in an ice bath for 2 hours, and then, poured into water and extracted with dichloromethane. The organic layer was successively washed with water and brine, and dried over anhydrous magnesium sulfate. The solvent was distilled off and the obtained residue was purified by preparative thin-layer chromatography (available from MERCK CO., 1.05744, 2 plates were used, developed by hexane:ethyl acetate=2:1) to obtain 76.9 mg (0.354 mmol, Yield: 80.1%) of 2-(2,2-dichlorocyclopropyl)-6-methylphenol.

(3) 6-Chloro-3-[2-(2,2-dichlorocyclopropyl)-6-methylphenoxy]pyridazine 1-oxide (Step B-2)

198 mg (0.912 mmol) of 2-(2,2-dichlorocyclopropyl)-6-methylphenol obtained in (2) was mixed with 1,4-dioxane (3 mL) and dimethylsulfoxide (3 mL), 113 mg (1.01 mmol) of potassium tert-butoxide was added to the mixture in an ice bath, and the resulting mixture was stirred for 10 minutes.

To the mixture was added 151 mg (0.915 mmol) of 3,6-dichloropyridazine 1-oxide, and the resulting mixture was stirred at room temperature overnight. The reaction mixture was poured into ice-cold water, and extracted with ethyl acetate. The organic layers were combined, washed successively with water and brine, and dried over anhydrous magnesium sulfate. The solvent was distilled off and the residue was purified by preparative thin-layer chromatography (available from MERCK CO., 1.05744, 3 plates were used, developed by hexane:ethyl acetate=2:1 three times) to obtain 257 mg of a crude product of 6-chloro-3-[2-(2,2-dichlorocyclopropyl)-6-methylphenoxy]pyridazine 1-oxide.

(4) 4,6-Dichloro-3-[2-(2,2-dichlorocyclopropyl)-6-methylphenoxy]pyridazine (Step B-3)

257 mg of a crude product of 6-chloro-3-[2-(2,2-dichlorocyclopropyl)-6-methylphenoxy]pyridazine 1-oxide obtained in (3) was mixed with phosphorus oxychloride (3 mL), and the mixture was stirred at room temperature overnight. To the reaction mixture were added water and dichloromethane, and the resulting mixture was stirred for 30 minutes. This mixture was separated, the organic layer was successively washed with water and brine, and dried over anhydrous magnesium sulfate. The solvent was distilled off and the residue was purified by preparative thin-layer chromatography (available from MERCK CO., 1.05744, 3 plates were used, developed by hexane:ethyl acetate=2:1) to obtain 209 mg (0.574 mmol, Yield from 2-(2,2-dichlorocyclopropyl)-6-methylphenol with 2 Steps: 62.9%) of 4,6-dichloro-3-[2-(2,2-dichlorocyclopropyl)-6-methylphenoxy]pyridazine.

(5) 6-Chloro-3-[2-(2,2-dichlorocyclopropyl)-6-methylphenoxy]-4-pyridazinol (Compound No. 827, Step B-4)

209 mg (0.574 mmol)-of 4,6-dichloro-3-[2-(2,2-dichlorocyclopropyl)-6-methylphenoxy]pyridazine obtained in (4) was mixed with 1,4-dioxane (3 mL) and dimethylsulfoxide (3 mL), 1.43 mL (2.86 mmol) of 2 mol/L aqueous sodium hydroxide solution was added to the mixture, and the resulting mixture was stirred at room temperature over-night. The reaction mixture was poured into water, and made acidic with diluted hydrochloric acid. This mixture was extracted with dichloromethane. The organic layers were combined, washed successively with water and brine, and dried over anhydrous magnesium sulfate. The solvent was distilled off and the residue was purified by preparative thin-layer chromatography (available from MERCK CO., 1.05744, 3 plates were used, developed by ethyl acetate) to obtain 120 mg (0.349 mmol, Yield: 60.8%) of 6-chloro-3-[2-(2,2-dichlorocyclopropyl)-6-methylphenoxy]-4-pyridazinol (Compound No. 827).

$^1$H-NMR (200 MHz, CD$_3$OD) δ ppm: 7.25 (1H, br.d, J=6.3 Hz), 7.16 (1H, t, J=7.7 Hz), 6.98 (1H, d, J=7.7 Hz), 6.72 (1H, s), 2.85 (1H, dd, J=10.6, 8.8 Hz), 2.22 (3H, s), 2.05-1.86 (2H, m). Melting point (° C.): 213-215.

EXAMPLE 25

6-Chloro-3-[(5-methyl-1-benzofuran-4-yl)oxy]-4-pyridazinol (Compound No. 1109)

(1) 6,7-Dihydro-1-benzofuran-4(5H)-one

In methanol (40 mL) was dissolved 11.2 g (0.100 mol) of 1,3-cyclohexanedione, an aqueous solution (8 mL) containing 6.60 g (0.100 mol) of 85% potassium hydroxide was added dropwise to the solution, and the resulting mixture was stirred at room temperature for 30 minutes. This mixture was cooled in an ice bath, 21.6 g (0.110 mol) of 40% chloroacetaldehyde aqueous solution was added to the mixture with stirring and the resulting mixture was stirred at room temperature overnight. To the reaction mixture was added dropwise 2 mol/L hydrochloric acid aqueous solution, and the resulting mixture was stirred at room temperature for 30 minutes and extracted with ether. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 8.63 g (0.0635 mol, Yield: 63.5%) of 6,7-dihydro-1-benzofuran-4(5H)-one.

(2) Methyl 4-oxo-4,5,6,7-tetrahydro-1-benzofuran-5-carboxylate

In dry tetrahydrofuran (10 mL) was dissolved 3.00 g (22.1 mmol) of 6,7-dihydro-1-benzofuran-4(5H)-one obtained in (1), and 48.5 mL (48.5 mmol) of lithium bis(trimethylsilyl)amide (1.0 M tetrahydrofuran solution) was added dropwise to the solution under nitrogen atmosphere at −78° C. After stirring at −78° C. for 30 minutes, 1.87 mL (24.1 mmol) of methyl chlorocarbonate was added dropwise to the mixture, and the reaction mixture was warmed to room temperature and stirred for 10 minutes. The reaction mixture was poured into water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 3.93 g (20.3 mmol, Yield: 91.9%) of methyl 4-oxo-4,5,6,7-tetrahydro-1-benzofuran-5-carboxylate.

(3) Methyl 4-hydroxy-1-benzofuran-5-carboxylate

In 1,4-dioxane (100 mL) was dissolved 3.93 g (20.3 mmol) of methyl 4-oxo-4,5,6,7-tetrahydro-1-benzofuran-5-carboxylate obtained in (2), 5.51 g (24.3 mmol) of 2,3-dichloro-5,6-dicyano-1,4-benzoquinone was added to the solution, and the resulting mixture was stirred at 120° C. for 3 hours. The reaction mixture was allowed to stand for cooling, insoluble materials were filtered off through Celite, and the filtrate was concentrated. The residue was purified by silica gel column chromatography (Wako gel C-100, hexane-ethyl acetate, gradient) to obtain 2.04 g (10.6 mmol, Yield: 52.2%) of methyl 4-hydroxy-1-benzofuran-5-carboxylate.

(4) Methyl 4-methoxy-1-benzofuran-5-carboxylate

To an acetonitrile (60 mL) solution containing 2.04 g (10.6 mmol) of methyl 4-hydroxy-1-benzofuran-5-carboxylate obtained in (3) were added 2.53 g (18.3 mmol) of potassium carbonate, and then, 2.85 mL (45.8 mmol) of methyl iodide, and the resulting mixture was refluxed for 3 hours. After allowing to stand at room temperature overnight, the reaction mixture was poured into water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 2.01 g (9.76 mmol, Yield: 92.1%) of methyl 4-methoxy-1-benzofuran-5-carboxylate.

(5) (4-Methoxy-1-benzofuran-5-yl)methanol

To a dry tetrahydrofuran (20 mL) solution containing 1.01 g (4.90 mmol) of methyl 4-methoxy-1-benzofuran-5-carboxylate obtained in (4), 0.479 g (12.6 mmol) of lithium aluminum hydride was added little by little to the mixture in an ice bath with stirring. The reaction mixture was stirred in an ice bath for 2 hours, and ethyl acetate was added little by little to the mixture. Subsequently, water (0.5 mL), 3N sodium hydroxide (0.5 mL), and water (1.5 mL) were successively added to the mixture and the resulting mixture was stirred for 30 minutes. This mixture was filtered through Celite, and the filtrate was concentrated to obtain 0.89 g of a crude product of (4-methoxy-1-benzofuran-5-yl)methanol.

(6) 4-Methoxy-5-methyl-1-benzofuran

In dichloromethane (10 mL) was dissolved 0.65 g of a crude product of (4-methoxy-1-benzofuran-5-yl)methanol obtained in (5), 0.56 mL (4.03 mmol) of triethylamine, and then, 0.31 mL (3.99 mmol) of methanesulfonyl chloride were added dropwise to the solution in an ice bath with stirring, and the resulting mixture was stirred in an ice bath for 1 hour. The reaction mixture was poured into water, and extracted with ethyl acetate. The organic layer was successively washed with water and brine, and dried over anhydrous magnesium sulfate. The solvent was removed, dry dimethylsulfoxide (20 mL) was added to the obtained residue, and 0.276 g (7.30 mmol) of sodium borohydride was added little by little. This mixture was stirred at room temperature for 1 hour, then poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05717, 3 plates were used, developed by hexane:ethyl acetate=9:1) to obtain 0.284 g (1.75 mmol, Yield from methyl 4-methoxy-1-benzofuran-5-carboxylate: 48.9%) of 4-methoxy-5-methyl-1-benzofuran.

(7) 5-Methyl-1-benzofuran-4-ol

In dry N,N-dimethylformamide (11 mL) was suspended 268 mg (6.71 mmol) of 60% sodium hydride, 0.51 mL (6.9 mmol) of ethanethiol was added dropwise to the suspension under nitrogen atmosphere, and the resulting mixture was stirred at room temperature for 10 minutes. To the mixture was added a N,N-dimethylformamide (7 mL) solution containing 362 mg (2.23 mmol) of 4-methoxy-5-methyl-1-benzofuran obtained in (6), and the resulting mixture was refluxed for 1 hour and 30 minutes. The reaction mixture was allowed to stand for cooling, and 1 mol/L potassium hydroxide aqueous solution and diethyl ether were added thereto. The aqueous layer was washed with diethyl ether, and a pH thereof was adjusted by adding diluted hydrochloric acid thereto to a pH 2. The mixture was extracted with diethyl ether, the obtained organic layer was successively washed with water and brine, and dried over anhydrous magnesium sulfate. The solvent was distilled off and the obtained residue was purified by preparative thin-layer chromatography (available from MERCK CO., 1.05744, 3 plates were used, developed by hexane:ethyl acetate=2:1) to obtain 276 mg (1.86 mmol, Yield: 83.4%) of 5-methyl-1-benzofuran-4-ol.

(8) 6-Chloro-3-[(5-methyl-1-benzofuran-4-yl)oxy]pyridazine 1-oxide (Step B-2)

121 mg (0.818 mmol) of 5-methyl-1-benzofuran-4-ol obtained in (7) was mixed with 1,4-dioxane (3 mL) and dimethylsulfoxide (3 mL), 101 mg (0.902 mmol) of potassium tert-butoxide was added to the mixture in an ice bath, and the resulting mixture was stirred for 10 minutes. To the mixture was added 134 mg (0.812 mmol) of 3,6-dichloropyridazine 1-oxide, and the resulting mixture was stirred at room temperature overnight. The reaction mixture was poured into ice-cold water, and extracted with ethyl acetate. The organic layers were combined, washed successively with water and brine, and dried over anhydrous magnesium sulfate. The solvent was distilled off and the residue was purified by preparative thin-layer chromatography (available from MERCK CO., 1.05744, 3 plates were used, developed by hexane:ethyl acetate=2:1 three times) to obtain 199 mg of a crude product of 6-chloro-3-[(5-methyl-1-benzofuran-4-yl)oxy]pyridazine 1-oxide.

(9) 4,6-Dichloro-3-[(5-methyl-1-benzofuran-4-yl)oxy]-pyridazine (Step B-3)

199 mg of a crude product of 6-chloro-3-[(5-methyl-1-benzofuran-4-yl)oxy]pyridazine 1-oxide obtained in (8) and 3 mL of phosphorus oxychloride were mixed, and the mixture was stirred at room temperature overnight. To the reaction mixture were added water and dichloromethane, and the resulting mixture was stirred for 30 minutes. The mixture was separated, the organic layer was successively washed with water and brine, and dried over anhydrous magnesium sulfate. The solvent was distilled off and the residue was purified by preparative thin-layer chromatography (available from MERCK CO., 1.05744, 3 plates were used, developed by hexane:ethyl acetate=2:1 three times, subsequently available from MERCK CO., 1.05717, 2 plates were used, developed by hexane:ethyl acetate=2:1 three times) to obtain 120 mg (0.407 mmol, Yield from 4-hydroxy-5-methyl-1-benzofuran with 2 Steps: 49.8%) of 4,6-dichloro-3-[(5-methyl-1-benzofuran-4-yl)oxy]pyridazine.

(10) 6-Chloro-3-[(5-methyl-1-benzofuran-4-yl)oxy]-4-pyridazinol (Compound No. 1109, Step B-4)

120 mg (0.407 mmol) of 4,6-dichloro-3-[(5-methyl-1-benzofuran-4-yl)oxy]pyridazine obtained in (9) was mixed with 1,4-dioxane (3 mL) and dimethylsulfoxide (3 mL), 1.01 mL (2.02 mmol) of 2 mol/L aqueous sodium hydroxide solution was added to the mixture, and the resulting mixture was stirred at room temperature overnight. The reaction mixture was poured into water, and made acidic with diluted hydrochloric acid. This mixture was extracted with dichloromethane. The organic layers were combined, washed successively with water and brine, and dried over anhydrous magnesium sulfate. The solvent was distilled off and the residue was purified by preparative thin-layer chromatography (available from MERCK CO., 1.05744, 2 plates were used, developed by ethyl acetate) to obtain 70.0 mg (0.253 mmol, Yield: 62.2%) of 6-chloro-3-[(5-methyl-1-benzofuran-4-yl)oxy]-4-pyridazinol (Compound No. 1109).

$^1$H-NMR (200 MHz, CD$_3$OD) δ ppm: 7.65 (1H, d, J=2.2 Hz), 7.32 (1H, d, J=8.8 Hz), 7.18 (1H, d, J=8.8 Hz), 6.73 (1H, s), 6.60 (1H, dd, J=2.2, 0.7 Hz), 2.23 (3H, s). Melting point (° C.): 222-225.

EXAMPLE 26

6-Chloro-3-(2-cyclopropylphenoxy)-4-pyridazinyl trifluoromethanesulfonate (Compound No. 2081, Step I-1)

In methylene chloride (2 mL) was dissolved 50.3 mg (0.191 mmol) of 6-chloro-3-(2-cyclopropylphenoxy)-4-pyridazinol (Compound No. 139) obtained in Example 6, 0.027 mL (0.19 mmol) of triethylamine was added dropwise to the solution, then, 0.031 mL (0.19 mmol) of trifluoromethanesulfonic acid anhydride was added dropwise to the same, and the resulting mixture was stirred at room temperature for 30 minutes. The reaction mixture was purified as such by preparative thin-layer chromatography (available from MERCK Co., 1.05744, 2 plates were used, developed by ethyl acetate: hexane=2:1) to obtain 64.7 mg (0.164 mmol, Yield: 85.8%) of 6-chloro-3-(2-cyclopropylphenoxy)-4-pyridazinyl trifluoromethanesulfonate (Compound No. 2081).

$^1$H-NMR (200 MHz, CDCl$_3$) δ ppm: 7.51 (1H, s), 7.26-7.19 (2H, m), 7.14-7.05 (2H, m), 1.89-1.81 (1H, m), 0.85-0.62 (4H, m). Melting point (° C.): 54-61.

EXAMPLE 27

6-Chloro-3-(2-cyclopropylphenoxy)-4-pyridazinyl 4-methylbenzene sulfonate (Compound No. 2225, Step I-1)

In acetonitrile (3 mL) was dissolved 53.4 mg (0.203 mmol) of 6-chloro-3-(2-cyclopropylphenoxy)-4-pyridazinol (Compound No. 139) obtained in Example 6, 23.1 mg (0.206 mmol) of 1,4-diazabicyclo[2,2,2]octane was added to the solution, then, 39.2 mg (0.205 mmol) of 4-methylbenzene sulfonyl chloride was added to the same, and the resulting mixture was stirred at room temperature for 1 hour and 30 minutes. The reaction mixture was poured into water, and extracted with ethyl acetate. The organic layer was successively washed with water and brine, and dried over anhydrous magnesium sulfate. The solvent was distilled off and the obtained residue was purified by preparative thin-layer chromatography (available from MERCK CO., 1.05744, ethyl acetate:hexane=2:1) to obtain 68.8 mg (0.165 mmol, Yield: 81.3%) of 6-chloro-3-(2-cyclopropylphenoxy)-4-pyridazinyl 4-methylbenzene sulfonate (Compound No. 2225).

H$^1$-NMR (200 MHz, CDCl$_3$) δ ppm: 7.87 (2H, d, J=8.1 Hz), 7.58 (1H, s), 7.36 (2H, d, J=8.1 Hz), 7.26-7.11 (2H, m), 6.97-6.93 (1H, m), 6.74-6.70 (1H, m), 2.45 (3H, s), 1.67-1.59 (1H, m), 0.71-0.56 (4H, m). Appearance: oily product.

EXAMPLE 28

2-[(6-Chloro-4-{[(4-methylphenyl)sulfonyl]oxy}-3-pyridazinyl)oxy]phenyl 4-methylbenzene sulfonate (Compound No. 2233, Step I-1)

0.60 g (2.5 mmol) of 6-chloro-3-(2-hydroxyphenoxy)-4-pyridazinol (Compound No. 384) obtained in Example 10, 1.06 g (5.5 mmol) of 4-methylbenzene sulfonyl chloride, 0.56 g (5.0 mmol) of 1,4-diazabicyclo[2,2,2]octane and acetonitrile (30 mL) were mixed, and the mixture was stirred under reflux for 3 hours, and at room temperature for 4 days. Acetonitrile was removed by distillation, water was added to the residue, and the mixture was extracted with ethyl acetate. The organic layers were combined, washed with water, and dried over anhydrous sodium sulfate. The solvent was removed, and the residue was washed with a mixed solvent of hexane-ethyl acetate (3:1) to obtain 1.0 g (1.8 mmol, Yield: 72%) of 2-[(6-chloro-4-{[(4-methylphenyl)sulfonyl]oxy}-3-pyridazinyl)oxy]phenyl 4-methylbenzene sulfonate (Compound No. 2233).

$^1$H-NMR (60 MHz, CDCl$_3$) δ ppm: 7.98-6.65 (13H, m), 2.40 (3H, s), 2.36 (3H, s). Melting point (° C.): 125.5-126.5.

EXAMPLE 29

6-Chloro-5-methyl-3-(2-methylphenoxy)-4-pyridazinol (Compound No. 2372)

(1) 3-Chloro-4-methyl-2,5-furandione and 3-chloro-4-(chloromethyl)-2,5-furandione 224 g (2.00 mol) of 3-methyl-2,5-furandione and 11.2 g (0.415 mol) of iron chloride (III) hexahydrate were mixed, and the mixture was heated to 140° C., and 346 g (4.88 mol) of a chlorine gas was passed through the mixture with stirring over 7 hours and 30 minutes. Thereafter, the mixture was heated at 175° C. for 3 hours and 30 minutes. The reaction mixture was evaporated under reduced pressure (5 mmHg) to collect fractions of 80° C. to 85° C. Thus, 223.5 g of a crude product (containing 3-chloro-4-methyl-2,5-furandione and 3-chloro-4-(chloromethyl)-2,5-furandione) was obtained.

(2) 4-Chloro-5-methyl-1,2-dihydro-3,6-pyridazinedione and 4-chloro-5-(chloromethyl)-1,2-dihydro-3,6-pyridazinedione 147 g of a material (containing 3-chloro-4-methyl-2,5-furandione and 3-chloro-4-(chloromethyl)-2,5-furandione) obtained in (1) was mixed with 400 mL of water, and the mixture was refluxed to make a solution. To the solution heated at reflux was added dropwise an aqueous solution containing 116 g (1.10 mol) of hydrazine dihydrochloride (the hydrazine dihydrochloride was dissolved in 400 mL of water) over 40 minutes. Thereafter, the mixture was refluxed for 1 hour and 30 minutes, and then allowed to stand for cooling. Precipitated crystals were collected by filtration, washed with hot water, and then, with ethyl acetate, to obtain 81.8 g of 4-chloro-5-methyl-1,2-dihydro-3,6-pyridazinedione (m.p. 305-310° C.). On the other hand, the filtrate was extracted with ethyl acetate, the organic layers were combined, washed with water, and dried over anhydrous sodium sulfate. The solvent was removed, and a mixture containing 8.06 g of 4-chloro-5-(chloromethyl)-1,2-dihydro-3,6-pyridazinedione was obtained as a residue.

(3) 3,4,6-Trichloro-5-methylpyridazine 24.1 g (0.150 mol) of 4-chloro-5-methyl-1,2-dihydro-3,6-pyridazinedione obtained in (2) was mixed with 250 mL (2.76 mol) of phosphorus oxychloride, and the mixture was refluxed for 1 hour and 40 minutes. Excess phosphorus oxychloride was removed from the reaction mixture by distillation, and the residue was mixed with ice water. Crystals were collected by filtration, and extracted with ethyl acetate. The organic layer was washed with water, and the solvent was removed. The obtained residue was distilled under reduced pressure (0.7 mmHg) and fractions at 105° C. to 110° C. were collected to obtain 25.1 g (0.127 mol, Yield: 84.7%, m.p. 67.5-70° C.) of 3,4,6-trichloro-5-methylpyridazine.

(4) 3,6-Dichloro-4-methoxy-5-methylpyridazine 7.90 g (40.1 mmol) of 3,4,6-trichloro-5-methylpyridazine obtained in (3) was mixed with methanol (100 mL), a methanol solution (50 mL) containing 0.92 g (40 mmol) of sodium was added dropwise to the mixture in an ice bath, thereafter in an ice bath, the mixture was stirred for 1 hour, and then, for 15 minutes under reflux. In an ice bath, 0.20 g (8.7 mmol) of sodium was additionally added to the mixture, and the resulting mixture was further refluxed for 15 minutes. The reaction mixture was allowed to stand for cooling, and methanol was distilled off. The residue was mixed with ice water and extracted with ethyl acetate. The organic layers were combined, washed with water, and the solvent was removed. The obtained residue was purified by silica gel column chromatography (Wako gel C-100, eluted with hexane:ethyl acetate=5:1) to obtain 5.1 g of a crude product. This product was distilled under reduced pressure (0.07 mmHg) and fractions at 125° C. were collected to obtain 4.50 g (23.3 mmol, Yield: 58.1%) of 3,6-dichloro-4-methoxy-5-methylpyridazine.

(5) Mixture of 3-chloro-5-methoxy-4-methyl-6-(2-methylphenoxy)pyridazine and 3-chloro-4-methoxy-5-methyl-6-(2-methylphenoxy)pyridazine (Step D-1)

To 30.8 g (285 mmol) of 2-methylphenol was gradually added 1.66 g (38.0 mmol) of 55% sodium hydride with stirring. After stirring at room temperature for 20 minutes, the mixture was heated to 90° C. to disappear a solid of sodium hydride. This mixture was cooled to 50° C., 3.69 g (19.1 mmol) of 3,6-dichloro-4-methoxy-5-methylpyridazine obtained in (4) was added thereto, and the resulting mixture was stirred at 110° C. for 3 hours and 30 minutes. The reaction mixture was allowed to stand for cooling, water was added thereto, and then, the mixture was extracted with ethyl acetate. The organic layer was washed with 20% aqueous sodium hydroxide solution, and the solvent was removed. The obtained residue was purified by silica gel column chromatography to obtain 1.38 g (5.21 mmol, Yield: 27.3%) of a mixture of 3-chloro-5-methoxy-4-methyl-6-(2-methylphenoxy)pyridazine and 3-chloro-4-methoxy-5-methyl-6-(2-methylphenoxy)pyridazine.

(6) 6-Chloro-5-methyl-3-(2-methylphenoxy)-4-pyridazinol (Compound No. 2372, Step D-2)

1.38 g (5.21 mmol) of a mixture of 3-chloro-5-methoxy-4-methyl-6-(2-methylphenoxy)pyridazine and 3-chloro-4-methoxy-5-methyl-6-(2-methylphenoxy)pyridazine obtained in (5) was mixed with 1,4-dioxane (8 mL), an aqueous solution (using 13 mL of water) containing 0.282 g (6.78 mmol) of 96% sodium hydroxide was added to the mixture, and the resulting mixture was stirred at 110° C. for 4.5 hours. Water was poured into the reaction mixture, and the mixture was extracted with ethyl acetate. The aqueous layer was made acidic with hydrochloric acid, and precipitated crystals were collected by filtration to obtain 0.249 g (0.992 mmol, Yield: 19.0%, m.p. 209-213° C.) of 6-chloro-5-methyl-3-(2-methylphenoxy)-4-pyridazinol (Compound No. 2372).

$^1$H-NMR (60 MHz, DMF-$d_7$) δ ppm: 7.50-6.95 (4H, m), 2.28 (3H, m), 2.11 (3H, m). Melting point (° C.): 209-213.

Incidentally, crystals precipitated from the filtrate were collected by filtration to obtain 0.187 g (0.745 mmol, Yield: 14.3%) of 3-chloro-5-methyl-6-(2-methylphenoxy)-4-pyridazinol. On the other hand, the organic layer was dried over anhydrous sodium sulfate, and the solvent was removed to recover 0.57 g (Recovery: 41%) of the starting material.

EXAMPLE 30

6-Chloro-5-(methoxymethyl)-3-(2-methylphenoxy)-4-pyridazinol (Compound No. 2378)

(1) 3,4,6-Trichloro-5-(chloromethyl)pyridazine 7.8 g of a mixture containing 4-chloro-5-(chloromethyl)-1,2-dihydro-3,6-pyridazinedione obtained in Example 29 was added 50 mL of phosphorus oxychloride, and the mixture was refluxed for 1 hour. Excess phosphorus oxychloride was distilled off from the reaction mixture, and the residue was mixed with ice water. The mixture was extracted with ethyl acetate, the organic layers were combined, washed with water, and dried over anhydrous sodium sulfate. The solvent was removed, and the obtained residue was purified by silica gel column chromatography (available from Merck Co., 9385, eluted with hexane:ethyl acetate=10:1) to obtain 3.63 g (15.6 mmol, m.p. 102-104° C.) of 3,4,6-trichloro-5-(chloromethyl)pyridazine.

(2) 3,6-Dichloro-4-methoxy-5-(methoxymethyl)pyridazine

In methanol (50 ml) was added 2.32 g (10.0 mmol) of 3,4,6-trichloro-5-(chloromethyl)pyridazine obtained in (1) and the mixture was heated to make a solution. Then, the solution was cooled to −60° C. and a methanol solution of sodium methoxide (prepared from 0.23 g of sodium and 5 mL of methanol, 10.0 mmol) was added dropwise to the solution. The solution was stirred at −10° C. for 2 hours and 30 minutes, and a methanol solution of sodium methoxide (prepared from 0.23 g of sodium and 5 mL of methanol, 10.0 mmol) was further added dropwise to the solution. After stirring for 2 hours at −10° C., and the mixture was allowed to stand at room temperature overnight. The reaction mixture was concentrated, and the residue was purified by silica gel column chromatography (available from Merck Co., 9385, eluted with hexane:ethyl acetate=5:1) to obtain 1.85 g (8.30 mmol, Yield: 83.0%, m.p. 28-32° C.) of 3,6-dichloro-4-methoxy-5-(methoxymethyl)pyridazine.

(3) 3-Chloro-5-methoxy-4-(methoxymethyl)-6-(2-methylphenoxy)pyridazine(Step D-1)

432 mg (4.00 mmol) of 2-methylphenol, methanol (20 mL) and 92 mg (4.0 mmol) of sodium were mixed, and the mixture was stirred at room temperature until sodium was disappeared. Methanol in the mixture was distilled off, 50 mL of toluene was added to the residue and the mixture was refluxed. The mixture was cooled in an ice bath, a toluene solution (10 mL) containing 892 mg (4.00 mmol) of 3,6-dichloro-4-methoxy-5-(methoxymethyl)pyridazine obtained in (2) was added dropwise to the mixture, and the resulting mixture was refluxed for 3 hours. The reaction mixture was allowed to stand at room temperature overnight, washed with water, and then with brine, and dried over anhydrous sodium sulfate. The solvent was removed, and the residue was purified by silica gel column chromatography (First time; available from Merck Co., 9385, eluted with hexane:ethyl acetate=5:1. Second time; available from Merck Co., 9385, eluted with hexane:ethyl acetate=8:1) to obtain 0.487 g (1.65 mmol, Yield: 41.3%) of 3-chloro-5-methoxy-4-(methoxymethyl)-6-(2-methylphenoxy)pyridazine and 0.266 g (0.902 mmol, Yield: 22.6%) of 3-chloro-4-methoxy-5-(methoxymethyl)-6-(2-methylphenoxy)pyridazine.

(4) 6-Chloro-5-(methoxymethyl)-3-(2-methylphenoxy)-4-pyridazinol (Compound No. 2378, Step D-2)

0.354 g (1.20 mmol) of 3-chloro-5-methoxy-4-(methoxymethyl)-6-(2-methylphenoxy)pyridazine obtained in (3), 1,4-dioxane (2 mL), 62 mg (1.49 mmol) of 96% sodium hydroxide and water (8 mL) were mixed, and the mixture was stirred at room temperature for 2 days, and further for 3 hours under reflux. Hydrochloric acid was added to the reaction mixture to make a pH 1, and then, the mixture was extracted with ethyl acetate. The organic layers were combined, washed with water, and dried over anhydrous sodium sulfate. The solvent was removed to obtain 0.336 g (1.20 mmol, Yield: 100%) of 6-chloro-5-(methoxymethyl)-3-(2-methylphenoxy)-4-pyridazinol (Compound No. 2378).

$^1$H-NMR (60 MHz, DMF-$d_7$) δ ppm: 8.92 (1H, brs), 7.45-6.80 (4H, m), 4.39 (2H, s), 3.25 (3H, s), 2.25 (3H, s). Melting point (° C.): 123-126.

EXAMPLE 31

Ethyl 6-(2-tert-butylphenoxy)-3-chloro-5-hydroxy-4-pyridazinecarboxylate (Compound No. 2386)

(1) 3-(2-Tert-butylphenoxy)-6-chloro-4-methoxypyridazine 5.87 g (39.1 mmol) of 2-tert-butylphenol, dimethylsulfoxide (80 mL) and 4.38 g (39.0 mmol) of potassium t-butoxide were mixed, and the mixture was stirred at room temperature for 20 minutes. To the mixture was added a dimethylsulfoxide solution (60 mL) containing 6.92 g (38.7 mmol) of 3,6-dichloro-4-methoxypyridazine, and the resulting mixture was stirred at room temperature for 40 minutes, and at 80° C. for 45 minutes. The reaction mixture was poured into a saturated aqueous ammonium chloride solution, and extracted with ethyl acetate. The organic layers were combined, washed with water, and then, with brine, and dried over anhydrous sodium sulfate. The solvent was removed, and the residue was purified by silica gel column chromatography (available from Merck Co., 9385, hexane:ethyl acetate, gradient) to obtain 2.66 g (9.09 mmol, Yield: 23.5%) of 3-(2-tert-butylphenoxy)-6-chloro-4-methoxypyridazine and 1.82 g (6.22 mmol, Yield: 16.1%) of 6-(2-tert-butylphenoxy)-3-chloro-4-methoxypyridazine.

(2) Ethyl 6-(2-tert-butylphenoxy)-3-chloro-5-methoxy-4-pyridazinecarboxylate (Step G-1)

In dry tetrahydrofuran (26 mL) was dissolved 783 mg (2.68 mmol) of 3-(2-tert-butylphenoxy)-6-chloro-4-methoxypyridazine obtained in (1). The solution was cooled to −78° C., 1.20 mL (2.80 mmol) of a n-butyl lithium-hexane solution (2.33M) was added to the solution and the resulting mixture was stirred for 20 minutes. To the mixture was added 0.330 mL (3.45 mmol) of ethyl chlorocarbonate, and the resulting mixture was stirred at the same temperature for 30 minutes. The reaction mixture was poured into a saturated aqueous ammonium chloride solution, and extracted with ether. The organic layers were combined, washed successively with water and brine, and dried over anhydrous sodium sulfate. The solvent was removed, and the obtained residue was purified by silica gel column chromatography (eluted with hexane:ethyl acetate=5:1) to obtain 603 mg (1.65 mmol, Yield: 61.6%) of ethyl 6-(2-tert-butylphenoxy)-3-chloro-5-methoxy-4-pyridazinecarboxylate.

(3) Eethyl 6-(2-tert-butylphenoxy)-3-chloro-5-hydroxy-4-pyridazinecarboxylate (Compound No. 2386, Step G-2)

419 mg (1.15 mmol) of ethyl 6-(2-tert-butylphenoxy)-3-chloro-5-methoxy-4-pyridazinecarboxylate obtained in (2), 1,4-dioxane, 1 mol/L aqueous sodium hydroxide solution (2.0 mL, 2.0 mmol) and dimethylsulfoxide (2.0 mL) were mixed, and the mixture was stirred at room temperature for 2 hours and 30 minutes, and at 80° C. for 4 hours and 30 minutes. After allowing to stand for cooling, the reaction mixture was made acidic with hydrochloric acid, and extracted with dichloromethane. The organic layers were combined, washed with brine, and dried over anhydrous sodium sulfate. The solvent was removed, and the residue was purified by silica gel column chromatography to obtain 337 mg (0.960 mmol, Yield: 83.5%) of ethyl 6-(2-tert-butylphenoxy)-3-chloro-5-hydroxy-4-pyridazinecarboxylate (Compound No. 2386). Appearance: amorphous.

EXAMPLE 32

3,6-Bis(2-methylphenoxy)-4-pyridazinol (Compound No. 2395)

(1) 3-chloro-5-methoxy-4,6-bis(2-methylphenoxy) pyridazine (Step D-1)

In toluene (100 mL) was dissolved 5.32 g (49.3 mmol) of 2-methylphenol, and 1.13 g (49.1 mmol) of sodium, and then, 5.80 g (27.2 mmol) of 3,4,6-trichloro-5-methoxypyridazine were added to the solution and the resulting mixture was stirred for 4 hours under reflux. The reaction mixture was poured into ice-cold water, and extracted with ethyl acetate. The organic layers were combined, washed successively with water and brine, and dried over anhydrous sodium sulfate. The solvent was removed, and the residue was purified by silica gel column chromatography (hexane:ethyl acetate, gradient) and recrystallized from isopropyl ether to obtain 3.0 g (8.4 mmol, Yield: 31%) of 3-chloro-5-methoxy-4,6-bis(2-methylphenoxy)pyridazine.

(2) 6-Chloro-3,5-bis(2-methylphenoxy)-4-pyridazinol (Compound No. 2395, Step D-2)

0.72 g (2.0 mmol) of 3-chloro-5-methoxy-4,6-bis(2-methylphenoxy)pyridazine obtained in (1) was added to a mixture comprising 0.60 mL (4.7 mmol) of trimethylsilyl chloride, 0.60 g (4.0 mmol) of sodium iodide and acetonitrile (15ml), and the resulting mixture was stirred overnight. The reaction mixture was poured into ice-cold water, and extracted with methylene chloride. The organic layers were combined, washed successively with water and brine, and dried over anhydrous sodium sulfate. The solvent was removed, and the residue was purified by silica gel column chromatography (chloroform: methanol, gradient) to obtain 0.45 g (1.3 mmol, Yield: 65%) of 6-chloro-3,5-(2-methylphenoxy)-4-pyridazinol (Compound No. 2395).

$^1$H-NMR (200 MHz, CD$_3$OD) δ ppm: 7.32-7.05 (7H, m), 6.91 (1H, br.d, J=7.3 Hz), 2.29 (3H, s), 2.19 (3H, s). Melting point (° C.): 110-115.

EXAMPLE 33

3-(2-tert-Butylphenoxy)-6-chloro-5-(trimethylsilyl)-4-pyridazinol (Compound No. 2405)

(1) 3-(2-tert-Butylphenoxy)-6-chloro-4-methoxy-5-(trimethylsilyl)pyridazine(Step G-1)

In dry tetrahydrofuran (15 mL) was dissolved 498 mg (1.70 mmol) of 3-(2-tert-butylphenoxy)-6-chloro-4-methoxypyridazine obtained in Example 31 (1), the solution was cooled to −78° C., 1.10 mL (1.87 mmol) of a n-butyl lithium-hexane solution (1.70M) was added to the solution and the resulting mixture was stirred for 20 minutes. To the mixture was added 0.370 mL (2.91 mmol) of trimethylsilyl chloride, and the resulting mixture was stirred at the same temperature for 10 minutes. The reaction mixture was poured into a saturated aqueous ammonium chloride solution, extracted with ether. The organic layers were combined, washed successively with water and brine, and dried over anhydrous sodium sulfate. The solvent was removed, and the obtained residue was purified by silica gel column chromatography to obtain 596 mg (1.63 mmol, Yield: 95.9%) of 3-(2-tert-butylphenoxy)-6-chloro-4-methoxy-5-(trimethylsilyl)pyridazine.

(2) 3-(2-tert-Butylphenoxy)-6-chloro-5-(trimethylsilyl)-4-pyridazinol (Compound No. 2405, Step G-2)

0.17 g (1.1 mmol) of sodium iodide, 0.14 mL (1.1 mmol) of trimethylsilyl chloride and acetonitrile (3.5 mL) were mixed, and to the mixture was added with stirring 340 mg (0.932 mmol) of 3-(2-tert-butylphenoxy)-6-chloro-4-methoxy-5-(trimethylsilyl)pyridazine obtained in (1), and the resulting mixture was stirred at room temperature for 1 hour and 35 minutes. The reaction mixture was poured into a saturated aqueous sodium sulfite solution, and ice-cold diluted hydrochloric acid was added to the mixture. The mixture was extracted with ethyl acetate, the organic layers were combined and washed with brine. The solvent was removed, and the residue was purified by silica gel column chromatography to obtain 275 mg (0.783 mmol, Yield: 84.0%) of 3-(2-tert-butylphenoxy)-6-chloro-5-(trimethylsilyl)-4-pyridazinol (Compound No. 2405).

$^1$H-NMR (90 MHz, CDCl$_3$) δ ppm: 10.12 (1H, brs), 7.39-6.75 (4H, m), 1.24 (9H, s), 0.31 (9H, s). Melting point (° C.): 160-163.

EXAMPLE 34

6-Bromo-3-(2-methylphenoxy)-4-pyridazinol (Compound No. 2411)

(1) 5-chloro-6-(2-methylphenoxy)-3-pyridazinol (Step P-1)

A mixture comprising 578 mg (2.27 mmol) of 4,6-dichloro-3-(2-methylphenoxy)pyridazine obtained in Example 1 (2), acetic acid (10 mL) and 0.45 g (4.6 mmol) of potassium acetate was refluxed for 5 hours. The reaction mixture was allowed to stand for cooling, and after adding 50 mL of water, the mixture was extracted with ethyl acetate. The organic layers were combined, and washed successively with water and brine. After drying over anhydrous sodium sulfate, the solvent was removed to obtain 461 mg (1.95 mmol, Yield: 85.9%) of 5-chloro-6-(2-methylphenoxy)-3-pyridazinol.

(2) 4,6-Dibromo-3-(2-methylphenoxy)pyridazine (Step P-2)

151 mg (0.637 mmol) of 5-chloro-6-(2-methylphenoxy)-3-pyridazinol obtained in (1), chloroform(3 mL) and 913 mg (3.18 mmol) of phosphorus oxybromide were mixed, and the mixture was refluxed for 5 hours. The reaction mixture was allowed to stand for cooling, water and dichloromethane were added to the mixture and the resulting mixture was stirred at room temperature for 1 hour. The mixture was extracted with dichloromethane. The organic layers were combined, and washed successively with water and brine. After drying over anhydrous sodium sulfate, the solvent was removed. The obtained residue was purified by silica gel column chromatography to obtain 176 mg (0.512 mmol, Yield: 80.4%) of 4,6-dibromo-3-(2-methylphenoxy)pyridazine.

(3) 6-Bromo-3-(2-methylphenoxy)-4-pyridazinol (Compound No. 2411, Step P-3)

In dimethylsulfoxide (3 mL) was dissolved 114 mg (0.331 mmol) of 4,6-dibromo-3-(2-methylphenoxy)pyridazine obtained in (2), 0.80 mL (1.6 mmol) of 2 mol/L aqueous sodium hydroxide solution was added to the solution, and the resulting mixture was stirred at room temperature for 3 hours. Water was added to the reaction mixture, and the resulting mixture was washed with ethyl acetate. The aqueous layer was made acidic with 4 mol/L hydrochloric acid, and extracted with ethyl acetate. The organic layers were combined, washed with brine and dried over anhydrous sodium sulfate. The solvent was removed, and the residue was washed with a mixed solvent of ethyl acetate-ether to obtain 56.0 mg (0.199 mmol, Yield: 60.1%) of 6-bromo-3-(2-methylphenoxy)-4-pyridazinol (Compound No. 2411).

$^1$H-NMR (200 MHz, DMSO-d$_6$) δ ppm: 7.35-7.05 (4H, m), 6.82 (1H, brs), 2.10 (3H, s). Melting point (° C.): 197-198.

EXAMPLE 35

6-Cyclopropyl-3-(2-methylphenoxy)-4-pyridazinol (Compound No. 2423)

(1) 6-Cyclopropyl-4-methoxy-3-(2-methylphenoxy) pyridazine (Step L-1)

To a tetrahydrofuran solution (2.94 mL) containing of 9-borabicyclo[3.3.1]nonane (0.5 mol/l, 1.47 mmol) was added 87.5 mg (0.735 mmol) of propargyl bromide, and the resulting mixture was refluxed for 2 hours. The reaction mixture was cooled to room temperature, 0.74 mL (2.2 mmol) of 3 mol/L aqueous sodium hydroxide solution was added to the mixture, and the resulting mixture was stirred at room temperature for 70 minutes. To the mixture were successively added 168 mg (0.669 mmol) of 6-chloro-4-methoxy-3-(2-methylphenoxy)pyridazine obtained in Example 2 (1) and 38.7 mg (0.00334 mmol) of tetrakis(triphenylphosphine)-palladium, and the resulting mixture was refluxed overnight. The reaction mixture was allowed to stand for cooling, water was added to the mixture, and the resulting mixture was extracted with ethyl acetate. The organic layers were combined, and washed successively with water and brine. After drying over anhydrous sodium sulfate, the solvent was removed. The obtained residue was purified by silica gel column chromatography to obtain 121 mg (0.473 mmol, Yield: 70.1%) of 6-cyclopropyl-4-methoxy-3-(2-methylphenoxy)pyridazine.

(2) 6-Cyclopropyl-3-(2-methylphenoxy)-4-pyridazinol (Compound No. 2423, Step L-2)

In dimethylsulfoxide (2 mL) was dissolved 45.6 mg (0.479 mmol) of 2-hydroxypyridine, 53.8 mg (0.480 mmol) of potassium tert-butoxide was added the solution at room temperature, and the resulting mixture was stirred at room temperature for 10 minutes. To the mixture was added a dimethylsulfoxide (1 mL) solution containing 112 mg (0.438 mmol) of 6-cyclopropyl-4-methoxy-3-(2-methylphenoxy)-pyridazine obtained in (1), and the resulting mixture was stirred at 60° C. for 5 hours, and at 80° C. for 15 hours. Moreover, 45.6 mg (0.479 mmol) of 2-hydroxypyridine and then 53.8 mg (0.480 mmol) of potassium tert-butoxide were additionally added to the mixture, and the resulting mixture was stirred at 80° C. for 4 hours and 30 minutes. The reaction mixture was allowed to stand for cooling, water was added to the mixture, and and the resulting mixture was washed with ethyl acetate. The aqueous layer was made acidic with 4 mol/L hydrochloric acid, and extracted with ethyl acetate. The organic layers were combined, and washed successively with water and brine. After drying over anhydrous sodium sulfate, the solvent was removed. The obtained residue was purified by preparative thin-layer chromatography (available from Merck Co., 1.05744, developed by ethyl acetate) to obtain 28.6 mg (0.118 mmol, Yield: 26.9%) of 6-cyclopropyl-3-(2-methylphenoxy)-4-pyridazinol (Compound No. 2423).
$^1$H-NMR (200 MHz, CD$_3$OD) δ ppm: 7.30-7.01 (4H, m), 6.19 (1H, s), 1.98-1.82 (1H, m), 1.23-1.12 (2H, m), 0.99-0.88 (2H, m). Melting point (° C.): 214-215.

EXAMPLE 36

3-(2-Methylphenoxy)-6-vinyl-4-pyridazinol (Compound No. 2436)

(1) 4-Methoxy-3-(2-methylphenoxy)-6-vinylpyridazine (Step L-1)

In toluene (2 mL) was dissolved 123 mg (0.490 mmol) of 6-chloro-4-methoxy-3-(2-methylphenoxy)pyridazine obtained in Example 2 (1), 246 mg (0.776 mmol) of tributyl-(vinyl)tin, and then, 119 mg (0.103 mmol) of tetrakis(triphenylphosphine)palladium were successively added to the solution at room temperature, and the resulting mixture was refluxed for 3 hours. The reaction mixture was allowed to stand for cooling, ethyl acetate (5 mL), water (3 mL) and sodium fluoride were added to the mixture, and the resulting mixture was stirred for 30 minutes and allowed to stand at at room temperature overnight. The mixture was filtered through Celite, ethyl acetate was added to the filtrate, then the organic layer was separated and washed with brine. After drying over anhydrous sodium sulfate, the solvent was removed. The obtained residue was purified by silica gel column chromatography (eluted with hexane:ethyl acetate=1:2) to obtain 105 mg (0.434 mmol, Yield: 88.6%) of 4-methoxy-3-(2-methylphenoxy)-6-vinylpyridazine.

(2) 3-(2-Methylphenoxy)-6-vinyl-4-pyridazinol (Compound No. 2436, Step L-2)

In dimethylsulfoxide (1 mL) was dissolved 33.7 mg (0.354 mmol) of 2-hydroxypyridine, 39.7 mg (0.354 mmol) of potassium tert-butoxide was added to the solution at room temperature, and the resulting mixture was stirred at room temperature for 10 minutes. To the mixture was added a dimethylsulfoxide (1 mL) solution containing 85.8 mg (0.354 mmol) of 4-methoxy-3-(2-methylphenoxy)-6-vinylpyridazine obtained in (1), and the resulting mixture was stirred at room temperature overnight and at 50° C. for 4 hours and 30 minutes. The reaction mixture was allowed to stand for cooling, water was added thereto, and the resulting mixture was washed with ethyl acetate. The aqueous layer was made acidic with 4 mol/L hydrochloric acid, and extracted with ethyl acetate. The organic layers were combined, dried over anhydrous sodium sulfate, and the solvent was removed. The obtained residue was purified by silica gel column chromatography (eluted with hexane:ethyl acetate=1:4) to obtain 51.7 mg (0.227 mmol, Yield: 64.1%) of 3-(2-methylphenoxy)-6-vinyl-4-pyridazinol (Compound No. 2436).
$^1$H-NMR (200 MHz, DMSO-d$_6$) δ ppm: 7.35-7.03 (4H, m), 6.56-6.43 (2H, m), 6.16 (1H, d, J=17.9 Hz), 6.16 (1H, d, J=11.4 Hz), 2.11 (3H, s). Melting point (° C.): 195-197.

EXAMPLE 37

3-(2-Methylphenoxy)-6-(1-propenyl)-4-pyridazinol (Compound No. 2442)

(1) 6-Allyl-4-methoxy-3-(2-methylphenoxy)pyridazine (Step L-1)

In toluene (4 mL) was dissolved 200 mg (0.797 mmol) of 6-chloro-4-methoxy-3-(2-methylphenoxy)pyridazine obtained in Example 2 (1), 305 mg (0.921 mmol) of allyl-(tributyl)tin, and then, 96.8 mg (0.0838 mmol) of tetrakis-(triphenylphosphine)palladium were successively added to the solution at room temperature, and the resulting mixture was refluxed for 3 hours and 20 minutes. The reaction mixture was allowed to stand at room temperature overnight, and then, ethyl acetate, water and sodium fluoride were added to the mixture and the resulting mixture was stirred for 2 hours. The mixture was filtered through Celite, ethyl acetate was added to the filtrate, then the organic layer was separated, and washed successively with water and brine. After drying over anhydrous sodium sulfate, the solvent was removed. The obtained residue was purified by silica gel column chromatography (hexane:ethyl acetate, gradient) to obtain 62.1 mg (0.243 mmol, Yield: 30.5%) of 6-allyl-4-methoxy-3-(2-methylphenoxy)pyridazine.

(2) 3-(2-Methylphenoxy)-6-(1-propenyl)-4-pyridazinol (Compound No. 2442, Step L-2)

In dimethylsulfoxide (2 mL) was dissolved 25.3 mg (0.267 mmol) of 2-hydroxypyridine, 29.9 mg (0.267 mmol) of potassium tert-butoxide was added to the solution at room temperature, and the resulting mixture was stirred at room temperature for 10 minutes. To the mixture was added a dimethylsulfoxide (3 mL) solution containing 62.1 mg (0.243 mmol) of 6-allyl-4-methoxy-3-(2-methylphenoxy)pyridazine obtained in (1), and the resulting mixture was stirred at 100° C. for 8 hours and at 130° C. for 5 hours and 30 minutes. Moreover, 25.3 mg (0.267 mmol) of 2-hydroxypyridine, and then, 29.9 mg (0.267 mmol) of potassium tert-butoxide were additionally added to the mixture, and the resulting mixture was stirred at 130° C. for 5 hours. The reaction mixture was allowed to stand for cooling, and after adding water, the mixture was washed with ethyl acetate. The aqueous layer was made acidic with 4 mol/L hydrochloric acid, and extracted with ethyl acetate. The organic layers were combined, dried over anhydrous sodium sulfate, and the solvent was removed. The obtained residue was purified by preparative thin-layer chromatography (available from Merck Co., 1.05744, 3 plates were used, developed by ethyl acetate) to obtain 21.3 mg (0.0880 mmol, Yield: 36.2%) of 3-(2-methylphenoxy)-6-(1-propenyl)-4-pyridazinol (Compound No. 2442).

$^1$H-NMR (200 MHz, DMSO-d$_6$) δ ppm: 7.32-7.03 (4H, m), 6.75-6.60 (1H, m), 6.44 (1H, s), 6.22-6.10 (1H, m), 2.10 (3H s), 1.86 (3H, br.d, J=6.6 Hz). Melting point (° C.): 208-210.

EXAMPLE 38

6-(2,6-Dimethylphenoxy)-5-hydroxy-3-pyridazinecarbonitrile (Compound No. 2453)

(1) 6-Chloro-3-(2,6-dimethylphenoxy)-4-methoxypyridazine 1-oxide (Step K-1)

3.42 g (12.9 mmol) of 6-chloro-3-(2,6-dimethylphenoxy)-4-methoxypyridazine, dichloromethane (110 mL) and 3.34 g (15.4 mmol) of 80% m-chloroperbenzoic acid were mixed, and the mixture was stirred at at room temperature for 16 days. The reaction mixture was poured into ice-cold saturated aqueous sodium sulfite solution, and extracted with dichloromethane. The organic layers were combined, washed successively with a saturated aqueous sodium hydrogen carbonate solution, water and brine, and dried over anhydrous sodium sulfate. The solvent was removed, and the residue was purified by silica gel column chromatography to obtain 2.06 g (7.33 mmol, Yield: 56.8%) of 6-chloro-3-(2,6-dimethylphenoxy)-4-methoxypyridazine 1-oxide.

(2) 3-(2,6-Dimethylphenoxy)-4-methoxypyridazine 1-oxide (Step K-2)

6.00 g (21.4 mmol) of 6-chloro-3-(2,6-dimethylphenoxy)-4-methoxypyridazine 1-oxide obtained in (1), methanol (200 mL), 3.0 mL of triethylamine, acetone (5 mL) and 0.5 g of 5% palladium carbon were mixed, and the mixture was shaked by using a Parr reducing device under a hydrogen pressure of 3.5 atm for 2 hours. The reaction mixture was filtered, and the filtrate was concentrated. Water was added to the residue, and the mixture was extracted with chloroform. The organic layers were combined, washed with brine, and dried over anhydrous sodium sulfate. The solvent was removed, and the residue was crystallized from an ether-dichloromethane mixed solvent to obtain 4.32 g (17.6 mmol, Yield: 82.2%) of 3-(2,6-dimethylphenoxy)-4-methoxypyridazine 1-oxide.

(3) 6-(2,6-Dimethylphenoxy)-5-methoxy-3-pyridazinecarbonitrile (Step M-1)

In dry N,N-dimethylformamide (15 mL) was dissolved 0.720 g (2.92 mmol) of 3-(2,6-dimethylphenoxy)-4-methoxypyridazine 1-oxide obtained in (2), 1.10 mL (8.25 mmol) of trimethylsilylcyanide and 2.00 mL (14.4 mmol) of triethylamine were added to the solution, and the resulting mixture was stirred at 90° C. for 1 hour and 30 minutes. The reaction mixture was poured into a saturated aqueous ammonium chloride solution, and extracted with ethyl acetate. The organic layers were combined, washed successively with water and brine, and dried over anhydrous sodium sulfate. The solvent was removed, and the residue was purified by silica gel column chromatography to obtain 0.675 g (2.65 mmol, Yield: 90.8%) of 6-(2,6-dimethylphenoxy)-5-methoxy-3-pyridazinecarbonitrile.

(4) 6-(2,6-Dimethylphenoxy)-5-hydroxy-3-pyridazinecarbonitrile (Compound No. 2453, Step M-2)

In acetonitrile (5 mL) was dissolved 0.500 g (1.96 mmol) of 6-(2,6-dimethylphenoxy)-5-methoxy-3-pyridazinecarbonitrile obtained in (3), 0.300 mL (2.36 mmol) of trimethylsilyl chloride and 0.350 g (2.33 mmol) of sodium iodide were added to the solution, and the resulting mixture was stirred at room temperature. 5 mL of acetonitrile was additionally added and the resulting mixture was stirred for 1 hour, then, 3 mL of 1,4-dioxane was added thereto, and the resulting mixture was stirred overnight. The reaction mixture was poured into an aqueous sodium sulfite solution, and made acidic by adding 1 mol/L hydrochloric acid. The resulting mixture was extracted with dichloromethane, washed with brine, and dried over anhydrous sodium sulfate. The solvent was removed, and the residue was purified by silica gel column chromatography to obtain 0.121 g (0.502 mmol, Yield: 25.6%) of 6-(2,6-dimethylphenoxy)-5-hydroxy-3-pyridazinecarbonitrile (Compound No. 2453).

$^1$H-NMR (90 MHz, CDCl$_3$) δ ppm: 11.3 (1H, brs), 7.09-6.99 (4H, m), 1.90 (6H, s). Appearance: amorphous.

EXAMPLE 39

1-[5-Hydroxy-6-(2-methylphenoxy)-3-pyridazinyl]-ethanone (Compound No. 2455)

(1) 6-(1-Ethoxyvinyl)-4-methoxy-3-(2-methylphenoxy)-pyridazine (Step L-1)

In toluene (6.5 mL) was dissolved 321 mg (1.28 mmol) of 6-chloro-4-methoxy-3-(2-methylphenoxy)pyridazine obtained in Example 2 (1), 534 mg (1.48 mmol) of (1-ethoxyvinyl)(tributyl)tin, then 155.3 mg (0.134 mmol) of tetrakis (triphenylphosphine)palladium were successively added to the solution at room temperature, and the resulting mixture was refluxed for 3 hours and 20 minutes. The reaction mixture was allowed to stand at room temperature overnight, then, ethyl acetate, water and sodium fluoride were added to the mixture and the resulting mixture was stirred for 2 hours. The mixture was filtered through Celite, ethyl acetate was added to the filtrate, and the organic layer was separated, and washed successively with water and brine. After drying over anhydrous sodium sulfate, the solvent was removed. The obtained residue was purified by silica gel column chromatography (hexane:ethyl acetate, gradient) to obtain 51.8 mg (0.181 mmol, Yield: 14.1%) of 6-(1-ethoxyvinyl)-4-methoxy-3-(2-methylphenoxy)pyridazine.

(2) 1-[5-Hydroxy-6-(2-methylphenoxy)-3-pyridazinyl]ethanone (Compound No. 2455, Step L-2)

In dimethylsulfoxide (2 mL) was dissolved 18.4 mg (0.194 mmol) of 2-hydroxypyridine, 21.7 mg (0.194 mmol) of potassium tert-butoxide was added to the solution at room temperature, and the resulting mixture was stirred at room temperature for 10 minutes. To the mixture was added a dimethylsulfoxide (3 mL) solution containing 50.4 mg (0.176 mmol) of 6-(1-ethoxyvinyl)-4-methoxy-3-(2-methylphenoxy)-pyridazine obtained in (1), and the resulting mixture was stirred at 100° C. for 8 hours and at 130° C. for 5 hours and 30 minutes. Moreover, 18.4 mg (0.194 mmol) of 2-hydroxypyridine, then 21.7 mg (0.194 mmol) of potassium tert-butoxide were additionally added to the mixture, and the resulting mixture was stirred at 130° C. for 2 hours. The reaction mixture was allowed to stand for cooling, and after adding water, and the mixture was washed with ethyl acetate. The aqueous layer was made acidic with 4 mol/L hydrochloric acid, and extracted with ethyl acetate. The organic layers were combined, dried over anhydrous sodium sulfate, and the solvent was removed. The obtained residue was purified by preparative thin-layer chromatography (available from Merck Co., 1.05744, 3 plates were used, developed by ethyl acetate) to obtain 28.5 mg (0.117 mmol, Yield: 66.5%) of 1-[5-hydroxy-6-(2-methylphenoxy)-3-pyridazinyl]ethanone (Compound No. 2455).

$^1$H-NMR (200 MHz, DMSO-$d_6$) δ ppm: 7.48-7.05 (5H, m), 2.58 (3H, s), 2.10 (3H, s). Melting point (° C.): 182-185.

EXAMPLE 40

3-(2-Methylphenoxy)-6-phenyl-4-pyridazinol (Compound No. 2464)

(1) 4-Methoxy-3-(2-methylphenoxy)-6-phenylpyridazine (Step L-1)

210 mg (0.837 mmol) of 6-chloro-4-methoxy-3-(2-methylphenoxy)pyridazine obtained in Example 2 (1), toluene (4 mL) and water (0.5 mL) were mixed, 161 mg (1.32 mmol) of phenylboronic acid, 365 mg (2.64 mmol) of potassium carbonate and 102 mg (0.0879 mmol) of tetrakis(triphenylphosphine)palladium were successively added to the mixture at room temperature, and the resulting mixture was refluxed for 2 hours and 50 minutes. The reaction mixture was allowed to stand at room temperature overnight, the mixture was filtered through Celite, and ethyl acetate and water were added to the filtrate. The organic layer was separated, washed with brine. After drying over anhydrous sodium sulfate, the solvent was removed. The obtained residue was purified by silica gel column chromatography (eluted with hexane:ethyl acetate=3:1) to obtain 146 mg (0.500 mmol, Yield: 59.7%) of 4-methoxy-3-(2-methylphenoxy)-6-phenylpyridazine.

(2) 3-(2-Methylphenoxy)-6-phenyl-4-pyridazinol (Compound No. 2464, Step L-2)

In dimethylsulfoxide (1.5 mL) was dissolved 91.9 mg (0.966 mmol) of 2-hydroxypyridine, 95.4 mg (0.850 mmol) of potassium tert-butoxide was added to the solution at room temperature, and the resulting mixture was stirred at room temperature for 10 minutes. To the mixture was added a dimethylsulfoxide (1 mL) solution containing 82.8 mg (0.283 mmol) of 4-methoxy-3-(2-methylphenoxy)-6-phenylpyridazine obtained in (1), and the resulting mixture was stirred at 60° C. for 3 hours. The reaction mixture was allowed to stand for cooling, and after adding water, the mixture was washed with ethyl acetate. The aqueous layer was made acidic with 4 mol/L hydrochloric acid, and extracted with ethyl acetate. The organic layers were combined, washed with brine, and dried over anhydrous sodium sulfate. The solvent was distilled off and the obtained residue was purified by preparative thin-layer chromatography (available from Merck Co., 1.05744, 3 plates were used, developed by ethyl acetate) to obtain 70.8 mg (0.255 mmol, Yield: 90.1%) of 3-(2-methylphenoxy)-6-phenyl-4-pyridazinol (Compound No. 2464).

$^1$H-NMR (200 MHz, DMSO-$d_6$) δ ppm: 7.78-7.66 (2H, m), 7.58-7.48 (3H, m), 7.35-7.08 (4H, m), 6.69 (1H, s), 2.15 (3H s). Melting point (° C.): 236-237.

EXAMPLE 41

3,6-Bis(2-fluorophenoxy)-4-pyridazinol (Compound No. 2485)

(1) 3,6-Bis(2-fluorophenoxy)pyridazine

In dimethylsulfoxide (20 mL) was dissolved 2.69 g (24.0 mmol) of 2-fluorophenol, and 2.69 g (24.0 mmol) of potassium tert-butoxide was added to the solution at room temperature. To the mixture was added 1.49 g (10.0 mmol) of 2,6-dichloropyridazine, and the resulting mixture was stirred at 100° C. for 3 hours. The reaction mixture was allowed to stand for cooling, pouted into ice-cold water, and extracted with ethyl acetate. The organic layers were combined, washed successively with 1 mol/L aqueous sodium hydroxide solution, water and brine, and dried over anhydrous sodium sulfate. The solvent was removed, the obtained residue was washed with a hot hexane, and then with a hot isopropyl ether to obtain 1.71 g (5.70 mmol, Yield: 57.0%) of 3,6-bis(2-fluorophenoxy)pyridazine.

(2) 3,6-Bis(2-fluorophenoxy)pyridazine 1-oxide (Step C-1)

In dry dichloromethane (40 mL) was dissolved 4.14 g (13.8 mmol) of 3,6-bis(2-fluorophenoxy)pyridazine obtained in (1), 3.19 g (14.8 mmol) of 80% m-chloroperbenzoic acid was added to the solution, and the resulting mixture was stirred at room temperature for 7 days. The reaction mixture was poured into ice-cold 1 mol/L aqueous sodium hydroxide solution, and extracted with ethyl acetate. The organic layers were combined, washed successively with water and brine, and dried over anhydrous sodium sulfate. The solvent was removed, and the obtained residue was purified by silica gel column chromatography (eluted with hexane:ethyl acetate=3:1) to obtain 2.24 g (7.09 mmol, Yield: 51.4%) of 3,6-bis(2-fluorophenoxy)pyridazine 1-oxide.

(3) 4-Chloro-3,6-bis(2-fluorophenoxy)pyridazine (Step C-2)

2.20 g (6.96 mmol) of 3,6-bis(2-fluorophenoxy)pyridazine 1-oxide obtained in (2) and 50 mL of phosphorus oxychloride were mixed, and the mixture was stirred at 90° C. for 1 hour. The reaction mixture was allowed to stand for cooling, poured into ice-cold water, and extracted with ethyl acetate. The organic layers were combined, washed successively with 1 mol/L aqueous sodium hydroxide solution, water and brine, and dried over anhydrous sodium sulfate. The solvent was removed, and the obtained residue was purified by silica gel column chromatography (hexane:ethyl acetate=10:1) to obtain 1.95 g (5.82 mmol, Yield: 83.6%) of 4-chloro-3,6-bis(2-fluorophenoxy)pyridazine.

(4) 3,6-Bis(2-fluorophenoxy)-4-methoxypyridazine (Step C-3)

In methanol (20 mL) was dissolved 1.44 g (4.30 mmol) of 4-chloro-3,6-bis(2-fluorophenoxy)pyridazine obtained in (3), 0.206 g (4.72 mmol) of 55% sodium hydride was added to the solution, and the resulting mixture was stirred at 60° C. for 1 hour. The reaction mixture was allowed to stand for cooling, poured into ice-cold water, and extracted with ethyl acetate. The organic layers were combined, washed successively with water and brine, and dried over anhydrous sodium sulfate. The solvent was removed, and the obtained residue was purified by silica gel column chromatography (eluted with hexane:ethyl acetate=10:1) to obtain 1.03 g (3.12 mmol, Yield: 72.6%) of 3,6-bis(2-fluorophenoxy)-4-methoxypyridazine.

(5) 3,6-Bis(2-fluorophenoxy)-4-pyridazinol (Compound No. 2485, Step C-4)

450 mg (1.36 mmol) of 3,6-bis(2-fluorophenoxy)-4-methoxypyridazine obtained in (4), 77 mg (1.85 mmol) of 96% sodium hydroxide, dimethylsulfoxide (5 mL) and water (1 mL) were mixed, and the mixture was stirred at 90° C. for 2 hours. The reaction mixture was poured into ice-cold water, and made acidic with hydrochloric acid. The mixture was extracted with ethyl acetate, washed with water, and dried over anhydrous sodium sulfate. The solvent was removed to obtain 0.380 g (1.20 mmol, Yield: 88.2%) of 3,6-bis(2-fluorophenoxy)-4-pyridazinol (Compound No. 2485).

$^1$H-NMR. (60 MHz, DMSO-$d_6$) δ ppm: 7.60-7.08 (8H, m), 6.34 (1H, brs). Melting point (° C.): 228.

EXAMPLE 42

(2,4-Dichlorophenyl)(5-{[5-hydroxy-6-(2-methylphenoxy)-3-pyridazinyl]oxy}-1,3-dimethyl-1H-pyrazol-4-yl)methanone (Compound No. 2506)

(1) (5-{[5-Chloro-6-(2-methylphenoxy)-3-pyridazinyl]oxy}-1,3-dimethyl-1H-pyrazol-4-yl)(2,4-dichlorophenyl)meth 109 mg (0.382 mmol) of (2,4-dichlorophenyl)(5-hydroxy-1,3-dimethyl-1H-pyrazol-4-yl)methanone, 1.62 g (6.35 mmol) of 4,6-dichloro-3-(2-methylphenoxy)pyridazine obtained in Example 1 (2) and 107 mg (0.775 mmol) of potassium carbonate were mixed, and the mixture was stirred at 130° C. for 14 hours. The reaction mixture was cooled up to room temperature, and purified by silica gel column chromatography (hexane:ethyl acetate, gradient) to obtain 155 mg (0.308 mmol, Yield: 80.6%) of (5-{[5-chloro-6-(2-methylphenoxy)-3-pyridazinyl]oxy}-1,3-dimethyl-1H-pyrazol-4-yl)(2,4-dichlorophenyl)methanone.

(2) (2,4-Dichlorophenyl)(5-{[5-hydroxy-6-(2-methylphenoxy)-3-pyridazinyl]oxy}-1,3-dimethyl-1H-pyrazol-4-yl)met (Compound No. 2506, A-3 Step)

12.3 mg (0.0244 mmol) of (5-{[5-chloro-6-(2-methylphenoxy)-3-pyridazinyl]oxy}-1,3-dimethyl-1H-pyrazol-4-yl)(2,4-dichlorophenyl)methanone obtained in (1), 0.2 mL of dimethylsulfoxide and 0.012 mL of 10% (W/V) aqueous sodium hydroxide solution were mixed, and the mixture was stirred at room temperature overnight. The reaction mixture was poured into ice-cold water, made acidic by hydrochloric acid, and extracted with ethyl acetate. The organic layers were combined, and dried over anhydrous sodium sulfate. The solvent was distilled off and the residue was purified by preparative thin-layer chromatography (available from Merck Co., 1.05744, developed by dichloromethane:methanol=10:1) to obtain 3.2 mg (0.00784 mmol, Yield: 32%) of (2,4-dichlorophenyl)(5-{[5-hydroxy-6-(2-methylphenoxy)-3-pyridazinyl]oxy}-1,3-dimethyl-1H-pyrazol-4-yl)methanone (Compound No. 2506) and 10.5 mg (0.0208 mmol, Yield: 85.4%) of 4-[{[5-chloro-6-(2-methylphenoxy)-3-pyridazinyl]oxy}-(2,4-dichlorophenyl)methylene]-2,5-dimethyl-2,4-dihydro-3H-pyrazol-3-one.

$^1$H-NMR (200 MHz, CDCl$_3$) δ ppm: 7.36-7.04 (7H, m), 6.20 (1H, brs), 3.64 (3H, s), 2.31 (3H, s), 2.20 (3H, s). Appearance: amorphous.

Also, the following compounds were produced in accordance with the above-mentioned Examples 1 to 42 or by the methods or in accordance with the methods described in the following Examples 622 to 646.

EXAMPLE 43

3-Phenoxy-4-pyridazinol (Compound No. 1)

$^1$H-NMR (90 MHz, DMSO-$d_6$) δ ppm: 12.66 (1H, brs), 8.21 (1H, d, J=6.6 Hz), 7.09-7.54 (5H, m), 6.38 (1H, d, J=6.6 Hz). Melting point (° C.): 193.5.

EXAMPLE 44

6-Chloro-3-{2-[1-(methoxymethyl)cyclopropyl]phenoxy}-4-pyridazinol (Compound No. 163)

$^1$H-NMR (200 MHz, CD$_3$OD) δ ppm: 7.47-7.35 (1H, m), 7.32-7.02 (3H, m), 6.71 (1H, s), 3.47 (2H, s), 3.21 (3H, s), 0.80-0.70 (4H, m). Melting point (° C.): 187-190.

EXAMPLE 45

3-(2-Isopropylphenoxy)-4-pyridazinol (Compound No. 6)

$^1$H-NMR (90 MHz, DMSO-$d_6$) δ ppm: 12.65 (1H, brs), 8.29 (2H, d, J=6.6 Hz), 7.49-6.98 (4H, m), 6.36 (1H, d, J=6.6 Hz), 3.20-2.89 (1H, m, J=6.6 Hz), 1.16 (6H, d, J=6.6 Hz). Melting point (° C.): 181.5-182.

EXAMPLE 46

6-Chloro-3-[2-(1-methoxycyclopropyl)phenoxy]-4-pyridazinol (Compound No. 202)

$^1$H-NMR (200 MHz, CD$_3$OD) δ ppm: 7.50-7.10 (4H, m), 6.67 (1H, s), 3.03 (3H, s), 1.00-0.85 (4H, m). Melting point (° C.): 157-165.

EXAMPLE 47

2-{2-[(6-Chloro-4-hydroxy-3-pyridazinyl)oxy]phenyl}-cyclopropanecarbonitrile (Compound No. 226)

Trans isomer:
$^1$H-NMR (200 MHz, CD$_3$OD) δ ppm: 7.40-7.10 (4H, m), 6.75 (1H, s), 2.65-2.50 (1H, m), 1.65-1.45 (3H, m). Melting point (° C.): 203-207.

Cis isomer:
$^1$H-NMR (200 MHz, CD$_3$OD) δ ppm: 7.40-7.15 (4H, m), 6.64 (1H, s), 2.59 (1H, q, J=8.4 Hz), 2.05-1.90 (1H, m), 1.67-1.40 (2H, m). Melting point (° C.): 225-227.

EXAMPLE 48

6-Chloro-3-phenoxy-4-pyridazinol (Compound No. 123)

$^1$H-NMR (60 MHz, DMF-$d_7$) δ ppm: 7.60-7.00 (5H, m), 6.87 (1H, s). Melting point (° C.): 222-224.

EXAMPLE 49

6-Chloro-3-(2-fluorophenoxy)-4-pyridazinol
(Compound No. 124)

$^1$H-NMR (90 MHz, CD$_3$OD) δ ppm: 7.50-7.05 (4H, m), 6.70 (1H, s). Melting point (° C.): 210-212.

EXAMPLE 50

6-Chloro-3-(2-chlorophenoxy)-4-pyridazinol
(Compound No. 125)

$^1$H-NMR (60 MHz, DMF-d$_7$) δ ppm: 7.70-7.10 (4H, m), 6.95 (1H, s). Melting point (° C.): 208-212.

EXAMPLE 51

3-(2-Bromophenoxy)-6-chloro-4-pyridazinol
(Compound No. 126)

$^1$H-NMR (90 MHz, CD$_3$OD) δ ppm: 7.68 (1H, dd, J=7.5, 1.8 Hz), 7.53-7.10 (3H, m), 6.73 (1H, s). Melting point (° C.): 201-203.

EXAMPLE 52

6-Chloro-3-(2-iodophenoxy)-4-pyridazinol
(Compound No. 127)

$^1$H-NMR (200 MHz, CD$_3$OD) δ ppm: 7.89 (1H, dd, J=7.7, 1.5 Hz) 7.45 (1H, td, J=7.7, 1.5 Hz), 7.22 (1H, dd, J=7.7, 1.5 Hz), 7.04 (1H, td, J=7.7, 1.5 Hz), 6.74 (1H, s). Melting point (° C.): 216-217.

EXAMPLE 53

6-Chloro-3-[2-(2-ethoxycyclopropyl)phenoxy]-4-pyridazinol (Compound No. 249)

$^1$H-NMR (200 MHz, CD$_3$OD) δ ppm: 7.26-7.05 (4H, m), 6.68 (1H, s), 3.46 (1H, q, J=5.2 Hz), 3.30-3.15 (2H, m), 2.17-1.96 (1H, m), 1.10 (2H, dd, J=5.2 Hz, 8.5 Hz), 0.93 (3H, t, J=7.0 Hz). Melting point (° C.): 145-152.

EXAMPLE 54

6-Chloro-3-[2-(2,2-difluorocyclopropyl)phenoxy]-4-pyridazinol (Compound No. 264)

$^1$H-NMR (200 MHz, CD$_3$OD) δ ppm: 7.40-7.15 (4H, m), 6.72 (1H, s), 2.85-2.65 (1H, m), 1.90-1.65 (2H, s). Melting point (° C.): 215-216.

EXAMPLE 55

6-Chloro-3-(2-ethylphenoxy)-4-pyridazinol
(Compound No. 130)

$^1$H-NMR (200 MHz, CD$_3$OD) δ ppm: 7.35-7.15 (3H, m), 7.10-7.02 (1H, m), 6.70 (1H, s), 2.56 (2H, q, J=7.7 Hz), 1.17 (3H, t, J=7.7 Hz). Melting point (° C.): 217-218.

EXAMPLE 56

6-Chloro-3-(2-propylphenoxy)-4-pyridazinol
(Compound No. 131)

$^1$H-NMR (60 MHz, DMF-d$_7$) δ ppm: 7.45-7.05 (4H, m), 6.90 (1H, s), 3.00-2.35 (2H, m), 1.95-1.26 (2H, m), 1.05-0.68 (3H, m). Melting point (° C.): 170-172.

EXAMPLE 57

6-Chloro-3-(2-isopropylphenoxy)-4-pyridazinol
(Compound No. 132)

$^1$H-NMR (60 MHz, DMF-d$_7$) δ ppm: 7.60-7.00 (4H, m), 6.92 (1H, s), 3.11 (1H, septet, J=7.0 Hz), 1.18 (6H, d, J=7.0 Hz). Melting point (° C.): 183.

EXAMPLE 58

3-(2-Butylphenoxy)-6-chloro-4-pyridazinol
(Compound No. 133)

$^1$H-NMR (60 MHz, CDCl$_3$) δ ppm: 11.8 (1H, brs), 7.30-6.70 (4H, m), 6.53 (1H, s), 2.60-2.00 (2H, m), 1.80-0.60 (7H, m). Melting point (° C.): 149.5-150.

EXAMPLE 59

6-Chloro-3-(2-isobutylphenoxy)-4-pyridazinol
(Compound No. 134)

$^1$H-NMR (60 MHz, CDCl$_3$) δ ppm: 12.90 (1H, brs), 7.40-6.85 (4H, m), 6.50 (1H, s), 2.25 (2H, d, J=10.0 Hz), 2.20-1.45 (1H, m, J=10.0 Hz), 0.75 (6H, d, J=10.0 Hz). Melting point (° C.): 151.5-152.5.

EXAMPLE 60

3-(2-s-Butylphenoxy)-6-chloro-4-pyridazinol (Compound No. 135)

$^1$H-NMR (60 MHz, CDCl$_3$+DMF-d$_7$) δ ppm: 7.35-6.80 (4H, m), 6.60 (1H, s), 3.05-2.50 (1H, m), 1.80-1.25 (2H, m), 1.13 (3H, d, J=6.2 Hz), 0.95-0.50 (3H, m). Melting point (° C.): 158-159.

EXAMPLE 61

3-(2-tert-Butylphenoxy)-6-chloro-4-pyridazinol
(Compound No. 136)

$^1$H-NMR (60 MHz, DMF-d$_7$) δ ppm: 7.55-6.85 (4H, m), 6.91 (1H, s), 5.32 (1H, brs), 1.35 (9H, s). Melting point (° C.): 215-216.

EXAMPLE 62

6-Chloro-3-(2-pentylphenoxy)-4-pyridazinol
(Compound No. 137)

$^1$H-NMR (60 MHz, CDCl$_3$) δ ppm: 11.70 (1H, brs), 7.40-6.80 (4H, m), 6.50 (1H, s), 2.60-2.20 (2H, m), 1.80-0.60 (9H, m). Melting point (° C.): 151.5-152.5.

EXAMPLE 63

6-Chloro-3-(2-hexylphenoxy)-4-pyridazinol (Compound No. 138)

$^1$H-NMR (60 MHz, CDCl$_3$) δ ppm: 7.40-6.70 (4H, m), 6.53 (1H, s), 2.70-2.20 (2H, m), 2.00-0.60 (11H, m). Melting point (° C.): 118-118.5.

EXAMPLE 64

6-Chloro-3-[2-(2,2-dichlorocyclopropyl)phenoxy]-4-pyridazinol (Compound No. 265)

$^1$H-NMR (200 MHz, CD$_3$OD) δ ppm: 7.55-7.15 (4H, m), 6.69 (1H, s), 2.90 (1H, dd, J=11.0, 10.8 Hz), 2.05-1.85 (2H, m). Melting point (° C.): 158-163.

EXAMPLE 65

6-Chloro-3-[2-(2,2-dibromocyclopropyl)phenoxy]-4-pyridazinol (Compound No. 266)

$^1$H-NMR (200 MHz, CD$_3$OD) δ ppm: 7.41-7.36 (1H, m), 7.29-7.13 (3H, m), 6.71 (1H, s), 2.97-2.87 (1H, dd, J=11.0, 8.4 Hz), 2.21-2.01 (2H, m). Melting point (° C.): 208-210 (decomposed).

EXAMPLE 66

6-Chloro-3-[2-(1-methylcyclopropyl)phenoxy]-4-pyridazinol (Compound No. 144)

$^1$H-NMR (200 MHz, CDCl$_3$) δ ppm: 7.40-7.35 (1H, m), 7.22-7.17 (2H, m), 6.99-6.94 (1H, m), 6.59 (1H, s), 1.25 (3H, s), 0.85-0.60 (2H, m), 0.60-0.45 (2H, m). Melting point (° C.): 196-198.

EXAMPLE 67

6-Chloro-3-[2-(1-ethylcyclopropyl)phenoxy]-4-pyridazinol (Compound No. 145)

$^1$H-NMR (200 MHz, CDCl$_3$) δ ppm: 7.35-7.10 (3H, m), 6.98 (1H, br.d, J=7.3 Hz), 6.59 (1H, s), 1.50 (2H, q, J=7.0 Hz), 1.26 (3H, t, J=7.0 Hz), 0.67-0.50 (4H, m). Melting point (° C.): 162-165.

EXAMPLE 68

6-Chloro-3-{2-[1-(cyclopropyl)cyclopropyl]phenoxy}-4-pyridazinol (Compound No. 151)

$^1$H-NMR (200 MHz, CDCl$_3$) δ ppm: 7.35-7.29 (1H, m), 7.26-7.10 (2H m), 7.00-6.92 (1H, m), 6.58 (1H, s), 1.30-1.15 (1H, m), 0.60-0.40 (4H, m), 0.27-0.15 (2H, m), 0.07-0.00 (2H, m). Melting point (° C.): 180-182.

EXAMPLE 69

1-{2-[(6-Chloro-4-hydroxy-3-pyridazinyl)oxy]phenyl}-cyclopropanecarbonitrile (Compound No. 173)

$^1$H-NMR (200 MHz, DMSO-d$_6$) δ ppm: 7.55-7.15 (5H, m), 1.65-1.20 (4H, m). Melting point (° C.): 63-64.

EXAMPLE 70

6-Chloro-3-[2-(1-phenylcyclopropyl)phenoxy]-4-pyridazinol (Compound No. 184)

$^1$H-NMR (200 MHz, CDCl$_3$) δ ppm: 7.65-7.55 (1H, m), 7.28-7.20 (2H, m), 7.17-6.95 (6H, m), 6.41 (1H, s), 1.19 (4H, s). Melting point (° C.): 172-173.

EXAMPLE 71

6-Chloro-3-(2-isopropenylphenoxy)-4-pyridazinol (Compound No. 304)

$^1$H-NMR (200 MHz, CD$_3$OD) δ ppm: 7.36-7.10 (4H, m), 6.66 (1H, s), 5.06 (1H, br.s), 5.02 (1H, br.s), 2.01 (3H, d, J=1.5 Hz). Melting point (° C.): 187-188.

EXAMPLE 72

6-Chloro-3-[2-(2-methylcyclopropyl)phenoxy]-4-pyridazinol (Compound No. 217)

$^1$H-NMR (200 MHz, DMSO-d$_6$) δ ppm: 7.32-6.97 (4H, m), 6.82 (1H, brs), 1.89-1.78 (0.8H, m), 1.52-1.43 (0.2H, m), 1.05-0.60 (6H, m). Melting point (° C.): 192-208.

EXAMPLE 73

6-Chloro-3-[2-(2-ethoxycyclopropyl)phenoxy]-4-pyridazinol (Compound No. 249)

$^1$H-NMR (200 MHz, CD$_3$OD) δ ppm: 7.30-7.05 (4H, m), 6.68 (1H, s), 3.51-3.15 (3H, m), 2.07-1.95 (1H, m), 1.13-1.06 (2H, m), 0.93 (3H, t, J=7.1 Hz). Melting point (° C.): 145-152.

EXAMPLE 74

(2E)-3-{2-[(6-Chloro-4-hydroxy-3-pyridazinyl)oxy-phenyl}acrylonitrile (Compound No. 306)

$^1$H-NMR (200 MHz, CD$_3$OD) δ ppm: 7.80-7.40 (3H, m), 7.35-7.15 (2H, m), 6.72 (1H, s), 6.30 (1H, d, J=6.9 Hz). Melting point (° C.): 190-192.

EXAMPLE 75

6-Chloro-3-[2-(2,2-dimethylcyclopropyl)phenoxy]-4-pyridazinol (Compound No. 267)

$^1$H-NMR (200 MHz, DMSO-d$_6$) δ ppm: 7.30-7.10 (4H, m), 1.57 (1H, dd, J=8.4, 6.2 Hz), 0.91-0.85 (1H, m), 0.85 (3H, s), 0.72-0.65 (1H, m), 0.65 (3H, s). Melting point (° C.): 187-188.

EXAMPLE 76

6-Chloro-3-{2-[(cis-2, cis-3-dimethyl)-ref-1-cyclopropyl]phenoxy}-4-pyridazinol (Compound No. 269)

$^1$H-NMR (200 MHz, CD$_3$OD) δ ppm: 7.36-7.11 (4H, m), 6.68 (1H, s), 1.60 (1H, t, J=8.4 Hz), 1.09-0.93 (8H, m). Appearance: amorphous.

EXAMPLE 77

6-Chloro-3-{2-[(cis-2, trans-3-dimethyl)-ref-1-cyclopropyl]phenoxy}-4-pyridazinol (Compound No. 270)

$^1$H-NMR (200 MHz, DMSO-d$_6$) δ ppm: 7.30-7.09 (4H, m), 6.80 (1H, brs), 1.56-1.50 (1H, m), 1.10-0.95 (1H, m), 1.03 (3H, s), 0.80-0.67 (1H, m), 0.71 (3H, s). Melting point (° C.): 157-160.

EXAMPLE 78

6-Chloro-3-{2-[(trans-2, trans-3-dimethyl)-ref-1-cyclopropyl]phenoxy}-4-pyridazinol (Compound No. 271)

$^1$H-NMR (200 MHz, CD$_3$OD) δ ppm: 7.22-6.96 (4H, m), 6.70 (1H, s), 1.18-0.95 (9H, m) Melting point (° C.): 181-183.

EXAMPLE 79

3-{2-[(ref-1,cis-5,cis-6)-Bicyclo[3.1.0]hex-6-yl]phenoxy}-6-chloro-4-pyridazinol (Compound No. 272)

$^1$H-NMR (200 MHz, CD$_3$OD) δ ppm: 7.40-7.05 (4H, m), 6.68 (1H, s), 2.05-1.60 (5H, m), 1.53 (2H, s), 1.35-1.20 (1H, m), 0.25-0.05 (1H, m). Melting point (° C.): 215-240.

EXAMPLE 80

3-{2-[(ref-1,cis-5,trans-6)-Bicyclo[3.1.0]hex-6-yl]phenoxy}-6-chloro-4-pyridazinol (Compound No. 273)

$^1$H-NMR (200 MHz, CDCl$_3$) δ ppm: 7.20-7.10 (2H, m), 7.10-6.90 (2H, m), 6.58 (1H, s), 1.80-1.40 (8H, m), 1.20-1.00 (1H, m). Melting point (° C.): 137-139.

EXAMPLE 81

3-{2-[(ref-1,cis-6,cis-7)-Bicyclo[4.1.0]hept-7-yl]phenoxy}-6-chloro-4-pyridazinol (Compound No. 274)

$^1$H-NMR (200 MHz, CD$_3$OD) δ ppm: 7.44 (1H, br.d, J=6.3 Hz), 7.35-7.10 (3H, m), 6.66 (1H, s), 2.00-1.50 (5H, m), 1.20-1.00 (4H, m), 0.90-0.65 (2H, m). Melting point (° C.): >260.

EXAMPLE 82

3-{2-[(ref-1,cis-6,trans-7)-Bicyclo[4.1.0]hept-7-yl]phenoxy}-6-chloro-4-pyridazinol (Compound No. 275)

$^1$H-NMR (200 MHz, CDCl$_3$) δ ppm: 7.20-7.10 (2H, m), 7.05-6.85 (2H, m), 6.58 (1H, s), 1.90-1.70 (2H, m), 1.60-1.40 (3H, m), 1.30-1.05 (6H, m). Melting point (° C.): 191-193.

EXAMPLE 83

6-Chloro-3-{2-[(2,2, cis-3-trimethyl)-ref-1-cyclopropyl]phenoxy}-4-pyridazinol (Compound No. 279)

$^1$H-NMR (200 MHz, CDCl$_3$) δ ppm: 7.30-7.00 (4H, m), 6.56 (1H, s), 1.42-1.22 (2H, m), 1.05-0.70 (9H, m). Melting point (° C.): 118-120.

EXAMPLE 84

6-Chloro-3-{2-[(2,2, trans-3-trimethyl)-ref-1-cyclopropyl]phenoxy}-4-pyridazinol (Compound No. 280)

$^1$H-NMR (200 MHz, CDCl$_3$) δ ppm: 7.26-7.06 (4H, m), 6.59 (1H, s), 1.70-1.50 (1H, m), 1.30-1.25 (1H, m), 1.09 (3H, s), 0.96 (3H, s), 0.75 (3H, s). Melting point (C): 160-162.

EXAMPLE 85

6-Chloro-3-(2-cyclobutylphenoxy)-4-pyridazinol (Compound No. 284)

$^1$H-NMR (200 MHz, CD$_3$OD) δ ppm: 7.43-7.30 (1H, m), 7.30-7.18 (2H, m), 7.08-6.98 (1H, m), 6.69 (1H, s), 3.68-3.50 (1H, m), 2.25-1.70 (6H, m). Melting point (° C.): 188-189.

EXAMPLE 86

1-{2-[(6-Chloro-4-hydroxy-3-pyridazinyl)oxy]phenyl}-cyclobutanecarbonitrile (Compound No. 287)

$^1$H-NMR (200 MHz, DMSO-d$_6$) δ ppm: 7.50-7.20 (5H, m), 2.70-1.80 (6H, m) Melting point (° C.): 213-215.

EXAMPLE 87

1-{2-[(6-Chloro-4-hydroxy-3-pyridazinyl)oxy]phenyl}-cyclobutanecarboxylicacid (Compound No. 288)

$^1$H-NMR (200 MHz, CD$_3$OD) δ ppm: 7.42-7.35 (1H, m), 7.35-7.20 (2H, m), 7.08-7.03 (1H, m), 6.66 (1H, s), 2.80-2.45 (4H, m), 2.22-1.95 (1H, m), 1.90-1.70 (1H, m). Melting point (° C.): 173-175.

EXAMPLE 88

6-Chloro-3-(2-cyclopentylphenoxy)-4-pyridazinol (Compound No. 292)

$^1$H-NMR (200 MHz, CD$_3$OD) δ ppm: 7.41-7.35 (1H, m), 7.25-7.17 (2H, m), 7.08-7.02 (1H, m), 6.70 (1H, s), 3.14-3.06 (1H, m), 1.98-1.52 (8H, m). Melting point (° C.): 178-180.

EXAMPLE 89

6-Chloro-3-(2-cyclohexylphenoxy)-4-pyridazinol (Compound No. 293)

$^1$H-NMR (60 MHz, CDCl$_3$+DMF-d$_7$) δ ppm: 7.40-6.70 (4H, m), 6.55 (1H s), 2.75 (1H, brs), 2.10-0.90 (10H, m). Melting point (° C.): 158-159.

EXAMPLE 90

6-Chloro-3-[2-(trifluoromethyl)phenoxy]-4-pyridazinol (Compound No. 300)

$^1$H-NMR (90 MHz, CD30D) δ ppm: 7.76-7.27 (4H, m), 6.75 (1H, s), 5.47 (1H, s). Melting point (° C.): 188.

EXAMPLE 91

6-Chloro-3-[2-(1-propenyl)phenoxy}-4-pyridazinol (Compound No. 305)

$^1$H-NMR (60 MHz, DMF-d$_7$) δ ppm: 7.70-6.90 (5H, m), 6.76 (1H, m), 6.50-6.20 (2H, m), 1.81 (3H, d, J=5.0 Hz). Melting point (° C.): 204-206.

EXAMPLE 92

3-(2-Allylphenoxy)-6-chloro-4-pyridazinol. (Compound No. 307)

$^1$H-NMR (60 MHz, DMF-d$_7$) δ ppm: 7.46-7.24 (4H, m), 6.96 (1H s), 6.20-5.60 (1H, m), 5.20-4.80 (2H, m), 3.46-3.26 (2H, m). Melting point (° C.): 200-202.5.

EXAMPLE 93

6-Chloro-3-[2-(1-propynyl)phenoxy]-4-pyridazinol (Compound No. 309)

$^1$H-NMR (200 MHz, CD$_3$OD) δ ppm: 7.43-7.32 (2H, m), 7.23-7.16 (2H, m), 6.73 (1H, s), 1.87 (3H, s). Melting point (° C.): 182-184.

EXAMPLE 94

6-Chloro-3-[2-(cyclopropylmethyl)phenoxy]-4-pyridazinol (Compound No. 311)

$^1$H-NMR (200 MHz, DMSO-d$_6$) δ ppm: 7.45 (1H, dd, J=7.3, 1.8 Hz), 7.31-7.17 (2H, m), 7.10 (1H, dd, J=7.3, 1.8 Hz), 2.38 (2H, d, J=7.0 Hz), 1.00-0.88 (1H, m), 0.50-0.40 (2H, m), 0.22-0.11 (2H, m) Melting point (° C.): 165-168.

EXAMPLE 95

3-(2-Benzylphenoxy)-6-chloro-4-pyridazinol (Compound No. 315) Melting point (° C.): 185-187.

EXAMPLE 96

6-Chloro-3-[2-(methoxymethyl)phenoxy]-4-pyridazinol (Compound No. 324)

$^1$H-NMR (200 MHz, DMSO-d$_6$) δ ppm: 7.47 (1H, br.d, J=7.7 Hz), 7.42-7.20 (2H, m), 7.15 (1H, br.d, J=7.7 Hz), 6.83 (1H, brs), 4.35 (2H, s), 3.23 (3H, s) Melting point (° C.): 211-212.

EXAMPLE 97

6-Chloro-3-[2-(ethoxymethyl)phenoxy]-4-pyridazinol (Compound No. 325)

$^1$H-NMR (200 MHz, DMSO-d$_6$) δ ppm: 7.47 (1H, br.d, J=7.7 Hz), 7.42-7.20 (2H, m), 7.16 (1H, br.d, J=7.7 Hz), 6.82 (1H, brs), 4.38 (2H, s), 3.39 (2H, q, J=7.0 Hz), 1.03 (3H, t, J=7.0 Hz). Melting point (° C.): 173-174.

EXAMPLE 98

6-Chloro-3-[2-(1,3-dioxolan-2-yl)phenoxy]-4-pyridazinol (Compound No. 329) Melting point (° C.): 143-145.

EXAMPLE 99

1-{2-[(6-Chloro-4-hydroxy-3-pyridazinyl)oxy]phenyl}-ethanone O-methyloxime (Compound No. 334)

$^1$H-NMR (200 MHz, DMSO-d$_6$) δ ppm: 7.47 (2H, t, J=7.7 Hz), 7.31 (1H, d, J=7.7 Hz), 7.24 (1H, d, J=7.7 Hz), 6.85 (1H, brs), 3.76 (2.8H, s), 3.58 (0.2H, s), 2.02 (2.8H, s), 1.99 (0.2H, Melting point (° C.): 165-167.

EXAMPLE 100

Methyl 2-[(6-chloro-4-hydroxy-3-pyridazinyl)oxy]-benzoate (Compound No. 339)

$^1$H-NMR (60 MHz, CDCl$_3$+DMF-d$_7$) δ ppm: 8.10-7.18 (4H, m), 6.80 (1H, s), 5.75 (1H, brs), 3.70 (3H, s). Melting point (° C.): 188-191.

EXAMPLE 101

3-([1,1'-Biphenyl]-2-yloxy)-6-chloro-4-pyridazinol (Compound No. 344)

$^1$H-NMR (60 MHz, CDCl$_3$) δ ppm: 7.30-6.70 (10H, m), 6.25 (1H, s). Melting point (° C.): 98-100.

EXAMPLE 102

6-Chloro-3-{[3'-(trifluoromethyl)[1,1'-biphenyl]-2-yl]oxy}-4-pyridazinol (Compound No. 348)

$^1$H-NMR (200 MHz, CDCl$_3$) δ ppm: 7.65-7.58 (2H, m), 7.51-7.26 (5H, m), 7.12-7.06 (1H, m), 6.41 (1H, brs). Appearance: paste state.

EXAMPLE 103

6-Chloro-3-{[3'-(trifluoromethyl)[1,1'-biphenyl]-2-yl]oxy}-4-pyridazinol (Compound No. 349)

$^1$H-NMR (200 MHz, CDCl$_3$) δ ppm: 7.71-7.64 (2H, m), 7.55-7.30 (5H, m), 7.20-7.13 (1H, m), 6.43 (1H, s). Appearance: paste state.

EXAMPLE 104

6-Chloro-3-[2-(1-pyrrolidinyl)phenoxy]-4-pyridazinol (Compound No. 355)

$^1$H-NMR (200 MHz, CD$_3$OD) δ ppm: 7.19-6.73 (4H, m), 5.64 (1H, s), 3.32-3.25 (4H, m), 1.91-1.84 (4H, m). Appearance: amorphous.

EXAMPLE 105

6-Chloro-3-[2-(1H-pyrrol-1-yl)phenoxy]-4-pyridazinol (Compound No. 356)

$^1$H-NMR (200 MHz, CD$_3$OD) δ ppm: 7.41-7.27 (4H, m), 6.95-6.93 (2H, m), 6.46 (1H, m), 6.10-6.08 (2H, m). Appearance: amorphous.

EXAMPLE 106

6-Chloro-3-[2-(2-thienyl)phenoxy]-4-pyridazinol (Compound No. 359)

$^1$H-NMR (200 MHz, CDCl$_3$) δ ppm: 7.68-7.60 (1H, m), 7.45-7.05 (5H, m), 7.01-6.95 (1H, m), 6.52 (1H, s). Appearance: amorphous.

EXAMPLE 107

6-Chloro-3-[2-(3-thienyl)phenoxy]-4-pyridazinol (Compound No. 361)

$^1$H-NMR (200 MHz, CD$_3$OD) δ ppm: 7.46-7.37 (3H, m), 7.30-7.15 (4H, m). Melting point (° C.): 207-209.

EXAMPLE 108

6-Chloro-3-[2-(1H-pyrazol-1-yl)phenoxy]-4-pyridazinol (Compound No. 362)

$^1$H-NMR (200 MHz, CD$_3$OD) δ ppm: 8.09 (1H, d, J=2.2 Hz), 7.70 (1H, dd, J=7.5, 2.4 Hz), 7.62 (1H, d, J=2.2 Hz), 7.50-7.27 (3H, m), 6.55 (1H, s), 6.39 (1H, t, J=2.2 Hz). Appareance: amorphous.

EXAMPLE 108

6-Chloro-3-[2-(3,5-dimethyl-1H-pyrazol-1-yl)phenoxy]-4-pyridazinol (Compound No. 364)

$^1$H-NMR (200 MHz, CD$_3$OD) δ ppm: 7.60-7.32 (4H, m), 6.52 (1H, s), 5.86 (1H, s), 2.17 (3H, s), 2.10 (3H, s). Appareance: amorphous.

EXAMPLE 109

6-Chloro-3-{2-[3-(trifluoromethyl)-1H-pyrazol-1-yl]phenoxy}-4-pyridazinol (Compound No. 365)

$^1$H-NMR (200 MHz, DMSO-d$_6$) δ ppm: 7.79 (1H, brs), 7.70-7.35 (5H, m), 7.06 (1H, brs), 6.68 (1H, s). Appareance: amorphous.

EXAMPLE 111

6-Chloro-3-{2-[4-(trifluoromethyl)-1H-pyrazol-1-yl]phenoxy}-4-pyridazinol (Compound No. 366)

$^1$H-NMR (200 MHz, DMSO-d$_6$) δ ppm: 8.75 (1H, s), 8.11 (1H, s), 7.80-7.74 (1H, m), 7.58-7.38 (3H, m), 6.77 (1H, s). Appareance: oily product.

EXAMPLE 112

6-Chloro-3-{2-[5-(trifluoromethyl)-1H-pyrazol-1-yl]phenoxy}-4-pyridazinol (Compound No. 367)

$^1$H-NMR (200 MHz, DMSO-d$_6$) δ ppm: 8.30 (1H, brs), 7.83-7.72 (1H, m), 7.60-7.40 (3H, m), 6.91 (1H, br.d, J=2.6 Hz), 6.78 (1H, s). Appearance: amorphous.

EXAMPLE 113

5-{2-[(6-Chloro-4-hydroxy-3-pyridazinyl)oxy]phenyl}-N,N-dimethyl-1H-pyrazole-1-sulfonamide (Compound No. 369)

$^1$H-NMR (200 MHz, CDCl$_3$) δ ppm: 8.87 (1H, d, J=2.6 Hz), 7.78 (1H, dd, J=7.3, 1.8 Hz), 7.65-7.35 (3H, m), 7.20 (1H, s), 7.03 (1H, d, J=2.6 Hz), 2.86 (6H, s). Melting point (° C.): 151-152.

EXAMPLE 114

3-{2-[(6-Chloro-4-hydroxy-3-pyridazinyl)oxy]phenyl}-N,N-dimethyl-1H-pyrazole-1-sulfonamide (Compound No. 368)

$^1$H-NMR (200 MHz, CDCl$_3$) δ ppm: 9.19 (1H, d, J=2.9 Hz), 8.12 (1H, s), 7.97 (1H, dd, J=7.3, 2.2 Hz), 7.61 (1H, d, J=1.5 Hz), 7.50-7.33 (2H, m), 6.98 (1H, d, J=2.9 Hz), 2.83 (6H, s). Melting point (° C.): 210-212.

EXAMPLE 115

6-Chloro-3-[2-(4-methyl-1,3-thiazol-2-yl)phenoxy]-4-pyridazinol (Compound No. 370)

$^1$H-NMR (200 MHz, CDCl$_3$) δ ppm: 8.17 (1H, d, J=7.7 Hz), 7.73 (1H, d, J=7.7 Hz), 7.47 (1H, t, J=7.7 Hz), 7.28 (1H, t, J=7.7 Hz), 7.02 (1H, s), 6.98 (1H, s), 2.56 (3H, s). Appearance: amorphous.

EXAMPLE 116

3-[2-(1,3-Benzoxazol-2-yl)phenoxy]-6-chloro-4-pyridazinol (Compound No. 375)

$^1$H-NMR (200 MHz, CD$_3$OD) δ ppm: 8.31 (1H, dd, J=7.9, 1.6 Hz), 7.73-7.30 (7H, m), 6.78 (1H, s). Melting point (° C.): 165-167.

EXAMPLE 117

35 3-[2-(1,3-Benzothiazol-2-yl)phenoxy]-6-chloro-4-pyridazinol (Compound No. 376)

$^1$H-NMR (200 MHz, CDCl$_3$) δ ppm: 8.12 (1H, d, J=7.7 Hz), 8.00-7.84 (1H, m), 7.78 (1H, d, J=7.7 Hz), 7.62-7.05 (1H, brs). Melting point (° C.): 215-217.

EXAMPLE 118

6-Chloro-3-[2-(dimethylamino)phenoxy]-4-pyridazinol (Compound No. 379)

$^1$H-NMR (200 MHz, CD$_3$OD) δ ppm: 7.17-6.96 (4H, m), 6.61 (1H, s), 2.75 (6H, s). Appearance: amorphous.

EXAMPLE 119

6-Chloro-3-(2-nitrophenoxy)-4-pyridazinol (Compound No. 383)

$^1$H-NMR (200 MHz, CD$_3$OD) δ ppm: 8.16 (1H, d, J=6.0 Hz), 7.90-7.33 (3H, m), 6.78 (1H, s). Melting point (° C.): 99-100.

EXAMPLE 120

6-Chloro-3-(2-ethynylphenoxy)-4-pyridazinol (Compound No. 308)

$^1$H-NMR (200 MHz, CD$_3$OD) δ ppm: 7.57-7.41 (2H, m), 7.30-7.20 (2H, m), 6.71 (1H, s), 3.60 (1H, s). Melting point (° C.): 189-191.

EXAMPLE 121

6-Chloro-3-(2-methoxyphenoxy)-4-pyridazinol (Compound No. 385)

$^1$H-NMR (60 MHz, CDCl$_3$+DMF-d$_7$) δ ppm: 7.30-6.80 (4H, m), 6.55 (1H, s), 3.69 (3H, s) Melting point (° C.): 191-194.

EXAMPLE 122

6-Chloro-3-(2-ethoxyphenoxy)-4-pyridazinol
(Compound No. 386)

$^1$H-NMR (200 MHz, CDCl$_3$) δ ppm: 7.26-7.02 (2H, m), 6.98-6.85 (2H, m), 6.57 (1H, s), 5.35 (1H, brs), 3.92 (2H, q, J=7.0 Hz), 1.18 (t, 3H, J=7.0 Hz). Melting point (° C.): 155-175.

EXAMPLE 123

6-Chloro-3-(2-isopropoxyphenoxy)-4-pyridazinol
(Compound No. 387)

$^1$H-NMR (200 MHz, DMSO-d$_6$) δ ppm: 7.28-7.10 (3H, m), 6.97 (1H, td, J=7.3, 2.3 Hz), 6.83 (1H, brs), 4.52 (1H, septet, J=6.2 Hz), 1.07 (6H, d, J=6.2 Hz). Melting point (° C.): 178-1.79.

EXAMPLE 124

6-Chloro-3-[2-(difluoromethoxy)phenoxy]-4-pyridazinol (Compound No. 390)

$^1$H-NMR (200 MHz, CDCl$_3$) δ ppm: 7.40 (4H, s), 6.63 (1H, s) 6.53 (1H, t, J=73.8 Hz). Melting point (° C.): 210-212.

EXAMPLE 125

6-Chloro-3-[2-(trifluoromethoxy)phenoxy]-4-pyridazinol (Compound No. 391)

$^1$H-NMR (200 MHz, CDCl$_3$+CD$_3$OD) δ ppm: 7.38-7.20 (4H, m), 6.60 (1H, s). Melting point (° C.): 215.

EXAMPLE 126

6-Chloro-3-[2-(2-methoxyethoxy)phenoxy]-4-pyridazinol (Compound No. 396)

$^1$H-NMR (200 MHz, CD$_3$OD) δ ppm: 7.26-6.93 (4H, m), 6.62 (1H, s), 4.78-4.03 (2H, m), 3.55-3.50 (2H, m), 3.24 (3H, s). Appearance: paste state.

EXAMPLE 127

6-Chloro-3-[2-(2-hydroxyphenoxy)phenoxy]-4-pyridazinol (Compound No. 399)

$^1$H-NMR (200 MHz, CD$_3$OD) δ ppm: 7.27-6.75 (8H, m), 6.61 (1H, s). Appearance: amorphous.

EXAMPLE 128

6-Chloro-3-{2-{2-[(6-chloro-4-ethoxy-3-pyridazinyl)-oxy]phenoxy}phenoxy}-4-pyridazinol (Compound No. 400)

$^1$H-NMR (200 MHz, CDCl$_3$) δ ppm: 7.65-6.70 (8H, m), 6.63-6.59 (2H, m), 4.19 (2H, q, J=7.0 Hz), 1.50 (3H, t, J=7.0 Hz). Appearance: amorphous.

EXAMPLE 129

6-Chloro-3-[2-(methylsulfanyl)phenoxy]-4-pyridazinol (Compound No. 401)

$^1$H-NMR (200 MHz, CD$_3$OD) δ ppm: 7.43-7.11 (4H, m), 6.71 (1H, s), 2.40 (3H, s). Melting point (° C.): 174-175.

EXAMPLE 130

6-Chloro-3-[2-(isopropylsulfanyl)phenoxy]-4-pyridazinol (Compound No. 403) Melting point (° C.): 176-177.

EXAMPLE 131

6-Chloro-3-(2-cyanophenoxy)-4-pyridazinol
(Compound No. 330)

$^1$H-NMR (200 MHz, CD$_3$OD) δ ppm: 7.82-7.68 (2H, m), 7.46-7.34 (2H, m), 6.79 (1H, s) Appareance: amorphous.

EXAMPLE 132

1-{2-[6-Chloro-4-hydroxy-3-pyridazinyl] oxy}phenyl}-ethanone(Compound No. 336)

$^1$H-NMR (200 MHz, CDCl$_3$) δ ppm: 7.88-7.85 (1H, m), 7.65-7.57 (1H, m), 7.43-7.26 (2H, m), 6.73 (1H, s), 2.50 (3H, br.s). Melting point (° C.): 186-189.

EXAMPLE 133

6-Chloro-3-(3-chlorophenoxy)-4-pyridazinol
(Compound No. 410)

$^1$H-NMR (200 MHz, CD$_3$OD) δ ppm: 7.45-7.10 (5H, m), 6.72 (1H, s). Melting point (° C.): 217.

EXAMPLE 134

6-Chloro-3-(3-iodophenoxy)-4-pyridazinol
(Compound No. 412)

$^1$H-NMR (200 MHz, DMSO-d$_6$) δ ppm: 7.64-7.53 (2H, m), 7.28-6.70 (3H, m). Melting point (° C.): 202-203.

EXAMPLE 135

6-Chloro-3-(3-methylphenoxy)-4-pyridazinol
(Compound No. 413)

$^1$H-NMR (60 MHz, DMF-d$_7$) δ ppm: 7.35-6.80 (4H, m), 6.95 (1H, s), 2.35 (3H, s). Melting point (° C.): 205-208.

EXAMPLE 136

6-Chloro-3-(3-isopropylphenoxy)-4-pyridazinol
(Compound No. 415) Melting point (° C.): 176-177.

EXAMPLE 137

3-(3-tert-Butylphenoxy)-6-chloro-4-pyridazinol
(Compound No. 416)

$^1$H-NMR (60 MHz, DMSO-d$_6$) δ ppm: 7.40-6.65 (4H, m), 6.67 (1H, s), 1.27 (9H, s). Melting point (° C.): 203-207.

EXAMPLE 138

6-Chloro-3-(3-cyclopropylphenoxy)-4-pyridazinol
(Compound No. 417)

$^1$H-NMR (200 MHz, DMSO-d$_6$) δ ppm: 7.35-7.20 (1H, m), 6.98-6.85 (3H, m), 6.78 (1H, brs), 2.00-1.88 (1H, m), 0.98-0.87 (2H, m), 0.70-0.60 (2H, m). Melting point (° C.): 179-181.

EXAMPLE 139

6-Chloro-3-[3-(trifluoromethyl)phenoxy]-4-pyridazinol (Compound No. 418)

$^1$H-NMR (60 MHz, DMF-d$_7$) δ ppm: 7.70-7.40 (4H, m), 6.95 (1H, s). Melting point (° C.): 213-216.

EXAMPLE 140

6-Chloro-3-[3-(2-furyl)phenoxy]-4-pyridazinol (Compound No. 419)

$^1$H-NMR (200 MHz, CDCl$_3$+CD$_3$OD) δ ppm: 7.55-7.35 (4H, m), 7.08-7.02 (1H, m), 6.67 (1H, d, J=3.3 Hz), 6.59 (1H, brs), 6.48 (1H, dd, J=3.3, 1.8 Hz). Melting point (° C.): 200-202.

EXAMPLE 141

3-[(6-Chloro-4-hydroxy-3-pyridazinyl)oxy]benzonitrile (Compound No. 420)

$^1$H-NMR (90 MHz, CD$_3$OD) δ ppm: 7.70-7.40 (4H, m), 6.75 (1H, s). Melting point (° C.): 226-229.

EXAMPLE 142

3-[(6-Chloro-4-hydroxy-3-pyridazinyl)oxy]benzaldehyde (Compound No. 421)

$^1$H-NMR (200 MHz, CD$_3$OD) δ ppm: 9.96 (1H, s), 7.72-7.53 (3H, m), 7.46-7.41 (1H, m), 6.54 (1H, s). Melting point (° C.): 188-192.

EXAMPLE 143

1-{3-[(6-Chloro-4-hydroxy-3-pyridazinyl)oxy]phenyl}-ethanone(Compound No. 422)

Melting point (° C.): 195-198.

EXAMPLE 144

Methyl 3-[(6-chloro-4-hydroxy-3-pyridazinyl)oxy]-benzoate (Compound No. 423)

$^1$H-NMR (90 MHz, CD$_3$OD) δ ppm: 8.00-7.70 (2H, m), 7.70-7.30 (2H, m), 6.75 (1H, s), 3.30 (3H, s). Melting point (° C.): 207.

EXAMPLE 145

6-Chloro-3-(3-nitrophenoxy)-4-pyridazinol (Compound No. 424)

$^1$H-NMR (60 MHz, DMF-d$_7$) δ ppm: 8.30-7.90 (2H, m), 7.90-7.70 (2H, m), 6.50 (1H, s), 5.80-5.15 (1H, brs). Melting point (° C.): 217-219.

EXAMPLE 146

6-Chloro-3-(3-methoxyphenoxy)-4-pyridazinol (Compound No. 425)

$^1$H-NMR (60 MHz, CDCl$_3$+DMF-d$_7$) δ ppm: 7.50-7.10 (1H, m), 6.90-6.60 (3H, m), 6.70 (1H, s), 5.88 (1H, brs), 3.77Melting point (° C.): 199-203.

EXAMPLE 147

6-Chloro-3-(4-chlorophenoxy)-4-pyridazinol (Compound No. 427).

$^1$H-NMR (200 MHz, CD$_3$OD) δ ppm: 7.45-7.38 (2H, m), 7.23-7.15 (2H, m), 6.70 (1H, s). Melting point (° C.): 226-231.

EXAMPLE 148

6-Chloro-3-(4-methylphenoxy)-4-pyridazinol (Compound No. 430)

$^1$H-NMR (60 MHz, DMSO-d$_6$) δ ppm: 7.25-6.83 (4H, m), 6.68 (1H, s), 2.25. (3H, s). Melting point (° C.): 261-263.

EXAMPLE 149

6-Chloro-3-(4-isopropylphenoxy)-4-pyridazinol (Compound No. 432)

Melting point (° C.): 233-235.

EXAMPLE 150

3-(4-tert-Butylphenoxy)-6-chloro-4-pyridazinol (Compound No. 433)

Melting point (° C.): 224-225.

EXAMPLE 151

6-Chloro-3-(4-cyclopropylphenoxy)-4-pyridazinol (Compound No. 434)

$^1$H-NMR (200 MHz, DMSO-d$_6$) δ ppm: 7.15-7.02 (4H, m), 6.82 (1H, brs), 2.01-1.90 (1H, m), 0.99-0.90 (2H, m), 0.70-0.62 (2H, m) Melting point (° C.): 221-227.

EXAMPLE 152

6-Chloro-3-(4-methoxyphenoxy)-4-pyridazinol (Compound No. 435)

$^1$H-NMR (60 MHz, DMF-d$_7$) δ ppm: 7.26-6.85 (4H, m), 6.80 (1H, brs), 3.81 (3H, s). Melting point (° C.): 260-263.5.

EXAMPLE 153

6-Chloro-3-[4-(trimethylsilyl)phenoxy]-4-pyridazinol (Compound No. 436)

Melting point (° C.): 197-199.

EXAMPLE 154

6-Chloro-3-(2,3-difluorophenoxy)-4-pyridazinol (Compound No. 437)

$^1$H-NMR (200 MHz, CD$_3$OD) δ ppm: 7.24-7.05 (3H, m), 6.73 (1H, s). Melting point. (C): 188-193.

EXAMPLE 155

6-Chloro-3-(3-chloro-2-fluorophenoxy)-4-pyridazinol (Compound No. 438)

$^1$H-NMR (200 MHz, CD$_3$OD) δ ppm: 7.43-7.21 (3H, m), 6.75 (1H, s). Melting point (° C.): 187-195.

EXAMPLE 156

6-Chloro-3-[2-fluoro-3-(trifluoromethyl)phenoxy]-4-pyridazinol (Compound No. 441)

$^1$H-NMR (200 MHz, DMSO-d$_6$) δ ppm: 7.78-7.66 (2H, m), 7.48 (1H, t, J=8.1 Hz), 6.83 (1H, s). Melting point (° C.): 185-189.

EXAMPLE 157

6-Chloro-3-(2,3-dichlorophenoxy)-4-pyridazinol (Compound No. 443)

$^1$H-NMR (200 MHz, DMSO-d$_6$) δ ppm: 7.62-7.57 (1H, m), 7.50-7.37 (2H, m), 6.89 (1H, s). Melting point (° C.): 233-238.

EXAMPLE 158

6-Chloro-3-[2-chloro-3-(trifluoromethyl)phenoxy]-4-pyridazinol (Compound No. 446)

$^1$H-NMR (200 MHz, CD$_3$OD) δ ppm: 7.74-7.55 (3H, m), 6.76 (1H, s). Melting point (° C.): 170-200.

EXAMPLE 159

3-(2-Bromo-3-methylphenoxy)-6-chloro-4-pyridazinol (Compound No. 450)

$^1$H-NMR (200 MHz, DMSO-d$_6$) δ ppm: 7.35 (1H, t, J=7.5 Hz), 7.27 (1H, dd, J=7.5, 2.2 Hz), 7.16 (1H, dd, J=7.5, 2.2 Hz), 6.87 (1H, brs), 2.41 (3H, s). Melting point (° C.): 140-141.

EXAMPLE 160

6-Chloro-3-(3-fluoro-2-methylphenoxy)-4-pyridazinol (Compound No. 453)

$^1$H-NMR (200 MHz, CD$_3$OD) δ ppm: 7.30-7.15 (1H, m), 7.08-6.85 (2H, m), 6.73 (1H, s), 2.09 (3H, d, J=1.8 Hz). Melting point (° C.): 242-244.

EXAMPLE 161

6-Chloro-3-(3-chloro-2-methylphenoxy)-4-pyridazinol (Compound No. 454)

$^1$H-NMR (200 MHz, DMSO-d$_6$) δ ppm: 7.39-7.12 (4H, m), 2.14 (3H, s). Melting point (° C.): 250-252.

EXAMPLE 162

6-Chloro-3-(2,3-dimethylphenoxy)-4-pyridazinol (Compound No. 456)

$^1$H-NMR (60 MHz, DMSO-d$_6$) δ ppm: 7.22-6.98 (3H, m), 6.77 (1H, s), 2.30 (3H, s), 2.02 (3H, s). Melting point (° C.): 240-241.

EXAMPLE 163

6-Chloro-3-(2-methyl-3-nitrophenoxy)-4-pyridazinol (Compound No. 458)

$^1$H-NMR (200 MHz, DMSO-d$_6$) δ ppm: 7.89-7.84 (1H, m), 7.58-7.47 (2H, m), 6.90 (1H, brs), 2.25 (3H, s). Melting point (° C.): 241-244.

EXAMPLE 164

6-Chloro-3-(3-methoxy-2-methylphenoxy)-4-pyridazinol (Compound No. 459)

$^1$H-NMR (200 MHz, CD$_3$OD) δ ppm: 7.14 (1H, t, J=8.4 Hz), 6.78 (1H, d, J=8.4 Hz), 6.63 (1H, d, J=8.4 Hz), 6.55 (1H, s), 3.83 (3H, s), 2.00 (3H, s). Melting point (° C.): 224-237.

EXAMPLE 165

6-Chloro-3-{3-[(6-chloro-4-hydroxy-3-pyridazinyl)oxy]-2-methylphenoxy}-4-pyridazinol (Compound No. 460)

$^1$H-NMR (200 MHz, CD$_3$OD) δ ppm: 7.16 (1H, t, J=8.4 Hz), 6.85 (2H, d, J=8.4 Hz), 6.48 (2H, s), 2.15 (3H, s). Melting point (° C.): >290.

EXAMPLE 166

6-Chloro-3-(2-cyclopropyl-3-methylphenoxy)-4-pyridazinol (Compound No. 472)

$^1$H-NMR (200 MHz, DMSO-d$_6$) δ ppm: 7.18 (1H, t, J=7.7 Hz), 7.07 -(1H, br.d, J=7.7 Hz), 6.91 (1H, br.d, J=7.7 Hz), 6.82 (1H, brs), 2.40 (3H, s), 1.43-1.28 (1H, m), 0.79-0.68 (2H, m), 0.59-0.48 (2H, m). Melting point (° C.): 197-198.

EXAMPLE 167

6-Chloro-3-(2-cyclopropyl-6-methylphenoxy)-4-pyridazinyl tetrahydro-2H-pyran-4-carboxylate (Compound No. 3856)

$^1$H-NMR (200 MHz, CDCl$_3$) δ ppm: 7.38 (1H, s), 7.15-7.04 (2H, m), 6.90-6.78 (1H, m), 4.10-3.95 (2H, m), 3.60-3.43 (2H, m), 3.03-2.86 (1H, m), 2.11 (3H, s), 2.06-1.90 (4H, m), 1.80-1.60 (1H, m), 0.80-0.50 (4H, m). Appareance: caramel-like.

EXAMPLE 168

Methyl 2-[(6-chloro-4-hydroxy-3-pyridazinyl)oxy]-6-fluorobenzoate (Compound No. 491)

$^1$H-NMR (270 MHz, CDCl$_3$) δ ppm: 7.62 (1H, td, J=8.4, 5.6 Hz), 7.23 (1H, t, J=8.4 Hz), 7.02 (1H, d, J=8.4 Hz), 3.83 (3H, s). Appareance: amorphous.

EXAMPLE 169

6-Chloro-3-(3-methyl-2-nitrophenoxy)-4-pyridazinol (Compound No. 498)

$^1$H-NMR (200 MHz, CD$_3$OD) δ ppm: 7.48 (1H, t, J=8.1 Hz), 7.26 (1H, d, J=8.1 Hz), 7.19 (1H, d, J=8.1 Hz), 6.66 (1H, s), 2.37 (3H, s). Melting point (° C.): 191-200.

EXAMPLE 170

6-Chloro-3-(2,3-dimethoxyphenoxy)-4-pyridazinol (Compound No. 503)

$^1$H-NMR (200 MHz, DMSO-d$_6$) δ ppm: 7.14-6.78 (4H, m), 3.84 (3H, s), 3.61 (3H, s). Melting point (° C.): 199-201.

EXAMPLE 171

6-Chloro-3-(2,3-dihydro-1H-inden-4-yloxy)-4-pyridazinol (Compound No. 506)

$^1$H-NMR (200 MHz, DMSO-$d_6$) δ ppm: 7.20 (1H, t, J=7.3 Hz), 7.14 (1H, d, J=7.3 Hz), 6.92 (1H, d, J=7.3 Hz), 6.83 (1H, brs), 2.92 (1H, t, J=7.3 Hz), 2.64 (1H, t, J=7.3 Hz), 2.00 (1H, quintet, J=7.3 Hz). Melting point (° C.): 230-232.

EXAMPLE 172

6-Chloro-3-[(3-methyl-2,3-dihydro-1H-inden-4-yl)oxy]-4-pyridazinol (Compound No. 507)

$^1$H-NMR (200 MHz, CD$_3$OD) δ ppm: 7.17 (1H, t, J=7.7 Hz), 7.08 (1H, d, J=7.7 Hz), 6.88 (1H, d, J=7.7 Hz), 6.69 (1H, s), 3.35-3.15 (1H, m), 3.10-2.70 (2H, m), 2.40-2.15 (1H, m), 1.80-1.55 (1H, m), 1.15 (3H, d, J=7.0 Hz). Melting point (° C.): 232.

EXAMPLE 173

6-Chloro-3-[(1-methyl-2,3-dihydro-1H-inden-4-yl)oxy]-4-pyridazinol (Compound No. 510)

$^1$H-NMR (200 MHz, CD$_3$OD) δ ppm: 7.21 (1H, dd, J=8.1, 7.3 Hz) 7.09 (1H, d, J=7.3 Hz), 6.91 (1H, d, J=8.1 Hz), 6.70 (1H, s), 3.30-3.05 (1H, m), 2.85-2.50 (2H, m), 2.40-2.20 (1H, m), 1.70-1.45 (1H, m), 1.29 (3H, d, J=7.0 Hz). Melting point (° C.): 228-230.

EXAMPLE 174

6-Chloro-3-[(2,2-dimethyl-2,3-dihydro-1H-inden-4-yl)oxy]-4-pyridazinol (Compound No. 513)

$^1$H-NMR (200 MHz, CD$_3$OD) δ ppm: 7.17 (1H, t, J=7.7 Hz), 7.05 (1H, d, J=7.7 Hz), 6.89 (1H, d, J=7.7 Hz), 6.69 (1H, s), 2.76 (2H, s), 2.53 (2H, s), 1.13 (6H, s). Melting point (° C.): 220-223.

EXAMPLE 175

6-Chloro-3-{spiro[cyclopropane-1,3'-(2',3'-dihydro-1'H-inden)]-4'-yloxy}-4-pyridazinol (Compound No. 514)

$^1$H-NMR (200 MHz, CD$_3$OD) δ ppm: 7.15-6.95 (2H, m), 6.75 (1H, dd, J=6.6, 2.6 Hz), 6.66 (1H, s), 3.02 (2H, dd, J=7.7, 7.3 Hz), 2.15-1.95 (2H, m), 1.28-1.15 (2H, m), 0.80-0.70 (2H, m) Appearence: amorphous.

EXAMPLE 176

6-Chloro-3-(4-fluorophenoxy)-4-pyridazinol (Compound No. 426)

$^1$H-NMR (200 MHz, CD$_3$OD) δ ppm: 7.26-7.05 (4H, m), 6.70 (1H, s). Melting point (° C.): 241-248.

EXAMPLE 177

3-(Bicyclo[4.2.0]octa-1,3,5-trien-2-yloxy)-6-chloro-4-pyridazinol (Compound No. 505)

$^1$H-NMR (200 MHz, CD$_3$OD) δ ppm: 7.22 (1H, dd, J=8.2, 7.3 Hz), 6.96 (1H, d, J=8.2 Hz), 6.91 (1H, d, J=7.3 Hz), 6.69 (1H, s), 3.19-3.11 (2H, m), 3.10-3.00 (2H, m). Melting point (° C.): 145-155.

EXAMPLE 178

7-[(6-Chloro-4-hydroxy-3-pyridazinyl)oxy]-2,3-dihydro-1H-inden-1-one 0-methyloxime (Compound No. 520)

$^1$H-NMR (200 MHz, CD$_3$OD) δ ppm: 7.50-7.15 (2H, m), 7.07 (1H, dd, J=8.1, 7.3 Hz), 6.55 (0.4H, s), 5.77 (0.6H, s), 3.73 (1.8H, s), 3.67 (1.2H, s), 3.15-3.00 (2H, m), 2.90-2.73 (2H, m). Melting point (° C.): >250.

EXAMPLE 179

6-Chloro-3-(5,6,7,8-tetrahydro-1-naphthalenyloxy)-4-pyridazinol (Compound No. 521)

$^1$H-NMR (200 MHz, DMSO-$d_6$) δ ppm: 7.14 (1H, t, J=7.7 Hz), 6.98 (1H, d, J=7.7 Hz), 6.89 (1H, d, J=7.7 Hz), 6.82 (1H, brs), 2.80-2.70 (2H, m), 2.50-2.40 (2H, m), 1.85-1.70 (4H, m).

Melting point. (C): 232-237.

EXAMPLE 180

6-Chloro-3-(1-naphthyloxy)-4-pyridazinol (Compound No. 527)

$^1$H-NMR (60 MHz, DMSO-$d_6$) δ ppm: 8.10-7.20 (7H, m), 6.85 (1H, s), 6.20 (1H, brs). Melting point (° C.): 243-245.

EXAMPLE 181

6-Chloro-3-(2,3-dihydro-1-benzofuran-4-yloxy)-4-pyridazinol (Compound No. 528)

$^1$H-NMR (200 MHz, DMSO-$d_6$) δ ppm: 7.11 (1H, t, J=8.1 Hz), 6.65 (1H, s), 6.60 (1H, d, J=8.1 Hz), 6.56 (1H d, J=8.1 Hz), 4.53 (2H, t, J=8.5 Hz), 2.97 (2H, t, J=8.5 Hz). Melting point (° C.): 219-221.

EXAMPLE 182

6-Chloro-3-[(3-methyl-2,3-dihydro-1-benzofuran-4-yl)oxy]-4-pyridazinol (Compound No. 529)

$^1$H-NMR (200 MHz, DMSO-$d_6$) δ ppm: 7.15 (1H, t, J=8.1 Hz), 6.85 (1H, brs), 6.67 (1H, d, J=8.1 Hz), 6.62 (1H, d, J=8.1 Hz), 4.65 (1H, t, J=8.8 Hz), 4.12-4.04 (1H, m), 3.50-3.39 (1H, m), 1.14 (3H, d, J=7.0 Hz). Melting point (° C.): 238-245.

EXAMPLE 183

3-(1-benzofuran-4-yloxy)-6-chloro-4-pyridazinol (Compound No. 531)

$^1$H-NMR (200 MHz, DMSO-$d_6$) δ ppm: 7.99 (1H, d, J=2.0 Hz), 7.52 20 (1H, d, J=7.8 Hz), 7.35 (1H, t, J=7.8 Hz), 7.06 (1H, d, J=7.8 Hz), 6.87 (1H, s), 6.81 (1H, d, J=2.0 Hz). Melting point (° C.): 220-225.

EXAMPLE 184

6-Chloro-3-[(3-methyl-1-benzofuran-4-yl)oxy]-4-pyridazinol (Compound No. 532)

$^1$H-NMR (200 MHz, CD$_3$OD) δ ppm: 7.44 (1H, d, J=1.5 Hz), 7.33-7.20 (2H, m), 6.91 (1H, dd, J=7.0, 1.5 Hz), 6.61 (1H, s), 2.01 (3H, s). Melting point (° C.): 218-225.

EXAMPLE 185

3-(1-Benzothien-4-yloxy)-6-chloro-4-pyridazinol
(Compound No. 534)

$^1$H-NMR (200 MHz, CD$_3$OD) δ ppm: 7.75 (1H, d, J=8.1 Hz), 7.53 (1H, d, J=5.5 Hz), 7.35 (1H, dd, J=8.1, 7.7 Hz), 7.28 (1H, 35 dd, J=5.5, 0.7 Hz), 7.10 (1H, dd, J=7.7, 0.7 Hz), 6.64 (1H, s). Melting point (° C.): 181-183.

EXAMPLE 186

6-Chloro-3-(8-quinolynyloxy)-4-pyridazinol
(Compound No. 535)

$^1$H-NMR (200 MHz, DMSO-d$_6$) δ ppm: 8.80 (1H, dd, J=4.0, 1.5 Hz), 8.46 (1H, dd, J=8.4, 1.5 Hz), 7.93-7.87 (1H, m), 7.70-7.63 (2H, m), 7.57 (1H, dd, J=8.4, 4.0 Hz), 6.82 (1H, s). Melting point (° C.): >200 (dec.).

EXAMPLE 187

6-Chloro-3-(8-quinolynyloxy)-4-pyridazinol
(Compound No. 536)

$^1$H-NMR (200 MHz, DMSO-d$_6$) δ ppm: 8.81 (1H, dd, J=4.0, 1.5 Hz), 8.41 (1H, dd, J=8.4, 1.5 Hz), 7.81 (1H, d, J=7.0 Hz), 7.62-7.52 (2H, m), 7.41 (1H, d, J=7.7 Hz), 6.43 (1H, s). Melting point (° C.): >180 (dec.).

EXAMPLE 188

6-Chloro-3-[(2-methyl-1,3-benzoxazol-4-yl)oxy]-4-pyridazinol (Compound No. 538)

$^1$H-NMR (200 MHz, CD$_3$OD) δ ppm: 7.55-7.32 (2H, m), 7.22-7.10 (1H, m), 6.73 (1H, s), 2.59 (3H, s). Melting point (° C.): 221-222.

EXAMPLE 189

6-Chloro-3-(2,3-dihydro-1-benzofuran-7-yloxy)-4-pyridazinol (Compound No. 539)

$^1$H-NMR (200 MHz, CD$_3$OD) δ ppm: 7.13-7.08 (1H, m), 6.95 (1H, d, J=7.3 Hz), 6.85 (1H, dd, J=8.1, 7.3 Hz), 6.67 (1H, s), 4.54 (2H, t, J=8.4 Hz), 3.30-3.20 (2H, m). Appearance: amorphous.

EXAMPLE 190

6-Chloro-3-[(2,2-dimethyl-2,3-dihydro-1-benzofuran-7-yl)oxy]-4-pyridazinol (Compound No. 540)

$^1$H-NMR (200 MHz, DMSO-d$_6$) δ ppm: 7.08 (1H, d, J=7.3 Hz), 6.96 (1H, d, J=8.1 Hz), 6.87-6.79 (2H, m), 3.06 (2H, s), 1.37 (6H, s). Melting point (° C.): 228-229.5.

EXAMPLE 191

3-(1-Benzofuran-7-yloxy)-6-chloro-4-pyridazinol
(Compound No. 541)

$^1$H-NMR (200 MHz, CD$_3$OD) δ ppm: 7.73 (1H, d, J=2.2 Hz), 7.53 (1H, dd, J=7.7, 1.4 Hz), 7.26 (1H, t, J=7.7 Hz), 7.15 (1H, dd, J=7.7, 1.4 Hz), 6.90 (1H, d, J=2.2 Hz), 6.76 (1H, s). Melting point (° C.): 201-202.

EXAMPLE 192

3-(1,3-Benzodioxol-4-yloxy)-6-chloro-4-pyridazinol
(Compound No. 544)

$^1$H-NMR (200 MHz, DMSO-d$_6$) δ ppm: 6.94-6.75 (4H, m), 6.01 (2H, s). Melting point (° C.): 206-211.

EXAMPLE 193

6-Chloro-3-(2,3-dihydro-1,4-benzodioxyn-5-yloxy)-4-pyridazinol (Compound No. 547)

$^1$H-NMR (200 MHz, DMSO-d$_6$) δ ppm: 6.90-6.72 (4H, m), 4.27-4.15 (4H, m). Melting point (° C.): 218-223.5.

EXAMPLE 194

6-Chloro-3-[(2-methyl-1,3-benzoxazol-7-yl)oxy]-4-pyridazinol (Compound No. 549)

$^1$H-NMR (200 MHz, CD$_3$OD) δ ppm: 7.52 (1H, dd, J=8.1, 1.1 Hz) 7.37 (1H, t, J=8.1 Hz), 7.21 (1H, dd, J=8.1, 1.1 Hz), 6.76 (1H, s), 2.65 (3H, s). Melting point (° C.): 197-202.

EXAMPLE 195

6-Chloro-3-(2,4-dichlorophenoxy)-4-pyridazinol
(Compound No. 552)

$^1$H-NMR (60 MHz, DMF-d$_7$) δ ppm: 7.55 (1H, t, J=1.8 Hz), 7.35 (2H, d, J=1.8 Hz), 6.88 (1H, s). Melting point (° C.): 233-237.

EXAMPLE 196

3-(2-Bromo-4-tert-butylphenoxy)-6-chloro-4-pyridazinol (Compound No. 556)

$^1$H-NMR (60 MHz, DMSO-d$_6$) δ ppm: 7.61 (1H, d, J=2.0 Hz), 7.43 (1H, dd, J=8.4, 2.0 Hz), 7.17 (1H, d, J=8.4 Hz), 6.73 (1H, s), 1.32 (9H, s). Melting point (° C.): >202 (dec.).

EXAMPLE 197

6-Chloro-3-(4-chloro-2-methylphenoxy)-4-pyridazinol (Compound No. 558)

$^1$H-NMR (60 MHz, DMSO-d$_6$+CDCl$_3$) δ ppm: 7.40-7.10 (3H, m), 6.65 (1H, s), 2.18 (3H, s). Melting point (° C.): 235-235.5.

EXAMPLE 198

6-Chloro-3-(2,4-dimethylphenoxy)-4-pyridazinol
(Compound No. 559)

$^1$H-NMR (60 MHz, CDCl$_3$) δ ppm: 7.17-6.98 (3H, m), 6.85 (1H, s), 2.29 (3H, s), 2.07 (3H, s). Melting point (° C.): 217.5.

EXAMPLE 199

6-Chloro-3-(2-ethyl-4-iodophenoxy)-4-pyridazinol
(Compound No. 562)

$^1$H-NMR (200 MHz, CD$_3$OD) δ ppm: 7.59 (1H, d, J=2.2 Hz), 7.49 (1H, dd, J=8.4, 2.2 Hz), 6.75 (1H, d, J=8.4 Hz), 6.48 (1H, s), 2.65-1.95 (2H, m), 1.16 (3H, t, J=7.7 Hz). Melting point (° C.): 199-201.

EXAMPLE 200

3-(4-Bromo-2-isopropylphenoxy)-6-chloro-4-pyridazinol (Compound No. 566)

$^1$H-NMR (60 MHz, DMSO-d$_6$) δ ppm: 7.44 (1H, brs), 7.37 (1H, dd, J=8.0, 2.2 Hz), 7.00 (1H, d, J=8.0 Hz), 6.73 (1H, s), 3.01 (1H, septet, J=6.8 Hz), 1.15 (6H, d, J=6.8 Hz). Melting point (° C.): 215-225.

EXAMPLE 201

3-(2-tert-Butyl-4-methylphenoxy)-6-chloro-4-pyridazinol (Compound No. 567)

$^1$H-NMR (90 MHz, CD$_3$OD) δ ppm: 7.25 (1H, d, J=2.0 Hz), 7.05 (1H, dd, J=8.0, 2.0 Hz), 6.85 (1H, d, J=8.0 Hz), 6.70 (1H, s), 2.30 (3H, s), 1.35 (9H, s). Melting point (° C.): 230-236.

EXAMPLE 202

6-Chloro-3-(2-cyclopropyl-4-methylphenoxy)-4-pyridazinol (Compound No. 571)

$^1$H-NMR (200 MHz, CD$_3$OD) δ ppm: 7.05-6.95 (1H, m), 6.96 (1H, s), 6.81 (1H, s), 6.68 (1H, m), 2.30 (3H, s), 1.90-1.75 (1H, m), 0.90-0.70 (2H, m), 0.70-0.50 (2H, m). Melting point (IC): 239.

EXAMPLE 203

6-Chloro-3-(2-chloro-5-methylphenoxy)-4-pyridazinol (Compound No. 614)

$^1$H-NMR (90 MHz, CD$_3$OD) δ ppm: 7.40 (1H, d, J=8.5 Hz), 7.15 (1H, s), 7.10 (1H, d, J=8.5 Hz), 6.70 (1H, s), 2.35 (3H, s). Melting point (° C.): 170.

EXAMPLE 204

6-Chloro-3-(5-chloro-2-methylphenoxy)-4-pyridazinol (Compound No. 618)

$^1$H-NMR (200 MHz, CD$_3$OD) δ ppm: 7.28 (1H, d, J=8.8 Hz), 7.21-7.15 (1H, m), 7.16 (1H, s), 6.72 (1H, s), 2.15 (3H, Melting point (° C.): 174-180.

EXAMPLE 205

6-Chloro-3-(2,5-dimethylphenoxy)-4-pyridazinol (Compound No. 621)

$^1$H-NMR (90 MHz, CD$_3$OD) δ ppm: 7.16 (1H, d, J=9.0 Hz), 7.08 (1H, d, J=9.0 Hz), 6.90 (1H, s), 6.70 (1H, s), 2.30 (3H, s) 2.10 (3H, s). Melting point (° C.): 80-83.

EXAMPLE 206

6-Chloro-3-(5-isopropyl-2-methylphenoxy)-4-pyridazinol (Compound No. 623)

$^1$H-NMR (90 MHz, CD$_3$OD) δ ppm: 7.20 (1H, d, J=7.5 Hz), 7.15-6.98 (1H, m), 6.95 (1H, s), 6.70 (1H, s), 2.88 (1H, s J=7.5 Hz), 2.10 (3H, s), 1.23 (6H, d, J=7.5 Hz). Melting point (° C.): 168-169.

EXAMPLE 207

3-[(6-Chloro-4-hydroxy-3-pyridazinyl)oxy]-4-methylbenzoic acid (Compound No. 626) Melting point (° C.): 238-240.

EXAMPLE 208

3-(5-Amino-2-methylphenoxy)-6-chloro-4-pyridazinol (Compound No. 627) Melting point (° C.): >310.

EXAMPLE 209

6-Chloro-3-[5-(dimethylamino)-2-methylphenoxy]-4-pyridazinol (Compound No. 628)

$^1$H-NMR (200 MHz, CD$_3$OD) δ ppm: 7.08 (1H, d, J=8.4 Hz), 6.68 (1H, s), 6.61 (1H, dd, J=8.4, 2.6 Hz), 6.50 (1H, d, J=2.6 Hz), 2.88 (6H, s), 2.02 (3H, s). Melting point (° C.): 181-182.

EXAMPLE 210

6-Chloro-3-(5-methoxy-2-methylphenoxy)-4-pyridazinol (Compound No. 629)

$^1$H-NMR (200 MHz, CD$_3$OD) δ ppm: 7.16 (1H, d, J=8.4 Hz), 6.78-6.67 (3H, m), 3.75 (3H, s), 2.07 (3H, s). Melting point (° C.): 170-172.

EXAMPLE 211

6-Chloro-3-(2-ethyl-5-methoxyphenoxy)-4-pyridazinol (Compound No. 635)

$^1$H-NMR (60 MHz, DMF-d$_7$) δ ppm: 7.15 (1H, br.d, J=8.0 Hz), 6.74 (1H, brs), 6.73 (1H, br.d, J=8.0 Hz), 6.63 (1H, s), 3.73 (3H, s), 2.46 (2H, q, J=7.0 Hz), 1.10 (3H, t, J=7.0 Hz). Melting point (° C.): 124-126.

EXAMPLE 212

6-Chloro-3-(2-isopropyl-5-methylphenoxy)-4-pyridazinol (Compound No. 640)

$^1$H-NMR (60 MHz, CDCl$_3$+DMF-d$_7$) δ ppm: 7.50-6.70 (3H, m), 6.58 (1H, s), 3.30-2.60 (1H, m), 2.26 (3H, s), 1.13 (6H, d, J=6.60 Hz). Melting point (° C.): 193-195.

EXAMPLE 213

6-Chloro-3-(3,5-diisopropylphenoxy)-4-pyridazinol (Compound No. 642)

$^1$H-NMR (60 MHz, DMSO-d$_6$) δ ppm: 7.25 (1H, d, J=8.0 Hz), 7.11 (1H, d, J=1.8 Hz), 6.92 (1H, dd, J=8.0, 1.8 Hz), 6.73 (1H, s), 2.84 (2H, septet, J=7.0 Hz), 1.18 (6H, d, J=7.0 Hz), 1.12 (6H, d, J=7.0 Hz). Melting point (° C.): 231-235.

EXAMPLE 214

3-(2-tert-Butyl-5-methylphenoxy)-6-chloro-4-pyridazinol (Compound No. 650)

$^1$H-NMR (90 MHz, CD$_3$OD) δ ppm: 7.35 (1H, d, J=8.0 Hz), 6.95 (1H, dd, J=8.0, 1.5 Hz), 6.80 (1H, s), 6.70 (1H, s), 2.27 (3H, s), 1.35 (9H, s). Melting point (° C.): 226.

EXAMPLE 215

6-Chloro-3-(2,5-di-tert-butylphenoxy)-4-pyridazinol (Compound No. 653)

¹H-NMR (60 MHz, DMF-d₇) δ ppm: 7.50-7.10 (3H, m), 6.94 (1H, s), 4.98 (1H brs), 1.37 (9H, s), 1.28 (9H, s). Melting point (° C.): 249-258.

EXAMPLE 216

6-Chloro-3-(2-cyclopropyl-5-fluorophenoxy)-4-pyridazinol (Compound No. 658)

¹H-NMR (200 MHz, CD₃OD) δ ppm: 7.10-6.85 (3H, m), 6.72 (1H, s), 1.92-1.75 (1H, m), 0.85-0.70 (2H, m), 0.70-0.54 (2H, m). Melting point (° C.): 227-228.

EXAMPLE 217

6-Chloro-3-(5-chloro-2-cyclopropylphenoxy)-4-pyridazinol (Compound No. 659)

¹H-NMR (200 MHz, CD₃OD) δ ppm: 7.19 (1H, d, J=7.7 Hz), 7.16 (1H, s), 7.01 (1H, d, J=7.7 Hz), 6.72 (1H, s), 1.94-1.79 (1H, m), 0.90-0.75 (2H, m), 0.75-0.58 (2H, m). Melting point (° C.): 194-195.

EXAMPLE 218

6-Chloro-3-(2-cyclopropyl-5-methylphenoxy)-4-pyridazinol (Compound No. 662)

¹H-NMR (200 MHz, CD₃OD) δ ppm: 6.96 (1H, d, J=7.7 Hz), 6.89 (1H, s), 6.87 (1H, d, J=7.7 Hz), 6.68 (1H, s), 2.28 (3H, s), 1.87-1.73 (1H, m), 0.80-0.51 (4H, m) Melting point (° C.): 150-159.

EXAMPLE 219

6-Chloro-3-(2-cyclopropyl-5-ethylphenoxy)-4-pyridazinol (Compound No. 663)

¹H-NMR (200 MHz, CD₃OD) δ ppm: 7.01 (1H, d, J=8.0 Hz), 6.92 (1H, s), 6.92 (1H, d, J=8.0 Hz), 6.69 (1H, s), 2.61 (2H, t, J=7.7 Hz), 1.88-1.72 (1H, m), 1.20 (3H, q, J=7.7 Hz), 0.82-0.66 (2H, m), 0.65-0.52 (2H, m). Appearance: amorphous.

EXAMPLE 220

6-Chloro-3-(2-cyclopropyl-5-isopropylphenoxy)-4-pyridazinol (Compound No. 664)

¹H-NMR (200 MHz, CD₃OD) δ ppm: 7.05 (1H, dd, J=7.7, 1.8 Hz), 7.00 (1H, brs), 6.93 (1H, d, J=7.7 Hz), 6.70 (1H, s), 2.87 (1H, septet, J=7.0 Hz), 1.90-1.72 (1H, m), 1.22 (6H, d, J=7.0 Hz), 0.85-0.68 (2H, m), 0.68-0.52 (2H, m). Melting point (° C.): 211-212.

EXAMPLE 221

3-[(6-Chloro-4-hydroxy-3-pyridazinyl)oxy]-4-cyclopropylbenzonitrile (Compound No. 667)

¹H-NMR (200 MHz, CD₃OD) δ ppm: 7.58-7.48 (2H, m), 7.15 (1H, d, J=8.8 Hz), 6.74 (1H, s), 2.10-1.90 (1H, m), 1.05-0.93 (2H, m), 0.83-0.70 (2H, m). Melting point (° C.): 211-212.

EXAMPLE 222

6-Chloro-3-[5-fluoro-2-(1-propenyl)phenoxy]-4-pyridazinol (Compound No. 679)

¹H-NMR (200 MHz, CD₃OD) δ ppm: 7.61-7.53 (1H, m), 7.03-6.90 (2H, m), 6.72 (1H, s), 6.44-6.19 (2H, m), 1.80 (3H, d, J=5.5 Hz). Melting point (° C.): 210-217.

EXAMPLE 223

6-Chloro-3-[5-chloro-2-(1-propenyl)phenoxy]-4-pyridazinol (Compound No. 680)

¹H-NMR (200 MHz, CD₃OD) δ ppm: 7.55 (1H, d, J=8.4 Hz), 7.24-7.17 (2H, m), 6.72 (1H, s), 6.46-6.30 (2H, m), 1.81 (3H, d, J=5.1 Hz). Melting point (° C.): 221-224.

EXAMPLE 224

2-[(6-Chloro-4-hydroxy-3-pyridazinyl)oxy]-4-(dimethylamino)benzaldehyde (Compound No. 692)

¹H-NMR (90 MHz, DMSO-d₆) δ ppm: 9.78 (1H, s), 7.69 (1H, d, J=6.0 Hz), 6.81 (1H, s), 6.78-6.46 (2H, m), 3.05 (6H, s). Melting point (° C.): 124-127.

EXAMPLE 225

3-(5-Chloro-2-methoxyphenoxy)-6-chloro-4-pyridazinol (Compound No. 701)

¹H-NMR (200 MHz, CD₃OD) δ ppm: 7.23-7.18 (2H, m), 7.05 (1H, d, J=8.8 Hz), 6.66 (1H, s), 3.73 (3H, s). Melting point (° C.): 143-155.

EXAMPLE 226

3-(5-Bromo-2-methoxyphenoxy)-6-chloro-4-pyridazinol (Compound No. 702)

¹H-NMR (200 MHz, CD₃OD) δ ppm: 7.39-7.31 (2H, m), 7.02 (1H, d, J=8.4 Hz), 6.67 (1H, s), 3.74 (3H, s). Melting point (° C.): 135-137.

EXAMPLE 227

6-Chloro-3-(4-fluoro-2-methylphenoxy)-4-pyridazinol (Compound No. 557)

¹H-NMR (200 MHz, CD₃OD) δ ppm: 7.14-6.88 (3H, m), 6.71 (1H, s), 2.16 (3H, s). Melting point (° C.): 249-250.

EXAMPLE 228

3-[(6-Chloro-4-hydroxy-3-pyridazinyl)oxy]-4-methoxybenzonitrile (Compound No. 707)

¹H-NMR (200 MHz, CD₃OD) δ ppm: 7.66 (1H, dd, J=8.4, 2.2 Hz), 7.58 (1H, d, J=2.2 Hz), 7.26 (1H, d, J=8.4 Hz), 6.71 (1H, s), 3.85 (3H, s). Melting point (° C.): 187-192.

EXAMPLE 229

6-Chloro-3-(2-methoxy-5-nitrophenoxy)-4-pyridazinol (Compound No. 708)

¹H-NMR (200 MHz, CD₃OD) δ ppm: 8.18 (1H, dd, J=9.2, 2.6 Hz) 8.04 (1H, d, J=2.6 Hz), 7.27 (1H, d, J=9.2 Hz), 6.59 (1H, s), 3.89 (3H, s). Appearance: amorphous.

EXAMPLE 230

6-Chloro-3-(2,5-dimethoxyphenoxy)-4-pyridazinol (Compound No. 709)

$^1$H-NMR (200 MHz, CD$_3$OD) δ ppm: 7.04-6.99 (1H, m), 6.81-6.78 (2H, m), 6.68 (1H, s), 3.76 (3H, s), 3.70 (3H, s). Melting point (° C.): 150-152.

EXAMPLE 231

6-Chloro-3-(2,6-difluorophenoxy)-4-pyridazinol (Compound No. 710)

$^1$H-NMR (200 MHz, DMSO-d$_6$) δ ppm: 7.54-7.20 (3H, m), 6.88 (1H, s). Melting point (° C.): 209-213.

EXAMPLE 232

6-Chloro-3-(2-chloro-6-fluorophenoxy)-4-pyridazinol (Compound No. 711)

$^1$H-NMR (200 MHz, CD$_3$OD) δ ppm: 7.35-7.13 (3H, m), 6.61 (1H, s). Melting point (° C.): 235.

EXAMPLE 233

3-(2-Bromo-6-fluorophenoxy)-6-chloro-4-pyridazinol (Compound No. 712)

$^1$H-NMR (200 MHz, CD$_3$OD) δ ppm: 7.31-7.15 (3H, m), 6.65 (1H, s). Appearance: amorphous.

EXAMPLE 234

6-Chloro-3-(2-fluoro-6-propylphenoxy)-4-pyridazinol (Compound No. 716) Melting point (° C.): 134-137.

EXAMPLE 235

6-Chloro-3-(2-fluoro-6-isopropylphenoxy)-4-pyridazinol (Compound No. 717)

$^1$H-NMR (200 MHz, DMSO-d$_6$) δ ppm: 7.35-7.15 (3H, m), 6.89 (1H, brs), 3.02 (1H, septet, J=7.0 Hz), 1.14 (6H, J=7.0 Hz). Melting point (° C.): 215-220.

EXAMPLE 236

6-Chloro-3-(2-cyclopropyl-6-fluorophenoxy)-4-pyridazinol (Compound No. 719)

$^1$H-NMR (200 MHz, CD$_3$OD) δ ppm: 7.22-6.96 (2H, m), 6.81-6.71 (1H, m), 6.72 (1H, s), 2.03-1.89 (1H, m), 0.93-0.80 (2H, m), 0.69-0.62 (2H, m). Melting point (° C.): 200-203.

EXAMPLE 237

6-Chloro-3-{2-[1-(ethylsulfanyl)ethyl]-6-fluorophenoxy}-4-pyridazinol (Compound No. 728)

$^1$H-NMR (200 MHz, CD$_3$OD) δ ppm: 7.42 (1H, d, J=8.1 Hz), 7.26-7.15 (1H, m), 7.07-6.97 (1H, m), 6.46 (1H, s), 4.33 (1H, q, J=7.0 Hz), 2.42-2.20 (2H, m), 1.43 (3H, d, J=7.0 Hz), 1.02 (3H, t, J=7.0 Hz) Physical property: amorphous.

EXAMPLE 238

6-Chloro-3-(2-fluoro-6-nitrophenoxy)-4-pyridazinol (Compound No. 731)

$^1$H-NMR (200 MHz, CD$_3$OD) δ ppm: 8.03-7.99 (1H, m), 7.78-7.53 (2H, m), 6.89 (1H, s) Melting point (° C.): 210 (sublimation).

EXAMPLE 239

6-Chloro-3-(2-fluoro-6-methoxyphenoxy)-4-pyridazinol (Compound No. 732)

$^1$H-NMR (200 MHz, DMSO-d$_6$) δ ppm: 7.26 (1H, dd, J=15.0, 8.1 Hz), 7.02-6.91 (2H, m), 6.84 (1H, s), 3.75 (3H, s). Melting point (° C.): 190-194 (sublimation).

EXAMPLE 240

6-Chloro-3-(2,6-dichlorophenoxy)-4-pyridazinol (Compound No. 733)

$^1$H-NMR (90 MHz, DMSO-d$_6$) δ ppm: 7.70-7.10 (3H, m), 6.80 (1H, s). Melting point (° C.): 265.

EXAMPLE 241

6-Chloro-3-(2-chloro-6-iodophenoxy)-4-pyridazinol (Compound No. 735)

$^1$H-NMR (200 MHz, DMSO-d$_6$) δ ppm: 7.90 (1H, d, J=8.1 Hz), 7.64 (1H, d, J=8.1 Hz), 7.12 (1H, t, J=8.1 Hz), 7.02-6.80 (1H, br.m). Melting point (° C.): 262-264.

EXAMPLE 242

6-Chloro-3-(2-chloro-6-methylphenoxy)-4-pyridazinol (Compound No. 736)

$^1$H-NMR (90 MHz, CD$_3$OD) δ ppm: 7.50-7.00 (3H, m), 6.75 (1H, s), 2.22 (3H, s). Melting point (° C.): 235.

EXAMPLE 243

6-Chloro-3-(2-chloro-6-ethylphenoxy)-4-pyridazinol (Compound No. 737)

Melting point (° C.): 194-195.

EXAMPLE 244

6-Chloro-3-(5-fluoro-2-methoxyphenoxy)-4-pyridazinol (Compound No. 700)

$^1$H-NMR (200 MHz, CD$_3$OD) δ ppm: 7.13-6.94 (3H, m), 6.71 (1H, s), 3.74 (1H, s). Melting point (° C.): 187-191.

EXAMPLE 245

6-Chloro-3-(2-chloro-6-cyclopropylphenoxy)-4-pyridazinol (Compound No. 740)

$^1$H-NMR (200 MHz, CD$_3$OD) δ ppm: 7.30 (1H, dd, J=8.1, 1.5 Hz), 7.17 (1H, dd, J=8.1, 7.7 Hz), 6.96 (1H, dd, J=7.7, 1.5 Hz), 6.76 (1H, s), 2.00-1.84 (1H, m), 0.95-0.80 (2H, m), 0.70-0.60 (2H, m). Melting point (° C.): 224-225.

EXAMPLE 246

6-Chloro-3-[2-chloro-6-(2-methyl-2-propenyl)phenoxy]-4-pyridazinol (Compound No. 746)

Melting point (° C.): 198-200.

EXAMPLE 247

6-Chloro-3-(2-chloro-6-nitrophenoxy)-4-pyridazinol (Compound No. 754)

$^1$H-NMR (200 MHz, CD$_3$OD) δ ppm: 8.12 (1H, dd, J=8.1, 1.5 Hz), 7.95 (1H, dd, J=8.1, 1.5 Hz), 7.59 (1H, t, J=8.1 Hz), 6.76 (1H, s). Appearance: amorphous.

EXAMPLE 248

6-Chloro-3-(2,6-dibromophenoxy)-4-pyridazinol (Compound No. 756)

$^1$H-NMR (200 MHz, CD$_3$OD) δ ppm: 7.65 (2H, d, J=8.1 Hz), 7.11 (1H, t, J=8.1 Hz), 6.74 (1H, brs). Melting point (° C.): 274-278.

EXAMPLE 249

3-(2-Bromo-6-methylphenoxy)-6-chloro-4-pyridazinol (Compound No. 758)

$^1$H-NMR (200 MHz, DMSO-d$_6$) δ ppm: 7.56 (1H, br.d, J=7.7 Hz) 7.36 (1H, br.d, J=7.7 Hz), 7.16 (1H, t, J=7.7 Hz), 6.92 (1H, brs), 2.14 (3H, s). Melting point (° C.): 242-243.

EXAMPLE 250

3-(2-Bromo-6-ethylphenoxy)-6-chloro-4-pyridazinol (Compound No. 759)

$^1$H-NMR (200 MHz, CD$_3$OD) δ ppm: 7.49 (1H, dd, J=7.9, 1.6 Hz), 7.32 (1H, dd, J=7.9, 1.6 Hz), 7.14 (1H, t, J=7.9 Hz), 6.75 (1H, s), 2.58 (2H, q, J=7.5 Hz), 1.18 (3H, t, J=7.5 Hz). Melting point (° C.): 215-217.

EXAMPLE 251

3-[(6-Chloro-4-hydroxy-3-pyridazinyl)oxy]-4-methoxybenzonitrile (Compound No. 707)

$^1$H-NMR (200 MHz, CD$_3$OD) δ ppm: 7.66 (1H, dd, J=8.4, 2.2 Hz), 7.58 (1H, d, J=2.2 Hz), 7.26 (1H, d, J=8.4 Hz), 6.71 (1H, s), 3.85 (3H, s). Melting point (° C.): 187-192.

EXAMPLE 252

3-(2-Bromo-6-chlorophenoxy)-6-chloro-4-pyridazinol (Compound No. 734)

$^1$H-NMR (200 MHz, CD$_3$OD) δ ppm: 7.64 (1H, dd, J=1.5 Hz, 8.1 Hz), 7.52 (1H, dd, J=1.5 Hz, 8.0 Hz), 7.21 (1H, t, J=8.1 Hz), 6.76 (1H, s). Melting point (° C.): 266-274.

EXAMPLE 253

3-(2-Bromo-6-cyclopropylphenoxy)-6-chloro-4-pyridazinol (Compound No. 762)

$^1$H-NMR (200 MHz, DMSO-d$_6$) δ ppm: 7.51 (1H, d, J=7.8 Hz), 7.14 (1H, t, J=7.8 Hz), 7.02 (1H, d, J=7.8 Hz), 6.89 (1H, s), 1.89-1.75 (1H, m), 0.88-0.75 (2H, m), 0.75-0.58 (2H, m). Melting point (° C.): 230-232.

EXAMPLE 254

3-Bromo-2-[(6-chloro-4-hydroxy-3-pyridazinyl)oxy]-benzonitrile (Compound No. 775)

$^1$H-NMR (200 MHz, CD$_3$OD) δ ppm: 8.00 (1H, dd, J=8.1, 1.5 Hz), 7.82 (1H, dd, J=8.1, 1.5 Hz), 7.37 (1H, t, J=8.1 Hz), 6.75 (1H, s). Melting point (° C.): 188 (dec.).

EXAMPLE 255

3-(2-Bromo-6-methoxyphenoxy)-6-chloro-4-pyridazinol (Compound No. 778)

$^1$H-NMR (200 MHz, CD$_3$OD) δ ppm: 7.26-7.05 (3H, m), 6.70 (1H, s), 3.78 (3H, s). Melting point (° C.): 220-221.

EXAMPLE 256

6-Chloro-3-(2-iodo-6-methylphenoxy)-4-pyridazinol (Compound No. 780)

$^1$H-NMR (200 MHz, CD$_3$OD) δ ppm: 7.70 (1H, d, J=7.7 Hz), 7.29 (1H, d, J=8.1 Hz), 6.95 (1H, t, J=7.7 Hz), 6.76 (1H, s), 2.20 (3H, s). Melting point (° C.): 250-252.

EXAMPLE 257

6-Chloro-3-(2-ethyl-6-iodophenoxy)-4-pyridazinol (Compound No. 781)

$^1$H-NMR (200 MHz, CD$_3$OD) δ ppm: 7.72 (1H, dd, J=7.7, 1.5 Hz), 7.33 (1H, dd, J=7.7, 1.5 Hz), 7.00 (1H, t, J=7.7 Hz), 6.76 (1H, s), 2.57 (2H, q, J=7.7 Hz), 1.17 (3H, t, J=7.7 Hz). Melting point (° C.): 242-244.

EXAMPLE 258

6-Chloro-3-(2-iodo-6-isopropylphenoxy)-4-pyridazinol (Compound No. 782)

$^1$H-NMR (200 MHz, CD$_3$OD) δ ppm: 7.70 (1H, dd, J=8.0, 1.5 Hz) 7.40 (1H, dd, J=8.0, 1.5 Hz), 7.03 (1H, t, J=8.0 Hz), 6.76 (1H, s), 3.01 (1H, septet, J=7.0 Hz), 1.18 (6H, d, J=7.0 Hz). Melting point (° C.): 250-255.

EXAMPLE 259

3-Bromo-2-[(6-chloro-4-hydroxy-3-pyridazinyl)oxy]-benzonitrile (Compound No. 775)

$^1$H-NMR (200 MHz, CD$_3$OD) δ ppm: 8.00 (1H, dd, J=8.1, 1.5 Hz), 7.82 (1H, dd, J=8.1, 1.5 Hz), 7.37 (1H, t, J=8.1 Hz), 6.75 (1H, s). Melting point (° C.): 188 (dec.).

EXAMPLE 260

6-Chloro-3-(2-ethyl-6-methylphenoxy)-4-pyridazinol (Compound No. 802)

$^1$H-NMR (200 MHz, CDCl$_3$) δ ppm: 7.12-6.97 (3H, m), 6.52 (1H, s), 2.37 (2H, q, J=7.6 Hz), 1.95 (3H, s), 1.04 (3H, t, J=7.6 Hz). Appearance: amorphous.

EXAMPLE 261

6-Chloro-3-(2-isopropyl-6-methylphenoxy)-4-pyridazinol (Compound No. 803)

$^1$H-NMR (200 MHz, CD$_3$OD) δ ppm: 7.23-7.06 (3H, m), 6.72 (1H, s), 2.96 (1H, septet, J=7.0 Hz), 2.10 (3H, s), 1.16 (6H, d, J=7.0 Hz). Melting point (° C.): 215-220.

EXAMPLE 262

3-(2-s-Butyl-6-methylphenoxy)-6-chloro-4-pyridazinol (Compound No. 804)

Melting point (° C.): 187-189.

EXAMPLE 263

6-Chloro-3-[2-(2,2-dichlorocyclopropyl)-6-methylphenoxy]-4-pyridazinol (Compound No. 827)

$^1$H-NMR (200 MHz, CD$_3$OD) δ ppm: 7.25 (1H, br.d, J=6.2 Hz), 7.16 (1H, dd, J=7.7, 7.3 Hz), 6.98 (1H, br.d, J=7.7 Hz), 6.72 (1H, s), 2.85 (1H, dd, J=11.0, 10.6 Hz), 2.22 (3H, s). Melting point (° C.): 213-215.

EXAMPLE 264

6-Chloro-3-(2-methyl-6-vinylphenoxy)-4-pyridazinol (Compound No. 834)

$^1$H-NMR (200 MHz, CD$_3$OD) δ ppm: 7.46 (1H, dd, J=6.6, 2.6 Hz), 7.25-7.05 (2H, m), 6.71 (1H, dd, J=17.6, 11.4 Hz), 6.70 (1H, s), 5.74 (1H, dd, J=17.6, 1.5 Hz), 5.21 (1H, dd, J=11.4, 1.5 Hz), 2.11 (3H, s). Appearance: amorphous.

EXAMPLE 265

6-Chloro-3-(6-cyclopropyl-3-fluoro-2-methylphenoxy)-4-pyridazinol (Compound No. 1052)

$^1$H-NMR (200 MHz, CD$_3$OD) δ ppm: 6.92-6.70 (3H, m), 2.06 (3H, d, J=2.2 Hz), 1.85-1.70 (1H, m), 0.79-0.45 (4H, m). Melting point (° C.): 230-231.

EXAMPLE 266

6-Chloro-3-(2-methyl-6-nitrophenoxy)-4-pyridazinol (Compound No. 844)

$^1$H-NMR (200 MHz, DMSO-d$_6$) δ ppm: 7.95 (1H, d, J=8.1 Hz), 7.76 (1H, d, J=7.7 Hz), 7.45 (1H, dd, J=8.1, 7.7 Hz), 6.80 (1H, s), 2.20 (3H, s). Appearance: paste state.

EXAMPLE 267

6-Chloro-3-(2-methoxy-6-methylphenoxy)-4-pyridazinol (Compound No. 845)

$^1$H-NMR (200 MHz, CDCl$_3$) δ ppm: 7.10-7.01 (1H, m), 6.79-6.72 (2H, m), 6.55 (1H, s), 3.64 (3H, s), 2.08 (3H, s). Appearance: amorphous.

EXAMPLE 268

6-Chloro-3-(2,6-diethylphenoxy)-4-pyridazinol (Compound No. 846)

$^1$H-NMR (60 MHz, CDCl$_3$) δ ppm: 10.21 (1H, brs), 7.02 (3H, brs), 6.47 (1H, s), 2.27 (4H, q, J=7.6 Hz), 0.98 (6H, t, J=7.6 Hz). Melting point (° C.): 181-185.

EXAMPLE 269

6-Chloro-3-(2-cyclopropyl-6-ethylphenoxy)-4-pyridazinol (Compound No. 850)

$^1$H-NMR (200 MHz, CD$_3$OD) δ ppm: 7.11 (2H, d, J=4.8 Hz), 6.85 (1H, t, J=4.8 Hz), 6.71 (1H, s), 2.52 (2H, q, J=7.5 Hz), 1.87-1.72 (1H, m), 1.16 (3H, t, J=7.5 Hz), 0.80-0.65 (2H, m), 0.65-0.50 (2H, m). Appearance: amorphous.

EXAMPLE 270

6-Chloro-3-(2,6-dipropylphenoxy)-4-pyridazinol (Compound No. 890)

Melting point (° C.): 191-193.

EXAMPLE 271

6-Chloro-3-(2,6-diisopropylphenoxy)-4-pyridazinol (Compound No. 894)

$^1$H-NMR (90 MHz, DMSO-d$_6$) δ ppm: 7.28 (3H, s), 6.80 (1H, s), 2.88 (2H, septet, J=7.0 Hz), 1.15 (12H, d, J=7.0 Hz). Melting point (° C.): >285.

EXAMPLE 272

6-Chloro-3-(2-cyclopropyl-6-isopropylphenoxy)-4-pyridazinol (Compound No. 896)

$^1$H-NMR (200 MHz, DMSO-d$_6$) δ ppm: 7.22-7.12 (2H, m), 6.83 (1H, brs), 6.82 (1H, dd, J=6.6, 2.2 Hz), 2.91 (1H, septet, J=7.0 Hz), 1.74-1.63 (1H, m), 1.11 (6H, d, J=7.0 Hz), 0.75-0.71 (2H, m), 0.58-0.50 (2H, m). Melting point (° C.): 242-245.

EXAMPLE 273

6-Chloro-3-(2-isopropyl-6-nitrophenoxy)-4-pyridazinol (Compound No. 911)

$^1$H-NMR (200 MHz, DMSO-d$_6$) δ ppm: 8.00 (1H, d, J=7.7 Hz), 7.88 (1H, d, J=7.7 Hz), 7.54 (1H, t, J=7.7 Hz), 6.96 (1H, brs), 3.07 (1H, septet, J=7.0 Hz), 1.16 (6H, d, J=7.0 Hz). Melting point (° C.): 205-209.

EXAMPLE 274

3-(2-tert-Butyl-6-cyclopropylphenoxy)-6-chloro-4-pyridazinol (Compound No. 914)

$^1$H-NMR (200 MHz, CD$_3$OD) δ ppm: 7.28 (1H, br.d, J=8.1 Hz), 7.10 (1H, dd, J=8.1 and 7.7 Hz), 6.90 (1H, d, J=7.7 Hz), 6.70 (1H, s), 1.80-1.55 (1H, m), 1.34 (9H, s), 0.85-0.60 (2H, m), 0.50-0.20 (2H, m) Melting point (° C.): 230-231.

EXAMPLE 275

6-Chloro-3-(2,6-dicyclopropylphenoxy)-4-pyridazinol (Compound No. 931)

$^1$H-NMR (200 MHz, CD$_3$OD) δ ppm: 7.08 (1H, t, J=7.7 Hz), 6.81 (2H, d, J=7.7 Hz), 6.71 (1H, s), 1.95-1.75 (2H, m), 0.85-0.70 (4H, m), 0.70-0.50 (4H, m). Melting point (° C.): 232-234.

EXAMPLE 276

6-Chloro-3-(2-cyclopropyl-6-methoxyphenoxy)-4-pyridazinol (Compound No. 964)

$^1$H-NMR (200 MHz, DMSO-d$_6$) δ ppm: 7.13 (1H, t, J=8.1 Hz), 6.92 (1H, d, J=8.1 Hz), 6.81 (1H, brs), 6.54 (1H, d, J=8.1 Hz), 3.68 (3H, s), 1.87-1.78 (1H, m), 0.87-0.78 (2H, m), 0.64-0.56 (2H, m). Melting point (° C.): 194-199.

EXAMPLE 277

6-Chloro-3-(2-cyclopropyl-6-ethoxyphenoxy)-4-pyridazinol (Compound No. 965)

$^1$H-NMR (200 MHz, CD$_3$OD) δ ppm: 7.07 (1H, t, J=8.1 Hz), 6.84 (1H, dd, J=8.4, 1.5 Hz), 6.71 (1H, s), 6.54 (1H, dd, J=8.4, 1.5 Hz), 3.97 (2H, q, J=7.0 Hz), 2.04-1.91 (1H, m), 1.18 (3H, t, J=7.0 Hz), 0.89-0.79 (2H, m), 0.66-0.60 (2H, m). Melting point (° C.): 174-179.

EXAMPLE 278

6-Chloro-3-{2,6-di[(1E)-1-propenyl]phenoxy}-4-pyridazinol (Compound No. 979)

$^1$H-NMR (200 MHz, CD$_3$OD) δ ppm: 7.40 (2H, d, J=7.8 Hz), 7.15 (1H, t, J=7.8 Hz), 6.72 (1H, s), 6.34 (2H, d, J=16.4 Hz), 6.27 (2H, dd, J=16.4, 4.9 Hz), 1.79 (6H, d, J=4.9 Hz) Melting point (° C.): 163-164.

EXAMPLE 279

6-Chloro-3-(2,6-diallylphenoxy)-4-pyridazinol (Compound No. 982)

$^1$H-NMR (200 MHz, CD$_3$OD) δ ppm: 7.20-7.15 (3H, m), 6.70 (1H, s), 5.95-5.75 (2H, m), 5.02-4.87 (4H, m), 3.26 (4H, d, J=6.8 Hz). Melting point (° C.): 131-135.

EXAMPLE 280

6-Chloro-3-(2,6-dimethoxyphenoxy)-4-pyridazinol (Compound No. 987)

$^1$H-NMR (200 MHz, DMSO-d$_6$) δ ppm: 7.19 (1H t, J=8.3 Hz), 6.79-6.75 (3H m), 3.71 (6H, s). Melting point (° C.): 199-201.

EXAMPLE 281

6-Chloro-3-(3,5-dimethylphenoxy)-4-pyridazinol (Compound No. 998)

$^1$H-NMR (60 MHz, DMSO-d$_6$) δ ppm: 6.90-6.65 (4H, m), 2.27 (6H, s). Melting point (° C.): 178-182.

EXAMPLE 282

6-Chloro-3-(3-isopropyl-5-methylphenoxy)-4-pyridazinol (Compound No. 1000)

$^1$H-NMR (200 MHz, CD$_3$OD) δ ppm: 6.94 (1H, s), 6.84 (1H, s) 6.81 (1H, s), 6.69 (1H, s), 2.87 (1H, septet, J=7.0 Hz), 2.32 (3H, s), 1.23 (6H, d, J=7.0 Hz). Melting point (° C.): 204-206.

EXAMPLE 283

6-Chloro-3-(3,5-diisopropylphenoxy)-4-pyridazinol (Compound No. 1007)

$^1$H-NMR (200 MHz, CD$_3$OD) δ ppm: 6.98 (1H, s), 6.87 (1H, s) 6.86 (1H, s), 6.68 (1H, s), 2.90 (2H, septet, J=7.0 Hz), 1.24 (12H, d, J=7.0 Hz). Melting point (° C.): 249-253.

EXAMPLE 284

3-[3,5-Bis(trifluoromethyl)phenoxy]-6-chloro-4-pyridazinol (Compound No. 1009)

$^1$H-NMR (200 MHz, DMF-d$_7$) δ ppm: 8.20-7.80 (3H, m), 6.94 (1H, s), 5.50-4.50 (1H, brs). Melting point (° C.): 237-242.

EXAMPLE 285

3-(2-Bromo-3,5-dimethylphenoxy)-6-chloro-4-pyridazinol (Compound No. 1013)

$^1$H-NMR (200 MHz, DMSO-d$_6$) δ ppm: 7.11 (1H, s), 7.00 (1H, s), 6.86 (1H, brs), 2.37 (3H, s), 2.27 (3H, s). Melting point (° C.): 240-244.

EXAMPLE 286

6-Chloro-3-(2,3,5-trimethylphenoxy)-4-pyridazinol (Compound No. 1016)

$^1$H-NMR (90 MHz, CD$_3$OD) δ ppm: 6.90 (1H, s), 6.75 (1H, s) 6.70 (1H, s), 2.30 (6H, s), 2.02 (3H, s). Melting point (° C.): 223-224.

EXAMPLE 287

6-Chloro-3-(3,5-dimethyl-2-propylphenoxy)-4-pyridazinol (Compound No. 1020)

$^1$H-NMR (90 MHz, DMSO-d$_6$) δ ppm: 6.90 (1H, s), 6.81 (1H, s), 6.77 (1H, s), 2.29 (3H, s), 2.21 (3H, s), 2.53-2.19 (2H, m), 1.57-1.29 (2H, m), 0.86 (3H, t, J=6.6 Hz). Melting point (° C.): 154.5.

EXAMPLE 288

6-Chloro-3-(2-cyclopropyl-3,5-dimethylphenoxy)-4-pyridazinol (Compound No. 1023)

$^1$H-NMR (200 MHz, CD$_3$OD) δ ppm: 6.89 (1H, s), 6.73 (1H, s) 6.69 (1H, s), 2.39 (3H, s), 2.26 (3H, s), 1.45-1.28 (1H, m), 0.78-0.67 (2H, m), 0.65-0.51 (2H, m). Melting point (° C.): 200-203.

EXAMPLE 289

6-Chloro-3-[3,5-dimethyl-2-(methylsulfanyl)phenoxy]-4-pyridazinol (Compound No. 1027)

Melting point (° C.): 213-214.

EXAMPLE 290

3-(2-Bromo-3,6-dimethylphenoxy)-6-chloro-4-pyridazinol (Compound No. 1040)

$^1$H-NMR (200 MHz, CD$_3$OD) δ ppm: 7.16 (1H, d, J=7.9 Hz), 7.10 (1H, d, J=7.9 Hz), 6.72 (1H, s), 2.38 (3H, s), 2.16 (3H, s). Melting point (° C.): 255-257.

EXAMPLE 291

3-(6-Bromo-3-fluoro-2-methylphenoxy)-6-chloro-4-pyridazinol (Compound No. 1050)

$^1$H-NMR (200 MHz, CD$_3$OD) δ ppm: 7.51 (1H, dd, J=8.8, 5.9 Hz), 7.00 (1H, t, J=8.8 Hz), 6.96 (1H, s), 2.13 (3H, d, J=2.2 Hz). Appearance: amorphous.

EXAMPLE 292

3-(6-Bromo-3-chloro-2-methylphenoxy)-6-chloro-4-pyridazinol (Compound No. 1053)

$^1$H-NMR (200 MHz, CD$_3$OD) δ ppm: 7.47 (1H, d, J=8.1 Hz), 7.23 (1H, d, J=8.1 Hz), 6.64 (1H, s), 2.24 (3H, s). Melting point (° C.): 254-260.

EXAMPLE 293

6-Chloro-3-(3-chloro-6-cyclopropyl-2-methylphenoxy)-4-pyridazinol (Compound No. 1055)

$^1$H-NMR (200 MHz, CD$_3$OD) δ ppm: 7.18 (1H, d, J=8.4 Hz), 6.81 (1H, d, J=8.4 Hz), 6.64 (1H, s), 2.17 (3H, s), 1.89-1.76 (1H, m), 0.80-0.71 (2H, m), 0.68-0.51 (2H, m). Melting point (° C.): 233.

EXAMPLE 294

3-(6-Bromo-2,3-dimethylphenoxy)-6-chloro-4-pyridazinol (Compound No. 1058)

$^1$H-NMR (200 MHz, CD$_3$OD) δ ppm: 7.34 (1H, d, J=8.1 Hz), 6.99 (1H, d, J=8.1 Hz), 6.71 (1H, s), 2.28 (3H, s), 2.12 (3H, s). Melting point (° C.): 263-268.

EXAMPLE 295

6-Chloro-3-(2,3,6-trimethylphenoxy)-4-pyridazinol (Compound No. 1060)

$^1$H-NMR (90 MHz, CD$_3$OD) δ ppm: 7.0 (2H, s), 6.73 (1H, s), 2.27 (3H, s), 2.07 (3H, s), 2.03 (3H, s). Melting point (° C.): 228.

EXAMPLE 296

6-Chloro-3-(6-cyclopropyl-2,3-dimethylphenoxy)-4-pyridazinol (Compound No. 1061)

$^1$H-NMR (200 MHz, CD$_3$OD) δ ppm: 6.96 (1H, d, J=8.1 Hz), 6.72 (1H, d, J=8.1 Hz), 6.69 (1H, s), 2.24 (3H, s), 2.04 (3H, s), 1.85-1.70 (1H, m), 0.75-0.46 (4H, m). Melting point (° C.): 229-234.

EXAMPLE 297

2-[(6-Chloro-4-hydroxy-3-pyridazinyl)oxy]-3,4-dimethylbenzaldehyde O-methyloxime (Compound No. 1063)

$^1$H-NMR (200 MHz, CD$_3$OD) δ ppm: 7.98 (1H, s), 7.50 (1H, d, J=8.1 Hz), 7.11 (1H, d, J=8.1 Hz), 6.69 (1H, s), 3.81 (3H, s), 2.32 (3H, s), 2.06 (3H, s). Appearance: amorphous.

EXAMPLE 298

6-Chloro-3-(6-methoxy-2,3-dimethylphenoxy)-4-pyridazinol (Compound No. 1064)

$^1$H-NMR (200 MHz, CD$_3$OD) δ ppm: 7.00 (1H, d, J=8.4 Hz), 6.78 (1H, d, J=8.4 Hz), 6.66 (1H, s), 3.69 (3H, s), 2.23 (3H, s), 2.08 (3H, s). Appearance: amorphous.

EXAMPLE 299

3-(6-Bromo-3-methoxy-2-methylphenoxy)-6-chloro-4-pyridazinol (Compound No. 1066)

$^1$H-NMR (200 MHz, CD$_3$OD) δ ppm: 7.42 (1H, d, J=9.2 Hz), 6.82 (1H, d, J=9.2 Hz), 6.69 (1H, s), 3.86 (3H, s), 2.05 (3H, s). Melting point (° C.): 246-253.

EXAMPLE 300

6-Chloro-3-(6-cyclopropyl-3-methoxy-2-methylphenoxy)-4-pyridazinol (Compound No. 1069)

$^1$H-NMR (200 MHz, CD$_3$OD) δ ppm: 6.83 (1H, d, J=8.8 Hz), 6.75 (1H, d, J=8.8 Hz), 6.66 (1H, s), 3.81 (3H, s), 1.99 (3H, s), 1.78-1.70 (1H, m), 0.69-0.63 (2H, m), 0.52-0.47 (2H, m). Melting point (° C.): 250-253.

EXAMPLE 301

6-Chloro-3-(2-cyclopropyl-3,6-dimethylphenoxy)-4-pyridazinol (Compound No. 1073)

$^1$H-NMR (200 MHz, CD$_3$OD) δ ppm: 7.20 (1H, d, J=7.6 Hz), 6.95 (1H, d, J=7.6 Hz), 6.68 (1H, s), 2.39 (3H, s), 2.10 (3H, s), 1.50-1.25 (1H, m), 0.90-0.70 (2H, m), 0.70-0.50 (2H, m). Melting point (° C.): 171-175.

EXAMPLE 302

3-(2-Allyl-6-ethyl-3-methoxyphenoxy)-6-chloro-4-pyridazinol (Compound No. 1080)

$^1$H-NMR (60 MHz, DMF-d$_7$) δ ppm: 7.11 (1H, d, J=8.4 Hz), 6.85 (1H, s), 6.83 (1H, d, J=8.4 Hz), 6.10-5.30 (1H, m), 5.00-4.60 (2H, m), 3.83 (3H, s), 3.30-3.10 (2H, m), 2.40 (2H, q, J=7.6 Hz), 1.10 (3H, t, J=7.6 Hz). Melting point (° C.): 183-186.

EXAMPLE 303

6-Chloro-3-{3,6-dimethyl-2-[(methylsulfanyl)methyl]-phenoxy}-4-pyridazinol (Compound No. 1083)

$^1$H-NMR (90 MHz, CD$_3$OD) δ ppm: 7.21-6.90 (2H, m), 6.71 (1H, s), 3.68 (2H, s), 2.38 (3H, s), 2.09 (3H, s), 2.00 (3H, s). Appearance: amorphous.

EXAMPLE 304

3-[(5-Bromo-2,3-dihydro-1H-inden-4-yl)oxy]-6-chloro-4-pyridazinol (Compound No. 1086)

$^1$H-NMR (200 MHz, CD$_3$OD) δ ppm: 7.39 (1H, d, J=8.1 Hz), 7.05 (1H, d, J=8.1 Hz), 6.71 (1H, s), 2.94 (2H, t, J=7.3 Hz), 2.79 (2H, t, J=7.3 Hz), 2.10-2.00 (2H, m). Appearance: amorphous.

EXAMPLE 305

6-Chloro-3-[(5-methyl-2,3-dihydro-1H-inden-4-yl)oxy]-4-pyridazinol (Compound No. 1088)

$^1$H-NMR (200 MHz, DMSO-d$_6$) δ ppm: 7.11-7.01 (2H, m), 6.83 (1H, brs), 2.88 (3H, t, J=7.3 Hz), 2.59 (3H, t, J=7.3 Hz), 2.06 (3H, s), 2.06-1.91 (2H, m). Melting point (° C.): 222-225.

EXAMPLE 306

6-Chloro-3-[(5-ethyl-2,3-dihydro-1H-inden-4-yl)oxy]-4-pyridazinol (Compound No. 1089)

$^1$H-NMR (200 MHz, CD$_3$OD) δ ppm: 7.06 (2H, s), 6.71 (1H, S) 2.91 (2H, t, J=7.3 Hz), 2.67 (2H, t, J=7.3 Hz), 2.51 (2H, q, J=7.7 Hz), 2.04 (2H, quintet, J=7.3 Hz), 1.13 (3H, t, J=7.7 Hz). Melting point (° C.): 193-196.

EXAMPLE 307

6-Chloro-3-[(5-cyclopropyl-2,3-dihydro-1H-inden-4-yl)oxy]-4-pyridazinol (Compound No. 1091)

$^1$H-NMR (200 MHz, CD$_3$OD) δ ppm: 7.02 (1H, d, J=7.7 Hz), 6.79 (1H, d, J=7.7 Hz), 6.71 (1H, s), 2.90 (2H, t, J=7.3 Hz), 2.72 (2H, t, J=7.3 Hz), 2.18-1.98 (2H, m), 1.92-1.75 (1H, m), 0.82-0.70 (2H, m), 0.60-0.47 (2H, m). Melting point (° C.): 218-220.

EXAMPLE 308

6-Chloro-3-[(6-methyl-2,3-dihydro-1-benzofuran-7-yl)oxy]-4-pyridazinol (Compound No. 1096)

$^1$H-NMR (200 MHz, CD$_3$OD) δ ppm: 6.99 (1H, d, J=7.7 Hz), 6.72 (1H, d, J=7.7 Hz), 6.70 (1H, s), 4.53 (2H, t, J=8.8 Hz), 3.20 (2H, br.t, J=8.8 Hz), 2.15 (3H, s). Melting point (° C.): 217-219.

EXAMPLE 309

3-[(6-Bromo-1-benzofuran-7-yl)oxy]-6-chloro-4-pyridazinol (Compound No. 1099)

$^1$H-NMR (200 MHz, CD$_3$OD) δ ppm: 7.75 (1H, d, J=2.2 Hz), 7.48 (1H, d, J=8.4 Hz), 7.47 (1H, d, J=8.4 Hz), 6.92 (1H, d, J=2.2 Hz), 6.78 (1H, s) Appearance: amorphous.

EXAMPLE 310

6-Chloro-3-[(6-methyl-1-benzofuran-7-yl)oxy]-4-pyridazinol (Compound No. 1100)

$^1$H-NMR (200 MHz, CD$_3$OD) δ ppm: 7.65 (1H, d, J=2.2 Hz), 7.40 (1H, d, J=8.1 Hz), 7.14 (1H, d, J=8.1 Hz), 6.82 (1H, d, J=2.2 Hz), 6.75 (1H, s), 2.31 (3H, s). Appearance: oily product.

EXAMPLE 311

6-Chloro-3-[(6-cyclopropyl-1-benzofuran-7-yl)oxy]-4-pyridazol (Compound No. 1102)

$^1$H-NMR (200 MHz, CD$_3$OD) δ ppm: 7.65 (1H, d, J=2.2 Hz), 7.40 (1H, d, J=8.1 Hz), 6.87 (1H, d, J=8.1 Hz), 6.81 (1H, d, J=2.2 Hz), 6.75 (1H, s), 2.10-1.98 (1H, m), 0.98-0.80 (2H, m), 0.80-0.64 (2H, m) Melting point (° C.): 175-180.

EXAMPLE 312

6-Chloro-3-[(5-methyl-1-benzofuran-4-yl)oxy]-4-pyridazinol (Compound No. 1109)

$^1$H-NMR (200 MHz, CD$_3$OD) δ ppm: 7.65 (1H, d, J=2.2 Hz), 7.32 (1H, d, J=8.4 Hz), 7.18 (1H, d, J=8.4 Hz), 6.73 (1H, s), 6.60 (1H, d, J=2.2 Hz), 2.23 (3H, s). Melting point (° C.): 222-225.

EXAMPLE 313

6-Chloro-3-(2,4-dicyclopropyl-6-fluorophenoxy)-4-pyridazinol (Compound No. 1115)

$^1$H-NMR (200 MHz, CD$_3$OD) δ ppm: 6.71-6.65 (2H, m), 6.54 (1H, s), 2.02-1.81 (2H, m), 1.01-0.72 (4H, m), 0.68-0.60 (4H, m). Appearance: amorphous.

EXAMPLE 314

6-Chloro-3-(2,4-dibromo-3,6-dimethylphenoxy)-4-pyridazinol (Compound No. 1118)

$^1$H-NMR (200 MHz, CD$_3$OD) δ ppm: 7.54 (1H, s), 6.71 (1H, s), 2.56 (3H, s), 2.16 (3H, s). Melting point (° C.): 241-248.

EXAMPLE 315

3-(2-Bromo-4,6-dimethylphenoxy)-6-chloro-4-pyridazinol (Compound No. 1119)

$^1$H-NMR (200 MHz, CD$_3$OD) δ ppm: 7.31 (1H, brs), 7.10 (1H, brs), 6.74 (1H, s), 2.31 (3H, s), 2.17 (3H, s). Melting point (° C.): 254-256.

EXAMPLE 316

6-Chloro-3-(2-ethyl-4,6-diiodophenoxy)-4-pyridazinol (Compound No. 1120)

$^1$H-NMR (200 MHz, CD$_3$OD) δ ppm: 8.03 (1H, d, J=2.2 Hz), 7.66 (1H, d, J=2.2 Hz), 6.74 (1H, s), 2.52 (2H, q, J=7.7 Hz), 1.17 (3H, t, J=7.7 Hz). Melting point (° C.): 142-144.

EXAMPLE 317

6-Chloro-3-(2,4,6-trimethylphenoxy)-4-pyridazinol (Compound No. 1122)

$^1$H-NMR (200 MHz, CD$_3$OD) δ ppm: 6.90 (2H, s), 6.71 (1H, s), 2.27 (3H, s), 2.07 (6H, s). Melting point (° C.): 235-239.

EXAMPLE 318

6-Chloro-3-(2-cyclopropyl-4,6-dimethylphenoxy)-4-pyridazinol (Compound No. 1123)

$^1$H-NMR (200 MHz, CD$_3$OD) δ ppm: 6.88 (1H, brs), 6.69 (1H, s), 6.63 (1H, brs), 2.26 (3H, s), 2.09 (3H, s), 1.85-1.70 (1H, m), 0.80-0.65 (2H, m), 0.65-0.50 (2H, m). Melting point (° C.): 215-217.

EXAMPLE 319

3-(2-Bromo-3,5,6-trimethylphenoxy)-6-chloro-4-pyridazinol (Compound No. 1124)

$^1$H-NMR (200 MHz, DMSO-d$_6$) δ ppm: 7.13 (1H, s), 6.88 (1H, brs), 2.32 (3H, s), 2.23 (3H, s), 2.01 (3H, s). Melting point (° C.): 280-290.

EXAMPLE 320

6-Chloro-3-(2,3,5,6-tetramethylphenoxy)-4-pyridazinol (Compound No. 1125)

$^1$H-NMR (200 MHz, CD$_3$OD) δ ppm: 6.88 (1H, s), 6.69 (1H, s), 2.22 (6H, s), 1.98 (6H, s). Melting point (° C.): 278-283.

EXAMPLE 321

6-Chloro-3-[(5,6-dimethyl-2,3-dihydro-1H-inden-4-yl)oxy]-4-pyridazinol (Compound No. 1129)

$^1$H-NMR (200 MHz, CD$_3$OD) δ ppm: 6.72 (1H, s), 6.68 (1H, s), 2.88 (2H, t, J=7.4 Hz), 2.70 (2H, t, J=7.4 Hz), 2.24 (3H, s), 2.17 (3H, s), 2.05 (2H, quintet, J=7.4 Hz). Melting point (° C.): 210-213.

EXAMPLE 322

6-Chloro-3-(1,2,3,5,6,7-hexahydro-s-indacen-4-yloxy)-4-pyridazinol (Compound No. 1133)

$^1$H-NMR (200 MHz, CD$_3$OD) δ ppm: 7.95 (1H, s), 6.65 (1H, s), 2.88 (4H, t, J=7.3 Hz), 2.68 (4H, t, J=7.3 Hz), 2.20-1.90 (4H, m). Appearance: amorphous.

EXAMPLE 323

6-Chloro-3-(2-cyclopropylphenoxy)-4-pyridazinyl acetate (Compound No. 1140)

$^1$H-NMR (200 MHz, CDCl$_3$) δ ppm: 7.40 (1H, s), 7.26-6.98 (4H, m), 2.40 (3H, s), 1.93-1.76 (1H, m), 0.85-0.59 (4H, m). Appearance: amorphous.

EXAMPLE 324

6-Chloro-3-(2-cyclopropyl-6-methylphenoxy)-4-pyridazinyl acetate (Compound No. 1151)

$^1$H-NMR (200 MHz, CDCl$_3$) δ ppm: 7.39 (1H, s), 7.15-7.00 (2H, m), 6.90-6.75 (1H, m), 2.42 (3H, s), 2.12 (3H, s), 1.90-1.67 (1H, m), 0.85-0.50 (4H, m). Melting point (° C.): 98-101.

EXAMPLE 325

6-Chloro-3-(2-cyclopropyl-6-methylphenoxy)-4-pyridazinyl pivalate (Compound No. 1207)

$^1$H-NMR (200 MHz, CDCl$_3$) δ ppm: 7.38 (1H, s), 7.15-7.05 (2H, m), 6.90-6.84 (1H, m), 2.13 (3H, s), 1.81-1.65 (1H, m), 1.41 (9H, s), 0.90-0.50 (4H, m). Melting point (° C.): 84-87.

EXAMPLE 326

6-Chloro-3-(2-cyclopropyl-6-methylphenoxy)-4-pyridazinyl decanoate (Compound No. 1251)

$^1$H-NMR (200 MHz, CDCl$_3$) δ ppm: 7.38 (1H, s), 7.15-7.05 (2H, m), 6.93-6.80 (1H, m), 2.67 (2H, t, J=7.3 Hz), 2.12 (3H, s), 1.85-1.65 (3H, m), 1.55-1.10 (12H, m), 0.95-0.80 (3H, m), 0.80-0.65 (2H, m), 0.65-0.52 (2H, m). Appearance: oily product.

EXAMPLE 327

6-Chloro-3-(2-cyclopropylphenoxy)-4-pyridazinyl cyclopropanecarboxylate (Compound No. 1266)

$^1$H-NMR (200 MHz, CDCl$_3$) δ ppm: 7.43 (1H, s), 7.22-6.98 (4H, m), 2.00-1.75 (2H, m), 1.30-1.08 (4H, m), 0.86-0.51 (4H, m). Melting point (° C.): 122-125.

EXAMPLE 328

6-Chloro-3-(2-methylphenoxy)-4-pyridazinyl benzoate (Compound No. 1387)

$^1$H-NMR (200 MHz, CDCl$_3$) δ ppm: 8.23-8.18 (2H, m), 7.75-7.50 (3H, m), 7.60 (1H, s) 7.30-7.08 (4H, m), 2.18 (3H, s). Appearance: oily product.

EXAMPLE 329

6-Chloro-3-(2-cyclopropylphenoxy)-4-pyridazinyl benzoate (Compound No. 1391)

$^1$H-NMR (200 MHz, CDCl$_3$) δ ppm: 8.20 (2H, d, J=7.3 Hz), 7.74-7.50 (4H, m), 7.26-7.01 (3H, m), 6.98-6.97 (1H, m), 1.91-1.80 (1H, m), 0.83-0.57 (4H, m). Appearance: amorphous.

EXAMPLE 330

6-Chloro-3-[4-(trimethylsilyl)phenoxy]-4-pyridazinyl benzoate (Compound No. 1396)

Melting point (° C.): 100-102.

EXAMPLE 331

6-Chloro-3-(2-cyclopropyl-6-methylphenoxy)-4-pyridazinyl benzoate (Compound No. 1417)

$^1$H-NMR (200 MHz, CDCl$_3$) δ ppm: 8.24-8.20 (2H, m), 7.75-7.68 (2H, m), 7.67-7.52 (3H, m), 7.09-7.07 (2H, m), 6.87-6.82 (1H, m), 2.16 (3H, s), 1.82-1.71 (1H, m), 0.75-0.71 (2H, m), 0.62-0.53 (2H, m) Appearance: amorphous.

EXAMPLE 332

6-Chloro-3-(2-methylphenoxy)-4-pyridazinyl 2-methylbenzoate (Compound No. 1446)

$^1$H-NMR (60 MHz, CDCl$_3$) δ ppm: 8.35-8.08 (2H, m), 7.59 (1H, s), 7.68-7.00 (6H, m), 2.70 (3H, s), 2.21 (3H, s). Melting point (° C.): 91-93.

EXAMPLE 333

6-Chloro-3-(2-isopropylphenoxy)-4-pyridazinyl 2-methylbenzoate (Compound No. 1448)

$^1$H-NMR (60 MHz, CDCl$_3$) δ ppm: 8.15-8.00 (2H, m), 7.58 (1H, s), 7.75-6.90 (6H, m), 3.40-2.85 (1H, m), 2.69 (3H, s), 1.15 (6H, d, J=7.0 Hz).

Refractive index: $n_D^{22}$ 1.5709.

EXAMPLE 334

3-(2-s-Butylphenoxy)-6-chloro-4-pyridazinyl 2-methylbenzoate (Compound No. 1450)

$^1$H-NMR (60 MHz, CDCl$_3$) δ ppm: 8.28-8.05 (1H, m), 7.60-7.05 (7H, m), 7.52 (1H, s), 3.05-2.60 (1H, m), 2.65 (3H, s), 1.70-1.00 (2H, m), 1.10 (3H, d, J=7.0 Hz), 0.90-0.50 (3H, m). Appearance: paste state.

EXAMPLE 335

6-Chloro-3-(2-cyclohexylphenoxy)-4-pyridazinyl 2-methylbenzoate (Compound No. 1455)

$^1$H-NMR (60 MHz, CDCl$_3$) δ ppm: 8.30-7.00 (8H, m), 7.54 (1H, s), 2.68 (1H, brs), 2.67 (3H, s), 2.00-1.00 (10H, m). Melting point (° C.): 89-91.

EXAMPLE 336

3-([1,1'-Biphenyl]-2-yloxy)-6-chloro-4-pyridazinyl 2-methylbenzoate (Compound No. 1456)

$^1$H-NMR (60 MHz, CDCl$_3$) δ ppm: 8.20-7.90 (1H, m), 7.60-7.10 (13H, m), 2.58 (3H, s).

Refractive index: $n_D^{28}$ 1.6055.

EXAMPLE 337

3-(3-tert-Butylphenoxy)-6-chloro-4-pyridazinyl 2-methylbenzoate (Compound No. 1457)

$^1$H-NMR (60 MHz, CDCl$_3$) δ ppm: 8.28-8.02 (1H, m), 7.55 (1H, s), 7.65-6.85 (7H, m), 2.64 (3H, s), 1.28 (9H, s). Melting point (° C.): 63-64.

EXAMPLE 338

6-Chloro-3-(3-methoxyphenoxy)-4-pyridazinyl 2-methylbenzoate (Compound No. 1458)

$^1$H-NMR (60 MHz, CDCl$_3$) δ ppm: 8.30-8.00 (1H, m), 7.70-7.10 (4H, m), 7.55 (1H, s), 6.90-6.60 (3H, m), 3.74 (3H, s), 2.64 (3H, s). Melting point (° C.): 66-67.

EXAMPLE 339

6-Chloro-3-(2-isopropyl-5-methylphenoxy)-4-pyridazinyl 2-methylbenzoate (Compound No. 1459)

$^1$H-NMR (60 MHz, CDCl$_3$) δ ppm: 8.30-8.00 (1H, m), 7.54 (1H, s), 7.50-6.80 (6H, m), 3.30-2.75 (1H, m), 2.65 (3H, s), 2.28 (3H, s), 1.15 (6H, d, J=7.00 Hz). Melting point (° C.): 95-97.

EXAMPLE 340

6-Chloro-3-(1-naphthyloxy)-4-pyridazinyl 2-methylbenzoate (Compound No. 1461)

$^1$H-NMR (60 MHz, CDCl$_3$) δ ppm: 8.20-7.00 (12H, m), 2.65 (3H, s) Melting point (° C.): 133-134.

EXAMPLE 341

6-Chloro-3-(2-methylphenoxy)-4-pyridazinyl 2-methoxybenzoate (Compound No. 1509)

$^1$H-NMR (60 MHz, CDCl$_3$) δ ppm: 8.11-7.89 (2H, m), 7.70-6.80 (4H, m), 7.50 (1H, s), 3.84 (3H, s), 2.10 (3H, s). Melting point (° C.): 114-116.

EXAMPLE 342

6-Chloro-3-(2-methylphenoxy)-4-pyridazinyl 4-methylbenzoate (Compound No. 1553)

$^1$H-NMR (60 MHz, CDCl$_3$) δ ppm: 8.07 (2H, d, J=8.0 Hz), 7.58 (1H, s), 7.40-7.03 (4H, m), 7.36 (2H, d, J=8.0 Hz), 2.51 (3H, s), 2.23 (3H, s). Melting point (° C.): 105-108.

EXAMPLE 343

6-Chloro-3-(2-isopropylphenoxy)-4-pyridazinyl 4-methylbenzoate (Compound No. 1554)

$^1$H-NMR (60 MHz, CDCl$_3$) δ ppm: 8.28-7.82 (2H, m), 7.61 (1H, s), 7.51-6.90 (6H, m), 3.30-2.80 (1H, m), 2.46 (3H, s), 1.19 (6H, d, J=7.0 Hz).

Refractive index: $n_D^{22}$ 1.5731.

EXAMPLE 344

6-Chloro-3-(2-methylphenoxy)-4-pyridazinyl 2,4-dichlorobenzoate (Compound No. 1603)

$^1$H-NMR (60 MHz, CDCl$_3$) δ ppm: 8.04 (1H, d, J=8.4 Hz), 7.58 (1H, s), 7.58-6.92 (6H, m), 2.20 (3H, s). Melting point (° C.): 81-82.5.

EXAMPLE 345

6-Chloro-3-(2-cyclopropylphenoxy)-4-pyridazinyl methyl carbonate (Compound No. 1658)

$^1$H-NMR (200 MHz, CDCl$_3$) δ ppm: 7.51 (1H, s), 7.23-6.98 (4H, m), 3.99 (3H, s), 1.91-1.82 (1H, m), 0.84-0.61 (4H, m). Appearance: amorphous.

EXAMPLE 346

6-Chloro-3-(2-methylphenoxy)-4-pyridazinyl ethyl carbonate (Compound No. 1706)

$^1$H-NMR (60 MHz, CDCl$_3$) δ ppm: 7.51 (1H, s), 7.38-7.00 (4H, m), 4.40 (2H, q, J=7.0 Hz), 2.20 (3H, s), 1.40 (3H, t, J=7.0 Hz). Melting point (° C.): 73-74.

EXAMPLE 347

6-Chloro-3-(2-cyclopropylphenoxy)-4-pyridazinyl ethyl carbonate (Compound No. 1710)

$^1$H-NMR (200 MHz, CDCl$_3$) δ ppm: 7.51 (1H s), 7.26-6.98 (4H, m), 4.40 (2H, q, J=7.0 Hz), 1.90-1.80 (1H, m), 1.41 (3H, t, J=7.0 Hz), 0.84-0.60 (4H, m). Appearance: amorphous.

EXAMPLE 348

6-Chloro-3-(2-methylphenoxy)-4-pyridazinyl isobutyl carbonate (Compound No. 1757)

$^1$H-NMR (60 MHz, CDCl$_3$) δ ppm: 7.45 (1H, s), 7.30-7.00 (4H, m), 4.08 (2H, d, J=5.8 Hz), 2.16 (3H, s), 2.20-1.70 (1H, m), 0.96 (6H, d, J=5.8 Hz). Melting point (° C.): 46-47.

EXAMPLE 349

6-Chloro-3-(2-methylphenoxy)-4-pyridazinyl 2,2,2-trichloroethyl carbonate (Compound No. 1789)

$^1$H-NMR (200 MHz, CDCl$_3$) δ ppm: 7.52 (1H, s), 7.28-7.03 (4H, m), 4.94 (2H, s), 2.18 (3H, s). Appearance: amorphous.

EXAMPLE 350

6-Chloro-3-(2-cyclopropyl-6-methylphenoxy)-4-pyridazinyl phenyl carbonate (Compound No. 1840)

$^1$H-NMR (200 MHz, CDCl$_3$) δ ppm: 7.58 (1H, s), 7.50-7.20 (5H, m), 7.20-7.05 (2H, m), 6.92-6.82 (1H, m), 2.16 (3H, s), 1.88-1.72 (1H, m), 0.80-0.55 (4H, m). Appearance: oily product.

EXAMPLE 351

6-Chloro-3-(2-methylphenoxy)-4-pyridazinyl dimethylcarbamate (Compound No. 1877)

$^1$H-NMR (60 MHz, CDCl$_3$) δ ppm: 7.55 (1H, s), 7.40-6.92 (4H, m), 3.10 (3H, s), 3.01 (3H, s), 2.19 (3H, s). Melting point (° C.): 107-109.

EXAMPLE 352

6-Chloro-3-(2-cyclopropylphenoxy)-4-pyridazinyl dimethylcarbamate (Compound No. 1879)

$^1$H-NMR (200 MHz, CDCl$_3$) δ ppm: 7.57 (1H, s), 7.22-6.98 (4H, m), 3.13 (3H, s), 3.04 (3H, s), 1.97-1.80 (1H, m), 0.85-0.63 (4H, m). Melting point (° C.): 137-138.

EXAMPLE 353

6-Chloro-3-[3-(trifluoromethyl)phenoxy]-4-pyridazinyl dimethylcarbamate (Compound No. 1881)

$^1$H-NMR (60 MHz, CDCl$_3$) δ ppm: 7.60 (1H, s), 7.65-7.22 (4H, m), 3.11 (3H s), 3.05 (3H s). Melting point (° C.): 92-93.

EXAMPLE 354

6-Chloro-3-(2-methylphenoxy)-4-pyridazinyl diethylcarbamate (Compound No. 1898)

$^1$H-NMR (60 MHz, CDCl$_3$) δ ppm: 7.55 (1H, s), 7.40-6.92 (4H, m), 3.41 (4H, q, J=6.2 Hz), 2.20 (3H, s), 1.27 (6H, t, J=6.2 Hz). Melting point (° C.): 74-75.5.

EXAMPLE 355

6-Chloro-3-(2-methylphenoxy)-4-pyridazinyl 1-pyrrolidinecarboxylate (Compound No. 1924)

$^1$H-NMR (60 MHz, CDCl$_3$) δ ppm: 7.58 (1H, s), 7.42-7.02 (4H, m), 3.67-3.37 (4H, m), 2.19 (3H, s), 2.07-1.72 (4H, m). Melting point (° C.): 126-127.

EXAMPLE 356

6-Chloro-3-(2-methylphenoxy)-4-pyridazinyl methanesulfonate (Compound NO. 1981)

$^1$H-NMR (200 MHz, CDCl$_3$) δ ppm: 7.55 (1H, s), 7.33-7.06 (4H, m), 3.43 (3H, s), 2.20 (3H, s) Appearance: oily product.

EXAMPLE 357

6-Chloro-3-(2-cyclopropylphenoxy)-4-pyridazinyl methanesulfonate (Compound No. 1985)

$^1$H-NMR (200 MHz, CDCl$_3$) δ ppm: 7.55 (1H, s), 7.26-7.23 (2H, m), 7.21-7.02 (2H, m), 3.44 (3H, s), 1.89-1.80 (1H, m), 0.86-0.61 (4H, m) Melting point (° C.): 162-172.

EXAMPLE 358

6-Chloro-3-(2-cyclopropyl-6-methylphenoxy)-4-pyridazinyl methanesulfonate (Compound No. 2010)

$^1$H-NMR (200 MHz, CDCl$_3$) δ ppm: 7.56 (1H, s), 7.18-7.09 (2H, m), 6.91-6.86 (1H, m), 3.47 (3H, s), 2.16 (3H, s), 1.82-1.68 (1H, m), 0.75-0.69 (2H, m), 0.67-0.55 (2H, m). Appearance: amorphous.

EXAMPLE 359

6-Chloro-3-(2-methylphenoxy)-4-pyridazinyl 1-propanesulfonate (Compound No. 2038)

$^1$H-NMR (200 MHz, CDCl$_3$) δ ppm: 7.57 (1H, s), 7.34-7.05 (4H, m), 3.48 (2H, t, J=7.7 Hz), 2.20 (3H, s), 2.10 (2H, sixtet, J=7.7 Hz), 1.14 (3H, t, J=7.7 Hz). Melting point (° C.): 72-73.

EXAMPLE 360

6-Chloro-3-(2-cyclopropylphenoxy)-4-pyridazinyl 1-propanesulfonate (Compound No. 2040)

$^1$H-NMR (200 MHz, CDCl$_3$) δ ppm: 7.57 (1H, s), 7.28-7.15 (2H, m), 7.12-6.99 (2H, m), 3.52-3.45 (2H, m), 2.17-1.98 (2H, m), 1.92-1.78 (1H, m), 1.11 (3H, t, J=7.3 Hz), 0.85-0.73 (2H, m), 0.69-0.60 (2H, m). Appearance: paste state.

EXAMPLE 361

6-Chloro-3-(2,3-dihydro-1H-inden-4-yloxy)-4-pyridazinyl 1-propanesulfonate (Compound No. 2042)

$^1$H-NMR (200 MHz, CDCl$_3$) δ ppm: 7.56 (1H, s), 7.26-7.14 (2H, m), 6.94 (1H, dd, J=7.0, 1.8 Hz), 3.50-3.42 (2H, m), 2.98 (2H, t, J=7.3 Hz), 2.74 (2H, t, J=7.3 Hz), 2.17-1.98 (4H, m), 1.12 (3H, t, J=7.3 Hz). Appearance: paste state.

EXAMPLE 362

6-Chloro-3-(2-cyclopropyl-6-methylphenoxy)-5-iodo-4-pyridazinol (Compound No. 3849)

$^1$H-NMR (200 MHz, CD$_3$OD) δ ppm: 7.08-7.05 (2H, m), 6.84-6.80 (1H, m), 2.14 (3H, s), 1.86-1.75 (1H, m), 0.81-0.65 (2H, m), 0.60-0.52 (2H, m) Appearance: amorphous.

EXAMPLE 363

6-Chloro-3-(2-cyclopropyl-6-methylphenoxy)-4-pyridazinyl trifluoromethanesulfonate (Compound No. 2106)

$^1$H-NMR (200 MHz, CDCl$_3$) δ ppm: 7.52 (1H, s), 7.19-7.09 (2H, m), 6.96-6.89 (1H, m), 2.15 (3H, s), 1.81-1.67 (1H, m), 0.73-0.58 (4H, m) Melting point (° C.): 64-67.

EXAMPLE 364

6-Chloro-3-(2-methylphenoxy)-4-pyridazinyl benzenesulfonate (Compound No. 2147)

$^1$H-NMR (60 MHz, CDCl$_3$) δ ppm: 8.10-7.83 (2H, m), 7.80-7.40 (3H, m), 7.59 (1H, s), 7.30-7.00 (3H, m), 6.90-6.60 (1H, m). Melting point (° C.): 91.5-92.

EXAMPLE 365

6-Chloro-3-(2-cyclopropylphenoxy)-4-pyridazinyl benzenesulfonate (Compound No. 2151)

$^1$H-NMR (200 MHz, CDCl$_3$) δ ppm: 8.02-7.98 (2H, m), 7.78-7.70 (1H, m), 7.62-7.54 (2H, m), 7.58 (1H, s), 7.26-7.09 (2H, m), 6.98-6.93 (1H, m), 6.78-6.69 (1H, m), 1.68-1.54 (1H, m), 0.74-0.52 (4H, m). Appearance: oily product.

EXAMPLE 366

6-Chloro-3-(2-cyclopropyl-6-methylphenoxy)-4-pyridazinyl benzenesulfonate (Compound No. 2176)

$^1$H-NMR (200 MHz, CDCl$_3$) δ ppm: 8.07-8.01 (2H, m), 7.80-7.71 (1H, m), 7.65-7.56 (2H, m), 7.60 (1H, s), 7.11-6.99 (2H, m), 6.80 (1H, dd, J=4.4, 2.4 Hz), 1.93 (3H, s), 1.61-1.45 (1H, m), 0.65-0.45 (4H, m). Melting point (° C.): 105-106.

EXAMPLE 367

6-Chloro-3-(2-methylphenoxy)-4-pyridazinyl 4-chlorobenzenesulfonate (Compound No. 2198)

$^1$H-NMR (60 MHz, CDCl$_3$) δ ppm: 7.94 (2H, d, J=8.4 Hz), 7.60 (1H, s), 7.59 (2H, d, J=8.4 Hz), 7.23-7.09 (3H, m), 6.90-6.60 (1H, m), 2.93 (3H, s). Melting point (° C.): 93-94.

EXAMPLE 368

3-(2-Isopropylphenoxy)-4-pyridazinyl 4-chlorobenzenesulfonate (Compound No. 2199)

$^1$H-NMR (60 MHz, CDCl$_3$) δ ppm: 7.91 (2H, d, J=8.4 Hz), 7.62 (1H, s), 7.55 (2H, d, J=8.4 Hz), 7.50-7.00 (3H, m), 6.80-6.60 (1H, m), 3.20-2.50 (1H, m), 1.14 (6H, d, J=7.0 Hz). Refractive index: $n_D^{22}$ 1.5315.

EXAMPLE 369

3-(2-tert-Butylphenoxy)-6-chloro-4-pyridazinyl 4-chlorobenzenesulfonate (Compound No. 2200)

$^1$H-NMR (60 MHz, CDCl$_3$) δ ppm: 8.05-7.05 (8H, m), 6.70-6.40 (1H, m), 1.26. (9H, s) Melting point (° C.): 83.5-84.5.

EXAMPLE 370

6-Chloro-3-(2-methylphenoxy)-4-pyridazinyl 4-methylbenzenesulfonate (Compound No. 2220)

$^1$H-NMR (60 MHz, CDCl$_3$) δ ppm: 7.83 (2H, d, J=8.4 Hz), 7.47 (2H, d, J=8.4 Hz), 7.32-6.95 (4H, m), 6.85-6.55 (1H, m), 2.43 (3H, s), 1.98 (3H, s). Melting point (° C.): 102-104.

EXAMPLE 371

6-Chloro-3-(2-ethylphenoxy)-4-pyridazinyl 4-methylbenzenesulfonate (Compound No. 2221)

Refractive index: $n_D^{28}$ 1.5847.

EXAMPLE 372

6-Chloro-3-(2-isopropylphenoxy)-4-pyridazinyl 4-methylbenzenesulfonate (Compound No. 2222)

$^1$H-NMR (60 MHz, CDCl$_3$) δ ppm: 8.00-6.50 (8H, m), 7.55 (1H, s), 2.85 (1H, septet, J=7.0 Hz), 2.42 (3H, s), 1.11 (6H, d, J=7.0 Hz). Melting point (° C.): 99-100.

EXAMPLE 373

3-(2-s-Butylphenoxy)-6-chloro-4-pyridazinyl 4-methylbenzenesulfonate (Compound No. 2223)

$^1$H-NMR (60 MHz, CDCl$_3$) δ ppm: 7.98-6.50 (8H, m), 7.52 (1H, s), 2.99-2.31 (1H, m), 2.41 (3H, s), 1.82-0.95 (2H, m), 1.08 (3H, d, J=7.0 Hz), 0.90-0.35 (3H, m). Melting point (° C.): 65-66.

EXAMPLE 374

3-(2-tert-Butylphenoxy)-6-chloro-4-pyridazinyl 4-methylbenzenesulfonate (Compound No. 2224)

$^1$H-NMR (60 MHz, CDCl$_3$) δ ppm: 7.98-7.00 (7H, m), 7.61 (1H s), 6.78-6.45 (1H, m), 2.40 (3H, s), 1.29 (9H, s). Melting point (° C.): 98-99.

EXAMPLE 375

5,6-Dichloro-3-(2-cyclopropyl-6-methylphenoxy)-4-pyridazinol (Compound No. 3837)

$^1$H-NMR (200 MHz, CD$_3$OD) δ ppm: 7.08-7.06 (2H, m), 6.85-6.80 (1H, m), 2,14 (3H, m), 1.87-1.78 (1H, m), 0.81-0.72 (2H, m), 0.64-0.52 (2H, m) Appearance: amorphous.

EXAMPLE 376

6-Chloro-3-(2-cyclohexylphenoxy)-4-pyridazinyl 4-methylbenzenesulfonate (Compound No. 2230)

$^1$H-NMR (60 MHz, CDCl$_3$) δ ppm: 8.00-6.50 (8H, m), 7.50 (1H, s), 2.50 (1H, brs), 2.40 (3H, s), 2.00-0.90 (1OH, m). Melting point (° C.): 120-121.

EXAMPLE 377

3-([1,1'-Biphenyl]-2-yloxy)-6-chloro-4-pyridazinyl 4-methylbenzenesulfonate (Compound No. 2231)

$^1$H-NMR (60 MHz, CDCl$_3$) δ ppm: 7.80-6.60 (14H, m), 2.42 (3H, s). Melting point (° C.): 106-108.

EXAMPLE 378

6-Chloro-3-(2-methoxyphenoxy)-4-pyridazinyl 4-methylbenzenesulfonate (Compound No. 2232)

$^1$H-NMR (60 MHz, CDCl$_3$) δ ppm: 8.00-6.70 (8H, m), 7.56 (1H, s), 3.62 (3H, s), 2.44 (3H, s). Melting point (° C.): 153-157.

EXAMPLE 379

6-Chloro-3-(2-cyclopropyl-6-methylphenoxy)-4-pyridazinyl propionate (Compound No. 1160)

$^1$H-NMR (200 MHz, CDCl$_3$) δ ppm: 7.39 (1H, s), 7.14-7.05 (2H, m), 6.89-6.82 (1H, m), 2.72 (2H, q, J=7.6 Hz), 2.12 (3H, s), 1.82-1.68 (1H, m), 1.31 (3H, t, J=7.6 Hz), 0.77-0.53 (4H, m). Melting point (° C.): 75-77.

EXAMPLE 380

6-Chloro-3-(3-chlorophenoxy)-4-pyridazinyl 4-methylbenzenesulfonate (Compound No. 2234)

Refractive index: $n_D^{28}$ 1.5970.

EXAMPLE 381

3-(3-tert-Butylphenoxy)-6-chloro-4-pyridazinyl 4-methylbenzenesulfonate (Compound No. 2235)

$^1$H-NMR (60 MHz, CDCl$_3$) δ ppm: 7.73 (2H, d, J=8.2 Hz), 7.49 (1H, s), 7.23 (2H, d, J=8.2 Hz), 7.14 (1H, d, J=4.0 Hz), 6.90-6.45 (3H, m), 2.38 (3H, s), 1.26 (9H, s). Melting point (° C.): 56-57.

EXAMPLE 382

6-Chloro-3-[3-(trifluoromethyl)phenoxy]-4-pyridazinyl 4-methylbenzenesulfonate (Compound No. 2236)

$^1$H-NMR (60 MHz, CDCl$_3$) δ ppm: 7.95-6.93 (9H, m), 2.40 (3H, s).

Refractive index: $n_D^{25.5}$ 1.5556.

EXAMPLE 383

6-Chloro-3-(3-cyanophenoxy)-4-pyridazinyl 4-methylbenzenesulfonate (Compound No. 2237)

$^1$H-NMR (90 MHz, CDCl$_3$) δ ppm: 7.85 (2H, d, J=8.0 Hz), 7.70-7.00 (7H, m), 2.49 (3H, s). Appearance: paste state.

EXAMPLE 384

6-Chloro-3-(3-methoxyphenoxy)-4-pyridazinyl 4-methylbenzenesulfonate (Compound No. 2238)

$^1$H-NMR (60 MHz, CDCl$_3$) δ ppm: 7.90-6.30 (8H, m), 7.47 (1H, s), 3.71 (3H, s), 2.40 (3H, s). Melting point (° C.): 89-90.

EXAMPLE 385

6-Chloro-3-(1-naphthyloxy)-4-pyridazinyl 4-methylbenzenesulfonate (Compound No. 2240)

$^1$H-NMR (60 MHz, CDCl$_3$) δ ppm: 7.90-6.80 (12H, m), 2.38 (3H, s). Melting point (° C.): 92-94.

EXAMPLE 386

3-(2-Bromo-4-tert-butylphenoxy)-6-chloro-6-4-pyridazinyl 4-methylbenzenesulfonate (Compound No. 2245)

$^1$H-NMR (60 MHz, CDCl$_3$) δ ppm: 7.89 (2H, d, J=8.4 Hz), 7.63 (1H, s), 7.62-7.18 (3H, m), 6.84 (2H, d, J=8.4 Hz), 2.43 (3H, s), 1.29 (9H, s) Melting point (° C.): 110-112.

EXAMPLE 387

6-Chloro-3-(4-chloro-2-methylphenoxy)-4-pyridazinyl 4-methylbenzenesulfonate (Compound No. 2246)

$^1$H-NMR (60 MHz, CDCl$_3$) δ ppm: 7.95-7.75 (2H, m), 7.60-7.00 (5H, m), 6.80-6.60 (1H, m), 2.46 (3H, s), 2.00 (3H, s). Melting point (° C.): 115-116.

EXAMPLE 388

6-Chloro-3-(2,4-dimethylphenoxy)-4-pyridazinyl 4-methylbenzenesulfonate (Compound No. 2247)

$^1$H-NMR (60 MHz, CDCl$_3$) δ ppm: 7.94-7.78 (2H, m), 7.54 (1H, s), 7.41-7.23 (2H, m), 7.02-6.53 (3H, m), 2.46 (3H, s), 2.30 (3H, s), 1.96 (3H, s). Melting point (° C.): 80-81.

EXAMPLE 389

3-(4-Bromo-2-isopropylphenoxy)-6-chloro-4-pyridazinyl 4-methylbenzenesulfonate (Compound No. 2248)

$^1$H-NMR (60 MHz, CDCl$_3$) δ ppm: 7.80 (2H, d, J=8.4 Hz), 7.51 (1H, s), 7.45-7.10 (3H, m), 6.56 (2H, d, J=8.4 Hz), 2.85 (1H, septet, J=6.8 Hz), 2.43 (3H, s), 1.10 (6H, d, J=6.8 Hz). Melting point (° C.): 119-122.

EXAMPLE 390

6-Chloro-3-(2-isopropyl-5-methylphenoxy)-4-pyridazinyl 4-methylbenzenesulfonate (Compound No. 2249)

$^1$H-NMR (60 MHz, CDCl$_3$) δ ppm: 8.00-6.80 (6H, m), 7.56 (1H, s), 6.46 (1H, brs), 2.95-2.50 (1H, m), 2.44 (3H, s), 2.25 (3H, s), 1.09. (6H, d, J=7.0 Hz). Melting point (° C.): 90-92.

EXAMPLE 391

6-Chloro-3-(2,6-dimethylphenoxy)-4-pyridazinyl 4-methylbenzenesulfonate (Compound No. 2263)
Melting point (° C.): 89-90.

EXAMPLE 392

6-Chloro-3-(2-cyclopropyl-6-methylphenoxy)-4-pyridazinyl 4-methylbenzenesulfonate (Compound No. 2265)

$^1$H-NMR (200 MHz, CDCl$_3$) δ ppm: 7.90 (2H, d, J=8.1 Hz), 7.60 (1H, s), 7.38 (2H, d, J=8.1 Hz), 7.11-7.01 (2H, m), 6.80 (1H, dd, J=6.6, 2.6 Hz), 2.47 (3H, s), 1.93 (3H, s), 1.59-1.46 (1H, m), 0.64-0.45 (4H, m). Melting point (° C.): 85-87.

EXAMPLE 393

6-Chloro-3-(2-methylphenoxy)-4-pyridazinyl 4-nitrobenzenesulfonate (Compound No. 2287)

$^1$H-NMR (60 MHz, CDCl$_3$) δ ppm: 8.41 (2H, d, J=8.4 Hz), 8.33 (2H, d, J=8.4 Hz), 7.61 (1H, s), 7.30-7.02 (3H, m), 6.95-6.63 (1H, m), 2.03 (3H, s). Melting point (° C.): 166-169.

EXAMPLE 394

6-Chloro-3-(2-cyclopropylphenoxy)-4-pyridazinyl 4-nitrobenzenesulfonate (Compound No. 2289)

$^1$H-NMR (200 MHz, CDCl$_3$) δ ppm: 8.39 (2H, d, J=8.8 Hz), 8.23 (2H, d, J=8.8 Hz), 7.59 (1H, s), 7.20-7.09 (2H, m), 6.97-6.92 (1H, m), 6.77-6.73 (1H, m), 1.67-1.59 (1H, m), 0.78-0.54 (4H, m). Melting point (° C.): 158.

EXAMPLE 395

6-Chloro-3-(2-cyclopropylphenoxy)-4-pyridazinyl dimethylsulfamate (Compound No. 2351)

$^1$H-NMR (200 MHz, CDCl$_3$) δ ppm: 7.60 (1H, s), 7.26-7.01 (4H, m), 3.09 (6H, s), 1.95-1.78 (1H, m), 0.85-0.63 (4H, m). Appearance: oily product.

EXAMPLE 396

6-Chloro-3-(2-cyclopropyl-6-methylphenoxy)-4-pyridazinyl 2-methylpropanoate (Compound No. 1172)

$^1$H-NMR (200 MHz, CDCl$_3$) δ ppm: 7.38 (1H, s), 7.14-7.05 (2H, m), 6.90-6.83 (1H, m), 2.93 (1H, septet, J=7.0 Hz), 2.13 (3H, s), 1.80-1.66 (1H, m), 1.36 (6H, d, J=7.0 Hz), 0.78-0.56 (4H, m). Melting point (° C.): 38-39.

EXAMPLE 397

6-Chloro-3-(2-cyclopropyl-6-methylphenoxy)-4-pyridazinyl pentanoate (Compound No. 1178)

$^1$H-NMR (200 MHz, CDCl$_3$) δ ppm: 7.38 (1H, s), 7.13-7.00 (2H, m), 6.90-6.77 (1H, m), 2.68 (2H, t, J=7.3 Hz), 2.12 (3H, s), 1.88-1.65 (3H, m), 1.60-1.35 (2H, m), 0.95 (3H, t, J=7.3 Hz), 0.80-0.50 (4H, m). Appearance: caramel-like.

EXAMPLE 398

6-Chloro-3-(2-cyclopropyl-6-methylphenoxy)-4-pyridazinyl 3-methylbutanoate (Compound No. 1184)

$^1$H-NMR (200 MHz, CDCl$_3$) δ ppm: 7.37 (1H, s), 7.14-7.07 (2H, m), 6.89-6.82 (1H, m), 2.55 (2H, d, J=7.0 Hz), 2.27 (1H, br.septet, J=6.8 Hz), 2.12 (3H, s), 1.80-1.67 (1H, m), 1.07 (6H, d, J=6.6 Hz), 0.77-0.55 (4H, m). Melting point (° C.): 71-74.

EXAMPLE 399

6-Chloro-3-(2-cyclopropyl-6-methylphenoxy)-4-pyridazinyl pentadecanoate (Compound No. 1260)

$^1$H-NMR (200 MHz, CDCl$_3$) δ ppm: 7.37 (1H, s), 7.10-7.00 (2H, m), 6.87-6.77 (1H, m), 2.66 (2H, t, J=6.4 Hz), 2.12 (3H, s), 1.85-1.65 (3H, m), 1.35-1.18 (22H, m), 0.95-0.82 (3H, m), 0.80-0.50 (4H, m). Melting point (° C.): 35-37.

EXAMPLE 400

6-Chloro-3-phenoxy-5-(trimethylsilyl)-4-pyridazinol (Compound No. 2402)

$^1$H-NMR (90 MHz, CDCl$_3$) δ ppm: 12.0 (1H, brs), 7.30-6.81 (5H, m), 0.28 (9H, s). Melting point (° C.): 119-120.

EXAMPLE 401

6-Chloro-3-(2-cyclopropyl-6-methylphenoxy)-4-pyridazinyl cyclobutanecarboxylate (Compound No. 1286)

$^1$H-NMR (200 MHz, CDCl$_3$) δ ppm: 7.38 (1H, s), 7.14-7.05 (2H, m), 6.89-6.79 (1H, m), 3.58-3.40 (1H, m), 2.60-1.85 (6H, m), 2.13 (3H, s), 1.82-1.67 (1H, m), 0.80-0.67 (2H, m), 0.64-0.53 (2H, m). Appearance: paste state.

EXAMPLE 402

6-Chloro-3-(2-cyclopropyl-6-methylphenoxy)-4-pyridazinyl cyclohexanecarboxylate (Compound No. 1298)

$^1$H-NMR (200 MHz, CDCl$_3$) δ ppm: 7.37 (1H, s), 7.15-7.05 (2H, m), 6.90-6.80 (1H, m), 2.78-2.60 (1H, m), 2.12 (3H, s), 1.90-1.20 (1OH, m), 0.80-0.50 (4H, m). Melting point (° C.): oily product.

EXAMPLE 403

3-(2-Isopropylphenoxy)-6-methyl-4-pyridazinol (Compound No. 2418)

$^1$H-NMR (200 MHz, CD$_3$OD) δ ppm: 7.40-7.35 (1H, m), 7.25-7.16 (2H, m), 7.04-6.98 (1H, m), 6.43 (1H, s), 3.06 (1H, septet, J=7.0 Hz), 2.36 (3H, s), 1.18 (6H, d, J=7.0 Hz). Melting point (° C.): 259-260.

EXAMPLE 404

6-Chloro-3-(2-cyclopropyl-6-methylphenoxy)-4-pyridazinyl 2-bromobutanoate (Compound No. 1334)

$^1$H-NMR (200 MHz, CDCl$_3$) δ ppm: 7.44 (1H, s), 7.14-7.05 (2H, m), 6.90-6.83 (1H, m), 4.45 (1H, t, J=7.6 Hz), 2.22 (1H, dq, J=7.3, 7.6 Hz), 2.13 (3H, s), 1.81-1.69 (1H, m), 1.17 (3H, t, J=7.3 Hz), 0.74-0.69 (2H, m), 0.58-0.56 (2H, m). Appearance: paste state.

EXAMPLE 405

3-(2-Isopropylphenoxy)-6-(trifluoromethyl)-4-pyridazinol (Compound No. 2431)

$^1$H-NMR (60 MHz, CDCl$_3$) δ ppm: 7.60-6.70 (4H, m), 6.87 (1H, s), 2.97 (1H, septet, J=7.0 Hz), 1.10 (6H, d, J=7.0 Hz). Melting point (° C.): 126.5.

EXAMPLE 406

6-Chloro-3-(2-cyclopropyl-6-methylphenoxy)-4-pyridazinyl 4-chlorobutanoate (Compound No. 1340)

$^1$H-NMR (200 MHz, CDCl$_3$) δ ppm: 7.40 (1H, s), 7.14-7.05 (2H, m), 6.89-6.82 (1H, m), 3.68 (2H, t, J=6.2 Hz), 2.91 (2H, t, J=7.0 Hz), 2.31-2.18 (2H, m), 2.11 (3H, s), 1.79-1.65 (1H, m), 0.80-0.67 (2H, m), 0.63-0.53 (2H, m). Appearance: paste state.

EXAMPLE 407

6-Chloro-3-(2-cyclopropyl-6-methylphenoxy)-4-pyridazinyl 3-methyl-2-butenoate (Compound No. 1358)

$^1$H-NMR (200 MHz, CDCl$_3$) δ ppm: 7.44 (1H, s), 7.12-7.05 (2H, m), 6.88-6.80 (1H, m), 5.99-5.97 (1H, m), 2.26 (3H, d, J=1.1 Hz), 2.13 (3H, s) 2.04 (3H, d, J=1.1 Hz), 1.83-1.70 (1H, m), 0.77-0.64 (2H, m), 0.60-0.53 (2H, m). Appearance: paste state.

EXAMPLE 408

6-Chloro-3-(2-cyclopropyl-6-methylphenoxy)-4-pyridazinyl (2E)-3-phenyl-2-propenoate (Compound No. 1364)

$^1$H-NMR (200 MHz, CDCl$_3$) δ ppm: 7.96 (1H, d, J=16.0 Hz), 7.63-7.59 (2H, m), 7.53 (1H, s), 7.48-7.43 (3H, m), 7.09-7.05 (2H, m), 6.86-6.81 (1H, m), 6.66 (1H, d, J=16.0 Hz), 2.16 (3H, s), 1.83-1.75 (1H, m), 0.79-0.54 (4H, m). Appearance: amorphous.

EXAMPLE 409

6-Chloro-3-(2-cyclopropyl-6-methylphenoxy)-4-pyridazinyl methyl succinate (Compound No. 1382)

$^1$H-NMR (200 MHz, CDCl$_3$) δ ppm: 7.44 (1H, s), 7.08-7.02 (2H, m), 6.88-6.74 (1H, m), 3.69 (3H, s), 3.01 (2H, t, J=7.3 Hz), 2.78 (2H, t, J=7.3 Hz), 2.11 (3H, s), 1.85-1.65 (1H, m), 0.80-0.50 (4H, m). Appearance: oily product.

EXAMPLE 410

6-Chloro-3-(2-cyclopropyl-6-methylphenoxy)-4-pyridazinyl 2-chlorobenzoate (Compound No. 1441)

$^1$H-NMR (200 MHz, CDCl$_3$) δ ppm: 8.14 (1H, d, J=8.8 Hz), 7.58 (1H, s), 7.59-7.39 (3H, m), 7.10-7.05 (2H, m), 6.88-6.80 (1H, m), 2.16 (3H, s), 1.90-1.70 (1H, m), 0.85-0.50 (4H, m). Appearance: oily product.

EXAMPLE 411

3-(2-Methylphenoxy)-6-(2-thienyl)-4-pyridazinol (Compound No. 2478)

$^1$H-NMR (200 MHz, CDCl$_3$) δ ppm: 7.56-7.48 (2H, m), 7.21-7.00 (4H, m), 6.97-6.90 (1H, m), 6.69 (1H, s), 2.11 (3H, s). Melting point (° C.): 86-87.

EXAMPLE 412

6-Chloro-3-(2-cyclopropyl-6-methylphenoxy)-4-pyridazinyl 2-methylbenzoate (Compound No. 1481)

$^1$H-NMR (200 MHz, CDCl$_3$) δ ppm: 8.20 (1H, d, J=7.0 Hz), 7.56 (1H, s), 7.52 (1H, d, J=7.7 Hz), 7.40-7.28 (2H, m), 7.10-7.00 (2H, m), 6.90-6.88 (1H, m), 2.69 (3H, s), 2.16 (3H, s), 1.90-1.70 (1H, m), 0.82-0.65 (2H, m), 0.65-0.50 (2H, m). Appearance: oily product.

EXAMPLE 413

3,6-Bis(2-methylphenoxy)-4-pyridazinol (Compound No. 2492)

$^1$H-NMR (60 MHz, DMF-d$_7$) δ ppm: 7.40-6.90 (8H, m), 5.79 (1H, s), 2.19 (6H, brs) Melting point (° C.): 247-250.

EXAMPLE 414

6-Chloro-3-(2-cyclopropyl-6-methylphenoxy)-4-pyridazinyl 2-methoxybenzoate (Compound No. 1522)

$^1$H-NMR (200 MHz, CDCl$_3$) δ ppm: 8.09 (1H, dd, J=7.9, 2.0 Hz) 7.68-7.57 (1H, m), 7.59 (1H, s), 7.15-7.03 (4H, m), 6.90-6.82 (1H, m), 3.96 (3H, s), 2.17 (3H, s), 1.96-1.72 (1H, m), 0.78-0.65 (2H, m), 0.65-0.51 (2H, m). Appearance: gum state.

EXAMPLE 415

6-Chloro-3-(2-cyclopropyl-6-methylphenoxy)-4-pyridazinyl 3-methylbenzoate (Compound No. 1531)

$^1$H-NMR (200 MHz, CDCl$_3$) δ ppm: 8.05-8.00 (2H, m), 7.58 (1H, s), 7.55-7.38 (2H, m), 7.10-7.05 (2H, m), 6.88-6.80 (1H, m), 2.46 (3H, s), 2.16 (3H, s), 1.90-1.68 (1H, m), 0.80-0.50 (4H, m). Appearance: oily product.

EXAMPLE 416

6-Chloro-3-(2-cyclopropyl-6-methylphenoxy)-4-pyridazinyl 4-chlorobenzoate (Compound No. 1537)

$^1$H-NMR (200 MHz, CDCl$_3$) δ ppm: 8.16 (2H, d, J=8.8 Hz), 7.59 (1H, s), 7.54 (2H, d, J=8.8 Hz), 7.14-7.07 (2H, m), 6.88-6.83 (1H, m), 2.15 (3H, s), 1.84-1.69 (1H, m), 0.80-0.70 (2H, m), 0.62-0.55 (2H, m). Appearance: amorphous.

EXAMPLE 417

6-Chloro-3-(2-cyclopropyl-6-methylphenoxy)-4-pyridazinyl 4-bromobenzoate (Compound No. 1543)

$^1$H-NMR (200 MHz, CDCl$_3$) δ ppm: 8.07 (2H, d, J=8.6 Hz), 7.70 (2H, d, J=8.6 Hz), 7.59 (1H, s), 7.12-7.03 (2H, m), 6.89-6.82 (1H, m), 2.15 (3H, s), 1.83-1.67 (1H, m), 0.78-0.50 (4H, m). Appearance: amorphous.

EXAMPLE 418

6-Chloro-3-(2-cyclopropyl-6-methylphenoxy)-4-pyridazinyl 4-iodobenzoate (Compound No. 1549)

$^1$H-NMR (200 MHz, CDCl$_3$) δ ppm: 7.94 (2H, s), 7.93 (1H, m) 7.62 (1H, s), 7.29 (1H, s), 7.12-7.09 (2H, m), 6.89-6.87 (1H, m), 2.17 (3H, s), 1.84-1.73 (1H, m), 0.79-0.70 (2H, m), 0.62-0.55 (2H, m). Appearance: paste state.

EXAMPLE 419

6-Chloro-3-(2-cyclopropyl-6-methylphenoxy)-4-pyridazinyl 4-methylbenzoate (Compound No. 1566)

$^1$H-NMR (200 MHz, CDCl$_3$) δ ppm: 8.10 (2H, d, J=8.1 Hz), 7.60 (1H, s), 7.34 (2H, d, J=8.1 Hz), 7.12-7.03 (2H, m), 6.88-6.81 (1H, m), 2.46 (3H, s), 2.15 (3H, s), 1.85-1.71 (1H, m), 0.78-0.65 (2H, m), 0.62-0.52 (2H, m). Melting point (° C.): 77.5-78.

EXAMPLE 420

6-Chloro-3-(2-cyclopropyl-6-methylphenoxy)-4-pyridazinyl 4-tert-butylbenzoate (Compound No. 1575)

$^1$H-NMR (200 MHz, CDCl$_3$) δ ppm: 8.15 (2H, d, J=8.8 Hz), 7.59 (1H, s), 7.56 (2H, d, J=8.8 Hz), 7.09-7.06 (2H, m), 6.86-6.82 (1H, m), 2.15 (3H, s), 1.37 (9H, s), 1.82-1.73 (1H, m), 0.76-0.69 (2H, m), 0.60-0.56 (2H, m). Melting point (° C.): 139-142.

EXAMPLE 421

6-Chloro-3-(2-cyclopropyl-6-methylphenoxy)-4-pyridazinyl 4-nitrobenzoate (Compound No. 1593)

$^1$H-NMR (200 MHz, CDCl$_3$) δ ppm: 8.41 (4H, s), 7.61 (1H, s) 7.14-7.08 (2H, m), 6.89-6.83 (1H, m), 2.17 (3H, s), 1.81-1.70 (1H, m), 0.80-0.71 (2H, m), 0.62-0.54 (2H, m). Appearance: amorphous.

EXAMPLE 422

6-Chloro-3-(2-cyclopropyl-6-methylphenoxy)-4-pyridazinyl 4-methoxybenzoate (Compound No. 1599)

$^1$H-NMR (200 MHz, CDCl$_3$) δ ppm: 8.17 (2H, d, J=8.8 Hz), 7.60 (1H, s), 7.12-7.04 (2H, m), 7.01 (2H, d, J=8.8 Hz), 6.88-6.82 (1H, m), 3.90 (1H, s), 2.16 (3H, s), 1.85-1.71 (1H, m), 0.78-0.69 (2H, m), 0.60-0.52 (2H, m). Appearance: amorphous.

EXAMPLE 423

6-Chloro-3-(2-cyclopropyl-6-methylphenoxy)-4-pyridazinyl 2,4-dichlorobenzoate (Compound No. 1616)

$^1$H-NMR (200 MHz, CDCl$_3$) δ ppm: 8.11 (1H, d, J=8.4 Hz), 7.60-7.57 (2H, m), 7.42 (1H, dd, J=8.4, 2.2 Hz), 7.14-7.08 (2H, m), 6.89-6.83 (1H, m), 2.15 (3H, s), 1.85-1.72 (1H, m), 0.78-0.67 (2H, m), 0.63-0.54 (2H, m). Appearance: amorphous.

EXAMPLE 424

6-Chloro-3-(2-methylphenoxy)-4-pyridazinyl 4-(2,4-dichlorobenzoyl)-1,3-dimethyl-1H-pyrazol-5-yl phthalate (Compound No. 1620)

$^1$H-NMR (200 MHz, CDCl$_3$) δ ppm: 7.98-7.94 (1H, m), 7.88-7.84 (1H, m), 7.81-7.71 (2H, m), 7.57 (1H, s), 7.28-7.17 (6H, m), 7.08-7.03 (1H, m), 3.70 (3H, s), 2.26 (3H, s), 2.15 (3H, s). Appearance: amorphous.

EXAMPLE 425

Potassium 6-chloro-3-(2-cyclopropyl-6-methylphenoxy)-4-pyridazinoate (Compound No. 3811)

$^1$H-NMR (200 MHz, CD$_3$OD) δ ppm: 7.05-6.95 (2H, m), 6.83-6.72 (1H, m), 6.47 (1H, s), 2.00-1.83 (1H, m), 0.80-0.64 (2H, m), 0.64-0.48 (2H, m). Melting point (° C.): 187-189.

EXAMPLE 426

6-Chloro-3-(2-cyclopropyl-6-methylphenoxy)-4-pyridazinyl 4-(2,4-dichlorobenzoyl)-1,3-dimethyl-1H-pyrazol-5-yl isophthalate (Compound No. 1631)

$^1$H-NMR (200 MHz, CDCl$_3$) δ ppm: 8.61 (1H, t, J=1.5 Hz), 8.54-8.47 (1H, m), 8.22-8.16 (1H, m), 7.71 (1H, t, J=8.1 Hz), 7.61 (1H, s), 7.15-6.96 (4H, m), 6.89-6.82 (1H, m), 3.67 (3H, s), 2.44 (3H, s), 2.17 (3H, s), 1.88-1.72 (1H, m), 0.83-0.71 (2H, m), 0.64-0.53 (2H, m). Appearance: amorphous.

EXAMPLE 427

6-Chloro-3-(2-cyclopropyl-6-methylphenoxy)-4-pyridazinyl 2-furoate (Compound No. 1643)

$^1$H-NMR (200 MHz, CDCl$_3$) δ ppm: 7.74-7.73 (1H, m), 7.56 (1H, s), 7.50 (1H, dd, J=3.7, 0.7 Hz), 7.13-7.04 (2H, m), 6.88-6.81 (1H, m), 6.65-6.63 (1H, m), 2.15 (3H, s), 1.85-1.71 (1H, m), 0.78-0.69 (2H, m), 0.62-0.52 (2H, m). Appearance: paste state.

EXAMPLE 428

6-Chloro-3-(2-cyclopropyl-6-methylphenoxy)-4-pyridazinyl 2-thiophenecarboxylate (Compound No. 1649)

$^1$H-NMR (200 MHz, CDCl$_3$) δ ppm: 8.07-8.05 (1H, m), 7.78-7.75 (1H, m), 7.58 (1H, s), 7.24-7.20 (1H, m), 7.13-7.06 (2H, m), 6.89-6.83 (1H, m), 2.16 (3H, s), 1.83-1.71 (1H, m), 0.80-0.70 (2H, m), 0.65-0.55 (2H, m). Appearance: amorphous.

EXAMPLE 429

6-Chloro-3-(2-cyclopropyl-6-methylphenoxy)-4-pyridazinyl isobutyl carbonate (Compound No. 1770)

$^1$H-NMR (200 MHz, CDCl$_3$) δ ppm: 7.49 (1H, s), 7.15-7.05 (2H, m), 6.89-6.82 (1H, m), 4.13 (2H, d, J=6.6 Hz), 2.14 (3H, s), 2.09 (1H, br.septet, J=7.0 Hz), 1.88-1.68 (1H, m), 1.01 (6H, d, J=7.0 Hz), 0.78-0.52 (4H, m). Melting point (° C.): 72-74.

EXAMPLE 430

Allyl 6-chloro-3-(2-cyclopropyl-6-methylphenoxy)-4-pyridazinyl carbonate (Compound No. 1811)

$^1$H-NMR (200 MHz, CDCl$_3$) δ ppm: 7.50 (1H, s), 7.15-7.06 (2H, m), 6.89-6.82 (1H, m), 6.10-5.90 (1H, m), 5.51-5.35 (2H, m), 4.84-4.80 (2H, m), 2.14 (3H, s), 1.85-1.70 (1H, m), 0.78-0.53 (4H, m). Appearance: oily product.

EXAMPLE 431

6-Chloro-3-(2-cyclopropyl-6-methylphenoxy)-4-pyridazinyl dimethylcarbamate (Compound No. 1891)

$^1$H-NMR (200 MHz, CDCl$_3$) δ ppm: 7.56 (1H s), 7.13-7.05 (2H, m), 6.89-6.82 (1H, m), 3.16 (3H, s), 3.05 (3H, s), 2.15 (3H, s), 1.85-1.71 (1H, m), 0.78-0.54 (4H, m). Melting point (° C.): 136-138.

EXAMPLE 432

6-Chloro-3-(2-cyclopropyl-6-methylphenoxy)-4-pyridazinyl diethylcarbamate (Compound No. 1911)

$^1$H-NMR (200 MHz, CDCl$_3$) δ ppm: 7.58 (1H, s), 7.10-7.07 (2H, m), 6.87-6.83 (1H, m), 3.48 (2H, q, J=7.3 Hz), 3.41 (2H, q, J=7.0 Hz), 2.15 (3H, s), 1.82-1.72 (1H, m), 1.29 (3H, t, J=7.3 Hz), 1.23 (3H, t, J=7.0 Hz), 0.74-0.57 (4H, m). Melting point (° C.): 119-121.

EXAMPLE 433

6-Chloro-3-(2-cyclopropyl-6-methylphenoxy)-4-pyridazinyl diisopropylcarbamate (Compound No. 1920)

$^1$H-NMR (200 MHz, CDCl$_3$) δ ppm: 7.61 (1H, s), 7.10-7.00 (2H, m), 6.90-6.85 (1H, m), 4.20-3.90 (2H, m), 2.14 (3H, s), 1.87-1.67 (1H, m), 1.45-1.20 (12H, m), 0.80-0.50 (4H, m). Melting point (° C.): 103-105.

EXAMPLE 434

6-Chloro-3-(2-cyclopropyl-6-methylphenoxy)-4-pyridazinyl 2-thiophenesulfonate (Compound No. 3792)

$^1$H-NMR (200 MHz, CDCl$_3$) δ ppm: 7.89-7.82 (2H, m), 7.58 (1H, s), 7.22-7.13 (1H, m), 7.13-7.02 (2H, m), 6.84-6.79 (1H, m), 1.99 (3H, s), 1.69-1.53 (1H, m), 0.70-0.48 (4H, m). Appearance: amorphous.

EXAMPLE 435

6-Chloro-3-(2-cyclopropyl-6-methylphenoxy)-4-pyridazinyl methyl(phenyl)carbamate (Compound No. 1946)

$^1$H-NMR (200 MHz, CDCl$_3$) δ ppm: 7.40-7.25 (6H, m), 7.11-7.08 (2H, m), 6.87-6.82 (1H, m), 3.42 (3H, br.s), 2.15 (3H, br.s), 1.82-1.68 (1H, m), 0.71-0.56 (4H, m). Appearance: amorphous.

EXAMPLE 436

6-Chloro-3-(2-cyclopropyl-6-methylphenoxy)-4-pyridazinyl diphenylcarbamate (Compound No. 1952)

$^1$H-NMR (200 MHz, CDCl$_3$) δ ppm: 7.45-7.28 (11H, m), 7.16-7.09 (2H, m), 6.87-6.82 (1H, m), 2.11 (3H, s), 1.79-1.66 (1H, m), 0.69-0.56 (4H, m). Appearance: amorphous.

EXAMPLE 437

O-[6-Chloro-3-(2-cyclopropyl-6-methylphenoxy)-4-pyridazinyl] S-methyl thiocarbonate (Compound No. 1958)

$^1$H-NMR (200 MHz, CDCl$_3$) δ ppm: 7.47 (1H, s), 7.13-7.06 (2H, m), 6.89-6.83 (1H, m), 2.49 (3H, s), 2.14 (3H, s), 1.83-1.69 (1H, m), 0.78-0.65 (2H, m), 0.63-0.55 (2H, m). Appearance: paste state.

EXAMPLE 438

6-Chloro-3-(2-cyclopropyl-6-methylphenoxy)-4-pyridazinyl ethanesulfonate (Compound No. 2034)

$^1$H-NMR (200 MHz, CDCl$_3$) δ ppm: 7.58 (1H, s), 7.15-7.05 (2H, m), 6.92-6.82 (1H, m), 3.58 (2H, q, J=7.4 Hz), 2.15 (3H, s), 1.82-1.68 (1H, m), 1.64 (3H, t, J=7.4 Hz), 0.78-0.52 (4H, m). Melting point (° C.): 96-97.

EXAMPLE 439

6-Chloro-3-(2-cyclopropyl-6-methylphenoxy)-4-pyridazinyl 1-propanesulfonate (Compound No. 2051)

$^1$H-NMR (200 MHz, CDCl$_3$) δ ppm: 7.58 (1H, s), 7.18-7.05 (2H, m), 6.94-6.83 (1H, m), 3.53 (2H, t, J=7.7 Hz), 2.20-2.00 (2H, m), 2.15 (3H, s), 1.82-1.67 (1H, m), 1.15 (3H, t, J=7.7 Hz), 0.80-0.50 (4H, m). Melting point (° C.): 70.5-71.5.

EXAMPLE 440

6-Chloro-3-(2-cyclopropyl-6-methylphenoxy)-4-pyridazinyl 2-propanesulfonate (Compound No. 2060)

$^1$H-NMR (200 MHz, CDCl$_3$) δ ppm: 7.59 (1H, s), 7.18-7.07 (2H, m), 6.93-6.82 (1H, m), 3.75 (1H, septet, 7.0 Hz), 2.15 (3H, S), 1.85-1.65 (1H, m), 1.65 (6H, d, J=7.0 Hz), 0.78-0.50 (4H, m). Appearance: oily product.

EXAMPLE 441

6-Chloro-3-(2-cyclopropyl-6-methylphenoxy)-4-pyridazinyl 1-octanesulfonate (Compound No. 2066)

$^1$H-NMR (200 MHz, CDCl$_3$) δ ppm: 7.57 (1H, s), 7.15-7.07 (2H, m), 6.89-6.85 (1H, s), 3.60-3.50 (2H, m), 2.15 (3H, s), 2.15-1.98 (2H, m), 1.83-1.67 (1H, m), 1.58-1.15 (1OH, m), 0.95-0.83 (3H, m), 0.80-0.68 (2H, m), 0.65-0.55 (2H, m). Appearance: paste state.

EXAMPLE 442

6-Chloro-3-(2-cyclopropyl-6-methylphenoxy)-4-pyridazinyl chloromethanesulfonate (Compound No. 2072)

$^1$H-NMR (200 MHz, CDCl$_3$) δ ppm: 7.58 (1H, s), 7.18-7.09 (2H, m), 6.92-6.85 (1H, m), 5.02 (2H, s), 2.16 (3H, s), 1.83-1.68 (1H, m), 0.80-0.68 (2H, m), 0.65-0.55 (2H, m). Appearance: paste state.

EXAMPLE 443

6-Chloro-3-(2-cyclopropyl-6-methylphenoxy)-4-pyridazinyl 2,2,2-trifluoroethanesulfonate (Compound No. 2136)

$^1$H-NMR (200 MHz, CDCl$_3$) δ ppm: 7.55 (1H, s), 7.19-7.05 (2H, m), 6.90 (1H, dd, J=6.6, 2.9 Hz), 4.39 (2H, q, J=8.2 Hz), 2.15 (3H, s), 1.80-1.65 (1H, m), 0.80-0.50 (4H, m). Appearance: amorphous.

EXAMPLE 444

6-Chloro-3-(2-cyclopropyl-6-methylphenoxy)-4-pyridazinyl 4-chlorobenzenesulfonate (Compound No. 2212)

$^1$H-NMR (200 MHz, CDCl$_3$) δ ppm: 8.01-7.92 (2H, m), 7.62-7.53 (3H, m), 7.13-7.00 (2H, m), 6.85-6.77 (1H, m), 2.04 (3H, s), 1.58-1.45 (1H, m), 0.70-0.45 (4H, m). Appearance: gum state.

EXAMPLE 445

6-Chloro-3-(2-cyclopropyl-6-methylphenoxy)-4-pyridazinyl 4-nitrobenzenesulfonate (Compound No. 2300)

$^1$H-NMR (200 MHz, CDCl$_3$) δ ppm: 8.50-8.39 (2H, m), 8.33-8.20 (2H, m), 7.59 (1H, s), 7.15-7.00 (2H, m), 6.85-6.75 (1H, m), 1.94 (3H, s), 1.65-1.45 (1H, m), 0.75-0.45 (4H, m). Appearance: gum state.

EXAMPLE 446

6-Chloro-3-(2-cyclopropyl-6-methylphenoxy)-4-pyridazinyl 4-methoxybenzenesulfonate (Compound No. 2309)

$^1$H-NMR (200 MHz, CDCl$_3$) δ ppm: 7.99-7.91 (2H, m), 7.61 (1H, s), 7.11-6.98 (4H, m), 6.80 (1H, dd, J=2.6 Hz, 6.6 Hz), 3.90 (3H, s), 1.95 (3H, s), 1.60-1.45 (1H, m), 0.70-0.45 (4H, m). Appearance: caramel-like.

EXAMPLE 447

6-Chloro-3-(2-cyclopropyl-6-methylphenoxy)-4-pyridazinyl 2,4,6-trimethylbenzenesulfonate (Compound No. 2315)

$^1$H-NMR (200 MHz, CDCl$_3$) δ ppm: 7.59 (1H, s), 7.13-6.98 (4H, m), 6.85-6.75 (1H, m), 2.70 (6H, s), 2.32 (3H, s), 2.04 (3H, s), 1.65-1.45 (1H, m), 0.78-0.44 (4H, m). Appearance: amorphous.

EXAMPLE 448

6-Chloro-3-(2-cyclopropyl-6-methylphenoxy)-4-pyridazinyl 2,4,6-triisopropylbenzenesulfonate (Compound No. 2321)

$^1$H-NMR (200 MHz, CDCl$_3$) δ ppm: 7.52 (1H, s), 7.28-7.20 (2H, m), 7.10-6.98 (2H, m), 6.85-6.75 (1H, m), 4.16 (2H, septet, J=6.6 Hz), 2.93 (1H, septet, J=6.6 Hz), 1.93 (3H, s), 1.75-1.50 (1H, m), 1.35-1.20 (18H, m), 0.75-0.45 (4H, m). Appearance: amorphous.

EXAMPLE 449

6-Chloro-3-(2-cyclopropyl-6-methylphenoxy)-4-pyridazinyl 4-(2,4-dichlorobenzoyl)-1,3-dimethyl-1H-pyrazol-5-yl 1,2-benzenedisulfonate (Compound No. 2327)

$^1$H-NMR (200 MHz, CDCl$_3$) δ ppm: 8.52-8.40 (1H, m), 8.15-8.07 (1H, m), 8.00-7.82 (2H, m), 7.63 (1H, s), 7.18 (2H, s), 7.15-6.97 (3H, m), 6.79 (1H, dd, J=7.0, 2.6 Hz), 3.84 (3H, s), 2.11 (3H, s), 1.99 (3H, s), 1.75-1.57 (1H, m), 0.74-0.45 (4H, m). Appearance: caramel-like.

EXAMPLE 450

6-Chloro-3-(2-cyclopropyl-6-methylphenoxy)-4-pyridazinyl 4-chloro-3-nitrobenzenesulfonate (Compound No. 3786)

$^1$H-NMR (200 MHz, CDCl$_3$) δ ppm: 8.55 (1H, d, J=2.2 Hz), 8.18 (1H, dd, J=8.8, 2.2 Hz), 7.81 (1H, d, J=8.8 Hz), 7.59 (1H, s), 7.13-7.06 (2H, m), 6.84-6.79 (1H, m), 1.98 (3H, s), 1.61-1.48 (1H, m), 0.68-0.52 (4H, m). Appearance: amorphous.

EXAMPLE 451

6-Chloro-3-[2-(2-chloro-2-fluorocyclopropyl)phenoxy]-4-pyridazinol (Compound No. 2519)

$^1$H-NMR (200 MHz, CD$_3$OD) δ ppm: 7.42-7.15 (4H, m), 6.70 (1H, s), 2.80-2.62 (1H, m), 2.18-1.65 (2H, m). Melting point (° C.): 175-177.

EXAMPLE 452

6-Chloro-3-(2-cyclopropyl-6-methylphenoxy)-4-pyridazinyl 2,5-dichlorobenzenesulfonate (Compound No. 3780)

$^1$H-NMR (200 MHz, CDCl$_3$) δ ppm: 8.09-8.08 (1H, m), 7.61-7.52 (3H, m), 7.12-7.01 (2H, m), 6.81-6.76 (1H, m), 1.98 (3H, s), 1.67-1.49 (1H, m), 0.82-0.60 (2H, m), 0.58-0.48 (2H, m). Appearance: amorphous.

EXAMPLE 453

6-Chloro-3-(2-cyclopropyl-6-methylphenoxy)-4-pyridazinyl 10H-phenothiazine-10-carboxylate (Compound No. 3720)

$^1$H-NMR (200 MHz, CDCl$_3$) δ ppm: 7.76-7.67 (3H, m), 7.49-7.40 (3H, m), 7.40-7.23 (3H, m), 7.20-7.10 (2H, m), 6.95-6.83 (1H, m), 2.19 (3H, s), 1.88-1.70 (1H, m), 0.85-0.57 (4H, m). Appearance: amorphous.

EXAMPLE 454

6-Chloro-3-(2-cyclopropyl-6-methylphenoxy)-4-pyridazinyl 9H-carbazole-9-carboxylate (Compound No. 3714)

$^1$H-NMR (200 MHz, CDCl$_3$) δ ppm: 8.40 (2H, d, J=7.4 Hz), 8.02 (2H, d, J=7.0 Hz), 7.99 (1H, s), 7.60-7.35 (4H, m), 7.13-7.03 (2H, m), 6.92-6.80 (1H, m), 2.19 (3H, s), 1.90-1.73 (1H, m), 0.84-0.50 (4H, m). Melting point (° C.): 157-159.

EXAMPLE 455

6-Chloro-3-(2-cyclopropyl-6-methylphenoxy)-4-pyridazinyl 3,4-dihydro-2(1H)-isoquinolinecarboxylate (Compound No. 3708)

$^1$H-NMR (200 MHz, CDCl$_3$) δ ppm: 7.59 (1H, s), 7.32-7.02 (6H, m), 6.90-6.78 (1H, m), 4.86 (1H, s), 4.72 (1H, s), 3.92 (1H, t, J=5.9 Hz), 3.81 (1H, t, J=5.9 Hz), 3.05-2.95 (2H, m), 2.14 (3H, s), 1.86-1.67 (1H, m), 0.80-0.50 (4H, m). Appearance: caramel-like.

EXAMPLE 456

3-[3-(Benzyloxy)phenoxy]-6-chloro-4-pyridazinol (Compound No. 2547)

$^1$H-NMR (200 MHz, CD$_3$OD) δ ppm: 7.48-7.25 (6H, m), 6.94-6.66 (4H, m), 5.07 (2H, s). Melting point (° C.): 184-185.

EXAMPLE 457

3-[4-(Benzyloxy)phenoxy]-6-chloro-4-pyridazinol (Compound No. 2548)

$^1$H-NMR (200 MHz, CD$_3$OD) δ ppm: 7.48-7.28 (5H, m), 7.12-6.96 (4H, m), 6.58 (1H, s), 5.07 (2H, s). Melting point (° C.): 170-180.

EXAMPLE 458

6-Chloro-3-(2-cyclopropyl-6-methylphenoxy)-4-pyridazinyl 4-thiomorpholinecarboxylate (Compound No. 3702)

$^1$H-NMR (200 MHz, CDCl$_3$) δ ppm: 7.53 (1H, s), 7.15-7.04 (2H, m), 6.92-6.80 (1H, m), 4.05-3.78 (4H, m), 2.75-2.64 (4H, m), 2.13 (3H, s), 1.85-1.65 (1H, m), 0.80-0.54 (4H, m). Appearance: caramel-like.

EXAMPLE 459

6-Chloro-3-(2-cyclopropyl-6-methylphenoxy)-4-pyridazinyl 2,6-dimethyl-4-morpholinecarboxylate (Compound No. 3696)

$^1$H-NMR (200 MHz, CDCl$_3$) δ ppm: 7.54 (1H, s), 7.18-7.05 (2H, m), 6.94-6.80 (1H, m), 4.17-3.97 (2H, m), 3.78-3.55 (2H, m), 2.95-2.60 (2H, m), 2.14 (3H, s), 1.85-1.67 (1H, m), 1.35-1.15 (6H, m), 0.80-0.54 (4H, m). Appearance: caramel-like.

EXAMPLE 460

6-Chloro-3-(2-cyclopropyl-6-methylphenoxy)-4-pyridazinyl 4-morpholinecarboxylate (Compound No. 3690)

$^1$H-NMR (200 MHz, CDCl$_3$) δ ppm: 7.57 (1H, s), 7.13-7.06 (2H, m), 6.90-6.83 (1H, m), 3.70-3.55 (8H, m), 2.14 (3H, s), 1.83-1.68 (1H, m), 0.80-0.65 (2H, m), 0.65-0.53 (2H, m). Melting point (° C.): 102.5-103.5.

EXAMPLE 461

6-Chloro-3-[(1-methyl-1H-indol-4-yl)oxy]-4-pyridazinol (Compound No. 2565)

$^1$H-NMR (200 MHz, CD$_3$OD) δ ppm: 7.29 (1H, d, J=8.4 Hz), 7.17 (1H, t, J=7.7 Hz), 7.13 (1H, d, J=2.9 Hz), 6.85 (1H, d, J=7.7 Hz), 6.72 (1H, s), 6.23 (1H, d, J=2.9 Hz), 4.87 (3H, s). Melting point (° C.): 203-206.

EXAMPLE 462

6-Chloro-3-[(1-methyl-1H-indol-7-yl)oxy]-4-pyridazinol (Compound No. 2568)

$^1$H-NMR (200 MHz, CD$_3$OD) δ ppm: 7.42 (1H, d, J=7.0 Hz), 7.07 (1H, d, J=2.9 Hz), 6.99 (1H, t, J=7.7 Hz), 6.86 (1H, d, J=6,6 Hz), 6.74 (1H, s), 6.44 (1H, d, J=2.9 Hz), 3.80 (3H, s). Melting point (° C.): 219-221.

EXAMPLE 463

1-{4-[(6-Chloro-4-hydroxy-3-pyridazinyl)oxy]-3-methylphenyl}ethanone (Compound No. 2570)

$^1$H-NMR (200 MHz, CD$_3$OD) δ ppm: 7.94-7.86 (2H, m), 7.21-7.16 (1H, m), 6.75 (1H, s), 2.60 (3H, s), 2.25 (3H, s). Melting point (° C.): 182-184.

EXAMPLE 464

1-{4-[(6-Chloro-4-hydroxy-3-pyridazinyl)oxy]-3-methylphenyl}ethanone O-methyloxime (Compound No. 2571)

$^1$H-NMR (200 MHz, CD$_3$OD) δ ppm: 7.59-7.51 (2H, m), 7.11-7.06 (1H, m), 6.71 (1H, s), 3.95 (3H, s), 2.20 (3H, s). Melting point (° C.): 189-192.

EXAMPLE 465

6-Chloro-3-(2-cyclopropyl-6-methylphenoxy)-4-pyridazinyl 4-phenyl-1-piperazinecarboxylate (Compound No. 3684)

$^1$H-NMR (200 MHz, CDCl$_3$) δ ppm: 7.60 (1H, s), 7.35-7.23 (2H, m), 7.13-7.04 (2H, m), 7.00-6.80 (4H, m), 3.95-3.84 (2H, m), 3.84-3.72 (2H, m), 3.31-3.18 (4H, m), 2.15 (3H, s), 1.86-1.66 (1H, m), 0.80-0.53 (4H, m). Appearance: caramel-like.

EXAMPLE 466

4-{[4-(Benzoyloxy)-6-chloro-3-pyridazinyl]oxy}-3-methylphenyl benzoate (Compound No. 3850)

$^1$H-NMR (200 MHz, CDCl$_3$) δ ppm: 8.21-8.17 (4H, m), 7.72-7.48 (7H, m), 7.22-7.07 (3H, m), 2.21 (3H, s). Melting point (° C.): 118-120.

EXAMPLE 467

Methyl 3-[(6-chloro-4-hydroxy-3-pyridazinyl)oxy]-4-methoxybenzoate (Compound No. 2574)

$^1$H-NMR (200 MHz, CD$_3$OD) δ ppm: 7.95 (1H, dd J=8.6, 2.2 Hz), 7.78 (1H, d, J=1.8 Hz), 7.19 (1H, d, J=8.8 Hz), 6.71 (1H, s), 3.87 (3H, s), 3.84 (3H, s). Melting point (° C.): 115-123.

EXAMPLE 468

6-Chloro-3-(2-cyclopropyl-6-methylphenoxy)-4-pyridazinyl 4-methyl-1-piperazinecarboxylate (Compound No. 3678)

$^1$H-NMR (200 MHz, CDCl$_3$) δ ppm: 7.59 (1H, s), 7.15-7.04 (2H, m), 6.90-6.80 (1H, m), 3.80-3.55 (4H, m), 2.54-2.40 (4H, m), 2.32 (3H, s), 2.14 (3H, s), 1.85-1.67 (1H, m), 0.80-0.52 (4H, m). Appearance: caramel-like.

EXAMPLE 469

6-Chloro-3-(2-isopropenyl-6-methylphenoxy)-4-pyridazinol (Compound No. 2577)

$^1$H-NMR (200 MHz, CD$_3$OD) δ ppm: 7.20-7.10 (3H, m), 6.66 (1H, s), 5.01 (1H, m), 4.95 (1H, m), 2.15 (3H, s), 1.99 (3H, s). Melting point (° C.): 183-186.

EXAMPLE 470

6-Chloro-3-[(1,1-dimethyl-2,3-dihydro-1H-inden-5-yl)oxy-4-pyridazinol (Compound No. 2585)

$^1$H-NMR (200 MHz, CD$_3$OD) δ ppm: 7.15 (1H, d, J=8.1 Hz), 6.95 (2H, br.d, J=8.1 Hz), 6.68 (1H, s), 2.89 (2H, t, J=7.3 Hz), 1.96 (2H, t, J=7.3 Hz), 1.27 (6H, s). Melting point (° C.): 209-212.

EXAMPLE 471

3-(3-Bromo-6-cyclopropyl-2-methylphenoxy)-6-chloro-4-pyridazinol (Compound No. 2587)

$^1$H-NMR (200 MHz, CD$_3$OD) δ ppm: 7.38 (1H, d, J=8.4 Hz), 6.78 (1H, d, J=8.4 Hz), 6.72 (1H, s), 2.22 (3H, s), 1.85-1.72 (1H, m), 0.85-0.72 (2H, m), 0.65-0.50 (2H, m). Melting point (° C.): 234-235.

EXAMPLE 472

6-Chloro-3-(6-cyclopropyl-2-methyl-3-nitrophenoxy)-4-pyridazinol (Compound No. 2589)

$^1$H-NMR (200 MHz, CD$_3$OD) δ ppm: 7.80 (1H, d, J=8.4 Hz), 7.02 (1H, d, J=8.4 Hz), 6.77 (1H, s), 2.32 (3H, s), 1.99-1.88 (1H, m), 0.95-0.88 (2H, m), 0.74-0.70 (2H, m). Melting point (° C.): 140-143.

EXAMPLE 473

6-Chloro-3-[(5-methyl-1,3-dihydro-2-benzofuran-4-yl)oxy]-4-pyridazinol (Compound No. 2592)

$^1$H-NMR (200 MHz, CD$_3$OD) δ ppm: 7.20 (1H, d, J=7.7 Hz), 7.08 (1H, d, J=7.7 Hz), 5.06 (2H, br.s), 4.88 (2H, br.s), 2.16 (3H, s). Melting point (° C.): 188-200.

EXAMPLE 474

6-Chloro-3-(2-cyclopropyl-6-methylphenoxy)-4-pyridazinyl 2,2,6,6-tetramethyl-1-piperidinecarboxylate (Compound No. 3672)

$^1$H-NMR (200 MHz, CDCl$_3$) δ ppm: 7,53 (1H, s), 7.14-7.03 (2H, m), 6.90-6.78 (1H, m), 2.13 (3H, s), 1.90-1.62 (7H, m), 1.55 (12H, s), 0.80-0.52 (4H, m). Appearance: caramel-like.

EXAMPLE 475

6-Chloro-3-(2-fluoro-3,5,6-trimethylphenoxy)-4-pyridazinol (Compound No. 2597)

$^1$H-NMR (200 MHz, CD$_3$OD) δ ppm: 6.92 (1H, d, J=7.0 Hz), 6.73 (1H, s), 2.24 (3H, s), 2.21 (3H, s), 2.06 (3H, s). Melting point (° C.): 258-260.

EXAMPLE 476

6-Chloro-3-(2-chloro-3,5,6-trimethylphenoxy)-4-pyridazinol (Compound No. 2599)

$^1$H-NMR (200 MHz, DMSO-d$_6$) δ ppm: 7.11 (1H, s), 6.86 (1H, br.s), 2.29 (3H, s), 2.24 (3H, s), 1.99 (3H, s). Melting point (° C.): 298-300.

EXAMPLE 477

6-Chloro-3-(2-iodo-3,5,6-trimethylphenoxy)-4-pyridazinol (Compound No. 2600)

$^1$H-NMR (200 MHz, CD$_3$OD) δ ppm: 7.06 (1H, s), 6.75 (1H, s) 2.40 (3H, s), 2.26 (3H, s), 2.09 (3H, s). Melting point (° C.): 235 (decomposed).

EXAMPLE 478

6-Chloro-3-(2-ethyl-3,5,6-trimethylphenoxy)-4-pyridazinol (Compound No. 2601)

$^1$H-NMR (200 MHz, DMSO-d$_6$) δ ppm: 6.95 (1H, s), 6.81 (1H, br.s), 2.32 (2H, q, J=7.5 Hz), 2.24 (3H, s), 2.12 (3H, s), 1.94 (3H, s), 1.04 (3H, t, J=7.5 Hz). Melting point (° C.): 188-195.

EXAMPLE 479

6-Chloro-3-(2-cyclopropyl-6-methylphenoxy)-4-pyridazinyl 1,4-dioxa-8-azaspiro[4.5]decan-8-carboxylate (Compound No. 3666)

$^1$H-NMR (200 MHz, CDCl$_3$) δ ppm: 7.57 (1H, s), 7.15-7.04 (2H, m), 6.92-6.80 (1H, m), 3.99 (4H, s), 3.85-3.62 (4H, m), 2.14 (3H, s), 1.85-1.65 (5H, m), 0.80-0.50 (4H, m). Appearance: caramel-like.

EXAMPLE 480

6-Chloro-3-(2-isopropenyl-3,5,6-trimethylphenoxy)-4-pyridazinol (Compound No. 2605)

$^1$H-NMR (200 MHz, CD$_3$OD) δ ppm: 6.91 (1H, s), 6.58 (1H, s), 5.00-4.90 (2H, bm), 2.27 (3H, s), 2.20 (3H, s), 2.07 (3H, s), 1.96 (3H, s). Appearance: amorphous.

EXAMPLE 481

1-[6-Chloro-3-(2-cyclopropyl-6-methylphenoxy)-4-pyridazinyl] 4-ethyl 1,4-piperidinedicarboxylate (Compound No. 3660)

$^1$H-NMR (200 MHz, CDCl$_3$) δ ppm: 7.56 (1H, s) 7.13-7.04 (2H, m), 6.90-6.80 (1H, m), 4.30-4.00 (2H, m), 3.35-3.02 (2H, m), 2.65-2.45 (1H, m), 2.14 (3H, s), 2.10-1.93 (3H, m), 1.93-1.65 (4H, m), 1.25 (3H, t, J=7.0 Hz), 0.80-0.54 (4H, m). Appearance: caramel-like.

EXAMPLE 482

1-{2-[(6-Chloro-4-hydroxy3-pyridazinyl)oxy]-3,4,6-trimethylphenyl}ethanone (Compound No. 2607)

$^1$H-NMR (200 MHz, CD$_3$OD) δ ppm: 7.55 (1H, s), 6.72 (1H, s) 2.45 (3H, s), 2.36 (3H, s), 2.29 (3H, s), 2.11 (3H, s). Appearance: amorphous.

EXAMPLE 483

6-Chloro-3-(2,3,5-trimethyl-6-nitrophenoxy)-4-pyridazinol (Compound No. 2608)

$^1$H-NMR (200 MHz, CD$_3$OD) δ ppm: 7.11 (1H, s), 6.65 (1H, s), 2.33 (3H, s), 2.28 (3H, s), 2.05 (3H, s). Melting point (° C.): 172-174.

EXAMPLE 484

6-Chloro-3-(2,4-dichloro-3,5,6-trimethylphenoxy)-4-pyridazinol (Compound No. 2609)

$^1$H-NMR (200 MHz, DMSO-d$_6$) δ ppm: 6.91 (1H, s), 2.46 (3H, s), 2.36 (3H, s), 2.10 (3H, s).

EXAMPLE 485

6-Chloro-3-(2,3,4,5,6-pentamethylphenoxy)-4-pyridazinol (Compound No. 2614)

¹H-NMR (200 MHz, CD$_3$OD) δ ppm: 6.69 (1H, s), 2.23 (3H, s), 2.21 (6H, s), 2.02 (6H, s). Melting point (° C.): 238-240 (decomposed).

EXAMPLE 486

6-Chloro-3-(2-cyclopropyl-6-methylphenoxy)-4-pyridazinyl 3,3-dimethylbutanoate (Compound No. 2662)

¹H-NMR (200 MHz, CDCl$_3$) δ ppm: 7.37 (1H, s), 7.13-7.05 (2H, s), 6.88-6.82 (1H, s), 2.55 (2H, s), 2.12 (3H, s), 1.82-1.67 (1H, m), 1.15 (9H, s), 0.80-0.65 (2H, m), 0.63-0.52 (2H, m). Melting point (° C.): 91-92.

EXAMPLE 487

6-Chloro-3-(2-cyclopropyl-6-methylphenoxy)-4-pyridazinyl 1-adamantanecarboxylate (Compound No. 2671)

¹H-NMR (200 MHz, CDCl$_3$) δ ppm: 7.37 (1H, s), 7.12-7.05 (2H, m), 6.92-6.80 (1H, m), 2.13 (3H, s), 2.08 (9H, s), 1.76 (7H, br.s), 0.85-0.45 (4H, m). Appearance: oily product.

EXAMPLE 488

6-Chloro-3-(2-cyclopropyl-6-methylphenoxy)-4-pyridazinyl 2-methylacrylate (Compound No. 2677)

¹H-NMR (200 MHz, CDCl$_3$) δ ppm: 7.48 (1H, s), 7.14-7.05 (2H, m), 6.89-6.83 (1H, m), 6.46 (1H, br.s), 5.91 (1H, br.s), 2.13 (3H, s), 2.09 (3H, s), 1.81-1.68 (1H, m), 0.78-0.53 (4H, m). Melting point (° C.): 98-100.

EXAMPLE 489

6-Chloro-3-(2-cyclopropyl-6-methylphenoxy)-4-pyridazinyl 2-bromo-2-methylpropanoate (Compound No. 2697)

¹H-NMR (200 MHz, CDCl$_3$) δ ppm: 7.47 (1H, s), 7.11-7.08 (2H, m), 6.89-6.85 (1H, m), 2.13 (3H, s), 2.10 (6H, s), 1.77-1.69 (1H, m), 0.74-0.58 (4H, m). Melting point (° C.): 69-71.

EXAMPLE 490

6-Chloro-3-(2-cyclopropyl-6-methylphenoxy)-4-pyridazinyl 3-chloro-2,2-dimethylpropanoate (Compound No. 2703)

¹H-NMR (200 MHz, CDCl$_3$) δ ppm: 7.43 (1H, s), 7.13-7.05 (2H, m), 6.90-6.84 (1H, m), 3.76 (2H, s), 2.13 (3H, s), 1.83-1.65 (1H, m), 1.50 (6H, s), 0.85-0.45 (4H, br.s). Melting point (° C.): 112-115.

EXAMPLE 491

6-Chloro-3-(2-cyclopropyl-6-methylphenoxy)-4-pyridazinyl 5-bromopentanoate (Compound No. 2709)

¹H-NMR (200 MHz, CDCl$_3$) δ ppm: 7.83 (1H, s), 7.11-7.05 (2H, m), 6.86-6.82 (1H, m), 3.43 (2H, d, J=6.2 Hz), 2.73 (2H, d, J=7.0 Hz), 2.12 (3H, s), 2.04-1.93 (4H, m), 1.77-1.69 (1H, m), 0.74-0.56 (4H, m). Appearance: caramel-like.

EXAMPLE 492

6-Chloro-3-(2-cyclopropyl-6-methylphenoxy)-4-pyridazinyl hydratropate (Compound No. 2715)

¹H-NMR (200 MHz, CDCl$_3$) δ ppm: 7.42-7.20 (5H, m), 7.32 (1H, s), 7.15-7.02 (2H, m), 6.86-6.75 (1H, m), 4.20-4.00 (1H, m), 2.04 (3H, s), 1.66 (3H, d, J=7.0 Hz), 1.70-1.50 (1H, m), 0.70-0.42 (4H, m). Appearance: oily product.

EXAMPLE 493

6-Chloro-3-(2-cyclopropyl-6-methylphenoxy)-4-pyridazinyl (4-methoxyphenyl)acetate (Compound No. 2721)

¹H-NMR (200 MHz, CDCl$_3$) δ ppm: 7.37 (1H, s), 7.27 (2H, d, J=8.2 Hz), 7.13-7.05 (2H, m), 6.89-6.80 (3H, m), 3.91 (2H, s), 3.76 (3H, s), 2.07 (3H, s), 1.73-1.60 (1H, m), 0.75-0.50 (4H, m). Appearance: paste state.

EXAMPLE 494

6-Chloro-3-(2-cyclopropyl-6-methylphenoxy)-4-pyridazinyl ethyl succinate (Compound No. 2727)

¹H-NMR (200 MHz, CDCl$_3$) δ ppm: 7.08-6.92 (2H, m), 6.85-6.68 (1H, m), 6.55 (1H, s), 4.14 (2H, br.q, J=7.1 Hz), 3.00 (1H, t, J=7.0 Hz), 2.76 (1H, t, J=7.0 Hz), 2.61 (2H, br.s), 1.98 (3H, s), 1.78-1.60 (1H, m), 1.25 (3H, t, J=7.1 Hz), 0.75-0.40 (4H, m). Appearance: amorphous.

EXAMPLE 495

6-Chloro-3-(2-cyclopropyl-6-methylphenoxy)-4-pyridazinyl 4-methyl-1-piperidinecarboxylate (Compound No. 3654)

¹H-NMR (200 MHz, CDCl$_3$) δ ppm: 7.56 (1H, s), 7.14-7.04 (2H, m), 6.90-6.80 (1H, m), 4.35-4.10 (2H, m), 3.15-2.80 (2H, m), 2.14 (3H, s), 1.85-1.50 (4H, m), 1.35-1.06 (2H, m), 0.96 (3H, d, J=6.2 Hz), 0.80-0.50 (4H, m). Appearance: caramel-like.

EXAMPLE 496

6-Chloro-3-(2-cyclopropyl-6-methylphenoxy)-4-pyridazinyl 4-bromo-1-piperidinecarboxylate (Compound No. 3648)

¹H-NMR (200 MHz, CDCl$_3$) δ ppm: 7.55 (1H, s), 7.15-7.04 (2H, m), 6.90-6.80 (1H, m), 4.54-4.38 (1H, m), 4.00-3.53 (4H, m), 2.30-1.90 (7H, m), 1.85-1.67 (1H, m), 0.80-0.50 (4H, m). Appearance: caramel-like.

EXAMPLE 497

Bis[6-chloro-3-(2-cyclopropyl-6-methylphenoxy)-4-pyridazinyl] succinate (Compound No. 2733)

¹H-NMR (200 MHz, CDCl$_3$) δ ppm: 7.32 (2H, s), 7.14-7.03 (4H, m), 6.88-6.81 (2H, m), 3.17 (4H, s), 2.10 (6H, s), 1.80-1.65 (2H, m), 0.78-0.53 (8H, m). Appearance: caramel-like.

EXAMPLE 498

6-Chloro-3-(2-cyclopropyl-6-methylphenoxy)-4-pyridazinyl methoxyacetate (Compound No. 2752)

¹H-NMR (200 MHz, CDCl$_3$) δ ppm: 7.43 (1H, s), 7.15-7.04 (2H, m), 6.90-6.82 (1H, m), 4.41 (2H, s), 3.55 (3H, s), 2.12 (3H, s), 1.82-1.67 (1H, m), 0.80-0.67 (2H, m), 0.64-0.55 (2H, m). Appearance: paste state.

EXAMPLE 499

6-Chloro-3-(2-cyclopropyl-6-methylphenoxy)-4-pyridazinyl phenoxyacetate (Compound No. 2758)

$^1$H-NMR (200 MHz, CDCl$_3$) δ ppm: 7.42 (1H, s), 7.29-7.25 (2H, m), 7.23-6.96 (5H, m), 6.89-6.83 (1H, m), 5.00 (2H, s), 2.08 (3H, s), 1.73-1.64 (1H, m), 0.71-0.54 (4H, m). Appearance: caramel-like.

EXAMPLE 500

6-Chloro-3-(2-cyclopropyl-6-methylphenoxy)-4-pyridazinyl 2-phenoxypropanoate (Compound No. 2764)

$^1$H-NMR (200 MHz, CDCl$_3$) δ ppm: 7.33 (1H, s), 7.25-7.19 (2H, m), 7.17-7.04 (2H, m), 7.00-6.91 (3H, m), 6.86-6.82 (1H, m), 5.09 (1H, q, J=6.6 Hz), 2.05 (3H, s), 1.84 (3H, d, J=6.6 Hz), 1.64-1.58 (1H, m), 0.68-0.52 (4H, m). Appearance: caramel-like.

EXAMPLE 501

6-Chloro-3-(2-cyclopropyl-6-methylphenoxy)-4-pyridazinyl methoxy(phenyl)acetate (Compound No. 2770)

$^1$H-NMR (200 MHz, CDCl$_3$) δ ppm: 7.56-7.51 (2H, m), 7.40-7.30 (4H, m), 7.12-7.02 (2H, m), 6.83-6.78 (1H, m), 5.10 (1H, s), 3.52 (3H, s), 2.01 (3H, s), 1.67-1.50 (1H, m), 0.70-0.43 (4H, m). Appearance: paste state.

EXAMPLE 502

6-Chloro-3-(2-cyclopropyl-6-methylphenoxy)-4-pyridazinyl 3-(methylsulfanyl)propanoate (Compound No. 2776)

$^1$H-NMR (200 MHz, CDCl$_3$) δ ppm: 7.42 (1H, s), 7.10-7.00 (2H, m), 6.90-6.77 (1H, m), 3.07-2.83 (4H, m), 2.17 (3H, s), 2.12 (3H, s), 1.85-1.65 (1H, m), 0.80-0.50 (4H, m). Appearance: caramel-like.

EXAMPLE 503

6-Chloro-3-(2-cyclopropyl-6-methylphenoxy)-4-pyridazinyl oxo(2-thienyl)acetate (Compound No. 2782)

$^1$H-NMR (200 MHz, CDCl$_3$) δ ppm: 8.07 (1H, dd, J=1.5 Hz, 4.1 Hz), 7.77 (1H, dd, J=1.5 Hz, 4.1 Hz), 7.58 (1H, s), 7.22 (1H, t, J=4.0 Hz), 7.10-7.02 (2H, m), 6.90-6.77 (1H, m), 2.15 (3H, s), 1.90-1.70 (1H, m), 0.85-0.50 (4H, m). Appearance: caramel-like.

EXAMPLE 504

6-Chloro-3-(2-cyclopropyl-6-methylphenoxy)-4-pyridazinyl 2-fluorobenzoate (Compound No. 2788)

$^1$H-NMR (200 MHz, CDCl$_3$) δ ppm: 8.17-8.09 (1H, m), 7.73-7.62 (1H, m), 7.57 (1H, s), 7.36-7.20 (2H, m), 7.09-7.07 (2H, m), 6.87-6.82 (1H, m), 2.16 (3H, s), 1.85-1.72 (1H, m), 0.76-0.56 (4H, m). Appearance: amorphous.

EXAMPLE 505

6-Chloro-3-(2-cyclopropyl-6-methylphenoxy)-4-pyridazinyl 2-bromobenzoate (Compound No. 2805)

$^1$H-NMR (200 MHz, CDCl$_3$) δ ppm: 8.20-8.05 (1H, m), 7.85-7.70 (1H, m), 7.59 (1H, s), 7.55-7.38 (2H, m), 7.15-7.00 (2H, m), 6.90-6.80 (1H, m), 2.17 (3H, s), 1.88-1.70 (1H, m), 0.80-0.50 (4H, m). Appearance: caramel-like.

EXAMPLE 506

6-Chloro-3-(2-cyclopropyl-6-methylphenoxy)-4-pyridazinyl 2-iodobenzoate (Compound No. 2814)

$^1$H-NMR (200 MHz, CDCl$_3$) δ ppm: 8.20-8.05 (2H, m), 7.60-7.44 (2H, m), 7.35-7.20 (1H, m), 7.13-7.00 (2H, m), 6.90-6.78 (1H, m), 2.17 (3H, s), 1.90-1.72 (1H, m), 0.85-0.50 (4H, m). Appearance: caramel-like.

EXAMPLE 507

6-Chloro-3-(2-cyclopropyl-6-methylphenoxy)-4-pyridazinyl 2-(trifluoromethyl)benzoate (Compound No. 2820)

$^1$H-NMR (200 MHz, CDCl$_3$) δ ppm: 8.13-8.09 (1H, m), 7.91-7.86 (1H, m), 7.76-7.72 (2H, m), 7.55 (1H, s), 7.11-7.06 (2H, m), 6.88-6.83 (1H, m), 2.16 (3H, s), 1.86-1.71 (1H, m), 0.75-0.56 (4H, m). Appearance: caramel-like.

EXAMPLE 508

6-Chloro-3-(2-cyclopropyl-6-methylphenoxy)-4-pyridazinyl 2-benzylbenzoate (Compound No. 2826)

$^1$H-NMR (200 MHz, CDCl$_3$) δ ppm: 8.22-8.18 (1H, d, J=7.2 Hz) 7.62-7.54 (1H, t, J=7.6 Hz), 7.44-7.06 (1OH, m), 6.85-6.81 (1H, m), 4.46 (1H, s), 2.11 (3H, s), 1.80-1.67 (1H, m), 0.75-0.64 (2H, m), 0.60-0.52 (2H, m). Appearance: paste state.

EXAMPLE 509

Bis[6-chloro-3-(2-methylphenoxy)-4-pyridazinyl] phthalate (Compound No. 2827)

$^1$H-NMR (200 MHz, CDCl$_3$) δ ppm: 8.06 (2H, dd, J=6.0, 3.4 Hz) 7.57 (2H, s), 7.25-7.15 (8H, m), 7.05-7.01 (2H, m), 2.14 (6H, s). Melting point (° C.): 157-158.

EXAMPLE 510

1-[6-Chloro-3-(2-cyclopropyl-6-methylphenoxy)-4-pyridazinyl] 2-methyl 1,2-piperidinedicarboxylate (Compound No. 3642)

$^1$H-NMR (200 MHz, CDCl$_3$) δ ppm: 7.60 (0.5H, s), 7.59 (0.5H, s), 7.14-7.03 (2H, m), 6.92-6.80 (1H, m), 5.10-4.90 (1H, m), 4.32-4.06 (1H, m), 3.73 (1.5H, s), 3.71 (1.5H, s), 3.40-3.05 (1H, m), 2.43-2.20 (1H, m), 2.15 (1.5H, s), 2.13 (1.5H, s), 2.00-1.20 (6H, m), 0.80-0.50 (4H, m). Appearance: caramel-like.

EXAMPLE 511

6-Chloro-3-(2-cyclopropyl-6-methylphenoxy)-4-pyridazinyl 2-nitrobenzoate (Compound No. 2850)

$^1$H-NMR (200 MHz, CDCl$_3$) δ ppm: 8.15-8.05 (1H, m), 7.95-7.72 (3H, m), 7.65 (1H, s), 7.14-7.05 (2H, m), 6.90-6.80 (1H, m), 2.15 (3H, s), 1.85-1.70 (1H, m), 0.78-0.65 (2H, m), 0.65-0.50 (2H, m). Appearance: oily product.

EXAMPLE 512

6-Chloro-3-(2-cyclopropyl-6-methylphenoxy)-4-pyridazinyl 2-phenoxybenzoate (Compound No. 2856)

$^1$H-NMR (200 MHz, CDCl$_3$) δ ppm: 8.35 (1H, dd, J=8.2, 1.8 Hz), 8.15 (1H, dd, J=8.0, 1.8 Hz), 7.74 (1H, dt, J=7.0, 1.4 Hz), 7.61-7.21 (5H, m), 7.15-6.98 (4H, m), 6.84-6.79 (1H, m), 2.09 (3H, s), 1.80-1.68 (1H, m), 0.70-0.71 (2H, m), 0.59-0.51 (2H, m). Appearance: paste state.

EXAMPLE 513

6-Chloro-3-(2-cyclopropyl-6-methylphenoxy)-4-pyridazinyl 3-chlorobenzoate (Compound No. 2868)

$^1$H-NMR (200 MHz, CDCl$_3$) δ ppm: 8.18 (1H, d, J=1.8 Hz), 8.10 (1H, d, J=8.1 Hz), 7.68 (1H, br.d, J=9.2 Hz), 7.57 (1H, s), 7.50 (1H, t, J=8.1 Hz), 7.08 (1H, d, J=5.8 Hz), 7.07 (1H, d, J=3.7 Hz), 6.85 (1H, dd, J=5.8, 3.7 Hz), 2.15 (3H, s), 1.85-1.66 (1H, m), 0.80-0.50 (4H, m). Appearance: amorphous.

EXAMPLE 514

6-Chloro-3-(2-cyclopropyl-6-methylphenoxy)-4-pyridazinyl 3-fluorobenzoate (Compound No. 2862)

$^1$H-NMR (200 MHz, CDCl$_3$) δ ppm: 8.02 (1H, dd, J=6.2, 1.5 Hz), 7.89 (1H, br.d, J=8.8 Hz), 7.60-7.34 (2H, m), 7.59 (1H, s), 7.13-7.04 (2H, m), 6.90-6.78 (1H, m), 2.15 (3H, s), 1.83-1.68 (1H, m), 0.80-0.50 (4H, m). Appearance: oily product.

EXAMPLE 515

6-Chloro-3-(2-cyclopropyl-6-methylphenoxy)-4-pyridazinyl 3-bromobenzoate (Compound No. 2874)

$^1$H-NMR (200 MHz, CDCl$_3$) δ ppm: 8.33 (1H, s), 8.14 (1H, d, J=8.0 Hz), 7.82 (1H, d, J=8.0 Hz), 7.56 (1H, s), 7.43 (1H, t, J=8.0 Hz), 7.13-7.03 (2H, m), 6.90-6.80 (1H, m), 2.15 (3H, s), 1.85-1.68 (1H, m), 0.80-0.50 (4H, m). Appearance: caramel-like.

EXAMPLE 516

6-Chloro-3-(2-cyclopropyl-6-methylphenoxy)-4-pyridazinyl 3-iodobenzoate (Compound No. 2880)

$^1$H-NMR (200 MHz, CDCl$_3$) δ ppm: 8.54 (1H, d, J=1.8 Hz), 8.20-8.15 (1H, m), 8.03 (1H, d, J=8.1 Hz), 7.56 (1H, s), 7.34-7.26 (1H, m), 7.13-7.05 (2H, m), 6.89-6.82 (1H, m), 2.15 (3H, s), 1.83-1.71 (1H, m), 0.80-0.68 (2H, m), 0.65-0.52 (2H, m). Appearance: amorphous.

EXAMPLE 517

6-Chloro-3-(2-cyclopropyl-6-methylphenoxy)-4-pyridazinyl 3-(trifluoromethyl)benzoate (Compound No. 2900)

$^1$H-NMR (200 MHz, CDCl$_3$) δ ppm: 8.47 (1H, s), 8.41 (1H, d, J=7.7 Hz), 7.96 (1H, d, J=7.3 Hz), 7.75-7.67 (1H, m), 7.58 (1H, s), 7.12-7.06 (2H, m), 6.89-6.82 (1H, m), 2.16 (3H, s), 1.84-1.71 (1H, m), 0.80-0.53 (4H, m). Appearance: caramel-like.

EXAMPLE 518

Bis[6-chloro-3-(2-cyclopropyl-6-methylphenoxy)-4-pyridazinyl] isophthalate (Compound No. 2906)

$^1$H-NMR (200 MHz, CDCl$_3$) δ ppm: 9.02 (1H, s), 8.53 (2H, d, J=8.2 Hz), 7.78 (1H, t, J=7.8 Hz), 7.58 (2H, s), 7.08-7.06 (4H, m), 6.86-6.82 (2H, m), 2.14 (6H, s), 1.83-1.68 (2H, m), 0.78-0.69 (4H, m), 0.60-0.53 (4H, m). Appearance: paste state.

EXAMPLE 519

6-Chloro-3-(2-cyclopropyl-6-methylphenoxy)-4-pyridazinyl 3-nitrobenzoate (Compound No. 2918)

$^1$H-NMR (200 MHz, CDCl$_3$) δ ppm: 9.05-9.04 (1H, m), 8.59-8.52 (2H, m), 7.79 (1H, t, J=7.7 Hz), 7.59 (1H, s), 7.13-7.07 (2H, m), 6.89-6.82 (1H, m), 2.15 (3H, s), 1.83-1.72 (1H, m), 0.80-0.54 (4H, m). Appearance: caramel-like.

EXAMPLE 520

6-Chloro-3-(2-cyclopropyl-6-methylphenoxy)-4-pyridazinyl 3-phenoxybenzoate (Compound No. 2924)

$^1$H-NMR (200 MHz, CDCl$_3$) δ ppm: 7.95-7.90 (1H, m), 7.80-7.78 (1H, m), 7.57 (1H, s), 7.50 (1H, t, J=8.0 Hz), 7.40-7.30 (3H, m), 7.17-7.10 (1H, m), 7.09-7.03 (3H, m), 7.07 (1H, s), 6.87-6.82 (1H, m), 2.13 (3H, s), 1.81-1.67 (1H, m), 0.78-0.66 (2H, m). 0.59-0.54 (2H, m). Appearance: paste state.

EXAMPLE 521

6-Chloro-3-(2-cyclopropyl-6-methylphenoxy)-4-pyridazinyl 4-fluorobenzoate (Compound No. 2930)

$^1$H-NMR (200 MHz, CDCl$_3$) δ ppm: 8.30-8.18 (2H, m), 7.59 (1H, s), 7.30-7.15 (2H, m), 7.15-7.02 (2H, m), 6.90-6.78 (1H, m), 2.15 (3H, s), 1.85-1.70 (1H, m), 0.80-0.50 (4H, m). Appearance: caramel-like.

EXAMPLE 522

6-Chloro-3-(2-cyclopropyl-6-methylphenoxy)-4-pyridazinyl 4-ethylbenzoate (Compound No. 2961)

$^1$H-NMR (200 MHz, CDCl$_3$) δ ppm: 8.13 (2H, d, J=8.5 Hz), 7.60 (1H, s), 7.36 (2H, d, J=8.5 Hz), 7.12-7.04 (2H, m), 6.88-6.81 (1H, m), 2.75 (2H, q, J=7.6 Hz), 2.04 (3H, s), 1.85-1.71 (1H, m), 1.28 (3H, t, J=7.6 Hz), 0.79-0.65 (2H, m), 0.61-0.52 (2H, m) Appearance: paste state.

EXAMPLE 523

6-Chloro-3-(2-cyclopropyl-6-methylphenoxy)-4-pyridazinyl 4-propylbenzoate (Compound No. 2970)

$^1$H-NMR (200 MHz, CDCl$_3$) δ ppm: 8.12 (2H, d, J=8.4 Hz), 7.59 (1H, s), 7.34 (2H, d, J=8.4 Hz), 7.12-7.05 (2H, m), 6.88-6.81 (1H, m), 2.69 (2H, t, J=7.3 Hz), 2.16 (3H, s), 1.85-1.60 (3H, m), 0.96 (3H, t, J=7.3 Hz), 0.80-0.68 (2H, m), 0.63-0.52 (2H, m). Appearance: paste state.

EXAMPLE 524

6-Chloro-3-(2-cyclopropyl-6-methylphenoxy)-4-pyridazinyl 4-isopropylbenzoate (Compound No. 2976)

$^1$H-NMR (200 MHz, CDCl$_3$) δ ppm: 8.14 (2H, d, J=8.4 Hz), 7.59 (1H, s), 7.40 (2H, d, J=8.4 Hz), 7.12-7.05 (2H, m), 6.90-6.82 (1H, m), 3.01 (1H, septet, J=7.0 Hz), 2.15 (3H, s), 1.85-1.70 (1H, m), 1.29 (6H, d, J=7.0 Hz), 0.80-0.65 (2H, m), 0.63-0.52 (2H, m). Appearance: paste state.

EXAMPLE 525

6-Chloro-3-(2-cyclopropyl-6-methylphenoxy)-4-pyridazinyl 4-butylbenzoate (Compound No. 2982)

$^1$H-NMR (200 MHz, CDCl$_3$) δ ppm: 8.12 (2H, d, J=8.1 Hz), 7.59 (1H, s), 7.35 (2H, d, J=8.1 Hz), 7.12-7.03 (2H, m), 6.89-6.81 (1H, m), 2.72 (2H, t, J=7.3 Hz), 2.16 (3H, s), 1.85-1.57 (3H, m), 1.47-1.22 (2H, m), 0.94 (3H, t, J=7.3 Hz), 0.80-0.68 (2H, m), 0.65-0.55 (2H, m). Appearance: paste state.

EXAMPLE 526

6-Chloro-3-(2-cyclopropyl-6-methylphenoxy)-4-pyridazinyl 4-(trifluoromethyl)benzoate (Compound No. 2988)

$^1$H-NMR (200 MHz, CDCl$_3$) δ ppm: 8.34 (2H, d, J=8.8 Hz), 7.83 (2H, d, J=8.8 Hz), 7.60 (1H, s), 7.14-7.07 (2H, m), 6.89-6.83 (1H, m), 2.15 (3H, s), 1.83-1.72 (1H, m), 0.79-0.71 (2H, m), 0.63-0.54 (2H, m). Melting point (° C.): 127-128.

EXAMPLE 527

6-Chloro-3-(2-cyclopropyl-6-methylphenoxy)-4-pyridazinyl 4-cyanobenzoate (Compound No. 2994)

$^1$H-NMR (200 MHz, CDCl$_3$) δ ppm: 8.33 (2H, d, J=8.8 Hz), 7.86 (2H, d, J=8.8 Hz), 7.60 (1H, s), 7.14-7.07 (2H, m), 6.89-6.83 (1H, m), 2.14. (3H, s), 1.82-1.68 (1H, m), 0.79-0.53 (4H, m). Appearance: caramel-like.

EXAMPLE 528

Bis[6-chloro-3-(2-cyclopropyl-6-methylphenoxy)-4-pyridazinyl] terephthalate (Compound No. 3001)

$^1$H-NMR (200 MHz, CDCl$_3$) δ ppm: 8.39 (4H, s), 7.62 (2H, s) 7.10-7.07 (4H, m), 6.87-6.83 (2H, m), 2.15 (6H, s), 1.81-1.68 (2H, m), 0.78-0.70 (4H, m), 0.61-0.53 (4H, m). Melting point (° C.): 247-249.

EXAMPLE 529

6-Chloro-3-(2-cyclopropyl-6-methylphenoxy)-4-pyridazinyl [1,1'-biphenyl]-4-carboxylate (Compound No. 3016)

$^1$H-NMR (200 MHz, CDCl$_3$) δ ppm: 8.31-8.23 (2H, m), 7.79-7.74 (2H, m), 7.67-7.62 (3H, m), 7.54-7.42 (3H, m), 7.09-7.06 (2H, m), 6.87-6.82 (1H, m), 2.17 (3H, s), 1.84-1.75 (1H, m), 0.77-0.56 (4H, m). Melting point (° C.): 135-137.

EXAMPLE 530

6-Chloro-3-(2-cyclopropyl-6-methylphenoxy)-4-pyridazinyl 4-(trifluoromethoxy)benzoate (Compound No. 3022)

$^1$H-NMR (200 MHz, CDCl$_3$) δ ppm: 8.28 (2H, d, J=9.2 Hz), 7.59 (1H, s), 7.38 (2H, d, J=9.2 Hz), 7.14-7.04 (2H, m), 6.89-6.82 (1H, m), 2.15 (3H, s), 1.83-1.69 (1H, m), 0.78-0.65 (2H, m), 0.62-0.53 (2H, m) Appearance: paste state.

EXAMPLE 531

6-Chloro-3-(2-cyclopropyl-6-methylphenoxy)-4-pyridazinyl 4-(benzyloxy)benzoate (Compound No. 3028)

$^1$H-NMR (200 MHz, CDCl$_3$) δ ppm: 8.16 (2H, d, J=9.2 Hz), 7.60 (1H, s), 7.50-7.30 (5H, m), 7.10-7.03 (4H, m), 6.89-6.82 (1H, m), 5.17 (2H, s), 2.15 (3H, s), 1.85-1.72 (1H, m), 0.80-0.68 (2H, m), 0.65-0.53 (2H, m). Appearance: paste state.

EXAMPLE 532

6-Chloro-3-(2-cyclopropyl-6-methylphenoxy)-4-pyridazinyl 2,3-difluorobenzoate (Compound No. 3034)

$^1$H-NMR (200 MHz, CDCl$_3$) δ ppm: 7.93-7.85 (1H, m), 7.57 (1H, s), 7.57-7.44 (1H, m), 7.32-7.21 (1H, m), 7.10-7.05 (2H, m), 6.87-6.82 (1H, m), 2.15 (3H, s), 1.81-1.73 (1H, m), 0.76-0.72 (2H, m), 0.60-0.56 (2H, m). Appearance: paste state.

EXAMPLE 533

6-Chloro-3-(2-cyclopropyl-6-methylphenoxy)-4-pyridazinyl 2-fluoro-3-(trifluoromethyl)benzoate (Compound No. 3040)

$^1$H-NMR (200 MHz, CDCl$_3$) δ ppm: 8.36-8.28 (1H, m), 7.99-7.92 (1H, m), 7.56 (1H, s), 7.49-7.41 (1H, m), 7.13-7.05 (2H, m), 6.89-6.83 (1H, m), 2.15 (3H, s), 1.84-1.72 (1H, m), 0.80-0.54 (4H, m). Appearance: amorphous.

EXAMPLE 534

6-Chloro-3-(2-cyclopropyl-6-methylphenoxy)-4-pyridazinyl 2,3-dimethylbenzoate (Compound No. 3046)

$^1$H-NMR (200 MHz, CDCl$_3$) δ ppm: 8.00-7.96 (1H, m), 7.54 (1H, s), 7.45-7.41 (1H, m), 7.27-7.20 (1H, m), 7.14-7.05 (2H, m), 6.89-6.82 (1H, m), 2.57 (3H, s), 2.37 (3H, s), 2.16 (3H, s), 1.86-1.72 (1H, m), 0.79-0.69 (2H, m), 0.61-0.53 (2H, m). Appearance: paste state.

EXAMPLE 535

6-Chloro-3-(2-cyclopropyl-6-methylphenoxy)-4-pyridazinyl 3-chloro-2-methylbenzoate (Compound No. 3052)

$^1$H-NMR (200 MHz, CDCl$_3$) δ ppm: 8.04 (1H, d, J=8.1 Hz), 7.65 (1H, d, J=8.1 Hz), 7.54 (1H, s), 7.33-7.25 (1H, m), 7.13-7.06 (2H, m), 6.89-6.83 (1H, m), 2.73 (3H, s), 2.15 (3H, s), 1.83-1.71 (1H, m), 0.79-0.68 (2H, m), 0.65-0.53 (2H, m). Appearance: amorphous.

EXAMPLE 536

6-Chloro-3-(2-cyclopropyl-6-methylphenoxy)-4-pyridazinyl 2,4-difluorobenzoate (Compound No. 3058)

$^1$H-NMR (200 MHz, CDCl$_3$) δ ppm: 8.23-8.12 (1H, m), 7.56 (1H, s), 7.10-6.94 (4H, m), 6.87-6.82 (1H, m), 2.15 (3H, s), 1.81-1.73 (1H, m), 0.75-0.56 (4H, m). Appearance: amorphous.

EXAMPLE 537

6-Chloro-3-(2-cyclopropyl-6-methylphenoxy)-4-pyridazinyl 4-chloro-2-fluorobenzoate (Compound No. 3064)

$^1$H-NMR (200 MHz, CDCl$_3$) δ ppm: 8.07 (1H, dd, J=7.4 Hz, 8.5 Hz), 7.55 (1H, s), 7.38-7.22 (2H, m), 7.14-7.03 (2H, m), 6.90-6.78 (1H, m), 2.15 (3H, s), 1.85-1.68 (1H, m), 0.80-0.50 (4H, m). Appearance: caramel-like.

EXAMPLE 538

6-Chloro-3-(2-cyclopropyl-6-methylphenoxy)-4-pyridazinyl 2-fluoro-4-(trifluoromethyl)benzoate (Compound No. 3070)

$^1$H-NMR (200 MHz, CDCl$_3$) δ ppm: 8.30-8.22 (1H, m), 7.61-7.52 (2H, m), 7.57 (1H, s), 7.14-7.05 (2H, m), 6.87-6.82 (1H, m), 2.15 (3H, m), 1.83-1.69 (1H, m), 0.78-0.70 (2H, m), 0.65-0.55 (2H, m). Appearance: paste state.

EXAMPLE 539

6-Chloro-3-(2-cyclopropyl-6-methylphenoxy)-4-pyridazinyl 2-chloro-4-fluorobenzoate (Compound No. 3076)

$^1$H-NMR (200 MHz, CDCl$_3$) δ ppm: 8.25-8.18 (1H, m), 7.57 (1H, s), 7.34-7.29 (1H, m), 7.19-7.05 (3H, m), 6.89-6.82 (1H, m), 2.15 (3H, m), 1.84-1.70 (1H, m), 0.79-0.68 (2H, m), 0.64-0.53 (2H, m). Appearance: paste state.

EXAMPLE 540

6-Chloro-3-(2-cyclopropyl-6-methylphenoxy)-4-pyridazinyl 4-bromo-2-chlorobenzoate (Compound No. 3082)

$^1$H-NMR (200 MHz, CDCl$_3$) δ ppm: 8.01 (1H, d, J=8.4 Hz), 7.76 (1H, d, J=1.8 Hz), 7.60-7.55 (2H, m), 7.10-7.07 (2H, m), 6.87-6.83 (1H, m), 2.15 (3H, s), 1.83-1.71 (1H, m), 0.77-0.71 (2H, m), 0.62-0.56 (2H, m). Appearance: paste state.

EXAMPLE 541

6-Chloro-3-(2-cyclopropyl-6-methylphenoxy)-4-pyridazinyl 4-bromo-2-methylbenzoate (Compound No. 3088)

$^1$H-NMR (200 MHz, CDCl$_3$) δ ppm: 8.05 (1H, d, J=8.4 Hz), 7.56-7.48 (3H, m), 7.09-7.07 (2H, m), 6.86-6.82 (1H, m), 2.14 (3H, s), 2.04 (3H, s), 1.85-1.72 (1H, m), 0.79-0.71 (2H, m), 0.64-0.55 (2H, m). Appearance: paste state.

EXAMPLE 542

6-Chloro-3-(2-cyclopropyl-6-methylphenoxy)-4-pyridazinyl 2,4-dimethylbenzoate (Compound No. 3094)

$^1$H-NMR (200 MHz, CDCl$_3$) δ ppm: 8.11 (1H, d, J=8.9 Hz), 7.57 (1H, s), 7.16-7.13 (2H, m), 7.09-7.05 (2H, m), 6.88-6.81 (1H, m), 2.65 (3H, s), 2.41 (3H, s), 2.15 (3H, s), 1.85-1.71 (1H, m), 0.80-0.68 (2H, m), 0.67-0.55 (2H, m). Appearance: paste state.

EXAMPLE 543

6-Chloro-3-(2-cyclopropyl-6-methylphenoxy)-4-pyridazinyl 2,5-dichlorobenzoate (Compound No. 3100)

$^1$H-NMR (200 MHz, CDCl$_3$) δ ppm: 8.10 (1H, d, J=2.2 Hz), 7.60-7.45 (3H, m), 7.15-7.04 (2H, m), 6.90-6.78 (1H, m), 2.15 (3H, s), 1.85-1.70 (1H, m), 0.80-0.50 (4H, m). Melting point (° C.): 128-130.

EXAMPLE 544

6-Chloro-3-(2-cyclopropyl-6-methylphenoxy)-4-pyridazinyl 5-bromo-2-chlorobenzoate (Compound No. 3106)

$^1$H-NMR (200 MHz, CDCl$_3$) δ ppm: 8.20 (1H, d, J=2.2 Hz), 7.68 (1H, dd, J=2.2 Hz, 8.4 Hz), 7.54 (1H, s), 7.43 (1H, d, J=8.4 Hz), 7.14-7.03 (2H, m), 6.92-6.80 (1H, m), 2.15 (3H, s), 1.87-1.70 (1H, m), 0.85-0.50 (4H, m). Appearance: caramel-like.

EXAMPLE 545

6-Chloro-3-(2-cyclopropyl-6-methylphenoxy)-4-pyridazinyl 2-bromo-5-methoxybenzoate (Compound No. 3112)

$^1$H-NMR (200 MHz, CDCl$_3$) δ ppm: 7.67-7.57 (3H, m), 7.12-7.00 (3H, m), 6.87-6.82 (1H, m), 3.85 (3H, s), 2.16 (3H, s), 1.87-1.75 (1H, m), 0.80-0.68 (2H, m), 0.65-0.55 (2H, m). Appearance: paste state.

EXAMPLE 546

6-Chloro-3-(2-cyclopropyl-6-methylphenoxy)-4-pyridazinyl 2,5-dimethylbenzoate (Compound No. 3129)

$^1$H-NMR (200 MHz, CDCl$_3$) δ ppm: 7.99 (1H, s), 7.54 (1H, s) 7.37-7.30 (1H, m), 7.25-7.21 (1H, m), 7.13-7.05 (2H, m), 6.89-6.82 (1H, m), 2.63 (3H, s), 2.40 (3H, s), 2.16 (3H, s), 1.86-1.72 (1H, m), 0.80-0.70 (2H, m), 0.62-0.54 (2H, m). Appearance: oily product.

EXAMPLE 547

6-Chloro-3-(2-cyclopropyl-6-methylphenoxy)-4-pyridazinyl 2,6-difluorobenzoate (Compound No. 3138)

$^1$H-NMR (200 MHz, CDCl$_3$) δ ppm: 7.68-7.50 (2H, m), 7.15-7.00 (4H, m), 6.90-6.77 (1H, m), 2.15 (3H, s), 1.90-1.70 (1H, m), 0.85-0.50 (4H, m). Appearance: caramel-like.

EXAMPLE 548

6-Chloro-3-(2-cyclopropyl-6-methylphenoxy)-4-pyridazinyl 2-chloro-6-fluorobenzoate (Compound No. 3144)

$^1$H-NMR (200 MHz, CDCl$_3$) δ ppm: 7.57 (1H, s), 7.57-7.00 (5H, m), 6.90-6.78 (1H, m), 2.16 (3H, s), 1.90-1.75 (1H, m), 0.80-0.50 (4H, m). Appearance: caramel-like.

EXAMPLE 549

6-Chloro-3-(2-cyclopropyl-6-methylphenoxy)-4-pyridazinyl 2,6-dichlorobenzoate (Compound No. 3150)

$^1$H-NMR (200 MHz, CDCl$_3$) δ ppm: 7.58 (1H, s), 7.43-7.41 (3H, m), 7.11-7.08 (2H, m), 6.88-6.83 (1H, m), 2.17 (3H, s), 1.85-1.77 (1H, m), 0.74-0.56 (4H, m). Appearance: amorphous.

EXAMPLE 550

6-Chloro-3-(2-cyclopropyl-6-methylphenoxy)-4-pyridazinyl 2,6-dimethylbenzoate (Compound No. 3156)

$^1$H-NMR (200 MHz, CDCl$_3$) δ ppm: 7.48 (1H, s), 7.32 (1H, dd, J=8.4, 7.0 Hz), 7.15-7.07 (3H, m), 6.87-6.83 (1H, m), 2.53 (6H, s), 2.16 (3H, s), 1.84-1.76 (1H, m), 0.75-0.69 (2H, m), 0.62-0.57 (2H, m). Appearance: paste state.

EXAMPLE 551

6-Chloro-3-(2-cyclopropyl-6-methylphenoxy)-4-pyridazinyl 2,6-dimethoxybenzoate (Compound No. 3162)

$^1$H-NMR (200 MHz, CDCl$_3$) δ ppm: 7.59 (1H, s), 7.39 (1H, t, J=8.8 Hz), 7.09-7.07 (2H, m), 6.85-6.81 (1H, m), 6.62 (2H, d, J=6.6 Hz), 3.84 (6H, s), 2.17 (3H, s), 1.96-1.81 (1H, m), 0.74-0.55 (4H, m). Melting point (° C.): 127-128.

EXAMPLE 552

6-Chloro-3-(2-cyclopropyl-6-methylphenoxy)-4-pyridazinyl 3,4-difluorobenzoate (Compound No. 3168)

$^1$H-NMR (200 MHz, CDCl$_3$) δ ppm: 8.10-7.99 (2H, m), 7.58 (1H, s), 7.43-7.25 (1H, m), 7.15-7.02 (2H, m), 6.90-6.80 (1H, m), 2.15 (3H, s), 1.83-1.67 (1H, m), 0.80-0.50 (4H, m). Appearance: caramel-like.

EXAMPLE 553

6-Chloro-3-(2-cyclopropyl-6-methylphenoxy)-4-pyridazinyl 3-fluoro-4-methylbenzoate (Compound No. 3185)

$^1$H-NMR (200 MHz, CDCl$_3$) δ ppm: 7.90 (1H, d, J=8.1 Hz), 7.83 (1H, d, J=9.9 Hz), 7.59 (1H, s), 7.37 (1H, dd, J=7.3 Hz, 7.7 Hz), 7.15-7.00 (2H, m), 6.90-6.78 (1H, m), 2.39 (3H, d, 1.5 Hz), 2.15 (3H, s), 1.85-1.67 (1H, m), 0.80-0.50 (4H, m). Appearance: caramel-like.

EXAMPLE 554

6-Chloro-3-(2-cyclopropyl-6-methylphenoxy)-4-pyridazinyl 3,4-dichlorobenzoate (Compound No. 3194)

$^1$H-NMR (200 MHz, CDCl$_3$) δ ppm: 8.29 (1H, d, J=1.8 Hz), 8.03 (1H, dd, J=8.4, 2.2 Hz), 7.65 (1H, d, J=8.4 Hz), 7.57 (1H, s), 7.15-7.02 (2H, m), 6.90-6.80 (1H, m), 2.15 (3H, s), 1.82-1.68 (1H, m), 0.78-0.47 (4H, m). Appearance: amorphous.

EXAMPLE 555

6-Chloro-3-(2-cyclopropyl-6-methylphenoxy)-4-pyridazinyl 4-chloro-3-nitrobenzoate (Compound No. 3200)

$^1$H-NMR (200 MHz, CDCl$_3$) δ ppm: 8.69 (1H, d, J=1.8 Hz), 8.33 (1H, dd, J=8.4, 1.8 Hz), 7.78 (1H, d, J=8.4 Hz), 7.57 (1H, s), 7.10-7.05 (2H, m), 6.87-6.82 (1H, m), 2.14 (3H, s), 1.77-1.69 (1H, m), 0.75-0.56 (4H, m). Appearance: amorphous.

EXAMPLE 556

6-Chloro-3-(2-cyclopropyl-6-methylphenoxy)-4-pyridazinyl 3,5-difluorobenzoate (Compound No. 3217)

$^1$H-NMR (200 MHz, CDCl$_3$) δ ppm: 7.80-7.65 (2H, m), 7.58 (1H, s), 7.32-7.00 (3H, m), 6.90-6.80 (1H, m), 2.15 (3H, s), 1.85-1.65 (1H, m), 0.80-0.50 (4H, m). Appearance: amorphous.

EXAMPLE 557

6-Chloro-3-(2-cyclopropyl-6-methylphenoxy)-4-pyridazinyl 3,5-dichlorobenzoate (Compound No. 3226)

$^1$H-NMR (200 MHz, CDCl$_3$) δ ppm: 8.07 (2H, d, J=2.0 Hz), 7.69 (1H, t, J=2.0 Hz), 7.55 (1H, s), 7.13-7.00 (2H, m), 6.89-6.82 (1H, m), 2.15 (3H, s), 1.83-1.60 (1H, m), 0.80-0.70 (2H, m), 0.63-0.55 (2H, m). Melting point (° C.): 168-174.

EXAMPLE 558

6-Chloro-3-(2-cyclopropyl-6-methylphenoxy)-4-pyridazinyl 3,5-dimethylbenzoate (Compound No. 3243)

$^1$H-NMR (200 MHz, CDCl$_3$) δ ppm: 7.82 (2H, s), 7.56 (1H, s) 7.32 (1H, s,), 7.13-7.04 (2H, m), 6.89-6.82 (1H, m), 2.41 (6H, s), 2.16 (3H, s), 1.85-1.72 (1H, m), 0.80-0.70 (2H, m), 0.63-0.53 (2H, m). Melting point (° C.): 117-119.

EXAMPLE 559

6-Chloro-3-(2-cyclopropyl-6-methylphenoxy)-4-pyridazinyl 3,5-dimethoxybenzoate (Compound No. 3252)

$^1$H-NMR (200 MHz, CDCl$_3$) δ ppm: 7.57 (1H, s), 7.34 (1H, s) 7.33 (1H, s), 7.08-7.06 (2H, m), 6.87-6.82 (1H, m), 6.78-6.75 (1H, m), 3.86 (6H, s), 2.16 (3H, s), 1.86-1.72 (1H, m), 0.80-0.72 (2H, m), 0.63-0.54 (2H, m). Appearance: paste state.

EXAMPLE 560

6-Chloro-3-(2-cyclopropyl-6-methylphenoxy)-4-pyridazinyl 2,4,6-trichlorobenzoate (Compound No. 3258)

$^1$H-NMR (200 MHz, CDCl$_3$) δ ppm: 7.55 (1H, s), 7.46 (2H, s) 7.15-7.05 (2H, m), 6.90-6.82 (1H, m), 2.16 (3H, s), 1.86-1.72 (1H, m), 0.78-0.67 (2H, m), 0.65-0.55 (2H, m). Appearance: paste state.

EXAMPLE 561

6-Chloro-3-(2-cyclopropyl-6-methylphenoxy)-4-pyridazinyl 3,4,5-trimethoxybenzoate (Compound No. 3264)

$^1$H-NMR (200 MHz, CDCl$_3$) δ ppm: 7.57 (1H, s), 7.45 (2H, s), 7.14-7.04 (2H, m), 6.89-6.83 (1H, m), 3.96 (3H, s), 3.94 (6H, s), 2.16 (3H, s), 1.85-1.72 (1H, m), 0.80-0.67 (2H, m), 0.63-0.54 (2H, m). Appearance: amorphous.

EXAMPLE 562

6-Chloro-3-(2-cyclopropyl-6-methylphenoxy)-4-pyridazinyl 1-naphthoate (Compound No. 3270)

$^1$H-NMR (200 MHz, CDCl$_3$) δ ppm: 9.02 (1H, d, J=8.4 Hz), 8.55 (1H, d, J=7.3 Hz), 8.17 (1H, d, J=8.0 Hz), 7.95 (1H, d, J=8.0 Hz), 7.75-7.54 (4H, m), 7.13-7.00 (2H, m), 6.90-6.80 (1H, m), 2.18 (3H, s), 1.93-1.75 (1H, m), 0.83-0.52 (4H, m). Appearance: amorphous.

EXAMPLE 563

6-Chloro-3-(2-cyclopropyl-6-methylphenoxy)-4-pyridazinyl 2-naphthoate (Compound No. 3276)

$^1$H-NMR (200 MHz, CDCl$_3$) δ ppm: 8.81 (1H, s), 8.18 (1H, dd, J=1.5 Hz, 8.5 Hz), 8.05-7.87 (3H, m), 7.70-7.52 (3H, m), 7.10-7.00 (2H, m), 6.90-6.77 (1H, m), 2.18 (3H, s), 1.90-1.73 (1H, m), 0.83-0.53 (4H, m). Appearance: amorphous.

EXAMPLE 564

6-Chloro-3-(2-cyclopropyl-6-methylphenoxy)-4-pyridazinyl 1-methyl-1H-pyrrole-2-carboxylate (Compound No. 3282)

$^1$H-NMR (200 MHz, CDCl$_3$) δ ppm: 7.57 (1H, s), 7.25 (1H, s), 7.08-7.06 (2H, m), 6.96 (1H, s), 6.86-6.81 (1H, m), 6.24-6.21 (1H, m), 3.97 (3H, s), 2.15 (3H, s), 1.87-1.72 (1H, m), 0.80-0.70 (2H, m), 0.63-0.52 (2H, m). Melting point (° C.): 143-144.

EXAMPLE 565

6-Chloro-3-(2-cyclopropyl-6-methylphenoxy)-4-pyridazinyl 5-bromo-2-furoate (Compound No. 3288)

$^1$H-NMR (200 MHz, CDCl$_3$) δ ppm: 7.53 (1H, s), 7.43 (1H, d, J=3.7 Hz), 7.15-7.03 (2H, m), 6.90-6.78 (1H, m), 6.59 (1H, d, J=3.7 Hz), 2.15 (3H, s), 1.83-1.70 (1H, m), 0.80-0.50 (4H, m). Appearance: caramel-like.

EXAMPLE 566

6-Chloro-3-(2-cyclopropyl-6-methylphenoxy)-4-pyridazinyl 3-furoate (Compound No. 3294)

$^1$H-NMR (200 MHz, CDCl$_3$) δ ppm: 8.30 (1H, t, J=0.7 Hz), 7.57-7.53 (1H, m), 7.55 (1H, s), 7.13-7.04 (2H, m), 6.92-6.81 (2H, m), 2.15 (3H, s), 1.83-1.69 (1H, m), 0.80-0.53 (4H, m). Appearance: paste state.

EXAMPLE 567

6-Chloro-3-(2-cyclopropyl-6-methylphenoxy)-4-pyridazinyl 5-tert-butyl-2-methyl-3-furoate (Compound No. 3300)

$^1$H-NMR (200 MHz, CDCl$_3$) δ ppm: 7.57 (1H, s), 7.09-7.07 (2H, m), 6.87-6.83 (1H, m), 6.33 (1H, s), 2.64 (3H, s), 2.15 (3H, s), 1.78-1.73 (1H, m), 1.29 (9H, s), 0.75-0.57 (4H, m). Appearance: caramel-like.

EXAMPLE 568

6-Chloro-3-(2-cyclopropyl-6-methylphenoxy)-4-pyridazinyl 5-methyl-2-(trifluoromethyl)-3-furoate (Compound No. 3306)

$^1$H-NMR (200 MHz, CDCl$_3$) δ ppm: 7.53 (1H, s), 7.13-7.04 (2H, m), 6.89-6.82 (1H, m), 6.64 (1H, s), 2.42 (3H, s), 2.13 (3H, s), 1.81-1.67 (1H, m), 0.78-0.68 (2H, m), 0.65-0.53 (2H, m). Appearance: paste state.

EXAMPLE 569

6-Chloro-3-(2-cyclopropyl-6-methylphenoxy)-4-pyridazinyl 5-(4-chlorophenyl)-2-(trifluoromethyl)-3-furoate (Compound No. 3312)

$^1$H-NMR (200 MHz, CDCl$_3$) δ ppm: 7.70-7.66 (2H, m), 7.56 (1H, s), 7.47-7.42 (2H, m), 7.19 (1H, s), 7.14-7.05 (2H, m), 6.90-6.82 (1H, m), 2.14 (3H, s), 1.83-1.69 (1H, m), 0.80-0.68 (2H, m), 0.65-0.53 (2H, m). Appearance: paste state.

EXAMPLE 570

6-Chloro-3-(2-cyclopropyl-6-methylphenoxy)-4-pyridazinyl 3-chloro-2-thiophenecarboxylate (Compound No. 3318)

$^1$H-NMR (200 MHz, CDCl$_3$) δ ppm: 7.68 (1H, d, J=5.5 Hz), 7.58 (1H, s), 7.14 (1H, d, J=5.5 Hz), 7.11-7.03 (2H, m), 6.90-6.80 (1H, m), 2.16 (3H, s), 1.85-1.70 (1H, m), 0.85-0.50 (4H, m). Appearance: caramel-like.

EXAMPLE 571

6-Chloro-3-(2-cyclopropyl-6-methylphenoxy)-4-pyridazinyl 3-methyl-2-thiophenecarboxylate (Compound No. 3324)

$^1$H-NMR (200 MHz, CDCl$_3$) δ ppm: 7.65-7.55 (2H, m), 7.13-6.95 (3H, m), 6.90-6.80 (1H, m), 2.63 (3H, s), 2.16 (3H, s), 1.90-1.70 (1H, m), 0.85-0.50 (4H, m). Appearance: amorphous.

EXAMPLE 572

6-Chloro-3-(2-cyclopropyl-6-methylphenoxy)-4-pyridazinyl 3-ethoxy-2-thiophenecarboxylate (Compound No. 3330)

$^1$H-NMR (200 MHz, CDCl$_3$) δ ppm: 7.62 (1H, s), 7.59 (1H, d, J=5.5 Hz), 7.08-7.06 (2H, m), 6.90 (1H, d, J=5.5 Hz), 6.86-6.81 (1H, m), 4.26 (2H, q, J=7.0 Hz), 2.17 (3H, s), 1.86-1.75 (1H, m), 1.46 (3H, t, J=7.0 Hz), 0.75-0.55 (4H, m). Appearance: caramel-like.

EXAMPLE 573

6-Chloro-3-(2-cyclopropyl-6-methylphenoxy)-4-pyridazinyl 5-chloro-2-thiophenecarboxylate (Compound No. 3336)

$^1$H-NMR (200 MHz, CDCl$_3$) δ ppm: 7.86 (1H, d, J=4.0 Hz), 7.57 (1H, s), 7.14-7.03 (3H, m), 6.90-6.83 (1H, m), 2.15 (3H, m), 1.83-1.68 (1H, m), 0.80-0.68 (2H, m), 0.65-0.53 (2H, m). Appearance: paste state.

EXAMPLE 574

6-Chloro-3-(2-cyclopropyl-6-methylphenoxy)-4-pyridazinyl 5-bromo-2-thiophenecarboxylate (Compound No. 3342)

$^1$H-NMR (200 MHz, CDCl$_3$) δ ppm: 7.80 (1H, d, J=4.0 Hz), 7.57 (1H, s), 7.19 (1H, d, J=4.0 Hz), 7.10-7.00 (2H, m), 6.90-6.80 (1H, m), 2.15 (3H, s), 1.85-1.65 (1H, m), 0.80-0.50 (4H, m). Appearance: caramel-like.

EXAMPLE 575

6-Chloro-3-(2-cyclopropyl-6-methylphenoxy)-4-pyridazinyl 5-methyl-2-thiophenecarboxylate (Compound No. 3348)

$^1$H-NMR (200 MHz, CDCl$_3$) δ ppm: 7.87 (1H, d, J=3.7 Hz), 7.57 (1H, s), 7.12-7.00 (2H, m), 6.93-6.87 (2H, m), 2.58 (3H, s), 2.15 (3H, s), 1.85-1.70 (1H, m), 0.80-0.50 (4H, m). Appearance: caramel-like.

EXAMPLE 576

6-Chloro-3-(2-cyclopropyl-6-methylphenoxy)-4-pyridazinyl 5-acetyl-2-thiophenecarboxylate (Compound No. 3354)

$^1$H-NMR (200 MHz, CDCl$_3$) δ ppm: 8.02 (1H, d, J=4.0 Hz), 7.72 (1H, d, J=4.0 Hz), 7.58 (1H, s), 7.10-7.07 (2H, m), 6.87-6.83 (1H, m), 2.63 (3H, s), 2.15 (3H, s), 1.79-1.71 (1H, m), 0.75-0.56 (4H, m). Appearance: amorphous.

EXAMPLE 577

6-Chloro-3-(2-cyclopropyl-6-methylphenoxy)-4-pyridazinyl 5-nitro-3-thiophenecarboxylate (Compound No. 3360)

$^1$H-NMR (200 MHz, CDCl$_3$) δ ppm: 8.52 (1H, d, J=1.8 Hz), 8.43 (1H, d, J=1.8 Hz), 7.56 (1H, s), 7.13-7.05 (2H, m), 6.90-6.80 (1H, m), 2.14 (3H, m), 1.85-1.65 (1H, m), 0.85-0.50 (4H, m). Appearance: amorphous.

EXAMPLE 578

6-Chloro-3-(2-cyclopropyl-6-methylphenoxy)-4-pyridazinyl 4,5-dibromo-2-thiophenecarboxylate (Compound No. 3366)

$^1$H-NMR (200 MHz, CDCl$_3$) δ ppm: 7.84 (1H, s), 7.56 (1H, s) 7.14-7.05 (2H, m), 6.90-6.83 (1H, m), 2.14 (3H, s), 1.83-1.69 (1H, m), 0.79-0.68 (2H, m), 0.65-0.55 (2H, m). Appearance: amorphous.

EXAMPLE 579

6-Chloro-3-(2-cyclopropyl-6-methylphenoxy)-4-pyridazinyl 3-thiophenecarboxylate (Compound No. 3372)

$^1$H-NMR (200 MHz, CDCl$_3$) δ ppm: 8.42-8.40 (1H, m), 7.70-7.66 (1H, m), 7.58 (1H, s), 7.47-7.41 (1H, m), 7.13-7.05 (2H, m), 6.88-6.82 (1H, m), 2.15 (3H, s), 1.84-1.70 (1H, m), 0.80-0.68 (2H, m), 0.64-0.55 (2H, m). Appearance: paste state.

EXAMPLE 580

6-Chloro-3-(2-cyclopropyl-6-methylphenoxy)-4-pyridazinyl 4-methoxy-3-thiophenecarboxylate (Compound No. 3378)

$^1$H-NMR (200 MHz, CDCl$_3$) δ ppm: 8.33 (1H, d, J=3.5 Hz), 7.59 (1H, s), 7.09-7.06 (2H, m), 6.87-6.82 (1H, m), 6.38 (1H, d, J=3.5 Hz), 3.93 (3H, s), 2.16 (3H, s), 1.82-1.74 (1H, m), 0.75-0.56 (4H, m). Melting point (° C.): 146-149.

EXAMPLE 581

6-Chloro-3-(2-cyclopropyl-6-methylphenoxy)-4-pyridazinyl 1-benzyl-3-tert-butyl-1H-pyrazole-5-carboxylate (Compound No. 3384)

$^1$H-NMR (200 MHz, CDCl$_3$) δ ppm: 7.44 (1H, s), 7.21 (5H, s), 7.09-7.06 (2H, m), 6.98 (1H, s), 6.85-6.80 (1H, m), 5.72 (2H, s), 2.08 (3H, s), 1.76-1.64 (1H, m), 1.36 (9H, s), 0.75-0.64 (2H, m), 0.59-0.50 (2H, m). Appearance: paste state.

EXAMPLE 582

6-Chloro-3-(2-cyclopropyl-6-methylphenoxy)-4-pyridazinyl 5-chloro-1,3-dimethyl-1H-pyrazole-4-carboxylate (Compound No. 3390)

$^1$H-NMR (200 MHz, CDCl$_3$) δ ppm: 7.62 (1H, s), 7.09-7.07 (2H, m), 6.87-6.82 (1H, m), 3.86 (3H, s), 2.52 (3H, s), 2.14 (3H, s), 1.84-1.77 (1H, m), 0.75-0.67 (2H, m), 0.60-0.53 (2H, m). Appearance: paste state.

EXAMPLE 583

6-Chloro-3-(2-cyclopropyl-6-methylphenoxy)-4-pyridazinyl 3-(2-chlorophenyl)-5-methyl-4-isoxazolecarboxylate (Compound No. 3396)

$^1$H-NMR (200 MHz, CDCl$_3$) δ ppm: 7.53 (1H, s), 7.48-7.42 (2H, m), 7.41-7.30 (2H, m), 7.08-7.06 (2H, m), 6.83-6.78 (1H, m), 2.89 (3H, s), 2.02 (3H, s), 1.67-1.53 (1H, m), 0.68-0.50 (4H, m). Appearance: amorphous.

EXAMPLE 584

6-Chloro-3-(2-cyclopropyl-6-methylphenoxy)-4-pyridazinyl 4-methyl-1,2,3-thiadizaole-5-carboxylate (Compound No. 3402)

$^1$H-NMR (200 MHz, CDCl$_3$) δ ppm: 7.57 (1H, s), 7.15-7.05 (2H, m), 6.91-6.84 (1H, m), 3.08 (3H, s), 2.14 (3H, s), 1.80-1.65 (1H, m), 0.80-0.72 (2H, m), 0.64-0.53 (2H, m). Appearance: paste state.

EXAMPLE 585

6-Chloro-3-(2-cyclopropyl-6-methylphenoxy)-4-pyridazinyl 6-methyl-2-pyridinecarboxylate (Compound No. 3408)

$^1$H-NMR (200 MHz, CDCl$_3$) δ ppm: 8.12 (1H, d, J=7.7 Hz), 7.82 (1H, t, J=7.7 Hz), 7.55 (1H, s), 7.46 (1H, d, J=7.7 Hz), 7.12-7.02 (2H, m), 6.85-6.76 (1H, m), 2.71 (3H, s), 2.15 (3H, s), 1.87-1.74 (1H, m), 0.82-0.52 (4H, m). Appearance: caramel-like.

EXAMPLE 586

6-Chloro-3-(2-cyclopropyl-6-methylphenoxy)-4-pyridazinyl 5-butyl-2-pyridinecarboxylate (Compound No. 3414)

$^1$H-NMR (200 MHz, CDCl$_3$) δ ppm: 8.67 (1H, br.s), 8.22 (1H, d, J=7.7 Hz), 7.74 (1H, br.d, J=7.7 Hz), 7.53 (1H, s), 7.08-7.05 (2H, m), 6.83-6.78 (1H, m), 2.75 (2H, t, J=7.7 Hz), 2.15 (3H, s), 1.84-1.59 (3H, m), 1.48-1.32 (2H, m), 0.95 (3H, t, J=7.0 Hz), 0.75-0.54 (4H, m). Appearance: caramel-like.

EXAMPLE 587

6-Chloro-3-(2-cyclopropyl-6-methylphenoxy)-4-pyridazinyl nicotinate (Compound No. 3420)

$^1$H-NMR (200 MHz, CDCl$_3$) δ ppm: 9.42-9.41 (1H, m), 8.91 (1H, dd, J=4.8, 0.8 Hz), 8.50-8.44 (1H, m), 7.60 (1H, s), 7.56-7.49 (1H, m), 7.13-7.04 (2H, m), 6.88-6.78 (1H, m), 2.15 (3H, s), 1.90-1.70 (1H, m), 0.81-0.70 (2H, m), 0.63-0.55 (2H, m). Appearance: paste state.

EXAMPLE 588

6-Chloro-3-(2-cyclopropyl-6-methylphenoxy)-4-pyridazinyl 2-chloronicotinate (Compound No. 3426)

$^1$H-NMR (200 MHz, CDCl$_3$) δ ppm: 8.66 (1H, dd, J=4.8, 2.0 Hz), 8.45 (1H, dd, J=7.7, 2.0 Hz), 7.59 (1H, s), 7.45 (1H, dd, J=7.7, 4.8 Hz), 7.14-7.06 (2H, m), 6.89-6.83 (1H, m), 2.15 (3H, s), 1.84-1.70 (1H, m), 0.80-0.52 (4H, m). Appearance: caramel-like.

EXAMPLE 589

6-Chloro-3-(2-cyclopropyl-6-methylphenoxy)-4-pyridazinyl 2-methylnicotinate (Compound No. 3432)

$^1$H-NMR (200 MHz, CDCl$_3$) δ ppm: 8.74 (1H, dd, J=4.8, 1.5 Hz), 8,46 (1H, dd, J=7.7, 1.5 Hz), 7.58 (1H, s), 7.34 (1H, dd, J=7.7, 4.8 Hz), 7.13-7.05 (2H, m), 6.89-6.83 (1H, m), 2.93 (3H, s), 2.15 (3H, s), 1.83-1.67 (1H, m), 0.80-0.68 (2H, m), 0.65-0.55 (2H, m). Appearance: paste state.

EXAMPLE 590

6-Chloro-3-(2-cyclopropyl-6-methylphenoxy)-4-pyridazinyl 2-phenoxynicotinate (Compound No. 3438)

$^1$H-NMR (200 MHz, CDCl$_3$) δ ppm: 8.50 (1H, dd, J=7.8, 2.2 Hz), 8.39 (1H, dd, J=4.8, 2.2 Hz), 7.61 (1H, s), 7.46-7.38 (2H, m), 7.29-7.20 (1H, m), 7.19-7.04 (5H, m), 6.86-6.81 (1H, m), 2.14 (3H, s), 1.85-1.72 (1H, m), 1.36 (9H, s), 0.75-0.65 (2H, m), 0.58-0.52 (2H, m). Appearance: paste state.

EXAMPLE 591

6-Chloro-3-(2-cyclopropyl-6-methylphenoxy)-4-pyridazinyl 2-(methylsulfanyl)nicotinate (Compound No. 3444)

$^1$H-NMR (200 MHz, CDCl$_3$) δ ppm: 8.70 (1H, dd, J=4.9, 1.8 Hz), 8.47 (1H, dd, J=7.7, 1.8 Hz), 7.63 (1H, s), 7.16 (1H, dd, J=7.7, 4.8 Hz) 7.12-7.05 (2H, m), 6.89-6.82 (1H, m), 2.59 (3H, s), 2.16 (3H, s), 1.84-1.71 (1H, m), 0.80-0.70 (2H, m), 0.65-0.53 (2H, m). Appearance: paste state.

EXAMPLE 592

6-Chloro-3-(2-cyclopropyl-6-methylphenoxy)-4-pyridazinyl 2-(allylsulfanyl)nicotinate (Compound No. 3450)

$^1$H-NMR (200 MHz, CDCl$_3$) δ ppm: 8.67 (1H, dd, J=4.8, 1.8 Hz), 8.46 (1H, dd, J=8.2, 1.8 Hz), 7.62 (1H, s), 7.16 (1H, dd, J=8.2, 4.8 Hz), 7.09-7.04 (2H, m), 6.89-6.82 (1H, m), 6.10-5.90 (1H, m), 5.33 (1H, dd, J=16.8, 1.6 Hz), 5.12 (1H, dd, J=11.0, 1.2 Hz), 3.91 (1H, dd, J=6.8, 1.2 Hz), 2.15 (3H, s), 1.85-1.70 (1H, m), 0.78-0.71 (2H, m), 0.60-0.51 (2H, m). Appearance: paste state.

EXAMPLE 593

6-Chloro-3-(2-cyclopropyl-6-methylphenoxy)-4-pyridazinyl 2-(phenylsulfanyl)nicotinate (Compound No. 3456)

$^1$H-NMR (200 MHz, CDCl$_3$) δ ppm: 8.50 (1H, s), 8.47 (1H, d, J=2.6 Hz), 7.65 (1H, s), 7.59-7.51 (2H, m), 7.48-7.41 (3H, m), 7.17-7.05 (3H, m), 6.90-6.82 (1H, m), 2.18 (3H, s), 1.89-1.74 (1H, m), 0.82-0.70 (2H, m), 0.65-0.54 (2H, m). Appearance: paste state.

EXAMPLE 594

6-Chloro-3-(2-cyclopropyl-6-methylphenoxy)-4-pyridazinyl 4-(trifluoromethyl)nicotinate (Compound No. 3462)

$^1$H-NMR (200 MHz, CDCl$_3$) δ ppm: 9.42 (1H, s), 9.08 (1H, d, J=5.1 Hz), 7.79 (1H, d, J=5.1 Hz), 7.57 (1H, s), 7.14-7.06 (2H, m), 6.90-6.84 (1H, m), 2.16 (3H, s), 1.84-1.72 (1H, m), 0.79-0.71 (2H, m), 0.63-0.55 (2H, m). Melting point (° C.): 92-93.

EXAMPLE 595

6-Chloro-3-(2-cyclopropyl-6-methylphenoxy)-4-pyridazinyl 6-chloronicotinate (Compound No. 3468)

$^1$H-NMR (200 MHz, CDCl$_3$) δ ppm: 9.19 (1H, d, J=2.0), 8.40 (1H, dd, J=8.4, 2.6), 7.59 (1H, s), 7.54 (1H, d, J=8.4 Hz), 7.10-7.08 (1H, m), 7.07 (1H, s), 6.87-6.82 (1H, m), 2.14 (3H, s), 1.79-1.65 (1H, m), 0.79-0.70 (2H, m), 0.62-0.53 (2H, m). Appearance: paste state.

EXAMPLE 596

6-Chloro-3-(2-cyclopropyl-6-methylphenoxy)-4-pyridazinyl 2,6-dichloronicotinate (Compound No. 3474)

$^1$H-NMR (200 MHz, CDCl$_3$) δ ppm: 8.46 (1H, d, J=8.1 Hz), 7.67 (1H, s), 7.52 (1H, d, J=8.1 Hz), 7.13-7.02 (2H, m), 6.90-6.75 (1H, m), 2.14 (3H, s), 1.85-1.68 (1H, m), 0.85-0.48 (4H, m). Appearance: amorphous.

EXAMPLE 597

6-Chloro-3-(2-cyclopropyl-6-methylphenoxy)-4-pyridazinyl 2-chloro-6-methylnicotinate (Compound No. 3480)

$^1$H-NMR (200 MHz, CDCl$_3$) δ ppm: 8.37 (1H, d, J=7.7 Hz), 7.58 (1H, s), 7.27 (1H, d, J=7.7 Hz), 7.14-7.08 (2H, m), 6.89-6.80 (1H, m), 2.65 (3H, s), 2.15 (3H, s), 1.83-1.69 (1H, m), 0.80-0.70 (2H, m), 0.68-0.55 (2H, m). Appearance: paste state.

EXAMPLE 598

6-Chloro-3-(2-cyclopropyl-6-methylphenoxy)-4-pyridazinyl 5,6-dichloronicotinate (Compound No. 3486)

$^1$H-NMR (200 MHz, CDCl$_3$) δ ppm: 9.07 (1H, d, J=2.2 Hz), 8.50 (1H, d, J=2.2 Hz), 7.57 (1H, s), 7.10-7.07 (2H, m), 6.87-6.82 (1H, m), 2.13 (3H, s), 1.80-1.65 (1H, m), 0.75-0.70 (2H, m), 0.58-0.55 (2H, m). Appearance: paste state.

EXAMPLE 599

6-Chloro-3-(2-cyclopropyl-6-methylphenoxy)-4-pyridazinyl 2-chloroisonicotinate (Compound No. 3492)

$^1$H-NMR (200 MHz, CDCl$_3$) δ ppm: 8.68 (1H, d, J=5.0 Hz), 8.05 (1H, s), 7.95-7.92 (1H, m), 7.57 (1H, s), 7.10-7.07 (2H, m), 6.87-6.83 (1H, m), 2.14 (3H, s), 1.77-1.68 (1H, m), 0.75-0.71 (2H, m), 0.58-0.56 (2H, m). Appearance: paste state.

EXAMPLE 600

6-Chloro-3-(2-cyclopropyl-6-methylphenoxy)-4-pyridazinyl 1-benzofuran-2-carboxylate (Compound No. 3498).

$^1$H-NMR (200 MHz, CDCl$_3$) δ ppm: 7.86-7.75 (2H, m), 7.68-7.51 (3H, m), 7.38 (1H, dd, J=7.7, 7.0 Hz), 7.12-7.05 (2H, m), 6.89-6.80 (1H, m), 2.17 (3H, s), 1.86-1.73 (1H, m), 0.80-0.68 (2H, m), 0.64-0.55 (2H, m). Appearance: amorphous.

EXAMPLE 601

6-Chloro-3-(2-cyclopropyl-6-methylphenoxy)-4-pyridazinyl 1-benzothiophene-2-carboxylate (Compound No. 3504)

$^1$H-NMR (200 MHz, CDCl$_3$) δ ppm: 8.34 (1H, s), 7.94 (2H, m), 7.64 (1H, s), 7.59-7.42 (2H, m), 7.09-7.07 (2H, m), 6.87-6.83 (1H, m), 2.18 (3H, s), 1.88-1.72 (1H, m), 0.77-0.71 (2H, m), 0.61-0.53 (2H, m). Melting point (° C.): 105-107.

EXAMPLE 602

6-Chloro-3-(2-cyclopropyl-6-methylphenoxy)-4-pyridazinyl 1,3-benzothiazole-6-carboxylate (Compound No. 3510)

$^1$H-NMR (200 MHz, CDCl$_3$) δ ppm: 9.24 (1H, s), 8.89 (1H, d, J=1.4 Hz), 8.36 (1H, dd, J=8.4, 1.4 Hz), 8.28 (1H, d, J=8.4 Hz), 7.65 (1H, s), 7.09-7.06 (2H, m), 6.87-6.82 (1H, m), 2.17 (3H, s), 1.86-1.73 (1H, m), 0.78-0.72 (2H, m), 0.63-0.55 (2H, m). Appearance: amorphous.

EXAMPLE 603

6-Chloro-3-(2-cyclopropyl-6-methylphenoxy)-4-pyridazinyl 1,3-benzodioxole-5-carboxylate (Compound No. 3516)

$^1$H-NMR (200 MHz, CDCl$_3$) δ ppm: 7.85 (1H, dd, J=8.4, 1.8 Hz), 7.60-7.59 (2H, m), 7.09-7.06 (2H, m), 6.93 (1H, d, J=8.0 Hz), 6.86-6.82 (1H, m), 6.10 (2H, s), 2.15 (3H, s), 1.86-1.74 (1H, m), 0.79-0.70 (2H, m), 0.62-0.53 (2H, m). Appearance: paste state.

EXAMPLE 604

6-Chloro-3-(2-cyclopropyl-6-methylphenoxy)-4-pyridazinyl 1-isoquinolinecarboxylate (Compound No. 3522)

$^1$H-NMR (200 MHz, CDCl$_3$) δ ppm: 8.45 (1H, d, J=8.1 Hz), 7.78-7.70 (2H, m), 7.61-7.53 (2H, m), 7.16 (1H, d, J=7.7 Hz), 7.12-7.05 (2H, m), 6.90-6.83 (1H, m), 6.66 (1H, d, J=7.3 Hz), 2.15 (3H, s), 1.81-1.66 (1H, m), 0.79-0.67 (2H, m), 0.63-0.53 (2H, m). Appearance: amorphous.

EXAMPLE 605

6-Chloro-3-(2-cyclopropyl-6-methylphenoxy)-4-pyridazinyl tert-butyl(methyl)carbamate (Compound No. 3528)

$^1$H-NMR (200 MHz, CDCl$_3$) δ ppm: 7.51 (1H, s), 7.15-7.03 (2H, m), 6.90-6.80 (1H, m), 3.11 (3H, s), 2.14 (3H, s), 1.85-1.70 (1H, m), 1.47 (9H, S), 0.80-0.50 (4H, m) Melting point (° C.): 113-115.

EXAMPLE 606

6-Chloro-3-(2-cyclopropyl-6-methylphenoxy)-4-pyridazinyl dibutylcarbamate (Compound No. 3534)

$^1$H-NMR (200 MHz, CDCl$_3$) δ ppm: 7.58 (1H, s), 7.15-7.03 (2H, m), 6.90-6.78 (1H, m), 3.50-3.26 (4H, m), 2.13 (3H, s), 1.87-1.50 (5H, m), 1.50-1.15 (4H, m), 1.10-0.85 (6H, m), 0.80-0.54 (4H, m). Appearance: caramel-like.

EXAMPLE 607

6-Chloro-3-(2-cyclopropyl-6-methylphenoxy)-4-pyridazinyl benzyl(methyl)carbamate (Compound No. 3540)

$^1$H-NMR (200 MHz, CDCl$_3$) δ ppm: 7.58 (0.5H, s), 7.57 (0.5H, s), 7.40-7.20 (5H, m), 7.15-7.03 (2H, m), 6.92-6.80 (1H, m), 4.68 (1H, s), 4.57 (1H, s), 3.08 (1.5H, s), 3.02 (1.5H,

EXAMPLE 608

6-Chloro-3-(2-cyclopropyl-6-methylphenoxy)-4-pyridazinyl cyanomethyl(methyl)carbamate (Compound No. 3546)

$^1$H-NMR (200 MHz, CDCl$_3$) δ ppm: 7.59 (0.4H, s), 7.56 (0.6H, s), 7.15-7.04 (2H, m), 6.90-6.80 (1H, m), 4.42 (0.8H, s), 4.36 (1.2H, s), 3.30 (1.8H, s), 3.19 (1.2H, s), 2.14 (3H, s), 1.85-1.62 (1H, m), 0.80-0.53 (4H, m). Appearance: caramel-like.

EXAMPLE 609

Ethyl N-({[6-chloro-3-(2-cyclopropyl-6-methylphenoxy)-4-pyridazinyl]oxy}carbonyl)-N-methylglycinate (Compound No. 3552)

$^1$H-NMR (200 MHz, CDCl$_3$) δ ppm: 7.61 (0.5H, s), 7.60 (0.5H, s), 7.15-7.02 (2H, m), 6.90-6.80 (1H, m), 4.28-4.11 (4H, m), 3.23 (1.5H, s), 3.13 (1.5H, s), 2.15 (1.5H, s), 2.13 (1.5H, s), 1.85-1.65 (1H, m), 1.31-1.18 (3H, m), 0.80-0.50 (4H, m) Appearance: caramel-like.

EXAMPLE 610

6-Chloro-3-(2-cyclopropyl-6-methylphenoxy)-4-pyridazinyl methyl(2-pyridinyl)carbamate (Compound No. 3558)

$^1$H-NMR (200 MHz, CDCl$_3$) δ ppm: 8.35-8.25 (1H, m), 7.70-7.55 (1H, m), 7.05-6.90 (5H, m), 6.85-6.74 (1H, m), 3.56 (3H, s), 2.03 (3H, s), 1.72-1.55 (1H, m), 0.75-0.45 (4H, m). Melting point (° C.): 140-147.

EXAMPLE 611

6-Chloro-3-(2-cyclopropyl-6-methylphenoxy)-4-pyridazinyl 1-piperidinecarboxylate (Compound No. 3636)

$^1$H-NMR (200 MHz, CDCl$_3$) δ ppm: 7.56 (1H, s), 7.15-7.03 (2H, m), 6.90-6.80 (1H, m), 3.70-3.60 (2H, m), 3.60-3.45 (2H, m), 2.15 (3H, s), 1.86-1.70 (1H, m), 1.70-1.50 (6H, m), 0.80-0.53 (4H, m). Appearance: caramel-like.

EXAMPLE 612

6-Chloro-3-(2-cyclopropyl-6-methylphenoxy)-4-pyridazinyl bis(2-chloroethyl)carbamate (Compound No. 3570)

$^1$H-NMR (200 MHz, CDCl$_3$) δ ppm: 7.58 (1H, s), 7.15-7.05 (2H, m), 6.92-6.82 (1H, m), 3.98-3.70 (8H, m), 2.13 (3H, s), 1.82-1.65 (1H, m), 0.80-0.50 (4H, m). Melting point (° C.): 166-167.

EXAMPLE 613

6-Chloro-3-(2-cyclopropyl-6-methylphenoxy)-4-pyridazinyl diallylcarbamate (Compound No. 3576)

$^1$H-NMR (200 MHz, CDCl$_3$) δ ppm: 7.56 (1H, s), 7.12-7.04 (2H, m), 6.88-6.80 (1H, m), 6.00-5.70 (2H, m), 5.30-5.15 (4H, m), 4.10-3.93 (4H, m), 2.13 (3H, s), 1.85-1.68 (1H, m), 0.80-0.52 (4H, m). Appearance: caramel-like.

EXAMPLE 614

6-Chloro-3-(2-cyclopropyl-6-methylphenoxy)-4-pyridazinyl bis(cyanomethyl)carbamate (Compound No. 3582)

$^1$H-NMR (200 MHz, CDCl$_3$) δ ppm: 7.59 (1H, s), 7.18-7.05 (2H, m), 6.90-6.80 (1H, m), 4.54 (2H, s), 4.48 (2H, s), 2.13 (3H, s), 1.80-1.65 (1H, m), 0.80-0.50 (4H, m). Appearance: caramel-like.

EXAMPLE 615

6-Chloro-3-(2-cyclopropyl-6-methylphenoxy)-4-pyridazinyl bis(2-cyanoethyl)carbamate (Compound No. 3588)

$^1$H-NMR (200 MHz, CDCl$_3$) δ ppm: 7.61 (1H, s), 7.18-7.05 (2H, m), 6.92-6.82 (1H, m), 3.91 (2H, t, J=6.6 Hz), 3.77 (2H, t, J=6.2 Hz), 2.85 (2H, t, J=6.6 Hz), 2.78 (2H, t, J=6.2 Hz), 2.13 (3H, s), 1.80-1.63 (1H, m), 0.82-0.53 (4H, m). Melting point (° C.): 159-161.

EXAMPLE 616

Ethyl N-({[6-chloro-3-(2-cyclopropyl-6-methylphenoxy)-4-pyridazinyl]oxy}carbonyl)-N-(2-ethoxy-2-oxoethyl)glycinate (Compound No. 3594)

$^1$H-NMR (200 MHz, CDCl$_3$) δ ppm: 7.65 (1H, s), 7.13-7.03 (2H, m), 6.90-6.80 (1H, m), 4.33-4.05 (8H, m), 2.12 (3H, s), 1.83-1.65 (1H, m), 1.28 (3H, t, J=7.3 Hz), 1.19 (3H, t, J=7.3 Hz), 0.80-0.50 (4H, m). Appearance: caramel-like.

EXAMPLE 617

6-Chloro-3-(2-cyclopropyl-6-methylphenoxy)-4-pyridazinyl bis(2-methoxyethyl)carbamate (Compound No. 3600)

$^1$H-NMR (200 MHz, CDCl$_3$) δ ppm: 7.59 (1H, s), 7.15-7.05 (2H, m), 6.90-6.80 (1H, m), 3.80-3.50 (8H, m), 3.32 (6H, s), 2.15 (3H, s), 1.86-1.69 (1H, m), 0.80-0.52 (4H, m). Appearance: caramel-like.

EXAMPLE 618

6-Chloro-3-(2-cyclopropyl-6-methylphenoxy)-4-pyridazinyl bis(2-ethoxyethyl)carbamate (Compound No. 3606)

$^1$H-NMR (200 MHz, CDCl$_3$) δ ppm: 7.57 (1H, s), 7.15-7.03 (2H, m), 6.90-6.80 (1H, m), 3.78-3.55 (8H, m), 3.46 (4H, q, J=6.9 Hz), 2.14 (3H, s), 1.87-1.65 (1H, m), 1.15 (3H, t, J=6.9 Hz), 1.14 (3H, t, J=6.9 Hz), 0.80-0.53 (4H, m). Appearance: caramel-like.

EXAMPLE 619

6-Chloro-3-(2-cyclopropyl-6-methylphenoxy)-4-pyridazinyl 1-azetizinecarboxylate (Compound No. 3612)

$^1$H-NMR (200 MHz, CDCl$_3$) δ ppm: 7.53 (1H, s), 7.13-7.02 (2H, m), 6.90-6.78 (1H, m), 4.38-4.05 (4H, m), 2.45-2.29 (2H, m), 2.15 (3H, s), 1.85-1.67 (1H, m), 0.80-0.50 (4H, m). Melting point (° C.): 134-136.

EXAMPLE 620

1-[6-Chloro-3-(2-cyclopropyl-6-methylphenoxy)-4-pyridazinyl] 2-methyl 1,2-pyrrolidinedicarboxylate (Compound No. 3618)

$^1$H-NMR (200 MHz, CDCl$_3$) δ ppm: 7.65 (0.5H, s), 7.62 (0.5H, s), 7.15-7.02 (2H, m), 6.90-6.78 (1H, m), 4.63-4.57 (0.5H, m), 4.51-4.44 (0.5H, m), 3.91-3.55 (2H, m), 3.75 (1.5H, s), 3.65 (1.5H, s), 2.50-1.90 (4H, m), 2.15 (1.5H, s), 2.13 (1.5H, s), 1.90-1.69 (1H, m), 0.80-0.50 (4H, m). Appearance: caramel-like.

EXAMPLE 621

6-Chloro-3-(2-cyclopropyl-6-methylphenoxy)-4-pyridazinyl 3-hydroxy-1-pyrrolidinecarboxylate (Compound No. 3624)

$^1$H-NMR (200 MHz, CDCl$_3$) δ ppm: 7.60 (1H, s), 7.13-7.03 (2H, m), 6.90-6.80 (1H, m), 4.65-4.52 (1H, m), 3.85-3.55 (4H, m), 2.14 (3H, s), 2.13-2.00 (2H, m), 1.87-1.70 (2H, m), 0.80-0.50 (4H, m). Appearance: caramel-like.

EXAMPLE 622

6-Chloro-3-(2-cyclopropyl-3,5,6-trimethylphenoxy)-4-pyridazinol (Compound No. 1126)

(1) 2,3,5-Trimethylphenyl acetate

In dichloromethane (150 mL) was dissolved 15.09 g (0.1108 mol) of 2,3,5-trimethylphenol, and 17.82 mL (0.2204 mol) of pyridine, then 20.78 mL (0.2202 mol) of acetic anhydride were added to the solution, and the mixture was stirred at room temperature overnight. The reaction mixture was poured into water, and extracted with dichloro-methane. The organic layer was successively washed with water and brine, and dried over anhydrous magnesium sulfate. The solvent was removed, and the residue was purified by silica gel column chromatography (Wako gel C-100, hexane:ethyl acetate, gradient) to obtain 20.08 g (0.1127 mol, Yield: quantitative) of 2,3,5-trimethylphenyl acetate.

(2) 1-(2-Hydroxy-3,4,6-trimethylphenyl)ethanone

To 13.83 g (77.60 mmol) of 2,3,5-trimethylphenyl acetate obtained in (1) was added 20.69 g (155.2 mmol) of aluminum chloride little by little in an ice bath with stirring. The mixture was stirred while heating to 100° C. overnight. After cooling, the reaction mixture was added to ice water little by little. The mixture was extracted with dichloromethane, the organic layers were combined, washed with water, and dried over anhydrous magnesium sulfate. The solvent was removed, and the residue was purified by silica gel column chromatography (Wako gel C-100, hexane:ethyl acetate, gradient) to obtain 12.75 g (71.55 mmol, Yield: 92.20%) of 1-(2-hydroxy-3,4,6-trimethylphenyl)ethanone.

(3) 1-(2-Methoxy-3,4,6-trimethylphenyl)ethanone

In acetone (100 mL) was dissolved 8.00 g (44.9 mmol) of 1-(2-hydroxy-3,4,6-trimethylphenyl)ethanone obtained in (2), to the mixture were added 18.6 g (135 mmol) of potassium carbonate, and then, 8.40 mL (135 mmol) of methyl iodide, and the resulting mixture was refluxed for 27 hours and 30 minutes. Moreover, 18.6 g (135 mmol) of potassium carbonate, and 8.40 mL (135 mmol) of methyl iodide were additionally added to the mixture, and the resulting mixture was refluxed for 6 hours. The reaction mixture was concentrated under reduced pressure, water (100 mL) was added to the residue, and the mixture was extracted with ethyl acetate. The organic layers were combined, washed successively with water and brine, and dried over anhydrous sodium sulfate. The solvent was removed, and the residue was purified by silica gel column chromatography (Daisogel 1001W, hexane:ethyl acetate, gradient) to obtain 8.04 g (41.9 mmol, Yield: 93.3%) of 1-(2-methoxy-3,4,6-trimethylphenyl)ethanone.

(4) 1-(2-Methoxy-3,4,6-trimethylphenyl)ethanol

In methanol (100 mL) was dissolved 5.01 g (26.1 mmol) of 1-(2-methoxy-3,4,6-trimethylphenyl)ethanone obtained in (3), and in an ice bath, 1.00 g (26.5 mmol) of sodium borohydride was added to the solution and the mixture was stirred in an ice bath for 2 hours and 30 minutes. The reaction mixture was poured into 400 mL of ice water, and extracted with ethyl acetate. The organic layers were combined, washed successively with water and brine, and dried over anhydrous sodium sulfate. The solvent was removed to obtain 4.35g (22.4 mmol, Yield: 85.8%) of 1-(2-methoxy-3,4,6-trimethylphenyl)ethanol.

(5) 2-(1-Chloroethyl)-3-methoxy-1,4,5-trimethylbenzene

To 0.652 g (3.36 mmol) of 1-(2-methoxy-3,4,6-trimethylphenyl)ethanol obtained in (4) was added dropwise with stirring 0.150 mL (1.72 mmol) of oxalyl chloride, and the mixture was stirred at 100° C. for 2 hours. Then, dichloromethane (1 mL) and triethylamine (3 mL) were added to the reaction mixture, and the resulting mixture was stirred at 100° C. for 3 hours. The reaction mixture was poured into 60 ml of ice water, and extracted with ethyl acetate. The organic layers were combined, washed successively with water and brine, and dried over anhydrous sodium sulfate. The solvent was removed to obtain 0.620 g (2.91 mmol, Yield: 86.6%) of 2-(1-chloroethyl)-3-methoxy-1,4,5-trimethylbenzene.

(6) 3-Methoxy-1,2,5-trimethyl-4-vinylbenzene

In N,N-dimethylformamide (DMF, 6 mL) was dissolved 0.620 g (2.91 mmol) of 2-(1-chloroethyl)-3-methoxy-1,4,5-trimethylbenzene obtained in (5), and 1.20 g (8.70 mmol) of potassium carbonate was added to the solution and the resulting mixture was refluxed for 9 hours. The reaction mixture was poured into 50 ml of ice water, and extracted with hexane. The organic layers were combined, washed successively with water and brine, and dried over anhydrous sodium sulfate. The solvent was removed, and the residue was purified by silica gel column chromatography (Daisogel 1001W, hexane:ethyl acetate, gradient) to obtain 0.360 g (2.05 mmol, Yield: 70.4%) of 3-methoxy-1,2,5-trimethyl-4-vinylbenzene.

(7) 2-Cyclopropyl-3-methoxy-1,4,5-trimethylbenzene

To dry dichloromethane (5 mL) was added 3.07 mL (3.04 mmol) of diethyl zinc (0.99 mol/L hexane solution), a dichloromethane (2.5 mL) solution containing 0.23 mL (3.0 mmol) of trifluoroacetic acid was gradually added dropwise with stirring in an ice bath. After completion of the dropwise addition, the mixture was stirred in an ice bath for 30 minutes, and 0.24 mL (3.0 mmol) of diiodomethane was added dropwise to the mixture. Then, a dichloromethane (3 mL) solution containing 0.268 g (1.52 mmol) of 3-methoxy-1,2,5-trimethyl-4-vinylbenzene obtained in (6) was added dropwise, and the mixture was stirred in an ice bath for 1 hour. The reaction mixture was poured into water, made acidic with diluted hydrochloric acid, and then, extracted with dichloromethane. The organic layers were combined, washed with water, and dried over anhydrous magnesium sulfate. The solvent was distilled off and the obtained residue was purified by preparative thin-layer chromatography (available from MERCK CO., 1.05717, 2 plates were used, developed by hexane:ethyl acetate=25:1) to obtain 0.212 g (1.12 mmol, Yield: 73.7%) of 2-cyclopropyl-3-methoxy-1,4,5-trimethylbenzene.

(8) 2-Cyclopropyl-3,5,6-trimethylphenol

Under nitrogen atmosphere, in dry N,N-dimethylformamide (5 mL) was suspended 134 mg (3.35 mmol) of 60% sodium hydride, and 0.26 mL (3.5 mmol) of ethanethiol was gradually added dropwise to the suspension. After stirring for 30 minutes, a dry N,N-dimethylformamide (5 mL) solution containing 0.212 g (1.12 mmol) of 2-cyclopropyl-3-methoxy-1,4,5-trimethylbenzene obtained in (7) was added dropwise to the mixture, and the resulting mixture was stirred at 160° C. for 5 hours. After allowing to stand for cooling, the reaction mixture was poured into water, made acidic by adding diluted hydrochloric acid, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=25:1) to obtain 179 mg (1.02 mmol, Yield: 91.1%) of 2-cyclopropyl-3,5,6-trimethylphenol.

(9) Mixture of 6-chloro-3-(2-cyclopropyl-3,5,6-trimethylphenoxy)pyridazine 1-oxide and 3-chloro-6-(2-cyclopropyl-3,5,6-trimethylphenoxy)pyridazine 1-oxide (Step B-2)

179 mg (1.02 mmol) of 2-cyclopropyl-3,5,6-trimethylphenol, 1,4-dioxane (5 mL) and dimethylsulfoxide (5 mL) were mixed, 125 mg (1.12 mmol) of potassium tert-butoxide was added to the mixture, and the resulting mixture was stirred for 10 minutes. To the mixture was added 167 mg (1.01 mmol) of 3,6-dichloropyridazine 1-oxide, and the mixture was allowed to stand at room temperature for 3 days. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05717, 2 plates were used, developed by hexane:ethyl acetate=2:1) to obtain 263 mg of a mixture of 6-chloro-3-(2-cyclopropyl-3,5,6-trimethylphenoxy)pyridazine 1-oxide and 3-chloro-6-(2-cyclopropyl-3,5,6-trimethylphenoxy)pyridazine 1-oxide.

(10) 4,6-Dichloro-3-(2-cyclopropyl-3,5,6-trimethylphenoxy)pyridazine (Step B-3)

263 mg of a mixture of 6-chloro-3-(2-cyclopropyl-3,5,6-trimethylphenoxy)pyridazine 1-oxide and 3-chloro-6-(2-cyclopropyl-3,5,6-trimethylphenoxy)pyridazine 1-oxide obtained in (9) and 3.0 mL (32 mmol) of phosphorus oxychloride were mixed, and the mixture was stirred at room temperature overnight. Dichloromethane and water were added to the reaction mixture, and after stirring, the mixture was extracted with dichloromethane. The organic layers were combined, washed with water, and dried over anhydrous magnesium sulfate. The solvent was distilled off and the obtained residue was purified by preparative thin-layer chromatography (available from MERCK CO., 1.05717, 2 plates were used, developed by hexane:ethyl acetate=2:1) to obtain 198 mg (0.613 mmol, Yield from 3,6-dichloropyridazine 1-oxide: 60.7%) of 4,6-dichloro-3-(2-cyclopropyl-3,5,6-trimethylphenoxy)pyridazine. Also, 43.8 mg (0.144 mmol, Yield from 3,6-dichloropyridazine 1-oxide: 14.2%) of 3-chloro-6-(2-cyclopropyl-3,5,6-trimethylphenoxy)pyridazine 1-oxide was obtained.

(11) 6-Chloro-3-(2-cyclopropyl-3,5,6-trimethylphenoxy)-4-pyridazinol (Compound No. 1126, Step A-3 and A-4)

In dimethylsulfoxide (10 mL) was dissolved 198 mg (0.613 mmol) of 4,6-dichloro-3-(2-cyclopropyl-3,5,6-trimethylphenoxy)pyridazine obtained in (10), 251 mg (3.06 mmol) of sodium acetate was added to the solution and the mixture was stirred at 120° C. for 4 hours. The reaction mixture was cooled, poured into water, and made acidic with diluted hydrochloric acid. The mixture was extracted with ethyl acetate, the organic layers were combined, washed with water, and dried over anhydrous magnesium sulfate. The solvent was distilled off and the obtained residue was purified by preparative thin-layer chromatography (available from MERCK CO., 1.05717, 2 plates were used, developed by hexane:ethyl acetate=1:2) to obtain 116 mg (0.380 mmol, Yield: 62.0%) of 6-chloro-3-(2-cyclopropyl-3,5,6-trimethylphenoxy)-4-pyridazinol (Compound No. 1126).

$^1$H-NMR (200 MHz, CD$_3$OD) δ ppm: 6.67 (1H, s), 6.62 (1H, s), 2.22 (3H, s), 2.16 (3H, s), 2.05 (3H, s), 1.85-1.65 (1H, m), 0.75-0.62 (2H, m), 0.60-0.45 (2H, m). Melting point (° C.): 212-219.

EXAMPLE 623

6-Chloro-3-(2-methoxy-3,5,6-trimethylphenoxy)-4-pyridazinol (Compound No. 1128)

(1)
1-[2-(Benzyloxy)-3,4,6-trimethylphenyl]ethanone

In N,N-dimethylformamide (8 mL) was dissolved 2.00 g (11.2 mmol) of 1-(2-hydroxy-3,4,6-trimethylphenyl)ethanone obtained in Example 622 (2). To the solution was added in an ice bath 0.488 g (11.2 mmol) of 60% sodium hydride, and after stirring in an ice bath for 10 minutes, 1.92 g (11.2 mmol) of benzyl bromide was gradually added dropwise and the mixture was stirred at room temperature overnight. The reaction mixture was poured into ice water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 2.36 g (8.81 mmol, Yield: 78.7%) of 1-[2-(benzyloxy)-3,4,6-trimethylphenyl]ethanone.

(2) 2-(Benzyloxy)-3,4,6-trimethylphenyl acetate

In dichloromethane (3 mL) was dissolved 500 mg (1.87 mmol) of 1-[2-(benzyloxy)-3,4,6-trimethylphenyl]ethanone obtained in (1), a dichloromethane (6 mL) solution containing 921 mg (purity 70-75%, 3.73-3.99 mmol) of m-chloroperbenzoic acid was added to the solution, and the resulting mixture was stirred at room temperature for 2 days. The reaction mixture was poured into a saturated aqueous sodium sulfite solution, and extracted with ethyl acetate. The organic layer was washed with a saturated aqueous sodium hydrogen carbonate solution, and dried over anhydrous sodium sulfate. The solvent was removed to obtain 560 mg of 2-(benzyloxy)-3,4,6-trimethylphenyl acetate.

(3) 2-(Benzyloxy)-3,4,6-trimethylphenol

In ethanol (15 mL) was dissolved 560 mg of 2-(benzyloxy)-3,4,6-trimethylphenyl acetate obtained in (2), 2N aqueous sodium hydroxide solution was added to the solution and the resulting mixture was stirred at room temperature overnight and at 60° C. for 4 hours. The reaction mixture was cooled up to room temperature, and poured into water. To the mixture was added 1N hydrochloric acid to make the mixture acidic, and the mixture was extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane-ethyl acetate, gradient) to obtain 290 mg (1.20 mmol, Yield from 1-[2-(benzyloxy)-3,4,6-trimethylphenyl]ethanone: 64.2%) of 2-(benzyloxy)-3,4,6-trimethylphenol.

(4) 3-(Benzyloxy)-2-methoxy-1,4,5-trimethylbenzene

In acetone (3 mL) was dissolved 290 mg (1.20 mmol) of 2-(benzyloxy)-3,4,6-trimethylphenol obtained in (3), 350 mg (2.54 mmol) of potassium carbonate was added to the solution, and the mixture was stirred at room temperature for 15 minutes. Then, 0.180 mL (2.89 mmol) of methyl iodide was added to the mixture, and the resulting mixture was stirred at room temperature overnight. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by ethyl acetate:hexane=10:1) to obtain 196 mg (0.766 mmol, Yield: 63.8%) of 3-(benzyloxy)-2-methoxy-1,4,5-trimethylbenzene.

(5) 2-Methoxy-3,5,6-trimethylphenol

In methanol (3 mL) was dissolved 180 mg (0.703 mmol) of 3-(benzyloxy)-2-methoxy-1,4,5-trimethylbenzene obtained in (4), 0.10 g of 5% palladium-carbon was added to the solution, and the mixture was stirred under hydrogen atmosphere (1 atm) for 4 hours. The reaction mixture was filtered through Celite, and the filtrate was concentrated. 90.7 mg (0.546 mmol, Yield: 77.7%) of 2-methoxy-3,5,6-trimethylphenol was obtained.

(6) Mixture of 6-chloro-3-(2-methoxy-3,5,6-trimethylphenoxy)pyridazine 1-oxide and 3-chloro-6-(2-methoxy-3,5,6-trimethylphenoxy)pyridazine 1-oxide (Step B-2)

90.0 mg (0.542 mmol) of 2-methoxy-3,5,6-trimethylphenol obtained in (5), 1,4-dioxane (1.5 mL) and dimethylsulfoxide (1.5 mL) were mixed, 73.5 mg (0.656 mmol) of potassium tert-butoxide was added to the mixture, and the resulting mixture was stirred in an ice bath for 15 minutes. To the mixture was added 93.2 mg (0.565 mmol) of 3,6-dichloropyridazine 1-oxide, and the resulting mixture was stirred at room temperature for 3 hours. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by hexane:ethyl acetate=2:1) to obtain 140 mg of a mixture of 6-chloro-3-(2-methoxy-3,5,6-trimethylphenoxy)pyridazine 1-oxide and 3-chloro-6-(2-methoxy-3,5,6-trimethylphenoxy)pyridazine 1-oxide.

(7) 4,6-Dichloro-3-(2-methoxy-3,5,6-trimethylphenoxy)pyridazine (Step B-3)

140 mg of a mixture of 6-chloro-3-(2-methoxy-3,5,6-trimethylphenoxy)pyridazine 1-oxide and 3-chloro-6-(2-methoxy-3,5,6-trimethylphenoxy)pyridazine 1-oxide obtained in (6) and 0.25 mL (2.7 mmol) of phosphorus oxychloride were mixed, and the mixture was stirred at room temperature overnight. The reaction mixture was poured into water, and extracted with dichloromethane. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by hexane:ethyl acetate=2:1) to obtain 111 mg (0.355 mmol, Yield from 3,6-dichloropyridazine 1-oxide: 62.8%) of 4,6-dichloro-3-(2-methoxy-3,5,6-trimethylphenoxy)pyridazine. Also, 38.3 mg (0.130 mmol, Yield from 3,6-dichloropyridazine 1-oxide: 23.0%) of 3-chloro-6-(2-methoxy-3,5,6-trimethylphenoxy)pyridazine 1-oxide was obtained.

(8) 6-Chloro-3-(2-methoxy-3,5,6-trimethylphenoxy)-4-pyridazinol (Compound No. 1128, Step B-4)

To a dimethylsulfoxide (10 mL) solution containing 111 mg (0.355 mmol) of 4,6-dichloro-3-(2-methoxy-3,5,6-trimethylphenoxy)pyridazine obtained in (7) was added 0.3 mL (0.6 mmol) of 2 mol/L aqueous sodium hydroxide solution, and the mixture was stirred at room temperature for 2 hours and 30 minutes. The reaction mixture was poured into ice-cooled 1 mol/L aqueous sodium hydroxide solution, and extracted with ethyl acetate. The aqueous layer was separated, made acidic by adding conc. hydrochloric acid in an ice bath, and extracted with ethyl acetate. The organic layers were combined, washed successively with water and brine, and dried over magnesium sulfate. The solvent was removed, and the obtained residue was washed with ether to obtain 38.9 mg (0.132 mmol, Yield: 37.2%) of 6-chloro-3-(2-methoxy-3,5,6-trimethylphenoxy)-4-pyridazinol (Compound No. 1128).

$^1$H-NMR (200 MHz, CD$_3$OD) δ ppm: 6.73 (1H, s), 6.67 (1H, s), 3.69 (3H, s), 2.29 (3H, s), 2.15 (3H, s),-2.09 (3H, s). Melting point (° C.): 209-210.

EXAMPLE 624

6-Chloro-3-[2-(1-isopropylvinyl)phenoxy]-4-pyridazinol (Compound No. 2529) and 6-chloro-3-[2-(1,2-dimethyl-1-propenyl)phenoxy]-4-pyridazinol (Compound No. 2542)

(1) 1-[2-(Methoxymethoxy)phenyl]ethanone

In N,N-dimethylformamide (25 mL) was dissolved 3.39 g (24.9 mmol) of commercially available 1-(2-hydroxyphenyl)-ethanone, 1.52 g (38.0 mmol) of 60% sodium hydride was added to the solution in an ice bath, and the resulting mixture was stirred in an ice bath for 20 minutes. To the mixture was gradually added dropwise 3.00 mL (39.5 mmol) of chloro(methoxy)methane, and the resulting mixture was stirred at room temperature overnight. The reaction mixture was poured into water, and extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 4.33 g (24.1 mmol, Yield: 96.8%) of 1-[2-(methoxymethoxy)phenyl]ethanone.

(2) 2-[2-(Methoxymethoxy)phenyl]-3-methyl-2-butanol

In dry tetrahydrofuran (3 mL) was dissolved 1.00 g (5.56 mmol) of 1-[2-(methoxymethoxy)phenyl]ethanone obtained in (1), and under nitrogen atmosphere and ice-cooling, 2.8 mL (5.6 mmol) of a tetrahydrofuran solution containing 2 mol/L isopropylmagnesium bromide was added dropwise. After completion of dropwise addition, the reaction mixture was stirred at room temperature for 1 hour and 30 minutes. The reaction mixture was poured into water, made acidic with diluted hydrochloric acid, and then, extracted with ether. The organic layers were combined, washed successively with water and brine, and dried over anhydrous magnesium sulfate. The solvent was removed, and the obtained residue was purified by silica gel column chromatography (Wako gel C-100, hexane-ethyl acetate, gradient) to obtain 0.522 g (2.33 mmol, Yield: 41.9%) of 2-[2-(methoxymethoxy)phenyl]-3-methyl-2-butanol.

(3) Mixture containing 6-chloro-3-[2-(1-isopropylvinyl)phenoxy]pyridazine 1-oxide and 6-chloro-3-[2-(1,2-dimethyl-1-propenyl)phenoxy]pyridazine 1-oxide, etc.

In dichloromethane (3 mL) was dissolved 0.522 g (2.33 mmol) of 2-[2-(methoxymethoxy)phenyl]-3-methyl-2-butanol obtained in (2), and in an ice bath, 0.50 mL (3.6 mmol) of triethylamine, then, 0.25 mL (3.2 mmol) of methanesulfonyl chloride were added to the solution, and the resulting mixture was stirred at room temperature overnight. The reaction mixture was poured into water, and extracted with dichloromethane. The organic layer was successively washed with water and brine, and dried over anhydrous magnesium sulfate. The solvent was removed, and the residue was purified by silica gel column chromatography (Wako gel C-100, hexane:ethyl acetate, gradient) to obtain 186 mg of a crude product containing 2-(1,2-dimethyl-1-propenyl)phenol, etc. 132 mg of the crude product was mixed with 1,4-dioxane (2 mL) and dimethylsulfoxide (2 mL), and 100 mg (0.893 mmol) of potassium tert-butoxide was added to the mixture. Then, to the mixture was added 119 mg (0.721 mmol) of 3,6-dichloropyridazine 1-oxide, and the resulting mixture was stirred at room temperature for 5 hours. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane:ethyl acetate, gradient) to obtain 220 mg of a mixture containing 6-chloro-3-[2-(1-isopropylvinyl)phenoxy]pyridazine 1-oxide and 6-chloro-3-[2-(1,2-dimethyl-1-propenyl)phenoxy]pyridazine 1-oxide, etc.

(4) 4,6-Dichloro-3-[2-(1-isopropylvinyl)phenoxy]pyridazine and 4,6-dichloro-3-[2-(1,2-dimethyl-1-propenyl)phenoxy]-pyridazine (Step B-3)

In chloroform (0.4 mL) was dissolved 200 mg of a mixture containing 6-chloro-3-[2-(1-isopropylvinyl)phenoxy]pyridazine 1-oxide and 6-chloro-3-[2-(1,2-dimethyl-1-propenyl)phenoxy]pyridazine 1-oxide, etc. obtained in (3), 0.40 mL (4.3 mmol) of phosphorus oxychloride was mixed with the mixture and the resulting mixture was stirred at 70° C. for 2 hours. The reaction mixture was poured into water, and extracted with dichloromethane. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by hexane:acetone =20:1 three times) to obtain 23 mg of 4,6-dichloro-3-[2-(1-isopropylvinyl)phenoxy]pyridazine (purity 86%, containing 14% of 4,6-dichloro-3-[2-(1,2-dimethyl-1-propenyl)phenoxy]pyridazine), and 50 mg of 4,6-dichloro-3-[2-(1,2-dimethyl-1-propenyl)phenoxy]pyridazine (purity 81%, containing 19% of 4,6-dichloro-3-[2-(1-isopropylvinyl)phenoxy]pyridazine).

(5) 6-Chloro-3-[2-(1-isopropylvinyl)phenoxy]-4-pyridazinol (Compound No. 2529, Step A-3 and A-4)

In dimethylsulfoxide (1 mL) was dissolved 23 mg of 4,6-dichloro-3-[2-(1-isopropylvinyl)phenoxy]pyridazine (purity 86%, containing 14% of 4,6-dichloro-3-[2-(1,2-dimethyl-1-propenyl)phenoxy]pyridazine) obtained in (4), 80 mg (0.98 mmol) of sodium acetate was added to the solution and the mixture was stirred at 60° C. for 9 hours. The reaction mixture was cooled, poured into water, and made acidic with diluted hydrochloric acid. The mixture was extracted with ethyl acetate, the organic layers were combined, washed successively with water and brine, and dried over anhydrous magnesium sulfate. The solvent was distilled off and the obtained residue was purified by preparative thin-layer chromatography (available from MERCK CO., 1.05744, 2 plates were used, developed by hexane:ethyl acetate=1:1) to obtain 4.5 mg of 6-chloro-3-[2-(1-isopropylvinyl)phenoxy]-4-pyridazinol (Compound No. 2529, purity 91%, containing 9% 6-chloro-3-[2-(1,2-dimethyl-1-propenyl)phenoxy]-4-pyridazinol). Also, 11.0 mg of 6-chloro-3-[2-(1-isopropylvinyl)phenoxy]-4-pyridazinol (containing 23% 6-chloro-3-[2-(1,2-dimethyl-1-propenyl)phenoxy]-4-pyridazinol) with a purity of 77% was obtained.

$^1$H-NMR (200 MHz, CD$_3$OD) δ ppm: 7.40-7.05 (4H, m), 6.59 (1H, s), 5.90 (1H, s), 5.04 (1H, s), 2.71 (1H, septet, J=6.9 Hz), 0.98 (6H, d, J=6.9 Hz). Appearance: amorphous.

(6) 6-Chloro-3-[2-(1,2-dimethyl-1-propenyl)phenoxy]-4-pyridazinol (Compound No. 2542, Step A-3 and A-4)

In dimethylsulfoxide (2 mL) was dissolved 50 mg of 4,6-dichloro-3-[2-(1,2-dimethyl-1-propenyl)phenoxy]-pyridazine (purity 81%, containing 19% of 4,6-dichloro-3-[2-(1-isopropylvinyl)phenoxy]pyridazine) obtained in (4), 68 mg (0.83 mmol) of sodium acetate was added to the solution and the resulting mixture was stirred at 50° C. for 11 hours. The reaction mixture was cooled, poured into water, and made acidic with diluted hydrochloric acid. The mixture was extracted with ethyl acetate, the organic layers were combined, washed successively with water and brine, and dried over anhydrous magnesium sulfate. The solvent was distilled off and the obtained residue was purified by preparative thin-layer chromatography (available from MERCK CO., 1.05744, 2 plates were used, developed by hexane:ethyl acetate=2:1) to obtain 40.2 mg of 6-chloro-3-[2-(1,2-dimethyl-1-propenyl)phenoxy]-4-pyridazinol (Compound No. 2542, purity 86%, containing 14% of 6-chloro-3-[2-(1-isopropylvinyl)phenoxy]-4-pyridazinol). Also, 3.7 mg of 6-chloro-3-[2-(1,2-dimethyl-1-propenyl)phenoxy]-4-pyridazinol (containing 27% of 6-chloro-3-[2-(1-isopropylvinyl)phenoxy]-4-pyridazinol) with a purity of 73% was obtained.

$^1$H-NMR (200 MHz, CD$_3$OD) δ ppm: 7.38-7.05 (4H, m), 6.59 (1H, s), 1.78 (3H, s), 1.62 (3H, s), 1.46 (3H, s). Appearance: amorphous.

EXAMPLE 625

6-Chloro-3-[2-(2-methyl-1-propenyl)phenoxy]-4-pyridazinol (Compound No. 2540)

(1) 1-(2-Methoxyphenyl)-2-methyl-1-propanol

Dry tetrahydrofuran (3 mL) was added to 1.01 g (7.43 mmol) of commercially available 2-methoxybenzaldehyde under nitrogen atmosphere, and the mixture was ice-cooled. To the mixture was added dropwise a 3.8 mL (7.6 mmol) of tetrahydrofuran solution containing 2 mol/L isopropyl-magnesium bromide. After completion of dropwise addition, the reaction mixture was stirred in an ice bath for 1 hour. The reaction mixture was poured into water, made acidic with diluted hydrochloric acid, and then, extracted with ether. The organic layers were combined, washed successively with water and brine, and dried over anhydrous magnesium sulfate. The solvent was removed, and the obtained residue was purified by silica gel column chromatography (Wako gel C-100, hexane-ethyl acetate, gradient) to obtain 1.00 g (5.56 mmol, Yield: 74.8%) of 1-(2-methoxyphenyl)-2-methyl-1-propanol.

(2) 1-(1-Chloro-2-methylpropyl)-2-methoxybenzene

In dichloromethane (3 mL) was dissolved 630 mg (3.50 mmol) of 1-(2-methoxyphenyl)-2-methyl-1-propanol obtained in (1), and then, 0.70 mL (5.0 mmol) of triethylamine, then 0.35 mL (4.5 mmol) of methanesulfonyl chloride were added to the solution, and the resulting mixture was stirred for 1 hour. The reaction mixture was poured into water, and extracted with dichloromethane. The organic layer was successively washed with water and brine, and dried over anhydrous magnesium sulfate. The solvent was removed to obtain 720 mg of 1-(1-chloro-2-methylpropyl)-2-methoxybenzene.

(3) 1-Methoxy-2-(2-methyl-1-propenyl)benzene

In dry N,N-dimethylformamide (8 mL) was dissolved 410 mg of 1-(1-chloro-2-methylpropyl)-2-methoxybenzene obtained in (2), and to the solution was added 395 mg (3.52 mmol) of potassium tert-butoxide in an ice bath. The reaction mixture was refluxed for 2 hours, then cooled to room temperature, and poured into water. The mixture was extracted with hexane, the obtained organic layers were combined, washed successively with water and brine. The organic layer was dried over anhydrous magnesium sulfate, and the solvent was removed to obtain 460 mg of 1-methoxy-2-(2-methyl-1-propenyl)benzene.

(4) 2-(2-Methyl-1-propenyl)phenol

Under nitrogen atmosphere, in dry N,N-dimethylformamide (3 mL) was suspended 60.0 mg (1.50 mmol) of 60% sodium hydride, and to the suspension was gradually added dropwise 0.11 mL (1.5 mmol) of ethanethiol in an ice bath. After stirring for 10 minutes, a dry N,N-dimethylformamide (0.5 mL) solution containing 200 mg of 1-methoxy-2-(2-methyl-1-propenyl)benzene obtained in (3) was added dropwise to the mixture, and the resulting mixture was refluxed for 2 hours and 30 minutes. After allowing to stand for cooling, the reaction mixture was poured into water, made acidic by adding diluted hydrochloric acid, and extracted with hexane. The organic layers were combined, washed successively with water and brine, and dried over anhydrous magnesium sulfate. The solvent was removed to obtain 220 mg of 2-(2-methyl-1-propenyl)phenol.

(5) Mixture of 6-chloro-3-[2-(2-methyl-1-propenyl)phenoxy]-pyridazine 1-oxide and 3-chloro-6-[2-(2-methyl-1-propenyl)phenoxy]pyridazine 1-oxide (Step B-2)

200 mg of 2-(2-methyl-1-propenyl)phenol obtained in (4), 1,4-dioxane (2 mL) and dimethylsulfoxide (2 mL) were mixed, 151 mg (1.35 mmol) of potassium tert-butoxide was added to the mixture, and the resulting mixture was stirred in an ice bath for 15 minutes. To the mixture was added 207 mg (1.25 mmol) of 3,6-dichloropyridazine 1-oxide, and the mixture was stirred in an ice bath for 15 minutes, and then, at room temperature for 4 hours. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane-ethyl acetate, gradient) to obtain 90.0 mg (0.325 mmol, Yield from 1-(2-methoxyphenyl)-2-methyl-1-propanol: 41.2%) of a mixture of 6-chloro-3-[2-(2-methyl-1-propenyl)phenoxy]pyridazine 1-oxide and 3-chloro-6-[2-(2-methyl-1-propenyl)phenoxy]-pyridazine 1-oxide.

(6) 4,6-Dichloro-3-[2-(2-methyl-1-propenyl)phenoxy]-pyridazine (Step B-3)

In chloroform (0.2 mL) was dissolved 90.0 mg (0.325 mmol) of a mixture of 6-chloro-3-[2-(2-methyl-1-propenyl)phenoxy]pyridazine 1-oxide and 3-chloro-6-[2-(2-methyl-1-propenyl)phenoxy]pyridazine 1-oxide obtained in (5), 0.20 mL (2.2 mmol) of phosphorus oxychloride was mixed with the above mixture, and the resulting mixture was stirred at 70° C. for 2 hours. The reaction mixture was poured into water, extracted with dichloromethane. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed by hexane:ethyl acetate=9:1) to obtain 85.0 mg (0.288 mmol, Yield: 88.6%) of 4,6-dichloro-3-[2-(2-methyl-1-propenyl)phenoxy]pyridazine.

(7) 6-Chloro-3-[2-(2-methyl-1-propenyl)phenoxy]-4-pyridazinol (Compound No. 2540, Step A-3 and A-4)

In dimethylsulfoxide (3 mL) was dissolved 85.0 mg (0.288 mmol) of 4,6-dichloro-3-[2-(2-methyl-1-propenyl)phenoxy] pyridazine obtained in (6), 122 mg (1.49 mmol) of sodium acetate was added to the solution and the resulting mixture was stirred at 120° C. for 2 hours. The reaction mixture was cooled up to room temperature, poured into water, and made acidic with diluted hydrochloric acid. The mixture was extracted with ethyl acetate, and the organic layers were combined, washed successively with water and brine, and dried over anhydrous magnesium sulfate. The solvent was distilled off and the obtained residue was purified by preparative thin-layer chromatography (available from MERCK CO., 1.05744, 2 plates were used, developed by ethyl acetate) to obtain 39.6 mg (0.143 mmol, Yield: 49.7%) of 6-chloro-3-[2-(2-methyl-1-propenyl)phenoxy]-4-pyridazinol (Compound No. 2540).

$^1$H-NMR (200 MHz, $CD_3OD$) δ ppm: 7.35-7.15 (3H, m), 7.15-7.05 (1H, m), 6.65 (1H, s), 6.05 (1H, s), 1.76 (3H, s), 1.70 (3H, s). Melting point (° C.): 149-152.

EXAMPLE 626

6-Chloro-3-(3-hydroxyphenoxy)-4-pyridazinol (Compound No. 2544)

(1) Mixture of 1-{3-[(6-chloro-1-oxide-3-pyridazinyl)oxy]-phenyl}ethanone and 1-{3-[(6-chloro-2-oxide-3-pyridazinyl)oxy]phenyl}ethanone 306 mg (2.25 mmol) of 1-(3-hydroxyphenyl)ethanone, 1,4-dioxane (6 mL) and dimethylsulfoxide (6 mL) were mixed, 297 mg (2.65 mmol) of potassium tert-butoxide was added to the mixture, and the resulting mixture was stirred in an ice bath for 15 minutes. To the mixture was added 342 mg (2.07 mmol) of 3,6-dichloropyridazine 1-oxide in an ice bath, and the resulting mixture was stirred at room temperature for 4 hours. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane-ethyl acetate, gradient) to obtain 400 mg (1.51 mmol, Yield: 72.9%) of a mixture of 1-{3-[(6-chloro-1-oxide-3-pyridazinyl)oxy] phenyl}ethanone and 1-{3-[(6-chloro-2-oxide-3-pyridazinyl)oxy]phenyl}ethanone.

(2) Mixture of 3-[(6-chloro-1-oxide-3-pyridazinyl) oxy]-phenyl acetate and 3-[(6-chloro-2-oxide-3-pyridazinyl)oxy]phenyl acetate In 3 mL of dichloromethane was dissolved was dissolved 400 mg (1.51 mmol) of a mixture of 1-{3-[(6-chloro-1-oxide-3-pyridazinyl)oxy]phenyl}ethanone and 1-{3-[(6-chloro-2-oxide-3-pyridazinyl)oxy]phenyl}ethanone obtained in (1), a dichloromethane (3 mL) solution containing 1.1 g (purity 70-75%, 4.5-4.8 mmol) of m-chloroperbenzoic acid was added to the solution, and the resulting mixture was stirred at room temperature for 4 days. To the reaction mixture was added a saturated aqueous sodium sulfite solution, and after stirring, the mixture was extracted with ethyl acetate. The organic layer was successively washed with water and brine, and dried over anhydrous sodium sulfate. The solvent was removed, and the obtained residue was purified by silica gel column chromatography (Wako gel C-100, hexane-ethyl acetate, gradient) to obtain 330 mg of a mixture of the starting material, 3-[(6-chloro-1-oxide-3-pyridazinyl)oxy]phenyl acetate, and 3-[(6-chloro-2-oxide-3-pyridazinyl)oxy]phenyl acetate. In dichloromethane (3 mL) was dissolved 280 mg of the mixture, 1.1 g (purity 70-75%, 4.5-4.8 mmol) of m-chloroperbenzoic acid was added to the solution, and the resulting mixture was stirred at room temperature overnight. The reaction mixture was poured into 10% aqueous sodium sulfite solution, and extracted with dichloromethane. The organic layer was washed with water, and dried over anhydrous sodium sulfate. The solvent was removed, and the obtained residue was washed with hexane to obtain 310 mg of a mixture of 3-[(6-chloro-1-oxide-3-pyridazinyl)oxy]phenyl acetate and 3-[(6-chloro-2-oxide-3-pyridazinyl)oxy]phenyl acetate.

(3) 3-[(4,6-Dichloro-3-pyridazinyl)oxy]phenyl acetate (Step B-3)

With chloroform (0.4 mL) was mixed 310 mg of a mixture of 3-[(6-chloro-1-oxide-3-pyridazinyl)oxy]phenyl acetate and 3-[(6-chloro-2-oxide-3-pyridazinyl)oxy]phenyl acetate obtained in (2), 0.40 mL (4.3 mmol) of phosphorus oxychloride was mixed with the above mixture, and the resulting mixture was stirred at 70° C. for 3 hours. The reaction mixture was poured into water and after stirring, the mixture was extracted with dichloromethane. The organic layers were combined, washed with water, and dried over anhydrous magnesium sulfate. The solvent was removed, and the obtained residue was purified by silica gel column chromatography (Wako gel C-100, hexane-ethyl acetate, gradient) to obtain 46.0 mg (0.154 mmol, Yield from a mixture of 1-{3-[(6-chloro-1-oxide-3-pyridazinyl)oxy]-phenyl}ethanone and 1-{3-[(6-chloro-2-oxide-3-pyridazinyl)oxy] phenyl}ethanone: 9.6%) of 3-[(4,6-dichloro-3-pyridazinyl) oxy]phenyl acetate.

(4) 6-Chloro-3-(3-hydroxyphenoxy)-4-pyridazinol (Compound No. 2544, Step A-3 and A-4)

In dimethylsulfoxide (1 mL) was dissolved 40.0 mg (0.134 mmol) of 3-[(4,6-dichloro-3-pyridazinyl)oxy]phenyl acetate obtained in (3), 56.0 mg (0.683 mmol) of sodium acetate was added to the solution and the resulting mixture was stirred at 120° C. for 1 hour. After cooling up to room temperature, the reaction mixture was poured into 0.5 mol/L aqueous sodium hydroxide solution, and washed with ethyl acetate. The aqueous layer was made acidic with 4 mol/L hydrochloric acid, and extracted with ethyl acetate. The organic layers were combined, washed successively with water and brine. After drying over anhydrous magnesium sulfate, the solvent was removed to obtain 30 mg (0.126 mmol, Yield: 94.0%) of 6-chloro-3-(3-hydroxyphenoxy)-4-pyridazinol (Compound No. 2544).

$^1$H-NMR (200 MHz, $CD_3OD$) δ ppm: 7.25-7.10 (1H, m), 6.70-6.57 (4H, m). Melting point (° C.): 248-251.

EXAMPLE 627

6-Chloro-3-(2-iodo-3-methoxyphenoxy)-4-pyridazinol (Compound No. 2551)

(1) 1-Methoxy-3-(methoxymethoxy)benzene

In N,N-dimethylformamide(50 mL) was dissolved 3.68 g (29.7 mmol) of commercially available 3-methoxyphenol, 1.81 g (45.4 mmol) of 60% sodium hydride was added to the solution in an ice bath, and the resulting mixture was stirred in an ice bath for 20 minutes. To the mixture was gradually added dropwise in an ice bath 4.05 mL (53.3 mmol) of chloro(methoxy)methane, and the resulting mixture was stirred at room temperature overnight. To the reaction mixture was added a saturated aqueous ammonium chloride solution, and the mixture was extracted with ethyl acetate. The organic layer was successively washed with water and brine, and dried over anhydrous magnesium sulfate. The solvent was removed, and the obtained residue was purified by silica gel column chromatography (Wako gel C-100, hexane-ethyl acetate, gradient) to obtain 4.81 g (28.6 mmol, Yield: 96.3%) of 1-methoxy-3-(methoxymethoxy)benzene.

(2) 2-Iodo-1-methoxy-3-(methoxymethoxy)benzene

In dry ether (50 mL) was dissolved 3.70 g (22.0 mmol) of 1-methoxy-3-(methoxymethoxy)benzene obtained in (1), the solution was cooled to −78° C. under nitrogem atmosphere, and 5.60 mL (37.2 mmol) of tetramethylethylenediamine, then, 22.0 mL (35.2 mmol) of n-butyl lithium-hexane solution (1.60 M) were added to the solution. The resulting mixture was stirred at −78° C. for 30 minutes, then at 0C for 30 minutes, and cooled to −78° C., 9.80 g (38.6 mmol) of iodine was added to the mixture. The mixture was stirred at −78° C. for 30 minutes, a saturated aqueous ammonium chloride solution was added to the reaction mixture, and the mixture was extracted with ethyl acetate. The organic layer was washed with a saturated aqueous sodium thiosulfate solution, and dried over anhydrous magnesium sulfate. The solvent was removed to obtain 6.59 g of 2-iodo-1-methoxy-3-(methoxymethoxy)benzene.

(3) 2-Iodo-3-methoxyphenol

In methanol (70 mL) was dissolved 6.59 g of 2-iodo-1-methoxy-3-(methoxymethoxy)benzene obtained in (2), conc. hydrochloric acid (0.18 mL) was added dropwise to the solution, and the resulting mixture was stirred at 65° C. for 1 hour and 15 minutes. Moreover, conc. hydrochloric acid (0.20 mL) was additionally added thereto, and the resulting mixture was stirred at 65° C. for 2 hours and 40 minutes. The reaction mixture was poured into water, and extracted with ethyl acetate. The organic layer was washed with brine, and dried over anhydrous magnesium sulfate. The solvent was removed, and the obtained residue was purified by silica gel column chromatography (Wako gel C-100, hexane-ethyl acetate, gradient) to obtain 4.61 g (18.4 mmol, Yield from 1-methoxy-3-(methoxymethoxy)benzene: 83.6%) of 2-iodo-3-methoxyphenol.

(4) Mixture of 6-chloro-3-(2-iodo-3-methoxyphenoxy)pyridazine 1-oxide and 3-chloro-6-(2-iodo-3-methoxyphenoxy)pyridazine 1-oxide (Step B-2)

298 mg (1.19 mmol) of 2-iodo-3-methoxyphenol obtained in (3), 1,4-dioxane (2.5 mL) and dimethylsulfoxide (2.5 mL) were mixed, 215 mg (1.92 mmol) of potassium tert-butoxide was added to the mixture, and the resulting mixture was stirred in an ice bath for 10 minutes. To the mixture was added 196 mg (1.19 mmol) of 3,6-dichloropyridazine 1-oxide in an ice bath, and the resulting mixture was stirred at at room temperature for 3 days. To the reaction mixture was added a saturated aqueous ammonium chloride solution, and the mixture was extracted with ethyl acetate. The organic layers were combined, washed successively with water and brine, and dried over anhydrous magnesium sulfate. The solvent was distilled off and the obtained residue was purified by preparative thin-layer chromatography (developed by hexane:ethyl acetate=3:1, then, hexane:ethyl acetate=1:1) to obtain 324 mg (0.855 mmol, Yield: 71.8%) of a mixture of 6-chloro-3-(2-iodo-3-methoxyphenoxy)pyridazine 1-oxide and 3-chloro-6-(2-iodo-3-methoxyphenoxy)pyridazine 1-oxide.

(5) 4,6-Dichloro-3-(2-iodo-3-methoxyphenoxy)pyridazine (Step B-3)

1.0 mL (1.1 mmol) of phosphorus oxychloride was added to 324 mg (0.855 mmol) of a mixture of 6-chloro-3-(2-iodo-3-methoxyphenoxy)pyridazine 1-oxide and 3-chloro-6-(2-iodo-3-methoxyphenoxy)pyridazine 1-oxide obtained in (4), and the resulting mixture was stirred at room temperature overnight. The reaction mixture was poured into water, and extracted with ethyl acetate. The organic layers were combined, washed successively with a saturated aqueous sodium hydrogen carbonate solution and brine, and dried over anhydrous magnesium sulfate. The solvent was removed, and the residue was purified by silica gel column chromatography (Wako gel C-100, hexane-ethyl acetate=5:1) to obtain 225 mg (0.567 mmol, Yield: 66.3%) of 4,6-dichloro-3-(2-iodo-3-methoxyphenoxy)pyridazine.

(6) 6-Chloro-3-(2-iodo-3-methoxyphenoxy)-4-pyridazinol (Compound No. 2551, Step A-3 and A-4)

In dimethylsulfoxide (2 mL) was dissolved 105 mg (0.264 mmol) of 4,6-dichloro-3-(2-iodo-3-methoxyphenoxy)-pyridazine obtained in (5), 118 mg (1.44 mmol) of sodium acetate was added to the solution and the resulting mixture was stirred at 120° C. for 1 hour and 30 minutes. After cooling the mixture up to room temperature, 4 mol/L hydrochloric acid was added to the reaction mixture, and the mixture was extracted with ethyl acetate. The organic layers were combined, and washed with brine. After drying over anhydrous magnesium sulfate, the solvent was removed, and the obtained residue was washed with isopropyl ether to obtain 51.2 mg (0.135 mmol, Yield: 51.1%) of 6-chloro-3-(2-iodo-3-methoxyphenoxy)-4-pyridazinol (Compound No. 2551).

$^1$H-NMR (200 MHz, CD$_3$OD) δ ppm: 7.39 (1H, t, J=8.4 Hz), 6.84 (2H, br.t, J=8.4 Hz), 6.73 (1H, s), 3.90 (3H, s). Melting point (° C.): 231-234.

EXAMPLE 628

6-Chloro-3-{[7-(3-hydroxypropyl)bicyclo[4.2.0]octa-1,3,5-trien-2-yl]oxy}-4-pyridazinol (Compound No. 2555)

(1) 2-Iodo-3-methoxyphenyl trifluoromethanesulfonate

In dry dichloromethane was dissolved 3.75 g (15.0 mmol) of 2-iodo-3-methoxyphenol obtained in Example 627(3), and 7.28 mL (90.0 mmol) of pyridine was added to the solution.

The mixture was cooled to −20° C., 5.40 mL (32.2 mmol) of trifluoromethanesulfonic anhydride was added thereto, and the resulting mixture was stirred for 3 hours and 50 minutes. The reaction mixture was poured into water, and extracted with dichloromethane, then with ethyl acetate. The organic layers were combined, washed successively with 4 mol/L hydrochloric acid, water and brine, and dried over anhydrous magnesium sulfate. The solvent was removed, and the residue was purified by silica gel column chromatography (Wako gel C-100, hexane-ethyl acetate=10:1) to obtain 5.52 g (14.5 mmol, Yield: 96.7%) of 2-iodo-3-methoxyphenyl trifluoromethanesulfonate.

(2) tert-Butyl[(8-methoxy-2,3,4,4a-tetrahydro-8bH-benzo-[3,4]cyclobuta[1,2-b]pyran-8b-yl)oxy]dimethylsilane In dry tetrahydrofuran (15 mL) was dissolved 1.10 g (2.88 mmol) of 2-iodo-3-methoxyphenyl trifluoromethanesulfonate obtained in (1), and 1.00 mL (4.37 mmol) of commercially available tert-butyl(3,4-dihydro-2H-pyran-6-yloxy)dimethylsilane was added to the solution under nitrogen atmosphere. The mixture was cooled to −78° C., 4.50 mL (7.20 mmol) of n-butyl lithium-hexane solution (1.60 M) was added to the mixture and the resulting mixture was stirred for 20 minutes. The reaction mixture was poured into a buffer (prepared by dissolving 9.1 g of $KH_2PO_4$ and 4.3 g of $Na_2HPO_4$ in 1 L of water) with a pH of 7, and extracted with ethyl acetate. The organic layers were combined, washed successively with water and brine, and dried over anhydrous magnesium sulfate. The solvent was removed, and the residue was purified by silica gel column chromatography (Wako gel C-100, hexane-ethyl acetate=50:1) to obtain 0.897 g (2.79 mmol, Yield: 96.9%) of tert-butyl[(8-methoxy-2,3,4,4a-tetrahydro-8bH -benzo[3,4]cyclobuta[1,2-b]pyran-8b-yl) oxy]dimethylsilane.

(3) 8-(3-Hydroxypropyl)-5-methoxybicyclo[4.2.0]octa-1,3,5-trien-7-one

In acetonitrile (12 mL) was dissolved 897 mg (2.79 mmol) of tert-butyl[(8-methoxy-2,3,4,4a-tetrahydro-8bH -benzo[3,4]cyclobuta[1,2-b]pyran-8b-yl)oxy]dimethylsilane obtained in (2), 0.30 mL (7.96-8.30 mmol) of 46-47% hydrofluoric acid aqueous solution was added to the solution in an ice bath, and the resulting mixture was stirred for 30 minutes. The reaction mixture was poured into a saturated aqueous sodium hydrogen carbonate solution, and extracted with ethyl acetate. The organic layers were combined, washed successively with water and brine, and dried over anhydrous magnesium sulfate. The solvent was removed, and the residue was purified by silica gel column chromatography (Wako gel C-100, hexane-ethyl acetate=7:3) to obtain 446 mg (2.17 mmol, Yield: 77.8%) of 8-(3-hydroxypropyl)-5-methoxybicyclo[4.2.0]octa-1,3,5-trien-7-one.

(4) 8-(3-Chloropropyl)-5-methoxybicyclo[4.2.0]octa-1,3,5-trien-7-one

In dichloromethane (22 mL) was dissolved 474 mg (2.30 mmol) of 8-(3-hydroxypropyl)-5-methoxybicyclo[4.2.0]octa-1,3,5-trien-7-one obtained in (3), 467 mg (3.49 mmol) of N-chlorosuccinimide and 917 mg (3.5 mmol) of triphenylphosphine were added to the solution, and the resulting mixture was stirred at room temperature for 1 hour. The reaction mixture was poured into water, a saturated aqueous sodium hydrogen carbonate solution was added thereto, and the mixture was extracted with ethyl acetate. The organic layers were combined, washed with brineand dried over anhydrous magnesium sulfate. The solvent was removed, and the residue was purified by silica gel column chromatography (Wako gel C-100, hexane-ethyl acetate=20:1) to obtain 409 mg (1.82 mmol, Yield: 79.1%) of 8-(3-chloropropyl)-5-methoxybicyclo[4.2.0]octa-1,3,5-trien-7-one.

(5) 7-(3-Chloropropyl)-2-methoxybicyclo[4.2.0]octa-1,3,5-triene

Water (6 mL) was added to 111 mg (0.408 mmol) of mercury chloride ($HgCl_2$) to dissolve therein, 4.00 g (6.12 mmol) of zinc powder was added to the solution and the resulting mixture was stirred at room temperature for 50 minutes. After removing the supernatant, the remained solid was washed once with water. To the material were gradually added water (6.0 mL), and then, conc. hydrochloric acid (5.0 mL), and further added acetic acid (2.4 mL), and finally 409 mg (1.82 mmol) of 8-(3-chloropropyl)-5-methoxybicyclo[4.2.0]octa-1,3,5-trien-7-one obtained in (4) dissolved in toluene (2 mL) and ethanol (2 mL). The mixture was stirred at 115° C. overnight, and cooled up to room temperature. Toluene (20 mL) was added to the mixture and the resulting mixture was stirred at 30 minutes, and the organic layer was separated. The obtained organic layer was washed with water, and dried over anhydrous magnesium sulfate. The solvent was removed, and the residue was purified by silica gel column chromatography (Wako gel C-100, hexane-ethyl acetate=20:1) to obtain 304 mg (1.44 mmol, Yield: 79.1%) of 7-(3-chloropropyl)-2-methoxybicyclo[4.2.0]octa-1,3,5-triene.

(6) 7-(3-Chloropropyl)bicyclo[4.2.0]octa-1,3,5-trien-2-ol

In dichloromethane(2.0 mL) was dissolved 304 mg (1.44 mmol) of 7-(3-chloropropyl)-2-methoxybicyclo[4.2.0]octa-1,3,5-triene obtained in (5), 0.50 mL (5.32 mmol) of boron tribromide was added to the solution in an ice bath with stirring, and the resulting mixture was stirred in an ice bath for 1 hour. The reaction mixture was poured into ice-water and extracted with ethyl acetate. The organic layers were combined, washed with brineand dried over anhydrous magnesium sulfate. The solvent was removed, and the residue was purified by silica gel column chromatography (Wako gel C-100, hexane-ethyl acetate=4:1) to obtain 303 mg (1.54 mmol, Yield: quantitative) of 7-(3-chloropropyl)bicyclo[4.2.0]octa-1,3,5-trien-2-ol.

(7) Mixture of 6-chloro-3-{[7-(3-chloropropyl)bicyclo[4.2.0]octa-1,3,5-trien-2-yl]oxy}pyridazine 1-oxide and 3-chloro-6-{[7-(3-chloropropyl)bicyclo[4.2.0]octa-1,3,5-trien-2-yl]oxy}pyridazine 1-oxide (Step B-2)

303 mg (1.54 mmol) of 7-(3-chloropropyl)bicycle[4.2.0]octa-1,3,5-trien-2-ol obtained in (6), 1,4-dioxane (2.0 mL) and dimethylsulfoxide (2.0 mL) were mixed, 275 mg (2.46 mmol) of potassium tert-butoxide was added to the mixture, and the resulting mixture was stirred in an ice bath for 10 minutes. To the mixture was added 254 mg (1.54 mmol) of 3,6-dichloropyridazine 1-oxide in an ice bath, and the resulting mixture was stirred at room temperature overnight. To the reaction mixture was added a saturated aqueous ammonium chloride solution, and the mixture was extracted with ethyl acetate. The organic layers were combined, washed successively with water and brine, and dried over anhydrous magnesium sulfate. The solvent was distilled off and the obtained residue was purified by preparative thin-layer chromatography (developed by hexane:ethyl acetate=3:1) to obtain 364 mg (1.12 mmol, Yield: 72.7%) of a mixture of 6-chloro-3-{[7-(3-chloropropyl)bicyclo[4.2.0]octa-1,3,5-trien-2-yl]oxy}pyridazine 1-oxide and 3-chloro-6-{[7-(3-chloropropyl)bicyclo[4.2.0]octa-1,3,5-trien-2-yl]oxy}pyridazine 1-oxide.

(8) 4,6-Dichloro-3-{[7-(3-chloropropyl)bicyclo[4.2.0]octa-1,3,5-trien-2-yl]oxy}pyridazine (Step B-3)

1.0 mL (11 mmol) of phosphorus oxychloride was added to 364 mg (1.12 mmol) of a mixture of 6-chloro-3-{[7-(3-chloropropyl)bicyclo[4.2.0]octa-1,3,5-trien-2-yl]oxy}pyridazine 1-oxide and 3-chloro-6-{[7-(3-chloropropyl)bicyclo[4.2.0]octa-1,3,5-trien-2-yl]oxy}pyridazine 1-oxide obtained in (7), and the resulting mixture was stirred at room temperature for 7 hours and 15 minutes. The reaction mixture was poured into water, and extracted with ethyl acetate. The organic layers were combined, washed successively with a saturated aqueous sodium hydrogen carbonate solution and brine, and dried over anhydrous magnesium sulfate. The solvent was distilled off and the residue was purified by preparative thin-layer chromatography (developed by hexane:ethyl acetate=2:1) to obtain 253 mg (0.735 mmol, Yield: 65.6%) of 4,6-dichloro-3-{[7-(3-chloropropyl)bicyclo[4.2.0]octa-1,3,5-trien-2-yl]oxy}pyridazine.

(9) 6-Chloro-3-{[7-(3-hydroxypropyl)bicyclo[4.2.0]octa-1,3,5-trien-2-yl]oxy}-4-pyridazinol (Compound No. 2555, Step A-3 and A-4)

In dimethylsulfoxide (5.0 mL) was dissolved 253 mg (0.735 mmol) of 4,6-dichloro-3-{[7-(3-chloropropyl)bicycle[4.2.0]octa-1,3,5-trien-2-yl]oxy}pyridazine obtained in (8), 250 mg (3.05 mmol) of sodium acetate was added to the solution and the resulting mixture was stirred at 120° C. for 2 hours. After cooling up to room temperature, 4 mol/L hydrochloric acid was added to the reaction mixture, and the mixture was extracted with ethyl acetate. The organic layers were combined, and washed with brine. After drying over anhydrous magnesium sulfate, the solvent was distilled off and the obtained residue was purified by preparative thin-layer chromatography (developed by hexane:ethyl acetate=2:1) to obtain 48.5 mg (0.158 mmol, Yield: 21.5%) of 6-chloro-3-{[7-(3-hydroxypropyl)bicyclo[4.2.0]octa-1,3,5-trien-2-yl]oxy}-4-pyridazinol (Compound No. 2555). Also, 28.2 mg of a mixture of 6-chloro-3-{[7-(3-chloropropyl)bicycle[4.2.0]octa-1,3,5-trien-2-yl]oxy}-4-pyridazinol and 3-{2-[(6-chloro-4-hydroxy-3-pyridazinyl)oxy]bicyclo[4.2.0]octa-1,3,5-trien-7-yl}propyl acetate was obtained.

$^1$H-NMR (200 MHz, CD$_3$OD) δ ppm: 7.22-7.18 (1H, m), 6.98-6.94 (2H, m), 6.70 (1H, s), 3.62-3.56 (2H, m), 3.46 (1H, br.s), 3.34 (1H, br.s), 3.18 (1H, dd, J=13.9, 5.5 Hz), 2.62 (1H, dd, J=13.9, 2.2 Hz), 1.81-1.62 (4H, m). Appearance: oily product.

EXAMPLE 629

6-Chloro-3-[(7,7-dimethylbicyclo[4.2.0]octa-1,3,5-trien-2-yl)oxy]-4-pyridazinol (Compound No. 2556)

(1) 5-Methoxy-8,8-dimethylbicyclo[4.2.0]octa-1,3,5-trien-7-one

In dry tetrahydrofuran(10 mL) was dissolved 723 mg (1.89 mmol) of 2-iodo-3-methoxyphenyl trifluoromethanesulfonate obtainable by the method of Example 628(1), and 0.50 mL (2.47 mmol) of commercially available [(1-methoxy-2-methyl-1-propynyl)oxy](trimethyl)silane was added to the solution under nitrogen atmosphere. The mixture was cooled to −78° C., 2.70 mL (4.32 mmol) of n-butyl lithium-hexane solution (1.60M) was added thereto and the resulting mixture was stirred for 20 minutes. The reaction mixture was poured into a buffer (prepared by dissolving 9.1 g of KH$_2$PO$_4$ and 4.3 g of Na$_2$HPO$_4$ in 1 L of water) with a pH of 7, and extracted with ethyl acetate. The organic layers were combined, washed successively with water and brine, and dried over anhydrous magnesium sulfate. The solvent was removed, and to the residue were added tetrahydrofuran (2.0 mL), water (0.2 mL) and acetic acid (2.0 mL), and the resulting mixture was stirred at room temperature for 1 hour. Ether was added to the reaction mixture, and the mixture was washed successively with a saturated aqueous sodium hydrogen carbonate solution and brine, and dried over anhydrous magnesium sulfate. The solvent was distilled off and the residue was purified by preparative thin-layer chromatography (developed by hexane:ethyl acetate=2:1) to obtain 182 mg (1.03 mmol, Yield: 54.5%) of 5-methoxy-8,8-dimethyl-bicyclo[4.2.0]octa-1,3,5-trien-7-one.

(2) 2-Methoxy-7,7-dimethylbicyclo[4.2.0]octa-1,3,5-triene

Water (6 mL) was added to 109 mg (0.401 mmol) of mercury chloride (HgCl$_2$) to dissolve therein, 3.98 g (6.09 mmol) of zinc powder was added thereto and the resulting mixture was stirred at room temperature for 1 hour. The supernatant was removed, and the remained solid was washed once with water. To the material were gradually added water (6.0 mL), then conc. hydrochloric acid (5.0 mL), and further acetic acid(2.4 mL), and finally 182 mg (1.03 mmol) of 5-methoxy-8,8-dimethylbicyclo[4.2.0]octa-1,3,5-trien-7-one obtained in (1) dissolved in toluene (2 mL) and ethanol (2 mL). The resulting mixture was stirred at 115° C. over-night, and cooled up to room temperature. Toluene (20 mL) was added to the mixture and the mixture was stirred for 20 minutes, and the organic layer was separated. The obtained organic layer was washed with water, and dried over anhydrous magnesium sulfate. The solvent was distilled off and the residue was purified by preparative thin-layer chromatography (developed by hexane:ethyl acetate=25:1) to obtain 85.1 mg (0.525 mmol, Yield: 51.0%) of 2-methoxy-7,7-dimethylbicyclo[4.2.0]octa-1,3,5-triene.

(3) 7,7-Dimethylbicyclo[4.2.0]octa-1,3,5-trien-2-ol

In dichloromethane(5.0 mL) was dissolved 85.1 mg (0.525 mmol) of 2-methoxy-7,7-dimethylbicyclo[4.2.0]octa-1,3,5-triene obtained in (2), 0.20 mL (2.12 mmol) of boron tribromide was added to the solution in an ice bath with stirring, and the resulting mixture was stirred in an ice bath for 2 hours and 10 minutes. The reaction mixture was poured into ice-water and extracted with ethyl acetate. The organic layers were combined, washed successively with water and brine, and dried over anhydrous magnesium sulfate. The solvent was removed to obtain 97.6 mg of 7,7-dimethylbicyclo[4.2.0]octa-1,3,5-trien-2-ol.

(4) 6-Chloro-3-[(7,7-dimethylbicyclo[4.2.0]octa-1,3,5-trien-2-yl)oxy]pyridazine 1-oxide and 3-chloro-6-[(7,7-dimethylbicyclo[4.2.0]octa-1,3,5-trien-2-yl)oxy]pyridazine 1-oxide (Step B-2)

97.6 mg of 7,7-dimethylbicyclo[4.2.0]octa-1,3,5-trien-2-ol obtained in (3), 1,4-dioxane (1.5 mL) and dimethylsulfoxide (1.5 mL) were mixed, 97.8 mg (0.873 mmol) of potassium tert-butoxide was added to the solution, and the resulting mixture was stirred in an ice bath for 10 minutes. To the mixture was added 90.2 mg (0.547 mmol) of 3,6-dichloropyridazine 1-oxide in an ice bath, and the mixture was stirred at room temperature overnight. To the reaction mixture was added a saturated aqueous ammonium chloride solution, and the mixture was extracted with ethyl acetate. The organic layers were combined, washed with brineand dried over anhydrous magnesium sulfate. The solvent was distilled off and the obtained residue was purified by preparative thin-layer chromatography (developed by hexane:ethyl acetate=3:1 two times) to obtain 61.7 mg (0.223 mmol, Yield from 2-methoxy-7,7-dimethylbicyclo[4.2.0]octa-1,3,5-triene: 42.5%) of a mixture of 6-chloro-3-[(7,7-dimethylbicyclo[4.2.0]octa-1,3,5-trien-2-yl)oxy]pyridazine 1-oxide and 3-chloro-6-[(7,7-dimethylbicyclo[4.2.0]octa-1,3,5-trien-2-yl)oxy]-pyridazine 1-oxide.

(5) 4,6-Dichloro-3-[(7,7-dimethylbicyclo[4.2.0]octa-1,3,5-trien-2-yl)oxy]pyridazine(Step B-3)

0.50 mL (5.4 mmol) of phosphorus oxychloride was added to 61.7 mg (0.223 mmol) of a mixture of 6-chloro-3-[(7,7-dimethylbicyclo[4.2.0]octa-1,3,5-trien-2-yl)oxy]-pyridazine 1-oxide and 3-chloro-6-[(7,7-dimethylbicyclo[4.2.0]octa-1,3,5-trien-2-yl)oxy]pyridazine 1-oxide obtained in (4), and the resulting mixture was stirred at room temperature overnight. The reaction mixture was poured into water, and extracted with ethyl acetate. The organic layers were combined, washed successively with a saturated aqueous sodium hydrogen carbonate solution and brine, and dried over anhydrous magnesium sulfate. The solvent was distilled off and the residue was purified by preparative thin-layer chromatography (developed by hexane:ethyl acetate=5:1) to obtain 43.7 mg (0.148 mmol, Yield: 66.4%) of 4,6-dichloro-3-[(7,7-dimethylbicyclo[4.2.0]octa-1,3,5-trien-2-yl)oxy]pyridazine.

(6) 6-Chloro-3-[(7,7-dimethylbicyclo[4.2.0]octa-1,3,5-trien-2-yl)oxy]-4-pyridazinol (Compound No. 2556, Step A-3 and Step A-4)

In dimethylsulfoxide(2.0 mL) was dissolved 43.7 mg (0.148 mmol) of 4,6-dichloro-3-[(7,7-dimethylbicyclo[4.2.0]octa-1,3,5-trien-2-yl)oxy]pyridazine obtained in (5), 63.1 mg (0.770 mmol) of sodium acetate was added to the solution and the resulting mixture was stirred at 120° C. for 2 hours. After cooling up to room temperature, 4 mol/L hydrochloric acid was added to the reaction mixture, and extracted with ethyl acetate. The organic layers were combined, washed successively with water and brine. After drying over anhydrous magnesium sulfate, the solvent was removed, and the obtained residue was washed with isopropyl ether to obtain 31.6 mg (0.114 mmol, Yield: 77.0%) of 6-chloro-3-[(7,7-dimethylbicyclo[4.2.0]octa-1,3,5-trien-2-yl)oxy]-4-pyridazinol (Compound No. 2556).
$^1$H-NMR (200 MHz, CD$_3$OD) δ ppm: 7.26-7.19 (1H, m), 6.97-6.89 (2H, m), 6.71 (1H, s), 2.81 (2H, s), 1.41 (6H, s). Melting point (° C.): 197-199.

EXAMPLE 630

4-[(6-Chloro-4-hydroxy-3-pyridazinyl)oxy]-3-methylphenyl acetate (Compound No. 2572)

(1) Mixture of 1-{4-[(6-chloro-1-oxide-3-pyridazinyl)oxy]-3-methylphenyl}ethanone and 1-{4-[(6-chloro-2-oxide-3-pyridazinyl)oxy]-3-methylphenyl}ethanone (Step B-2)

784 mg (5.23 mmol) of commercially available 1-(4-hydroxy-3-methylphenyl)ethanone, 1,4-dioxane (5 mL) and dimethylsulfoxide (5 mL) were mixed, 938 mg (8.38 mmol) of potassium tert-butoxide was added to the mixture and the resulting mixture was stirred in an ice bath for 10 minutes. To the mixture was added 861 mg (5.22 mmol) of 3,6-dichloropyridazine 1-oxide in an ice bath, and the mixture was stirred at room temperature overnight. To the reaction mixture was added a saturated aqueous ammonium chloride solution, and the mixture was extracted with ethyl acetate. The organic layers were combined, washed successively with water and brine, and dried over anhydrous magnesium sulfate. The solvent was removed, and the residue was purified by silica gel column chromatography (Wako gel C-100, hexane-ethyl acetate=5:1) to obtain 758 mg (2.74 mmol, Yield: 52.5%) of a mixture of 1-{4-[(6-chloro-1-oxide-3-pyridazinyl)oxy]-3-methylphenyl}ethanone and 1-{4-[(6-chloro-2-oxide-3-pyridazinyl)oxy]-3-methylphenyl}ethanone.

(2) Mixture of 4-[(6-chloro-1-oxide-3-pyridazinyl)oxy]-3-methylphenyl acetate and 4-[(6-chloro-2-oxide-3-pyridazinyl)oxy]-3-methylphenyl acetate In 1,2-dichloroethane (13 mL) was dissolved 758 mg (2.74 mmol) of a mixture of 1-{4-[(6-chloro-1-oxide-3-pyridazinyl)oxy]-3-methylphenyl}ethanone and 1-{4-[(6-chloro-2-oxide-3-pyridazinyl)oxy]-3-methylphenyl}ethanone obtained in (1), a dichloromethane (3 mL) solution containing 1.1 g (purity 70-75%, 4.5-4.8 mmol) of m-chloroperbenzoic acid was added to the solution, and the resulting mixture was stirred at room temperature for 4 hours and 45 minutes. Moreover, 1.20 g (purity 70-75%, 4.86-5.20 mmol) of m-chloroperbenzoic acid was added to the mixture, and the mixture was stirred at room temperature overnight. The reaction mixture was poured into 10% aqueous sodium sulfite solution, and extracted with ethyl acetate. The organic layer was washed successively with a saturated aqueous sodium carbonate and brine, and dried over anhydrous sodium sulfate. The solvent was removed, and the residue was purified by silica gel column chromatography (Wako gel C-100, hexane-ethyl acetate=5:1) to obtain the starting material and 330 mg of a mixture of 3-[(6-chloro-1-oxide-3-pyridazinyl)oxy]-phenyl acetate and 3-[(6-chloro-2-oxide-3-pyridazinyl)oxy]-phenyl acetate. In dichloromethane (3 mL) was dissolved 280 mg of the mixture, 2.62 g (purity 70-75%, 10.6-11.4 mmol) of m-chloroperbenzoic acid was added to the solution, and the resulting mixture was stirred at room temperature for 4 hours and 45 minutes. Moreover, 1.20 g (purity 70-75%, 4.86-5.20 mmol) of m-chloroperbenzoic acid was added to the mixture, and the mixture was stirred at room temperature overnight. The reaction mixture was poured into 10% aqueous sodium sulfite solution, and extracted with ethyl acetate. The organic layer was washed successively with a saturated aqueous sodium carbonate and a saturated saline solution, and dried over anhydrous sodium sulfate. The solvent was removed, and the residue was purified by silica gel column chromatography (Wako gel C-100, hexane-ethyl acetate=5:1) to obtain the starting material and 622 mg of a mixture of 4-[(6-chloro-1-oxide-3-pyridazinyl)oxy]-3-methylphenyl acetate and 4-[(6-chloro-2-oxide-3-pyridazinyl)oxy]-3-methylphenyl acetate. 0.5 mL (4.85 mmol) of 30% hydrogen peroxide aqueous solution was mixed with 1,2-dichloroethane (2.2 mL), 3.2 mL (22.7 mmol) of trifluoroacetic anhydride was added dropwise thereto in an ice bath, and the resulting mixture was stirred at room temperature. In an ice bath, this mixture was added to the mixture of the starting material, 4-[(6-chloro-1-oxide-3-pyridazinyl)oxy]-3-methylphenyl acetate, and 4-[(6-chloro-2-oxide-3-pyridazinyl)oxy]-3-methylphenyl acetate, which was previously obtained and dissolved in 1,2-dichloroethane (2.2 mL), and the resulting mixture was stirred in an ice bath for 1 hour, and at room temperature overnight. The reaction mixture was poured into 10% aqueous sodium sulfite solution, and extracted with ethyl acetate. The organic layer was washed successively with a saturated aqueous sodium carbonate, water and brine, and dried over anhydrous sodium sulfate. The solvent was removed, and the residue was purified by silica gel column chromatography (Wako gel C-100, hexane-ethyl acetate gradient) to obtain 413 mg (1.40 mmol, Yield: 51.1%) of a mixture of 4-[(6-chloro-1-oxide-3-pyridazinyl)oxy]-3-methylphenyl acetate and 4-[(6-chloro-2-oxide-3-pyridazinyl)oxy]-3-methylphenyl acetate.

(3) 4-[(4,6-Dichloro-3-pyridazinyl)oxy]-3-methylphenyl acetate (Step B-3)

In chloroform(2 mL) was dissolved 413 mg (1.40 mmol) of a mixture of 4-[(6-chloro-1-oxide-3-pyridazinyl)oxy]-3-methylphenyl acetate and 4-[(6-chloro-2-oxide-3-pyridazinyl)oxy]-3-methylphenyl acetate obtained in (2), 2.0 mL (22 mmol) of phosphorus oxychloride was mixed with the solution, and the resulting mixture was stirred at 80° C. for 3 hours. The reaction mixture was diluted with dichloromethane, and then, poured into water. The mixture was extracted with dichloromethane, and then, with ethyl acetate. The organic layers were combined, washed successively with a saturated aqueous sodium hydrogen carbonate solution and brine, and dried over anhydrous magnesium sulfate. The solvent was removed, and the obtained residue was purified by silica gel column chromatography (Wako gel C-100, hexane-ethyl acetate, hexane-ethyl acetate=6:1) to obtain 336 mg (1.07 mmol, Yield: 76.4%) of 4-[(4,6-dichloro-3-pyridazinyl) oxy]-3-methylphenyl acetate.

(4) 4-[(6-Chloro-4-hydroxy-3-pyridazinyl)oxy]-3-methylphenyl acetate (Compound No. 2572, Step A-3 and Step A-4)

In dimethylsulfoxide (1.5 mL) was dissolved 160 mg (0.511 mmol) of 4-[(4,6-dichloro-3-pyridazinyl)oxy]-3-methylphenyl acetate obtained in (3), 136 mg (1.66 mmol) of sodium acetate was added to the solution and the resulting mixture was stirred at 120° C. for 2 hours. After cooling up to room temperature, 4 mol/L hydrochloric acid was added to the reaction mixture, and the mixture was extracted with ethyl acetate. The organic layers were combined, washed successively with water and brine. After drying over anhydrous magnesium sulfate, the solvent was removed, and the obtained residue was washed with isopropyl ether to obtain 37.3 mg (0.126 mmol, Yield: 24.7%) of 4-[(6-chloro-4-hydroxy-3-pyridazinyl)oxy]-3-methylphenyl acetate (Compound No. 2572).

$^1$H-NMR (200 MHz, CD$_3$OD) δ ppm: 7.13-6.94 (3H, m), 6.70 (1H, s), 2.27 (3H, s), 2.17 (3H, s). Melting point (° C.): 255 (dec.).

EXAMPLE 631

6-Chloro-3-[2-(difluoromethyl)-6-methylphenoxy]-4-pyridazinol (Compound No. 2576)

(1) 2-(methoxymethoxy)-3-methylbenzaldehyde

In N,N-dimethylformamide(50 mL) was dissolved 4.96 g (36.5 mmol) of 2-hydroxy-3-methylbenzaldehyde, 2.19 g (54.6 mmol) of 60% sodium hydride was added to the solution in an ice bath and the resulting mixture was stirred for 10 minutes. To the mixture was added 3.59 mL (47.3 mmol) of chloro(methoxy)methane in an ice bath, and the resulting mixture was stirred at room temperature for 1 hour and 30 minutes. The reaction mixture was poured into a saturated aqueous ammonium chloride solution, and extracted with ethyl acetate. The organic layers were combined, washed successively with water and brine, and dried over anhydrous sodium sulfate. The solvent was removed, and the residue was purified by silica gel column chromatography (Daisogel 1001W, hexane:ethyl acetate=50:1) to obtain 6.60 g (36.6 mmol, Yield: 100%) of 2-(methoxymethoxy)-3-methylbenzaldehyde.

(2) 1-(Difluoromethyl)-2-(methoxymethoxy)-3-methylbenzene

In dichloromethane(10 mL) was dissolved 589 mg (3.27 mmol) of 2-(methoxymethoxy)-3-methylbenzaldehyde obtained in (1), 0.863 mL (6.52 mmol) of (diethylamino) sulfur trifluoride (DAST) was added to the solution under nitrogen atmosphere, and the resulting mixture was stirred at room temperature for 3 hours. After allowing to stand at room temperature overnight, the reaction mixture was poured into water, and extracted with dichloromethane. The organic layers were combined, washed with water, and dried over anhydrous sodium sulfate. The solvent was removed, and the residue was purified by silica gel column chromatography (Daisogel 1001W, hexane:ethyl acetate=10:1) to obtain 229 mg (1.13 mmol, Yield: 34.6%) of 1-(difluoromethyl)-2-(methoxymethoxy)-3-methylbenzene.

(3) 2-(Difluoromethyl)-6-methylphenol

In methanol (5 mL) was dissolved 229 mg (1.13 mmol) of 1-(difluoromethyl)-2-(methoxymethoxy)-3-methylbenzene obtained in (2), two drops of conc. hydrochloric acid was added to the solution at room temperature and the resulting mixture was stirred at 60° C. for 30 minutes. The reaction mixture was cooled to room temperature, and the solvent was removed under reduced pressure. Ethyl acetate was added to the residue, and the mixture was washed with brineand dried over anhydrous sodium sulfate. The solvent was removed to obtain 135 mg (0.854 mmol, Yield: 75.6%) of 2-(difluoromethyl)-6-methylphenol.

(4) 6-Chloro-3-[2-(difluoromethyl)-6-methylphenoxy]pyridazine 1-oxide and 3-chloro-6-[2-(difluoromethyl)-6-methylphenoxy]pyridazine 1-oxide (Step B-1)

In 1,4-dioxane (1.5 mL) and dimethylsulfoxide (1.5 mL) was dissolved 135 mg (0.854 mmol) of 2-(difluoromethyl)-6-methylphenol obtained in (3), 115 mg (1.03 mmol) of potassium tert-butoxide was added to the mixture in an ice bath, and the resulting mixture was stirred for 5 minutes. To the mixture was added 141 mg (0.855 mmol) of 3,6-dichloropyridazine 1-oxide in an ice bath, and the mixture was stirred at room temperature overnight. The reaction mixture was poured into water, and extracted with ethyl acetate. The organic layers were combined, washed successively with water and brine, and dried over anhydrous sodium sulfate. The solvent was removed, and the obtained residue was purified by silica gel column chromatography (eluted by hexane: ethyl acetate=2:1) and by preparative thin-layer chromatography (available from MERCK CO., 1.05744, 3 plates were used, developed by hexane:ethyl acetate=2:1) to obtain 28.6 mg (0.0997 mmol, Yield: 11.7%) of a mixture of 6-chloro-3-

[2-(difluoromethyl)-6-methylphenoxy]pyridazine 1-oxide and 3-chloro-6-[2-(difluoromethyl)-6-methylphenoxy]pyridazine 1-oxide.

(5) 4,6-Dichloro-3-[2-(difluoromethyl)-6-methylphenoxy]pyridazine(Step B-3)

In chloroform(0.5 mL) was dissolved 28.6 mg (0.0997 mmol) of a mixture of 6-chloro-3-[2-(difluoromethyl)-6-methylphenoxy]pyridazine 1-oxide and 3-chloro-6-[2-(difluoromethyl)-6-methylphenoxy]pyridazine 1-oxide obtained in (4), 76.5 mg (0.50 mmol) of phosphorus oxychloride was added to the solution and the resulting mixture was refluxed for 8 hours. After allowing to stand at room temperature overnight, water and dichloromethane were added to the reaction mixture, and the resulting mixture was stirred for 30 minutes. The mixture was extracted with dichloromethane, the organic layers were combined, washed with water, and dried over anhydrous sodium sulfate. The solvent was distilled off and the residue was purified by preparative thin-layer chromatography (available from MERCK CO., 1.05744, developed by hexane:ethyl acetate=4:1) to obtain 19.1 mg (0.0626 mmol, Yield: 62.8%) of 4,6-dichloro-3-[2-(difluoromethyl)-6-methylphenoxy]pyridazine.

(6) 6-Chloro-3-[2-(difluoromethyl)-6-methylphenoxy]-4-pyridazinol (Compound No. 2576)

In dimethylsulfoxide(0.5 mL) was dissolved 19.1 mg (0.0626 mmol) of 4,6-dichloro-3-[2-(difluoromethyl)-6-methylphenoxy]pyridazine obtained in (5), 25.7 mg (0.313 mmol) of sodium acetate was added to the solution and the resulting mixture was stirred at 120° C. for 2 hours. After cooling up to room temperature, water was added to the reaction mixture, and the mixture was extracted with ethyl acetate. The organic layers were combined, washed successively with water and brine. After drying over anhydrous sodium sulfate, the solvent was distilled off and the obtained residue was purified by preparative thin-layer chromatography (available from MERCK CO., 1.05744, developed by ethyl acetate) to obtain 17.8 mg (0.0620 mmol, Yield: 99.0%) of 6-chloro-3-[2-(difluoromethyl)-6-methylphenoxy-4-pyridazinol (Compound No. 2576).

$^1$H-NMR (200 MHz, CD$_3$OD) δ ppm: 7.55-7.25 (3H, m), 6.83 (1H, t, J=55.1 Hz). 2.15 (3H, s). Melting point (° C.): 204-205.

EXAMPLE 632

6-Chloro-3-[2,4-dibromo-5-(ethylsulfanyl)phenoxy]-4-pyridazinol (Compound No. 2596)

(1) 4,6-Dichloro-3-[2,4-dibromo-5-(ethylsulfanyl)phenoxy]pyridazine 2.05 g (8.84 mmol) of commercially available 1-bromo-2-methoxy-4-nitrobenzene and water (200 mL) were mixed, and 11.4 g (213 mmol) of ammonium chloride, then 4.78 g (73.2 mmol) of zinc powder were added to the mixture. After stirring at room temperature for 5 hours, the mixture was filtered through Celite, and the filtrate was extracted with ethyl acetate. The organic layers were combined, washed successively with water and brine, and dried over anhydrous magnesium sulfate. The solvent was removed to obtain 1.78 g of the residue.

The residue was mixed with water (9 mL) and 47% hydrobromic acid aqueous solution (3 mL), an aqueous solution (3.6 mL of water) containing 655 mg (9.49 mmol) of sodium nitrite was added dropwise to the mixture in an ice bath with stirring. After completion of the dropwise addition, the mixture was stirred for 10 minutes, and 973 mg (6.80 mmol) of cuprous bromide dissolved in 47% hydrobromic acid aqueous solution (3.6 mL) was added dropwise to the mixture. The reaction mixture was stirred at 110° C. for 2 hours and 30 minutes, then cooled up to room temperature, water was added thereto and the mixture was extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane: ethyl acetate=10:1) and by preparative thin-layer chromatography (available from MERCK CO., 1.05717, developed multiply by hexane:ethyl acetate=4:1) to obtain 751 mg of a crude product.

Under nitrogen atmosphere, in dry N,N-dimethylformamide (5 mL) was suspended 339 mg (8.46 mmol) of 60% sodium hydride, and 0.65 mL (8.78 mmol) of ethanethiol was gradually added dropwise to the suspension. After stirring for 30 minutes, 751 mg of the previously obtained crude product dissolved in N,N-dimethylformamide (8 mL) was added to the mixture, and the resulting mixture was stirred at 160° C. for 5 hours. After the reaction mixture was allowed to stand at room temperature overnight, it was poured into water, made acidic by adding diluted hydrochloric acid, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed multiply by hexane:ethyl acetate=4:1) to obtain 109 mg of a phenolic crude product.

109 mg of the obtained phenolic crude product was mixed with 1,4-dioxane (3 mL) and dimethylsulfoxide (3 mL), 53.5 mg (0.478 mmol) of potassium tert-butoxide was added to the mixture, and the resulting mixture was stirred in an ice bath for 15 minutes. To the mixture was added 71.2 mg (0.432 mmol) of 3,6-dichloropyridazine 1-oxide in an ice bath, and the resulting mixture was stirred at room temperature overnight. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 3 plates were used, developed multiply by hexane: ethyl acetate=2:1) to obtain 71.5 mg of an etheric crude product.

In phosphorus oxychloride (3 mL) was dissolved 44.8 mg of the etheric crude product, and the resulting mixture was stirred at 60° C. for 21 hours. Water and dichloromethane were added to the reaction mixture and after stirring, the mixture was extracted with dichloromethane. The organic layers were combined, washed with water, and dried over anhydrous magnesium sulfate. The solvent was distilled off and the residue was purified by preparative thin-layer chromatography (available from MERCK CO., 1.05744, 2 plates were used, developed by hexane:ethyl acetate=2:1) to obtain 14.4 mg (0.0314 mmol, Yield: 0.567%) of 4,6-dichloro-3-[2,4-dibromo-5-(ethylsulfanyl)phenoxy]pyridazine.

(2) 6-Chloro-3-[2,4-dibromo-5-(ethylsulfanyl)phenoxy]-4-pyridazinol (Compound No. 2596, Step A-3 and A-4)

In dimethylsulfoxide (3 mL) was dissolved 33.4 mg (0.0728 mmol) of 4,6-dichloro-3-[2,4-dibromo-5-(ethylsulfanyl)phenoxy]pyridazine obtained in (1), 29.8 mg (0.363 mmol) of sodium acetate was added to the solution and the resulting mixture was stirred at 120° C. for 4 hours and 30 minutes. After allowing to stand at room temperature overnight, water was added to the reaction mixture, the mixture was made acidic by adding diluted hydrochloric acid, and extracted with ethyl acetate. The organic layers were combined, washed successively with water and brine. After drying over anhydrous magnesium sulfate, the solvent was distilled off and the obtained residue was purified by preparative thin-layer chromatography (available from MERCK Co., 1.05744, developed multiply by ethyl acetate) to obtain 13.1 mg (0.0297 mmol, Yield: 40.8%) of 6-chloro-3-[2,4-dibromo-5-(ethylsulfanyl)phenoxy]-4-pyridazinol (Compound No. 2596).

$^1$H-NMR (200 MHz, CD$_3$OD) δ ppm: 7.84 (1H, s), 7.21 (1H, s) 6.72 (1H, s), 2.97 (2H, q, J=7.3 Hz), 1.33 (3H, t, J=7.3 Hz). Melting point (° C.): 225-228.

EXAMPLE 633

6-Chloro-3-(2,3,5-trimethyl-6-vinylphenoxy)-4-pyridazinol (Compound No. 2603)

(1) 1-(2-Methoxy-3,4,6-trimethylphenyl)ethanone

In acetone (30 mL) was dissolved 2.00 g (11.2 mmol) of 1-(2-hydroxy-3,4,6-trimethylphenyl)ethanone which can be produced by the method disclosed in Chemical Research in Toxicology, 1997, vol. 10, No. 3, pp. 335-343, 3.10 g (22.4 mmol) of potassium carbonate, then 1.40 mL (22.5 mmol) of methyl iodide were added to the solution, and the resulting mixture was refluxed for 5 hours. After cooling to room temperature, the reaction mixture was concentrated, and the residue was poured into water, and extracted with ethyl acetate. The organic layers were combined, washed successively with water and brine, and dried over anhydrous magnesium sulfate. The solvent was removed, and the residue was purified by silica gel column chromatography (Wako gel C-100, hexane:ethyl acetate gradient) to obtain 1.90 g (9.90 mmol, Yield: 88.4%) of 1-(2-methoxy-3,4,6-trimethylphenyl)ethanone.

(2) 1-(2-Methoxy-3,4,6-trimethylphenyl)ethanol

In methanol (8 mL) was dissolved 1.00 g (5.21 mmol) of 1-(2-methoxy-3,4,6-trimethylphenyl)ethanone obtained in (1), and 170 mg (4.50 mmol) of sodium borohydride was added to the solution little by little with stirring. After confirmation of disappearance of the starting materials by thin layer chromatography (TLC) for analysis, the reaction mixture was poured into water, and made acidic by adding hydrochloric acid. The mixture was extracted with hexane, the organic layers were combined, washed successively with water and brine, and dried over anhydrous magnesium sulfate. The solvent was removed to obtain 1.0 g of 1-(2-methoxy-3,4,6-trimethylphenyl)ethanol.

(3)
2-(l-Chloroethyl)-3-methoxy-1,4,5-trimethylbenzene

In dichloromethane(10 mL) was dissolved 1.0 g of 1-(2-methoxy-3,4,6-trimethylphenyl)ethanol obtained in (2), and 1.10 mL (7.91 mmol) of triethylamine, then, 0.56 mL (7.21 mmol) of methanesulfonyl chloride were added to the solution in an ice bath with stirring. The reaction mixture was stirred at room temperature for 20 minutes, poured into water, and extracted with dichloromethane. The organic layers were combined, washed successively with water and brine, and dried over anhydrous magnesium sulfate. The solvent was removed to obtain 1.2 g of 2-(1-chloroethyl)-3-methoxy-1,4, 5-trimethylbenzene.

(4) 3-Methoxy-1,2,5-trimethyl-4-vinylbenzene

In dry N,N-dimethylformamide (12 mL) was dissolved 1.2 g of 2-(1-chloroethyl)-3-methoxy-1,4,5-trimethylbenzene obtained in (3), and 1.14 g (10.2 mmol) of potassium tertbutoxide was added to the solution in an ice bath with stirring. The reaction mixture was stirred at room temperature for 30 minutes, then, under reflux for 30 minutes. After cooling to room temperature, the mixture was poured into water, and extracted with hexane. The organic layers were combined, washed successively with water and brine, and dried over anhydrous magnesium sulfate. The solvent was removed to obtain 870 mg of 3-methoxy-1,2,5-trimethyl-4-vinylbenzene.

(5) 2,3,5-Trimethyl-6-vinylphenol and 2-[1-(ethylsulfanyl)ethyl]-3,5,6-trimethylphenol Under nitrogen atmosphere, in dry N,N-dimethylformamide (8 mL) was suspended 270 mg (6.75 mmol) of 60% sodium hydride, and 0.60 mL (8.10 mmol) of ethanethiol was gradually added dropwise to the suspension. After stirring for 15 minutes, 400 mg (2.27 mmol) of 3-methoxy-1,2,5-trimethyl-4-vinylbenzene obtained in (4) and dissolved in dry N,N-dimethylformamide (1.5 mL) was added to the mixture, and the resulting mixture was refluxed for 1 hour. After cooling to room temperature, the reaction mixture was poured into water, made acidic by adding hydrochloric acid, and extracted with hexane. The organic layers were combined, washed successively with water and brine, and dried over anhydrous magnesium sulfate. The solvent was removed, and the residue was purified by silica gel column chromatography (Wako gel C-100, hexane:ethyl acetate=20:1) and by preparative thin-layer chromatography (available from MERCK CO., 1.05744, developed by hexane:ethyl acetate=8:1) to obtain 63.0 mg (0.389 mmol, Yield from 1-(2-methoxy-3,4, 6-trimethylphenyl)ethanone: 16.2%) of 2,3,5-trimethyl-6-vinylphenol and 330 mg (1.47 mmol, Yield from 1-(2-methoxy-3,4,6-trimethylphenyl)ethanone: 61.4%) of 2-[1-(ethylsulfanylethyl]-3,5,6-trimethylphenol.

(6) Mixture of 6-chloro-3-(2,3,5-trimethyl-6-vinylphenoxy)pyridazine 1-oxide and 3-chloro-6-(2,3, 5-trimethyl-6-vinylphenoxy)pyridazine 1-oxide
(Step B-2)

In 1,4-dioxane (0.4 mL) and dimethylsulfoxide (0.4 mL) was dissolved 43.0 mg (0.265 mmol) of 2,3,5-trimethyl-6-vinylphenol obtained in (5), 36.0 mg (0.321 mmol) of potassium tert-butoxide was added to the mixture in an ice bath, and the resulting mixture was stirred for 10 minutes. To the mixture was added 47.6 mg (0.288 mmol) of 3,6-dichloropyridazine 1-oxide in an ice bath, and the mixture was stirred at room temperature for 4 hours. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 2 plates were used, developed by hexane:ethyl acetate=2:1) to obtain 27.6 mg (0.0949 mmol, Yield: 35.8%) of a mixture of 6-chloro-3-(2, 3,5-trimethyl-6-vinylphenoxy)pyridazine 1-oxide and 3-chloro-6-(2,3,5-trimethyl-6-vinylphenoxy)pyridazine 1-oxide.

(7) 4,6-Dichloro-3-(2,3,5-trimethyl-6-vinylphenoxy) pyridazine (Step B-3)

0.02 mL (0.22 mmol) of phosphorus oxychloride was added to 27.6 mg (0.0949 mmol) of a mixture of 6-chloro-3-(2,3,5-trimethyl-6-vinylphenoxy)pyridazine 1-oxide and 3-chloro-6-(2,3,5-trimethyl-6-vinylphenoxy)pyridazine 1-oxide obtained in (6), and the resulting mixture was stirred at room temperature for 2 hours. To the mixture was added 0.4 mL of chloroform, and the resulting mixture was stirred at room temperature overnight. The reaction mixture was concentrated, 0.2 mL (2.2 mmol) of phosphorus oxychloride was added to the residue and the resulting mixture was stirred at room temperature for 5 hours. The reaction mixture was concentrated, the residue was purified by preparative thin-layer chromatography (available from MERCK CO., 1.05744, 1 plate was used, developed by hexane:ethyl acetate=5:1) to obtain 5.0 mg (0.016 mmol, Yield: 17%) of 4,6-dichloro-3-(2,3,5-trimethyl-6-vinylphenoxy)pyridazine.

(8) 6-Chloro-3-(2,3,5-trimethyl-6-vinylphenoxy)-4-pyridazinol (Compound No. 2603, Step A-3 and Step A-4)

In dimethylsulfoxide(1 mL) was dissolved 5.0 mg (0.016 mmol) of 4,6-dichloro-3-(2,3,5-trimethyl-6-vinylphenoxy)pyridazine obtained in (7), 10.3 mg (0.126 mmol) of sodium acetate was added to the solution and the resulting mixture was stirred at 120° C. for 2 hours. After cooling to room temperature, the reaction mixture was poured into water, made acidic by adding hydrochloric acid, and extracted with ethyl acetate. The organic layers were combined, washed successively with water and brine. After drying over anhydrous magnesium sulfate, the solvent was distilled off and the obtained residue was purified by preparative thin-layer chromatography (available from MERCK CO., 1.05744, 1 plate was used, developed by ethyl acetate) to obtain 1.5 mg (0.0052 mmol, Yield: 33%) of 6-chloro-3-(2,3,5-trimethyl-6-vinylphenoxy)-4-pyridazinol (Compound No. 2603).

$^1$H-NMR (200 MHz, CD$_3$OD) δ ppm: 7.25 (1H, s), 6.67 (1H, dd, J=11.0 Hz, 17.6 Hz), 6.56 (1H, s), 5.66 (1H, dd, J=1.5 Hz, 17.6 Hz), 5.10 (1H, dd, J=1.5 Hz, 11.0 Hz), 2.29 (3H, s), 2.20 (3H, s), 2.04 (3H, s). Appearance: amorphous.

EXAMPLE 634

6-Chloro-3-{2-[1-(ethylsulfanyl)ethyl]-3,5,6-trimethylphenoxy}-4-pyridazinol (Compound No. 2606)

(1) 6-Chloro-3-{2-[1-(ethylsulfanyl)ethyl]-3,5,6-trimethylphenoxy}-4-methoxypyridazine(Step D-1)

In a mixed solvent of 1,4-dioxane (2 mL) and dimethylsulfoxide (2 mL) was dissolved 150 mg (0.670 mmol) of 2-[1-(ethylsulfanyl)ethyl]-3,5,6-trimethylphenol obtained in Example 633(5), 93 mg (0.83 mmol) of potassium tert-butoxide was added to the solution in an ice bath, and the resulting mixture was stirred at room temperature for 20 minutes. The mixture was again cooled in an ice bath, 120 mg (0.670 mmol) of 3,6-dichloro-4-methoxypyridazine was added to the mixture, and the resulting mixture was stirred at room temperature overnight. The reaction mixture was poured into water, and extracted with ethyl acetate. The organic layers were combined, washed successively with water and brine, and dried over anhydrous magnesium sulfate. The solvent was removed, and the obtained residue was purified by silica gel chromatography (Wakogel C-100, hexane-ethyl acetate, gradient) and by preparative thin-layer chromatography (available from MERCK CO., 1.05744, 2 plates were used, developed by hexane:ethyl acetate=2:1) to obtain 26.7 mg (0.0728 mmol, Yield: 10.9%) of 6-chloro-3-{2-[1-(ethylsulfanyl)ethyl]-3,5,6-trimethylphenoxy}-4-methoxypyridazine. Also, 60.0 mg (0.163 mmol, Yield: 24.3%) of 3-chloro-6-{2-[1-(ethylsulfanyl)ethyl]-3,5,6-trimethylphenoxy}-4-methoxypyridazine was obtained.

(2) 6-Chloro-3-{2-[1-(ethylsulfanyl)ethyl]-3,5,6-trimethylphenoxy}-4-pyridazinol (Compound No. 2606, Step D-2)

In dimethylsulfoxide (1 mL) was dissolved 34.0 mg (0.358 mmol) of 2-hydroxypyridine, 41.0 mg (0.366 mmol) of potassium tert-butoxide was added to the solution at room temperature, and the resulting mixture was stirred at room temperature for 20 minutes. To the mixture was added a dimethylsulfoxide (1 mL) solution containing 26.7 mg (0.0728 mmol) of 6-chloro-3-{2-[1-(ethylsulfanyl)ethyl]-3,5,6-trimethylphenoxy}-4-methoxypyridazine obtained in (1), and the resulting mixture was stirred at 60° C. After completion of the reaction, the reaction mixture was allowed to stand for cooling, and poured into water. After making the mixture acidic by adding hydrochloric acid to the mixture, and the mixture was extracted with ethyl acetate. The organic layers were combined, and washed successively with water and brine. After drying over anhydrous magnesium sulfate, the solvent was removed. The obtained residue was purified by preparative thin-layer chromatography (available from Merck Co., 1.05744, developed by ethyl acetate) to obtain 6.6 mg (0.019 mmol, Yield: 26%) of 6-chloro-3-{2-[1-(ethylsulfanyl)ethyl]-3,5,6-trimethylphenoxy}-4-pyridazinol (Compound No. 2606).

$^1$H-NMR (200 MHz, CD$_3$OD) δ ppm: 7.20 (2H, s), 6.64 (1H, s), 2.40-2.15 (8H, m), 2.03 (3H, s), 1.40 (3H, d, J=7.0 Hz), 1.24 (1H, m), 1.03 (3H, t, J=7.3 Hz). Appearance: amorphous.

EXAMPLE 635

6-Chloro-3-(2-cyclopropyl-6-methylphenoxy)-4-pyridazinyl 4-(2,4-dichlorobenzoyl)-1,3-dimethyl-1H-pyrazol-5-yl phthalate (Compound No. 1625) and bis[6-chloro-3-(2-cyclopropyl-6-methylphenoxy)-4-pyridazinyl] phthalate (Compound No. 2838, Step I)

In acetonitrile (3 mL) was suspended 207 mg (0.726 mmol) of (2,4-dichlorophenyl)(5-hydroxy-1,3-dimethyl-1H-pyrazol-4-yl)methanone, 81.6 mg (0.729 mmol) of 1,4-diazabicyclo[2.2.2]octane was added to the suspension and the resulting mixture was stirred. To the mixture was added 105 iL (0.729 mmol) of phthaloyl dichloride, and after stirring at room temperature for 1 hour, 200 mg (0.722 mmol) of 6-chloro-3-(2-cyclopropyl-6-methylphenoxy)-4-pyridazinol was further added, and the resulting mixture was stirred at room temperature for 1 hour and 30 minutes. The reaction mixture was poured into ice-water, and extracted with ethyl acetate. The organic layers were combined, washed successively with water and brine, and dried over anhydrous sodium sulfate. The solvent was removed, and the obtained residue was purified by silica gel column chromatography (Daisogel 1001W, hexane:ethyl acetate, gradient) to obtain 28.0 mg (0.0405 mmol, Yield: 5.61%) of 6-chloro-3-(2-cyclopropyl-6-methylphenoxy)-4-pyridazinyl 4-(2,4-dichlorobenzoyl)-1,3-dimethyl-1H-pyrazol-5-yl phthalate (Compound No.

1625) and 163 mg (0.238 mmol, Yield: 33.0%) of bis[6-chloro-3-(2-cyclopropyl-6-methylphenoxy)-4-pyridazinyl] phthalate (Compound No. 2838).

6-Chloro-3-(2-cyclopropyl-6-methylphenoxy)-4-pyridazinyl 4-(2,4-dichlorobenzoyl)-1,3-dimethyl-1H-pyrazol-5-yl phthalate (Compound No. 1625):
$^1$H-NMR (200 MHz, CDCl$_3$) δ ppm: 8.01-7.96 (1H, m), 7.89-7.68 (3H, m), 7.57 (1H, s), 7.29-7.06 (5H, m), 6.90-6.83 (1H, m), 3.71 (3H, s), 2.27 (3H, s), 2.13 (3H, s), 1.82-1.68 (1H, m), 0.77-0.53 (4H, m). Appearance: amorphous.

Bis[6-chloro-3-(2-cyclopropyl-6-methylphenoxy)-4-pyridazinyl] phthalate (Compound No. 2838):
$^1$H-NMR (200 MHz, CDCl$_3$) δ ppm: 8.13-8.06 (2H, m), 7.84-7.78 (2H, m), 7.58 (2H, s), 7.15-7.06 (4H, m), 6.90-6.83 (2H, m), 2.13 (6H, s), 1.82-1.68 (2H, m), 0.73-0.52 (8H, m). Appearance: amorphous.

EXAMPLE 636

6-Chloro-3-(2-cyclopropyl-6-methylphenoxy)-4-pyridazinyl 4-(2,4-dichlorobenzoyl)-1,3-dimethyl-1H-pyrazol-5-yl 1,3-benzenedisulfonate (Compound No. 2333) and bis[6-chloro-3-(2-cyclopropyl-6-methylphenoxy)-4-pyridazinyl] 1,3-benzenedisulfonate (Compound No. 3755, Step I)

In acetonitrile (4 mL) was suspended 122 mg (0.428 mmol) of (2,4-dichlorophenyl)(5-hydroxy-1,3-dimethyl-1H-pyrazol-4-yl)methanone, 72.0 mg (0.643 mmol) of 1,4-diazabicyclo[2.2.2]octane, then 117 mg (0.425 mmol) of 1,3-benzenedisulfonyl dichloride were added to the suspension in an ice bath, and the resulting mixture was stirred at room temperature for 30 minutes. The reaction mixture was ice-cooled, and further 100 mg (0.361 mmol) of 6-chloro-3-(2-cyclopropyl-6-methylphenoxy)-4-pyridazinol was added to the mixture, and the mixture was stirred at room temperature for 1 hour. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane:ethyl acetate, gradient) to obtain 135 mg (0.177 mmol, Yield: 49.0%) of 6-chloro-3-(2-cyclopropyl-6-methylphenoxy)-4-pyridazinyl 4-(2,4-dichlorobenzoyl)-1,3-dimethyl-1H-pyrazol-5-yl 1,3-benzenedisulfonate (Compound No. 2333) and 38.0 mg (0.0503 mmol, Yield: 13.9%) of bis[6-chloro-3-(2-cyclopropyl-6-methylphenoxy)-4-pyridazinyl] 1,3-benzenedisulfonate (Compound No. 3755).

6-Chloro-3-(2-cyclopropyl-6-methylphenoxy)-4-pyridazinyl 4-(2,4-dichlorobenzoyl)-1,3-dimethyl-1H-pyrazol-5-yl 1,3-benzenedisulfonate (Compound No. 2333):
H-NMR (200 MHz, CDCl$_3$) δ ppm: 8.67 (1H, t, J=1.9 Hz), 8.40-8.34 (1H, m), 8.31-8.24 (1H, m), 7.86 (1H, t, J=8.0 Hz), 7.56 (1H, s), 7.37 (1H, d, J=1.9 Hz), 7.29-7.23 (1H, m), 7.15-7.00 (3H, m), 6.85-6.78 (1H, m), 3.81 (3H, s), 2.00 (3H, s), 1.94 (3H, s), 1.70-1.52 (1H, m), 0.73-0.45 (4H, m). Appearance: amorphous.

Bis[6-chloro-3-(2-cyclopropyl-6-methylphenoxy)-4-pyridazinyl] 1,3-benzenedisulfonate (Compound No. 3755):
$^1$H-NMR (200 MHz, CDCl$_3$) δ ppm: 8.77 (1H, dd, J=1.8 Hz, 1.8 Hz), 8.41 (2H, dd, J=7.7 Hz, 1.8 Hz), 7.88 (1H, t, J=8.0 Hz), 7.48 (2H, s), 7.15-6.95 (4H, m), 6.90-6.75 (2H, m), 1.97 (6H, s), 1.67-1.46 (2H, m), 0.75-0.44 (8H, m). Appearance: amorphous.

EXAMPLE 637

Bis[6-chloro-3-(2-cyclopropyl-6-methylphenoxy)-4-pyridazinyl] pentanedioate (Compound No. 2746) and 6-chloro-3-(2-cyclopropyl-6-methylphenoxy)-4-pyridazinyl 4-(2,4-dichlorobenzoyl)-1,3-dimethyl-1H-pyrazol-5-yl pentanedioate (Compound No. 2739)

In acetonitrile (8 mL) was suspended 241 mg (0.870 mmol) of 6-chloro-3-(2-cyclopropyl-6-methylphenoxy)-4-pyridazinol, in an ice bath 139 mg (1.23 mmol) of 1,4-diazabicyclo[2.2.2]octane, then 146 mg (0.864 mmol) of pentanedioyl dichloride, and further 244 mg (0.856 mmol) of (2,4-dichlorophenyl)(5-hydroxy-1,3-dimethyl-1H-pyrazol-4-yl)methanone were added to the suspension, and the resulting mixture was stirred at room temperature. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane: ethyl acetate, gradient) and by preparative thin-layer chromatography (available from MERCK CO., 1.05744, 2 plates were used, developed by hexane:ethyl acetate=2:1 or 1:1) to obtain 42.0 mg (0.0646 mmol, Yield: 7.48%) of bis[6-chloro-3-(2-cyclopropyl-6-methylphenoxy)-4-pyridazinyl] pentanedioate (Compound No. 2746) and 35.0 mg (0.0532 mmol, Yield: 6.21%) of 6-chloro-3-(2-cyclopropyl-6-methylphenoxy)-4-pyridazinyl 4-(2,4-dichlorobenzoyl)-1,3-dimethyl-1H-pyrazol-5-yl pentanedioate (Compound No. 2739).

Bis[6-chloro-3-(2-cyclopropyl-6-methylphenoxy)-4-pyridazinyl] pentanedioate (Compound No. 2746):
$^1$H-NMR (200 MHz, CDCl$_3$) δ ppm: 7.23 (2H, s), 7.14-7.02 (4H, m), 6.83 (2H, dd, J=6.6, 2.9 Hz), 2.89 (4H, t, J=7.0 Hz), 2.25 (2H, quintet, J=7.0 Hz), 2.10 (6H, s), 1.80-1.65 (2H, m), 0.78-0.52 (8H, m). Appearance: caramel-like.

6-Chloro-3-(2-cyclopropyl-6-methylphenoxy)-4-pyridazinyl 4-(2,4-dichlorobenzoyl)-1,3-dimethyl-1H-pyrazol-5-yl pentanedioate (Compound No. 2739):
$^1$H-NMR (200 MHz, CDCl$_3$) δ ppm: 7.45-7.17 (4H, m), 7.14-7.00 (2H, m), 6.90-6.75 (1H, m), 3.53 (3H, s), 2.83 (2H, t, J=7.0 Hz), 2.57 (2H, t, J=7.0 Hz), 2.20-2.00 (2H, m), 2.11 (3H, s), 2.10 (3H, s), 1.80-1.65 (1H, m), 0.80-0.50 (4H, m). Appearance: amorphous.

EXAMPLE 638

6-Chloro-3-(2-cyclopropyl-6-methylphenoxy)-4-pyridazinyl 1-pyrrolidinecarboxylate (Compound No. 1937)

200 mg (0.722 mmol) of 6-chloro-3-(2-cyclopropyl-6-methylphenoxy)-4-pyridazinol was mixed with toluene (3 mL) and the mixture was ice-cooled. To the mixture were added 60 ìL (0.742 mmol) of pyridine, then 0.67 mL (0.724 mmol) of 1.08 mol/L phosgene-toluene solution under nitrogen atmosphere with stirring, and the resulting mixture was stirred at room temperature for 15 minutes. The reaction mixture was ice-cooled, 60 ìL (0.722 mmol) of pyridine, then 60 ìL (0.719 mmol) of pyrrolidine were added to the mixture, and the resulting mixture was stirred at room temperature for 1 hour. The reaction mixture was poured into water, and extracted with ethyl acetate. The organic layers were combined, washed successively with water and brine, and dried over anhydrous magnesium sulfate. The solvent was distilled off and the obtained residue was purified by preparative thin-layer chromatography (available from MERCK CO., 1.05744, 4 plates were used, developed by hexane:ethyl acetate=2:1) to obtain 190 mg (0.508 mmol, Yield: 70.7%) of 6-chloro-3-(2-cyclopropyl-6-methylphenoxy)-4-pyridazinyl 1-pyrrolidinecarboxylate (Compound No. 1937).

$^1$H-NMR (200 MHz, CDCl$_3$) δ ppm: 7.59 (1H, s), 7.15-7.03 (2H, m), 6.90-6.80 (1H, m), 3.62 (2H, dd, J=6.6 Hz, 6.9 Hz), 3.51 (2H, dd, J=6.9 Hz, 6.6 Hz), 2.15 (3H, s), 2.05-1.90 (4H, m), 1.88-1.68 (1H, m), 0.80-0.50 (4H, m). Melting point (° C.): 115-118.

EXAMPLE 639

6-Chloro-3-(2-cyclopropyl-6-methylphenoxy)-4-pyridazinyl methoxy(methyl)carbamate (Compound No. 3564)

200 mg (0.722 mmol) of 6-chloro-3-(2-cyclopropyl-6-methylphenoxy)-4-pyridazinol was mixed with toluene (3 mL) and the mixture was ice-cooled. To the mixture were added 60 ìL (0.742 mmol) of pyridine, then 0.67 mL (0.724 mmol) of 1.08 mol/L phosgene-toluene solution under nitrogen atmosphere with stirring, and the resulting mixture was stirred at room temperature for 15 minutes. The reaction mixture was ice-cooled, 120 ìL (1.48 mmol) of pyridine, then 70.4 mg (0.722 mmol) of N,O-dimethylhydroxylamine hydrochloride were added to the mixture, and the resulting mixture was stirred at room temperature for 1 hour. The reaction mixture was poured into water, and extracted with ethyl acetate. The organic layers were combined, washed successively with water and brine, and dried over anhydrous magnesium sulfate. The solvent was removed, and the obtained residue was purified by silica gel column chromatography (Wako gel C-100, hexane: ethyl acetate, gradient) to obtain 100 mg (0.275 mmol, Yield: 38.1%) of 6-chloro-3-(2-cyclopropyl-6-methylphenoxy)-4-pyridazinyl methoxy(methyl)carbamate (Compound No. 3564).

$^1$H-NMR (200 MHz, CDCl$_3$) δ ppm: 7.53 (1H, s), 7.15-7.03 (2H, m), 6.90-6.82 (1H, m), 3.84 (3H, s), 3.35 (3H, s), 2.15 (3H, s), 1.87-1.67 (1H, m), 0.80-0.52 (4H, m). Melting point (° C.): 63-64.5.

EXAMPLE 640

6-Chloro-3-(2-cyclopropyl-6-methylphen6xy)-4-pyridazinyl 2,5-dimethyl-1H-pyrrole-1-carboxylate (Compound No. 3630)

37.4 mg (0.393 mmol) of 2,5-dimethyl-1H-pyrrole was mixed with toluene (1 mL), 40.0 ìL (0.407 mmol) of pyridine, then 0.34 mL (0.367 mmol) of 1.08 mol/L phosgene-toluene solution were added to the mixture in an ice bath with stirring, and the resulting mixture was stirred for 1 hour. To the mixture were added 40.0 ìL (0.407 mmol) of pyridine, then 100 mg (0.361 mmol) of 6-chloro-3-(2-cyclopropyl-6-methylphenoxy)-4-pyridazinol, and the resulting mixture was stirred for 3 hours. The reaction mixture was poured into water, and extracted with ethyl acetate. The organic layers were combined, washed with water, and dried over anhydrous magnesium sulfate. The solvent was distilled off and the obtained residue was purified by preparative thin-layer chromatography (available from MERCK CO., 1.05744, 2 plates were used, developed by hexane:ethyl acetate=2:1) to obtain 24.0 mg (0.0603 mmol, Yield: 16.7%) of 6-chloro-3-(2-cyclopropyl-6-methylphenoxy)-4-pyridazinyl 2,5-dimethyl-1H-pyrrole-1-carboxylate (Compound No. 3630).

$^1$H-NMR (200 MHz, CDCl$_3$) δ ppm: 8.20-8.03 (1H, m), 7.63 (1H, s), 7.13-7.00 (2H, m), 6.90-6.80 (1H, m), 6.36 (1H, d, J=2.9 Hz), 2.55 (3H, s), 2.22 (3H, s), 2.15 (3H, s), 1.90-1.70 (1H, m), 0.80-0.50 (4H, m). Melting point (° C.): 208-210.

EXAMPLE 641

4-{[4-(benzoyloxy)-6-chloro-3-pyridazinyl]oxy}-3-methylphenyl benzoate (Compound No. 3850)

(1) 6-Chloro-3-(4-hydroxy-2-methylphenoxy)-4-pyridazinol

In 1,4-dioxane(1.4 mL) was dissolved 173 mg (0.553 mmol) of 4-[(4,6-dichloro-3-pyridazinyl)oxy]-3-methylphenyl acetate obtained in Example 630(3), 0.7 mL (2.1 mmol) of 3 mol/L sodium hydroxide solution and dimethylsulfoxide (2.8 mL) were added to the solution and the resulting mixture was stirred at room temperature overnight. To the reaction mixture was added 4 mol/L hydrochloric acid, and the mixture was extracted with ethyl acetate. The organic layers were combined, washed successively with water and brine. After drying over anhydrous magnesium sulfate, the solvent was removed. The obtained residue was purified by preparative thin-layer chromatography (developed by dichloromethane:methanol=36:1) to obtain 66.8 mg of 6-chloro-3-(4-hydroxy-2-methylphenoxy)-4-pyridazinol.

(2) 4-{[4-(Benzoyloxy)-6-chloro-3-pyridazinyl]oxy}-3-methylphenyl benzoate (Compound No. 3850)

In acetonitrile (1.0 mL) was dissolved 66.8 mg of 6-chloro-3-(4-hydroxy-2-methylphenoxy)-4-pyridazinol obtained in (1), 60.0 mg (0.536 mmol) of 1,4-diazabicyclo[2.2.2]-octane, then, 61 ìL (0.523 mmol) of benzoyl chloride were added to the solution and the resulting mixture was stirred at room temperature for 1 hour and 30 minutes. The reaction mixture was poured into water, and extracted with ethyl acetate. The organic layers were combined, washed successively with water and brine. After drying over anhydrous magnesium sulfate, the solvent was removed. The obtained residue was purified by preparative thin-layer chromatography (developed by hexane:ethyl acetate=5:1) to obtain 36.9 mg (0.0800 mmol, Yield from 4-[(4,6-dichloro-3-pyridazinyl)oxy]-3-methylphenyl acetate: 14.5%) of 4-{[4-(benzoyloxy)-6-chloro-3-pyridazinyl]oxy}-3-methylphenyl benzoate (Compound No. 3850).

$^1$H-NMR (200 MHz, CDCl$_3$) δ ppm: 8.21-8.17 (4H, m), 7.72-7.48 (7H, m), 7.22-7.07 (3H, m), 2.21 (3H, s). Melting point (° C.): 118-120.

EXAMPLE 642

3-(2-Aminophenoxy)-3-chloro-4-pyridazinol (Compound No. 377)

(1) 2-[(6-chloro-4-methoxy-3-pyridazinyl)oxy] aniline(Step D-1)

In a mixed solvent of 1,4-dioxane (7 mL) and dimethylsulfoxide (7 mL) was dissolved 670 mg (6.15 mmol) of 2-aminophenol, 690 mg (6.16 mmol) of potassium tertbutoxide was added to the solution in an ice bath and the resulting mixture was stirred for 10 minutes. To the mixture was added 1000 mg (5.59 mmol) of 3,6-dichloro-4-methoxypyridazine, and the resulting mixture was stirred at room temperature for 5 hours.

The reaction mixture was poured into ice water, and after adding brine, the mixture was extracted with ethyl acetate. The organic layers were combined, washed successively with water and brine, and dried over anhydrous magnesium sulfate. The solvent was removed, and the obtained residue was purified by silica gel chromatography (Wakogel C-100, hexane-ethyl acetate, gradient) to obtain 328 mg (1.30 mmol, Yield: 23.3%) of 2-[(6-chloro-4-methoxy-3-pyridazinyl) oxy]aniline and 100 mg of a mixture of 2-[(6-chloro-4-methoxy-3-pyridazinyl)oxy]aniline and 2-[(6-chloro-5-methoxy-3-pyridazinyl)oxy]aniline.

(2) 3-(2-Aminophenoxy)-3-chloro-4-pyridazinol (Compound No. 377, Step D-2)

In dimethylsulfoxide (0.4 mL) was dissolved 50.0 mg (0.198 mmol) of 2-[(6-chloro-4-methoxy-3-pyridazinyl)oxy] aniline obtained in (1), (0.2 mL, 0.4 mmol) of 2 mol/L aqueous sodium hydroxide solution was added to the solution and the resulting mixture was stirred at room temperature for 5 hours. The reaction mixture was poured into brine, and extracted with tetrahydrofuran. The organic layers were combined, washed with brineand dried over anhydrous magnesium sulfate. The solvent was distilled off and the residue was purified by preparative thin-layer chromatography (available from MERCK CO., 1.05744, 2 plates were used, developed by dichloromethane:methanol=10:1) to obtain 17.0 mg (0.0714 mmol, Yield: 36.1%) of 3-(2-aminophenoxy)-3-chloro-4-pyridazinol (Compound No. 377).

$^1$H-NMR (200 MHz, CD$_3$OD) δ ppm: 7.50-6.94 (2H, m), 6.90-6.82 (1H, m), 6.85-6.63 (2H, m). Melting point (° C.): 249-250.

EXAMPLE 643

N-{2-[(6-Chloro-4-hydroxy-3-pyridazinyl)oxy] phenyl}acetamide (Compound No. 380)

18.0 mg (0.0756 mmol) of 3-(2-aminophenoxy)-3-chloro-4-pyridazinol obtained in Example 641 was mixed with dichloromethane (0.8 mL), 0.050 mL (0.36 mmol) of triethylamine, then 0.010 mL (0.14 mmol) of acetyl chloride were added to the mixture in an ice bath with stirring, and the resulting mixture was stirred at room temperature for 3 hours. The reaction mixture was poured into brine, and extracted with tetrahydrofuran. The organic layers were combined, washed with brineand dried over anhydrous magnesium sulfate. The solvent was distilled off and the residue was purified by preparative thin-layer chromatography (available from MERCK CO., 1.05715, developed by dichloromethane:methanol=10:1) to obtain 3.6 mg (0.0129 mmol, Yield: 17.1%) of N-{2-[(6-chloro-4-hydroxy-3-pyridazinyl)oxy] phenyl}acetamide (Compound No. 380).

$^1$H-NMR (200 MHz, CD$_3$OD) δ ppm: 8.10-8.00 (1H, m), 7.25-7.08 (3H, m), 6.60 (1H, s), 2.12 (3H, s). Melting point (° C.): 135.

EXAMPLE 644

N,N,N-Tributyl-1-butanaminium 6-chloro-3-(2-cyclopropyl-6-methylphenoxy)-4-pyridazinolate(Compound No. 3798)

To an ethanol (2 mL) solution containing 105 mg (0.379 mmol) of 6-chloro-3-(2-cyclopropyl-6-methylphenoxy)-4-pyridazinol were added 0.19 mL (0.38 mmol) of 2 mol/L aqueous sodium hydroxide solution, then, 106 mg (0.381 mmol) of tetrabutylammonium chloride, and the resulting mixture was stirred at 60° C. for 5 hours. The reaction mixture was allowed to stand at room temperature overnight, and the solid was removed by filtration. The filtrate was concentrated to obtain N,N,N-tributyl-1-butanaminium 6-chloro-3-(2-cyclopropyl-6-methylphenoxy)-4-pyridazinolate (Compound No. 3798).

$^1$H-NMR (200 MHz, CD$_3$OD) δ ppm: 7.05-6.95 (2H, m), 6.80-6.73 (1H, m), 6.43 (1H, s), 3.30-3.15 (8H, m), 2.14 (3H, s), 2.00-1.85 (1H, m), 1.76-1.53 (8H, m), 1.50-1.30 (8H, m), 1.02 (9H, t, J=7.1 Hz), 0.78-0.63 (2H, m), 0.63-0.48 (2H, m). Melting point (° C.): 113-114.

EXAMPLE 645

Sodium 6-chloro-3-(2-cyclopropyl-6-methylphenoxy)-4-pyridazinolate (Compound No. 3805)

0.18 mL (0.36 mmol) of 2 mol/L aqueous sodium hydroxide solution was added to an ethanol (2 mL) solution containing 100 mg (0.361 mmol) of 6-chloro-3-(2-cyclopropyl-6-methylphenoxy)-4-pyridazinol, and the resulting mixture was stirred at 50° C. for 4 hours. The reaction mixture was concentrated to obtain 108 mg (0.361 mmol, Yield: 100%) of sodium 6-chloro-3-(2-cyclopropyl-6-methylphenoxy)-4-pyridazinolate (Compound No. 3805).

$^1$H-NMR (200 MHz, CD$_3$OD) δ ppm: 7.05-6.95 (2H, m), 6.77 (1H, dd, J=6.4, 3.1 Hz), 6.43 (1H, s), 2.14 (3H, s), 2.00-1.82 (1H, m), 0.78-0.63 (2H, m), 0.63-0.48 (2H, m). Melting point (° C.): >260.

EXAMPLE 646

5-Bromo-6-chloro-3-(2-cyclopropyl-6-methylphenoxy)-4-pyridazinol (Compound No. 3843)

108 mg (0.607 mmol) of N-bromosuccinimide was added to a N,N-dimethylformamide (2 mL) solution containing 157 mg (0.567 mmol) of 6-chloro-3-(2-cyclopropyl-6-methylphenoxy)-4-pyridazinol, and the resulting mixture was stirred at room temperature for 3 hours and 30 minutes. Water, and then, 4 mol/L hydrochloric acid were added to the reaction mixture, and the mixture was extracted with ethyl acetate. The organic layers were combined, washed successively with water and brine, and dried over anhydrous magnesium sulfate. The solvent was distilled off and the residue was purified by preparative thin-layer chromatography (available from MERCK CO. 1.05744, developed by hexane:ethyl acetate=2:1) to obtain 123 mg (0.346 mmol, Yield: 61.0%) of 5-bromo-6-chloro-3-(2-cyclopropyl-6-methylphenoxy)-4-pyridazinol (Compound No. 3843).

$^1$H-NMR (200 MHz, CD$_3$OD) δ ppm: 7.08-7.05 (2H, m), 6.85-6.80 (1H, m), 2.14 (3H, s), 1.88-1.76 (1H, m), 0.82-0.72 (2H, m), 0.60-0.56 (2H, m). Appearance: amorphous.

Compounds of Compounds Nos. 1 and 6 can be produced in accordance with the method of Example 2.

Compounds of Compounds Nos. 123-127, 130-138, 144, 145, 151, 163, 173, 184, 202, 217, 226, 249, 264, 265, 266, 267, 269-275, 279, 280, 284, 287, 288, 292, 293, 300, 304, 305, 306, 307, 308, 309, 311, 315, 324, 325, 329, 330, 334, 336, 339, 344, 348, 349, 355, 356, 359, 361, 362, 364-370, 375, 376, 379, 383, 385-387, 390, 391, 396, 399-401, 403, 410, 412, 413, 415-425, 426, 427, 430, 432-438, 441, 443, 446, 450, 453, 454, 456, 458-460, 472, 491, 498, 503, 505, 506, 507, 510, 513, 514, 520, 521, 527-529, 531, 532, 534-536, 538-541, 544, 547, 549, 552, 556, 557, 558, 559, 562, 566, 567, 571, 614, 618, 621, 623, 626-629, 635, 640, 642, 650, 653, 658, 659, 662-664, 667, 679, 680, 692, 700, 701, 702, 707-712, 716, 71.7, 719, 731-733, 734, 735-737, 740, 746, 754, 756, 758, 759, 762, 775, 778, 780-782, 802-804, 834, 844-846, 850, 890, 894, 896, 911, 914, 931, 964, 965, 979, 982, 987, 998, 1000, 1007, 1009, 1013, 1016, 1020, 1023, 1027, 1040, 1050, 1052, 1053, 1055, 1058, 1060, 1061, 1063, 1064, 1066, 1069, 1073, 1080, 1083, 1086, 1088, 1089, 1091, 1096, 1099, 1100, 1102, 1115, 1118-1120, 1122-1125, 1129, 1133, 2519, 2547, 2548, 2565, 2568, 2570, 2571, 2574, 2577, 2585, 2587, 2589, 2592, 2597, 2599, 2600, 2601, 2605, 2607, 2608, 2609 and 2614 can be produced in accordance with the method of Example 1, Example 6, Example 13, Example 16, Example 21, Example 22 or Example 23.

Compounds of Compound No. 1140, 1151, 1160, 1172, 1178, 1184, 1207, 1251, 1260, 1266, 1286, 1298, 1334, 1340, 1358, 1364, 1382, 1387, 1391, 1396, 1417, 1441, 1446, 1448, 1450, 1455-1459, 1461, 1481, 1509, 1522, 1531, 1537, 1543, 1549, 1553, 1554, 1566, 1575, 1593, 1599, 1603, 1616, 1643, 1649, 1658, 1706, 1710, 1757, 1770, 1789, 1811, 1840, 1877, 1879, 1881, 1898, 1924, 1981, 1985, 2010, 2034, 2038, 2040, 2042, 2051, 2060, 2066, 2072, 2106, 2136, 2147, 2151, 2176, 2198-2200, 2212, 2220-2224, 2230-2232, 2234-2238, 2240, 2245-2249, 2263, 2265, 2287, 2289, 2300, 2309, 2315, 2321, 2351, 2662, 2671, 2677, 2697, 2703, 2709, 2715, 2721, 2727, 2752, 2758, 2764, 2770, 2776, 2782, 2788, 2805, 2814, 2820, 2826, 2850, 2856, 2862, 2868, 2874, 2880, 2900, 2906, 2918, 2924, 2930, 2961, 2970, 2976, 2982, 2988, 2994, 3016, 3022, 3028, 3034, 3040, 3046, 3052, 3058, 3064, 3070, 3076, 3082, 3088, 3094, 3100, 3106, 3112, 3129, 3138, 3144, 3150, 3156, 3162, 3168, 3185, 3194, 3200, 3217, 3226, 3243, 3252, 3258, 3264, 3270, 3276, 3282, 3288, 3294, 3300, 3306, 3312, 3318, 3324, 3330, 3336, 3342, 3348, 3354, 3360, 3366, 3372, 3378, 3384, 3390, 3396, 3402, 3408, 3414, 3420, 3426, 3432, 3438, 3444, 3450, 3456, 3462, 3468, 3474, 3480, 3486, 3492, 3498, 3504, 3510, 3516, 3780, 3786, 3792 and 3856 can be produced in accordance with the method of Example 26, Example 27 or Example 28.

A compound of Compound No. 2402 can be produced in accordance with the method of Example 33.

Compounds of Compound No. 2418 and 2431 can be produced in accordance with the method of Example 1, Example 6 or Example 22.

A compound of Compound No. 2478 can be produced in accordance with the method of Example 35, Example 36, Example 37, Example 39 or Example 40.

A compound of Compound No. 2492 can be produced in accordance with the method of Example 41.

Compounds of Compound No. 1620, 1631, 2827 and 3001 can be produced in accordance with the method of Example 635.

Compounds of Compound No. 1891, 1911, 1920, 1946, 1952, 1958, 3522, 3528, 3534, 3540, 3546, 35.52, 3558, 3570, 3576, 3582, 3588, 3594, 3600, 3606, 3612, 3618, 3624, 3636, 3642, 3648, 3654, 3660, 3666, 3672, 3678, 3684, 3690, 3696, 3702, 3708, 3714 and 3720 can be produced in accordance with the method of Example 26, Example 27, Example 28, Example 638, Example 639 or Example 640.

A compound of Compound No. 2327 can be produced in accordance with the method of Example 636.

A compound of Compound No. 2733 can be produced in accordance with the method of Example 637.

A compound of Compound No. 3811 can be produced in accordance with the method of Example 645.

Compounds of Compound No. 3837 and 3849 can be produced in accordance with the method of Example 646.

In the following Preparation example, all "%" mean % by weight.

PREPARATION EXAMPLE 1

Wettable Powder

A compound (10 parts by weight) of Example 1 (Compound No. 128), Carplex #80D (available from Shionogi & Co. Ltd., 10 parts by weight), GOHSENOL GL05 (available from The Nippon Synthetic Chemical Industry Co., Ltd., 2 parts by weight), Newcol 291PG (dioctylsulfosuccinate sodium salt, available from Nippon Nyukazai Co., Ltd., 0.5 part by weight), Neogen Powder (available from DAI-ICHI KOGYO SEIYAKU CO., LTD., 5 parts by weight), Radiolite #200 (available from SHOWA CHEMICAL CO., LTD., 10 parts by weight) and H Bifun (fine cray, available from Keiwa Rozai Co., Ltd, 62.5 parts by weight) were sufficiently mixed, and pulverized by Ecksample Mill Type KII-1 (available from Fuji Paudal Co., Ltd.) to obtain wettable powder.

PREPARATION EXAMPLE 2

Granule

A compound (5 parts by weight) of Example 61 (Compound No. 136), sodium tripolyphosphate (available from Mitsui Chemicals, Inc., 2 parts by weight), Amycol No. 1 (dextrin, available from NIPPON STARCH CHEMICAL CO., LTD., 1.5 parts by weight), bentonite (available from Hojun Co., Ltd., 25 parts by weight) and Calfin 600 (calcium carbonate, available from Ashidachi Sekkai K.K., 66.5 parts by weight) were mixed in a kneader (available from Fujisangyo Co., Ltd., Type FM-NW-5), and water (13 parts by weight) was added to the mixture to carry out further mixing, and subjected to extrusion granulation by using Dom Gran (available from Fuji Paudal Co., Ltd., screen 1.0 mmo). The obtained granules were dried by using a tray type dryer (available from Tabai K.K., PERFECT OVEN Type PS-222, 60° C.), and sieved to 600 to 1190 mm to obtain granules.

PREPARATION EXAMPLE 3

Water Dispersible Granules

A compound (80 parts by weight) of Example 7 (Compound No. 140), Geropon SC/213 (polycarboxylic acid type surfactant, available from Rohdia K.K., 7 parts by weight), Neopelex No. 6F Powder (dodecylbenzene sulfonate, KAO CORPORATION, 3 parts by weight), Amycol No. 1 (5 parts by weight) and titanium oxide (SAKAI CHEMICAL INDUSTRY CO., LTD., 5 parts by weight) are mixed, pulverized by air mill (SK-JET O MIZER model 0101, available from SEISHIN ENTERPRISE CO., LTD.,), then added to a rotary mixer, and granulated by spraying water. When almost all the part become a size of 1.00 mm to 0.15 mm, then the granules are taken out, and after drying in a tray type dryer, they are sieved to obtain a granular wettable powder with a size of 1.00 mm to 0.15 mm.

PREPARATION EXAMPLE 4

Suspension Consentrato

A compound (10 parts by weight) of Example 171 (Compound No. 506), Newcol 291PG (1 parts by weight), Pearlrex CP (lignin sulfonic acid calcium salt, available from NIPPON PAPER INDUSTRIES CO., LTD., 10 parts by weight), propylene glycol (available from Nippon Nyukazai Co., Ltd., 10 parts by weight) and water (69 parts by weight) were together mixed and pulverized in an attritor (MISUI MINING CO., LTD.) until the diameter of solid particles became 5 im or less. To the pulverized slurry (90 parts by weight) was added 0.05% (W/W) xanthane gum aqueous solution (10 parts by weight) and mixed to obtain an aqueous suspension.

PREPARATION EXAMPLE 5

Wettable Powder

A compound (10 parts by weight) of Example 6 (Compound No. 139), Compound A (10 parts by weight), Carplex #80D (available from Shionogi & Co. Ltd., 10 parts by weight), GOHSENOL GL05-S (available from The Nippon Synthetic Chemical Industry Co., Ltd., 2 parts by weight), Newcol 291PG (dioctylsulfosuccinate sodium salt, available from Nippon Nyukazai Co., Ltd., 0.5 parts by weight), Neogen Powder (available from DAI-ICHI KOGYO SEIYAKU CO., LTD., 5 parts by weight), Radiolite #200 (available from SHOWA CHEMICAL CO., LTD., 10 parts by weight) and H Bifun (fine cray, available from Keiwa Rozai Co., Ltd, 52.5 parts by weight) were sufficiently mixed. The mixture was pulverized by air mill (SK-JET O MIZER Model 0101, available from SEISHIN ENTERPRISE CO., LTD.,) to obtain mixed wettable powder of the compound (10%) of Example 6 and compound A (10%).

PREPARATION EXAMPLE 6

Wettable Powder

A compound (10 parts by weight) of Example 23 (Compound No. 806), Compound B (10 parts by weight), Carplex #80D (available from Shionogi & Co. Ltd., 10 parts by weight), GOHSENOL GL05-S (available from The Nippon Synthetic Chemical Industry Co., Ltd., 2 parts by weight), Newcol 291PG (dioctylsulfosuccinate sodium salt, available from Nippon Nyukazai Co., Ltd., 0.5 parts by weight), Neogen Powder (available from DAI-ICHI KOGYO SEIYAKU CO., LTD., 5 parts by weight), Radiolite #200 (available from SHOWA CHEMICAL CO., LTD., 10 parts by weight) and H Bifun (fine cray, available from Keiwa Rozai Co., Ltd, 52.5 parts by weight) were sufficiently mixed. The mixture was pulverized by air mill (SK-JET O MIZER Model 0101, available from SEISHIN ENTERPRISE CO., LTD.,) to obtain a mixed wettable powder of the compound (10%) of Example 23 and Compound B (10%).

PREPARATION EXAMPLE 7

Granules

Compound A (61.22 parts by weight), Newcol 291PG (0.85 parts by weight) and water (37.93 parts by weight) were mixed, and pulverized by using an attritor (available from MISUI MINING CO., LTD.) until the average particle size became about 2 im to obtain a slurry. To the slurry (98 parts by weight) was added Toxanone (available from Sanyo Chemical Industries, Ltd., 2 parts by weight) and then mixed to obtain Slurry 2. A compound (5 parts by weight) of Example 171 (Compound No. 506), sodium tripolyphosphate (available from Mitsui Chemicals, Inc., 2 parts by weight), Amycol No. 1 (dextrin, available from NIPPON STARCH CHEMICAL CO., LTD., 1.5 parts by weight), bentonite (available from Hojun Co., Ltd., 25 parts by weight) and Calfin 600 (calcium carbonate, available from Ashidachi Sekkai K.K., 61.27 parts by weight) were mixed in a kneader (available from Fujisangyo Co., Ltd., Type FM-NW-5), and further Slurry 2 (8.33 parts by weight) were added and mixed. The kneading material was subjected to extrusion granulation by using Dom Gran (available from Fuji Paudal Co., Ltd., screen 1.0 mmö), and the obtained granules were dried by using a tray type dryer (available from Tabai K.K., PERFECT OVEN Type PS-222, 60° C.), then sieved to a size of 600 to 1190 mm to obtain granules of the compound. (5%) of Example 171 and Ccompound A (5%).

PREPARATION EXAMPLE 8

Suspension Concentrato

A compound (11.11 parts by weight) of Example 1 (Compound No. 128), Compound C (11.11 parts by weight), Newcol 291PG (1 parts by weight), ligninsulfonic acid calcium salt (Pearlrex CP, available from NIPPON PAPER INDUSTRIES CO., LTD., 10 parts by weight), propylene glycol (available from Nippon Nyukazai Co., Ltd., 10 parts by weight) and water (56.78 parts by weight) were mixed and pulverized in an attritor (MISUI MINING CO., LTD.) until a diameter of solid particles became 5 im or less to obtain a slurry. To the slurry (90 parts) was added 0.05% xanthane gum aqueous solution (10 parts by weight) and mixed to obtain a mixed aqueous suspension of the compound (10%) of Example 1 and Compound C (10%).

PREPARATION EXAMPLE 9

Wettable Powder

A compound (10 parts by weight) of Example 23 (Compound No. 806), Compound D (2 parts by weight), Carplex #80D (available from Shionogi & Co. Ltd., 10 parts by weight), GOHSENOL GL05-S (available from The Nippon Synthetic Chemical Industry Co., Ltd., 2 parts by weight), Newcol 291PG (dioctylsulfosuccinate sodium salt, available from Nippon Nyukazai Co., Ltd., 0.5 parts by weight), Neogen Powder (available from DAI-ICHI KOGYO SEIYAKU CO., LTD., 5 parts by weight), Radiolite #200 (available from SHOWA CHEMICAL CO., LTD., 10 parts by weight) and H Bifun (fine cray, available from Keiwa Rozai Co., Ltd, 60.5 parts by weight) were sufficiently mixed. The mixture was pulverized by air mill (SK-JET O MIZER Model 0101, available from SEISHIN ENTERPRISE CO., LTD.,) to obtain a mixed wettable powder of the compound (10%) of Example 23 and Compound D (2%).

PREPARATION EXAMPLE 10

Wettable Powder

A compound (10 parts by weight) of Example 23 (Compound No. 806), Compound E (8 parts by weight), Carplex #80D (available from Shionogi & Co. Ltd., 10 parts by weight), GOHSENOL GL05-S (available from The Nippon Synthetic Chemical Industry Co., Ltd., 2 parts by weight), Newcol 291PG (dioctylsulfosuccinate sodium salt, available from Nippon Nyukazai Co., Ltd., 0.5 parts by weight), Neogen Powder (available from DAI-ICHI KOGYO SEIYAKU CO., LTD., 5 parts by weight), Radiolite #200 (available from SHOWA CHEMICAL CO., LTD., 10 parts by weight) and H Bifun (fine cray, available from Keiwa Rozai Co., Ltd, 54.5 parts by weight) were sufficiently mixed. The mixture was pulverized by air mill (SK-JET O MIZER Model 0101, available from SEISHIN ENTERPRISE CO., LTD.,) to obtain a mixed wettable powder of the compound (10%) of Example 23 and Compound E (8%).

PREPARATION EXAMPLE 11

Wettable Powder

In the same manner as in Preparation example 10 except for using Compound F in place of Compound E, a mixed wettable powder of the compound (10%) of Example 23 and Compound F (8%) was obtained.

TEST EXAMPLE 1

Tests of Herbicidal Effects and Crop Injury Against Paddy-field Rice

A paddy soil was filled in 1/10,000 are pot, and seeds of barnyardgrass (*Echinochloa oryzicola Vasing.*), *Scirpus joncoides* and annual broad-leaved weeds (*Lindernia* spp., *Rotala indica*) which are awaken from dormancy were mixed at the surface layer of 1 cm. Also, tuber of *Cyperus serotinus* which is germinated was planted, and further seedlings of paddy-field rice at 2.2-leaf stage were transplanted, and they were grown under the flooded condition in a greenhouse. After 3 days from transplanting, a predetermined chemical dosage of the wettable powder prepared in accordance with Preparation example 1 was diluted in water, and the solution was applied to the pot and herbicidal effects and crop injury against transplanted paddy-field rice were judged after 25 days from the treatment. Also, 3-(2-allylphenoxy)-6-chloro-4-methoxypyridazine described in Chemical Pharmaceutical Bulletin, 1972, vol. 20, No. 10, pp. 2191-2203 was used as Comparative compound. The results are shown in Table 2. Incidentally, herbicidal effects and crop injury against transplanted paddy-field rice were judged by the following judgment standard, and "-" in the table means no test was carried out.

Judgment standard
0: Growth inhibition rate; 0 to 10%
1: Growth inhibition rate; 11 to 30%
2: Growth inhibition rate; 31 to 50%
3: Growth inhibition rate; 51 to 70%
4: Growth inhibition rate; 71 to 90%
5: Growth inhibition rate; 91 to 100%.

TABLE 2

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 1 (Compound No. 128) | 25 | 5 | 5 | 5 | 5 | 0 |
| Compound of Example 1 (Compound No. 128) | 12.5 | 4 | 5 | 5 | 5 | 0 |
| Compound of Example 6 (Compound No. 139) | 20 | 3 | 5 | 5 | 5 | 0 |
| Compound of Example 6 (Compound No. 139) | 10 | 2 | 5 | 5 | 5 | 0 |
| Compound of Example 14 (Compound No. 515) | 10 | 0 | 5 | 4 | 5 | 0 |
| Compound of Example 15 (Compound No. 516) | 10 | 1 | 5 | — | 5 | 0 |
| Compound of Example 16 (Compound No. 704) | 20 | 1 | 5 | 5 | 5 | 0 |
| Compound of Example 16 (Compound No. 704) | 10 | 0 | 5 | 5 | 5 | 0 |
| Compound of Example 18 (Compound No. 738) | 25 | 1 | 5 | 4 | 5 | 2 |
| Compound of Example 18 (Compound No. 738) | 12.5 | 0 | 5 | 3 | 5 | 1 |
| Compound of Example 19 (Compound No. 760) | 25 | 1 | 5 | 4 | 5 | 1 |
| Compound of Example 19 (Compound No. 760) | 12.5 | 0 | 5 | 4 | 5 | 1 |
| Compound of Example 21 (Compound No. 801) | 10 | 2 | 5 | 5 | 5 | 0 |
| Compound of Example 22 (Compound No. 805) | 25 | 2 | 5 | 4 | 4 | 2 |
| Compound of Example 22 (Compound No. 805) | 12.5 | 1 | 5 | 2 | 3 | 1 |
| Compound of Example 23 (Compound No. 806) | 20 | 4 | 5 | 5 | 5 | 2 |
| Compound of Example 23 (Compound No. 806) | 10 | 3 | 5 | 5 | 5 | 0 |
| Compound of Example 26 (Compound No. 2081) | 20 | 4 | 5 | 5 | 5 | 0 |
| Compound of Example 26 (Compound No. 2081) | 10 | 4 | 5 | 5 | 5 | 0 |
| Compound of Example 27 (Compound No. 2225) | 20 | 4 | 5 | 5 | 5 | 0 |
| Compound of Example 27 (Compound No. 2225) | 10 | 2 | 5 | 4 | 5 | 0 |
| Compound of Example 34 (Compound No. 2411) | 20 | 2 | 4 | 4 | 5 | 0 |

TABLE 2-continued

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 34 (Compound No. 2411) | 10 | 1 | 2 | 2 | 5 | 0 |
| Compound of Example 49 (Compound No. 124) | 25 | 2 | 5 | 4 | 5 | 0 |
| Compound of Example 49 (Compound No. 124) | 12.5 | 1 | 3 | 3 | 5 | 0 |
| Compound of Example 50 (Compound No. 125) | 25 | 3 | 5 | 4 | 5 | 0 |
| Compound of Example 50 (Compound No. 125) | 12.5 | 2 | 5 | 3 | 5 | 0 |
| Compound of Example 51 (Compound No. 126) | 25 | 2 | 5 | 5 | 5 | 0 |
| Compound of Example 51 (Compound No. 126) | 12.5 | 2 | 4 | 3 | 5 | 0 |
| Compound of Example 52 (Compound No. 127) | 20 | 4 | 5 | 5 | 5 | 0 |
| Compound of Example 52 (Compound No. 127) | 10 | 3 | 5 | 5 | 5 | 0 |
| Compound of Example 55 (Compound No. 130) | 25 | 2 | 5 | 4 | 5 | 0 |
| Compound of Example 55 (Compound No. 130) | 12.5 | 2 | 5 | 3 | 5 | 0 |
| Compound of Example 56 (Compound No. 131) | 25 | 0 | 5 | 3 | 4 | 0 |
| Compound of Example 56 (Compound No. 131) | 12.5 | 0 | 4 | 2 | 4 | 0 |
| Compound of Example 57 (Compound No. 132) | 25 | 2 | 5 | 4 | 5 | 0 |
| Compound of Example 57 (Compound No. 132) | 12.5 | 2 | 5 | 3 | 5 | 0 |
| Compound of Example 61 (Compound No. 136) | 25 | 2 | 5 | 5 | 5 | 0 |
| Compound of Example 61 (Compound No. 136) | 12.5 | 1 | 5 | 5 | 5 | 0 |
| Compound of Example 72 (Compound No. 217) | 20 | 3 | 5 | 5 | 5 | 0 |
| Compound of Example 72 (Compound No. 217) | 10 | 3 | 5 | 5 | 4 | 0 |
| Compound of Example 85 (Compound No. 284) | 10 | 2 | 4 | 3 | 5 | 0 |
| Compound of Example 88 (Compound No. 292) | 25 | 0 | 5 | 5 | 5 | 0 |
| Compound of Example 88 (Compound No. 292) | 12.5 | 0 | 4 | 4 | 5 | 0 |
| Compound of Example 121 (Compound No. 385) | 25 | 3 | 5 | 4 | 5 | 0 |
| Compound of Example 121 (Compound No. 385) | 12.5 | 2 | 5 | 3 | 5 | 0 |
| Compound of Example 122 (Compound No. 386) | 20 | 0 | 5 | 5 | 5 | 0 |
| Compound of Example 122 (Compound No. 386) | 10 | 0 | 5 | 4 | 5 | 0 |
| Compound of Example 123 (Compound No. 387) | 20 | 1 | 5 | 4 | 5 | 0 |
| Compound of Example 123 (Compound No. 387) | 10 | 0 | 5 | 3 | 4 | 0 |
| Compound of Example 125 (Compound No. 391) | 20 | 2 | 5 | 4 | 5 | 0 |
| Compound of Example 125 (Compound No. 391) | 10 | 1 | 5 | 3 | 4 | 0 |
| Compound of Example 129 (Compound No. 401) | 25 | 2 | 5 | 4 | 5 | 0 |
| Compound of Example 129 (Compound No. 401) | 12.5 | 1 | 5 | 3 | 4 | 0 |
| Compound of Example 154 (Compound No. 437) | 20 | 2 | 5 | 5 | 5 | 0 |
| Compound of Example 154 (Compound No. 437) | 10 | 1 | 5 | 3 | 5 | 0 |
| Compound of Example 166 (Compound No. 472) | 20 | 1 | 5 | 5 | 5 | 0 |

TABLE 2-continued

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 166 (Compound No. 472) | 10 | 0 | 5 | 5 | 5 | 0 |
| Compound of Example 171 (Compound No. 506) | 20 | 4 | 5 | 5 | 5 | 0 |
| Compound of Example 171 (Compound No. 506) | 10 | 3 | 5 | 5 | 5 | 0 |
| Compound of Example 172 (Compound No. 507) | 20 | 5 | 5 | 5 | 5 | 0 |
| Compound of Example 172 (Compound No. 507) | 10 | 5 | 5 | 5 | 4 | 0 |
| Compound of Example 179 (Compound No. 521) | 20 | 1 | 4 | 4 | 5 | 0 |
| Compound of Example 179 (Compound No. 521) | 10 | 0 | 4 | 3 | 5 | 0 |
| Compound of Example 180 (Compound No. 527) | 25 | 0 | 5 | 3 | 5 | 0 |
| Compound of Example 180 (Compound No. 527) | 12.5 | 0 | 5 | 2 | 5 | 0 |
| Compound of Example 181 (Compound No. 528) | 20 | 2 | 5 | 4 | 5 | 0 |
| Compound of Example 181 (Compound No. 528) | 10 | 1 | 5 | 3 | 4 | 0 |
| Compound of Example 182 (Compound No. 529) | 20 | 2 | 5 | 4 | 5 | 0 |
| Compound of Example 183 (Compound No. 531) | 20 | 2 | 5 | 5 | 5 | 0 |
| Compound of Example 183 (Compound No. 531) | 10 | 1 | 5 | 5 | 5 | 0 |
| Compound of Example 184 (Compound No. 532) | 20 | 0 | 5 | 4 | 5 | 0 |
| Compound of Example 185 (Compound No. 534) | 5 | 1 | 3 | 2 | 3 | 0 |
| Compound of Example 189 (Compound No. 539) | 10 | 3 | 5 | 5 | 5 | 3 |
| Compound of Example 189 (Compound No. 539) | 5 | 2 | 5 | 4 | 5 | 0 |
| Compound of Example 191 (Compound No. 541) | 20 | 5 | 5 | 5 | 5 | 5 |
| Compound of Example 191 (Compound No. 541) | 10 | 4 | 5 | 5 | 5 | 2 |
| Compound of Example 192 (Compound No. 544) | 20 | 5 | 3 | 5 | 5 | 1 |
| Compound of Example 192 (Compound No. 544) | 10 | 2 | 2 | 5 | 5 | 0 |
| Compound of Example 202 (Compound No. 571) | 10 | 2 | 5 | — | 4 | 0 |
| Compound of Example 203 (Compound No. 614) | 25 | 2 | 5 | 5 | 5 | 0 |
| Compound of Example 203 (Compound No. 614) | 12.5 | 1 | 5 | 5 | 5 | 0 |
| Compound of Example 204 (Compound No. 618) | 25 | 2 | 5 | 5 | 5 | 0 |
| Compound of Example 204 (Compound No. 618) | 12.5 | 2 | 5 | 5 | 5 | 0 |
| Compound of Example 205 (Compound No. 621) | 25 | 1 | 5 | 5 | 5 | 0 |
| Compound of Example 205 (Compound No. 621) | 12.5 | 0 | 5 | 5 | 5 | 0 |
| Compound of Example 212 (Compound No. 640) | 25 | 2 | 5 | 5 | 5 | 0 |
| Compound of Example 212 (Compound No. 640) | 12.5 | 1 | 5 | 5 | 5 | 0 |
| Compound of Example 216 (Compound No. 658) | 20 | 4 | 5 | 5 | 5 | 2 |
| Compound of Example 216 (Compound No. 658) | 10 | 4 | 5 | 5 | 5 | 0 |
| Compound of Example 217 (Compound No. 659) | 20 | 4 | 5 | 5 | 5 | 0 |
| Compound of Example 217 (Compound No. 659) | 10 | 2 | 5 | 5 | 5 | 0 |

TABLE 2-continued

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 218 (Compound No. 662) | 20 | 1 | 5 | 5 | 5 | 0 |
| Compound of Example 218 (Compound No. 662) | 10 | 0 | 5 | 5 | 5 | 0 |
| Compound of Example 219 (Compound No. 663) | 20 | 4 | 5 | 5 | — | 0 |
| Compound of Example 219 (Compound No. 663) | 10 | 3 | 5 | 5 | — | 0 |
| Compound of Example 232 (Compound No. 711) | 20 | 4 | 5 | 4 | 5 | 0 |
| Compound of Example 232 (Compound No. 711) | 10 | 4 | 5 | 3 | 4 | 0 |
| Compound of Example 233 (Compound No. 712) | 20 | 4 | 5 | 5 | 5 | 0 |
| Compound of Example 233 (Compound No. 712) | 10 | 3 | 4 | 3 | 4 | 0 |
| Compound of Example 234 (Compound No. 716) | 25 | 0 | 5 | 4 | 5 | 0 |
| Compound of Example 234 (Compound No. 716) | 12.5 | 0 | 5 | 3 | 5 | 0 |
| Compound of Example 235 (Compound No. 717) | 20 | 3 | 5 | 5 | 5 | 0 |
| Compound of Example 235 (Compound No. 717) | 10 | 3 | 5 | 5 | 5 | 0 |
| Compound of Example 236 (Compound No. 719) | 20 | 4 | 5 | 5 | 5 | 0 |
| Compound of Example 236 (Compound No. 719) | 10 | 3 | 5 | 5 | 5 | 0 |
| Compound of Example 239 (Compound No. 732) | 20 | 0 | 5 | 5 | 4 | 0 |
| Compound of Example 240 (Compound No. 733) | 25 | 3 | 5 | 4 | 5 | 0 |
| Compound of Example 240 (Compound No. 733) | 12.5 | 2 | 5 | 3 | 5 | 0 |
| Compound of Example 241 (Compound No. 735) | 20 | 3 | 5 | 4 | 5 | 0 |
| Compound of Example 241 (Compound No. 735) | 10 | 1 | 5 | 3 | 5 | 0 |
| Compound of Example 242 (Compound No. 736) | 25 | 4 | 5 | 4 | 5 | 0 |
| Compound of Example 242 (Compound No. 736) | 12.5 | 3 | 5 | 3 | 5 | 0 |
| Compound of Example 243 (Compound No. 737) | 25 | 2 | 5 | 4 | 5 | 0 |
| Compound of Example 243 (Compound No. 737) | 12.5 | 1 | 5 | 4 | 5 | 0 |
| Compound of Example 245 (Compound No. 740) | 20 | 4 | 5 | 5 | 5 | 0 |
| Compound of Example 245 (Compound No. 740) | 10 | 4 | 5 | 5 | 5 | 0 |
| Compound of Example 248 (Compound No. 756) | 10 | 3 | 5 | — | 5 | 0 |
| Compound of Example 248 (Compound No. 756) | 5 | 1 | 5 | — | 5 | 0 |
| Compound of Example 249 (Compound No. 758) | 20 | 3 | 5 | 5 | 5 | 3 |
| Compound of Example 249 (Compound No. 758) | 10 | 2 | 5 | 5 | 5 | 0 |
| Compound of Example 250 (Compound No. 759) | 20 | 4 | 5 | 5 | 5 | 0 |
| Compound of Example 250 (Compound No. 759) | 10 | 3 | 5 | 5 | 5 | 0 |
| Compound of Example 253 (Compound No. 762) | 20 | 4 | 5 | 5 | 5 | 5 |
| Compound of Example 253 (Compound No. 762) | 10 | 3 | 5 | 5 | 5 | 5 |
| Compound of Example 255 (Compound No. 778) | 20 | 5 | 5 | 4 | 5 | 2 |
| Compound of Example 255 (Compound No. 778) | 10 | 5 | 5 | 4 | 5 | 0 |

TABLE 2-continued

| Test compound | Chemical dosage (g/a) | Herbicidal effects | | | | Crop injury against trans-planted rice |
|---|---|---|---|---|---|---|
| | | Barnyard grass | Broad leaf | *Scirpus joncoides* | *Cyperus serotinus* | |
| Compound of Example 256 (Compound No. 780) | 20 | 4 | 5 | 5 | 5 | 3 |
| Compound of Example 256 (Compound No. 780) | 10 | 3 | 5 | 5 | 5 | 2 |
| Compound of Example 258 (Compound No. 782) | 10 | 3 | 5 | — | — | 0 |
| Compound of Example 260 (Compound No. 802) | 20 | 3 | 5 | 5 | 5 | 0 |
| Compound of Example 260 (Compound No. 802) | 10 | 2 | 5 | 5 | 5 | 0 |
| Compound of Example 261 (Compound No. 803) | 20 | 2 | 5 | 5 | 5 | 0 |
| Compound of Example 261 (Compound No. 803) | 10 | 2 | 5 | 4 | 5 | 0 |
| Compound of Example 267 (Compound No. 845) | 20 | 2 | 5 | 5 | 5 | 0 |
| Compound of Example 267 (Compound No. 845) | 10 | 1 | 5 | 4 | 5 | 0 |
| Compound of Example 268 (Compound No. 846) | 25 | 1 | 5 | 5 | 5 | 1 |
| Compound of Example 268 (Compound No. 846) | 12.5 | 0 | 5 | 5 | 5 | 1 |
| Compound of Example 269 (Compound No. 850) | 20 | 3 | 5 | 5 | 5 | 5 |
| Compound of Example 269 (Compound No. 850) | 10 | 2 | 5 | 5 | 5 | 3 |
| Compound of Example 271 (Compound No. 894) | 25 | 2 | 5 | 4 | 4 | 1 |
| Compound of Example 271 (Compound No. 894) | 12.5 | 1 | 5 | 2 | 3 | 0 |
| Compound of Example 272 (Compound No. 896) | 20 | 0 | 5 | 5 | 4 | 0 |
| Compound of Example 272 (Compound No. 896) | 10 | 0 | 5 | 4 | 4 | 0 |
| Compound of Example 274 (Compound No. 914) | 20 | 3 | 5 | 4 | 4 | 0 |
| Compound of Example 274 (Compound No. 914) | 10 | 3 | 5 | 3 | 4 | 0 |
| Compound of Example 275 (Compound No. 931) | 20 | 4 | 5 | 5 | 5 | 3 |
| Compound of Example 275 (Compound No. 931) | 10 | 4 | 5 | 5 | 5 | 1 |
| Compound of Example 276 (Compound No. 964) | 20 | 4 | 5 | 4 | 5 | 0 |
| Compound of Example 276 (Compound No. 964) | 10 | 3 | 5 | 3 | 5 | 0 |
| Compound of Example 277 (Compound No. 965) | 20 | 1 | 5 | 5 | 5 | 0 |
| Compound of Example 277 (Compound No. 965) | 10 | 0 | 5 | — | 5 | 0 |
| Compound of Example 281 (Compound No. 998) | 25 | 0 | 5 | 3 | 5 | 0 |
| Compound of Example 281 (Compound No. 998) | 12.5 | 0 | 5 | 2 | 5 | 0 |
| Compound of Example 282 (Compound No. 1000) | 25 | 0 | 5 | 4 | 5 | 0 |
| Compound of Example 282 (Compound No. 1000) | 12.5 | 0 | 5 | 3 | 4 | 0 |
| Compound of Example 285 (Compound No. 1013) | 20 | 0 | 5 | 5 | 3 | 0 |
| Compound of Example 285 (Compound No. 1013) | 10 | 0 | 5 | 4 | 2 | 0 |
| Compound of Example 286 (Compound No. 1016) | 25 | 0 | 5 | 5 | 5 | 0 |
| Compound of Example 286 (Compound No. 1016) | 12.5 | 0 | 5 | 5 | 5 | 0 |
| Compound of Example 287 (Compound No. 1020) | 25 | 0 | 5 | 5 | 3 | 0 |
| Compound of Example 287 (Compound No. 1020) | 12.5 | 0 | 5 | 5 | 1 | 0 |

TABLE 2-continued

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 288 (Compound No. 1023) | 20 | 1 | 5 | 5 | 5 | 0 |
| Compound of Example 288 (Compound No. 1023) | 10 | 0 | 5 | 5 | 5 | 0 |
| Compound of Example 289 (Compound No. 1027) | 25 | 0 | 5 | 5 | 5 | 0 |
| Compound of Example 289 (Compound No. 1027) | 12.5 | 0 | 4 | 4 | 4 | 0 |
| Compound of Example 290 (Compound No. 1040) | 10 | 0 | 5 | 4 | 5 | 0 |
| Compound of Example 294 (Compound No. 1058) | 20 | 2 | 5 | 5 | 5 | 0 |
| Compound of Example 294 (Compound No. 1058) | 10 | 1 | 5 | 5 | 5 | 0 |
| Compound of Example 295 (Compound No. 1060) | 25 | 1 | 5 | 5 | 5 | 0 |
| Compound of Example 295 (Compound No. 1060) | 12.5 | 0 | 5 | 5 | 5 | 0 |
| Compound of Example 296 (Compound No. 1061) | 20 | 2 | 5 | 5 | 5 | 0 |
| Compound of Example 296 (Compound No. 1061) | 10 | 1 | 5 | 5 | 5 | 0 |
| Compound of Example 303 (Compound No. 1083) | 25 | 1 | 4 | 4 | 5 | 0 |
| Compound of Example 303 (Compound No. 1083) | 12.5 | 0 | 3 | 3 | 5 | 0 |
| Compound of Example 304 (Compound No. 1086) | 20 | 4 | 5 | 5 | 5 | 0 |
| Compound of Example 304 (Compound No. 1086) | 10 | 4 | 5 | 4 | 4 | 0 |
| Compound of Example 305 (Compound No. 1088) | 10 | 1 | 5 | 5 | 5 | 0 |
| Compound of Example 306 (Compound No. 1089) | 10 | 1 | 5 | 5 | 5 | 0 |
| Compound of Example 307 (Compound No. 1091) | 20 | 4 | 5 | 5 | 5 | 0 |
| Compound of Example 307 (Compound No. 1091) | 10 | 3 | 5 | 5 | 5 | 0 |
| Compound of Example 308 (Compound No. 1096) | 20 | 4 | 5 | 5 | 5 | 0 |
| Compound of Example 308 (Compound No. 1096) | 10 | 2 | 5 | 4 | 5 | 0 |
| Compound of Example 309 (Compound No. 1099) | 20 | 5 | 5 | 5 | 5 | 5 |
| Compound of Example 309 (Compound No. 1099) | 10 | 4 | 5 | 5 | 5 | 2 |
| Compound of Example 310 (Compound No. 1100) | 20 | 5 | 5 | 5 | 5 | 0 |
| Compound of Example 310 (Compound No. 1100) | 10 | 4 | 5 | 5 | 5 | 0 |
| Compound of Example 311 (Compound No. 1102) | 20 | 3 | 5 | 5 | 5 | 0 |
| Compound of Example 311 (Compound No. 1102) | 10 | 1 | 5 | 4 | 4 | 0 |
| Compound of Example 313 (Compound No. 1115) | 20 | 1 | 5 | — | — | 0 |
| Compound of Example 315 (Compound No. 1119) | 20 | 4 | 5 | — | 5 | 0 |
| Compound of Example 316 (Compound No. 1120) | 20 | 3 | 5 | — | — | 0 |
| Compound of Example 316 (Compound No. 1120) | 10 | 2 | 5 | — | — | 0 |
| Compound of Example 317 (Compound No. 1122) | 25 | 0 | 5 | 3 | 5 | 1 |
| Compound of Example 317 (Compound No. 1122) | 12.5 | 0 | 4 | 2 | 5 | 0 |
| Compound of Example 318 (Compound No. 1123) | 20 | 1 | 5 | 5 | 5 | 0 |
| Compound of Example 318 (Compound No. 1123) | 10 | 0 | 5 | 5 | 5 | 0 |

TABLE 2-continued

| Test compound | Chemical dosage (g/a) | Herbicidal effects | | | | Crop injury against transplanted rice |
|---|---|---|---|---|---|---|
| | | Barnyard grass | Broad leaf | *Scirpus joncoides* | *Cyperus serotinus* | |
| Compound of Example 319 (Compound No. 1124) | 20 | 3 | 5 | 5 | 5 | 0 |
| Compound of Example 319 (Compound No. 1124) | 10 | 2 | 5 | 5 | 5 | 0 |
| Compound of Example 320 (Compound No. 1125) | 25 | 2 | 5 | 5 | 5 | 0 |
| Compound of Example 320 (Compound No. 1125) | 12.5 | 1 | 5 | 5 | 5 | 0 |
| Compound of Example 323 (Compound No. 1140) | 20 | 4 | 5 | 5 | 5 | 0 |
| Compound of Example 323 (Compound No. 1140) | 10 | 3 | 5 | 5 | 5 | 0 |
| Compound of Example 327 (Compound No. 1266) | 20 | 4 | 5 | 5 | 5 | 0 |
| Compound of Example 327 (Compound No. 1266) | 10 | 4 | 5 | 5 | 5 | 0 |
| Compound of Example 328 (Compound No. 1387) | 20 | 4 | 5 | 5 | 5 | 0 |
| Compound of Example 328 (Compound No. 1387) | 10 | 3 | 3 | 3 | 5 | 0 |
| Compound of Example 329 (Compound No. 1391) | 20 | 4 | 5 | 5 | 5 | 0 |
| Compound of Example 329 (Compound No. 1391) | 10 | 2 | 5 | 5 | 5 | 0 |
| Compound of Example 345 (Compound No. 1658) | 20 | 4 | 5 | 5 | 5 | 0 |
| Compound of Example 345 (Compound No. 1658) | 10 | 3 | 5 | 5 | 5 | 0 |
| Compound of Example 347 (Compound No. 1710) | 20 | 4 | 5 | 5 | 5 | 0 |
| Compound of Example 347 (Compound No. 1710) | 10 | 3 | 5 | 5 | 5 | 0 |
| Compound of Example 349 (Compound No. 1789) | 20 | 4 | 5 | 5 | 5 | 0 |
| Compound of Example 349 (Compound No. 1789) | 10 | 3 | 4 | 4 | 5 | 0 |
| Compound of Example 352 (Compound No. 1879) | 20 | 4 | 5 | 5 | — | 0 |
| Compound of Example 356 (Compound No. 1981) | 20 | 3 | 5 | 5 | 5 | 0 |
| Compound of Example 356 (Compound No. 1981) | 10 | 2 | 4 | 3 | 5 | 0 |
| Compound of Example 357 (Compound No. 1985) | 20 | 3 | 5 | 5 | 5 | 0 |
| Compound of Example 357 (Compound No. 1985) | 10 | 2 | 5 | 5 | 5 | 0 |
| Compound of Example 359 (Compound No. 2038) | 20 | 5 | 5 | 4 | 5 | 0 |
| Compound of Example 359 (Compound No. 2038) | 10 | 4 | 3 | 3 | 5 | 0 |
| Compound of Example 360 (Compound No. 2040) | 20 | 4 | 5 | 5 | 5 | 0 |
| Compound of Example 360 (Compound No. 2040) | 10 | 3 | 5 | 5 | 5 | 0 |
| Compound of Example 361 (Compound No. 2042) | 20 | 3 | 5 | 5 | 5 | 0 |
| Compound of Example 361 (Compound No. 2042) | 10 | 2 | 5 | 5 | 4 | 0 |
| Compound of Example 365 (Compound No. 2151) | 20 | 3 | 5 | 5 | 5 | 0 |
| Compound of Example 365 (Compound No. 2151) | 10 | 2 | 5 | 4 | 5 | 0 |
| Compound of Example 394 (Compound No. 2289) | 20 | 3 | 5 | 5 | 5 | 0 |
| Compound of Example 394 (Compound No. 2289) | 10 | 2 | 5 | 4 | 5 | 0 |
| Comparative compound | 25 | 0 | 1 | 0 | 0 | 0 |

TEST EXAMPLE 2

Tests of Herbicidal Effects (Soil Treatment)

Upland soil was filled in 150 cm² pot, and seeds of barnyardgrass and indian mustard (*Brassica juncea* (*L.*) Czern. et Coss) were sowed, and grown in a greenhouse. At the next day of seeding, a predetermined chemical dosage of the wettable powder prepared in accordance with Preparation example 1 was diluted in water and applied to soil surface. After 21 days from the treatment, herbicidal effects were judged in accordance with the judgment standard of Test example 1, and the results were shown in Table 3.

TABLE 3

Test of herbicidal effects

| Test compound | Dosage (kg/a) | Herbicidal effects Barnyard-grass | indian mustard |
|---|---|---|---|
| Example 23 (Compound No. 806) | 2 | 4 | 5 |
| Example 171 (Compound No. 506) | 5 | 5 | 5 |
| Example 236 (Compound No. 719) | 5 | 3 | 5 |
| Example 245 (Compound No. 740) | 5 | 3 | 5 |
| Example 249 (Compound No. 758) | 5 | 4 | 5 |
| Example 256 (Compound No. 780) | 5 | 3 | 5 |
| Example 309 (Compound No. 1099) | 5 | 5 | 5 |
| Example 310 (Compound No. 1100) | 5 | 5 | 5 |

TEST EXAMPLE 3

Test of Herbicidal Effects (Foliar Treatment)

Upland soil was filled in 150 cm² pot, and seeds of velvetleaf, tall morningglory, indian mustard, black nightshade redroot pigweed were sowed, and grown in a greenhouse. After the weeds were grown with 10 to 15 cm or so, a predetermined chemical dosage of the wettable powder prepared in accordance with Preparation example 1 was diluted with water containing 0.05% of GRAMIN-S and applied as a foliar treatment. After 14 days from the treatment, herbicidal effects were judged in accordance with the judgment standard of Test example 1, and the results were shown in Table 4. Incidentally, "-" in the table means no test was carried out.

TABLE 4

Test of herbicidal effects

| Test compound | Chemical dosage (kg/a) | Herbicidal effects Velvet-leaf | Tall Morning glory | Indian mustard | Black Nightshade | Redroot pigweed |
|---|---|---|---|---|---|---|
| Example 23 (Compound No. 806) | 2 | 4 | 5 | 5 | 5 | 4 |
| Example 236 (Compound No. 719) | 0.5 | — | 4 | 3 | — | 3 |

TEST EXAMPLE 4

Tests of Herbicidal Effects and Crop Injury Against Transplanted Paddy-field Rice Paddy filed soil was filled in 1/5000 are Wagner pot, seeds of barnyardgrass (*Echinochloa oryzicola* Vasing.), *Scirpus joncoides* and annual broad-leaved weeds (*Lindernia* spp. and *Rotala indica*) which are awaken from dormancy were mixed at the surface layer of 1 cm. Also, tubers of *Cyperus serotinus*, *Sagittaria pygmaea* and *Eleocharis kuroguwai* which are awaken from dormancy were planted, and further seedlings of paddy-field ric at 2.2-leaf stage were transplantedand they were grown under the flooded condition in a greenhouse. After 3 days from the transplanting, a predetermined chemical dosage of the wettable powder prepared in accordance with Preparation example 5 was diluted with water, and applied to the pot. After 25 days, herbicidal effects and crop injury against transplanted paddy-field rice were judged according to the following judgment standard, and the results were shown in Table 5. Incidentally, "-" in the table means a composition containing no effective ingredient.

Judgment standard

0: Growth inhibition rate; 0 to 15%

1: Growth inhibition rate; 16 to 35%

2: Growth inhibition rate; 36 to 55%

3: Growth inhibition rate; 56 to 75%

4: Growth inhibition rate; 76 to 95%

5: Growth inhibition rate; 96 to 100%.

TABLE 5

Tests of herbicidal effects and crop injury against transplanted paddy-field rice

| Test No. | 3-phenoxy-4-pyridazinol derivatives (g/a) | Second herbicidally active compound (g/a) | Herbicidal effects | | | | | | Crop injury against transplanted rice |
|---|---|---|---|---|---|---|---|---|---|
| | | | Barnyard grass | Broad leaf | *Scirpus joncoides* | *Sagittaria pygmaea* | *Cyperus serotinus* | *Eleocharis kuroguwai* | |
| 1 | Example 1 (10) | A(5) | 5 | 5 | 5 | 5 | 5 | 5 | 0 |
| 2 | Example 1 (5) | A(5) | 5 | 5 | 5 | 5 | 5 | 4 | 0 |
| 3 | Example 1 (10) | B(5) | 5 | 5 | 5 | 5 | 5 | 4 | 0 |
| 4 | Example 1 (5) | B(5) | 5 | 5 | 5 | 5 | 5 | 4 | 0 |
| 5 | Example 1 (10) | C(5) | 5 | 5 | 5 | 5 | 5 | 4 | 0 |
| 6 | Example 1 (5) | C(5) | 5 | 5 | 5 | 5 | 5 | 4 | 0 |
| 7 | Example 1 (10) | — | 4 | 4 | 4 | 4 | 5 | 0 | 0 |
| 8 | Example 1 (5) | — | 2 | 3 | 2 | 4 | 4 | 0 | 0 |
| 9 | Example 6 (10) | A(5) | 5 | 5 | 5 | 5 | 5 | 5 | 0 |
| 10 | Example 6 (5) | A(5) | 5 | 5 | 5 | 5 | 5 | 5 | 0 |
| 11 | Example 6 (10) | C(5) | 5 | 5 | 5 | 5 | 5 | 5 | 0 |
| 12 | Example 6 (5) | C(5) | 5 | 5 | 5 | 5 | 5 | 5 | 0 |
| 13 | Example 6 (10) | — | 2 | 5 | 5 | 5 | 5 | 3 | 0 |
| 14 | Example 6 (5) | — | 1 | 5 | 5 | 5 | 5 | 2 | 0 |
| 15 | Example 16 (10) | A(5) | 5 | 5 | 5 | 5 | 5 | 2 | 0 |
| 16 | Example 16 (5) | A(5) | 5 | 5 | 5 | 5 | 5 | 2 | 0 |
| 17 | Example 16 (10) | B(5) | 5 | 5 | 5 | 5 | 5 | 3 | 0 |
| 18 | Example 16 (5) | B(5) | 5 | 5 | 5 | 5 | 5 | 2 | 0 |
| 19 | Example 16 (10) | — | 0 | 5 | 5 | 4 | 5 | 1 | 0 |
| 20 | Example 16 (5) | — | 0 | 5 | 3 | 3 | 4 | 0 | 0 |
| 21 | Example 23 (10) | A(5) | 5 | 5 | 5 | 5 | 5 | 5 | 0 |
| 22 | Example 23 (5) | A(5) | 5 | 5 | 5 | 5 | 5 | 3 | 0 |
| 23 | Example 23 (10) | B(5) | 5 | 5 | 5 | 5 | 5 | 5 | 0 |
| 24 | Example 23 (5) | B(5) | 5 | 5 | 5 | 5 | 5 | 3 | 0 |
| 25 | Example 23 (10) | C(5) | 5 | 5 | 5 | 5 | 5 | 5 | 0 |
| 26 | Example 23 (5) | C(5) | 5 | 5 | 5 | 5 | 5 | 2 | 0 |
| 27 | Example 23 (10) | — | 3 | 5 | 5 | 5 | 5 | 3 | 0 |
| 28 | Example 23 (5) | — | 2 | 5 | 5 | 5 | 5 | 2 | 0 |
| 29 | Example 47 (10) | A(5) | 5 | 5 | 5 | 5 | 5 | 5 | 0 |
| 30 | Example 47 (5) | A(5) | 5 | 5 | 5 | 5 | 5 | 5 | 0 |
| 31 | Example 47 (10) | — | 3 | 5 | 5 | 5 | 5 | 2 | 0 |
| 32 | Example 47 (5) | — | 3 | 5 | 4 | 5 | 5 | 1 | 0 |
| 33 | Example 171 (10) | A(5) | 5 | 5 | 5 | 5 | 5 | 4 | 0 |
| 34 | Example 171 (5) | A(5) | 5 | 5 | 5 | 5 | 5 | 4 | 0 |
| 35 | Example 171 (10) | B(5) | 5 | 5 | 5 | 5 | 5 | 4 | 0 |
| 36 | Example 171 (5) | B(5) | 5 | 5 | 5 | 5 | 5 | 4 | 0 |
| 37 | Example 171 (10) | C(5) | 5 | 5 | 5 | 5 | 5 | 4 | 0 |
| 38 | Example 171 (5) | C(5) | 5 | 5 | 5 | 5 | 5 | 3 | 0 |
| 39 | Example 171 (10) | — | 3 | 5 | 5 | 5 | 5 | 3 | 0 |
| 40 | Example 171 (5) | — | 2 | 5 | 5 | 5 | 5 | 2 | 0 |
| 41 | Example 191 (2.5) | A(5) | 5 | 5 | 5 | 5 | 5 | 3 | 0 |
| 42 | Example 191 (2.5) | B(5) | 5 | 5 | 5 | 5 | 5 | 3 | 0 |
| 43 | Example 191 (2.5) | C(5) | 5 | 5 | 5 | 5 | 5 | 3 | 0 |
| 44 | Example 191 (2.5) | — | 1 | 3 | 3 | 2 | 5 | 1 | 0 |
| 45 | Example 245 (10) | A(5) | 5 | 5 | 5 | 5 | 5 | 3 | 0 |

TABLE 5-continued

Tests of herbicidal effects and crop injury against transplanted paddy-field rice

| Test No. | 3-phenoxy-4-pyridazinol derivatives (g/a) | Second herbicidally active compound (g/a) | Herbicidal effects | | | | | | Crop injury against transplanted rice |
|---|---|---|---|---|---|---|---|---|---|
| | | | Barnyard grass | Broad leaf | *Scirpus joncoides* | *Sagittaria pygmaea* | *Cyperus serotinus* | *Eleocharis kuroguwai* | |
| 46 | Example 245 (5) | A(5) | 5 | 5 | 5 | 5 | 5 | 2 | 0 |
| 47 | Example 245 (10) | C(5) | 5 | 5 | 5 | 5 | 5 | 3 | 0 |
| 48 | Example 245 (5) | C(5) | 5 | 5 | 5 | 5 | 5 | 2 | 0 |
| 49 | Example 245 (10) | — | 4 | 5 | 5 | 5 | 5 | 1 | 0 |
| 50 | Example 245 (5) | — | 3 | 5 | 5 | 4 | 4 | 0 | 0 |
| 51 | Example 249 (10) | A(5) | 5 | 5 | 5 | 5 | 5 | 3 | 0 |
| 52 | Example 249 (5) | A(5) | 5 | 5 | 5 | 5 | 5 | 3 | 0 |
| 53 | Example 249 (10) | — | 2 | 5 | 5 | 5 | 5 | 2 | 0 |
| 54 | Example 249 (5) | — | 1 | 5 | 3 | 5 | 5 | 1 | 0 |
| 55 | Example 288 (10) | A(5) | 5 | 5 | 5 | 5 | 5 | 5 | 0 |
| 56 | Example 288 (5) | A(5) | 5 | 5 | 5 | 5 | 5 | 5 | 0 |
| 57 | Example 288 (10) | — | 0 | 5 | 5 | 5 | 5 | 3 | 0 |
| 58 | Example 288 (5) | — | 0 | 5 | 5 | 5 | 4 | 2 | 0 |
| 59 | — | A (30) | 5 | 5 | 4 | 5 | 4 | 2 | 0 |
| 60 | — | A(5) | 3 | 4 | 3 | 4 | 2 | 0 | 0 |
| 61 | — | B (30) | 5 | 5 | 4 | 5 | 4 | 2 | 0 |
| 62 | — | B(5) | 3 | 4 | 3 | 4 | 2 | 0 | 0 |
| 63 | — | C (30) | 5 | 5 | 4 | 5 | 4 | 2 | 0 |
| 64 | — | C(5) | 3 | 5 | 2 | 4 | 1 | 0 | 0 |

TEST EXAMPLE 5

Tests of Herbicidal Effects and Crop Injury Against Upland Crops (Soil Treatment)

Upland soil was filled in 150 cm² pot, and seeds of barnyardgrass, *Cyperus esculentus L.*, velvetleaf, black nightshade, tall morningglory and corn were sowed, and grown in a greenhouse. At the next day of seeding, a predetermined chemical dosage of the wettable powder prepared in accordance with Preparation example 5 was diluted with water and applied to soil surface. After 21 days from the treatment, herbicidal effects and crop injury against corn were judged according to the following judgment standard, and the results were shown in Tables 6 to 8. Incidentally, "-" in the table means that the composition does not contain the effective ingredient.

Judgment standard

0: Growth inhibition rate; 0 to 9%
1: Growth inhibition rate; 10 to 19%
2: Growth inhibition rate; 20 to 29%
3: Growth inhibition rate; 30 to 39%
4: Growth inhibition rate; 40 to 49%
5: Growth inhibition rate; 50 to 59%
6: Growth inhibition rate; 60 to 69%
7: Growth inhibition rate; 70 to 79%
8: Growth inhibition rate; 80 to 89%
9: Growth inhibition rate; 90 to 98%
10: Growth inhibition rate; 99 to 100%.

TABLE 6

Tests of herbicidal effects and crop injury against corn (Example 23 + compound D)

| Test No. | 3-phenoxy-4-pyridazinol derivatives (g/ha) | Second herbicidally active compound (g/ha) | Herbicidal effects | | | | Crop injury against corn |
|---|---|---|---|---|---|---|---|
| | | | Barnyard-grass | Velvetleaf | Tall Morningglory | Black Nightshade | |
| 1 | Example 23 (250) | D(25) | 10 | 10 | 9 | 10 | 0 |
| 2 | Example 23 (125) | D(25) | 10 | 10 | 7 | 10 | 0 |
| 3 | Example 23 (63) | D(25) | 10 | 10 | 8 | 10 | 0 |
| 4 | — | D(25) | 10 | 9 | 5 | 9 | 0 |
| 5 | Example 23 (250) | D(12.5) | 10 | 10 | 9 | 10 | 0 |
| 6 | Example 23 (125) | D(12.5) | 10 | 10 | 5 | 9 | 0 |
| 7 | Example 23 (63) | D(12.5) | 10 | 9 | 3 | 9 | 0 |
| 8 | — | D(12.5) | 10 | 7 | 0 | 9 | 0 |
| 9 | Example 23 (250) | D(6.3) | 10 | 10 | 6 | 9 | 0 |
| 10 | Example 23 (125) | D(6.3) | 9 | 10 | 5 | 10 | 0 |
| 11 | Example 23 (63) | D(6.3) | 5 | 9 | 1 | 9 | 0 |
| 12 | — | D(6.3) | 3 | 6 | 2 | 5 | 0 |

TABLE 7

Test of herbicidal effects and chemical damage against corn (Example 23 + compound E)

| Test No. | 3-phenoxy-4-pyridazinol derivatives (g/ha) | Second herbicidally active compound (g/ha) | Herbicidal effects | | | | | crop injury against corn |
|---|---|---|---|---|---|---|---|---|
| | | | Barnyard-grass | *Cyperus esculentus* | Velvet-leaf | TallMorning glory | Black Nightshade | |
| 1 | Example 23 (125) | E(200) | 10 | 9 | 10 | 10 | 10 | 0 |
| 2 | Example 23 (63) | E(200) | 10 | 9 | 10 | 10 | 10 | 0 |
| 3 | — | E(200) | 10 | 8 | 10 | 10 | 9 | 0 |
| 4 | Example 23 (125) | E(100) | 10 | 9 | 10 | 10 | 10 | 0 |
| 5 | Example 23 (63) | E(100) | 10 | 8 | 10 | 10 | 9 | 0 |
| 6 | — | E(100) | 9 | 8 | 7 | 7 | 6 | 0 |
| 7 | Example 23 (125) | E(50) | 9 | 8 | 10 | 8 | 10 | 0 |
| 8 | Example 23 (63) | E(50) | 10 | 9 | 9 | 7 | 9 | 0 |
| 9 | — | E(50) | 7 | 8 | 7 | 6 | 7 | 0 |

TABLE 8

Test of herbicidal effects and chemical damage against corn (Example 23 + compound F)

| Test No. | 3-phenoxy-4-pyridazinol derivatives (g/ha) | Second herbicidally active compound (g/ha) | Crop Herbicidal effects | | | | | injury against corn |
|---|---|---|---|---|---|---|---|---|
| | | | Barnyard-grass | *Cyperus esculentus* | Velvetleaf | Tall Morningglory | Black Nightshade | |
| 1 | Example 23 (125) | F(100) | 10 | 9 | 10 | 9 | 10 | 0 |

TABLE 8-continued

Test of herbicidal effects and chemical damage against corn (Example 23 + compound F)

| Test No. | 3-phenoxy-4-pyridazinol derivatives (g/ha) | Second herbicidally active compound (g/ha) | Crop Herbicidal effects | | | | | injury against corn |
|---|---|---|---|---|---|---|---|---|
| | | | Barnyard-grass | Cyperus esculentus | Velvetleaf | Tall Morningglory | Black Nightshade | |
| 2 | Example 23 (63) | F(100) | 10 | 9 | 10 | 9 | 10 | 0 |
| 3 | — | F(100) | 9 | 9 | 10 | 8 | 8 | 0 |
| 4 | Example 23 (125) | F(50) | 10 | 9 | 10 | 7 | 10 | 0 |
| 5 | Example 23 (63) | F(50) | 9 | 9 | 10 | 7 | 10 | 0 |
| 6 | — | F(50) | 8 | 9 | 10 | 5 | 3 | 0 |
| 7 | Example 23 (125) | F(25) | 9 | 9 | 10 | 7 | 9 | 0 |
| 8 | Example 23 (63) | F(25) | 7 | 8 | 9 | 5 | 10 | 0 |
| 9 | — | F(25) | 4 | 8 | 9 | 2 | 6 | 0 |

TEST EXAMPLE 6

Tests of Herbicidal Effects and Crop Injury Against Upland crops (foliar treatment)

Upland soil was filled in 150 cm² pot, and seeds of barnyardgrass, *Cyperus esculentus L.*, velvetleaf, black nightshade, tall morningglory and corn were sowed, and grown in a greenhouse. After the weeds were grown with 10 to 15 cm or so, a predetermined chemical dosage of the wettable powder prepared in accordance with Preparation example 5 was diluted with water containing 0.05% of GRAMIN S and applied as a foliar treatment. After 14 days from the treatment, herbicidal effects and crop injury were judged in accordance with the judgment standard of Test example 5, and the results were shown in Tables 9 and 10. Incedentally, "-" in the table means no effective ingredient was contained.

TABLE 9

Test of herbicidal effects and crop injury against corn (Example 23 + compound E)

| Test No. | 3-phenoxy-4-pyridazinol derivatives (g/ha) | Second herbicidally active compound (g/ha) | Herbicidal effects | | | | | crop injury against corn |
|---|---|---|---|---|---|---|---|---|
| | | | Barnyard grass | Cyperus esculentus | Velvet-leaf | TallMorning glory | Black Nightshade | |
| 1 | Example 23 (250) | E(200) | 9 | 8 | 10 | 9 | 10 | 0 |
| 2 | Example 23 (125) | E(200) | 9 | 9 | 10 | 9 | 10 | 0 |
| 3 | Example 23 (63) | E(200) | 9 | 9 | 10 | 8 | 10 | 0 |
| 4 | — | E(200) | 7 | 8 | 10 | 9 | 10 | 0 |
| 5 | Example 23 (250) | E(100) | 9 | 9 | 10 | 9 | 10 | 0 |
| 6 | Example 23 (125) | E(100) | 9 | 8 | 10 | 9 | 10 | 0 |
| 7 | Example 23 (63) | E(100) | 8 | 9 | 10 | 8 | 9 | 0 |
| 8 | — | E(100) | 2 | 7 | 10 | 7 | 10 | 0 |
| 9 | Example 23 (250) | E(50) | 8 | 9 | 10 | 7 | 10 | 0 |
| 10 | Example 23 (125) | E(50) | 5 | 8 | 10 | 9 | 10 | 0 |
| 11 | Example 23 (63) | E(50) | 2 | 8 | 10 | 8 | 10 | 0 |
| 12 | — | E(50) | 1 | 6 | 9 | 6 | 9 | 0 |

TABLE 10

Test of herbicidal effects and crop injury against corn (Example 23 + compound F)

| Test No. | 3-phenoxy-4-pyridazinol derivatives (g/ha) | Second herbicidally active compound (g/ha) | Barnyardgrass | *Cyperus esculentus* | Velvetleaf | TallMorning glory | Black Nightshade | Crop injury against corn |
|---|---|---|---|---|---|---|---|---|
| 1 | Example 23 (250) | F(100) | 8 | 7 | 10 | 9 | 10 | 0 |
| 2 | Example 23 (125) | F(100) | 6 | 7 | 9 | 9 | 10 | 0 |
| 3 | — | F(100) | 2 | 6 | 10 | 9 | 9 | 0 |
| 4 | Example 23 (250) | F(50) | 4 | 7 | 10 | 9 | 10 | 0 |
| 5 | Example 23 (125) | F(50) | 2 | 7 | 10 | 9 | 10 | 0 |
| 6 | — | F(50) | 0 | 5 | 10 | 5 | 10 | 0 |
| 7 | Example 23 (250) | F(25) | 1 | 7 | 10 | 6 | 10 | 0 |
| 8 | Example 23 (125) | F(25) | 1 | 6 | 10 | 5 | 10 | 0 |
| 9 | — | F(25) | 0 | 4 | 9 | 2 | 7 | 0 |

Utilizability in Industry

The compounds of the present invention have herbicidal activities, and can be used as a herbicidal composition for a paddy field, upland field, orchard, pasture, turf, forest or non-crop land.

The compounds of the present invention show herbicidal activities against various weeds which cause problems in a paddy field, for example, annual broad-leaved weeds such as *Lindernia* spp., *Vandellia angustifolia* Benth., *Rotala indica, Elatine triandra, Monochoria vaginaris, Murdannia keisak, Dopatirum junceum* (Roxb.) Hamilt, *Ammannia multiflora,* etc.; perennial arrowhead weeds such as *Sagittaria pygmaea* Miq., arrowhead (*Sagittaria trifolia* L.), *Alisma canaliculatum,* etc.; annual Cyperaceous weeds such as flatsedge, smallflower umbrellasedge, etc.; perennial Cyperaceous weeds such as needle spikerush, *Scirpus joncoides, Cyperus serotinus,* Scrips Nipponicus Makino, etc.; or annual perennial Graminaceous weeds such as barnyardgrass, *Leersia oryzoides* (L.) Swartz., and the like, and show no crop injury against rice which causes any problem.

Also, the compounds of the present invention show herbicidal activities both by foliar application and soil application agaist valious kinds of weeds, which are troublesome in upland fields.

Moreover, they can be used not only in a paddy field and an upland filed, but also in an orchard, a mulberry field and a non-crop land.

Also, weeding spectrum of the herbicidal composition of the present invention can be enlarged by using 3-phenoxy-4-pyridazinol derivatives and a second herbicidally active compound in admixture which are effective ingredients than its range to be applied which had been obtained with a single agent use. The weeding spectrum of the composition according to the present invention covers *Graminaceous* weeds, annual broad-leaved weeds and whole *perennial* weeds such as Arrowhead, *Cyperaceous* weeds, etc. Moreover, the composition of the present invention has high safety to paddyfield rice or upland crops, and has a wide application window. Also, the composition of the present invention shows synergistic effects in the herbicidal effects, and shows sufficient effects with a mixture of compounds with a markedly lower chemical dosage than the chemical dosage is used as a single agent in the case where each. As a result, the composition of the present invention is hightened in herbicidal activity so that it is sufficient with a one time treatment agent, and its effects are continued for a long period of time. Also, the composition of the present invention shows no crop injury against paddy-field rice, and it can be applied both of before transplanting and immediately after transplanting.

The invention claimed is:

1. A compound represented by the formula:

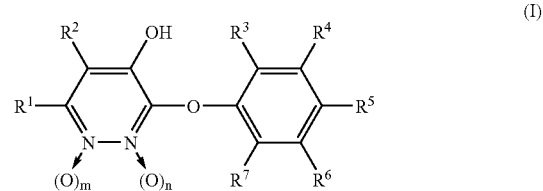

(I)

wherein $R^1$ is a chlorine atom or a bromine atom, $R^2$ is a hydrogen atom, $R^3$, $R^4$, $R^5$, $R^6$ and $R^7$ each independently represent a hydrogen atom, a fluorine atom, a chlorine atom, a bromine atom, an iodine atom, a $C_1$ to $C_4$ alkyl group, a $C_3$ to $C_4$ cycloalkyl group, a cyano group, a $C_2$ to $C_3$ alkoxycarbonyl group, a nitro group, a $C_1$ to $C_3$ alkoxy group or a trifluoromethoxy group, or $R^3$, $R^4$, $R^5$, $R^6$ and $R^7$ are a group represented by —$CH_2CH_2CH_2$—, —$CH(CH_3)CH_2CH_2$—, $OCH_2CH_2$, —$OCH$=$CH$— or

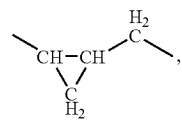

which is formed by two adjacent members of $R^3$, $R^4$, $R^5$, $R^6$ and $R^7$, provided that $R^3$ is not a hydrogen atom, and m and n are both zero, a salt thereof or an ester thereof.

2. The compound, a salt thereof or an ester thereof according to claim 1, wherein $R^1$ is a chlorine atom.

3. The compound, a salt thereof or an ester thereof according to claim 1, wherein $R^3$, $R^4$, $R^5$, $R^6$ and $R^7$ each independently represent a hydrogen atom, a fluorine atom, a chlorine atom, a bromine atom, an iodine atom, a $C_1$ to $C_3$ alkyl group, a $C_3$ to $C_4$ cycloalkyl group, a cyano group or a $C_1$ to $C_2$ alkoxy group, or $R^3$, $R^4$, $R^5$, $R^6$ and $R^7$ are a group represented by —$CH_2CH_2CH_2$— or —$OCH=CH$—, which is formed by two adjacent members of $R^3$, $R^4$, $R^5$, $R^6$ and $R^7$, provided that $R^3$ is not a hydrogen atom.

4. The compound, a salt thereof or an ester thereof according to claim 1, wherein $R^1$ is a chlorine atom, $R^3$, $R^4$, $R^5$, $R^6$ and $R^7$ each independently represent a hydrogen atom, a fluorine atom, a chlorine atom, a bromine atom, an iodine atom, a methyl group, an ethyl group, an isopropyl group, a cyclopropyl group or a methoxy group, or $R^3$, $R^4$, $R^5$, $R^6$ and $R^7$ are a group represented by —$CH_2CH_2CH_2$—, which is formed by two adjacent members of $R^3$, $R^4$, $R^5$, $R^6$ and $R^7$, provided that $R^3$ is not a hydrogen atom.

5. The compound according to claim 1, wherein the compound is selected from the group consisting of 6-chloro-3-(2-iodophenoxy)-4-pyridazinol, 6-chloro-3-(2-methyiphenoxy)-4-pyridazinol, 6-chloro-3-(2-cyclopropyiphenoxy)-4-pyridazinol, 6-chloro-3-(2,3-dihydro-1H-inden-4-yloxy)-4-pyridazinol, 3-(1-benzofuran-7-yloxy)-6-chloro-4-pyridazinol, 6-chloro-3-(2-methoxy-5-methylphenoxy)-4-pyridazinol, 6-chloro-3-(2-chloro-6-cyclopropylphenoxy)-4-pyridazinol, 3-(2-bromo-6-methylphenoxy)-6-chloro-4-pyridazinol, 6-chloro-3-(2-cyclopropyl-6-methylphenoxy)-4-pyridazinol and 6-chloro-3-(2-cyclopropyl-3,5-dimethyiphenoxy)-4-pyridaziflol, or a salt thereof or an ester thereof.

6. The ester of the compound according to claims 1, 2, 3, 4 or 5, in which a group bonded to the oxygen atom of the hydroxyl group at the 4-position of the pyrazine ring is a $C_2$ to $C_4$ alkylcarbonyl group; a benzoyl group which is unsubstituted or substituted with a methyl group or a 4-(2,4-dichlorobenzoyl)-1,3-dimethyl-1H-pyrazol-5-yloxycarbonyl group; a 1-azetidinylcarbonyl group; a 4-morpholinylcarbonyl group; a $C_2$ to $C_3$ alkoxycarbonyl group which is unsubstituted or substituted with 1 to 3 chlorine atoms; a dimethylcarbamoyl group; a methoxy(methyl)carbamoyl group; a $C_1$ to $C_3$ alkylsulfonyl group which is unsubstituted or substituted with 1 to 3 fluorine atoms; or a phenylsulfonyl group which is unsubstituted or substituted with a chlorine atom, a methyl group, a 4-(2,4-dichlorobenzoyl)-1,3-dimethyl-1H-pyrazol-5-yloxysulfonyl group or a nitro group.

7. The compound or a salt thereof or an ester thereof according to claim 1, wherein the compound is 6-chloro-3-(2-cyclopropyl-6-methylphenoxy)-4-pyridazinyl 4-methylbenzoate.

8. The compound or a salt thereof or an ester thereof according to claim 1, wherein the compound is 6-chloro-3-(2-cyclopropyl-6-methylphenoxy)-4-pyridazinyl dimethylcarbamate.

9. The compound or a salt thereof or an ester thereof according to claim 1, wherein the compound is 6-chloro-3-(2-cyclopropyl-6-methylphenoxy)-4-pyridazinyl 1-propanesulfonate.

10. The compound or a salt thereof or an ester thereof according to claim 1, wherein the compound is 6-chloro-3-(2-cyclopropyl-6-methylphenoxy)-4-pyridazinyl 4-methylbenzenesulfonate.

11. The compound or a salt thereof or an ester thereof according to claim 1, wherein the compound is 6-chloro-3-(2-cyclopropyl-6-methylphenoxy)-4-pyridazinyl 4-morpholinecarboxylate.

12. The compound or a salt thereof or an ester thereof according to claim 1, wherein the compound is 6-chloro-3-(2-cyclopropyl-6-methylphenoxy)-4-pyridazinyl 1-azetizinecarboxylate.

13. The compound or a salt thereof or an ester thereof according to claim 1, wherein the compound is 6-chloro-3-(2-cyclopropyl-6-methylphenoxy)-4-pyridazinyl benzenesulfonate.

14. An agricultural chemical composition which comprises the compound, a salt thereof or an ester thereof according to claim 1 as an effective ingredient in combination with a carrier.

15. A herbicidal composition which comprises (i) a herbicidally effective amount of at least one 3-phenoxy-4-pyridazinol compound selected from the group consisting of the compound, a salt thereof or an ester thereof according to claim 1, and (ii) a herbicidally effective amount of at least one herbicidally active compound selected from the group consisting of 4-(2,4-dichlorobenzoyl)-1,3-dimethyl-5-pyrazolyl-p-toluenesulfonate, 2-[4-(2,4-dichlorobenzoyl)-1,3-dimethylpyrazol-5-yloxy]acetophenone, 2-[4-(2,4-dichloro-m-toluoyl)-1,3-dimethylpyrazol-5-yloxy]-4'-methylacetophenone, 5-cyclopropyl-1,2-oxazol-4-yl α-α-α-trifluoro-2-mesyl-p-tolyl ketone, 2-(2-chloro-4-mesylbenzoyl)cyclohexan-1,3-dione, 2-(4-mesyl-2-nitrobenzoyl)cyclohexan-1,3-dione and 4-chloro-2-(methylsulfonyl)phenyl 5-cyclopropyl-4-isoxazolyl ketone.

16. The herbicidal composition according to claim 15, wherein the herbicidally active compound is 4-(2,4-dichlorobenzoyl)-1,3-dimethyl-5-pyrazolyl-p-toluenesulfonate.

17. A method for killing weeds comprising applying to weeds or a locus thereof a herbicidally effective amount of the compound, a salt thereof or an ester according to claim 1.

18. A method for killing weeds comprising applying to weeds or a locus thereof a herbicidally effective amount of the composition according to claim 15.

* * * * *

UNITED STATES PATENT AND TRADEMARK OFFICE
CERTIFICATE OF CORRECTION

PATENT NO. : 7,608,563 B2
APPLICATION NO. : 10/487013
DATED : October 27, 2009
INVENTOR(S) : Yoshihisa Tsukamoto et al.

It is certified that error appears in the above-identified patent and that said Letters Patent is hereby corrected as shown below:

Title Page, Item (73) Assignee, replace "MITSUI AGRO CHEMICALS, INC." with --MITSUI CHEMICALS AGRO, INC.--

Signed and Sealed this
Twenty-third Day of June, 2015

Michelle K. Lee
*Director of the United States Patent and Trademark Office*